United States Patent
Li

(10) Patent No.: US 11,357,869 B2
(45) Date of Patent: *Jun. 14, 2022

(54) COMPOSITIONS AND METHODS FOR TREATING LEBER'S HEREDITARY OPTIC NEUROPATHY WITH NADH DEHYDROGENASE PROTEINS

(71) Applicant: Wuhan Neurophth Biotechnology Limited Company, Hubei (CN)

(72) Inventor: Bin Li, Hubei (CN)

(73) Assignee: Wuhan Neurophth Biotechnology Limited Company, Hubei (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/361,884

(22) Filed: Jun. 29, 2021

(65) Prior Publication Data

US 2021/0353774 A1 Nov. 18, 2021

Related U.S. Application Data

(63) Continuation of application No. PCT/CN2020/134859, filed on Dec. 9, 2020.

(51) Int. Cl.
| | | |
|---|---|---|
| *A61K 48/00* | (2006.01) | |
| *A61K 31/573* | (2006.01) | |
| *A61K 31/664* | (2006.01) | |
| *A61K 47/10* | (2017.01) | |
| *C12N 15/86* | (2006.01) | |
| *C12N 7/00* | (2006.01) | |

(52) U.S. Cl.
CPC .......... *A61K 48/005* (2013.01); *A61K 31/573* (2013.01); *A61K 31/664* (2013.01); *A61K 47/10* (2013.01); *C12N 7/00* (2013.01); *C12N 15/86* (2013.01); *C12N 2750/14143* (2013.01)

(58) Field of Classification Search
None
See application file for complete search history.

(56) References Cited

U.S. PATENT DOCUMENTS

| | | |
|---|---|---|
| 3,625,214 A | 12/1971 | Higuchi |
| 4,789,734 A | 12/1988 | Pierschbacher |
| 4,897,268 A | 1/1990 | Tice et al. |
| 4,906,474 A | 3/1990 | Langer et al. |
| 4,925,673 A | 5/1990 | Steiner et al. |
| 5,075,109 A | 12/1991 | Tice et al. |
| 5,811,128 A | 9/1998 | Tice et al. |
| 5,814,344 A | 9/1998 | Tice et al. |
| 5,820,883 A | 10/1998 | Tice et al. |
| 5,853,763 A | 12/1998 | Tice et al. |
| 5,928,647 A | 7/1999 | Rock |
| 5,942,252 A | 8/1999 | Tice et al. |
| 6,207,392 B1 | 3/2001 | Weiss et al. |
| 7,704,721 B2 | 4/2010 | Wright et al. |
| 8,637,257 B2 | 1/2014 | Brys et al. |
| 9,701,961 B2 | 7/2017 | Feinstein et al. |
| 10,308,987 B2 | 6/2019 | Parr et al. |
| 10,906,931 B2 | 2/2021 | Moghadam |
| 11,034,954 B2 | 6/2021 | Li |
| 2008/0166724 A1 | 7/2008 | Gerber et al. |
| 2009/0306188 A1 | 12/2009 | Corral-Debrinski et al. |
| 2010/0272688 A1 | 10/2010 | Acland et al. |
| 2015/0250869 A1 | 9/2015 | Sene et al. |
| 2016/0206706 A1 | 7/2016 | Wright et al. |
| 2016/0289674 A1 | 10/2016 | Bancel et al. |
| 2018/0207293 A1 | 7/2018 | Shimizu et al. |
| 2020/0263172 A1 | 8/2020 | Li |
| 2021/0163898 A1 | 6/2021 | Towheed et al. |
| 2021/0189429 A1 | 6/2021 | Li |

FOREIGN PATENT DOCUMENTS

| | | |
|---|---|---|
| CN | 102517304 A | 6/2012 |
| CN | 102634527 A | 8/2012 |
| CN | 102634527 B | 8/2012 |
| CN | 104450747 B | 3/2015 |
| CN | 104450747 B | 2/2018 |
| EP | 2913403 A1 | 9/2015 |
| WO | WO-9739776 A1 | 10/1997 |
| WO | WO 2006/117250 A2 | 11/2006 |
| WO | WO 2008/063802 A2 | 5/2008 |
| WO | WO 2016/044023 A1 | 3/2016 |
| WO | WO 2017/011519 A1 | 1/2017 |
| WO | WO-2019033119 A1 | 2/2019 |
| WO | WO-2019241206 A1 | 12/2019 |
| WO | WO 2020/000641 A1 | 1/2020 |
| WO | WO 2020/001657 A1 | 1/2020 |
| WO | WO 2020/010491 A1 | 1/2020 |

(Continued)

OTHER PUBLICATIONS

Allocca et al., "Novel Adeno-Associated Virus Serotypes Efficiently Transduce Murine Photoreceptors," J Viol 81(20):11372-11380 (2007).

Altschul, et al. "A protein alignment scoring system sensitive at all evolutionary distances." J Mol Evol. (3):290-300. (1993).

Altschul, et al. "Gapped BLAST and PSI-BLAST: a new generation of protein database search programs." Nucleic Acids Res., 25:3389-3402 (1997).

Altschul, S, F et al., "Basic local alignment search tool," (1990) J Mol Biol 215:403-10 (1990).

Bainbridge et al., "Effect of gene therapy on visual function in Leber's congenital amaurosis," N Engl J Med. 358(21):2231-2239 (2008).

(Continued)

*Primary Examiner* — Robert M Kelly
(74) *Attorney, Agent, or Firm* — Cooley LLP

(57) ABSTRACT

Disclosed herein is a recombinant nucleic acid, comprising: a mitochondrial targeting sequence; a mitochondrial protein coding sequence, wherein said mitochondrial protein coding sequence encodes a polypeptide comprising a mitochondrial protein; and a 3'UTR nucleic acid sequence. Also disclosed is a pharmaceutical composition comprising the recombinant nucleic acid and a method of treating Leber's hereditary optic neuropathy (LHON) using the pharmaceutical composition.

29 Claims, 10 Drawing Sheets

Specification includes a Sequence Listing.

(56) References Cited

FOREIGN PATENT DOCUMENTS

| WO | WO 2020/037938 A1 | 2/2020 |
|---|---|---|
| WO | WO 2020/038352 A1 | 2/2020 |
| WO | WO 2020/077756 A1 | 4/2020 |
| WO | WO 2020/082417 A1 | 4/2020 |

OTHER PUBLICATIONS

Bangham et al., "Diffusion of univalent ions across the lamellae of swollen phospholipids," J. Mol. Biol. 13(1): 238-252 (1965).

Bonnet, Crystel et al. The optimized allotopic expression of ND1 or ND4 genes restores respiratory chain complex I activity in fibroblasts harboring mutations in these genes Biochimica et Biophysica Acta 31 No. 10(1783): 1707-1717 (2008).

Choi et al., "AAV hybrid serotypes: improved vectors for gene delivery," Curr Gene Ther. 5(3):299-310 (2005).

Coura, et al. "The state of the art of adeno-associated virus-based vectors in gene therapy." Virol J. Oct. 16, 2007;4:99, pp. 1-7. doi: 10.1186/1743-422X-4-99.

Cronin, et al., "Functional Genomics Study of the RdCVF-/- Mouse Model", Investigative Ophthalmology & Visual Science, vol. 49, No. 3058, 2008, D1048, 2 pages.

Cross et al., Characterization of Adsorption of Adeno-Associated Virus to Commonly Used Catheter Materials: AAV2 vs. AAVI/2.[J], Molecular Therapy, No. 512 (2006).

Croyle et al., "Development of formulations that enhance physical stability of viral vectors for gene therapy," Gene Therapy 8:1281-1290 (2001).

Cwerman-Thibault. et al. "Nuclear Expression of Mitochondrial Nd4 Leads to the Protein Assembling in Complex I and Prevents Optic Atrophy and Visual Loss," Molecular Therapy—Methods & Clinical Development. 2(15003):1-15 (2015).

Devereux et al., "A comprehensive set of sequence analysis programs for the VAX," Nucleic Acids Research 12, 387-395 (1984).

Gao et al., "Comparison of Immunosuppressive Effects and ND4 Expression among Different Immunosuppressive Strategies following AAV2-ND4 Gene Treatment for Leber Hereditary Optic Neuropathy," Acta Medicinae Universitatis Scientiae et Technologiae Huazhong 42(2):187-191 (2013), with English Abstract.

Greenwood et al. Current research into brain barriers and the delivery of therapeutics for neurological diseases: a report on CNS barrier congress London, UK Fluids Barriers CNS. 14: 31 (2017).

Gregoriadis. "Liposomes." Drug Carriers in Biology and Medicine. Chapter 14: p. 2.sup. 287-341 (Academic Press, 1979).

Guidance on nonclinical safety studies for the conduct of human clinical trials and marketing authorization for pharmaceuticals. ICH/M3 (R2), 2009.

Guy, et al. "Gene Therapy for Leber Hereditary Optic Neuropathy: Low- and Medium-Dose Visual Results." Ophthalmology 124(11):1621-1634 (2017).

Hocquemiller et al. "Adeno-Associated Virus-Based Gene Therapy for CNS Diseases." Hum Gene Ther. 27(7):478-496 (2016).

Hudry et al. "Therapeutic AAV Gene Transfer to the Nervous System: A Clinical Reality." Neuron. Mar. 6, 2019;101(5):839-862. (Year: 2019).

International Search Report and Written Opinion issued by the International Searching Authority for Application No. PCT/CN2018/095023, dated Apr. 9, 2019, 14 pages including English translation of ISR.

International Search Report and Written Opinion issued by the International Searching Authority for Application No. PCT/CN2018/103937, dated Apr. 3, 2019, 19 pages including English translation of Search Report.

International Search Report and Written Opinion issued by the International Searching Authority for Application No. PCT/CN2018/113799, dated Aug. 5, 2019, 15 pages including English translation of Search Report.

International Search Report and Written Opinion issued by the International Searching Authority for Application No. PCT/CN2018/118662, dated Jul. 18, 2019, 18 pages including English translation of ISR.

International Search Report and Written Opinion issued by the International Searching Authority for Application No. PCT/CN2019/070461, dated May 22, 2019, 13 pages including translation of ISR.

International Search Report and Written Opinion issued by the International Searching Authority for Application No. PCT/CN2019/094136, dated Oct. 10, 2019, 10 pages.

International Search Report and Written Opinion issued by the International Searching Authority for Application No. PCT/CN2019/101538, dated Nov. 29, 2019, 14 pages.

Karlin, S. and Altschul, S., "Applications and statistics for multiple high-scoring segments in molecular sequences," Proc. Natl. Acad. Sci. USA, 90-5873-5877 (1993).

Kim, et al. "Preparation of multilamellar vesicles of defined size-distribution by solvent-spherule evaporation." Biochim Biophys Acta. 812(3):793-801 (1985).

Koilkonda, R. D et al. "Safety and Effects of the Vector for the Leber Hereditary Optic Neuropathy Gene Therapy Clinical Trial." JAMA Ophthalmol. 132(4):409-420 (2014).

Kotterman et al. "Antibody Neutralization Poses a Barrier to Intravitreal Adena-Associated Viral Vector Gene Delivery to Non-Human Primates." Gene Ther. Feb. 2015; 22(2): 116-126. (Year: 2015).

Kraus, M. and Aaronson, S., "Detection and isolation of novel protein-tyrosine kinase genes employing reduced stringency hybridization," Methods Enzymol., 200:546-556 (1991).

Kushnareva et al., "Mitochondrial Dysfunction in an Opa1 Q285STOP Mouse Model of Dominant Optic Atrophy Results from Opa11 Haploinsufficiency," Cell Death and Disease Jul. 7, 2016(7):e-2309, 13 pages.

Laughlin et al., "Spliced adenovirus-associated virus RNA.," PNAS, 76:5567-5571 (1979).

Mancuso et al., "Gene therapy for red-green colour blindness in adult primates," Nature 461:784-787 (2009).

Manfredsson et al. "AAV9: a potential blood-brain barrier buster." Mol Ther. Mar. 2009; 17(3): 403-405. (Year: 2009).

NCBI Gene ID: 4535. MT-ND1 mitochondrially encoded NADH dehydrogenase 1 [ *Homo sapiens* (human) ]. Updated on Apr. 20, 2021, 8 pages.

NCBI Gene ID: 4538. "MT-ND4 mitochondrially encoded NADH dehydrogenase 4 [ *Homo sapiens* (human) ]." Updated on Apr. 20, 2021, 8 pages.

NCBI Gene ID: 4541. "MT-ND6 mitochondrially encoded NADH dehydrogenase 6 [ *Homo sapiens* (human) ]." Updated on Apr. 20, 2021, 7 pages.

NCBI Reference Sequence: NC_001829.1, dated Aug. 13, 2018, 3 pages.

NCBI Reference Sequence: NC_002077.1, dated Aug. 13, 2018, 3 pages.

NCBI Reference Sequence: NC_001729.1, dated Aug. 13, 2018, 3 pages.

NCBI Reference Sequence: NC_004828.1, Aug. 13, 2018, 3 pages.

NCBI Reference Sequence: NC_005889.1, Aug. 13, 2018, 3 pages.

NCBI. "Genbank Accession No. KP240659.1" dated Dec. 4, 2016, 8 pages.

NCBI. "Genbank Accession No. LX309664.1" dated Oct. 28, 2017, 2 pages.

NCBI. Genbank Accession No. LX309667, dated Oct. 28, 2017, 2 pages.

NCBI. "Genbank Accession No. LX309670.1" dated Oct. 28, 2017, 2 pages.

NCBI. "Genbank Accession No. MF522909.1" GenBank, Oct. 21, 2017 (Oct. 21, 2017), 8 pages.

NCBI. "Genbank Accession No. YP_003024026.1" GenBank, Oct. 31, 2014 (Oct. 31, 2014), 2 pages.

Patel et al., "Poloxamers: A pharmaceutical excipients with therapeutic behaviors," International Journal of PharmTech Research 1(2):299-303 (2009).

(56) References Cited

OTHER PUBLICATIONS

Ribera et al. "Biochemical, histological and functional correction of mucopolysaccharidosis type IIIB by intra-cerebrospinal fluid gen therapy" Hum Mol Genet Apr. 1, 2015;24(7):2078-95. (2015).
Sun et al., "Detection of Neutralizing Antibody to Human Adenovirus Type 5 in Marmosets," J. South Med. Univ., 36(4):582-587 (2016).
Szoka et al., "Procedure for preparation of liposomes with large internal aqueous space and high capture by reverse-phase evaporation," Proc. Natl Acad. Sci. USA 75: 4194-4198 (1978).
Vignal, et al. "Safety of rAAV2/2-ND4 Gene Therapy for Leber Hereditary Optic Neuropathy." Ophthalmology. Jun. 2018; 125(6):945-947. doi: 10.1016/j.ophtha.2017.12.036.
Wan et al., "Efficacy and Safety of rAAV2-ND4 Treatment for Leber's Hereditary Optic Neuropathy," Scientific Reports, vol. 6, Article 21587, pp. 1-10 (2016).
Wu et al., "Adeno-associated virus serotypes: vector toolkit for human gene therapy," Molecular Therapy. 14(3):316-327 (2006).
Yang et al., "Long-Term Outcomes of Gene Therapy for the Treatment of Leber's Hereditary Optic Neuropathy," Ebiomedicine 10:258-268 (2016).
Yang et al., "Study on transfection of adeno associated virus 2-ND4 gene into mitochondria," Chinese Journal of Experimental Ophthalmology 8(32):693-695 (2014).
Yang, S. et al. "Chemical and material communication between the optic nerves in rats," Clinical and Experimental Ophthalmology 43:742-748 (2015).
Yang, Y, Codon and Anticodon, Foreign Medical Molecular Biology Fascicule 7(4):156-163 (1985). (English translation included).
Yu et al. "Mutant NADH dehydrogenase subunit 4 gene delivery to mitochondria by targeting sequence-modified adeno-associated virus induces visual loss and optic atrophy in mice," Molecular Vision 18:1668-1683 (2012).
Yu et al., "Gene delivery to mitochondria by targeting modified adenoassociated virus suppresses Leber's hereditary optic neuropathy in a mouse model," PNAS, pp. EI238-EI247 (2012).
Daya S, Berns KI. Gene therapy using adeno-associated virus vectors. Clinical microbiology reviews. Oct. 2008;21(4):583-93. (Year: 2008).
Entezari et al., "High-dose intravenous methylprednisolone in recent traumatic optic neuropathy; a randomized double-masked placebo-controlled clinical triai." Graefe's Archive for Clinical and Experimental Ophthalmology vol. 245, pp. 1267-1271 (2007) (Year: 2007).
Fumoto, S. et al., "Targeted Gene Delivery: Importance of Administration Routes," Intech, Chapter 1:3-31 (2013).
Glerum DM, Tzagoloff A. Isolation of a human cDNA for heme A: farnesyltransferase by functional complementation of a yeast cox10 mutant. Proceedings of the National Academy of Sciences. Aug. 30, 1994;91(18):8452-6. (Year: 1994).
Guy J, Qi X, Koilkonda RD, Arguello T, Chou TH, Ruggeri M, Porciatti V, Lewin AS, Hauswirth WW. Efficiency and safety of AAV-mediated gene delivery of the human ND4 complex I subunit in the mouse visual system. Investigative ophthalmology & visual science. Sep. 1, 2009;50(9):4205-14. (Year: 2009).
Kattenhorn et al., Adeno-Associated Virus Gene Therapy for Liver Disease, 2016, Human Gene Therapy, vol. 27 No. 12, pp. 947-961 (Year: 2016).
Mingozzi et al. "Immune responses to AAV vectors: overcoming barriers to successful gene therapy" Blood, 122 (1):23-36 (2013).
Newman NJ. Treatment of hereditary optic neuropathies. Nature Reviews Neurology. Oct. 2012;8(10):545-56. (Year: 2012).
Perrin S. Preclinical research: Make mouse studies work. Nature News. Mar. 27, 2014;507(7493):423. (Year: 2014).
Sequence alignment SEQ ID No. 10 of 17181849 and SEQ ID No. 19870 of 15174219; US20160289674A1 Publ: Oct. 6, 2016. Alignment Aug. 2021 (Year: 2016), 4 pages.
Sequence alignment SEQ ID No. 12 of 17181849 and SEQ ID No. 19864 of 15174219; US20160289674A1 Publ: Oct. 6, 2016. Alignment Aug. 2021 (Year: 2016), 5 pages.
Yuan et al., "Preliminary clinical observation of creatine phosphate sodium treatment for Leber hereditary optic neuropathy." Mar. 2017 Ophthalmology in China 26(2):126-130 (Year: 2017).

Sequence Alignment of Opt_ND1 (upper line) and ND1 (lower line)
Identity=79.00%(756/957)   Gap=0.00%(0/957)

```
  1    ATGCCCATGGCCAACCTGCTGCTGCTGATCGTGCCCATCCTGATCGCCATGGCCTTCCTG
       ||||||||||||||||| || || || || || ||||| || ||||| ||||| |||||
  1    ATGCCCATGGCCAACCTCCTACTCCTCATTGTACCCATTCTAATCGCAATGGCATTCCTA
 61    ATGCTGACCGAGCGCAAGATCCTGGGCTACATGCAGCTGCGCAAGGGCCCCAACGTGGTG
       ||||| ||||| || || || || ||||| ||||| || ||||| |||||||||||| ||
 61    ATGCTTACCGAACGAAAAATTCTAGGCTATATGCAACTACGCAAAGGCCCCAACGTGTA
121    GGCCCCTACGGCCTGCTGCAGCCCTTCGCCGACGCCATGAAGCTGTTCACCAAGGAGCCC
       |||||||||| || || || ||||||||| |||||||||||| || ||||||||| ||||||
121    GGCCCCTACGGGCTACTACAACCCTTCGCTGACGCCATGAAACTCTTCACCAAAGAGCCC
181    CTGAAGCCCGCCACCAGCACCATCACCCTGTACATCACCGCCCCACCCTGGCCCTGACC
       || || |||||||||    ||||||||||| |||||||||||| ||| | || || |||
181    CTAAAACCCGCCACATCTACCATCACCCTCTACATCACCGCCCCGACCTTAGCTCTCACC
241    ATCGCCCTGCTGCTGTGGACCCCCCTGCCCATGCCCAACCCCCTGGTGAACCTGAACCTG
       ||||| || || || ||||||||||| |||||||||||||||||||| ||||| |||||
241    ATCGCTCTTCTACTATGGACCCCCCTCCCCATGCCCAACCCCCTGGTCAACCTCAACCTA
301    GGCCTGCTGTTCATCCTGGCCACCAGCAGCCTGGCCGTGTACAGCATCCTGTGGAGCGGC
       ||||| || || || || |||||    ||||| || ||||||    |||| ||||| ||
301    GGCCTCCTATTTATTCTAGCCACCTCTAGCCTAGCCGTTACTCAATCCTCTGGTCAGGG
361    TGGGCCAGCAACAGCAACTACGCCCTGATCGGCGCCCTGCGCGCCGTGGCCCAGACCATC
       |||||    |||    ||||||||||||||||||||||| ||||| || || ||||| |||
361    TGGGCATCAAACTCAAACTACGCCCTGATCGGCGCACTGCGAGCAGTAGCCCAAACAATC
421    AGCTACGAGGTGACCCTGGCCATCATCCTGCTGAGCACCCTGCTGATGAGCGGCAGCTTC
       || || || ||||| ||||||||| ||    || ||    | || ||||| ||| |||
421    TCATATGAAGTCACCCTAGCCATCATTCTACTATCAACATTACTAATGAGTGGCTCCTTT
481    AACCTGAGCACCCTGATCACCACCCAGGAGCACCTGTGGCTGCTGCTGCCCAGCTGGCCC
       |||||    |||||| |||||| || || || ||||| ||| ||| | || ||||| |||||
481    AACCTCTCCACCCTTATCACAACACAAGAACACCTCTGGTTACTCCTGCCATCATGGCCC
541    CTGGCCATGATGTGGTTCATCAGCACCCTGGCCGAGACCAACCGCACCCCCTTCGACCTG
       |||||||||||||||||| ||| || || ||||||||||||||| ||||||||||||||
541    TTGGCCATGATGTGGTTTATCTCCACACTAGCAGAGACCAACCGAACCCCCTTCGACCTT
601    GCCGAGGGCGAGAGCGAGCTGGTGAGCGGCTTCAACATCGAGTACGCCGCCGGCCCCTTC
       ||||| || ||| || || || ||     ||||||||||||| |||||||| ||||||||
601    GCCGAAGGGGAGTCCGAACTAGTCTCAGGCTTCAACATCGAATACGCCGCAGGCCCCTTC
661    GCCCTGTTCTTCATGGCCGAGTACACCAACATCATCATGATGAACACCCTGACCACCACC
       ||||| ||||||||||||||||  |||||| |||||||| |||||||||||||||| ||
661    GCCCTATTCTTCATGGCCGAATACACAAAACATTATTATGATGAACACCCTCACCACTACA
721    ATCTTCCTGGGCACCACCTACGACGCCCTGAGCCCCGAGCTGTACACCACCTACTTCGTG
       ||||||||| || || || || || |||||    || || || ||||| || || || ||
721    ATCTTCCTAGGAACAACATATGACGCACTCCCCTGAACTCTACAACATATTTGTC
781    ACCAAGACCCTGCTGCTGACCAGCCTGTTCCTGTGGATCCGCACCGCCTACCCCCGCTTC
       ||||||||| || || |||  ||||||| | ||||| || || || |||||||| |||
781    ACCAAGACCCTACTTCTAACCTCCCTGTTCTTATGGATTCGAACAGCATACCCCGATTC
841    CGCTACGACCAGCTGATGCACCTGCTGTGGAAGAACTTCCTGCCCCTGACCCTGGCCCTG
       |||||||||||| || || |||||||||| || |||||||||||| ||||| ||  |
841    CGCTACGACCAACTCATGCACCTCCTATGGAAAACTTCCTACCACTCACCCTAGCATTA
901    CTGATGGTGTACGTGAGCATGCCCATCACCATCAGCAGCATCCCCCCCAGACCTAA
       || ||||||||| ||    ||||||||| || ||||| ||||| || ||||||
901    CTTATGTGGTATGTCTCCATGCCCATTACAATCTCCAGCATTCCCCCTCAAACCTAA
```

FIG. 3

Sequence Alignment of COX10-opt_ND1 (upper line) and
COX10-ND1 (lower line)
Identity=81% (840/1041) Gap=0.00%(0/1041)

```
1     ATGGCCGCATCTCCGCACACTCTCTCCTCACGCCTCCTGACAGGTTGCGTAGGAGGCTCT
      ||||||||||||||||||||||||||||||||||||||||||||||||||||||||||||
1     ATGGCCGCATCTCCGCACACTCTCTCCTCACGCCTCCTGACAGGTTGCGTAGGAGGCTCT

61    GTCTGGTATCTTGAAAGAAGAACTATGCCCATGGCCAACCTGCTGCTGCTGATCGTGCCC
      |||||||||||| |||||||||||||||||||||||||||||  || || || ||  |||
61    GTCTGGTATCTTGAAAGAAGAACTATGCCCATGGCCAACCTCCTACTCCTCATTGTACCC

121   ATCCTGATCGCCATGGCCTTCCTGATGCTGACCGAGCGCAAGATCCTGGGCTACATGCAG
      || || |||||||||||||||||| ||||| ||||| ||||| || ||||| ||| |  
121   ATTCTAATCGCAATGGCATTCCTAATGCTTACCGAACGAAAAATTCTAGGCTATATGCAA

181   CTGCGCAAGGGCCCCAACGTGGTGGGCCCCTACGGCCTGCTGCAGCCCTTCGCCGACGCC
      || || |||||||||||||||| |||||||||||| |||| ||| ||||||||||||||
181   CTACGCAAAGGCCCCAACGTTGTAGGCCCCTACGGGCTACTACAACCCTTCGCTGACGCC

241   ATGAAGCTGTTCACCAAGGAGCCCCTGAAGCCCGCCACCAGCACCATCACCCTGTACATC
      |||||  | |||||||| |||||||| || |||||||| || ||||||||| |||||||
241   ATGAAACTCTTCACCAAAGAGCCCCTAAAACCCGCCACATCTACCATCACCCTCTACATC

301   ACCGCCCCCACCCTGGCCCTGACCATCGCCCTGCTGCTGTGGACCCCCCTGCCCATGCCC
      ||||||||  | ||  |||| ||||||| |||| ||||| ||||||||||| ||||||||
301   ACCGCCCCCGACCTTAGCTCTCACCATCGCTCTTCTACTATGGACCCCCCTCCCCATGCCC

361   AACCCCCTGGTGAACCTGAACCTGGGCCTGCTGTTCATCCTGGCCACCAGCAGCCTGGCC
      |||||||||||| ||||| ||| ||||||||| ||||  ||| ||||| || |||||||
361   AACCCCCTGGTCAACCTCAACCTAGGCCTCCTATTTATTCTAGCCACCTCTAGCCTAGCC

421   GTGTACAGCATCCTGTGGAGCGGCTGGGCCAGCAACAGCAACTACGCCCTGATCGGCGCC
      || | ||| |||| ||| |  ||| || ||||| ||| || |||||||||||||||||
421   GTTTACTCAATCCTCTGGTCAGGGTGGGCATCAAACTCAAACTACGCCCTGATCGGCGCA

481   CTGCGCGCCGTGGCCCAGACCATCAGCTACGAGGTGACCCTGGCCATCATCCTGCTGAGC
      ||||| ||| || ||   ||| ||| |||| |||| || ||| ||||||| | |||| |
481   CTGCGAGCAGTAGCCCAAACAATCTCATATGAAGTCACCCTAGCCATCATTCTACTATCA

541   ACCCTGCTGATGAGCGGCAGCTTCAACCTGAGCACCCTGATCACCACCCAGGAGCACCTG
      || |  || ||||||||| | |||  |||   ||||| |||| ||| || || |||||
541   ACATTACTAATGAGTGGCTCCTTTAACCTCTCCACCCTTATCACAACACAAGAACACCTC

601   TGGCTGCTGCTGCCCAGCTGGCCCCTGGCCATGATGTGGTTCATCAGCACCCTGGCCGAG
      |||  |   ||||| |||||||||||||||||| |||||||| | ||||||||||| |||
601   TGGTTACTCCTGCCATCATGGCCCTTGGCCATGATGTGGTTTATCTCCACACTAGCAGAG

661   ACCAACCGCACCCCCTTCGACCTGGCCGAGGGCGAGAGCGAGCTGGTGAGCGGCTTCAAC
      |||||| | |||||||||||||| || ||||| || || |||| || |||||||||||
661   ACCAACCGAACCCCCTTCGACCTTGCCGAAGGGGAGTCCGAACTAGTCTCAGGCTTCAAC

721   ATCGAGTACGCCGCCGGCCCCTTCGCCCTGTTCTTCATGGCCGAGTACACCAACATCATC
      ||||| |||||||||| ||||||||||| || ||||||||||||| ||||| ||| |||
721   ATCGAATACGCCGCAGGCCCCTTCGCCCTATTCTTCATGGCCGAATACACAAACATTATT

781   ATGATGAACACCCTGACCACCACCATCTTCCTGGGCACCACCTACGACGCCCTGAGCCCC
      ||||||||||||||| |||| || ||||||||  ||||| |||| ||||| || ||| 
781   ATGATGAACACCCTCACCACTACAATCTTCCTAGGAACAACATATGACGCACTCTCCCCT

841   GAGCTGTACACCACCTACTTCGTGACCAAGACCCTGCTGCTGACCAGCCTGTTCCTGTGG
      || || || || || | ||| |||||||||||||| ||| || ||  |||| || ||||
841   GAACTCTACACAACATATTTTGTCACCAAGACCCTACTTCTAACCTCCCTGTTCTTATGG

901   ATCCGCACCGCCTACCCCCGCTTCCGCTACGACCAGCTGATGCACCTGCTGTGGAAGAAC
      || ||||| || |||||||| || ||||||||||| ||||||| || || ||| |||||
901   ATTCGAACAGCATACCCCCGATTCCGCTACGACCAACTCATGCACCTCCTATGGAAAAAC

961   TTCCTGCCCCTGACCCTGGCCCTGCTGATGTGGTACGTGAGCATGCCCATCACCATCAGC
      |||||| |  |||||| |||| ||||| ||||| |||| || ||||||| || || |||
961   TTCCTACCACTCACCCTAGCATTACTTATGTGGTATGTCTCCATGCCCATTACAATCTCC

1021  AGCATCCCCCCCAGACCTAA
      ||||| |||| ||  |||||
1021  AGCATTCCCCCTCAAACCTAA
```

FIG. 4

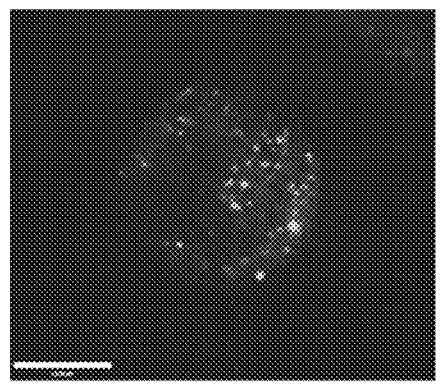
ND1-GFP
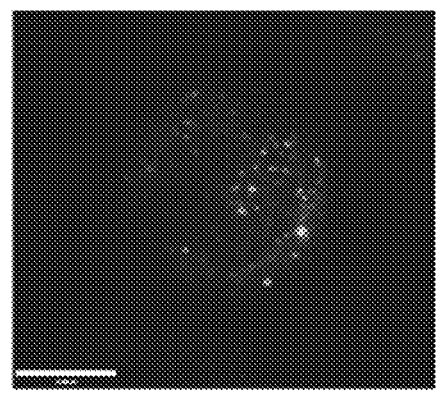
MitoTracker
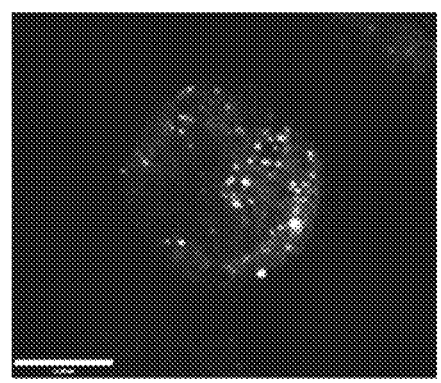
Merged
FIG. 6

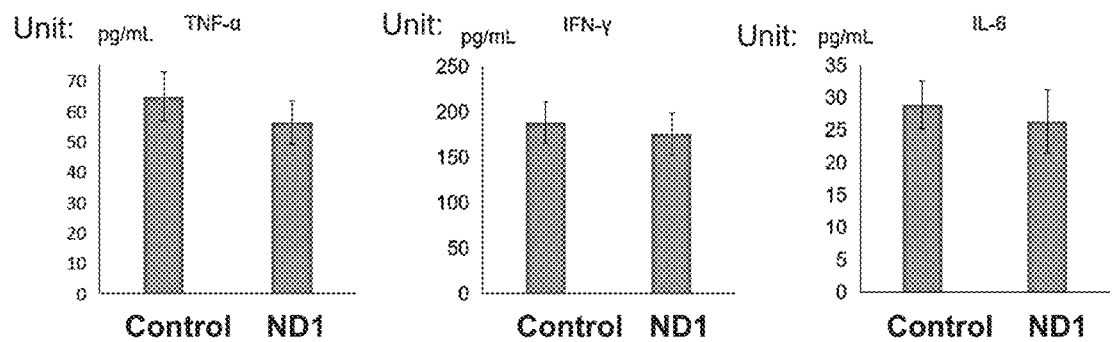
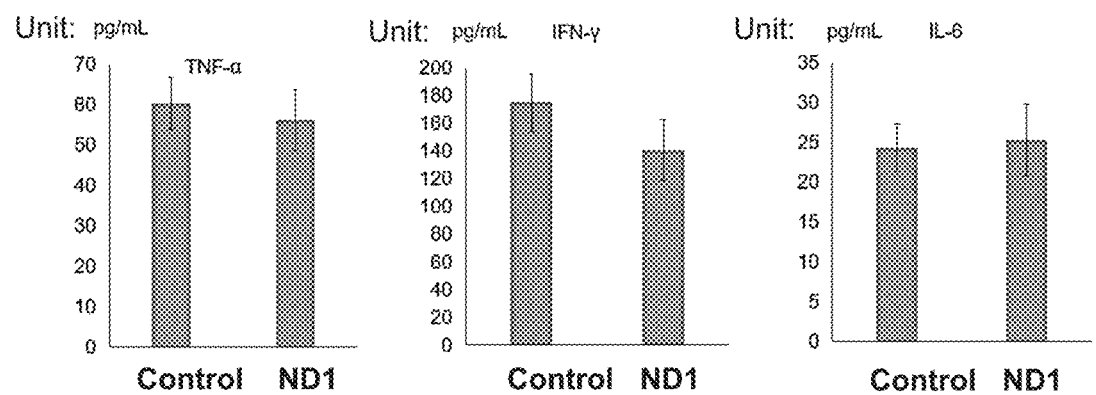
FIG. 10

```
SEQUENCE LISTING

<160> NUMBER OF SEQ ID NOS: 169

<210> SEQ ID NO 1
<211> LENGTH: 84
<212> TYPE: DNA
<213> ORGANISM: Homo sapiens

<400> SEQUENCE: 1
atggccgcat ctccgcacac tctctcctca cgcctcctga caggttgcgt aggaggctct    60
gtctggtatc ttgaaagaag aact                                          84

<210> SEQ ID NO 2
<211> LENGTH: 84
<212> TYPE: DNA
<213> ORGANISM: Artificial Sequence
<220> FEATURE:
<223> OTHER INFORMATION: opt_COX10

<400> SEQUENCE: 2
atggccgcct ctccacacac actgagtagc agactgctga ccggctgtgt tggcggctct    60
gtgtggtatc tggaacggcg gaca                                          84

<210> SEQ ID NO 3
<211> LENGTH: 84
<212> TYPE: DNA
<213> ORGANISM: Artificial Sequence
<220> FEATURE:
<223> OTHER INFORMATION: opt_COX10*

<400> SEQUENCE: 3
atggccgcca gccccacac cctgagcagc cgcctgctga ccggctgcgt gggcggcagc    60
gtgtggtacc tggagcgccg cacc                                          84

<210> SEQ ID NO 4
<211> LENGTH: 87
<212> TYPE: DNA
<213> ORGANISM: Artificial Sequence
<220> FEATURE:
<223> OTHER INFORMATION: COX8

<400> SEQUENCE: 4
```

```
atgtccgtcc tgacgcgcct gctgctgcgg ggcttgacac ggctcggctc ggcggctcca    60
gtgcggcgcg ccagaatcca ttcgttg                                        87

<210> SEQ ID NO 5
<211> LENGTH: 266
<212> TYPE: DNA
<213> ORGANISM: Homo sapiens

<400> SEQUENCE: 5
gtgctgcccg cctagaaagg gtgaagtggt tgtttccgtg acggactgag tacgggtgcc    60
tgtcaggctc ttgcggaagt ccatgcgcca ttgggagggc ctcggccgcg gctctgtgcc   120
cttgctgctg agggccactt cctgggtcat tcctggaccg ggagccgggc tggggctcac   180 acggggctc ccgcgtggcc gtctcggcgc ctgcgtgacc tccccgccgg cgggatgtgg    240
cgactacgtc gggccgctgt ggcctg                                        266

<210> SEQ ID NO 6
<211> LENGTH: 1380
<212> TYPE: DNA
<213> ORGANISM: Homo sapiens

<400> SEQUENCE: 6
atgctaaaac taatcgtccc aacaattatg ttactaccac tgacatggct ttccaaaaaa    60
cacatgattt ggatcaacac aaccacccac agcctaatta ttagcatcat ccctctacta   120 tttttttaacc aaatcaacaa caacctattt agctgttccc caacctttc ctccgacccc    180 ctaacaaccc ccctcctaat gctaactacc tggctcctac ccctcacaat catggcaagc   240
caacgccact tatccagtga accactatca cgaaaaaaac tctacctctc tatgctaatc   300
tccctacaaa tctccttaat tatgacattc acagccacag aactaatcat gttttatatc   360
ttcttcgaaa ccacacttat ccccaccttg gctatcatca cccgatgggg caaccagcca   420
gaacgcctga acgcaggcac atacttccta ttctacaccc tagtaggctc ccttcccta    480 ctcatcgcac taatttacac tcacaacacc ctaggctcac taaacattct actactcact   540
ctcactgccc aagaactatc aaactcctgg gccaacaact taatgtggct agcttacaca   600
atggctttta tggtaaagat gcctctttac ggactccact tatggctccc taaagcccat   660
gtcgaagccc ccatcgctgg gtcaatggta cttgccgcag tactcttaaa actaggcggc   720
tatggtatga tgcgcctcac actcattctc aacccctga caaaacacat ggcctacccc    780
ttccttgtac tatccctatg gggcatgatt atgacaagct ccatctgcct acgacaaaca   840
gacctaaaat cgctcattgc atactcttca atcagccaca tggccctcgt agtaacagcc   900
attctcatcc aaaccccctg gagcttcacc ggcgcagtca ttctcatgat cgcccacggg   960
cttacatcct cattactatt ctgcctagca aactcaaact acgaacgcac tcacagtcgc  1020
atcatgatcc tctctcaagg acttcaaact ctactcccac taatggcttt ttggtggctt  1080
ctagcaagcc tcgctaacct cgccttaccc cccactatta acctactggg agaactctct  1140
gtgctagtaa ccacgttctc ctggtcaaat atcactctcc tacttacagg actcaacatg  1200
ctagtcacag ccctatactc cctctacatg tttaccacaa cacaatgggg ctcactcacc  1260
caccacatta acaacatgaa accctcattc acacgagaaa acaccctcat gttcatgcac  1320
ctatccccca ttctcctcct atccctcaac cccgacatca ttaccgggtt ttcctcttaa  1380

<210> SEQ ID NO 7
```

<211> LENGTH: 1380
<212> TYPE: DNA
<213> ORGANISM: Artificial Sequence
<220> FEATURE:
<223> OTHER INFORMATION: opt_ND4

<400> SEQUENCE: 7

| | |
|---|---|
| atgctgaagc tgatcgtgcc caccatcatg ctgctgcctc tgacctggct gagcaagaaa | 60 |
| cacatgatct ggatcaacac caccacgcac agcctgatca tcagcatcat ccctctgctg | 120 |
| ttcttcaacc agatcaacaa caacctgttc agctgcagcc ccaccttcag cagcgaccct | 180 |
| ctgacaacac tctgctgat gctgaccacc tggctgctgc ccctcacaat catggcctct | 240 |
| cagagacacc tgagcagcga gcccctgagc cggaagaaac tgtacctgag catgctgatc | 300 |
| tccctgcaga tctctctgat catgaccttc accgccaccg agctgatcat gttctacatc | 360 |
| tttttcgaga caacgctgat ccccacactg gccatcatca ccagatgggg caaccagcct | 420 |
| gagagactga acgccggcac ctactttctg ttctacaccc tcgtgggcag cctgccactg | 480 |
| ctgattgccc tgatctacac ccacaacacc ctgggctccc tgaacatcct gctgctgaca | 540 |
| ctgacagccc aagagctgag caacagctgg ccaacaatc tgatgtggct ggcctacaca | 600 |
| atggccttca tggtcaagat gccctgtac ggcctgcacc tgtggctgcc taaagctcat | 660 |
| gtggaagccc ctatcgccgg ctctatggtg ctggctgcag tgctgctgaa actcggcggc | 720 |
| tacggcatga tgcggctgac cctgattctg aatcccctga ccaagcacat ggcctatcca | 780 |
| tttctggtgc tgagcctgtg gggcatgatt atgaccagca gcatctgcct gcggcagacc | 840 |
| gatctgaagt ccctgatcgc ctacagctcc atcagccaca tggccctggt ggtcaccgcc | 900 |
| atcctgattc agacccttg gagctttaca ggcgccgtga tcctgatgat gcccacggc | 960 |
| ctgacaagca gcctgctgtt tgtctggcc aacagcaact acgagcggac ccacagcaga | 1020 |
| atcatgatcc tgtctcaggg cctgcagacc ctcctgcctc ttatggcttt tggtggctg | 1080 |
| ctggcctctc tggccaatct ggcactgcct cctaccatca tctgctgggg cgagctgagc | 1140 |
| gtgctggtca ccacattcag ctggtccaat atcaccctgc tgctcaccgg cctgaacatg | 1200 |
| ctggttacag ccctgtactc cctgtacatg ttcaccacca cacagtgggg aagcctgaca | 1260 |
| caccacatca acaatatgaa gcccagcttc acccgcgaga cacccctgat gttcatgcat | 1320 |
| ctgagcccca ttctgctgct gtccctgaat cctgatatca tcaccggctt ctccagctga | 1380 |

<210> SEQ ID NO 8
<211> LENGTH: 1380
<212> TYPE: DNA
<213> ORGANISM: Artificial Sequence
<220> FEATURE:
<223> OTHER INFORMATION: opt_ND4*

<400> SEQUENCE: 8

| | |
|---|---|
| atgctgaagc tgatcgtgcc caccatcatg ctgctgcccc tgacctggct gagcaagaag | 60 |
| cacatgatct ggatcaacac caccacccac agcctgatca tcagcatcat ccccctgctg | 120 |
| ttcttcaacc agatcaacaa caacctgttc agctgcagcc ccaccttcag cagcgacccc | 180 |
| ctgaccaccc ccctgctgat gctgaccacc tggctgctgc ccctgaccat catggccagc | 240 |
| cagcgccacc tgagcagcga gcccctgagc cgcaagaagc tgtacctgag catgctgatc | 300 |
| agcctgcaga tcagcctgat catgaccttc accgccaccg agctgatcat gttctacatc | 360 |
| ttcttcgaga ccaccctgat ccccaccctg gccatcatca cccgctgggg caaccagccc | 420 |
| gagcgcctga acgccggcac ctacttcctg ttctacaccc tggtgggcag cctgcccctg | 480 |

-continued

```
ctgatcgccc tgatctacac ccacaacacc ctgggcagcc tgaacatcct gctgctgacc      540
ctgaccgcca aggagctgag caacagctgg gccaacaacc tgatgtggct ggcctacacc      600
atggccttca tggtgaagat gcccctgtac ggcctgcacc tgtggctgcc caaggcccac      660
gtggaggccc ccatcgccgg cagcatggtg ctggccgccg tgctgctgaa gctgggcggc      720
tacggcatga tgcgcctgac cctgatcctg aaccccctga ccaagcacat ggcctacccc      780
ttcctggtgc tgagcctgtg ggcatgatc atgaccagca gcatctgcct cgcgcagacc       840
gacctgaaga gcctgatcgc ctacagcagc atcagccaca tggccctggt ggtgaccgcc      900
atcctgatcc agacccctg gagcttcacc ggcgccgtga tcctgatgat cgcccacggc       960
ctgaccagca gcctgctgtt ctgcctggcc aacagcaact acgagcgcac ccacagccgc     1020
atcatgatcc tgagccaggg cctgcagacc ctgctgcccc tgatggcctt ctggtggctg     1080
ctggccagcc tggccaacct ggccctgccc ccaccatca acctgctggg cgagctgagc      1140
gtgctggtga ccaccttcag ctggagcaac atcaccctgc tgctgaccgg cctgaacatg     1200
ctggtgaccg ccctgtacag cctgtacatg ttcaccacca cccagtgggg cagcctgacc     1260
caccacatca acaacatgaa gcccagcttc acccgcgaga caccctgat gttcatgcac     1320 ctgagcccca tcctgctgct gagcctgaac cccgacatca tcaccggctt cagcagctaa    1380
```

```
<210> SEQ ID NO 9
<211> LENGTH: 525
<212> TYPE: DNA
<213> ORGANISM: Homo sapiens

<400> SEQUENCE: 9
```

```
atgatgtatg ctttgtttct gttgagtgtg ggtttagtaa tggggtttgt ggggttttct       60
tctaagcctt ctcctatta tgggggttta gtattgattg ttagcggtgt ggtcgggtgt       120
gttattattc tgaattttgg gggaggttat atgggtttaa tggttttttt aatttattta      180
gggggaatga tggttgtctt tggatatact acagcgatgg ctattgagga gtatcctgag      240
gcatgggggt caggggttga ggtcttggtg agtgttttag tggggttagc gatggaggta      300
ggattggtgc tgtgggtgaa agagtatgat gggtggtgg ttgtgtaaa ctttaatagt       360 gtaggaagct ggatgattta tgaaggagag gggtcagggt tgattcggga ggatcctatt      420
ggtgcggggg ctttgtatga ttatgggcgt tggttagtag tagttactgg ttggacattg      480
tttgttggtg tatatattgt aattgagatt gctcgggga attag                      525
```

```
<210> SEQ ID NO 10
<211> LENGTH: 525
<212> TYPE: DNA
<213> ORGANISM: Artificial Sequence
<220> FEATURE:
<223> OTHER INFORMATION: opt_ND6

<400> SEQUENCE: 10
```

```
atgatgtacg ccctgttcct gctgagcgtg ggcctggtga tgggcttcgt gggcttcagc      60
agcaagccca gccccatcta cggcggcctg gtgctgatcg tgagcggcgt ggtgggctgc     120
gtgatcatcc tgaacttcgg cggcggctac atgggcctga tggtgttcct gatctacctg     180
ggcggcatga tggtggtgtt cggctacacc accgccatgg ccatcgagga gtaccccgag     240
gcctggggca gcggcgtgga ggtgctggtg agcgtgctgg tgggcctggc catggaggtg     300
ggcctggtgc tgtgggtgaa ggagtacgac ggcgtggtgg tggtggtgaa cttcaacagc    360
```

```
gtgggcagct ggatgatcta cgagggcgag ggcagcggcc tgatccgcga ggaccccatc      420
ggcgccggcg ccctgtacga ctacggccgc tggctggtgg tggtgaccgg ctggaccctg      480
ttcgtgggcg tgtacatcgt gatcgagatc gcccgcggca actaa                     525

<210> SEQ ID NO 11
<211> LENGTH: 957
<212> TYPE: DNA
<213> ORGANISM: Homo sapiens

<400> SEQUENCE: 11
atgcccatgg ccaacctcct actcctcatt gtacccattc taatcgcaat ggcattccta       60
atgcttaccg aacgaaaaat tctaggctat atgcaactac gcaaaggccc caacgttgta      120 ggccccctacg ggctactaca acccttcgct gacgccatga aactcttcac caaagagccc     180
ctaaaacccg ccacatctac catcaccctc tacatcaccg ccccgacctt agctctcacc      240
atcgctcttc tactatggac ccccctcccc atgcccaacc cctggtcaa cctcaaccta       300 ggcctcctat ttattctagc cacctctagc ctagccgttt actcaatcct ctggtcaggg      360
tgggcatcaa actcaaacta cgccctgatc ggcgcactgc gagcagtagc ccaaacaatc      420
tcatatgaag tcaccctagc catcattcta ctatcaacat tactaatgag tggctccttt      480
aacctctcca cccttatcac aacacaagaa cacctctggt tactcctgcc atcatggccc      540
ttggccatga tgtggtttat ctccacacta gcagagacca accgaacccc cttcgacctt      600
gccgaagggg agtccgaact agtctcaggc ttcaacatcg aatacgccgc aggccccttc      660
gccctattct tcatggccga atacacaaac attattatga tgaacaccct caccactaca      720
atcttcctag gaacaacata tgacgcactc tcccctgaac tctacacaac atattttgtc      780
accaagaccc tacttctaac ctccctgttc ttatggattc gaacagcata cccccgattc      840
cgctacgacc aactcatgca cctcctatgg aaaaacttcc taccactcac cctagcatta      900
cttatgtggt atgtctccat gcccattaca atctccagca ttccccctca aacctaa        957

<210> SEQ ID NO 12
<211> LENGTH: 957
<212> TYPE: DNA
<213> ORGANISM: Artificial Sequence
<220> FEATURE:
<223> OTHER INFORMATION: opt_ND1

<400> SEQUENCE: 12
atgcccatgg ccaacctgct gctgctgatc gtgcccatcc tgatcgccat ggccttcctg       60
atgctgaccg agcgcaagat cctgggctac atgcagctgc gcaagggccc caacgtggtg      120 ggccccctacg gcctgctgca gcccttcgcc gacgccatga gctgttcac caaggagccc      180 ctgaagcccg ccaccagcac catcaccctg tacatcaccg ccccaccct ggccctgacc       240 atcgccctgc tgctgtggac ccccctgccc atgcccaacc cctggtgaa cctgaacctg       300 ggcctgctgt tcatcctggc caccagcagc ctggccgtgt acagcatcct gtggagcggc      360
tgggccagca acagcaacta cgccctgatc ggcgccctgc gcgccgtggc ccagaccatc      420
agctacgagg tgaccctggc catcatcctg ctgagcaccc tgctgatgag cggcagcttc      480
aacctgagca cccctgatcac cacccaggag cacctgtggc tgctgctgcc cagctggccc      540
ctggccatga tgtggttcat cagcacccctg gccgagacca accgcacccc cttcgacctg     600
gccgagggcg agagcgagct ggtgagcggc ttcaacatcg agtacgccgc cggcccccttc    660 gccctgttct tcatggccga gtacaccaac atcatcatga tgaacaccct gaccaccacc      720
```

| | |
|---|---|
| atcttcctgg gcaccaccta cgacgccctg agccccgagc tgtacaccac ctacttcgtg | 780 |
| accaagaccc tgctgctgac cagctgttc ctgtggatcc gcaccgccta ccccgcttc | 840 |
| cgctacgacc agctgatgca cctgctgtgg aagaacttcc tgcccctgac cctggccctg | 900 |
| ctgatgtggt acgtgagcat gcccatcacc atcagcagca tccccccccca gacctaa | 957 |

<210> SEQ ID NO 13
<211> LENGTH: 1425
<212> TYPE: DNA
<213> ORGANISM: Homo sapiens

<400> SEQUENCE: 13

| | |
|---|---|
| gagcactggg acgcccaccg cccctttccc tccgctgcca ggcgagcatg ttgtggtaat | 60 |
| tctggaacac aagaagagaa attgctgggt ttagaacaag attataaacg aattcggtgc | 120 |
| tcagtgatca cttgacagtt ttttttttt ttaaatatta cccaaaatgc tccccaaata | 180 |
| agaaatgcat cagctcagtc agtgaataca aaaaggaat tatttttccc tttgagggtc | 240 |
| ttttatacat ctctcctcca accccaccct ctattctgtt tcttcctcct cacatggggg | 300 |
| tacacataca cagcttcctc ttttggttcc atccttacca ccacaccaca cgcacactcc | 360 |
| acatgcccag cagagtggca cttggtggcc agaaagtgtg agcctcatga tctgctgtct | 420 |
| gtagttctgt gagctcaggt ccctcaaagg cctcggagca ccccttcct tgtgactgag | 480 |
| ccagggcctg cattttggt tttcccacc ccacacattc tcaaccatag tccttctaac | 540 |
| aataccaata gctaggaccc ggctgctgtg cactgggact ggggattcca catgtttgcc | 600 |
| ttgggagtct caagctggac tgccagcccc tgtcctccct tcaccccat tgcgtatgag | 660 |
| catttcagaa ctccaaggag tcacaggcat ctttatagtt cacgttaaca tatagacact | 720 |
| gttggaagca gttccttcta aaagggtagc cctggactta ataccagccg gatacctctg | 780 |
| gccccaccc cattactgta cctctggagt cactactgtg ggtcgccact cctctgctac | 840 |
| acagcacggc tttttcaagg ctgtattgag aagggaagtt aggaagaagg gtgtgctggg | 900 |
| ctaaccagcc cacagagctc acattcctgt cccttgggtg aaaaatacat gtccatcctg | 960 |
| atatctcctg aattcagaaa ttagcctcca catgtgcaat ggctttaaga gccagaagca | 1020 |
| gggttctggg aattttgcaa gttacctgtg gccaggtgtg gtctcggtta ccaaatacgg | 1080 |
| ttacctgcag cttttagtc ctttgtgctc ccacgggtct acagagtccc atctgcccaa | 1140 |
| aggtcttgaa gcttgacagg atgttttcga ttactcagtc tcccagggca ctactggtcc | 1200 |
| gtaggattcg attggtcggg gtaggagagt taaacaacat ttaaacagag ttctctcaaa | 1260 |
| aatgtctaaa gggattgtag gtagataaca tccaatcact gtttgcactt atctgaaatc | 1320 |
| ttccctcttg gctgccccca ggtatttact gtggagaaca ttgcatagga atgtctggaa | 1380 |
| aaagcttcta caacttgtta cagccttcac atttgtagaa gcttt | 1425 |

<210> SEQ ID NO 14
<211> LENGTH: 625
<212> TYPE: DNA
<213> ORGANISM: Homo sapiens

<400> SEQUENCE: 14

| | |
|---|---|
| gagcactggg acgcccaccg cccctttccc tccgctgcca ggcgagcatg ttgtggtaat | 60 |
| tctggaacac aagaagagaa attgctgggt ttagaacaag attataaacg aattcggtgc | 120 |
| tcagtgatca cttgacagtt ttttttttt ttaaatatta cccaaaatgc tccccaaata | 180 |

| | |
|---|---|
| agaaatgcat cagctcagtc agtgaataca aaaaaggaat tattttttccc tttgagggtc | 240 |
| ttttatacat ctctcctcca accccaccct ctattctgtt tcttcctcct cacatggggg | 300 |
| tacacataca cagcttcctc ttttggttcc atccttacca ccacaccaca cgcacactcc | 360 |
| acatgcccag cagagtggca cttggtggcc agaaagtgtg agcctcatga tctgctgtct | 420 |
| gtagttctgt gagctcaggt ccctcaaagg cctcggagca cccccttcct tgtgactgag | 480 |
| ccagggcctg cattttggt tttcccacc ccacacattc tcaaccatag tccttctaac | 540 |
| aataccaata gctaggaccc ggctgctgtg cactgggact ggggattcca catgtttgcc | 600 |
| ttgggagtct caagctggac tgcca | 625 |

```
<210> SEQ ID NO 15
<211> LENGTH: 2889
<212> TYPE: DNA
<213> ORGANISM: Artificial Sequence
<220> FEATURE:
<223> OTHER INFORMATION: COX10-ND4-3'UTR

<400> SEQUENCE: 15
```

| | |
|---|---|
| atggccgcat ctccgcacac tctctcctca cgcctcctga caggttgcgt aggaggctct | 60 |
| gtctggtatc ttgaaagaag aactatgcta aaactaatcg tcccaacaat tatgttacta | 120 |
| ccactgacat ggcttttccaa aaaacacatg atttggatca acacaaccac ccacagccta | 180 |
| attattagca tcatccctct actattttt aaccaaatca caacaaccct atttagctgt | 240 |
| tccccaacct tttcctccga cccccctaaca accccctcc taatgctaac tacctggctc | 300 |
| ctacccctca caatcatggc aagccaacgc cacttatcca gtgaaccact atcacgaaaa | 360 |
| aaactctacc tctctatgct aatctcccta caaatctcct taattatgac attcacagcc | 420 |
| acagaactaa tcatgtttta tcttcttc gaaaccacac ttatccccac cttggctatc | 480 |
| atcacccgat ggggcaacca gccagaacgc ctgaacgcag gcacatactt cctattctac | 540 |
| accctagtag gctcccttcc cctactcatc gcactaattt acactcacaa cccctaggc | 600 |
| tcactaaaca ttctactact cactctcact gcccaagaac tatcaaactc ctgggccaac | 660 |
| aacttaatgt ggctagctta cacaatggct tttatggtaa agatgcctct ttacggactc | 720 |
| cacttatggc tccctaaagc ccatgtcgaa gcccccatcg ctgggtcaat ggtacttgcc | 780 |
| gcagtactct taaaactagg cggctatggt atgatgcgcc tcacactcat tctcaacccc | 840 |
| ctgacaaaac acatggccta ccccttcctt gtactatccc tatggggcat gattatgaca | 900 |
| agctccatct gcctacgaca aacagaccta aaatcgctca ttgcatactc ttcaatcagc | 960 |
| cacatggccc tcgtagtaac agccattctc atccaaaccc cctggagctt caccggcgca | 1020 |
| gtcattctca tgatcgccca cgggcttaca tcctcattac tattctgcct agcaaactca | 1080 |
| aactacgaac gcactcacag tcgcatcatg atcctctctc aaggacttca aactctactc | 1140 |
| ccactaatgg cttttggtg gcttctagca agcctcgcta acctcgcctt accccccact | 1200 |
| attaacctac tgggagaact ctctgtgcta gtaaccacgt tctcctggtc aaatatcact | 1260 |
| ctcctactta caggactcaa catgctagtc acagccctat actccctcta catgtttacc | 1320 |
| acaacacaat ggggctcact cacccaccac attaacaaca tgaaaccctc attcacacga | 1380 |
| gaaaacaccc tcatgttcat gcacctatcc cccattctcc tcctatccct caaccccgac | 1440 |
| atcattaccg ggttttcctc ttaagagcac tgggacgccc accgcccctt tcctccgct | 1500 |
| gccaggcgag catgttgtgg taattctgga acacaagaag agaaattgct gggtttagaa | 1560 |
| caagattata aacgaattcg gtgctcagtg atcacttgac agttttttt ttttttaaat | 1620 |

-continued

```
attacccaaa atgctcccca aataagaaat gcatcagctc agtcagtgaa tacaaaaaag    1680
gaattatttt tcccttt gag ggtcttttat acatctctcc tccaacccca ccctctattc    1740
tgtttcttcc tcctcacatg ggggtacaca tacacagctt cctcttttgg ttccatcctt    1800
accaccacac cacacgcaca ctccacatgc ccagcagagt ggcacttggt ggccagaaag    1860
tgtgagcctc atgatctgct gtctgtagtt ctgtgagctc aggtccctca aaggcctcgg    1920
agcaccccct tccttgtgac tgagccaggg cctgcatttt tggttttccc caccccacac    1980
attctcaacc atagtccttc taacaatacc aatagctagg acccggctgc tgtgcactgg    2040
gactggggat tccacatgtt tgccttggga gtctcaagct ggactgccag ccctgtcct    2100
cccttcaccc ccattgcgta tgagcatttc agaactccaa ggagtcacag gcatctttat    2160
agttcacgtt aacatataga cactgttgga agcagttcct tctaaagggg tagccctgga    2220
cttaatacca gccggatacc tctggccccc accccattac tgtacctctg gagtcactac    2280
tgtgggtcgc cactcctctg ctacacagca cggcttttc aaggctgtat tgagaaggga    2340
agttaggaag aagggtgtgc tgggctaacc agcccacaga gctcacattc ctgtcccttg    2400
ggtgaaaaat acatgtccat cctgatatct cctgaattca gaaattagcc tccacatgtg    2460
caatggcttt aagagccaga agcagggttc tgggaatttt gcaagttacc tgtggccagg    2520
tgtggtctcg gttaccaaat acggttacct gcagcttttt agtcctttgt gctcccacgg    2580
gtctacagag tcccatctgc ccaaaggtct tgaagcttga caggatgttt tcgattactc    2640
agtctcccag ggcactactg gtccgtagga ttcgattggt cggggtagga gagttaaaca    2700
acatttaaac agagttctct caaaaatgtc taaagggatt gtaggtagat aacatccaat    2760
cactgtttgc acttatctga aatcttccct cttggctgcc cccaggtatt tactgtggag    2820
aacattgcat aggaatgtct ggaaaaagct tctacaactt gttacagcct tcacatttgt    2880
agaagcttt                                                            2889
```

<210> SEQ ID NO 16
<211> LENGTH: 2089
<212> TYPE: DNA
<213> ORGANISM: Artificial Sequence
<220> FEATURE:
<223> OTHER INFORMATION: COX10-ND4-3'UTR*

<400> SEQUENCE: 16

```
atggccgcat ctccgcacac tctctcctca cgcctcctga caggttgcgt aggaggctct      60
gtctggtatc ttgaaagaag aactatgcta aaactaatcg tcccaacaat tatgttacta    120
ccactgacat ggctttccaa aaaacacatg atttggatca acacaaccac ccacagccta    180
attattagca tcatccctct actatttttt aaccaaatca caacaaccct atttagctgt    240
tccccaacct tttcctccga ccccctaaca accccctcc taatgctaac tacctggctc    300
ctacccctca caatcatggc aagccaacgc acttatccca gtgaaccact atcacgaaaa    360
aaactctacc tctctatgct aatctcccta caaatctcct taattatgac attcacagcc    420
acagaactaa tcatgttta tatcttcttc gaaaccacac ttatccccac cttggctatc    480
atcacccgat ggggcaacca gccagaacgc ctgaacgcag gcatatactt cctattctac    540
accctagtag gctcccttcc cctactcatc gcactaattt acactcacaa cacctaggc    600
tcactaaaca ttctactact cactctcact gcccaagaac tatcaaactc ctgggccaac    660
aacttaatgt ggctagctta cacaatggct tttatggtaa agatgcctct ttacggactc    720
```

```
cacttatggc tccctaaagc ccatgtcgaa gccccatcg ctgggtcaat ggtacttgcc      780
gcagtactct taaaactagg cggctatggt atgatgcgcc tcacactcat tctcaacccc      840
ctgacaaaac acatggccta ccccttcctt gtactatccc tatggggcat gattatgaca      900
agctccatct gcctacgaca aacagaccta aaatcgctca ttgcatactc ttcaatcagc      960
cacatggccc tcgtagtaac agccattctc atccaaaccc cctggagctt caccggcgca     1020
gtcattctca tgatcgccca cgggcttaca tcctcattac tattctgcct agcaaactca     1080
aactacgaac gcactcacag tcgcatcatg atcctctctc aaggacttca aactctactc     1140
ccactaatgg cttttggtg gcttctagca agcctcgcta acctcgcctt accccccact      1200
attaacctac tgggagaact ctctgtgcta gtaaccacgt tctcctggtc aaatatcact     1260
ctcctactta caggactcaa catgctagtc acagccctat actccctcta catgtttacc     1320
acaacacaat ggggctcact cacccaccac attaacaaca tgaaaccctc attcacacga     1380
gaaaacaccc tcatgttcat gcacctatcc cccattctcc tcctatccct caaccccgac     1440
atcattaccg ggttttcctc ttaagagcac tgggacgccc accgcccctt ccctccgct      1500 gccaggcgag catgttgtgg taattctgga acacaagaag agaaattgct gggtttagaa     1560
caagattata aacgaattcg gtgctcagtg atcacttgac agtttttttt tttttttaaat    1620 attacccaaa atgctcccca ataagaaat gcatcagctc agtcagtgaa tacaaaaaag      1680
gaattatttt tcccttgtag ggtcttttat acatctctcc tccaaccca ccctctattc      1740 tgtttcttcc tcctcacatg ggggtacaca tacacagctt cctcttttgg ttccatcctt     1800
accaccacac cacacgcaca ctccacatgc ccagcagagt ggcacttggt ggccagaaag     1860
tgtgagcctc atgatctgct gtctgtagtt ctgtgagctc aggtccctca aaggcctcgg     1920 agcacccct tccttgtgac tgagccaggg cctgcatttt tggttttccc caccccacac      1980
attctcaacc atagtccttc taacaatacc aatagctagg accccggctgc tgtgcactgg    2040 gactggggat ccacatgtt tgccttggga gtctcaagct ggactgcca                  2089
```

<210> SEQ ID NO 17
<211> LENGTH: 2889
<212> TYPE: DNA
<213> ORGANISM: Artificial Sequence
<220> FEATURE:
<223> OTHER INFORMATION: COX10-opt_ND4-3'UTR

<400> SEQUENCE: 17

```
atggccgcat ctccgcacac tctctcctca cgcctcctga caggttgcgt aggaggctct       60
gtctggtatc ttgaaagaag aactatgctg aagctgatcg tgcccaccat catgctgctg      120
cctctgacct ggctgagcaa gaaacacatg atctggatca acaccaccac gcacagcctg      180
atcatcagca tcatccctct gctgttcttc aaccagatca caacaaccct gttcagctgc      240
agccccacct tcagcagcga ccctctgaca acacctctgc tgatgctgac cacctggctg      300
ctgcccctca caatcatggc ctctcagaga cacctgagca gcgagcccct gagccggaag      360
aaactgtacc tgagcatgct gatctccctg cagatctctc tgatcatgac cttcaccgcc      420
accgagctga tcatgttcta catcttttc gagacaacgc tgatcccac actggccatc      480 atcaccagat ggggcaacca gcctgagaga ctgaacgccg gcacctactt tctgttctac     540
accctcgtgg gcagcctgcc actgctgatt gccctgatct acacccacaa ccctgggc       600 tccctgaaca tcctgctgct gacactgaca gcccaagagc tgagcaacag ctgggccaac    660
aatctgatgt ggctggccta cacaatggcc ttcatggtca agatgcccct gtacggcctg    720
```

```
cacctgtggc tgcctaaagc tcatgtggaa gcccctatcg ccggctctat ggtgctggct    780
gcagtgctgc tgaaactcgg cggctacggc atgatgcggc tgaccctgat tctgaatccc    840
ctgaccaagc acatggccta tccatttctg gtgctgagcc tgtggggcat gattatgacc    900
agcagcatct gcctgcggca gaccgatctg aagtccctga tcgcctacag ctccatcagc    960
cacatggccc tggtggtcac cgccatcctg attcagaccc cttggagctt tacaggcgcc   1020
gtgatcctga tgattgccca cggcctgaca agcagcctgc tgttttgtct ggccaacagc   1080
aactacgagc ggacccacag cagaatcatg atcctgtctc agggcctgca gaccctcctg   1140
cctcttatgg cttttggtg gctgctggcc tctctggcca atctggcact gcctcctacc   1200
atcaatctgc tgggcgagct gagcgtgctg gtcaccacat cagctggtc aatatcacc    1260
ctgctgctca ccggcctgaa catgctggtt acagccctgt actccctgta catgttcacc   1320
accacacagt ggggaagcct gacacaccac atcaacaata tgaagcccag cttcacccgc   1380
gagaacaccc tgatgttcat gcatctgagc cccattctgc tgctgtccct gaatcctgat   1440
atcatcaccg gcttctccag ctgagagcac tgggacgccc accgcccctt ccctccgct   1500
gccaggcgag catgttgtgg taattctgga acacaagaag agaaattgct gggtttagaa   1560
caagattata aacgaattcg gtgctcagtg atcacttgac agttttttt ttttttaaat   1620
attacccaaa atgctcccca ataagaaat gcatcagctc agtcagtgaa tacaaaaaag   1680
gaattatttt tcccttttgag ggtctttttat acatctctcc tccaacccca ccctctattc   1740
tgtttcttcc tcctcacatg ggggtacaca tacacagctt cctcttttgg ttccatcctt   1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920
agcacccct tccttgtgac tgagccaggg cctgcatttt tggttttccc caccccacac   1980
attctcaacc atagtccttc taacaatacc aatagctagg accggctgc tgtgcactgg   2040
gactggggat tccacatgtt tgccttggga gtctcaagct ggactgccag ccctgtcct   2100
cccttcaccc ccattgcgta tgagcatttc agaactccaa ggagtcacag gcatctttat   2160
agttcacgtt aacatataga cactgttgga agcagttcct tctaaagggt tagccctgga   2220
cttaatacca gccggatacc tctggccccc accccattac tgtacctctg gagtcactac   2280
tgtgggtcgc cactcctctg ctacacagca cggctttttc aaggctgtat tgagaaggga   2340
agttaggaag aagggtgtgc tgggctaacc agcccacaga gctcacattc ctgtcccttg   2400
ggtgaaaaat acatgtccat cctgatatct cctgaattca gaaattagcc tccacatgtg   2460
caatggcttt aagagccaga agcagggttc tgggaatttt gcaagttacc tgtggccagg   2520
tgtggtctcg gttaccaaat acggttacct gcagcttttt agtcctttgt gctcccacgg   2580
gtctacagag tcccatctgc ccaaaggtct tgaagcttga caggatgttt tcgattactc   2640
agtctcccag ggcactactg gtccgtagga ttcgattggt cggggtagga gagttaaaca   2700
acatttaaac agagttctct caaaaatgtc taaagggatt gtaggtagat aacatccaat   2760
cactgtttgc acttatctga aatcttccct cttggctgcc cccaggtatt tactgtggag   2820
aacattgcat aggaatgtct ggaaaaagct tctacaactt gttacagcct tcacatttgt   2880
agaagcttt                                                           2889
```

<210> SEQ ID NO 18
<211> LENGTH: 2089
<212> TYPE: DNA

<213> ORGANISM: Artificial Sequence
<220> FEATURE:
<223> OTHER INFORMATION: COX10-opt_ND4-3'UTR*

<400> SEQUENCE: 18

```
atggccgcat ctccgcacac tctctcctca cgcctcctga caggttgcgt aggaggctct      60
gtctggtatc ttgaaagaag aactatgctg aagctgatcg tgcccaccat catgctgctg     120
cctctgacct ggctgagcaa gaaacacatg atctggatca acaccaccac gcacagcctg     180
atcatcagca tcatccctct gctgttcttc aaccagatca caacaaccct gttcagctgc     240
agccccacct tcagcagcga ccctctgaca acacctctgc tgatgctgac cacctggctg     300
ctgccctca caatcatggc ctctcagaga cacctgagca gcgagcccct gagccggaag     360
aaactgtacc tgagcatgct gatctccctg cagatctctc tgatcatgac cttcaccgcc     420
accgagctga tcatgttcta catctttttc gagacaacgc tgatccccac actggccatc     480
atcaccagat ggggcaacca gcctgagaga ctgaacgccg gcacctactt tctgttctac     540
accctcgtgg gcagcctgcc actgctgatt gccctgatct acacccacaa cacccctgggc     600
tccctgaaca tcctgctgct gacactgaca gcccaagagc tgagcaacag ctgggccaac     660
aatctgatgt ggctggccta cacaatggcc ttcatggtca gatgcccct gtacggcctg     720
cacctgtggc tgcctaaagc tcatgtggaa gcccctatcg ccggctctat ggtgctggct     780
gcagtgctgc tgaaactcgg cggctacggc atgatgcggc tgaccctgat tctgaatccc     840
ctgaccaagc acatggccta tccatttctg gtgctgagcc tgtggggcat gattatgacc     900
agcagcatct gcctgcggca gaccgatctg aagtccctga tcgcctacag ctccatcagc     960
cacatggccc tggtggtcac cgccatcctg attcagaccc cttggagctt tacaggcgcc    1020
gtgatcctga tgattgccca cggcctgaca agcagcctgc tgttttgtct ggccaacagc    1080
aactacgagc ggacccacag cagaatcatg atcctgtctc agggcctgca gaccctcctg    1140
cctcttatgg cttttggtg gctgctggcc tctctggcca atctggcact gcctcctacc    1200
atcaatctgc tgggcgagct gagcgtgctg gtcaccacat tcagctggtc caatatcacc    1260
ctgctgctca ccggcctgaa catgctggtt acagccctgt actccctgta catgttcacc    1320
accacacagt ggggaagcct gacacaccac atcaacaata tgaagcccag cttcacccgc    1380
gagaacaccc tgatgttcat gcatctgagc cccattctgc tgctgtccct gaatcctgat    1440
atcatcaccg gcttctccag ctgagagcac tgggacgccc accgcccctt tccctccgct    1500
gccaggcgag catgttgtgg taattctgga acacaagaag agaaattgct gggtttagaa    1560
caagattata aacgaattcg gtgctcagtg atcacttgac agttttttttt tttttttaaat    1620
attacccaaa atgctcccca aataagaaat gcatcagctc agtcagtgaa tacaaaaaag    1680
gaattatttt tccctttgag ggtctttat acatctctcc tccaaccca ccctctattc    1740
tgtttcttcc tcctcacatg ggggtacaca tacacagctt cctcttttgg ttccatcctt    1800
accaccacac cacacgcaca ctccacatgc ccagcagagt ggcacttggt ggccagaaag    1860
tgtgagcctc atgatctgct gtctgtagtt ctgtgagctc aggtccctca aaggcctcgg    1920
agcacccct tccttgtgac tgagccaggg cctgcatttt tggttttccc cacccacac    1980
attctcaacc atagtccttc taacaatacc aatagctagg accggctgc tgtgcactgg    2040
gactggggat ccacatgtt tgccttggga gtctcaagct ggactgcca                   2089
```

<210> SEQ ID NO 19
<211> LENGTH: 2889

```
<212> TYPE: DNA
<213> ORGANISM: Artificial Sequence
<220> FEATURE:
<223> OTHER INFORMATION: COX10-opt_ND4*-3'UTR

<400> SEQUENCE: 19
atggccgcat ctccgcacac tctctcctca cgcctcctga caggttgcgt aggaggctct       60
gtctggtatc ttgaaagaag aactatgctg aagctgatcg tgcccaccat catgctgctg      120
cccctgacct ggctgagcaa gaagcacatg atctggatca caccaccac ccacagcctg       180
atcatcagca tcatcccct gctgttcttc aaccagatca caacaacct gttcagctgc        240
agccccacct tcagcagcga ccccctgacc accccctgc tgatgctgac cacctggctg       300
ctgcccctga ccatcatggc cagccagcgc cacctgagca gcgagcccct gagccgcaag      360
aagctgtacc tgagcatgct gatcagcctg cagatcagcc tgatcatgac cttcaccgcc      420
accgagctga tcatgttcta catcttcttc gagaccaccc tgatccccac cctggccatc      480
atcacccgct ggggcaacca gcccgagcgc ctgaacgccg gcacctactt cctgttctac      540
accctggtgg gcagcctgcc cctgctgatc gccctgatct acacccacaa caccctgggc      600
agcctgaaca tcctgctgct gaccctgacc gcccaggagc tgagcaacag ctgggccaac      660
aacctgatgt ggctggccta ccatggcc ttcatggtga agatgccccct gtacggcctg       720
cacctgtggc tgcccaaggc ccacgtggag gcccccatcg ccggcagcat ggtgctggcc      780
gccgtgctgc tgaagctggg cggctacggc atgatgcgcc tgaccctgat cctgaacccc      840
ctgaccaagc acatggccta cccccttcctg gtgctgagcc tgtggggcat gatcatgacc     900
agcagcatct gcctgcgcca gaccgacctg aagagcctga tcgcctacag cagcatcagc      960
cacatggccc tggtggtgac cgccatcctg atccagaccc cctggagctt caccggcgcc     1020
gtgatcctga tgatcgccca cggcctgacc agcagcctgc tgttctgcct ggccaacagc     1080
aactacgagc gcacccacag ccgcatcatg atcctgagcc agggcctgca gaccctgctg     1140
cccctgatgg ccttctggtg gctgctggcc agcctggcca acctggccct gcccccacc      1200
atcaacctgc tgggcgagct gagcgtgctg gtgaccacct tcagctggag caacatcacc     1260
ctgctgctga ccggcctgaa catgctggtg accgccctgt acagcctgta catgttcacc     1320
accacccagt ggggcagcct gacccaccac atcaacaaca tgaagcccag cttcacccgc     1380
gagaacaccc tgatgttcat gcacctgagc cccatcctgc tgctgagcct gaaccccgac     1440
atcatcaccg gcttcagcag ctaagagcac tgggacgccc accgcccctt tccctccgct     1500
gccaggcgag catgttgtgg taattctgga acacaagaag agaaattgct gggtttagaa     1560
caagattata acgaattcg gtgctcagtg atcacttgac agtttttttt ttttttaaat      1620
attacccaaa atgctcccca ataagaaat gcatcagctc agtcagtgaa tacaaaaaag      1680
gaattatttt tccctttgag ggtcttttat acatctctcc tccaacccca cctctattc     1740
tgtttcttcc tcctcacatg ggggtacaca tacacagctt cctcttttgg ttccatcctt     1800
accaccacac cacacgcaca ctccacatgc ccagcagagt ggcacttggt ggccagaaag     1860
tgtgagcctc atgatctgct gtctgtagtt ctgtgagctc aggtccctca aaggcctcgg     1920
agcaccccct tccttgtgac tgagccaggg cctgcatttt tggttttccc caccccacac     1980
attctcaacc atagtccttc taacaatacc aatagctagg accggctgc tgtgcactgg      2040
gactggggat tccacatgtt tgccttggga gtctcaagct ggactgccag ccctgtcct     2100
cccttcaccc ccattgcgta tgagcatttc agaactccaa ggagtcacag gcatctttat    2160
```

```
agttcacgtt aacatataga cactgttgga agcagttcct tctaaaaggg tagccctgga    2220
cttaatacca gccggatacc tctggccccc accccattac tgtacctctg gagtcactac    2280
tgtgggtcgc cactcctctg ctacacagca cggcttttc aaggctgtat tgagaaggga    2340
agttaggaag aagggtgtgc tgggctaacc agcccacaga gctcacattc ctgtcccttg    2400
ggtgaaaaat acatgtccat cctgatatct cctgaattca gaaattagcc tccacatgtg    2460
caatggcttt aagagccaga agcagggttc tgggaatttt gcaagttacc tgtggccagg    2520
tgtggtctcg gttaccaaat acggttacct gcagcttttt agtcctttgt gctcccacgg    2580
gtctacagag tcccatctgc ccaaaggtct tgaagcttga caggatgttt tcgattactc    2640
agtctcccag ggcactactg gtccgtagga ttcgattggt cggggtagga gagttaaaca    2700
acatttaaac agagttctct caaaaatgtc taaagggatt gtaggtagat aacatccaat    2760
cactgtttgc acttatctga aatcttccct cttggctgcc cccaggtatt tactgtggag    2820
aacattgcat aggaatgtct ggaaaaagct tctacaactt gttacagcct tcacatttgt    2880
agaagcttt                                                            2889

<210> SEQ ID NO 20
<211> LENGTH: 2089
<212> TYPE: DNA
<213> ORGANISM: Artificial Sequence
<220> FEATURE:
<223> OTHER INFORMATION: COX10-opt_ND4*-3'UTR*

<400> SEQUENCE: 20
atggccgcat ctccgcacac tctctcctca cgcctcctga caggttgcgt aggaggctct      60
gtctggtatc ttgaaagaag aactatgctg aagctgatcg tgcccaccat catgctgctg     120
cccctgacct ggctgagcaa gaagcacatg atctggatca caccaccac ccacagcctg     180 atcatcagca tcatcccect gctgttcttc aaccagatca caacaacct gttcagctgc     240 agccccacct tcagcagcga ccccctgacc accccctgc tgatgctgac cacctggctg     300
ctgcccctga ccatcatggc cagccagcgc cacctgagca gcgagcccct gagccgcaag     360
aagctgtacc tgagcatgct gatcagcctg cagatcagcc tgatcatgac cttcaccgcc     420
accgagctga tcatgttcta catcttcttc gagaccaccc tgatccccac cctggccatc     480
atcacccgct ggggcaacca gcccgagcgc ctgaacgccg gcacctactt cctgttctac     540
accctggtgg gcagcctgcc cctgctgatc gccctgatct acacccacaa caccctgggc     600
agcctgaaca tcctgctgct gaccctgacc gcccaggagc tgagcaacag ctgggccaac     660
aacctgatgt ggctggccta ccatggcc ttcatggtga agatgcccct gtacggcctg     720
cacctgtggc tgcccaaggc ccacgtggag gcccccatcg ccggcagcat ggtgctggcc     780
gccgtgctgc tgaagctggg cggctacggc atgatgcgcc tgaccctgat cctgaacccc     840
ctgaccaagc acatggccta ccccttcctg gtgctgagcc tgtggggcat gatcatgacc     900
agcagcatct gcctgcgcca gaccgacctg aagagcctga tcgcctacag cagcatcagc     960
cacatggccc tggtggtgac cgccatcctg atccagaccc cctggagctt caccggcgcc    1020
gtgatcctga tgatcgccca cggcctgacc agcagcctgc tgttctgcct ggccaacagc    1080
aactacgagc gcacccacag ccgcatcatg atcctgagcc agggcctgca gaccctgctg    1140
cccctgatgg ccttctggtg gctgctggcc agcctggcca acctggcccct gccccccacc    1200 atcaacctgc tgggcgagct gagcgtgctg gtgaccacct tcagctggag caacatcacc    1260
ctgctgctga ccggcctgaa catgctggtg accgcccctgt acagcctgta catgttcacc    1320
```

```
accacccagt ggggcagcct gacccaccac atcaacaaca tgaagcccag cttcacccgc    1380
gagaacaccc tgatgttcat gcacctgagc cccatcctgc tgctgagcct gaaccccgac    1440
atcatcaccg gcttcagcag ctaagagcac tgggacgccc accgcccctt tccctccgct    1500
gccaggcgag catgttgtgg taattctgga acacaagaag agaaattgct gggtttagaa    1560
caagattata acgaattcg gtgctcagtg atcacttgac agttttttt ttttttaaat      1620 attacccaaa atgctcccca aataagaaat gcatcagctc agtcagtgaa tacaaaaaag    1680
gaattatttt tccctttgag ggtcttttat acatctctcc tccaaccca ccctctattc     1740 tgtttcttcc tcctcacatg ggggtacaca tacacagctc cctctttgg ttccatcctt     1800 accaccacac cacacgcaca ctccacatgc ccagcagagt ggcacttggt ggccagaaag    1860
tgtgagcctc atgatctgct gtctgtagtt ctgtgagctc aggtccctca aaggcctcgg    1920 agcacccct tccttgtgac tgagccaggg cctgcatttt tggttttccc caccccacac     1980
attctcaacc atagtccttc taacaatacc aatagctagg acccggctgc tgtgcactgg    2040
gactggggat tccacatgtt tgccttggga gtctcaagct ggactgcca               2089

<210> SEQ ID NO 21
<211> LENGTH: 2034
<212> TYPE: DNA
<213> ORGANISM: Artificial Sequence
<220> FEATURE:
<223> OTHER INFORMATION: COX10-ND6-3'UTR

<400> SEQUENCE: 21
atggccgcat ctccgcacac tctctcctca cgcctcctga caggttgcgt aggaggctct     60
gtctggtatc ttgaaagaag aactatgatg tatgctttgt ttctgttgag tgtgggttta    120
gtaatggggt ttgtggggtt ttcttctaag ccttctccta tttatggggg tttagtattg    180
attgttagcg gtgtggtcgg gtgtgttatt attctgaatt ttgggggagg ttatatgggt    240
ttaatggttt ttttaatta tttaggggga atgatggttg tctttggata tactacagcg     300
atggctattg aggagtatcc tgaggcatgg gggtcagggg ttgaggtctt ggtgagtgtt    360
ttagtggggt tagcgatgga ggtaggattg gtgctgtggg tgaaagagta tgatggggtg    420
gtggttgtgg taaactttaa tagtgtagga agctggatga tttatgaagg agaggggtca    480
gggttgattc gggaggatcc tattggtgcg ggggctttgt atgattatgg gcgttggtta    540
gtagtagtta ctggttggac attgtttgtt ggtgtatata ttgtaattga gattgctcgg    600
gggaattagg agcactggga cgcccaccgc cccttccct ccgctgccag gcgagcatgt     660
tgtggtaatt ctggaacaca agaagagaaa ttgctgggtt tagaacaaga ttataaacga    720
attcggtgct cagtgatcac ttgacagttt tttttttttt taaatattac ccaaaatgct    780
ccccaaataa gaaatgcatc agctcagtca gtgaatacaa aaaggaatt attttttccct    840 ttgagggtct tttatacatc tctcctccaa ccccacccct tattctgttt cttcctcctc    900
acatgggggt acacatacac agcttcctct tttggttcca tccttaccac cacaccacac    960
gcacactcca catgcccagc agagtggcac ttggtggcca gaaagtgtga gcctcatgat    1020
ctgctgtctg tagttctgtg agctcaggtc cctcaaaggc tcggagcac ccccttcctt    1080 gtgactgagc cagggcctgc attttttggtt tccccaccc cacacattct caaccatagt    1140
ccttctaaca ataccaatag ctaggacccg ctgctgtgc actgggactg gggattccac    1200
atgtttgcct tgggagtctc aagctggact gccagcccct gtcctccctt caccccatt    1260
```

| | |
|---|---|
| gcgtatgagc atttcagaac tccaaggagt cacaggcatc tttatagttc acgttaacat | 1320 |
| atagacactg ttggaagcag ttccttctaa aagggtagcc ctggacttaa taccagccgg | 1380 |
| atacctctgg cccccacccc attactgtac ctctggagtc actactgtgg gtcgccactc | 1440 |
| ctctgctaca cagcacggct ttttcaaggc tgtattgaga agggaagtta ggaagaaggg | 1500 |
| tgtgctgggc taaccagccc acagagctca cattcctgtc ccttgggtga aaaatacatg | 1560 |
| tccatcctga tatctcctga attcagaaat tagcctccac atgtgcaatg ctttaagag | 1620 |
| ccagaagcag ggttctggga attttgcaag ttacctgtgg ccaggtgtgg tctcggttac | 1680 |
| caaatacggt tacctgcagc ttttagtcc tttgtgctcc cacgggtcta cagagtccca | 1740 |
| tctgcccaaa ggtcttgaag cttgacagga tgttttcgat tactcagtct cccagggcac | 1800 |
| tactggtccg taggattcga ttggtcgggg taggagagtt aaacaacatt taaacagagt | 1860 |
| tctctcaaaa atgtctaaag ggattgtagg tagataacat ccaatcactg tttgcactta | 1920 |
| tctgaaatct tccctcttgg ctgccccag gtatttactg tggagaacat tgcataggaa | 1980 |
| tgtctggaaa aagcttctac aacttgttac agccttcaca tttgtagaag cttt | 2034 |

<210> SEQ ID NO 22
<211> LENGTH: 1234
<212> TYPE: DNA
<213> ORGANISM: Artificial Sequence
<220> FEATURE:
<223> OTHER INFORMATION: COX10-ND6-3'UTR*

<400> SEQUENCE: 22

| | |
|---|---|
| atggccgcat ctccgcacac tctctcctca cgcctcctga caggttgcgt aggaggctct | 60 |
| gtctggtatc ttgaaagaag aactatgatg tatgctttgt ttctgttgag tgtgggttta | 120 |
| gtaatggggt ttgtggggtt ttcttctaag ccttctccta tttatggggg tttagtattg | 180 |
| attgttagcg gtgtggtcgg gtgtgttatt attctgaatt ttgggggagg ttatatgggt | 240 |
| ttaatggttt ttttaatta tttaggggga atgatggttg tctttggata tactacagcg | 300 |
| atggctattg aggagtatcc tgaggcatgg gggtcagggg ttgaggtctt ggtgagtgtt | 360 |
| ttagtggggt tagcgatgga ggtaggattg gtgctgtggg tgaaagagta tgatggggtg | 420 |
| gtggttgtgg taaactttaa tagtgtagga agctggatga tttatgaagg agagggtca | 480 |
| gggttgattc gggaggatcc tattggtgcg gggctttgt atgattatgg gcgttggtta | 540 |
| gtagtagtta ctggttggac attgtttgtt ggtgtatata ttgtaattga gattgctcgg | 600 |
| gggaattagg agcactggga cgcccaccgc ccctttccct ccgctgccag gcgagcatgt | 660 |
| tgtggtaatt ctggaacaca agaagagaaa ttgctgggtt tagaacaaga ttataaacga | 720 |
| attcggtgct cagtgatcac ttgacagttt ttttttttt taaatattac ccaaaatgct | 780 |
| ccccaaataa gaaatgcatc agctcagtca gtgaatacaa aaaggaatt atttttccct | 840 |
| ttgagggtct tttatacatc tctcctccaa ccccacccctc tattctgttt cttcctcctc | 900 |
| acatgggggt acacatacac agcttcctct tttggttcca tccttaccac cacaccacac | 960 |
| gcacactcca catgcccagc agagtggcac ttggtggcca gaaagtgtga gcctcatgat | 1020 |
| ctgctgtctg tagttctgtg agctcaggtc cctcaaaggc ctcggagcac cccttcctt | 1080 |
| gtgactgagc cagggcctgc atttttggtt ttccccaccc cacacattct caaccatagt | 1140 |
| ccttctaaca ataccaatag ctaggacccg gctgctgtgc actgggactg gggattccac | 1200 |
| atgtttgcct tgggagtctc aagctggact gcca | 1234 |

<210> SEQ ID NO 23
<211> LENGTH: 2034
<212> TYPE: DNA
<213> ORGANISM: Artificial Sequence
<220> FEATURE:
<223> OTHER INFORMATION: COX10-opt_ND6-3'UTR

<400> SEQUENCE: 23

```
atggccgcat ctccgcacac tctctcctca cgcctcctga caggttgcgt aggaggctct      60
gtctggtatc ttgaaagaag aactatgatg tacgccctgt cctgctgag cgtgggcctg      120
gtgatgggct tcgtgggctt cagcagcaag cccagcccca tctacggcgg cctggtgctg     180
atcgtgagcg gcgtggtggg ctgcgtgatc atcctgaact cggcggcgg ctacatgggc      240
ctgatggtgt tcctgatcta cctgggcggc atgatggtgg tgttcggcta caccaccgcc     300
atggccatcg aggagtaccc cgaggcctgg ggcagcggcg tggaggtgct ggtgagcgtg     360
ctggtgggcc tggccatgga ggtgggcctg gtgctgtggg tgaaggagta cgacggcgtg     420
gtggtggtgg tgaacttcaa cagcgtgggc agctggatga tctacgaggg cgagggcagc     480
ggcctgatcc gcgaggaccc catcggcgcc ggcgccctgt acgactacgg ccgctggctg     540
gtggtggtga ccggctggac cctgttcgtg gcgtgtaca tcgtgatcga gatcgcccgc      600
ggcaactaag agcactggga cgcccaccgc ccctttccct ccgctgccag gcgagcatgt     660
tgtggtaatt ctggaacaca agaagagaaa ttgctgggtt tagaacaaga ttataaacga     720
attcggtgct cagtgatcac ttgacagttt ttttttttt taaatattac ccaaaatgct      780
ccccaaataa gaaatgcatc agctcagtca gtgaatacaa aaaggaatt atttttccct      840
ttgagggtct tttatacatc tctcctccaa ccccacccctc tattctgttt cttcctcctc    900
acatggggt acacatacac agcttcctct tttggttcca tccttaccac cacaccacac     960
gcacactcca catgcccagc agagtggcac ttggtggcca gaaagtgtga gcctcatgat     1020
ctgctgtctg tagttctgtg agctcaggtc cctcaaaggc ctcggagcac ccccttcctt    1080
gtgactgagc cagggcctgc atttttggtt ttccccaccc cacacattct caaccatagt    1140
ccttctaaca ataccaatag ctaggacccg gctgctgtgc actgggactg gggattccac    1200
atgtttgcct tgggagtctc aagctggact gccagcccct gtcctccctt cacccccatt    1260
gcgtatgagc atttcagaac tccaaggagt cacaggcatc tttatagttc acgttaacat    1320
atagacactg ttgaagcag ttccttctaa aagggtagcc ctggacttaa taccagccgg     1380
atacctctgg cccccacccc attactgtac ctctggagtc actactgtgg gtcgccactc    1440
ctctgctaca cagcacggct ttttcaaggc tgtattgaga agggaagtta ggaagaaggg    1500
tgtgctgggc taaccagccc acagagctca cattcctgtc ccttgggtga aaaatacatg    1560
tccatcctga tatctcctga attcagaaat tagcctccac atgtgcaatg ctttaagag    1620
ccagaagcag ggttctggga attttgcaag ttacctgtgg ccaggtgtgg tctcggttac    1680
caaatacggt tacctgcagc ttttagtcc tttgtgctcc cacgggtcta cagagtccca    1740
tctgcccaaa ggtcttgaag cttgacagga tgtttttcgat tactcagtct cccagggcac   1800
tactggtccg taggattcga ttggtcgggg taggagagtt aaacaacatt taaacagagt    1860
tctctcaaaa atgtctaaag ggattgtagg tagataacat ccaatcactg tttgcactta    1920
tctgaaatct tccctcttgg ctgcccccag gtatttactg tggagaacat tgcataggaa    1980
tgtctggaaa aagcttctac aacttgttac agccttcaca tttgtagaag cttt           2034
```

<210> SEQ ID NO 24

<211> LENGTH: 1234
<212> TYPE: DNA
<213> ORGANISM: Artificial Sequence
<220> FEATURE:
<223> OTHER INFORMATION: COX10-opt_ND6-3'UTR*

<400> SEQUENCE: 24

| | | |
|---|---|---|
| atggccgcat ctccgcacac tctctcctca cgcctcctga caggttgcgt aggaggctct | 60 |
| gtctggtatc ttgaaagaag aactatgatg tacgccctgt tcctgctgag cgtgggcctg | 120 |
| gtgatgggct tcgtgggctt cagcagcaag cccagcccca tctacggcgg cctggtgctg | 180 |
| atcgtgagcg gcgtggtggg ctgcgtgatc atcctgaact tcggcggcgg ctacatgggc | 240 |
| ctgatggtgt tcctgatcta cctgggcggc atgatggtgg tgttcggcta caccaccgcc | 300 |
| atggccatcg aggagtaccc cgaggcctgg ggcagcggcg tggaggtgct ggtgagcgtg | 360 |
| ctggtgggcc tggccatgga ggtgggcctg gtgctgtggg tgaaggagta cgacggcgtg | 420 |
| gtggtggtgg tgaacttcaa cagcgtgggc agctggatga tctacgaggg cgagggcagc | 480 |
| ggcctgatcc gcgaggaccc catcgcgccc ggcgccctgt acgactacgg ccgctggctg | 540 |
| gtggtggtga ccggctggac cctgttcgtg ggcgtgtaca tcgtgatcga gatcgcccgc | 600 |
| ggcaactaag agcactggga cgcccaccgc cccttccct ccgctgccag gcgagcatgt | 660 |
| tgtggtaatt ctggaacaca agaagagaaa ttgctgggtt tagaacaaga ttataaacga | 720 |
| attcggtgct cagtgatcac ttgacagttt tttttttttt taaatattac ccaaaatgct | 780 |
| ccccaaataa gaaatgcatc agctcagtca gtgaatacaa aaaggaatt attttttccct | 840 |
| ttgagggtct tttatacatc tctcctccaa ccccaccctc tattctgttt cttcctcctc | 900 |
| acatggggt acacatacac agcttcctct tttggttcca tccttaccac cacaccacac | 960 |
| gcacactcca catgcccagc agagtggcac ttggtggcca gaaagtgtga gcctcatgat | 1020 |
| ctgctgtctg tagttctgtg agctcaggtc cctcaaaggc ctcggagcac ccccttcctt | 1080 |
| gtgactgagc cagggcctgc attttttggtt ttccccaccc cacacattct caaccatagt | 1140 |
| ccttctaaca ataccaatag ctaggacccg gctgctgtgc actgggactg gggattccac | 1200 |
| atgtttgcct tgggagtctc aagctggact gcca | 1234 |

<210> SEQ ID NO 25
<211> LENGTH: 2466
<212> TYPE: DNA
<213> ORGANISM: Artificial Sequence
<220> FEATURE:
<223> OTHER INFORMATION: COX10-ND1-3'UTR

<400> SEQUENCE: 25

| | | |
|---|---|---|
| atggccgcat ctccgcacac tctctcctca cgcctcctga caggttgcgt aggaggctct | 60 |
| gtctggtatc ttgaaagaag aactatgccc atggccaacc tcctactcct cattgtaccc | 120 |
| attctaatcg caatggcatt cctaatgctt accgaacgaa aaattctagg ctatatgcaa | 180 |
| ctacgcaaag gccccaacgt tgtaggcccc tacgggctac tacaaccctt cgctgacgcc | 240 |
| atgaaactct tcaccaaaga gcccctaaaa cccgccacat ctaccatcac cctctacatc | 300 |
| accgccccga ccttagctct caccatcgct cttctactat ggaccccct ccccatgccc | 360 |
| aaccccctgg tcaacctcaa cctaggcctc ctatttattc tagccacctc tagcctagcc | 420 |
| gtttactcaa tcctctggtc agggtgggca tcaaactcaa actacgccct gatcggcgca | 480 |
| ctgcgagcag tagcccaaac aatctcatat gaagtcaccc tagccatcat tctactatca | 540 |
| acattactaa tgagtggctc ctttaacctc tccacccctta tcacaacaca agaacacctc | 600 |

```
tggttactcc tgccatcatg gcccttggcc atgatgtggt ttatctccac actagcagag    660
accaaccgaa ccccctccga ccttgccgaa ggggagtccg aactagtctc aggcttcaac    720
atcgaatacg ccgcaggccc cttcgcccta ttcttcatgg ccgaatacac aaacattatt    780
atgatgaaca ccctcaccac tacaatcttc ctaggaacaa catatgacgc actctcccct    840
gaactctaca caacatattt tgtcaccaag accctacttc taacctccct gttcttatgg    900
attcgaacag catacccccg attccgctac gaccaactca tgcacctcct atggaaaaac    960
ttcctaccac tcaccctagc attacttatg tggtatgtct ccatgcccat tacaatctcc   1020
agcattcccc ctcaaaccta agagcactgg gacgcccacc gccccttcc ctccgctgcc    1080
aggcgagcat gttgtggtaa ttctggaaca aagaagaga aattgctggg tttagaacaa    1140
gattataaac gaattcggtg ctcagtgatc acttgacagt tttttttttt tttaaatatt   1200
acccaaaatg ctccccaaat aagaaatgca tcagctcagt cagtgaatac aaaaaaggaa   1260
ttattttccc ctttgagggt cttttataca tctctcctcc aaccccaccc tctattctgt   1320
ttcttcctcc tcacatgggg gtacacatac acagcttcct cttttggttc catccttacc   1380
accacaccac acgcacactc cacatgccca gcagagtggc acttggtggc cagaaagtgt   1440
gagcctcatg atctgctgtc tgtagttctg tgagctcagg tccctcaaag gcctcggagc   1500
acccccttcc ttgtgactga gccagggcct gcattttttgg ttttcccac cccacacatt    1560
ctcaaccata gtccttctaa caataccaat agctaggacc cggctgctgt gcactgggac   1620
tggggattcc acatgtttgc cttgggagtc tcaagctgga ctgccagccc ctgtcctccc   1680
ttcaccccca ttgcgtatga gcatttcaga actccaagga gtcacaggca tctttatagt   1740
tcacgttaac atatagacac tgttggaagc agttccttct aaaagggtag ccctggactt   1800
aataccagcc ggatacctct ggccccccacc ccattactgt acctctggag tcactactgt   1860
gggtcgccac tcctctgcta cacagcacgg cttttttcaag gctgtattga aagggaagt    1920
taggaagaag ggtgtgctgg gctaaccagc ccacagagct cacattcctg tcccttgggt   1980
gaaaaataca tgtccatcct gatatctcct gaattcagaa attagcctcc acatgtgcaa   2040
tggctttaag agccagaagc agggttctgg gaattttgca agttacctgt ggccaggtgt   2100
ggtctcggtt accaaatacg gttacctgca gcttttttagt cctttgtgct cccacgggtc   2160
tacagagtcc catctgccca aaggtcttga agcttgacag gatgttttcg attactcagt   2220
ctcccagggc actactggtc cgtaggattc gattggtcgg ggtaggagag ttaaacaaca   2280
tttaaacaga gttctctcaa aaatgtctaa agggattgta ggtagataac atccaatcac   2340
tgtttgcact tatctgaaat cttccctctt ggctgccccc aggtatttac tgtggagaac   2400
attgcatagg aatgtctgga aaaagcttct acaacttgtt acagccttca catttgtaga   2460
agcttt                                                              2466

<210> SEQ ID NO 26
<211> LENGTH: 1666
<212> TYPE: DNA
<213> ORGANISM: Artificial Sequence
<220> FEATURE:
<223> OTHER INFORMATION: COX10-ND1-3'UTR*

<400> SEQUENCE: 26
atggccgcat ctccgcacac tctctcctca cgcctcctga caggttgcgt aggaggctct     60
gtctggtatc ttgaaagaag aactatgccc atggccaacc tcctactcct cattgtaccc    120
```

| | |
|---|---:|
| attctaatcg caatggcatt cctaatgctt accgaacgaa aaattctagg ctatatgcaa | 180 |
| ctacgcaaag gccccaacgt tgtaggcccc tacgggctac tacaacccct cgctgacgcc | 240 |
| atgaaactct tcaccaaaga gcccctaaaa cccgccacat ctaccatcac cctctacatc | 300 |
| accgccccga ccttagctct caccatcgct cttctactat ggaccccct ccccatgccc | 360 |
| aacccctgg tcaacctcaa cctaggcctc ctatttattc tagccacctc tagcctagcc | 420 |
| gtttactcaa tcctctggtc agggtgggca tcaaactcaa actacgccct gatcggcgca | 480 |
| ctgcgagcag tagcccaaac aatctcatat gaagtcaccc tagccatcat tctactatca | 540 |
| acattactaa tgagtggctc ctttaacctc tccacccta tcacaacaca agaacacctc | 600 |
| tggttactcc tgccatcatg gcccttggcc atgatgtggt ttatctccac actagcagag | 660 |
| accaaccgaa cccccttcga ccttgccgaa ggggagtccg aactagtctc aggcttcaac | 720 |
| atcgaatacg ccgcaggccc cttcgcccta ttcttcatgg ccgaatacac aaacattatt | 780 |
| atgatgaaca ccctcaccac tacaatcttc ctaggaacaa catatgacgc actctcccct | 840 |
| gaactctaca caacatattt tgtcaccaag accctacttc taacctccct gttcttatgg | 900 |
| attcgaacag catcccccg attccgctac gaccaactca tgcacctcct atggaaaaac | 960 |
| ttcctaccac tcaccctagc attacttatg tggtatgtct ccatgcccat tacaatctcc | 1020 |
| agcattcccc ctcaaaccta agagcactgg gacgcccacc gccccttcc ctccgctgcc | 1080 |
| aggcgagcat gttgtggtaa ttctggaaca caagaagaga aattgctggg tttagaacaa | 1140 |
| gattataaac gaattcggtg ctcagtgatc acttgacagt tttttttttt tttaaatatt | 1200 |
| acccaaaatg ctccccaaat aagaaatgca tcagctcagt cagtgaatac aaaaaaggaa | 1260 |
| ttattttttcc ctttgagggt cttttataca tctctcctcc aaccccaccc tctattctgt | 1320 |
| ttcttcctcc tcacatgggg gtacacatac acagcttcct cttttggttc catccttacc | 1380 |
| accacaccac acgcacactc cacatgccca gcagagtggc acttggtggc cagaaagtgt | 1440 |
| gagcctcatg atctgctgtc tgtagttctg tgagctcagg tccctcaaag gcctcggagc | 1500 |
| accccttcc ttgtgactga gccagggcct gcattttgg ttttcccac cccacacatt | 1560 |
| ctcaaccata gtccttctaa caataccaat agctaggacc cggctgctgt gcactgggac | 1620 |
| tggggattcc acatgtttgc cttgggagtc tcaagctgga ctgcca | 1666 |

<210> SEQ ID NO 27
<211> LENGTH: 2466
<212> TYPE: DNA
<213> ORGANISM: Artificial Sequence
<220> FEATURE:
<223> OTHER INFORMATION: COX10-opt_ND1-3'UTR

<400> SEQUENCE: 27

| | |
|---|---:|
| atggccgcat ctccgcacac tctctcctca cgcctcctga caggttgcgt aggaggctct | 60 |
| gtctggtatc ttgaaagaag aactatgccc atggccaacc tgctgctgct gatcgtgccc | 120 |
| atcctgatcg ccatggcctt cctgatgctg accgagcgca agatcctggg ctacatgcag | 180 |
| ctgcgcaagg gccccaacgt ggtgggcccc tacgcctgc tgcagcccct cgccgacgcc | 240 |
| atgaagctgt tcaccaagga gcccctgaag cccgccacca gcaccatcac cctgtacatc | 300 |
| accgccccca cctggccct gaccatcgcc ctgctgctgt gaccccct gcccatgccc | 360 |
| aaccccctgg tgaacctgaa cctgggcctg ctgttcatcc tggccaccag cagcctggcc | 420 |
| gtgtacagca tcctgtggag cggctgggcc agcaacagca ctacgccct gatcggcgcc | 480 |
| ctgcgcgccg tggcccagac catcagctac gaggtgaccc tggccatcat cctgctgagc | 540 |

```
accctgctga tgagcggcag cttcaacctg agcaccctga tcaccaccca ggagcacctg      600
tggctgctgc tgcccagctg gcccctggcc atgatgtggt tcatcagcac cctggccgag      660
accaaccgca ccccttcga cctggccgag ggcgagagcg agctggtgag cggcttcaac       720
atcgagtacg ccgccggccc cttcgccctg ttcttcatgg ccgagtacac caacatcatc      780
atgatgaaca ccctgaccac caccatcttc ctgggcacca cctacgacgc cctgagcccc      840
gagctgtaca ccacctactt cgtgaccaag accctgctgc tgaccagcct gttcctgtgg      900
atccgcaccg cctaccccg cttccgctac gaccagctga tgcacctgct gtggaagaac       960
ttcctgcccc tgaccctggc cctgctgatg tggtacgtga gcatgcccat caccatcagc     1020
agcatccccc cccagaccta gagcactgg gacgcccacc gcccctttcc ctccgctgcc      1080
aggcgagcat gttgtggtaa ttctggaaca caagaagaga aattgctggg tttagaacaa     1140
gattataaac gaattcggtg ctcagtgatc acttgacagt tttttttttt tttaaatatt     1200
acccaaaatg ctccccaaat aagaaatgca tcagctcagt cagtgaatac aaaaaaggaa     1260 ttattttcc ctttgagggt cttttataca tctctcctcc aaccccaccc tctattctgt      1320
ttcttcctcc tcacatgggg gtacacatac acagcttcct cttttggttc catccttacc     1380
accacaccac acgcacactc cacatgccca gcagagtggc acttggtggc cagaaagtgt     1440
gagcctcatg atctgctgtc tgtagttctg tgagctcagg tccctcaaag gcctcggagc     1500 accccttcc ttgtgactga gccagggcct gcattttgg ttttccccac cccacacatt       1560
ctcaaccata gtccttctaa caataccaat agctaggacc cggctgctgt gcactgggac     1620
tggggattcc acatgtttgc cttgggagtc tcaagctgga ctgccagccc ctgtcctccc     1680 ttcacccca ttgcgtatga gcatttcaga actccaagga gtcacaggca tctttatagt     1740
tcacgttaac atatagacac tgttggaagc agttccttct aaaagggtag ccctggactt     1800
aataccagcc ggatacctct ggcccccacc ccattactgt acctctggag tcactactgt     1860
gggtcgccac tcctctgcta cacagcacgg cttttttcaag gctgtattga aagggaagt    1920 taggaagaag ggtgtgctgg gctaaccagc ccacagagct cacattcctg tcccttgggt     1980
gaaaaataca tgtccatcct gatatctcct gaattcagaa attagcctcc acatgtgcaa     2040
tggctttaag agccagaagc agggttctgg gaattttgca agttacctgt ggccaggtgt     2100
ggtctcggtt accaaatacg gttacctgca gcttttagt cctttgtgct cccacgggtc      2160
tacagagtcc catctgccca aaggtcttga agcttgacag gatgttttcg attactcagt     2220
ctcccagggc actactggtc cgtaggattc gattggtcgg ggtaggagag ttaaacaaca     2280
tttaaacaga gttctctcaa aaatgtctaa agggattgta ggtagataac atccaatcac     2340
tgtttgcact tatctgaaat cttccctctt ggctgcccc aggtatttac tgtggagaac      2400
attgcatagg aatgtctgga aaaagcttct acaacttgtt acagccttca catttgtaga     2460
agcttt                                                                2466
```

<210> SEQ ID NO 28
<211> LENGTH: 1666
<212> TYPE: DNA
<213> ORGANISM: Artificial Sequence
<220> FEATURE:
<223> OTHER INFORMATION: COX10-opt_ND1-3'UTR*

<400> SEQUENCE: 28

```
atggccgcat ctccgcacac tctctcctca cgcctcctga caggttgcgt aggaggctct       60
```

| | |
|---|---|
| gtctggtatc ttgaaagaag aactatgccc atggccaacc tgctgctgct gatcgtgccc | 120 |
| atcctgatcg ccatggcctt cctgatgctg accgagcgca agatcctggg ctacatgcag | 180 |
| ctgcgcaagg gccccaacgt ggtgggcccc tacggcctgc tgcagcccct cgccgacgcc | 240 |
| atgaagctgt tcaccaagga gcccctgaag cccgccacca gcaccatcac cctgtacatc | 300 |
| accgccccca ccctggccct gaccatcgcc ctgctgctgt ggaccccct gcccatgccc | 360 |
| aaccccctgg tgaacctgaa cctgggcctg ctgttcatcc tggccaccag cagcctggcc | 420 |
| gtgtacagca tcctgtggag cggctgggcc agcaacagca actacgccct gatcggcgcc | 480 |
| ctgcgcgccg tggcccagac catcagctac gaggtgaccc tggccatcat cctgctgagc | 540 |
| accctgctga tgagcggcag cttcaacctg agcaccctga tcaccaccca ggagcacctg | 600 |
| tggctgctgc tgcccagctg gcccctggcc atgatgtggt tcatcagcac cctggccgag | 660 |
| accaaccgca ccccccttcga cctggccgag ggcgagagcg agctggtgag cggcttcaac | 720 |
| atcgagtacg ccgccggccc cttcgcccctg ttcttcatgg ccgagtacac caacatcatc | 780 |
| atgatgaaca ccctgaccac caccatcttc ctgggcacca cctacgacgc cctgagcccc | 840 |
| gagctgtaca ccacctactt cgtgaccaag accctgctgc tgaccagcct gttcctgtgg | 900 |
| atccgcaccg cctaccccccg cttccgctac gaccagctga tgcacctgct gtggaagaac | 960 |
| ttcctgcccc tgaccctggc cctgctgatg tggtacgtga gcatgcccat caccatcagc | 1020 |
| agcatccccc cccagaccta agagcactgg gacgcccacc gccccttttcc ctccgctgcc | 1080 |
| aggcgagcat gttgtggtaa ttctggaaca aagaagaga aattgctggg tttagaacaa | 1140 |
| gattataaac gaattcggtg ctcagtgatc acttgacagt tttttttttt tttaaatatt | 1200 |
| acccaaaatg ctccccaaat aagaaatgca tcagctcagt cagtgaatac aaaaaggaa | 1260 |
| ttattttttcc ctttgagggt cttttataca tctctcctcc aaccccaccc tctattctgt | 1320 |
| ttcttcctcc tcacatgggg gtacacatac acagcttcct cttttggttc catccttacc | 1380 |
| accacaccac acgcacactc cacatgccca gcagagtggc acttggtggc cagaaagtgt | 1440 |
| gagcctcatg atctgctgtc tgtagttctg tgagctcagg tccctcaaag gcctcggagc | 1500 |
| acccccttcc ttgtgactga gccagggcct gcatttttgg ttttccccac ccacacatt | 1560 |
| ctcaaccata gtccttctaa caataccaat agctaggacc cggctgctgt gcactgggac | 1620 |
| tggggattcc acatgttttgc cttgggagtc tcaagctgga ctgcca | 1666 |

<210> SEQ ID NO 29
<211> LENGTH: 2889
<212> TYPE: DNA
<213> ORGANISM: Artificial Sequence
<220> FEATURE:
<223> OTHER INFORMATION: opt_COX10-ND4-3'UTR

<400> SEQUENCE: 29

| | |
|---|---|
| atggccgcct ctccacacac actgagtagc agactgctga ccggctgtgt tggcggctct | 60 |
| gtgtggtatc tggaacggcg gacaatgcta aaactaatcg tcccaacaat tatgttacta | 120 |
| ccactgacat ggctttccaa aaaacacatg atttggatca acacaaccac ccacagccta | 180 |
| attattagca tcatccctct actatttttt aaccaaatca caacaaccct atttagctgt | 240 |
| tccccaacct tttcctccga ccccctaaca accccctcc taatgctaac tacctggctc | 300 |
| ctaccccctca caatcatggc aagccaacgc cacttatcca gtgaaccact atcacgaaaa | 360 |
| aaactctacc tctctatgct aatctcccta caaatctcct taattatgac attcacagcc | 420 |
| acagaactaa tcatgttta tcttcttc gaaaccacac ttatccccac cttggctatc | 480 |

```
atcacccgat ggggcaacca gccagaacgc ctgaacgcag gcacatactt cctattctac    540
accctagtag gctcccttcc cctactcatc gcactaattt acactcacaa caccctaggc    600
tcactaaaca ttctactact cactctcact gcccaagaac tatcaaactc ctgggccaac    660
aacttaatgt ggctagctta cacaatggct tttatggtaa agatgcctct ttacggactc    720
cacttatggc tccctaaagc ccatgtcgaa gccccatcg ctgggtcaat ggtacttgcc     780
gcagtactct taaaactagg cggctatggt atgatgcgcc tcacactcat tctcaacccc    840
ctgacaaaac acatggccta ccccttcctt gtactatccc tatggggcat gattatgaca    900
agctccatct gcctacgaca aacagaccta aaatcgctca ttgcatactc ttcaatcagc    960
cacatggccc tcgtagtaac agccattctc atccaaaccc cctggagctt caccggcgca   1020
gtcattctca tgatcgccca cgggcttaca tcctcattac tattctgcct agcaaactca   1080
aactacgaac gcactcacag tcgcatcatg atcctctctc aaggacttca aactctactc   1140
ccactaatgg cttttggtg gcttctagca agcctcgcta acctcgcctt accccccact    1200
attaacctac tgggagaact ctctgtgcta gtaaccacgt tctcctggtc aaatatcact   1260
ctcctactta caggactcaa catgctagtc acagccctat actccctcta catgtttacc   1320
acaacacaat ggggctcact caccccaccac attaacaaca tgaaaccctc attcacacga   1380
gaaaacaccc tcatgttcat gcacctatcc cccattctcc tcctatccct caaccccgac   1440
atcattaccg ggttttcctc ttaagagcac tgggacgccc accgccctt tccctccgct    1500 gccaggcgag catgttgtgg taattctgga acacaagaag agaaattgct gggtttagaa   1560
caagattata acgaattcg gtgctcagtg atcacttgac agttttttttt ttttttaaat   1620 attacccaaa atgctcccca aataagaaat gcatcagctc agtcagtgaa tacaaaaaag   1680
gaattatttt tcccttgag ggtcttttat acatctctcc tccaaccca ccctctattc    1740 tgtttcttcc tcctcacatg ggggtacaca tacacagctt cctcttttgg ttccatcctt   1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920 agcacccct tccttgtgac tgagccaggg cctgcatttt tggttttccc caccccacac    1980
attctcaacc atagtccttc taacaatacc aatagctagg accggctgc tgtgcactgg    2040 gactggggat tccacatgtt tgccttggga gtctcaagct ggactgccag ccctgtcct    2100 cccttcaccc ccattgcgta tgagcatttc agaactccaa ggagtcacag gcatctttat   2160
agttcacgtt aacatataga cactgttgga agcagttcct tctaaaaggg tagccctgga   2220
cttaatacca gccggatacc tctggccccc accccattac tgtacctctg gagtcactac   2280
tgtgggtcgc cactcctctg ctacacagca cggcttttc aaggctgtat tgagaaggga   2340
agttaggaag aagggtgtgc tgggctaacc agcccacaga gctcacattc ctgtcccttg   2400
ggtgaaaaat acatgtccat cctgatatct cctgaattca gaaattagcc tccacatgtg   2460
caatggcttt aagagccaga agcagggttc tgggaatttt gcaagttacc tgtggccagg   2520
tgtggtctcg gttaccaaat acggttacct gcagcttttt agtcctttgt gctcccacgg   2580
gtctacagag tccatctgc ccaaaggtct tgaagcttga caggatgttt tcgattactc    2640
agtctcccag ggcactactg gtccgtagga ttcgattggt cggggtagga gagttaaaca   2700
acatttaaac agagttctct caaaaatgtc taaagggatt gtaggtagat aacatccaat   2760
cactgtttgc acttatctga aatcttccct cttggctgcc cccaggtatt tactgtggag   2820
```

```
aacattgcat aggaatgtct ggaaaaagct tctacaactt gttacagcct tcacatttgt    2880
agaagcttt                                                            2889

<210> SEQ ID NO 30
<211> LENGTH: 2089
<212> TYPE: DNA
<213> ORGANISM: Artificial Sequence
<220> FEATURE:
<223> OTHER INFORMATION: opt_COX10-ND4-3'UTR*

<400> SEQUENCE: 30
atggccgcct ctccacacac actgagtagc agactgctga ccggctgtgt tggcggctct      60
gtgtggtatc tggaacggcg gacaatgcta aaactaatcg tcccaacaat tatgttacta    120
ccactgacat ggcttttccaa aaaacacatg atttggatca acacaaccac ccacagccta    180
attattagca tcatccctct actatttttt aaccaaatca caacaaccct atttagctgt    240
tccccaacct tttcctccga ccccctaaca acccccctcc taatgctaac tacctggctc    300
ctacccctca caatcatggc aagccaacgc cacttatcca gtgaaccact atcacgaaaa    360
aaactctacc tctctatgct aatctcccta caaatctcct taattatgac attcacagcc    420
acagaactaa tcatgtttta tatcttcttc gaaaccacac ttatccccac cttggctatc    480
atcacccgat ggggcaacca gccagaacgc ctgaacgcag gcacatactt cctattctac    540
accctagtag gctcccttcc cctactcatc gcactaattt acactcacaa caccctaggc    600
tcactaaaca ttctactact cactctcact gcccaagaac tatcaaactc ctgggccaac    660
aacttaatgt ggctagctta cacaatggct tttatggtaa agatgcctct ttacggactc    720
cacttatggc tccctaaagc ccatgtcgaa gccccatcg ctgggtcaat ggtacttgcc    780
gcagtactct taaaactagg cggctatggt atgatgcgcc tcacactcat tctcaacccc    840
ctgacaaaac acatggccta ccccttcctt gtactatccc tatggggcat gattatgaca    900
agctccatct gcctacgaca aacagaccta aaatcgctca ttgcatactc ttcaatcagc    960
cacatggccc tcgtagtaac agccattctc atccaaaccc cctggagctt caccggcgca   1020
gtcattctca tgatcgccca cgggcttaca tcctcattac tattctgcct agcaaactca   1080
aactacgaac gcactcacag tcgcatcatg atcctctctc aaggacttca aactctactc   1140
ccactaatgg ctttttggtg gcttctagca agcctgctta acctcgcctt accccccact   1200
attaacctac tgggagaact ctctgtgcta gtaaccacgt tctcctggtc aaatatcact   1260
ctcctactta caggactcaa catgctagtc acagccctat actccctcta catgtttacc   1320
acaacacaat ggggctcact cacccaccac attaacaaca tgaaaccctc attcacacga   1380
gaaacacccc tcatgttcat gcacctatcc cccattctcc tcctatccct caaccccgac   1440
atcattaccg ggttttcctc ttaagagcac tgggacgccc accgcccctt tccctccgct   1500
gccaggcgag catgttgtgg taattctgga acacaagaag agaaattgct gggtttagaa   1560
caagattata aacgaattcg gtgctcagtg atcacttgac agtttttttt tttttttaat   1620 attcccaaa atgctcccca aataagaaat gcatcagctc agtcagtgaa tacaaaaaag   1680
gaattatttt tcccttgag ggtcttttat acatctctcc tccaacccca ccctctattc   1740
tgtttcttcc tcctcacatg ggggtacaca tacacagctt cctcttttgg ttccatcctt   1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920
agcaccccct tccttgtgac tgagccaggg cctgcatttt tggttttccc caccccacac   1980
```

```
attctcaacc atagtccttc taacaatacc aatagctagg acccggctgc tgtgcactgg    2040
gactggggat tccacatgtt tgccttggga gtctcaagct ggactgcca               2089

<210> SEQ ID NO 31
<211> LENGTH: 2889
<212> TYPE: DNA
<213> ORGANISM: Artificial Sequence
<220> FEATURE:
<223> OTHER INFORMATION: opt_COX10-opt_ND4-3'UTR

<400> SEQUENCE: 31
atggccgcct ctccacacac actgagtagc agactgctga ccggctgtgt tggcggctct      60
gtgtggtatc tggaacggcg gacaatgctg aagctgatcg tgcccaccat catgctgctg    120
cctctgacct ggctgagcaa gaaacacatg atctggatca caccaccac gcacagcctg    180 atcatcagca tcatccctct gctgttcttc aaccagatca caacaaccct gttcagctgc    240
agccccacct tcagcagcga ccctctgaca cacctctgc tgatgctgac cacctggctg    300
ctgcccctca caatcatggc ctctcagaga cacctgagca gcgagcccct gagccggaag    360
aaactgtacc tgagcatgct gatctccctg cagatctctc tgatcatgac cttcaccgcc    420
accgagctga tcatgttcta catctttttc gagacaacgc tgatccccac actggccatc    480
atcaccagat ggggcaacca gcctgagaga ctgaacgccg gcacctactt tctgttctac    540
accctcgtgg gcagcctgcc actgctgatt gccctgatct acacccacaa cacctgggc    600 tccctgaaca tcctgctgct gacactgaca gcccaagagc tgagcaacag ctgggccaac    660
aatctgatgt ggctggccta cacaatggcc ttcatggtca agatgcccct gtacggcctg    720
cacctgtggc tgcctaaagc tcatgtggaa gccctatcg ccggctctat ggtgctggct    780
gcagtgctgc tgaaactcgg cggctacggc atgatgcggc tgaccctgat tctgaatccc    840
ctgaccaagc acatggccta tccatttctg tgtctgagcc tgtggggcat gattatgacc    900
agcagcatct gcctgcggca gaccgatctg aagtccctga tcgcctacag ctccatcagc    960
cacatggccc tggtggtcac cgccatcctg attcagaccc cttggagctt tacaggcgcc   1020
gtgatcctga tgattgccca cggcctgaca agcagcctgc tgttttgtct ggccaacagc   1080
aactacgagc ggacccacag cagaatcatg atcctgtctc agggcctgca gaccctcctg   1140
cctcttatgg cttttttggtg gctgctggcc tctctggcca atctggcact gcctcctacc   1200
atcaatctgc tgggcgagct gagcgtgctg gtcaccacat tcagctggtc aatatcacc   1260 ctgctgctca ccggcctgaa catgctggtt acagccctgt actccctgta catgttcacc   1320
accacacagt ggggaagcct gacacaccac atcaacaata tgaagcccag cttcacccgc   1380
gagaacaccc tgatgttcat gcatctgagc cccattctgc tgctgtccct gaatcctgat   1440
atcatcaccg gcttctccag ctgagagcac tgggacgccc accgcccctt tccctccgct   1500
gccaggcgag catgttgtgg taattctgga acacaagaag agaaattgct gggtttagaa   1560
caagattata aacgaattcg gtgctcagtg atcacttgac agtttttttt tttttaaat   1620 attacccaaa atgctcccca aataagaaat gcatcagctc agtcagtgaa tacaaaaaag   1680
gaattatttt tccctttgag ggtcttttat acatctctcc tccaaccca ccctctattc    1740 tgtttcttcc tcctcacatg ggggtacaca tacacagctt cctctttggg ttccatcctt   1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920
```

| | |
|---|---:|
| agcaccccct tccttgtgac tgagccaggg cctgcatttt tggttttccc caccccacac | 1980 |
| attctcaacc atagtccttc taacaatacc aatagctagg acccggctgc tgtgcactgg | 2040 |
| gactggggat tccacatgtt tgccttggga gtctcaagct ggactgccag ccctgtcct | 2100 |
| cccttcaccc ccattgcgta tgagcatttc agaactccaa ggagtcacag gcatctttat | 2160 |
| agttcacgtt aacatataga cactgttgga agcagttcct tctaaagggg tagccctgga | 2220 |
| cttaatacca gccggatacc tctggccccc accccattac tgtacctctg gagtcactac | 2280 |
| tgtgggtcgc cactcctctg ctacacagca cggcttttc aaggctgtat tgagaaggga | 2340 |
| agttaggaag aagggtgtgc tgggctaacc agcccacaga gctcacattc ctgtcccttg | 2400 |
| ggtgaaaaat acatgtccat cctgatatct cctgaattca gaaattagcc tccacatgtg | 2460 |
| caatggcttt aagagccaga agcagggttc tgggaatttt gcaagttacc tgtggccagg | 2520 |
| tgtggtctcg gttaccaaat acggttacct gcagcttttt agtcctttgt gctcccacgg | 2580 |
| gtctacagag tcccatctgc ccaaaggtct tgaagcttga caggatgttt tcgattactc | 2640 |
| agtctcccag ggcactactg gtccgtagga ttcgattggt cggggtagga gagttaaaca | 2700 |
| acatttaaac agagttctct caaaaatgtc taagggatt gtaggtagat aacatccaat | 2760 |
| cactgtttgc acttatctga aatcttccct cttggctgcc cccaggtatt tactgtggag | 2820 |
| aacattgcat aggaatgtct ggaaaaagct tctacaactt gttacagcct tcacatttgt | 2880 |
| agaagcttt | 2889 |

<210> SEQ ID NO 32
<211> LENGTH: 2089
<212> TYPE: DNA
<213> ORGANISM: Artificial Sequence
<220> FEATURE:
<223> OTHER INFORMATION: opt_COX10-opt_ND4-3'UTR*

<400> SEQUENCE: 32

| | |
|---|---:|
| atggccgcct ctccacacac actgagtagc agactgctga ccggctgtgt tggcggctct | 60 |
| gtgtggtatc tggaacggcg gacaatgctg aagctgatcg tgcccaccat catgctgctg | 120 |
| cctctgacct ggctgagcaa gaaacacatg atctggatca acaccaccac gcacagcctg | 180 |
| atcatcagca tcatccctct gctgttcttc aaccagatca caacaacct gttcagctgc | 240 |
| agccccacct tcagcagcga ccctctgaca cacctctgc tgatgctgac cacctggctg | 300 |
| ctgccccta caatcatggc ctctcagaga cacctgagca gcgagcccct gagccggaag | 360 |
| aaactgtacc tgagcatgct gatctccctg cagatctctc tgatcatgac cttcaccgcc | 420 |
| accgagctga tcatgttcta catctttttc gagacaacgc tgatccccac actggccatc | 480 |
| atcaccagat ggggcaacca gcctgagaga ctgaacgccg gcacctactt tctgttctac | 540 |
| accctcgtgg gcagcctgcc actgctgatt gccctgatct acacccacaa caccctgggc | 600 |
| tccctgaaca tcctgctgct gacactgaca gcccaagagc tgagcaacag ctgggccaac | 660 |
| aatctgatgt ggctggccta cacaatggcc ttcatggtca agatgcccct gtacggcctg | 720 |
| cacctgtggc tgcctaaagc tcatgtggaa gccctatcg ccggctctat ggtgctggct | 780 |
| gcagtgctgc tgaaactcgg cggctacggc atgatgcggc tgaccctgat tctgaatccc | 840 |
| ctgaccaagc acatggccta tccatttctg gtgctgagcc tgtggggcat gattatgacc | 900 |
| agcagcatct gcctgcggca gaccgatctg aagtccctga tcgcctacag ctccatcagc | 960 |
| cacatggccc tggtggtcac cgccatcctg attcagaccc cttggagctt tacaggcgcc | 1020 |
| gtgatcctga tgattgccca cggcctgaca agcagcctgc tgttttgtct ggccaacagc | 1080 |

```
aactacgagc ggacccacag cagaatcatg atcctgtctc agggcctgca gaccctcctg   1140
cctcttatgg cttttggtg gctgctggcc tctctggcca atctggcact gcctcctacc   1200
atcaatctgc tgggcgagct gagcgtgctg gtcaccacat tcagctggtc caatatcacc   1260
ctgctgctca ccggcctgaa catgctggtt acagccctgt actccctgta catgttcacc   1320
accacacagt ggggaagcct gacacaccac atcaacaata tgaagcccag cttcacccgc   1380
gagaacaccc tgatgttcat gcatctgagc cccattctgc tgctgtccct gaatcctgat   1440
atcatcaccg gcttctccag ctgagagcac tgggacgccc accgcccctt ccctccgct    1500 gccaggcgag catgttgtgg taattctgga acacaagaag agaaattgct gggtttagaa   1560
caagattata aacgaattcg gtgctcagtg atcacttgac agttttttt tttttaaat    1620 attacccaaa atgctcccca aataagaaat gcatcagctc agtcagtgaa tacaaaaaag   1680
gaattatttt tcccttgag ggtcttttat acatctctcc tccaacccca ccctctattc    1740
tgtttcttcc tcctcacatg ggggtacaca tacacagctt cctcttttgg ttccatcctt   1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920 agcacccct tccttgtgac tgagccaggg cctgcatttt tggttttccc caccccacac    1980
attctcaacc atagtccttc taacaatacc aatagctagg accggctgc tgtgcactgg    2040 gactggggat tccacatgtt tgccttggga gtctcaagct ggactgcca              2089

<210> SEQ ID NO 33
<211> LENGTH: 2889
<212> TYPE: DNA
<213> ORGANISM: Artificial Sequence
<220> FEATURE:
<223> OTHER INFORMATION: opt_COX10-opt_ND4*-3'UTR

<400> SEQUENCE: 33
atggccgcct ctccacacac actgagtagc agactgctga ccggctgtgt tggcggctct     60
gtgtggtatc tggaacggcg gacaatgctg aagctgatcg tgcccaccat catgctgctg    120
cccctgacct ggctgagcaa gaagcacatg atctggatca acaccaccac ccacagcctg    180
atcatcagca tcatccccct gctgttcttc aaccagatca caacaacct gttcagctgc     240 agccccacct tcagcagcga ccccctgacc acccccctgc tgatgctgac cacctggctg    300 ctgccctga ccatcatggc cagccagcgc cacctgagca gcgagccct gagccgcaag      360 aagctgtacc tgagcatgct gatcagcctg cagatcagcc tgatcatgac cttcaccgcc    420
accgagctga tcatgttcta catcttcttc gagaccaccc tgatcccac cctggccatc     480 atcacccgct ggggcaacca gcccgagcgc ctgaacgccg gcacctactt cctgttctac    540
accctggtgg gcagcctgcc cctgctgatc gccctgatct acacccacaa caccctgggc    600
agcctgaaca tctgctgct gaccctgacc gccaggagc tgagcaacag ctgggccaac     660
aacctgatgt ggctggccta ccatggcc ttcatggtga gatgcccct gtacggcctg     720 cacctgtggc tgcccaaggc ccacgtggag gccccatcg ccggcagcat ggtgctggcc    780
gccgtgctgc tgaagctggg cggctacggc atgatgcgcc tgaccctgat cctgaacccc    840
ctgaccaagc acatggccta ccccttcctg gtgctgagcc tgtggggcat gatcatgacc    900
agcagcatct gcctgcgcca gaccgacctg aagagcctga tcgcctacag cagcatcagc    960
cacatggccc tggtggtgac cgccatcctg atccagaccc cctggagctt caccggcgcc   1020
```

```
gtgatcctga tgatcgccca cggcctgacc agcagcctgc tgttctgcct ggccaacagc    1080
aactacgagc gcacccacag ccgcatcatg atcctgagcc agggcctgca gaccctgctg    1140
cccctgatgg ccttctggtg gctgctggcc agcctggcca acctggccct gcccccccacc   1200 atcaacctgc tgggcgagct gagcgtgctg gtgaccacct tcagctggag caacatcacc    1260
ctgctgctga ccggcctgaa catgctggtg accgccctgt acagcctgta catgttcacc    1320
accacccagt ggggcagcct gacccaccac atcaacaaca tgaagcccag cttcacccgc    1380
gagaacaccc tgatgttcat gcacctgagc cccatcctgc tgctgagcct gaaccccgac    1440
atcatcaccg gcttcagcag ctaagagcac tgggacgccc accgcccctt ccctccgct    1500 gccaggcgag catgttgtgg taattctgga acacaagaag agaaattgct gggtttagaa    1560
caagattata aacgaattcg gtgctcagtg atcacttgac agttttttt ttttttaaat     1620 attacccaaa atgctcccca ataagaaat gcatcagctc agtcagtgaa tacaaaaaag     1680
gaattatttt tcccttgag ggtcttttat acatctctcc tccaaccca ccctctattc      1740 tgtttcttcc tcctcacatg ggggtacaca tacacagctt cctcttttgg ttccatcctt    1800
accaccacac cacacgcaca ctccacatgc ccagcagagt ggcacttggt ggccagaaag    1860
tgtgagcctc atgatctgct gtctgtagtt ctgtgagctc aggtccctca aaggcctcgg    1920
agcaccccct tccttgtgac tgagccaggg cctgcatttt tggttttccc caccccacac    1980
attctcaacc atagtccttc taacaatacc aatagctagg accggctgc tgtgcactgg     2040 gactggggat ccacatgtt tgccttggga gtctcaagct ggactgccag ccctgtcct     2100 cccttcaccc ccattgcgta tgagcatttc agaactccaa ggagtcacag gcatctttat    2160
agttcacgtt aacatataga cactgttgga agcagttcct tctaaaggg tagccctgga    2220 cttaatacca gccggatacc tctggccccc accccattac tgtacctctg gagtcactac    2280
tgtgggtcgc cactcctctg ctacacagca cggcttttc aaggctgtat tgagaaggga    2340
agttaggaag aagggtgtgc tgggctaacc agcccacaga gctcacattc ctgtcccttg    2400
ggtgaaaaat acatgtccat cctgatatct cctgaattca gaaattagcc tccacatgtg    2460
caatggcttt aagagccaga agcagggttc tgggaatttt gcaagttacc tgtggccagg    2520
tgtggtctcg gttaccaaat acggttacct gcagcttttt agtcctttgt gctcccacgg    2580
gtctacagag tcccatctgc ccaaaggtct tgaagcttga caggatgttt tcgattactc     2640
agtctcccag ggcactactg gtccgtagga ttcgattggt cggggtagga gagttaaaca    2700
acatttaaac agagttctct caaaaatgtc taagggatt gtaggtagat aacatccaat     2760
cactgtttgc acttatctga aatcttccct cttggctgcc cccaggtatt tactgtggag    2820
aacattgcat aggaatgtct ggaaaaagct tctacaactt gttacagcct tcacatttgt    2880
agaagcttt                                                           2889
```

<210> SEQ ID NO 34
<211> LENGTH: 2089
<212> TYPE: DNA
<213> ORGANISM: Artificial Sequence
<220> FEATURE:
<223> OTHER INFORMATION: opt_COX10-opt_ND4*-3'UTR*

<400> SEQUENCE: 34

```
atggccgcct ctccacacac actgagtagc agactgctga ccggctgtgt tggcggctct      60
gtgtggtatc tggaacggcg gacaatgctg aagctgatcg tgcccaccat catgctgctg    120
cccctgacct ggctgagcaa gaagcacatg atctggatca acaccaccac ccacagcctg    180
```

```
atcatcagca tcatccccct gctgttcttc aaccagatca acaacaacct gttcagctgc      240
agccccacct tcagcagcga ccccctgacc acccccctgc tgatgctgac acctggctg       300 ctgcccctga ccatcatggc cagccagcgc cacctgagca gcgagcccct gagccgcaag      360
aagctgtacc tgagcatgct gatcagcctg cagatcagcc tgatcatgac cttcaccgcc      420
accgagctga tcatgttcta catcttcttc gagaccaccc tgatcccac cctggccatc       480 atcacccgct ggggcaacca gcccgagcgc ctgaacgccg caccta ctt cctgttctac      540 accctggtgg cagcctgcc cctgctgatc gccctgatct acacccacaa caccctgggc       600
agcctgaaca tcctgctgct gaccctgacc gccaggagc tgagcaacag ctgggccaac       660
aacctgatgt ggctggccta ccatggcc ttcatggtga agatgcccct gtacggcctg        720
cacctgtggc tgcccaaggc ccacgtggag gccccatcg ccggcagcat ggtgctggcc      780
gccgtgctgc tgaagctggg cggctacggc atgatgcgcc tgaccctgat cctgaacccc      840
ctgaccaagc acatggccta cccttcctg gtgctgagcc tgtggggcat gatcatgacc      900
agcagcatct gcctgcgcca accgacctg aagagcctga tcgcctacag cagcatcagc      960
cacatggccc tggtggtgac cgccatcctg atccagaccc cctggagctt caccggcgcc     1020
gtgatcctga tgatcgccca cggcctgacc agcagcctgc tgttctgcct ggccaacagc     1080
aactacgagc gcacccacag ccgcatcatg atcctgagcc agggcctgca gaccctgctg     1140 ccctgatgg ccttctggtg gctgctggcc agcctggcca acctggccct gccccccacc     1200
atcaacctgc tgggcgagct gagcgtgctg gtgaccacct tcagctggag caacatcacc     1260
ctgctgctga ccggcctgaa catgctggtg accgccctgt acagcctgta catgttcacc     1320
accacccagt ggggcagcct gacccaccac atcaacaaca tgaagcccag cttcacccgc     1380
gagaacaccc tgatgttcat gcacctgagc cccatcctgc tgctgagcct gaaccccgac     1440
atcatcaccg gcttcagcag ctaagagcac tgggacgccc accgccctt ccctccgct     1500 gccaggcgag catgttgtgg taattctgga acacaagaag agaaattgct gggtttagaa     1560
caagattata aacgaattcg gtgctcagtg atcacttgac agttttttt tttttaat      1620 attacccaaa atgctcccca ataagaaat gcatcagctc agtcagtgaa tacaaaaaag     1680 gaatttatttt tccctttgag ggtcttttat acatctctcc tccaaccca ccctctattc      1740 tgtttcttcc tcctcacatg ggggtacaca tacacagctt cctcttttgg ttccatcctt     1800
accaccacac cacacgcaca ctccacatgc ccagcagagt ggcacttggt ggccagaaag    1860
tgtgagcctc atgatctgct gtctgtagtt ctgtgagctc aggtccctca aaggcctcgg    1920
agcaccccct tccttgtgac tgagccaggg cctgcatttt tggttttccc cacccacac    1980 attctcaacc atagtccttc taacaatacc aatagctagg accggctgc tgtgcactgg    2040 gactggggat ccacatgtt tgccttggga gtctcaagct ggactgcca                  2089

<210> SEQ ID NO 35
<211> LENGTH: 2034
<212> TYPE: DNA
<213> ORGANISM: Artificial Sequence
<220> FEATURE:
<223> OTHER INFORMATION: opt_COX10-ND6-3'UTR

<400> SEQUENCE: 35
atggccgcct ctccacacac actgagtagc agactgctga ccggctgtgt tggcggctct        60
gtgtggtatc tggaacggcg gacaatgatg tatgctttgt ttctgttgag tgtgggttta      120
```

| | | | |
|---|---|---|---|
| gtaatggggt | tgtggggtt ttcttctaag | ccttctccta tttatggggg tttagtattg | 180 |
| attgttagcg | gtgtggtcgg gtgtgttatt | attctgaatt ttgggggagg ttatatgggt | 240 |
| ttaatggttt | ttttaatta tttagggga | atgatggttg tctttggata tactacagcg | 300 |
| atggctattg | aggagtatcc tgaggcatgg | gggtcagggg ttgaggtctt ggtgagtgtt | 360 |
| ttagtggggt | tagcgatgga ggtaggattg | gtgctgtggg tgaaagagta tgatggggtg | 420 |
| gtggttgtgg | taaactttaa tagtgtagga | agctggatga tttatgaagg agaggggtca | 480 |
| gggttgattc | gggaggatcc tattggtgcg | ggggctttgt atgattatgg gcgttggtta | 540 |
| gtagtagtta | ctggttggac attgtttgtt | ggtgtatata ttgtaattga gattgctcgg | 600 |
| gggaattagg | agcactggga cgcccaccgc | cccttcccct ccgctgccag gcgagcatgt | 660 |
| tgtggtaatt | ctggaacaca agaagagaaa | ttgctgggtt tagaacaaga ttataaacga | 720 |
| attcggtgct | cagtgatcac ttgacagttt | tttttttttt taaatattac ccaaaatgct | 780 |
| ccccaaataa | gaaatgcatc agctcagtca | gtgaatacaa aaaggaatt attttcct | 840 |
| ttgagggtct | tttatacatc tctcctccaa | ccccaccctc tattctgttt cttcctcctc | 900 |
| acatggggt | acacatacac agcttcctct | tttggttcca tccttaccac cacaccacac | 960 |
| gcacactcca | catgcccagc agagtggcac | ttggtggcca gaaagtgtga gcctcatgat | 1020 |
| ctgctgtctg | tagttctgtg agctcaggtc | cctcaaaggc ctcggagcac ccccttcctt | 1080 |
| gtgactgagc | cagggcctgc attttggtt | ttccccaccc cacacattct caaccatagt | 1140 |
| ccttctaaca | ataccaatag ctaggacccg | gctgctgtgc actgggactg gggattccac | 1200 |
| atgtttgcct | tgggagtctc aagctggact | gccagcccct gtcctccctt caccccatt | 1260 |
| gcgtatgagc | atttcagaac tccaaggagt | cacaggcatc tttatagttc acgttaacat | 1320 |
| atagacactt | tggaagcag ttccttctaa | aagggtagcc ctggacttaa taccagccgg | 1380 |
| atacctctgg | ccccccacccc attactgtac | ctctggagtc actactgtgg gtcgccactc | 1440 |
| ctctgctaca | cagcacggct tttcaaggc | tgtattgaga agggaagtta ggaagaaggg | 1500 |
| tgtgctgggc | taaccagccc acagagctca | cattcctgtc ccttgggtga aaaatacatg | 1560 |
| tccatcctga | tatctcctga attcagaaat | tagcctccac atgtgcaatg ctttaagag | 1620 |
| ccagaagcag | ggttctggga attttgcaag | ttacctgtgg ccaggtgtgg tctcggttac | 1680 |
| caaatacggt | tacctgcagc tttttagtcc | tttgtgctcc cacgggtcta cagagtccca | 1740 |
| tctgcccaaa | ggtcttgaag cttgacagga | tgttttcgat tactcagtct cccagggcac | 1800 |
| tactggtccg | taggattcga ttggtcgggg | taggagagtt aaacaacatt taaacagagt | 1860 |
| tctctcaaaa | atgtctaaag ggattgtagg | tagataacat ccaatcactg tttgcactta | 1920 |
| tctgaaatct | tccctcttgg ctgccccag | gtatttactg tggagaacat tgcataggaa | 1980 |
| tgtctggaaa | aagcttctac aacttgttac | agccttcaca tttgtagaag cttt | 2034 |

<210> SEQ ID NO 36
<211> LENGTH: 1234
<212> TYPE: DNA
<213> ORGANISM: Artificial Sequence
<220> FEATURE:
<223> OTHER INFORMATION: opt_COX10-ND6-3'UTR*

<400> SEQUENCE: 36

| | | | |
|---|---|---|---|
| atggccgcct | ctccacacac actgagtagc | agactgctga ccggctgtgt tgcggctct | 60 |
| gtgtggtatc | tggaacggcg gacaatgatg | tatgctttgt ttctgttgag tgtgggttta | 120 |
| gtaatggggt | ttgtggggtt ttcttctaag | ccttctccta tttatggggg tttagtattg | 180 |

```
attgttagcg gtgtggtcgg gtgtgttatt attctgaatt ttgggggagg ttatatgggt      240
ttaatggttt ttttaatta  tttaggggga atgatggttg tctttggata tactacagcg      300
atggctattg aggagtatcc tgaggcatgg gggtcagggg ttgaggtctt ggtgagtgtt      360
ttagtggggt tagcgatgga ggtaggattg gtgctgtggg tgaaagagta tgatggggtg      420
gtggttgtgg taaactttaa tagtgtagga agctggatga tttatgaagg agagggtca       480 gggttgattc gggaggatcc tattggtgcg ggggctttgt atgattatgg gcgttggtta      540
gtagtagtta ctggttggac attgtttgtt ggtgtatata ttgtaattga gattgctcgg      600
gggaattagg agcactggga cgcccaccgc cccttccct  ccgctgccag gcgagcatgt      660
tgtggtaatt ctggaacaca agaagagaaa ttgctgggtt tagaacaaga ttataaacga      720
attcggtgct cagtgatcac ttgacagttt ttttttttt  taaatattac ccaaaatgct      780
ccccaaataa gaaatgcatc agctcagtca gtgaatacaa aaaggaatt  attttttccct     840 ttgagggtct tttatacatc tctcctccaa ccccaccctc tattctgttt cttcctcctc      900 acatggggt  acacatacac agcttcctct tttggttcca tccttaccac cacaccacac      960
gcacactcca catgcccagc agagtggcac ttggtggcca gaaagtgtga gcctcatgat     1020
ctgctgtctg tagttctgtg agctcaggtc cctcaaaggc ctcggagcac ccccttcctt     1080
gtgactgagc cagggcctgc attttttggtt ttccccaccc cacacattct caaccatagt    1140
ccttctaaca ataccaatag ctaggacccg gctgctgtgc actgggactg gggattccac     1200
atgtttgcct tgggagtctc aagctggact gcca                                 1234
```

<210> SEQ ID NO 37
<211> LENGTH: 2034
<212> TYPE: DNA
<213> ORGANISM: Artificial Sequence
<220> FEATURE:
<223> OTHER INFORMATION: opt_COX10-opt_ND6-3'UTR

<400> SEQUENCE: 37

```
atggccgcct ctccacacac actgagtagc agactgctga ccggctgtgt tggcggctct       60
gtgtggtatc tggaacggcg gacaatgatg tacgccctgt tcctgctgag cgtgggcctg      120
gtgatgggct tcgtgggctt cagcagcaag cccagcccca tctacggcgg cctggtgctg      180
atcgtgagcg gcgtggtggg ctgcgtgatc atcctgaact tcgcggcgg  ctacatgggc      240 ctgatggtgt tcctgatcta cctgggcggc atgatggtgg tgttcggcta caccaccgcc      300
atggccatcg aggagtaccc cgaggcctgg ggcagcggcg tggaggtgct ggtgagcgtg      360
ctggtgggcc tggccatgga ggtgggcctg gtgctgtggg tgaaggagta cgacggcgtg      420
gtggtggtgg tgaacttcaa cagcgtgggc agctggatga tctacgaggg cgagggcagc      480
ggcctgatcc gcgaggaccc catcggcgcc ggcgccctgt acgactacgg ccgctggctg      540
gtggtggtga ccggctggac cctgttcgtg ggcgtgtaca tcgtgatcga tcgcccgc       600 ggcaactaag agcactggga cgcccaccgc cccttccct  ccgctgccag gcgagcatgt      660
tgtggtaatt ctggaacaca agaagagaaa ttgctgggtt tagaacaaga ttataaacga      720
attcggtgct cagtgatcac ttgacagttt ttttttttt  taaatattac ccaaaatgct      780
ccccaaataa gaaatgcatc agctcagtca gtgaatacaa aaaggaatt  attttttccct     840 ttgagggtct tttatacatc tctcctccaa ccccaccctc tattctgttt cttcctcctc      900 acatggggt  acacatacac agcttcctct tttggttcca tccttaccac cacaccacac      960
```

| | |
|---|---|
| gcacactcca catgcccagc agagtggcac ttggtggcca gaaagtgtga gcctcatgat | 1020 |
| ctgctgtctg tagttctgtg agctcaggtc cctcaaaggc ctcggagcac ccccttcctt | 1080 |
| gtgactgagc cagggcctgc attttggtt ttccccaccc cacacattct caaccatagt | 1140 |
| ccttctaaca ataccaatag ctaggacccg gctgctgtgc actgggactg gggattccac | 1200 |
| atgtttgcct tgggagtctc aagctggact gccagcccct gtcctccctt caccccatt | 1260 |
| gcgtatgagc atttcagaac tccaaggagt cacaggcatc tttatagttc acgttaacat | 1320 |
| atagacactg ttggaagcag ttccttctaa aagggtagcc ctggacttaa taccagccgg | 1380 |
| atacctctgg cccccacccc attactgtac ctctggagtc actactgtgg gtcgccactc | 1440 |
| ctctgctaca cagcacggct ttttcaaggc tgtattgaga agggaagtta ggaagaaggg | 1500 |
| tgtgctgggc taaccagccc acagagctca cattcctgtc ccttgggtga aaaatacatg | 1560 |
| tccatcctga tatctcctga attcagaaat tagcctccac atgtgcaatg ctttaagag | 1620 |
| ccagaagcag ggttctggga attttgcaag ttacctgtgg ccaggtgtgg tctcggttac | 1680 |
| caaatacggt tacctgcagc ttttagtcc tttgtgctcc cacgggtcta cagagtccca | 1740 |
| tctgcccaaa ggtcttgaag cttgacagga tgttttcgat tactcagtct cccagggcac | 1800 |
| tactggtccg taggattcga ttggtcgggg taggagagtt aaacaacatt taaacagagt | 1860 |
| tctctcaaaa atgtctaaag ggattgtagg tagataacat ccaatcactg tttgcactta | 1920 |
| tctgaaatct tccctcttgg ctgccccag gtatttactg tggagaacat tgcataggaa | 1980 |
| tgtctggaaa aagcttctac aacttgttac agccttcaca tttgtagaag cttt | 2034 |

<210> SEQ ID NO 38
<211> LENGTH: 1234
<212> TYPE: DNA
<213> ORGANISM: Artificial Sequence
<220> FEATURE:
<223> OTHER INFORMATION: opt_COX10-opt_ND6-3'UTR*

<400> SEQUENCE: 38

| | |
|---|---|
| atggccgcct ctccacacac actgagtagc agactgctga ccggctgtgt tggcggctct | 60 |
| gtgtggtatc tggaacggcg gacaatgatg tacgccctgt tcctgctgag cgtgggcctg | 120 |
| gtgatgggct tcgtgggctt cagcagcaag cccagcccca tctacggcgg cctggtgctg | 180 |
| atcgtgagcg gcgtggtggg ctgcgtgatc atcctgaact tcggcggcgg ctacatgggc | 240 |
| ctgatggtgt tcctgatcta cctgggcggc atgatggtgg tgttcggcta caccaccgcc | 300 |
| atggccatcg aggagtaccc cgaggcctgg ggcagcggcg tggaggtgct ggtgagcgtg | 360 |
| ctggtgggcc tggccatgga ggtgggcctg gtgctgtggg tgaaggagta cgacggcgtg | 420 |
| gtggtggtgg tgaacttcaa cagcgtgggc agctggatga tctacgaggg cgagggcagc | 480 |
| ggcctgatcc gcgaggaccc catcggcgcc ggcgccctgt acgactacgg ccgctggctg | 540 |
| gtggtggtga ccggctggac cctgttcgtg gcgtgtaca tcgtgatcga tcgccccgc | 600 |
| ggcaactaag agcactggga cgcccaccgc ccctttccct ccgctgccag gcgagcatgt | 660 |
| tgtggtaatt ctggaacaca agaagagaaa ttgctgggtt tagaacaaga ttataaacga | 720 |
| attcggtgct cagtgatcac ttgacagttt tttttttttt taaatattac ccaaaatgct | 780 |
| ccccaaataa gaaatgcatc agctcagtca gtgaatacaa aaaggaatt attttttccct | 840 |
| ttgagggtct tttatacatc tctcctccaa ccccaccctc tattctgttt cttcctcctc | 900 |
| acatgggggt acacatacac agcttcctct tttggttcca tccttaccac cacaccacac | 960 |
| gcacactcca catgcccagc agagtggcac ttggtggcca gaaagtgtga gcctcatgat | 1020 |

| | |
|---|---|
| ctgctgtctg tagttctgtg agctcaggtc cctcaaaggc ctcggagcac cccttcctt | 1080 |
| gtgactgagc cagggcctgc attttttggtt ttccccaccc cacacattct caaccatagt | 1140 |
| ccttctaaca ataccaatag ctaggacccg gctgctgtgc actgggactg gggattccac | 1200 |
| atgtttgcct tgggagtctc aagctggact gcca | 1234 |

<210> SEQ ID NO 39
<211> LENGTH: 2466
<212> TYPE: DNA
<213> ORGANISM: Artificial Sequence
<220> FEATURE:
<223> OTHER INFORMATION: opt_COX10-ND1-3'UTR

<400> SEQUENCE: 39

| | |
|---|---|
| atggccgcct ctccacacac actgagtagc agactgctga ccggctgtgt tggcggctct | 60 |
| gtgtggtatc tggaacggcg gacaatgccc atggccaacc tcctactcct cattgtaccc | 120 |
| attctaatcg caatggcatt cctaatgctt accgaacgaa aaattctagg ctatatgcaa | 180 |
| ctacgcaaag gccccaacgt tgtaggcccc tacgggctac tacaacccct cgctgacgcc | 240 |
| atgaaactct tcaccaaaga gcccctaaaa cccgccacat ctaccatcac cctctacatc | 300 |
| accgccccga ccttagctct caccatcgct cttctactat ggacccccct ccccatgccc | 360 |
| aaccccctgg tcaacctcaa cctaggcctc ctatttattc tagccacctc tagcctagcc | 420 |
| gtttactcaa tcctctggtc agggtgggca tcaaactcaa actacgccct gatcggcgca | 480 |
| ctgcgagcag tagcccaaac aatctctatat gaagtcaccc tagccatcat tctactatca | 540 |
| acattactaa tgagtggctc ctttaacctc tccacccttta tcacaacaca agaacacctc | 600 |
| tggttactcc tgccatcatg gcccttggcc atgatgtggt ttatctccac actagcagag | 660 |
| accaaccgaa cccccttcga ccttgccgaa ggggagtccg aactagtctc aggcttcaac | 720 |
| atcgaatacg ccgcaggccc cttcgcccta ttcttcatgg ccgaatacac aaacattatt | 780 |
| atgatgaaca ccctcaccac tacaatcttc ctaggaacaa catatgacgc actctcccct | 840 |
| gaactctaca acacatattt tgtcaccaag accctacttc taacctccct gttcttatgg | 900 |
| attcgaacag catacccccg attccgctac gaccaactca tgcacctcct atggaaaaac | 960 |
| ttcctaccac tcaccctagc attacttatg tggtatgtct ccatgcccat tacaatctcc | 1020 |
| agcattcccc ctcaaaccta agagcactgg gacgcccacc gcccctttcc ctccgctgcc | 1080 |
| aggcgagcat gttgtggtaa ttctggaaca caagaagaga aattgctggg tttagaacaa | 1140 |
| gattataaac gaattcggtg ctcagtgatc acttgacagt tttttttttt tttaaatatt | 1200 |
| acccaaaatg ctccccaaat aagaaatgca tcagctcagt cagtgaatac aaaaaaggaa | 1260 |
| ttatttttcc ctttgagggt cttttataca tctctcctcc aacccaccc tctattctgt | 1320 |
| ttcttcctcc tcacatgggg gtacacatac acagcttcct cttttggttc catccttacc | 1380 |
| accacaccac acgcacactc cacatgccca gcagagtggc acttgtggc cagaaagtgt | 1440 |
| gagcctcatg atctgctgtc tgtagttctg tgagctcagg tccctcaaag gcctcggagc | 1500 |
| acccccttcc ttgtgactga gccagggcct gcattttttgg ttttccccac cccacacatt | 1560 |
| ctcaaccata gtccttctaa caataccaat agctaggacc cggctgctgt gcactgggac | 1620 |
| tggggattcc acatgtttgc cttgggagtc tcaagctgga ctgccagccc ctgtcctccc | 1680 |
| ttcacccca ttgcgtatga gcatttcaga actccaagga gtcacaggca tctttatagt | 1740 |
| tcacgttaac atatagacac tgttggaagc agttccttct aaaagggtag ccctggactt | 1800 |

| | | | | |
|---|---|---|---|---|
| aataccagcc | ggatacctct | ggcccccacc | ccattactgt | acctctggag tcactactgt | 1860 |
| gggtcgccac | tcctctgcta | cacagcacgg | cttttcaag | gctgtattga gaagggaagt | 1920 |
| taggaagaag | ggtgtgctgg | gctaaccagc | ccacagagct | cacattcctg tcccttgggt | 1980 |
| gaaaaataca | tgtccatcct | gatatctcct | gaattcagaa | attagcctcc acatgtgcaa | 2040 |
| tggctttaag | agccagaagc | agggttctgg | gaattttgca | agttacctgt ggccaggtgt | 2100 |
| ggtctcggtt | accaaatacg | gttacctgca | gcttttagt | cctttgtgct cccacgggtc | 2160 |
| tacagagtcc | catctgccca | aggtcttga | agcttgacag | gatgttttcg attactcagt | 2220 |
| ctcccagggc | actactggtc | cgtaggattc | gattggtcgg | ggtaggagag ttaaacaaca | 2280 |
| tttaaacaga | gttctctcaa | aaatgtctaa | agggattgta | ggtagataac atccaatcac | 2340 |
| tgtttgcact | tatctgaaat | cttccctctt | ggctgccccc | aggtatttac tgtggagaac | 2400 |
| attgcatagg | aatgtctgga | aaaagcttct | acaacttgtt | acagccttca catttgtaga | 2460 |
| agcttt | | | | | 2466 |

<210> SEQ ID NO 40
<211> LENGTH: 1666
<212> TYPE: DNA
<213> ORGANISM: Artificial Sequence
<220> FEATURE:
<223> OTHER INFORMATION: opt_COX10-ND1-3'UTR*

<400> SEQUENCE: 40

| | | | | |
|---|---|---|---|---|
| atggccgcct | ctccacacac | actgagtagc | agactgctga | ccggctgtgt tggcggctct | 60 |
| gtgtggtatc | tggaacggcg | gacaatgccc | atggccaacc | tcctactcct cattgtaccc | 120 |
| attctaatcg | caatggcatt | cctaatgctt | accgaacgaa | aaattctagg ctatatgcaa | 180 |
| ctacgcaaag | gccccaacgt | tgtaggcccc | tacgggctac | tacaacccct cgctgacgcc | 240 |
| atgaaactct | tcaccaaaga | gcccctaaaa | cccgccacat | ctaccatcac cctctacatc | 300 |
| accgccccga | cctagctct | caccatcgct | cttctactat | ggacccccct ccccatgccc | 360 |
| aacccctgg | tcaacctcaa | cctaggcctc | ctatttattc | tagccacctc tagcctagcc | 420 |
| gtttactcaa | tcctctggtc | agggtgggca | tcaaactcaa | actacgccct gatcggcgca | 480 |
| ctgcgagcag | tagcccaaac | aatctcatat | gaagtcaccc | tagccatcat tctactatca | 540 |
| acattactaa | tgagtggctc | ctttaacctc | tccaccctta | tcacaacaca agaacacctc | 600 |
| tggttactcc | tgccatcatg | gcccttggcc | atgatgtggt | ttatctccac actagcagag | 660 |
| accaaccgaa | ccccttcga | ccttgccgaa | ggggagtccg | aactagtctc aggcttcaac | 720 |
| atcgaatacg | ccgcaggccc | cttcgcccta | ttcttcatgg | ccgaatacac aaacattatt | 780 |
| atgatgaaca | ccctcaccac | tacaatcttc | ctaggaacaa | catatgacgc actctcccct | 840 |
| gaactctaca | caacatattt | tgtcaccaag | accctacttc | taacctccct gttcttatgg | 900 |
| attcgaacag | catacccccg | attccgctac | gaccaactca | tgcacctcct atggaaaaac | 960 |
| ttcctaccac | tcaccctagc | attacttatg | tggtatgtct | ccatgcccat tacaatctcc | 1020 |
| agcattcccc | ctcaaaccta | agagcactgg | gacgcccacc | gcccctttcc ctccgctgcc | 1080 |
| aggcgagcat | gttgtggtaa | ttctggaaca | caagaagaga | aattgctggg tttagaacaa | 1140 |
| gattataaac | gaattcggtg | ctcagtgatc | acttgacagt | ttttttttt tttaaatatt | 1200 |
| acccaaaatg | ctccccaaat | aagaaatgca | tcagctcagt | cagtgaatac aaaaaaggaa | 1260 |
| ttattttcc | ctttgagggt | cttttataca | tctctcctcc | aacccaccc tctattctgt | 1320 |
| ttcttcctcc | tcacatgggg | gtacacatac | acagcttcct | cttttggttc catccttacc | 1380 |

```
accacaccac acgcacactc cacatgccca gcagagtggc acttggtggc cagaaagtgt    1440
gagcctcatg atctgctgtc tgtagttctg tgagctcagg tccctcaaag gcctcggagc    1500 accccccttcc ttgtgactga gccagggcct gcatttttgg ttttccccac cccacacatt   1560
ctcaaccata gtccttctaa caataccaat agctaggacc cggctgctgt gcactgggac    1620
tggggattcc acatgtttgc cttgggagtc tcaagctgga ctgcca                   1666
```

<210> SEQ ID NO 41
<211> LENGTH: 2466
<212> TYPE: DNA
<213> ORGANISM: Artificial Sequence
<220> FEATURE:
<223> OTHER INFORMATION: opt_COX10-opt_ND1-3'UTR

<400> SEQUENCE: 41

```
atggccgcct ctccacacac actgagtagc agactgctga ccggctgtgt tggcggctct     60
gtgtggtatc tggaacggcg gacaatgccc atggccaacc tgctgctgct gatcgtgccc    120
atcctgatcg ccatggcctt cctgatgctg accgagcgca agatcctggg ctacatgcag    180
ctgcgcaagg cccccaacgt ggtgggcccc tacggcctgc tgcagccctt cgccgacgcc    240
atgaagctgt tcaccaagga gcccctgaag cccgccacca gcaccatcac cctgtacatc    300
accgccccca ccctggccct gaccatcgcc ctgctgctgt ggaccccccct gcccatgccc    360 aaccccctgg tgaacctgaa cctgggcctg ctgttcatcc tggccaccag cagcctggcc    420
gtgtacagca tcctgtggag cggctgggcc agcaacagca actacgccct gatcggcgcc    480
ctgcgcgccg tgcccagac  catcagctac gaggtgaccc tggccatcat cctgctgagc    540
accctgctga tgagcggcag cttcaacctg agcaccctga tcaccaccca ggagcacctg    600
tggctgctgc tgcccagctg gccccctggcc atgatgtggt tcatcagcac cctggccgag    660
accaaccgca ccccccttcga cctggccgag ggcgagagcg agctggtgag cggcttcaac    720
atcgagtacg ccgccggccc cttcgccctg ttcttcatgg ccgagtacac caacatcatc    780
atgatgaaca ccctgaccac caccatcttc ctgggcacca cctacgacgc cctgagcccc    840
gagctgtaca ccacctactt cgtgaccaag accctgctgc tgaccagcct gttcctgtgg    900
atccgcaccg cctaccccccg cttccgctac gaccagctga tgcacctgct gtggaagaac    960 ttcctgccccc tgaccctggc cctgctgatg tggtacgtga gcatgcccat caccatcagc   1020
agcatccccc ccagaccta agagcactgg gacgcccacc gcccctttcc ctccgctgcc    1080
aggcgagcat gttgtggtaa ttctggaaca caagaagaga aattgctggg tttagaacaa    1140
gattataaac gaattcggtg ctcagtgatc acttgacagt ttttttttttt tttaaatatt   1200 acccaaaatg ctccccaaat aagaaatgca tcagctcagt cagtgaatac aaaaaaggaa   1260 ttattttttcc ctttgagggt cttttataca tctctcctcc aaccccaccc tctattctgt   1320
ttcttcctcc tcacatgggg gtacacatac acagcttcct cttttggttc catccttacc   1380
accacaccac acgcacactc cacatgccca gcagagtggc acttggtggc cagaaagtgt   1440
gagcctcatg atctgctgtc tgtagttctg tgagctcagg tccctcaaag gcctcggagc   1500 accccccttcc ttgtgactga gccagggcct gcatttttgg ttttccccac cccacacatt   1560
ctcaaccata gtccttctaa caataccaat agctaggacc cggctgctgt gcactgggac   1620
tggggattcc acatgtttgc cttgggagtc tcaagctgga ctgccagccc ctgtcctccc   1680 ttcacccccca ttgcgtatga gcatttcaga actccaagga gtcacaggca tctttatagt   1740
```

| | |
|---|---:|
| tcacgttaac atatagacac tgttggaagc agttccttct aaaagggtag ccctggactt | 1800 |
| aataccagcc ggatacctct ggcccccacc ccattactgt acctctggag tcactactgt | 1860 |
| gggtcgccac tcctctgcta cacagcacgg cttttcaag gctgtattga aagggaagt | 1920 |
| taggaagaag ggtgtgctgg gctaaccagc ccacagagct cacattcctg tcccttgggt | 1980 |
| gaaaaataca tgtccatcct gatatctcct gaattcagaa attagcctcc acatgtgcaa | 2040 |
| tggctttaag agccagaagc agggttctgg gaattttgca agttacctgt ggccaggtgt | 2100 |
| ggtctcggtt accaaatacg gttacctgca gcttttagt cctttgtgct cccacgggtc | 2160 |
| tacagagtcc catctgccca aaggtcttga agcttgacag gatgttttcg attactcagt | 2220 |
| ctcccagggc actactggtc cgtaggattc gattggtcgg ggtaggagag ttaaacaaca | 2280 |
| tttaaacaga gttctctcaa aaatgtctaa agggattgta ggtagataac atccaatcac | 2340 |
| tgtttgcact tatctgaaat cttccctctt ggctgccccc aggtatttac tgtggagaac | 2400 |
| attgcatagg aatgtctgga aaaagcttct acaacttgtt acagccttca catttgtaga | 2460 |
| agcttt | 2466 |

<210> SEQ ID NO 42
<211> LENGTH: 1666
<212> TYPE: DNA
<213> ORGANISM: Artificial Sequence
<220> FEATURE:
<223> OTHER INFORMATION: opt_COX10-opt_ND1-3'UTR*

<400> SEQUENCE: 42

| | |
|---|---:|
| atggccgcct ctccacacac actgagtagc agactgctga ccggctgtgt tggcggctct | 60 |
| gtgtggtatc tggaacggcg gacaatgccc atggccaacc tgctgctgct gatcgtgccc | 120 |
| atcctgatcg ccatggcctt cctgatgctg accgagcgca agatcctggg ctacatgcag | 180 |
| ctgcgcaagg gccccaacgt ggtgggcccc tacggcctgc tgcagcccct cgccgacgcc | 240 |
| atgaagctgt tcaccaagga gcccctgaag cccgccacca gcaccatcac cctgtacatc | 300 |
| accgccccca ccctggccct gaccatcgcc ctgctgctgt ggacccccct gcccatgccc | 360 |
| aaccccctgg tgaacctgaa cctgggcctg ctgttcatcc tggccaccag cagcctggcc | 420 |
| gtgtacagca tcctgtggag cggctgggcc agcaacagca actacgccct gatcggcgcc | 480 |
| ctgcgcgccg tggcccagac catcagctac gaggtgaccc tggccatcat cctgctgagc | 540 |
| accctgctga tgagcggcag cttcaacctg agcaccctga tcaccaccca ggagcacctg | 600 |
| tggctgctgc tgcccagctg gcccctggcc atgatgtggt catcagcac cctggccgag | 660 |
| accaaccgca cccccttcga cctggccgag ggcgagagcg agctggtgag cggcttcaac | 720 |
| atcgagtacg ccgccggccc cttcgccctg ttcttcatgg ccgagtacac caacatcatc | 780 |
| atgatgaaca ccctgaccac caccatcttc ctgggcacca cctacgacgc cctgagcccc | 840 |
| gagctgtaca ccacctactt cgtgaccaag accctgctgc tgaccagcct gttcctgtgg | 900 |
| atccgcaccg cctaccccccg cttccgctac gaccagctga tgcacctgct gtggaagaac | 960 |
| ttcctgcccc tgaccctggc cctgctgatg tggtacgtga gcatgcccat caccatcagc | 1020 |
| agcatccccc cccagaccta agagcactgg gacgccacc gccccttcc ctccgctgcc | 1080 |
| aggcgagcat gttgtggtaa ttctggaaca caagaagaga aattgctggg tttagaacaa | 1140 |
| gattataaac gaattcggtg ctcagtgatc acttgacagt tttttttttt tttaaatatt | 1200 |
| acccaaaatg ctccccaaat aagaaatgca tcagctcagt cagtgaatac aaaaaaggaa | 1260 |
| ttatttttcc ctttgagggt cttttataca tctctcctcc aaccccaccc tctattctgt | 1320 |

| | |
|---|---|
| ttcttcctcc tcacatgggg gtacacatac acagcttcct cttttggttc catccttacc | 1380 |
| accacaccac acgcacactc cacatgccca gcagagtggc acttggtggc cagaaagtgt | 1440 |
| gagcctcatg atctgctgtc tgtagttctg tgagctcagg tccctcaaag gcctcggagc | 1500 |
| accccctccc ttgtgactga gccagggcct gcatttttgg ttttccccac cccacacatt | 1560 |
| ctcaaccata gtccttctaa caataccaat agctaggacc cggctgctgt gcactgggac | 1620 |
| tggggattcc acatgtttgc cttgggagtc tcaagctgga ctgcca | 1666 |

<210> SEQ ID NO 43
<211> LENGTH: 2889
<212> TYPE: DNA
<213> ORGANISM: Artificial Sequence
<220> FEATURE:
<223> OTHER INFORMATION: opt_COX10*-ND4-3'UTR

<400> SEQUENCE: 43

| | |
|---|---|
| atggccgcca gccccacac cctgagcagc cgcctgctga ccggctgcgt gggcggcagc | 60 |
| gtgtggtacc tggagcgccg caccatgcta aaactaatcg tcccaacaat tatgttacta | 120 |
| ccactgacat ggcttttccaa aaaacacatg atttggatca acacaaccac ccacagccta | 180 |
| attattagca tcatccctct actatttttt aaccaaatca caacaaccct atttagctgt | 240 |
| tccccaacct tttcctccga ccccctaaca ccccccctcc taatgctaac tacctggctc | 300 |
| ctacccctca caatcatggc aagccaacgc acttatccca gtgaaccact atcacgaaaa | 360 |
| aaactctacc tctctatgct aatctcccta caaatctcct taattatgac attcacagcc | 420 |
| acagaactaa tcatgtttta tatcttcttc gaaaccacac ttatcccac cttggctatc | 480 |
| atcacccgat ggggcaacca gccagaacgc ctgaacgcag gcacatactt cctattctac | 540 |
| accctagtag gctcccttcc cctactcatc gcactaattt acactcacaa cccctaggc | 600 |
| tcactaaaca ttctactact cactctcact gcccaagaac tatcaaactc ctgggccaac | 660 |
| aacttaatgt ggctagctta cacaatggct tttatggtaa agatgcctct ttacggactc | 720 |
| cacttatggc tccctaaagc ccatgtcgaa gcccccatcg ctgggtcaat ggtacttgcc | 780 |
| gcagtactct taaaactagg cggctatggt atgatgcgcc tcacactcat tctcaacccc | 840 |
| ctgacaaaac acatggccta ccccttcctt gtactatccc tatggggcat gattatgaca | 900 |
| agctccatct gcctacgaca aacagaccta aaatcgctca ttgcatactc ttcaatcagc | 960 |
| cacatggccc tcgtagtaac agccattctc atccaaaccc cctggagctt caccggcgca | 1020 |
| gtcattctca tgatcgccca cgggcttaca tcctcattac tattctgcct agcaaactca | 1080 |
| aactacgaac gcactcacag tcgcatcatg atcctctctc aaggacttca aactctactc | 1140 |
| ccactaatgg cttttggtg gcttctagca agcctcgcta acctgccctt accccccact | 1200 |
| attaacctac tgggagaact ctctgtgcta gtaaccacgt tctcctggtc aaatatcact | 1260 |
| ctcctactta caggactcaa catgctagtc acagccctat actccctcta catgtttacc | 1320 |
| acaacacaat ggggctcact cacccaccac attaacaaca tgaaaccctc attcacacga | 1380 |
| gaaaacaccc tcatgttcat gcacctatcc cccattctcc tcctatccct caaccccgac | 1440 |
| atcattaccg ggttttcctc ttaagagcac tgggacgccc accgcccctt ccctccgct | 1500 |
| gccaggcgag catgttgtgg taattctgga acacaagaag agaaattgct gggtttagaa | 1560 |
| caagattata aacgaattcg gtgctcagtg atcacttgac agttttttt tttttaaat | 1620 |
| attacccaaa atgctcccca aataagaaat gcatcagctc agtcagtgaa tacaaaaaag | 1680 |

```
gaattatttt tcccttttgag ggtcttttat acatctctcc tccaaccccca ccctctattc   1740 tgtttcttcc tcctcacatg ggggtacaca tacacagctt cctcttttgg ttccatcctt   1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920 agcacccct tccttgtgac tgagccaggg cctgcatttt tggttttccc caccccacac   1980
attctcaacc atagtccttc taacaatacc aatagctagg accggctgc tgtgcactgg   2040 gactggggat tccacatgtt tgccttggga gtctcaagct ggactgccag ccctgtcct   2100 cccttcaccc ccattgcgta tgagcatttc agaactccaa ggagtcacag gcatctttat   2160
agttcacgtt aacatataga cactgttgga agcagttcct tctaaaaggg tagccctgga   2220
cttaatacca gccggatacc tctggcccc accccattac tgtacctctg gagtcactac   2280
tgtgggtcgc cactcctctg ctacacagca cggcttttc aaggctgtat tgagaaggga   2340
agttaggaag aagggtgtgc tgggctaacc agcccacaga gctcacattc ctgtcccttg   2400
ggtgaaaaat acatgtccat cctgatatct cctgaattca gaaattagcc tccacatgtg   2460
caatggcttt aagagccaga agcagggttc tgggaatttt gcaagttacc tgtggccagg   2520
tgtggtctcg gttaccaaat acggttacct gcagcttttt agtcctttgt gctcccacgg   2580
gtctacagag tcccatctgc ccaaaggtct tgaagcttga caggatgttt tcgattactc   2640
agtctcccag ggcactactg gtccgtagga ttcgattggt cggggtagga gagttaaaca   2700
acatttaaac agagttctct caaaaatgtc taaagggatt gtaggtagat aacatccaat   2760
cactgtttgc acttatctga aatcttccct cttggctgcc cccaggtatt tactgtggag   2820
aacattgcat aggaatgtct ggaaaaagct tctacaactt gttacagcct tcacatttgt   2880
agaagctttt                                                          2889
```

<210> SEQ ID NO 44
<211> LENGTH: 2089
<212> TYPE: DNA
<213> ORGANISM: Artificial Sequence
<220> FEATURE:
<223> OTHER INFORMATION: opt_COX10*-ND4-3'UTR*

<400> SEQUENCE: 44

```
atggccgcca gccccacac cctgagcagc cgcctgctga ccggctgcgt gggcggcagc    60
gtgtggtacc tggagcgccg caccatgcta aaactaatcg tcccaacaat tatgttacta   120
ccactgacat ggcttccaa aaaacacatg atttggatca cacaaccac ccacagccta   180 attattagca tcatccctct actatttttt aaccaaatca caacaacct atttagctgt   240 tccccaacct tttcctccga ccccctaaca acccccctcc taatgctaac tacctggctc   300 ctaccctca caatcatggc aagccaacgc cacttatcca gtgaaccact atcacgaaaa   360
aaactctacc tctctatgct aatctcccta caaatctcct taattatgac attcacagcc   420
acagaactaa tcatgttta tatcttcttc gaaaccacac ttatccccac cttggctatc   480
atcacccgat ggggcaacca gccagaacgc ctgaacgcag gcacatactt cctattctac   540
accctagtag gctcccttcc cctactcatc gcactaattt acactcacaa cccctaggc   600 tcactaaaca ttctactact cactctcact gcccaagaac tatcaaactc ctgggccaac   660
aacttaatgt ggctagctta cacaatggc tttatggtaa agatgcctct ttacggactc   720
cacttatggc tccctaaagc ccatgtcgaa gccccatcg ctgggtcaat ggtacttgcc   780
gcagtactct taaaactagg cggctatggt atgatgcgcc tcacactcat tctcaacccc   840
```

```
ctgacaaaac acatggccta ccccttcctt gtactatccc tatggggcat gattatgaca    900
agctccatct gcctacgaca aacagaccta aaatcgctca ttgcatactc ttcaatcagc    960
cacatggccc tcgtagtaac agccattctc atccaaaccc cctggagctt caccggcgca   1020
gtcattctca tgatcgccca cgggcttaca tcctcattac tattctgcct agcaaactca   1080
aactacgaac gcactcacag tcgcatcatg atcctctctc aaggacttca aactctactc   1140
ccactaatgg cttttggtg gcttctagca agcctcgcta acctcgcctt accccccact    1200
attaacctac tgggagaact ctctgtgcta gtaaccacgt tctcctggtc aaatatcact   1260
ctcctactta caggactcaa catgctagtc acagccctat actccctcta catgtttacc   1320
acaacacaat ggggctcact cacccaccac attaacaaca tgaaaccctc attcacacga   1380
gaaaacaccc tcatgttcat gcacctatcc cccattctcc tcctatccct caaccccgac   1440
atcattaccg ggttttcctc ttaagagcac tgggacgccc accgcccctt ccctccgct    1500 gccaggcgag catgttgtgg taattctgga acacaagaag agaaattgct gggtttagaa   1560
caagattata acgaattcg gtgctcagtg atcacttgac agtttttttt tttttaaat    1620 attacccaaa atgctcccca aataagaaat gcatcagctc agtcagtgaa tacaaaaaag   1680
gaattatttt tccctttgag ggtcttttat acatctctcc tccaacccca ccctctattc   1740
tgtttcttcc tcctcacatg ggggtacaca tacacagctt cctcttttgg ttccatcctt   1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920 agcacccct tccttgtgac tgagccaggg cctgcatttt tggttttccc caccccacac    1980
attctcaacc atagtccttc taacaatacc aatagctagg accggctgc tgtgcactgg    2040 gactggggat tccacatgtt tgccttggga gtctcaagct ggactgcca              2089
```

<210> SEQ ID NO 45
<211> LENGTH: 2889
<212> TYPE: DNA
<213> ORGANISM: Artificial Sequence
<220> FEATURE:
<223> OTHER INFORMATION: opt_COX10*-opt_ND4-3'UTR

<400> SEQUENCE: 45

```
atggccgcca gccccacac cctgagcagc cgcctgctga ccggctgcgt gggcggcagc      60
gtgtggtacc tggagcgccg caccatgctg aagctgatcg tgcccaccat catgctgctg    120
cctctgacct ggctgagcaa gaaacacatg atctggatca acaccaccac gcacagcctg    180
atcatcagca tcatccctct gctgttcttc aaccagatca acaacaacct gttcagctgc    240
agccccacct tcagcagcga ccctctgaca cacctctgc tgatgctgac cacctggctg    300
ctgcccctca caatcatggc ctctcagaga cacctgagca gcgagcccct gagccggaag   360
aaactgtacc tgagcatgct gatctccctg cagatctctc tgatcatgac cttcaccgcc    420
accgagctga tcatgttcta catctttttc gagacaacgc tgatccccac actggccatc   480
atcaccagat ggggcaacca gcctgagaga ctgaacgccg gcacctactt tctgttctac   540
accctcgtgg gcagcctgcc actgctgatt gccctgatct acacccacaa cacctgggc    600 tccctgaaca tcctgctgct gacactgaca gcccaagagc tgagcaacag ctgggccaac   660
aatctgatgt ggctggccta cacaatggcc ttcatggtca agatgccccct gtacggcctg   720 cacctgtggc tgcctaaagc tcatgtggaa gcccctatcg ccggctctat ggtgctggct   780
```

```
gcagtgctgc tgaaactcgg cggctacggc atgatgcggc tgaccctgat tctgaatccc    840
ctgaccaagc acatggccta tccatttctg gtgctgagcc tgtggggcat gattatgacc    900
agcagcatct gcctgcggca gaccgatctg aagtccctga tcgcctacag ctccatcagc    960
cacatggccc tggtggtcac cgccatcctg attcagaccc cttggagctt acaggcgcc    1020 gtgatcctga tgattgccca cggcctgaca agcagcctgc tgttttgtct ggccaacagc   1080
aactacgagc ggacccacag cagaatcatg atcctgtctc agggcctgca gaccctcctg   1140
cctcttatgg cttttggtg gctgctggcc tctctggcca atctggcact gcctcctacc    1200
atcaatctgc tgggcgagct gagcgtgctg gtcaccacat tcagctggtc caatatcacc   1260
ctgctgctca ccggcctgaa catgctggtt acagccctgt actccctgta catgttcacc   1320
accacacagt ggggaagcct gacacaccac atcaacaata tgaagcccag cttcacccgc   1380
gagaacaccc tgatgttcat gcatctgagc cccattctgc tgctgtccct gaatcctgat   1440
atcatcaccg gcttctccag ctgagagcac tgggacgccc accgccctt tccctccgct    1500 gccaggcgag catgttgtgg taattctgga acacaagaag agaaattgct gggtttagaa   1560
caagattata acgaattcg gtgctcagtg atcacttgac agtttttttt ttttttaaat    1620
attacccaaa atgctcccca aataagaaat gcatcagctc agtcagtgaa tacaaaaaag   1680
gaattatttt tcccttgag ggtcttttat acatctctcc tccaaccca ccctctattc     1740 tgtttcttcc tcctcacatg gggtacaca tacacagctt cctctttgg ttccatcctt     1800 accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920
agcaccccct tccttgtgac tgagccaggg cctgcatttt tggttttccc caccccacac   1980
attctcaacc atagtccttc taacaatacc aatagctagg acccggctgc tgtgcactgg   2040
gactggggat tccacatgtt tgccttggga gtctcaagct ggactgccag ccctgtcct    2100 cccttcaccc ccattgcgta tgagcatttc agaactccaa ggagtcacag gcatctttat   2160
agttcacgtt aacatataga cactgttgga agcagttcct tctaaagggg tagccctgga   2220
cttaatacca gccggatacc tctggccccc accccattac tgtacctctg gagtcactac   2280
tgtgggtcgc cactcctctg ctacacagca cggcttttc aaggctgtat tgagaaggga    2340
agttaggaag aagggtgtgc tgggctaacc agcccacaga gctcacattc ctgtcccttg   2400
ggtgaaaaat acatgtccat cctgatatct cctgaattca gaaattagcc tccacatgtg   2460
caatggcttt aagagccaga agcagggttc tgggaatttt gcaagttacc tgtggccagg   2520
tgtggtctcg gttaccaaat acggttacct gcagctttt agtcctttgt gctcccacgg    2580
gtctacagag tcccatctgc ccaaaggtct tgaagcttga caggatgttt tcgattactc   2640
agtctcccag ggcactactg gtccgtagga ttcgattggt cggggtagga gagttaaaca   2700
acatttaaac agagttctct caaaaatgtc taaagggatt gtaggtagat aacatccaat   2760
cactgtttgc acttatctga aatcttccct cttggctgcc cccaggtatt tactgtggag   2820
aacattgcat aggaatgtct ggaaaaagct tctacaactt gttacagcct tcacatttgt   2880
agaagcttt                                                           2889
```

<210> SEQ ID NO 46
<211> LENGTH: 2089
<212> TYPE: DNA
<213> ORGANISM: Artificial Sequence
<220> FEATURE:
<223> OTHER INFORMATION: opt_COX10*-opt_ND4-3'UTR*

<400> SEQUENCE: 46

```
atggccgcca gccccacac cctgagcagc cgcctgctga ccggctgcgt gggcggcagc      60
gtgtggtacc tggagcgccg caccatgctg aagctgatcg tgcccaccat catgctgctg    120
cctctgacct ggctgagcaa gaaacacatg atctggatca caccaccac gcacagcctg    180
atcatcagca tcatccctct gctgttcttc aaccagatca caacaacct gttcagctgc    240
agccccacct tcagcagcga ccctctgaca cacctctgc tgatgctgac cacctggctg    300
ctgcccctca caatcatggc ctctcagaga cacctgagca gcgagcccct gagccggaag    360
aaactgtacc tgagcatgct gatctccctg cagatctctc tgatcatgac cttcaccgcc    420
accgagctga tcatgttcta catcttttc gagacaacgc tgatccccac actggccatc    480
atcaccagat ggggcaacca gcctgagaga ctgaacgccg gcacctactt tctgttctac    540
accctcgtgg gcagcctgcc actgctgatt gccctgatct acacccacaa caccctgggc    600
tccctgaaca tcctgctgct gacactgaca gcccaagagc tgagcaacag ctgggccaac    660
aatctgatgt ggctggccta cacaatggcc ttcatggtca gatgcccct gtacggcctg    720
cacctgtggg tgcctaaagc tcatgtggaa gccctatcg ccggctctat ggtgctggct    780
gcagtgctgc tgaaactcgg cggctacggc atgatgcggc tgaccctgat tctgaatccc    840
ctgaccaagc acatggccta tccatttctg gtgctgagcc tgtggggcat gattatgacc    900
agcagcatct gcctgcggca gaccgatctg aagtccctga tcgcctacag ctccatcagc    960
cacatggccc tggtggtcac cgccatcctg attcagaccc cttggagctt acaggcgcc   1020
gtgatcctga tgattgccca cggcctgaca agcagcctgc tgttttgtct ggccaacagc   1080
aactacgagc ggacccacag cagaatcatg atcctgtctc agggcctgca gaccctcctg   1140
cctcttatgg cttttggtg gctgctggcc tctctggcca atctggcact gcctcctacc   1200
atcaatctgc tgggcgagct gagcgtgctg gtcaccacat tcagctggtc caatatcacc   1260
ctgctgctca ccggcctgaa catgctggtt acagccctgt actccctgta catgttcacc   1320
accacacagt ggggaagcct gacacaccac atcaacaata tgaagcccag cttcacccgc   1380
gagaacaccc tgatgttcat gcatctgagc cccattctgc tgctgtccct gaatcctgat   1440
atcatcaccg gcttctccag ctgagagcac tgggacgccc accgcccctt tccctccgct   1500
gccaggcgag catgttgtgg taattctgga acacaagaag agaaattgct gggtttagaa   1560
caagattata acgaattcg gtgctcagtg atcacttgac agttttttt ttttttaaat   1620
attacccaaa atgctcccca aataagaaat gcatcagctc agtcagtgaa tacaaaaaag   1680
gaattatttt tccctttgag ggtcttttat acatctctcc tccaaccca ccctctattc   1740
tgtttcttcc tcctcacatg ggggtacaca tacacagctt cctcttttgg ttccatcctt   1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920
agcaccccct tccttgtgac tgagccaggg cctgcatttt tggttttccc cacccacac   1980
attctcaacc atagtccttc taacaatacc aatagctagg acccggctgc tgtgcactgg   2040
gactggggat tccacatgtt tgccttggga gtctcaagct ggactgcca              2089
```

<210> SEQ ID NO 47
<211> LENGTH: 2889
<212> TYPE: DNA
<213> ORGANISM: Artificial Sequence
<220> FEATURE:

<223> OTHER INFORMATION: opt_COX10*-opt_ND4*-3'UTR

<400> SEQUENCE: 47

```
atggccgcca gcccccacac cctgagcagc cgcctgctga ccggctgcgt gggcggcagc        60
gtgtggtacc tggagcgccg caccatgctg aagctgatcg tgcccaccat catgctgctg       120
cccctgacct ggctgagcaa gaagcacatg atctggatca acaccaccac ccacagcctg       180
atcatcagca tcatccccct gctgttcttc aaccagatca caacaaccct gttcagctgc       240
agccccacct tcagcagcga ccccctgacc accccctgc tgatgctgac cacctggctg        300
ctgcccctga ccatcatggc cagcagcgc cacctgagca gcgagcccct gagccgcaag        360
aagctgtacc tgagcatgct gatcagcctg cagatcagcc tgatcatgac cttcaccgcc       420
accgagctga tcatgttcta catcttcttc gagaccaccc tgatcccac cctggccatc        480
atcacccgct ggggcaacca gcccgagcgc ctgaacgccg gcacctactt cctgttctac       540
accctggtgg gcagcctgcc cctgctgatc gccctgatct acacccacaa caccctgggc       600
agcctgaaca tcctgctgct gaccctgacc gcccaggagc tgagcaacag ctgggccaac       660
aacctgatgt ggctggccta ccatggcc ttcatggtga agatgcccct gtacggcctg         720
cacctgtggc tgcccaaggc ccacgtggag gcccccatcg ccggcagcat ggtgctggcc       780
gccgtgctgc tgaagctggg cggctacggc atgatgcgcc tgaccctgat cctgaacccc       840
ctgaccaagc acatggccta ccccttcctg gtgctgagcc tgtggggcat gatcatgacc       900
agcagcatct gcctgcgcca gaccgacctg aagagcctga tcgcctacag cagcatcagc       960
cacatggccc tggtggtgac cgccatcctg atccagaccc cctggagctt caccggcgcc      1020
gtgatcctga tgatcgccca cggcctgacc agcagcctgc tgttctgcct ggccaacagc      1080
aactacgagc gcacccacag ccgcatcatg atcctgagcc agggcctgca gacccttgctg     1140
cccctgatgg ccttctggtg gctgctggcc agcctggcca acctggccct gccccccacc      1200
atcaacctgc tgggcgagct gagcgtgctg gtgaccacct tcagctggag caacatcacc      1260
ctgctgctga ccggcctgaa catgctggtg accgccctgt acagcctgta catgttcacc      1320
accacccagt ggggcagcct gacccaccac atcaacaaca tgaagcccag cttcacccgc      1380
gagaacaccc tgatgttcat gcacctgagc cccatcctgc tgctgagcct gaaccccgac      1440
atcatcaccg gcttcagcag ctaagagcac tgggacgccc accgcccctt ccctccgct       1500
gccaggcgag catgttgtgg taattctgga acacaagaag agaaattgct gggtttagaa      1560
caagattata acgaattcg gtgctcagtg atcacttgac agttttttt ttttttaaat        1620
attacccaaa atgctcccca ataagaaat gcatcagctc agtcagtgaa tacaaaaaag      1680
gaattatttt tccctttgag ggtcttttat acatctctcc tccaacccca ccctctattc      1740
tgtttcttcc tcctcacatg ggggtacaca tacacagctt cctcttttgg ttccatcctt      1800
accaccacac cacacgcaca ctccacatgc ccagcagagt ggcacttggt ggccagaaag      1860
tgtgagcctc atgatctgct gtctgtagtt ctgtgagctc aggtccctca aaggcctcgg      1920
agcacccct tccttgtgac tgagccaggg cctgcatttt tggttttccc cacccccacac     1980
attctcaacc atagtccttc taacaatacc aatagctagg accggctgc tgtgcactgg       2040
gactggggat tccacatgtt tgccttggga gtctcaagct ggactgccag ccctgtcct       2100
cccttcaccc ccattgcgta tgagcatttc agaactccaa ggagtcacag gcatctttat      2160
agttcacgtt aacatataga cactgttgga agcagttcct tctaaaaggg tagccctgga      2220
cttaatacca gccggatacc tctggccccc accccattac tgtacctctg gagtcactac      2280
```

```
tgtgggtcgc cactcctctg ctacacagca cggcttttc aaggctgtat tgagaaggga    2340
agttaggaag aagggtgtgc tgggctaacc agcccacaga gctcacattc ctgtcccttg    2400
ggtgaaaaat acatgtccat cctgatatct cctgaattca gaaattagcc tccacatgtg    2460
caatggcttt aagagccaga agcagggttc tgggaatttt gcaagttacc tgtggccagg    2520
tgtggtctcg gttaccaaat acggttacct gcagcttttt agtcctttgt gctcccacgg    2580
gtctacagag tccatctgc ccaaaggtct tgaagcttga caggatgttt tcgattactc    2640
agtctcccag ggcactactg gtccgtagga ttcgattggt cggggtagga gagttaaaca    2700
acatttaaac agagttctct caaaaatgtc taaaggggatt gtaggtagat aacatccaat    2760
cactgtttgc acttatctga aatcttccct cttggctgcc cccaggtatt tactgtggag    2820
aacattgcat aggaatgtct ggaaaaagct tctacaactt gttacagcct tcacatttgt    2880
agaagcttt                                                          2889
```

<210> SEQ ID NO 48
<211> LENGTH: 2089
<212> TYPE: DNA
<213> ORGANISM: Artificial Sequence
<220> FEATURE:
<223> OTHER INFORMATION: opt_COX10*-opt_ND4*-3'UTR*

<400> SEQUENCE: 48

```
atggccgcca gccccacac cctgagcagc cgcctgctga ccggctgcgt gggcggcagc    60
gtgtggtacc tggagcgccg caccatgctg aagctgatcg tgcccaccat catgctgctg    120
cccctgacct ggctgagcaa gaagcacatg atctggatca caccaccac ccacagcctg    180 atcatcagca tcatccccct gctgttcttc aaccagatca caacaacct gttcagctgc    240 agccccacct tcagcagcga cccctgacc acccccctgc tgatgctgac cacctggctg    300
ctgcccctga ccatcatggc cagcagcgc cacctgagca gcgagcccct gagccgcaag    360
aagctgtacc tgagcatgct gatcagcctg cagatcagcc tgatcatgac cttcaccgcc    420
accgagctga tcatgttcta catcttcttc gagaccaccc tgatcccac cctggccatc    480 atcacccgct ggggcaacca gcccgagcgc ctgaacgccg gcacctactt cctgttctac    540
accctggtgg gcagcctgcc cctgctgatc gccctgatct acacccacaa cccctgggc    600 agcctgaaca tcctgctgct gaccctgacc gcccaggagc tgagcaacag ctgggccaac    660
aacctgatgt ggctggccta caccatggcc ttcatggtga agatgccccct gtacggcctg    720 cacctgtggc tgcccaaggc ccacgtggag ccccccatcg ccggcagcat ggtgctggcc    780
gccgtgctgc tgaagctggg cggctacggc atgatgcgcc tgaccctgat cctgaacccc    840
ctgaccaagc acatggccta cccccttcctg gtgctgagcc tgtggggcat gatcatgacc    900
agcagcatct gcctgcgcca gaccgacctg aagagcctga tcgcctacag cagcatcagc    960
cacatggccc tggtggtgac cgccatcctg atccagaccc cctggagctt caccggcgcc    1020
gtgatcctga tgatcgccca cggcctgacc agcagcctgc tgttctgcct ggccaacagc    1080
aactacgagc gcacccacag ccgcatcatg atcctgagcc agggcctgca gaccctgctg    1140
cccctgatgg ccttctggtg gctgctggcc agcctggcca acctggccct gccccccacc    1200
atcaacctgc tgggcgagct gagcgtgctg gtgaccacct tcagctggag caacatcacc    1260
ctgctgctga ccgccctgaa catgctggtg accgccctgt acagcctgta catgttcacc    1320
accacccagt ggggcagcct gacccaccac atcaacaaca tgaagcccag cttcacccgc    1380
```

| | |
|---|---|
| gagaacaccc tgatgttcat gcacctgagc cccatcctgc tgctgagcct gaaccccgac | 1440 |
| atcatcaccg gcttcagcag ctaagagcac tgggacgccc accgcccctt tccctccgct | 1500 |
| gccaggcgag catgttgtgg taattctgga acacaagaag agaaattgct gggtttagaa | 1560 |
| caagattata aacgaattcg gtgctcagtg atcacttgac agttttttt tttttttaaat | 1620 |
| attacccaaa atgctcccca ataagaaat gcatcagctc agtcagtgaa tacaaaaaag | 1680 |
| gaattatttt tcccttt gag ggtctttat acatctctcc tccaacccca ccctctattc | 1740 |
| tgtttcttcc tcctcacatg ggggtacaca tacacagctt cctcttttgg ttccatcctt | 1800 |
| accaccacac cacacgcaca ctccacatgc ccagcagagt ggcacttggt ggccagaaag | 1860 |
| tgtgagcctc atgatctgct gtctgtagtt ctgtgagctc aggtccctca aaggcctcgg | 1920 |
| agcacccct tccttgtgac tgagccaggg cctgcatttt tggttttccc cacccccacac | 1980 |
| attctcaacc atagtccttc taacaatacc aatagctagg acccggctgc tgtgcactgg | 2040 |
| gactggggat ccacatgtt tgccttggga gtctcaagct ggactgcca | 2089 |

<210> SEQ ID NO 49
<211> LENGTH: 2034
<212> TYPE: DNA
<213> ORGANISM: Artificial Sequence
<220> FEATURE:
<223> OTHER INFORMATION: opt_COX10*-ND6-3'UTR

<400> SEQUENCE: 49

| | |
|---|---|
| atggccgcca gcccccacac cctgagcagc cgcctgctga ccggctgcgt gggcggcagc | 60 |
| gtgtggtacc tggagcgccg caccatgatg tatgctttgt ttctgttgag tgtgggttta | 120 |
| gtaatggggt ttgtggggtt ttcttctaag ccttctccta tttatggggg tttagtattg | 180 |
| attgttagcg gtgtggtcgg gtgtgttatt attctgaatt ttggggagg ttatatgggt | 240 |
| ttaatggttt ttttaattta tttaggggga atgatggttg tctttggata tactacagcg | 300 |
| atggctattg aggagtatcc tgaggcatgg ggtcagggg ttgaggtctt ggtgagtgtt | 360 |
| ttagtggggt tagcgatgga ggtaggattg gtgctgtggg tgaaagagta tgatggggtg | 420 |
| gtggttgtgg taaactttaa tagtgtagga agctggatga tttatgaagg agaggggtca | 480 |
| gggttgattc gggaggatcc tattggtgcg ggggctttgt atgattatgg gcgttggtta | 540 |
| gtagtagtta ctggttggac attgtttgtt ggtgtatata ttgtaattga gattgctcgg | 600 |
| gggaattagg agcactggga cgcccaccgc ccctttccct ccgctgccag gcgagcatgt | 660 |
| tgtggtaatt ctggaacaca agaagagaaa ttgctgggtt tagaacaaga ttataaacga | 720 |
| attcggtgct cagtgatcac ttgacagttt ttttttttt taaatattac ccaaaatgct | 780 |
| ccccaaataa gaaatgcatc agctcagtca gtgaatacaa aaaggaatt attttttccct | 840 |
| ttgagggtct tttatacatc tcctccaa ccccaccctc tattctgttt cttcctcctc | 900 |
| acatggggt acatacac agcttcctct tttggttcca tccttaccac cacaccacac | 960 |
| gcacactcca catgcccagc agagtggcac ttggtggcca gaaagtgtga gcctcatgat | 1020 |
| ctgctgtctg tagttctgtg agctcaggtc cctcaaaggc tcggagcac ccccttcctt | 1080 |
| gtgactgagc cagggcctgc attttggtt tccccacccc cacacattct caaccatagt | 1140 |
| ccttctaaca ataccaatag ctaggacccg gctgctgtgc actgggactg gggattccac | 1200 |
| atgtttgcct tgggagtctc aagctggact gccagcccct gtcctccctt cacccccatt | 1260 |
| gcgtatgagc atttcagaac tccaaggagt cacaggcatc tttatagttc acgttaacat | 1320 |
| atagacactg ttggaagcag ttccttctaa aagggtagcc ctggacttaa taccagccgg | 1380 |

```
atacctctgg ccccaccccc attactgtac ctctggagtc actactgtgg gtcgccactc    1440
ctctgctaca cagcacggct ttttcaaggc tgtattgaga agggaagtta ggaagaaggg    1500
tgtgctgggc taaccagccc acagagctca cattcctgtc ccttgggtga aaaatacatg    1560
tccatcctga tatctcctga attcagaaat tagcctccac atgtgcaatg ctttaagag     1620 ccagaagcag ggttctggga attttgcaag ttacctgtgg ccaggtgtgg tctcggttac    1680
caaatacggt tacctgcagc tttttagtcc tttgtgctcc cacgggtcta cagagtccca    1740
tctgcccaaa ggtcttgaag cttgacagga tgttttcgat tactcagtct cccagggcac    1800
tactggtccg taggattcga ttggtcgggg taggagagtg aaacaacatt taaacagagt    1860
tctctcaaaa atgtctaaag ggattgtagg tagataacat ccaatcactg tttgcactta    1920
tctgaaatct tccctcttgg ctgcccccag gtatttactg tggagaacat tgcataggaa    1980
tgtctggaaa aagcttctac aacttgttac agccttcaca tttgtagaag cttt           2034
```

<210> SEQ ID NO 50
<211> LENGTH: 1234
<212> TYPE: DNA
<213> ORGANISM: Artificial Sequence
<220> FEATURE:
<223> OTHER INFORMATION: opt_COX10*-ND6-3'UTR*

<400> SEQUENCE: 50

```
atggccgcca gcccccacac cctgagcagc cgcctgctga ccggctgcgt gggcggcagc    60
gtgtggtacc tggagcgccg caccatgatg tatgctttgt ttctgttgag tgtgggttta    120
gtaatggggt tgtggggtt tccttctaag ccttctccta tttatggggg tttagtattg     180
attgttagcg gtgtggtcgg gtgtgttatt attctgaatt ttggggggagg ttatatgggt    240 ttaatggttt ttttaattta tttaggggga atgatggttg tctttggata tactacagcg    300
atggctattg aggagtatcc tgaggcatgg gggtcagggg ttgaggtctt ggtgagtgtt    360
ttagtggggt tagcgatgga ggtaggattg gtgctgtggg tgaaagagta tgatggggtg    420
gtggttgtgg taaactttaa tagtgtagga agctggatga tttatgaagg agaggggtca    480
gggttgattc ggaggatcc tattggtgcg ggggctttgt atgattatgg gcgttggtta    540
gtagtagtta ctggttggac attgtttgtt ggtgtatata ttgtaattga gattgctcgg    600
gggaattagg agcactggga cgcccaccgc cccttttccct ccgctgccag gcgagcatgt    660
tgtggtaatt ctggaacaca agaagagaaa ttgctgggtt tagaacaaga ttataaacga    720
attcggtgct cagtgatcac ttgacagttt tttttttttt taaatattac ccaaaatgct    780
ccccaaataa gaaatgcatc agctcagtca gtgaatacaa aaaggaatt attttttccct    840 ttgagggtct tttatacatc tctcctccaa ccccaccctc tattctgttt cttcctcctc    900
acatgggggt acacatacac agcttcctct tttggttcca tccttaccac cacaccacac    960
gcacactcca catgcccagc agagtggcac ttggtggcca gaaagtgtga gcctcatgat    1020
ctgctgtctg tagttctgtg agctcaggtc cctcaaaggc ctcggagcac cccttccttt   1080
gtgactgagc cagggcctgc atttttggtt ttccccaccc cacacattct caaccatagt    1140
ccttctaaca ataccaatag ctaggacccg gctgctgtgc actgggactg gggattccac    1200
atgtttgcct tgggagtctc aagctggact gcca                                1234
```

<210> SEQ ID NO 51
<211> LENGTH: 2034
<212> TYPE: DNA

<213> ORGANISM: Artificial Sequence
<220> FEATURE:
<223> OTHER INFORMATION: opt_COX10*-opt_ND6-3'UTR

<400> SEQUENCE: 51

```
atggccgcca gccccacac cctgagcagc cgcctgctga ccggctgcgt gggcggcagc      60
gtgtggtacc tggagcgccg caccatgatg tacgccctgt tcctgctgag cgtgggcctg     120
gtgatgggct tcgtgggctt cagcagcaag cccagcccca tctacggcgg cctggtgctg     180
atcgtgagcg gcgtggtggg ctgcgtgatc atcctgaact tcgcggcgg ctacatgggc      240
ctgatggtgt tcctgatcta cctgggcggc atgatggtgg tgttcggcta caccaccgcc     300
atggccatcg aggagtaccc cgaggcctgg ggcagcggcg tggaggtgct ggtgagcgtg     360
ctggtggggcc tggccatgga ggtgggcctg gtgctgtggg tgaaggagta cgacggcgtg     420
gtggtggtgg tgaacttcaa cagcgtgggc agctggatga tctacgaggg cgagggcagc     480
ggcctgatcc gcgaggaccc catcggcgcc ggcgccctgt acgactacgg ccgctggctg     540
gtggtggtga ccggctggac cctgttcgtg ggcgtgtaca tcgtgatcga gatcgcccgc     600
ggcaactaag agcactggga cgcccaccgc ccctttccct ccgctgccag gcgagcatgt     660
tgtggtaatt ctgaacaca agaagagaaa ttgctgggtt tagaacaaga ttataaacga     720
attcggtgct cagtgatcac ttgacagttt tttttttttt taaatattac ccaaaatgct     780
ccccaaataa gaaatgcatc agctcagtca gtgaatacaa aaaaggaatt atttttccct     840
ttgagggtct tttatacatc tctcctccaa ccccaccctc tattctgttt cttcctcctc     900
acatgggggg acacatacac agcttcctct tttggttcca tccttaccac cacaccacac     960
gcacactcca catgcccagc agagtggcac ttggtggcca gaaagtgtga gcctcatgat    1020
ctgctgtctg tagttctgtg agctcaggtc cctcaaaggc ctcggagcac ccccttcctt    1080
gtgactgagc cagggcctgc attttggtt ttccccaccc cacacattct caaccatagt     1140
ccttctaaca ataccaatag ctaggacccg gctgctgtgc actgggactg gggattccac    1200
atgtttgcct tgggagtctc aagctggact gccagcccct gtcctccctt cacccccatt    1260
gcgtatgagc atttcagaac tccaaggagt cacaggcatc tttatagttc acgttaacat    1320
atagacactg ttggaagcag ttccttctaa aagggtagcc ctggacttaa taccagccgg    1380
atacctctgg cccccacccc attactgtac ctctggagtc actactgtgg gtcgccactc    1440
ctctgctaca cagcacggct ttttcaaggc tgtattgaga agggaagtta ggaagaaggg    1500
tgtgctgggc taaccagccc acagagctca cattcctgtc ccttgggtga aaaatacatg    1560
tccatcctga tatctcctga attcagaaat tagcctccac atgtgcaatg ctttaagag     1620
ccagaagcag ggttctggga attttgcaag ttacctgtgg ccaggtgtgg tctcggttac    1680
caaatacggt tacctgcagc ttttagtcc tttgtgctcc cacgggtcta cagagtccca     1740
tctgcccaaa ggtcttgaag cttgacagga tgttttcgat tactcagtct cccagggcac    1800
tactggtccg taggattcga ttggtcgggg taggagagtt aaacaacatt taaacagagt    1860
tctctcaaaa atgtctaaag ggattgtagg tagataacat ccaatcactg tttgcactta    1920
tctgaaatct tccctcttgg ctgccccag gtatttactg tggagaacat tgcataggaa     1980
tgtctggaaa aagcttctac aacttgttac agccttcaca tttgtagaag cttt          2034
```

<210> SEQ ID NO 52
<211> LENGTH: 1234
<212> TYPE: DNA
<213> ORGANISM: Artificial Sequence
<220> FEATURE:
<223> OTHER INFORMATION: opt_COX10*-opt_ND6-3'UTR*

<400> SEQUENCE: 52

```
atggccgcca gccccacac cctgagcagc cgcctgctga ccggctgcgt gggcggcagc      60
gtgtggtacc tggagcgccg caccatgatg tacgccctgt tcctgctgag cgtgggcctg     120
gtgatgggct tcgtgggctt cagcagcaag cccagcccca tctacggcgg cctggtgctg     180
atcgtgagcg gcgtggtggg ctgcgtgatc atcctgaact cggcggcgg ctacatgggc      240
ctgatggtgt tcctgatcta cctgggcggc atgatggtgg tgttcggcta caccaccgcc     300
atggccatcg aggagtaccc cgaggcctgg ggcagcggcg tggaggtgct ggtgagcgtg     360
ctggtgggcc tggccatgga ggtgggcctg gtgctgtggg tgaaggagta cgacggcgtg     420
gtggtggtga tgaacttcaa cagcgtgggc agctggatga tctacgaggg cgagggcagc     480
ggcctgatcc gcgaggaccc catcggcgcc ggcgccctgt acgactacgg ccgctggctg     540
gtggtggtga ccggctggac cctgttcgtg ggcgtgtaca tcgtgatcga gatcgcccgc     600
ggcaactaag agcactggga cgcccaccgc cccttccct ccgctgccag gcgagcatgt      660
tgtggtaatt ctggaacaca agaagagaaa ttgctgggtt tagaacaaga ttataaacga     720
attcggtgct cagtgatcac ttgacagttt tttttttttt taaatattac ccaaaatgct     780
ccccaaataa gaaatgcatc agctcagtca gtgaatacaa aaaggaatt atttttccct      840
ttgagggtct tttatacatc tctcctccaa ccccaccctc tattctgttt cttcctcctc     900
acatgggggt acacatacac agcttcctct tttggttcca tccttaccac cacaccacac     960
gcacactcca catgcccagc agagtggcac ttggtggcca gaaagtgtga gcctcatgat    1020
ctgctgtctg tagttctgtg agctcaggtc cctcaaaggc ctcggagcac cccttcctt     1080
gtgactgagc cagggcctgc attttttggtt ttccccaccc cacacattct caaccatagt   1140
ccttctaaca ataccaatag ctaggacccg gctgctgtgc actgggactg gggattccac    1200
atgtttgcct tgggagtctc aagctggact gcca                                1234
```

<210> SEQ ID NO 53
<211> LENGTH: 2466
<212> TYPE: DNA
<213> ORGANISM: Artificial Sequence
<220> FEATURE:
<223> OTHER INFORMATION: opt_COX10*-ND1-3'UTR

<400> SEQUENCE: 53

```
atggccgcca gccccacac cctgagcagc cgcctgctga ccggctgcgt gggcggcagc      60
gtgtggtacc tggagcgccg caccatgccc atggccaacc tcctactcct cattgtaccc    120
attctaatcg caatggcatt cctaatgctt accgaacgaa aaattctagg ctatatgcaa    180
ctacgcaaag gccccaacgt tgtaggcccc tacgggctac tacaaccctt cgctgacgcc    240
atgaaactct tcaccaaaga gcccctaaaa ccgccacat ctaccatcac cctctacatc     300
accgccccga ccttagctct caccatcgct cttctactat ggacccccct ccccatgccc    360
aaccccctgg tcaacctcaa cctaggcctc ctatttattc tagccacctc tagcctagcc    420
gtttactcaa tcctctggtc agggtgggca tcaaactcaa actacgccct gatcggcgca    480
ctgcgagcag tagcccaaac aatctcatat gaagtcaccc tagccatcat tctactatca    540
acattactaa tgagtggctc ctttaacctc tccacccta tcacaacaca gaacaccctc     600
tggttactcc tgccatcatg gcccttggcc atgatgtggt ttatctccac actagcagag    660
```

```
accaaccgaa cccccttcga ccttgccgaa ggggagtccg aactagtctc aggcttcaac    720
atcgaatacg ccgcaggccc cttcgcccta ttcttcatgg ccgaatacac aaacattatt    780
atgatgaaca ccctcaccac tacaatcttc ctaggaacaa catatgacgc actctcccct    840
gaactctaca caacatattt tgtcaccaag accctacttc taacctccct gttcttatgg    900
attcgaacag catacccccg attccgctac gaccaactca tgcacctcct atggaaaaac    960
ttcctaccac tcaccctagc attacttatg tggtatgtct ccatgcccat tacaatctcc   1020
agcattcccc ctcaaaccta gagcactgg gacgcccacc gccccttttcc ctccgctgcc   1080 aggcgagcat gttgtggtaa ttctggaaca caagaagaga aattgctggg tttagaacaa   1140
gattataaac gaattcggtg ctcagtgatc acttgacagt ttttttttt  tttaaatatt   1200 acccaaaatg ctccccaaat aagaaatgca tcagctcagt cagtgaatac aaaaaaggaa   1260 ttattttttcc ctttgagggt cttttataca tctctcctcc aaccccaccc tctattctgt   1320
ttcttcctcc tcacatgggg gtacacatac acagcttcct cttttggttc catccttacc   1380
accacaccac acgcacactc cacatgccca gcagagtggc acttggtggc cagaaagtgt   1440
gagcctcatg atctgctgtc tgtagttctg tgagctcagg tccctcaaag gcctcggagc   1500 accccccttcc ttgtgactga gccagggcct gcattttttgg ttttccccac cccacacatt   1560
ctcaaccata gtccttctaa caataccaat agctaggacc cggctgctgt gcactgggac   1620
tggggattcc acatgtttgc cttggggagtc tcaagctgga ctgccagccc ctgtcctccc   1680
ttcaccccca ttgcgtatga gcatttcaga actccaagga gtcacaggca tctttatagt   1740
tcacgttaac atatagacac tgttggaagc agttccttct aaaagggtag ccctggactt   1800
aataccagcc ggatacctct ggcccccacc ccattactgt acctctggag tcactactgt   1860
gggtcgccac tcctctgcta cacagcacgg cttttttcaag gctgtattga aagggaagt    1920 taggaagaag ggtgtgctgg gctaaccagc ccacagagct cacattcctg tcccttgggt   1980
gaaaaataca tgtccatcct gatatctcct gaattcagaa attagcctcc acatgtgcaa   2040
tggctttaag agccagaagc agggttctgg gaattttgca agttacctgt ggccaggtgt   2100
ggtctcggtt accaaatacg gttacctgca gcttttttagt cctttgtgct cccacgggtc   2160
tacagagtcc catctgccca aaggtcttga agcttgacag gatgttttcg attactcagt   2220
ctcccagggc actactggtc cgtaggattc gattggtcgg ggtaggagag ttaaacaaca   2280
tttaaacaga gttctctcaa aaatgtctaa agggattgta ggtagataac atccaatcac   2340
tgtttgcact tatctgaaat cttccctctt ggctgccccc aggtatttac tgtggagaac   2400
attgcatagg aatgtctgga aaaagcttct acaacttgtt acagccttca catttgtaga   2460
agcttt                                                              2466
```

<210> SEQ ID NO 54
<211> LENGTH: 1666
<212> TYPE: DNA
<213> ORGANISM: Artificial Sequence
<220> FEATURE:
<223> OTHER INFORMATION: opt_COX10*-ND1-3'UTR*

<400> SEQUENCE: 54

```
atggccgcca gccccacac  cctgagcagc cgcctgctga ccggctgcgt gggcggcagc     60
gtgtggtacc tggagcgccg caccatgccc atggccaacc tcctactcct cattgtaccc    120
attctaatcg caatggcatt cctaatgctt accgaacgaa aaattctagg ctatatgcaa    180
ctacgcaaag gccccaacgt tgtaggcccc tacgggctac tacaacccct cgctgacgcc    240
```

```
atgaaactct tcaccaaaga gcccctaaaa cccgccacat ctaccatcac cctctacatc    300
accgccccga ccttagctct caccatcgct cttctactat ggaccccct ccccatgccc     360
aaccccctgg tcaacctcaa cctaggcctc ctatttattc tagccacctc tagcctagcc    420
gtttactcaa tcctctggtc agggtgggca tcaaactcaa actacgccct gatcggcgca    480
ctgcgagcag tagcccaaac aatctcatat gaagtcaccc tagccatcat tctactatca    540
acattactaa tgagtggctc ctttaacctc tccacccctta tcacaacaca gaacacctc    600
tggttactcc tgccatcatg gcccttggcc atgatgtggt ttatctccac actagcagag    660
accaaccgaa cccccttcga ccttgccgaa ggggagtccg aactagtctc aggcttcaac    720
atcgaatacg ccgcaggccc cttcgcccta ttcttcatgg ccgaatacac aaacattatt    780
atgatgaaca ccctcaccac tacaatcttc taggaacaa catatgacgc actctcccct     840
gaactctaca caacatattt tgtcaccaag accctacttc taacctccct gttcttatgg    900
attcgaacag cataccccg attccgctac gaccaactca tgcacctcct atggaaaaac     960
ttcctaccac tcaccctagc attacttatg tggtatgtct ccatgcccat tacaatctcc   1020
agcattcccc ctcaaaccta agagcactgg gacgcccacc gcccctttcc ctccgctgcc   1080
aggcgagcat gttgtggtaa ttctggaaca caagaagaga aattgctggg tttagaacaa   1140
gattataaac gaattcggtg ctcagtgatc acttgacagt ttttttttttt tttaaatatt   1200
acccaaaatg ctccccaaat aagaaatgca tcagctcagt cagtgaatac aaaaaaggaa   1260
ttatttttcc ctttgagggt cttttataca tctctcctcc aaccccaccc tctattctgt   1320
ttcttcctcc tcacatgggg gtacacatac acagcttcct cttttggttc catccttacc   1380
accacaccac acgcacactc cacatgccca gcagagtggc acttggtggc cagaaagtgt   1440
gagcctcatg atctgctgtc tgtagttctg tgagctcagg tccctcaaag gcctcggagc   1500
accccttcc ttgtgactga gccagggcct gcatttttgg ttttcccccac cccacacatt    1560
ctcaaccata gtccttctaa caataccaat agctaggacc cggctgctgt gcactgggac   1620
tggggattcc acatgtttgc cttgggagtc tcaagctgga ctgcca                  1666
```

<210> SEQ ID NO 55
<211> LENGTH: 2466
<212> TYPE: DNA
<213> ORGANISM: Artificial Sequence
<220> FEATURE:
<223> OTHER INFORMATION: opt_COX10*-opt_ND1-3'UTR

<400> SEQUENCE: 55

```
atggccgcca gccccacac cctgagcagc cgcctgctga ccggctgcgt gggcggcagc       60
gtgtggtacc tggagcgccg caccatgccc atggccaacc tgctgctgct gatcgtgccc     120
atcctgatcg ccatggcctt cctgatgctg accgagcgca agatcctggg ctacatgcag     180
ctgcgcaagg gccccaacgt ggtgggcccc tacggcctgc tgcagccctt cgccgacgcc     240
atgaagctgt tcaccaagga gcccctgaag cccgccacca gcaccatcac cctgtacatc     300
accgccccca ccctggccct gaccatcgcc ctgctgctgt ggaccccct gcccatgccc      360
aaccccctgg tgaacctgaa cctgggcctg ctgttcatcc tggccaccag cagcctggcc     420
gtgtacagca tcctgtggag cggctgggcc agcaacagca actacgccct gatcggcgcc    480
ctgcgcgccg tggcccagac catcagctac gaggtgaccc tggccatcat cctgctgagc    540
accctgctga tgagcggcag cttcaacctg agcacccctga tcaccaccca ggagcacctg    600
```

```
tggctgctgc tgcccagctg gcccctggcc atgatgtggt tcatcagcac cctggccgag      660
accaaccgca cccccttcga cctggccgag ggcgagagcg agctggtgag cggcttcaac      720
atcgagtacg ccgccggccc cttcgccctg ttcttcatgg ccgagtacac caacatcatc      780
atgatgaaca ccctgaccac caccatcttc ctgggcacca cctacgacgc cctgagcccc      840
gagctgtaca ccacctactt cgtgaccaag accctgctgc tgaccagcct gttcctgtgg      900
atccgcaccg cctaccccog cttccgctac gaccagctga tgcacctgct gtggaagaac      960
ttcctgcccc tgaccctggc cctgctgatg tggtacgtga gcatgcccat caccatcagc     1020
agcatccccc cccagaccta agagcactgg gacgcccacc gccccttttcc ctccgctgcc     1080 aggcgagcat gttgtggtaa ttctggaaca caagaagaga aattgctggg tttagaacaa     1140
gattataaac gaattcggtg ctcagtgatc acttgacagt ttttttttttt tttaaatatt     1200 acccaaaatg ctccccaaat aagaaatgca tcagctcagt cagtgaatac aaaaaaggaa     1260
ttatttttcc ctttgagggt cttttataca tctctcctcc aaccccaccc tctattctgt     1320
ttcttcctcc tcacatgggg gtacacatac acagcttcct cttttggttc catccttacc     1380
accacaccac acgcacactc cacatgccca gcagagtggc acttggtggc cagaaagtgt     1440
gagcctcatg atctgctgtc tgtagttctg tgagctcagg tccctcaaag gcctcggagc     1500
acccccttcc ttgtgactga gccagggcct gcattttttgg ttttcccccac cccacacatt     1560 ctcaaccata gtccttctaa caataccaat agctaggacc cggctgctgt gcactgggac     1620
tggggattcc acatgtttgc cttgggagtc tcaagctgga ctgccagccc ctgtcctccc     1680 ttcacccccca ttgcgtatga gcatttcaga actccaagga gtcacaggca tctttatagt     1740
tcacgttaac atatagacac tgttggaagc agttccttct aaaagggtag ccctggactt     1800
aataccagcc ggatacctct ggcccccacc ccattactgt acctctggag tcactactgt     1860
gggtcgccac tcctctgcta cacagcacgg ctttttcaag gctgtattga agggaagt      1920 taggaagaag ggtgtgctgg gctaaccagc ccacagagct cacattcctg tcccttgggt     1980
gaaaaataca tgtccatcct gatatctcct gaattcagaa attagcctcc acatgtgcaa     2040
tggctttaag agccagaagc agggttctgg gaattttgca agttacctgt ggccaggtgt     2100
ggtctcggtt accaaatacg gttacctgca gcttttttagt cctttgtgct cccacgggtc     2160
tacagagtcc catctgccca aaggtcttga agcttgacag gatgttttcg attactcagt     2220
ctcccagggc actactggtc cgtaggattc gattggtcgg ggtaggagag ttaaacaaca     2280
tttaaacaga gttctctcaa aaatgtctaa agggattgta ggtagataac atccaatcac     2340
tgtttgcact tatctgaaat cttccctctt ggctgccccc aggtatttac tgtggagaac     2400
attgcatagg aatgtctgga aaaagcttct acaacttgtt acagccttca catttgtaga     2460
agcttt                                                                 2466

<210> SEQ ID NO 56
<211> LENGTH: 1666
<212> TYPE: DNA
<213> ORGANISM: Artificial Sequence
<220> FEATURE:
<223> OTHER INFORMATION: opt_COX10*-opt_ND1-3'UTR*

<400> SEQUENCE: 56
atggccgcca gccccacac cctgagcagc cgcctgctga ccggctgcgt gggcggcagc       60
gtgtggtacc tggagcgccg caccatgccc atggccaacc tgctgctgct gatcgtgccc      120
atcctgatcg ccatggcctt cctgatgctg accgagcgca agatcctggg ctacatgcag      180
```

```
ctgcgcaagg gccccaacgt ggtgggcccc tacggcctgc tgcagcccct cgccgacgcc    240
atgaagctgt tcaccaagga gccctgaag cccgccacca gcaccatcac cctgtacatc    300
accgccccca ccctggccct gaccatcgcc ctgctgctgt ggaccccct gccatgccc    360 aaccccctgg tgaacctgaa cctgggcctg ctgttcatcc tggccaccag cagcctggcc    420
gtgtacagca tcctgtggag cggctgggcc agcaacagca actacgccct gatcggcgcc    480
ctgcgcgccg tggcccagac catcagctac gaggtgaccc tggccatcat cctgctgagc    540
accctgctga tgagcggcag cttcaacctg agcaccctga tcaccaccca ggagcacctg    600
tggctgctgc tgcccagctg gcccctggcc atgatgtggt tcatcagcac cctggccgag    660
accaaccgca ccccttcga cctggccgag ggcgagagcg agctggtgag cggcttcaac    720
atcgagtacg ccgccggccc cttcgccctg ttcttcatgg ccgagtacac caacatcatc    780
atgatgaaca ccctgaccac caccatcttc ctgggcacca cctacgacgc cctgagcccc    840
gagctgtaca ccacctactt cgtgaccaag accctgctgc tgaccagcct gttcctgtgg    900
atccgcaccg cctacccccg cttccgctac gaccagctga tgcacctgct gtggaagaac    960
ttcctgcccc tgaccctggc cctgctgatg tggtacgtga gcatgcccat caccatcagc    1020
agcatccccc cccagaccta agagcactgg gacgcccacc gccccttcc ctccgctgcc    1080 aggcgagcat gttgtggtaa ttctggaaca caagaagaga aattgctggg tttagaacaa    1140
gattataaac gaattcggtg ctcagtgatc acttgacagt ttttttttt tttaaatatt    1200 acccaaaatg ctccccaaat aagaaatgca tcagctcagt cagtgaatac aaaaaaggaa    1260
ttatttttcc ctttgagggt cttttataca tctctcctcc aaccccaccc tctattctgt    1320
ttcttcctcc tcacatgggg gtacacatac acagcttcct cttttggttc catccttacc    1380
accacaccac acgcacactc cacatgccca gcagagtggc acttggtggc cagaaagtgt    1440
gagcctcatg atctgctgtc tgtagttctg tgagctcagg tccctcaaag gcctcggagc    1500 accccttcc ttgtgactga gccagggcct gcattttgg ttttccccac cccacacatt    1560
ctcaaccata gtccttctaa caataccaat agctaggacc cggctgctgt gcactgggac    1620
tggggattcc acatgtttgc cttgggagtc tcaagctgga ctgcca               1666
```

<210> SEQ ID NO 57
<211> LENGTH: 2892
<212> TYPE: DNA
<213> ORGANISM: Artificial Sequence
<220> FEATURE:
<223> OTHER INFORMATION: COX8-ND4-3'UTR

<400> SEQUENCE: 57

```
atgtccgtcc tgacgcgcct gctgctgcgg ggcttgacac ggctcggctc ggcggctcca     60
gtgcggcgcg ccagaatcca ttcgttgatg ctaaaactaa tcgtcccaac aattatgtta    120
ctaccactga catggctttc caaaaaacac atgatttgga tcaacacaac cacccacagc    180
ctaattatta gcatcatccc tctactattt tttaaccaaa tcaacaacaa cctatttagc    240
tgttccccaa ccttttcctc cgaccccta acaaccccc tcctaatgct aactacctgg    300
ctcctacccc tcacaatcat ggcaagccaa cgccacttat ccagtgaacc actatcacga    360
aaaaaactct acctctctat gctaatctcc ctacaaatct ccttaattat gacattcaca    420
gccacagaac taatcatgtt ttatatcttc ttcgaaacca cacttatccc caccttggct    480
atcatcaccc gatggggcaa ccagccagaa cgcctgaacg caggcacata cttcctattc    540
```

```
tacaccctag taggctccct tcccctactc atcgcactaa tttacactca caacacccta    600
ggctcactaa acattctact actcactctc actgcccaag aactatcaaa ctcctgggcc    660
aacaacttaa tgtggctagc ttacacaatg gcttttatgg taaagatgcc tctttacgga    720
ctccacttat ggctccctaa agcccatgtc gaagccccca tcgctgggtc aatggtactt    780
gccgcagtac tcttaaaact aggcggctat ggtatgatgc gcctcacact cattctcaac    840
cccctgacaa acacatggc ctaccccttc cttgtactat ccctatgggg catgattatg    900
acaagctcca tctgcctacg acaaacagac ctaaaatcgc tcattgcata ctcttcaatc    960
agccacatgg ccctcgtagt aacagccatt ctcatccaaa cccctggag cttcaccggc    1020 gcagtcattc tcatgatcgc ccacgggctt acatcctcat tactattctg cctagcaaac    1080
tcaaactacg aacgcactca cagtcgcatc atgatcctct ctcaaggact tcaaactcta    1140
ctcccactaa tggctttttg gtggcttcta gcaagcctcg ctaacctcgc cttaccccc    1200 actattaacc tactgggaga actctctgtg ctagtaacca cgttctcctg gtcaaatatc    1260
actctcctac ttacaggact caacatgcta gtcacagccc tatactccct ctacatgttt    1320
accacaacac aatggggctc actcacccac cacattaaca acatgaaacc ctcattcaca    1380
cgagaaaaca ccctcatgtt catgcaccta tcccccattc cctcctatc cctcaacccc    1440 gacatcatta ccgggttttc ctcttaagag cactgggacg cccaccgccc ctttccctcc    1500
gctgccaggc gagcatgttg tggtaattct ggaacacaag aagagaaatt gctgggttta    1560
gaacaagatt ataaacgaat tcggtgctca gtgatcactt gacagttttt ttttttttta    1620
aatattaccc aaaatgctcc ccaaataaga aatgcatcag ctcagtcagt gaatacaaaa    1680
aaggaattat ttttcccttt gagggtcttt tatacatctc tcctccaacc ccaccctcta    1740
ttctgtttct tcctcctcac atgggggtac acatacacag cttcctcttt tggttccatc    1800
cttaccacca caccacacgc acactccaca tgcccagcag agtggcactt ggtggccaga    1860
aagtgtgagc ctcatgatct gctgtctgta gttctgtgag ctcaggtccc tcaaaggcct    1920
cggagcaccc ccttccttgt gactgagcca gggcctgcat ttttggtttt ccccacccca    1980
cacattctca accatagtcc ttctaacaat accaatagct aggacccggc tgctgtgcac    2040
tgggactggg gattccacat gttttgccttg ggagtctcaa gctggactgc cagcccctgt    2100
cctcccttca cccccattgc gtatgagcat ttcagaactc caaggagtca caggcatctt    2160
tatagttcac gttaacatat agacactgtt ggaagcagtt ccttctaaaa gggtagccct    2220
ggacttaata ccagccggat acctctggcc cccacccat tactgtacct ctggagtcac    2280
tactgtgggt cgccactcct ctgctacaca gcacggcttt ttcaaggctg tattgagaag    2340
ggaagttagg aagaagggtg tgctgggcta accagcccac agagctcaca ttcctgtccc    2400
ttgggtgaaa aatacatgtc catcctgata tctcctgaat tcagaaatta gcctccacat    2460
gtgcaatggc tttaagagcc agaagcaggg ttctgggaat tttgcaagtt acctgtggcc    2520
aggtgtggtc tcggttacca aatacggtta cctgcagctt tttagtcctt tgtgctccca    2580
cgggtctaca gagtcccatc tgcccaaagg tcttgaagct tgacaggatg ttttcgatta    2640
ctcagtctcc cagggcacta ctggtccgta ggattcgatt ggtcggggta ggagagttaa    2700
acaacattta aacagagttc tctcaaaaat gtctaaaggg attgtaggta gataacatcc    2760
aatcactgtt tgcacttatc tgaaatcttc cctcttggct gccccaggt atttactgtg    2820 gagaacattg cataggaatg tctggaaaaa gcttctacaa cttgttacag ccttcacatt    2880
tgtagaagct tt                                                       2892
```

<210> SEQ ID NO 58
<211> LENGTH: 2092
<212> TYPE: DNA
<213> ORGANISM: Artificial Sequence
<220> FEATURE:
<223> OTHER INFORMATION: COX8-ND4-3'UTR*

<400> SEQUENCE: 58

| | | | | | |
|---|---|---|---|---|---|
| atgtccgtcc | tgacgcgcct | gctgctgcgg | ggcttgacac | ggctcggctc | ggcggctcca | 60 |
| gtgcggcgcg | ccagaatcca | ttcgttgatg | ctaaaactaa | tcgtcccaac | aattatgtta | 120 |
| ctaccactga | catggctttc | caaaaaacac | atgatttgga | tcaacacaac | cacccacagc | 180 |
| ctaattatta | gcatcatccc | tctactattt | tttaaccaaa | tcaacaacaa | cctatttagc | 240 |
| tgttccccaa | cctttcctc | cgaccccta | caaccccc | tcctaatgct | aactacctgg | 300 |
| ctcctacccc | tcacaatcat | ggcaagccaa | cgccacttat | ccagtgaacc | actatcacga | 360 |
| aaaaaactct | acctctctat | gctaatctcc | ctacaaatct | ccttaattat | gacattcaca | 420 |
| gccacagaac | taatcatgtt | ttatatcttc | ttcgaaacca | cacttatccc | caccttggct | 480 |
| atcatcaccc | gatggggcaa | ccagccagaa | cgcctgaacg | caggcacata | cttcctattc | 540 |
| tacaccctag | taggctccct | tcccctactc | atcgcactaa | tttacactca | caacaccta | 600 |
| ggctcactaa | acattctact | actcactctc | actgcccaag | aactatcaaa | ctcctgggcc | 660 |
| aacaacttaa | tgtggctagc | ttacacaatg | gcttttatgg | taaagatgcc | tctttacgga | 720 |
| ctccacttat | ggctccctaa | agcccatgtc | gaagccccca | tcgctgggtc | aatggtactt | 780 |
| gccgcagtac | tcttaaaact | aggcggctat | ggtatgatgc | gcctcacact | cattctcaac | 840 |
| cccctgacaa | acacatggc | ctaccccttc | cttgtactat | ccctatgggg | catgattatg | 900 |
| acaagctcca | tctgcctacg | acaaacagac | ctaaaatcgc | tcattgcata | ctcttcaatc | 960 |
| agccacatgg | ccctcgtagt | aacagccatt | tcatccaaa | cccctggag | cttcaccggc | 1020 |
| gcagtcattc | tcatgatcgc | ccacgggctt | acatcctcat | tactattctg | cctagcaaac | 1080 |
| tcaaactacg | aacgcactca | cagtcgcatc | atgatcctct | ctcaaggact | tcaaactcta | 1140 |
| ctcccactaa | tggcttttg | gtggcttcta | gcaagcctcg | ctaacctcgc | cttacccccc | 1200 |
| actattaacc | tactgggaga | actctctgtg | ctagtaacca | cgttctcctg | gtcaaatatc | 1260 |
| actctcctac | ttacaggact | caacatgcta | gtcacagccc | tatactccct | ctacatgttt | 1320 |
| accacaacac | aatggggctc | actcacccac | cacattaaca | acatgaaacc | ctcattcaca | 1380 |
| cgagaaaaca | ccctcatgtt | catgcaccta | tccccattc | tcctcctatc | cctcaaccc | 1440 |
| gacatcatta | ccgggtttc | ctcttaagag | cactgggacg | cccaccgccc | ctttccctcc | 1500 |
| gctgccaggc | gagcatgttg | tggtaattct | ggaacacaag | aagagaaatt | gctgggttta | 1560 |
| gaacaagatt | ataaacgaat | tcggtgctca | gtgatcactt | gacagttttt | tttttttta | 1620 |
| aatattaccc | aaaatgctcc | ccaaataaga | aatgcatcag | ctcagtcagt | gaatacaaaa | 1680 |
| aaggaattat | ttttcccttt | gagggtcttt | tatacatctc | tcctccaacc | ccaccctcta | 1740 |
| ttctgtttct | tcctcctcac | atggggtac | acatacacag | cttcctcttt | tggttccatc | 1800 |
| cttaccacca | caccacacgc | acactccaca | tgcccagcag | agtggcactt | ggtggccaga | 1860 |
| aagtgtgagc | tcatgatct | gctgtctgta | gttctgtgag | ctcaggtccc | tcaaaggcct | 1920 |
| cggagcaccc | ccttccttgt | gactgagcca | gggcctgcat | ttttggtttt | ccccaccca | 1980 |
| cacattctca | accatagtcc | ttctaacaat | accaatagct | aggacccggc | tgctgtgcac | 2040 | tgggactggg gattccacat gtttgccttg ggagtctcaa gctggactgc ca        2092

<210> SEQ ID NO 59
<211> LENGTH: 2892
<212> TYPE: DNA
<213> ORGANISM: Artificial Sequence
<220> FEATURE:
<223> OTHER INFORMATION: COX8-opt_ND4-3'UTR

<400> SEQUENCE: 59

| | |
|---|---|
| atgtccgtcc tgacgcgcct gctgctgcgg ggcttgacac ggctcggctc ggcggctcca | 60 |
| gtgcggcgcg ccagaatcca ttcgttgatg ctgaagctga tcgtgcccac catcatgctg | 120 |
| ctgcctctga cctggctgag caagaaacac atgatctgga tcaacaccac cacgcacagc | 180 |
| ctgatcatca gcatcatccc tctgctgttc ttcaaccaga tcaacaacaa cctgttcagc | 240 |
| tgcagcccca ccttcagcag cgaccctctg acaacacctc tgctgatgct gaccacctgg | 300 |
| ctgctgcccc tcacaatcat ggcctctcag agacacctga gcagcgagcc cctgagccgg | 360 |
| aagaaactgt acctgagcat gctgatctcc ctgcagatct ctctgatcat gaccttcacc | 420 |
| gccaccgagc tgatcatgtt ctacatcttt ttcgagacaa cgctgatccc cacactggcc | 480 |
| atcatcacca gatgggggcaa ccagcctgag agactgaacg ccggcaccta ctttctgttc | 540 |
| tacaccctcg tgggcagcct gccactgctg attgccctga tctacaccca caacaccctg | 600 |
| ggctccctga acatcctgct gctgacactg acagcccaag agctgagcaa cagctgggcc | 660 |
| aacaatctga tgtggctggc ctacacaatg gccttcatgg tcaagatgcc cctgtacggc | 720 |
| ctgcacctgt ggctgcctaa agctcatgtg gaagccccta tcgccggctc tatggtgctg | 780 |
| gctgcagtgc tgctgaaaact cggcggctac ggcatgatgc ggctgaccct gattctgaat | 840 |
| cccctgacca gcacatggc ctatccattt ctggtgctga gcctgtgggg catgattatg | 900 |
| accagcagca tctgcctgcg gcagaccgat ctgaagtccc tgatcgccta cagctccatc | 960 |
| agccacatgg ccctggtggt caccgccatc ctgattcaga ccccttggag ctttacaggc | 1020 |
| gccgtgatcc tgatgattgc ccacggcctg acaagcagcc tgctgttttg tctggccaac | 1080 |
| agcaactacg agcggaccca cagcagaatc atgatcctgt ctcagggcct gcagaccctc | 1140 |
| ctgcctctta tggcttttttg gtggctgctg gcctctctgg ccaatctggc actgcctcct | 1200 |
| accatcaatc tgctgggcga gctgagcgtg ctggtcacca cattcagctg gtccaatatc | 1260 |
| accctgctgc tcaccggcct gaacatgctg gttacagccc tgtactccct gtacatgttc | 1320 |
| accaccacac agtggggaag cctgacacac cacatcaaca atatgaagcc cagcttcacc | 1380 |
| cgcgagaaca ccctgatgtt catgcatctg agccccattc tgctgctgtc cctgaatcct | 1440 |
| gatatcatca ccggcttctc cagctgagag cactgggacg cccaccgccc ctttccctcc | 1500 |
| gctgccaggc gagcatgttg tggtaattct ggaacacaag aagagaaatt gctgggttta | 1560 |
| gaacaagatt ataaacgaat tcggtgctca gtgatcactt gacagttttt ttttttttta | 1620 |
| aatattaccc aaaatgctcc ccaaataaga aatgcatcag ctcagtcagt gaatacaaaa | 1680 |
| aaggaattat tttcccttt gagggtcttt tatacatctc tcctccaacc ccaccctcta | 1740 |
| ttctgtttct tcctcctcac atgggggtac acatacacag cttcctcttt tggttccatc | 1800 |
| cttaccacca caccacacgc acactccaca tgcccagcag agtggcactt ggtggccaga | 1860 |
| aagtgtgagc ctcatgatct gctgtctgta gttctgtgag ctcaggtccc tcaaaggcct | 1920 |
| cggagcaccc ccttccttgt gactgagcca gggcctgcat ttttggtttt ccccacccca | 1980 |
| cacattctca accatagtcc ttctaacaat accaatagct aggacccggc tgctgtgcac | 2040 |

```
tgggactggg gattccacat gtttgccttg ggagtctcaa gctggactgc cagcccctgt    2100
cctcccttca cccccattgc gtatgagcat ttcagaactc caaggagtca caggcatctt    2160
tatagttcac gttaacatat agacactgtt ggaagcagtt ccttctaaaa gggtagccct    2220
ggacttaata ccagccggat acctctggcc cccaccccat tactgtacct ctggagtcac    2280
tactgtgggt cgccactcct ctgctacaca gcacggcttt ttcaaggctg tattgagaag    2340
ggaagttagg aagaagggtg tgctgggcta accagcccac agagctcaca ttcctgtccc    2400
ttgggtgaaa aatacatgtc catcctgata tctcctgaat tcagaaatta gcctccacat    2460
gtgcaatggc tttaagagcc agaagcaggg ttctgggaat tttgcaagtt acctgtggcc    2520
aggtgtggtc tcggttacca aatacggtta cctgcagctt tttagtcctt tgtgctccca    2580
cgggtctaca gagtcccatc tgcccaaagg tcttgaagct tgacaggatg ttttcgatta    2640
ctcagtctcc cagggcacta ctggtccgta ggattcgatt ggtcggggta ggagagttaa    2700
acaacattta aacagagttc tctcaaaaat gtctaaaggg attgtaggta gataacatcc    2760
aatcactgtt tgcacttatc tgaaatcttc cctcttggct gccccaggt atttactgtg     2820 gagaacattg cataggaatg tctggaaaaa gcttctacaa cttgttacag ccttcacatt    2880
tgtagaagct tt                                                        2892

<210> SEQ ID NO 60
<211> LENGTH: 2092
<212> TYPE: DNA
<213> ORGANISM: Artificial Sequence
<220> FEATURE:
<223> OTHER INFORMATION: COX8-opt_ND4-3'UTR*

<400> SEQUENCE: 60
atgtccgtcc tgacgcgcct gctgctgcgg ggcttgacac ggctcggctc ggcggctcca      60
gtgcggcgcg ccagaatcca ttcgttgatg ctgaagctga tcgtgcccac catcatgctg     120
ctgcctctga cctggctgag caagaaacac atgatctgga tcaacaccac cacgcacagc     180
ctgatcatca gcatcatccc tctgctgttc ttcaaccaga tcaacaacaa cctgttcagc     240
tgcagcccca ccttcagcag cgaccctctg acaaacacctc tgctgatgct gaccacctgg     300
ctgctgcccc tcacaatcat ggcctctcag agacacctga gcagcgagcc cctgagccgg     360
aagaaactgt acctgagcat gctgatctcc ctgcagatct ctctgatcat gaccttcacc     420
gccaccgagc tgatcatgtt ctacatcttt ttcgagacaa cgctgatccc cacactggcc     480
atcatcacca gatggggcaa ccagcctgag agactgaacg ccggcaccta ctttctgttc     540
tacaccctcg tgggcagcct gcccactgctg attgccctga tctacaccca caacaccctg     600
ggctccctga acatcctgct gctgacactg acagcccaag agctgagcaa cagctgggcc     660
aacaatctga tgtggctggc ctacacaatg gccttcatgg tcaagatgcc cctgtacggc     720
ctgcacctgt ggctgcctaa agctcatgtg gaagcccta tcgccggctc tatggtgctg     780
gctgcagtgc tgctgaaaact cggcggctac ggcatgatgc ggctgaccct gattctgaat    840 ccctgacca agcacatggc ctatccattt ctggtgctga gcctgtgggg catgattatg    900
accagcagca tctgcctgcg gcagaccgat ctgaagtccc tgatcgccta cagctccatc    960
agccacatgg gcctggtggt caccgccatc ctgattcaga ccccttggag ctttacaggc    1020
gccgtgatcc tgatgattgc ccacggcctg acaagcagcc tgctgttttg tctggccaac    1080
agcaactacg agcggaccca cagcagaatc atgatcctgt ctcagggcct gcagaccctc    1140
```

```
ctgcctctta tggcttttg gtggctgctg gcctctctgg ccaatctggc actgcctcct      1200
accatcaatc tgctgggcga gctgagcgtg ctggtcacca cattcagctg gtccaatatc      1260
accctgctgc tcaccggcct gaacatgctg gttacagccc tgtactccct gtacatgttc      1320
accaccacac agtggggaag cctgacacac acatcaaca atatgaagcc cagcttcacc      1380
cgcgagaaca ccctgatgtt catgcatctg agccccattc tgctgctgtc cctgaatcct      1440
gatatcatca ccggcttctc cagctgagag cactgggacg cccaccgccc ctttccctcc      1500
gctgccaggc gagcatgttg tggtaattct ggaacacaag aagagaaatt gctgggttta      1560
gaacaagatt ataaacgaat tcggtgctca gtgatcactt gacagttttt ttttttttta      1620
aatattaccc aaaatgctcc ccaaataaga aatgcatcag ctcagtcagt gaatacaaaa      1680
aaggaattat ttttcccttt gagggtcttt tatacatctc tcctccaacc ccaccctcta      1740
ttctgttct tcctcctcac atgggggtac acatacacag cttcctcttt tggttccatc      1800
cttaccacca caccacacgc acactccaca tgcccagcag agtggcactt ggtggccaga      1860
aagtgtgagc ctcatgatct gctgtctgta gttctgtgag ctcaggtccc tcaaaggcct      1920
cggagcaccc ccttccttgt gactgagcca gggcctgcat ttttggtttt ccccacccca      1980
cacattctca accatagtcc ttctaacaat accaatagct aggacccggc tgctgtgcac      2040
tgggactggg gattccacat gtttgccttg ggagtctcaa gctggactgc ca             2092
```

<210> SEQ ID NO 61
<211> LENGTH: 2892
<212> TYPE: DNA
<213> ORGANISM: Artificial Sequence
<220> FEATURE:
<223> OTHER INFORMATION: COX8-opt_ND4*-3'UTR

<400> SEQUENCE: 61

```
atgtccgtcc tgacgcgcct gctgctgcgg ggcttgacac ggctcggctc ggcggctcca       60
gtgcggcgcg ccagaatcca ttcgttgatg ctgaagctga tcgtgcccac catcatgctg      120
ctgcccctga cctggctgag caagaagcac atgatctgga tcaacaccac cacccacagc      180
ctgatcatca gcatcatccc cctgctgttc ttcaaccaga tcaacaacaa cctgttcagc      240
tgcagcccca ccttcagcag cgaccccctg accaccccc tgctgatgct gaccacctgg      300
ctgctgcccc tgaccatcat ggccagccag cgccacctga gcagcgagcc cctgagccgc      360
aagaagctgt acctgagcat gctgatcagc ctgcagatca gcctgatcat gaccttcacc      420
gccaccgagc tgatcatgtt ctacatcttc ttcgagacca ccctgatccc caccctggcc      480
atcatcaccc gctggggcaa ccagcccgag cgcctgaacg ccggcaccta cttcctgttc      540
tacaccctgg tgggcagcct gcccctgctg atcgccctga tctacacccca caacaccctg      600
ggcagcctga acatcctgct gctgacccctg accgcccagg agctgagcaa cagctgggcc      660
aacaacctga tgtggctggc ctacaccatg gccttcatgg tgaagatgcc cctgtacggc      720
ctgcacctgt ggctgcccaa ggcccacgtg gaggcccca tcgccggcag catggtgctg      780
gccgccgtgc tgctgaagct gggcggctac ggcatgatgc gcctgaccct gatcctgaac      840
cccctgacca agcacatggc ctaccccttc tggtgctga gctgtgggg catgatcatg      900
accagcagca tctgcctgcg ccagaccgac ctgaagagcc tgatcgccta cagcagcatc      960
agccacatgg ccctggtggt gaccgccatc ctgatccaga ccccctggag cttcaccggc     1020
gccgtgatcc tgatgatcgc ccacggcctg accagcagcc tgctgttctg cctggccaac     1080
agcaactacg agcgcaccca cagccgcatc atgatcctga gccagggcct gcagaccctg     1140
```

```
ctgcccctga tggccttctg gtggctgctg gccagcctgg ccaacctggc cctgccccc        1200 accatcaacc tgctgggcga gctgagcgtg ctggtgacca ccttcagctg gagcaacatc       1260
accctgctgc tgaccggcct gaacatgctg gtgaccgccc tgtacagcct gtacatgttc       1320
accaccaccc agtggggcag cctgacccac cacatcaaca acatgaagcc cagcttcacc       1380
cgcgagaaca ccctgatgtt catgcacctg agccccatcc tgctgctgag cctgaacccc       1440
gacatcatca ccggcttcag cagctaagag cactgggacg cccaccgccc ctttccctcc       1500
gctgccaggc gagcatgttg tggtaattct ggaacacaag aagagaaatt gctgggttta       1560
gaacaagatt ataaacgaat tcggtgctca gtgatcactt gacagttttt ttttttttta       1620
aatattaccc aaaatgctcc ccaaataaga aatgcatcag ctcagtcagt gaatacaaaa       1680
aaggaattat ttttccctttt gagggtcttt tatacatctc tcctccaacc ccaccctcta     1740
ttctgtttct tcctcctcac atgggggtac acatacacag cttcctcttt tggttccatc      1800
cttaccacca caccacacgc acactccaca tgcccagcag agtggcactt ggtggccaga      1860
aagtgtgagc ctcatgatct gctgtctgta gttctgtgag ctcaggtccc tcaaaggcct      1920
cggagcaccc ccttccttgt gactgagcca gggcctgcat ttttggtttt ccccacccca      1980
cacattctca accatagtcc ttctaacaat accaatagct aggacccggc tgctgtgcac      2040
tgggactggg gattccacat gtttgccttg ggagtctcaa gctggactgc cagcccctgt      2100
cctcccttca cccccattgc gtatgagcat tcagaactc caaggagtca caggcatctt       2160
tatagttcac gttaacatat agacactgtt ggaagcagtt ccttctaaaa gggtagccct      2220
ggacttaata ccagccggat acctctggcc cccacccat tactgtacct ctggagtcac       2280
tactgtgggt cgccactcct ctgctacaca gcacggcttt ttcaaggctg tattgagaag      2340
ggaagttagg aagaagggtg tgctgggcta accagcccac agagctcaca ttcctgtccc      2400
ttgggtgaaa aatacatgtc catcctgata tctcctgaat tcagaaatta gcctccacat      2460
gtgcaatggc tttaagagcc agaagcaggg ttctgggaat tttgcaagtt acctgtggcc      2520
aggtgtggtc tcggttacca aatacggtta cctgcagctt tttagtcctt tgtgctccca     2580
cgggtctaca gagtcccatc tgcccaaagg tcttgaagct tgacaggatg ttttcgatta      2640
ctcagtctcc cagggcacta ctggtccgta ggattcgatt ggtcggggta ggagagttaa      2700
acaacattta aacagagttc tctcaaaaat gtctaaaggg attgtaggta gataacatcc      2760
aatcactgtt tgcacttatc tgaaatcttc cctcttggct gccccaggt atttactgtg       2820 gagaacattg cataggaatg tctggaaaaa gcttctacaa cttgttacag ccttcacatt      2880
tgtagaagct tt                                                           2892
```

<210> SEQ ID NO 62
<211> LENGTH: 2092
<212> TYPE: DNA
<213> ORGANISM: Artificial Sequence
<220> FEATURE:
<223> OTHER INFORMATION: COX8-opt_ND4*-3'UTR*

<400> SEQUENCE: 62

```
atgtccgtcc tgacgcgcct gctgctgcgg ggcttgacac ggctcggctc ggcggctcca        60
gtgcggcgcg ccagaatcca ttcgttgatg ctgaagctga tcgtgcccac catcatgctg       120
ctgcccctga cctggctgag caagaagcac atgatctgga tcaacaccac cacccacagc       180
ctgatcatca gcatcatccc cctgctgttc ttcaaccaga tcaacaacaa cctgttcagc       240
```

```
tgcagcccca ccttcagcag cgaccccctg accaccccc tgctgatgct gaccacctgg    300
ctgctgcccc tgaccatcat ggccagccag cgccacctga gcagcgagcc cctgagccgc    360
aagaagctgt acctgagcat gctgatcagc ctgcagatca gcctgatcat gaccttcacc    420
gccaccgagc tgatcatgtt ctacatcttc ttcgagacca ccctgatccc caccctggcc    480
atcatcaccc gctggggcaa ccagcccgag cgcctgaacg ccggcaccta cttcctgttc    540
tacaccctgg tgggcagcct gcccctgcta tcgccctga tctacaccca caacaccctg    600
ggcagcctga acatcctgct gctgaccctg accgcccagg agctgagcaa cagctgggcc    660
aacaacctga tgtggctggc ctacaccatg gccttcatgg tgaagatgcc cctgtacggc    720
ctgcacctgt ggctgcccaa ggcccacgtg gaggccccca tcgccggcag catggtgctg    780
gccgccgtgc tgctgaagct gggcggctac ggcatgatgc gcctgaccct gatcctgaac    840 ccctgacca agcacatggc ctaccccttc ctggtgctga gctgtgggg catgatcatg    900 accagcagca tctgcctgcg ccagaccgac ctgaagagcc tgatcgccta cagcagcatc    960
agccacatgg ccctggtggt gaccgccatc ctgatccaga cccctggag cttcaccggc    1020 gccgtgatcc tgatgatcgc ccacggcctg accagcagcc tgctgttctg cctggccaac    1080
agcaactacg agcgcaccca cagccgcatc atgatcctga ccagggcct gcagaccctg    1140 ctgcccctga tggccttctg gtggctgctg gccagcctgg ccaacctggc cctgccccc    1200 accatcaacc tgctgggcga gctgagcgtg ctggtgacca ccttcagctg gagcaacatc    1260
accctgctgc tgaccggcct gaacatgctg gtgaccgccc tgtacagcct gtacatgttc    1320
accaccaccc agtggggcag cctgacccac cacatcaaca acatgaagcc cagcttcacc    1380
cgcgagaaca ccctgatgtt catgcacctg agccccatcc tgctgctgag cctgaaccc    1440 gacatcatca ccggcttcag cagctaagag cactgggacg cccaccgccc ctttccctcc    1500
gctgccaggc gagcatgttg tggtaattct ggaacacaag aagagaaatt gctgggttta    1560
gaacaagatt ataaacgaat tcggtgctca gtgatcactt gacagttttt ttttttttta    1620
aatattaccc aaaatgctcc ccaaataaga aatgcatcag ctcagtcagt gaatacaaaa    1680
aaggaattat ttttcccttt gagggtcttt tatacatctc tcctccaacc ccaccctcta    1740
ttctgtttct tcctcctcac atgggggtac acatacacag cttcctcttt tggttccatc    1800
cttaccacca caccacacgc acactccaca tgcccagcag agtggcactt ggtgccagca    1860
aagtgtgagc tcatgatcct gctgtctgta gttctgtgag ctcaggtccc tcaaaggcct    1920
cggagcaccc ccttccttgt gactgagcca gggcctgcat ttttggtttt ccccacccca    1980
cacattctca accatagtcc ttctaacaat accaatagct aggacccggc tgctgtgcac    2040
tgggactggg gattccacat gtttgccttg ggagtctcaa gctggactgc ca            2092
```

<210> SEQ ID NO 63
<211> LENGTH: 2037
<212> TYPE: DNA
<213> ORGANISM: Artificial Sequence
<220> FEATURE:
<223> OTHER INFORMATION: COX8-ND6-3'UTR

<400> SEQUENCE: 63

```
atgtccgtcc tgacgcgcct gctgctgcgg ggcttgacac ggctcggctc ggcggctcca     60
gtgcggcgcg ccagaatcca ttcgttgatg atgtatgctt tgtttctgtt gagtgtgggt    120
ttagtaatgg ggtttgtggg gttttcttct aagccttctc ctatttatgg gggtttagta    180
ttgattgtta gcggtgtggt cgggtgtgtt attattctga attttggggg aggttatatg    240
```

```
ggtttaatgg ttttttaat ttatttaggg ggaatgatgg ttgtctttgg atatactaca         300
gcgatggcta ttgaggagta tcctgaggca tgggggtcag ggggttgaggt cttggtgagt        360 gttttagtgg ggttagcgat ggaggtagga ttggtgctgt gggtgaaaga gtatgatggg        420
gtggtggttg tggtaaactt taatagtgta ggaagctgga tgatttatga aggagaggg         480 tcagggttga ttcgggagga tcctattggt gcggggcttt tgtatgatta tgggcgttgg       540
ttagtagtag ttactggttg gacattgttt gttggtgtat atattgtaat tgagattgct       600
cgggggaatt aggagcactg ggacgcccac cgccccttc cctccgctgc caggcgagca        660
tgttgtggta attctggaac acaagaagag aaattgctgg gttagaaca agattataaa        720 cgaattcggt gctcagtgat cacttgacag tttttttttt ttttaaatat acccaaaat       780 gctccccaaa taagaaatgc atcagctcag tcagtgaata caaaaaagga attattttc      840 cctttgaggg tcttttatac atctctcctc caaccccacc ctctattctg tttcttcctc      900
ctcacatggg ggtacacata cacagcttcc tcttttggtt ccatccttac caccacacca     960
cacgcacact ccacatgccc agcagagtgg cacttggtgg ccagaaagtg tgagcctcat    1020
gatctgctgt ctgtagttct gtgagctcag gtccctcaaa ggcctcggag cacccccttc    1080
cttgtgactg agccagggcc tgcattttg gtttcccca ccccacacat tctcaaccat      1140
agtccttcta acaataccaa tagctaggac ccggctgctg tgcactggga ctggggattc    1200
cacatgtttg ccttgggagt ctcaagctgg actgccagcc cctgtcctcc cttcaccccc    1260
attgcgtatg agcatttcag aactccaagg agtcacaggc atctttatag ttcacgttaa   1320
catatagaca ctgttggaag cagttccttc taaagggta gccctggact taataccagc     1380
cggatacctc tggcccccac cccattactg tacctctgga gtcactactg tgggtcgcca   1440
ctcctctgct acacagcacg gctttttcaa ggctgtattg agaagggaag ttaggaagaa   1500
gggtgtgctg ggctaaccag cccacagagc tcacattcct gtcccttggg tgaaaaatac   1560
atgtccatcc tgatatctcc tgaattcaga aattagcctc cacatgtgca atggctttaa   1620
gagccagaag cagggttctg ggaattttgc aagttacctg tggccaggtg tggtctcggt    1680
taccaaatac ggttacctgc agcttttag tcctttgtgc tcccacgggt ctacagagtc    1740
ccatctgccc aaaggtcttg aagcttgaca ggatgttttc gattactcag tctcccaggg  1800
cactactggt ccgtaggatt cgattggtcg gggtaggaga gttaaacaac atttaaacag  1860
agttctctca aaaatgtcta aagggattgt aggtagataa catccaatca ctgtttgcac  1920
ttatctgaaa tcttccctct tggctgcccc caggtattta ctgtggagaa cattgcatag  1980
gaatgtctgg aaaaagcttc tacaacttgt tacagccttc acatttgtag aagcttt       2037
```

<210> SEQ ID NO 64
<211> LENGTH: 1237
<212> TYPE: DNA
<213> ORGANISM: Artificial Sequence
<220> FEATURE:
<223> OTHER INFORMATION: COX8-ND6-3'UTR*

<400> SEQUENCE: 64

```
atgtccgtcc tgacgcgcct gctgctgcgg ggcttgacac ggctcggctc ggcggctcca         60
gtgcggcgcg ccagaatcca ttcgttgatg atgtatgctt tgtttctgtt gagtgtgggt        120
ttagtaatgg ggtttgtggg gttttcttct aagccttctc ctatttatgg gggtttagta       180
ttgattgtta gcggtgtggt cgggtgtgtt attattctga attttggggg aggttatatg      240
```

```
ggtttaatgg ttttttttaat ttatttaggg ggaatgatgg ttgtctttgg atatactaca    300
gcgatggcta ttgaggagta tcctgaggca tggggtcag gggttgaggt cttggtgagt      360
gttttagtgg ggttagcgat ggaggtagga ttggtgctgt gggtgaaaga gtatgatggg    420
gtggtggttg tggtaaactt taatagtgta ggaagctgga tgatttatga aggagagggg    480
tcagggttga ttcgggagga tcctattggt gcgggggctt tgtatgatta tgggcgttgg   540
ttagtagtag ttactggttg gacattgttt gttggtgtat atattgtaat tgagattgct    600
cgggggaatt aggagcactg ggacgcccac cgccccttcc cctccgctgc caggcgagca    660
tgttgtggta attctggaac acaagaagag aaattgctgg gtttagaaca agattataaa    720
cgaattcggt gctcagtgat cacttgacag tttttttttt ttttaaatat tacccaaaat   780
gctccccaaa taagaaatgc atcagctcag tcagtgaata caaaaaagga attatttttc    840
cctttgaggg tcttttatac atctctcctc caacccccacc ctctattctg tttcttcctc    900
ctcacatggg ggtacacata cacagcttcc tcttttggtt ccatccttac caccacacca   960
cacgcacact ccacatgccc agcagagtgg cacttggtgg ccagaaagtg tgagcctcat   1020
gatctgctgt ctgtagttct gtgagctcag gtccctcaaa ggcctcggag caccccttc    1080
cttgtgactg agccagggcc tgcatttttg gttttcccca ccccacacat tctcaaccat   1140
agtccttcta acaataccaa tagctaggac ccggctgctg tgcactggga ctggggattc   1200
cacatgtttg ccttgggagt ctcaagctgg actgcca                            1237
```

<210> SEQ ID NO 65  
<211> LENGTH: 2037  
<212> TYPE: DNA  
<213> ORGANISM: Artificial Sequence  
<220> FEATURE:  
<223> OTHER INFORMATION: COX8-opt_ND6-3'UTR

<400> SEQUENCE: 65

```
atgtccgtcc tgacgcgcct gctgctgcgg ggcttgacac ggctcggctc ggcggctcca     60
gtgcggcgcg ccagaatcca ttcgttgatg atgtacgccc tgttcctgct gagcgtgggc    120
ctggtgatgg gcttcgtggg cttcagcagc aagcccagcc ccatctacgg cggcctggtg    180
ctgatcgtga gcggcgtggt gggctgcgtg atcatcctga acttcggcgg cggctacatg    240
ggcctgatgg tgttcctgat ctacctgggc ggcatgatgg tggtgttcgg ctacaccacc    300
gccatggcca tcgaggagta ccccgaggcc tggggcagcg gcgtggaggt gctggtgagc    360
gtgctggtgg gcctggccat ggaggtgggc ctggtgctgt gggtgaagga gtacgacggc    420
gtggtggtgg tggtgaactt caacagcgtg ggcagctgga tgatctacga gggcgagggc    480
agcggcctga tccgcgagga ccccatcggc gccggcgccc tgtacgacta cggccgctgg    540
ctggtggtgg tgaccggctg gaccctgttc gtgggcgtgt acatcgtgat cgagatcgcc    600
cgcggcaact aagagcactg ggacgcccac cgccccttcc cctccgctgc caggcgagca    660
tgttgtggta attctggaac acaagaagag aaattgctgg gtttagaaca agattataaa    720
cgaattcggt gctcagtgat cacttgacag tttttttttt ttttaaatat tacccaaaat   780
gctccccaaa taagaaatgc atcagctcag tcagtgaata caaaaaagga attatttttc    840
cctttgaggg tcttttatac atctctcctc caacccccacc ctctattctg tttcttcctc    900
ctcacatggg ggtacacata cacagcttcc tcttttggtt ccatccttac caccacacca   960
cacgcacact ccacatgccc agcagagtgg cacttggtgg ccagaaagtg tgagcctcat  1020
gatctgctgt ctgtagttct gtgagctcag gtccctcaaa ggcctcggag caccccttc   1080
```

-continued

```
cttgtgactg agccagggcc tgcatttttg gttttcccca ccccacacat tctcaaccat   1140
agtccttcta acaataccaa tagctaggac ccggctgctg tgcactggga ctggggattc   1200
cacatgtttg ccttgggagt ctcaagctgg actgccagcc cctgtcctcc cttcaccccc   1260
attgcgtatg agcatttcag aactccaagg agtcacaggc atctttatag ttcacgttaa   1320
catatagaca ctgttggaag cagttccttc taaaagggta gccctggact taataccagc   1380 cggataccte tggcccccac cccattactg tacctctgga gtcactactg tgggtcgcca   1440
ctcctctgct acacagcacg gcttttcaa ggctgtattg agaagggaag ttaggaagaa   1500
gggtgtgctg ggctaaccag cccacagagc tcacattcct gtcccttggg tgaaaaatac   1560
atgtccatcc tgatatctcc tgaattcaga aattagcctc cacatgtgca atggctttaa   1620
gagccagaag cagggttctg ggaattttgc aagttacctg tggccaggtg tggtctcggt   1680
taccaaatac ggttacctgc agcttttag tcctttgtgc tcccacgggt ctacagagtc   1740
ccatctgccc aaaggtcttg aagcttgaca ggatgttttc gattactcag tctcccaggg   1800
cactactggt ccgtaggatt cgattggtcg gggtaggaga gttaaacaac atttaaacag   1860
agttctctca aaaatgtcta aagggattgt aggtagataa catccaatca ctgtttgcac   1920
ttatctgaaa tcttccctct tggctgcccc caggtattta ctgtggagaa cattgcatag   1980
gaatgtctgg aaaaagcttc tacaacttgt tacagccttc acatttgtag aagcttt    2037
```

<210> SEQ ID NO 66
<211> LENGTH: 1237
<212> TYPE: DNA
<213> ORGANISM: Artificial Sequence
<220> FEATURE:
<223> OTHER INFORMATION: COX8-opt_ND6-3'UTR*

<400> SEQUENCE: 66

```
atgtccgtcc tgacgcgcct gctgctgcgg ggcttgacac ggctcggctc ggcggctcca     60
gtgcggcgcg ccagaatcca ttcgttgatg atgtacgccc tgttcctgct gagcgtgggc    120
ctggtgatgg gcttcgtggg cttcagcagc aagcccagcc ccatctacgg cggcctggtg    180
ctgatcgtga gcggcgtggt gggctgcgtg atcatcctga acttcggcgg cggctacatg    240
ggcctgatgg tgttcctgat ctacctgggc ggcatgatgg tggtgttcgg ctacaccacc    300
gccatggcca tcgaggagta cccccgaggcc tggggcagcg cgtgggaggt gctggtgagc    360
gtgctggtgg gcctggccat ggaggtgggc ctggtgctgt gggtgaagga gtacgacggc    420
gtggtggtgg tggtgaactt caacagcgtg ggcagctgga tgatctacga gggcgagggc    480
agcggcctga tccgcgagga cccatcggc gccggcgccc tgtacgacta cggccgctgg    540
ctggtggtgg tgaccggctg gaccctgttc gtgggcgtgt acatcgtgat cgagatcgcc    600
cgcggcaact aagagcactg ggacgcccac cgccccttc cctccgctgc caggcgagca    660
tgttgtggta attctggaac acaagaagag aaattgctgg gttagaacaa agattataaa    720
cgaattcggt gctcagtgat cacttgacag ttttttttt ttttaaatat tacccaaaat    780
gctccccaaa taagaaatgc atcagctcag tcagtgaata caaaaaagga attattttc    840 cctttgaggg tcttttatac atctctcctc caaccccacc ctctattctg tttcttcctc    900
ctcacatggg ggtacacata cacagcttcc tcttttggtt ccatccttac caccacacca    960
cacgcacact ccacatgccc agcagagtgg cacttggtgg ccagaaagtg tgagcctcat   1020
gatctgctgt ctgtagttct gtgagctcag gtccctcaaa ggcctcggag cacccccttc   1080
```

| | |
|---|---|
| cttgtgactg agccagggcc tgcatttttg gttttcccca ccccacacat tctcaaccat | 1140 |
| agtccttcta acaataccaa tagctaggac ccggctgctg tgcactggga ctggggattc | 1200 |
| cacatgtttg ccttgggagt ctcaagctgg actgcca | 1237 |

<210> SEQ ID NO 67
<211> LENGTH: 2469
<212> TYPE: DNA
<213> ORGANISM: Artificial Sequence
<220> FEATURE:
<223> OTHER INFORMATION: COX8-ND1-3'UTR

<400> SEQUENCE: 67

| | |
|---|---|
| atgtccgtcc tgacgcgcct gctgctgcgg ggcttgacac ggctcggctc ggcggctcca | 60 |
| gtgcggcgcg ccagaatcca ttcgttgatg cccatggcca acctcctact cctcattgta | 120 |
| cccattctaa tcgcaatggc attcctaatg cttaccgaac gaaaaattct aggctatatg | 180 |
| caactacgca aaggccccaa cgttgtaggc ccctacgggc tactacaacc cttcgctgac | 240 |
| gccatgaaac tcttcaccaa agagccccta aaacccgcca catctaccat caccctctac | 300 |
| atcaccgccc cgaccttagc tctcaccatc gctcttctac tatggacccc cctccccatg | 360 |
| cccaaccccc tggtcaacct caacctaggc ctcctattta ttctagccac ctctagccta | 420 |
| gccgtttact caatcctctg gtcagggtgg gcatcaaact caaactacgc cctgatcggc | 480 |
| gcactgcgag cagtagccca acaatctca tatgaagtca ccctagccat cattctacta | 540 |
| tcaacattac taatgagtgg ctcctttaac ctctccaccc ttatcacaac acaagaacac | 600 |
| ctctggttac tcctgccatc atggcccttg gccatgatgt ggtttatctc cacactagca | 660 |
| gagaccaacc gaacccccctt cgaccttgcc gaaggggagt ccgaactagt ctcaggcttc | 720 |
| aacatcgaat acgccgcagg ccccttcgcc ctattcttca tggccgaata cacaaacatt | 780 |
| attatgatga acacccctcac cactacaatc ttcctaggaa caacatatga cgcactctcc | 840 |
| cctgaactct acacaacata ttttgtcacc aagaccctac ttctaacctc cctgttctta | 900 |
| tggattcgaa cagcataccc ccgattccgc tacgaccaac tcatgcacct cctatggaaa | 960 |
| aacttcctac cactcacccct agcattactt atgtggtatg tctccatgcc cattacaatc | 1020 |
| tccagcattc cccctcaaac ctaagagcac tgggacgccc accgcccctt ccctccgct | 1080 |
| gccaggcgag catgttgtgg taattctgga acacaagaag agaaattgct gggtttagaa | 1140 |
| caagattata acgaattcg gtgctcagtg atcacttgac agttttttttt tttttaaat | 1200 |
| attacccaaa atgctcccca aataagaaat gcatcagctc agtcagtgaa tacaaaaaag | 1260 |
| gaattatttt tcccttttgag ggtctttttat acatctctcc tccaacccca ccctctattc | 1320 |
| tgtttcttcc tcctcacatg ggggtacaca tacacagctt cctcttttgg ttccatcctt | 1380 |
| accaccacac cacacgcaca ctccacatgc ccagcagagt ggcacttggt ggccagaaag | 1440 |
| tgtgagcctc atgatctgct gtctgtagtt ctgtgagctc aggtccctca aaggcctcgg | 1500 |
| agcacccccct tccttgtgac tgagccaggg cctgcatttt tggttttccc caccccacac | 1560 |
| attctcaacc atagtccttc taacaatacc aatagctagg accggctgc tgtgcactgg | 1620 |
| gactggggat tccacatgtt tgccttggga gtctcaagct ggactgccag ccctgtcct | 1680 |
| cccttcaccc ccattgcgta tgagcatttc agaactccaa ggagtcacag gcatctttat | 1740 |
| agttcacgtt aacatataga cactgttgga agcagttcct tctaaagggg tagccctgga | 1800 |
| cttaatacca gccggatacc tctggccccc accccattac tgtacctctg gagtcactac | 1860 |
| tgtgggtcgc cactcctctg ctacacagca cggcttttc aaggctgtat tgagaaggga | 1920 |

```
agttaggaag aagggtgtgc tgggctaacc agcccacaga gctcacattc ctgtcccttg    1980
ggtgaaaaat acatgtccat cctgatatct cctgaattca gaaattagcc tccacatgtg    2040
caatggcttt aagagccaga agcagggttc tgggaatttt gcaagttacc tgtggccagg    2100
tgtggtctcg gttaccaaat acggttacct gcagcttttt agtcctttgt gctcccacgg    2160
gtctacagag tcccatctgc ccaaaggtct tgaagcttga caggatgttt tcgattactc    2220
agtctcccag ggcactactg gtccgtagga ttcgattggt cggggtagga gagttaaaca    2280
acatttaaac agagttctct caaaaatgtc taagggatt gtaggtagat aacatccaat     2340
cactgtttgc acttatctga aatcttccct cttggctgcc cccaggtatt tactgtggag    2400
aacattgcat aggaatgtct ggaaaaagct tctacaactt gttacagcct tcacatttgt    2460
agaagcttt                                                             2469

<210> SEQ ID NO 68
<211> LENGTH: 1669
<212> TYPE: DNA
<213> ORGANISM: Artificial Sequence
<220> FEATURE:
<223> OTHER INFORMATION: COX8-ND1-3'UTR*

<400> SEQUENCE: 68
atgtccgtcc tgacgcgcct gctgctgcgg ggcttgacac ggctcggctc ggcggctcca      60
gtgcggcgcg ccagaatcca ttcgttgatg cccatggcca acctcctact cctcattgta     120
cccattctaa tcgcaatggc attcctaatg cttaccgaac gaaaaattct aggctatatg     180
caactacgca aaggccccaa cgttgtaggc ccctacgggc tactacaacc cttcgctgac     240
gccatgaaac tcttcaccaa agagccccta aaacccgcca catctaccat caccctctac     300
atcaccgccc cgaccttagc tctcaccatc gctcttctac tatggacccc cctccccatg     360
cccaaccccc tggtcaacct caacctaggc ctcctattta ttctagccac ctctagccta     420
gccgtttact caatcctctg gtcagggtgg gcatcaaact caaactacgc cctgatcggc     480
gcactgcgag cagtagccca aacaatctca tatgaagtca ccctagccat cattctacta     540
tcaacattac taatgagtgg ctcctttaac ctctccaccc ttatcacaac acaagaacac     600
ctctggttac tcctgccatc atggcccttg gccatgatgt ggtttatctc cacactagca     660
gagaccaacc gaaccccctt cgaccttgcc gaagggagt ccgaactagt ctcaggcttc      720
aacatcgaat acgccgcagg ccccttcgcc ctattcttca tggccgaata cacaaacatt     780
attatgatga cacccctcac cactacaatc ttcctaggaa caacatatga cgcactctcc     840
cctgaactct acacaacata ttttgtcacc aagaccctac ttctaacctc cctgttctta     900
tggattcgaa cagcataccc ccgattccgc tacgaccaac tcatgcacct cctatggaaa     960
aacttcctac cactcacccct agcattactt atgtggtatg tctccatgcc cattacaatc    1020
tccagcattc cccctcaaac ctaagagcac tgggacgccc accgcccctt ccctccgct     1080 gccaggcgag catgttgtgg taattctgga acacaagaag agaaattgct gggtttagaa    1140
caagattata aacgaattcg gtgctcagtg atcacttgac agtttttttt ttttttaaat    1200
attacccaaa atgctcccca aataagaaat gcatcagctc agtcagtgaa tacaaaaaag    1260
gaattatttt tccctttgag ggtcttttat acatctctcc tccaacccca ccctctattc    1320
tgtttcttcc tcctcacatg ggggtacaca tacacagctt cctcttttgg ttccatcctt    1380
accaccacac cacacgcaca ctccacatgc ccagcagagt ggcacttggt ggccagaaag    1440
```

```
tgtgagcctc atgatctgct gtctgtagtt ctgtgagctc aggtccctca aaggcctcgg   1500 agcacccct  tccttgtgac tgagccaggg cctgcatttt tggttttccc caccccacac   1560
attctcaacc atagtccttc taacaatacc aatagctagg acccggctgc tgtgcactgg   1620
gactggggat tccacatgtt tgccttggga gtctcaagct ggactgcca              1669
```

<210> SEQ ID NO 69
<211> LENGTH: 2469
<212> TYPE: DNA
<213> ORGANISM: Artificial Sequence
<220> FEATURE:
<223> OTHER INFORMATION: COX8-opt_ND1-3'UTR

<400> SEQUENCE: 69

```
atgtccgtcc tgacgcgcct gctgctgcgg ggcttgacac ggctcggctc ggcggctcca     60
gtgcggcgcg ccagaatcca ttcgttgatg cccatggcca acctgctgct gctgatcgtg    120
cccatcctga tcgccatggc cttcctgatg ctgaccgagc gcaagatcct gggctacatg    180
cagctgcgca agggccccaa cgtggtgggc ccctacggcc tgctgcagcc cttcgccgac    240
gccatgaagc tgttcaccaa ggagcccctg aagcccgcca ccagcaccat caccctgtac    300
atcaccgccc ccaccctggc cctgaccatc gccctgctgc tgtggacccc cctgcccatg    360
cccaaccccc tggtgaacct gaacctgggc ctgctgttca tcctggccac cagcagcctg    420
gccgtgtaca gcatcctgtg gagcggctgg gccagcaaca gcaactacgc cctgatcggc    480
gccctgcgcg ccgtggccca gaccatcagc tacgaggtga ccctggccat catcctgctg    540
agcaccctgc tgatgagcgg cagcttcaac ctgagcaccc tgatcaccac caggagcac     600 ctgtggctgc tgctgcccag ctggcccctg gccatgatgt ggttcatcag caccctggcc    660
gagaccaacc gcaccccctt cgacctggcc gagggcgaga gcgagctggt gagcggcttc    720
aacatcgagt acgccgccgg ccccttcgcc ctgttcttca tggccgagta caccaacatc    780
atcatgatga caccctgac  caccaccatc ttcctgggca ccacctacga cgccctgagc    840
cccgagctgt acaccaccta cttcgtgacc aagaccctgc tgctgaccag cctgttcctg    900
tggatccgca ccgcctaccc ccgcttccgc tacgaccagc tgatgcacct gctgtggaag    960
aacttcctgc ccctgaccct ggccctgctg atgtggtacg tgagcatgcc catcaccatc   1020
agcagcatcc cccccagac  ctaagagcac tgggacgccc accgccctt  tccctccgct   1080 gccaggcgag catgttgtgg taattctgga acacaagaag agaaattgct gggtttagaa   1140
caagattata aacgaattcg gtgctcagtg atcacttgac agttttttt  tttttttaat    1200 attacccaaa atgctcccca aataagaaat gcatcagctc agtcagtgaa tacaaaaaag   1260
gaattatttt tcccttttgag ggtcttttat acatctctcc tccaacccca ccctctattc  1320
tgtttcttcc tcctcacatg ggggtacaca tacacagctt cctcttttgg ttccatcctt   1380
accaccacac cacacgcaca ctccacatgc ccagcagagt ggcacttggt ggccagaaag   1440
tgtgagcctc atgatctgct gtctgtagtt ctgtgagctc aggtccctca aaggcctcgg   1500 agcacccct  tccttgtgac tgagccaggg cctgcatttt tggttttccc caccccacac   1560
attctcaacc atagtccttc taacaatacc aatagctagg acccggctgc tgtgcactgg   1620
gactggggat tccacatgtt tgccttggga gtctcaagct ggactgccag ccctgtcct    1680 cccttcaccc ccattgcgta tgagcatttc agaactccaa ggagtcacag gcatctttat   1740
agttcacgtt aacatataga cactgttgga agcagttcct tctaaaggg  tagccctgga   1800 cttaatacca gccggatacc tctggccccc accccattac tgtacctctg gagtcactac   1860
```

| | |
|---|---|
| tgtgggtcgc cactcctctg ctacacagca cggcttttc aaggctgtat tgagaaggga | 1920 |
| agttaggaag aagggtgtgc tgggctaacc agcccacaga gctcacattc ctgtcccttg | 1980 |
| ggtgaaaaat acatgtccat cctgatatct cctgaattca gaaattagcc tccacatgtg | 2040 |
| caatggcttt aagagccaga agcagggttc tgggaatttt gcaagttacc tgtggccagg | 2100 |
| tgtggtctcg gttaccaaat acggttacct gcagcttttt agtcctttgt gctcccacgg | 2160 |
| gtctacagag tcccatctgc ccaaaggtct tgaagcttga caggatgttt tcgattactc | 2220 |
| agtctcccag ggcactactg gtccgtagga ttcgattggt cggggtagga gagttaaaca | 2280 |
| acatttaaac agagttctct caaaaatgtc taaagggatt gtaggtagat aacatccaat | 2340 |
| cactgtttgc acttatctga aatcttccct cttggctgcc cccaggtatt tactgtggag | 2400 |
| aacattgcat aggaatgtct ggaaaaagct tctacaactt gttacagcct tcacatttgt | 2460 |
| agaagcttt | 2469 |

<210> SEQ ID NO 70
<211> LENGTH: 1669
<212> TYPE: DNA
<213> ORGANISM: Artificial Sequence
<220> FEATURE:
<223> OTHER INFORMATION: COX8-opt_ND1-3'UTR*

<400> SEQUENCE: 70

| | |
|---|---|
| atgtccgtcc tgacgcgcct gctgctgcgg ggcttgacac ggctcggctc ggcggctcca | 60 |
| gtgcggcgcg ccagaatcca ttcgttgatg cccatggcca acctgctgct gctgatcgtg | 120 |
| cccatcctga tcgccatggc cttcctgatg ctgaccgagc gcaagatcct gggctacatg | 180 |
| cagctgcgca agggcccaa cgtggtgggc ccctacggcc tgctgcagcc cttcgccgac | 240 |
| gccatgaagc tgttcaccaa ggagcccctg aagcccgcca ccagcaccat caccctgtac | 300 |
| atcaccgccc ccaccctggc cctgaccatc gccctgctgc tgtggacccc cctgcccatg | 360 |
| cccaaccccc tggtgaacct gaacctgggc ctgctgttca tcctggccac cagcagcctg | 420 |
| gccgtgtaca gcatcctgtg gagcggctgg gccagcaaca gcaactacgc cctgatcggc | 480 |
| gccctgcgcg ccgtggccca gaccatcagc tacgaggtga ccctggccat catcctgctg | 540 |
| agcaccctgc tgatgagcgg cagcttcaac ctgagcaccc tgatcaccac ccaggagcac | 600 |
| ctgtggctgc tgctgcccag ctggcccctg gccatgatgt ggttcatcag caccctggcc | 660 |
| gagaccaacc gcacccccct cgacctggcc gagggcgaga gcgagctggt gagcggcttc | 720 |
| aacatcgagt acgccgccgg cccccttcgcc ctgttcttca tggccgagta caccaacatc | 780 |
| atcatgatga cacccctgac caccaccatc ttcctgggca ccacctacga cgccctgagc | 840 |
| cccgagctgt acaccaccta cttcgtgacc aagaccctgc tgctgaccag cctgttcctg | 900 |
| tggatccgca ccgcctaccc ccgcttccgc tacgaccagc tgatgcacct gctgtggaag | 960 |
| aacttcctgc ccctgaccct ggccctgctg atgtggtacg tgagcatgcc catcaccatc | 1020 |
| agcagcatcc ccccccagac ctaagagcac tgggacgccc accgccctt tccctccgct | 1080 |
| gccaggcgag catgttgtgg taattctgga acacaagaag agaaattgct gggtttagaa | 1140 |
| caagattata aacgaattcg gtgctcagtg atcacttgac agttttttt tttttaaat | 1200 |
| attacccaaa atgctcccca aataagaaat gcatcagctc agtcagtgaa tacaaaaaag | 1260 |
| gaattatttt tccctttgag ggtctttat acatctctcc tccaaccca ccctctattc | 1320 |
| tgtttcttcc tcctcacatg ggggtacaca tacacagctt cctcttttgg ttccatcctt | 1380 |

| | |
|---|---|
| accaccacac cacacgcaca ctccacatgc ccagcagagt ggcacttggt ggccagaaag | 1440 |
| tgtgagcctc atgatctgct gtctgtagtt ctgtgagctc aggtccctca aaggcctcgg | 1500 |
| agcaccccct tccttgtgac tgagccaggg cctgcatttt tggttttccc caccccacac | 1560 |
| attctcaacc atagtccttc taacaatacc aatagctagg acccggctgc tgtgcactgg | 1620 |
| gactggggat tccacatgtt tgccttggga gtctcaagct ggactgcca | 1669 |

<210> SEQ ID NO 71
<211> LENGTH: 3071
<212> TYPE: DNA
<213> ORGANISM: Artificial Sequence
<220> FEATURE:
<223> OTHER INFORMATION: OPA1-ND4-3'UTR

<400> SEQUENCE: 71

| | |
|---|---|
| gtgctgcccg cctagaaagg gtgaagtggt tgtttccgtg acggactgag tacgggtgcc | 60 |
| tgtcaggctc ttgcggaagt ccatgcgcca ttgggagggc ctcggccgcg gctctgtgcc | 120 |
| cttgctgctg agggccactt cctgggtcat tcctggaccg ggagccgggc tggggctcac | 180 |
| acggggctc ccgcgtggcc gtctcggcgc ctgcgtgacc tccccgccgg cgggatgtgg | 240 |
| cgactacgtc gggccgctgt ggcctgatgc taaaactaat cgtcccaaca attatgttac | 300 |
| taccactgac atggctttcc aaaaaacaca tgatttggat caacacaacc acccacagcc | 360 |
| taattattag catcatccct ctactatttt ttaaccaaat caacaacaac ctatttagct | 420 |
| gttccccaac ctttcctcc gaccccctaa caacccccct cctaatgcta actacctggc | 480 |
| tcctacccct cacaatcatg gcaagccaac gccacttatc cagtgaacca ctatcacgaa | 540 |
| aaaaactcta cctctctatg ctaatctccc tacaaatctc cttaattatg acattcacag | 600 |
| ccacagaact aatcatgttt tatatcttct tcgaaaccac acttatcccc accttggcta | 660 |
| tcatcacccg atggggcaac cagccagaac gcctgaacgc aggcacatac ttcctattct | 720 |
| acaccctagt aggctccctt cccctactca tcgcactaat ttacactcac aacaccctag | 780 |
| gctcactaaa cattctacta ctcactctca ctgcccaaga actatcaaac tcctgggcca | 840 |
| acaacttaat gtggctagct tacacaatgg cttttatggt aaagatgcct ctttacggac | 900 |
| tccacttatg gctccctaaa gcccatgtcg aagcccccat cgctgggtca atggtacttg | 960 |
| ccgcagtact cttaaaacta ggcggctatg gtatgatgcg cctcacactc attctcaacc | 1020 |
| ccctgacaaa acacatggcc taccccttcc ttgtactatc cctatggggc atgattatga | 1080 |
| caagctccat ctgcctacga caaacagacc taaaatcgct cattgcatac tcttcaatca | 1140 |
| gccacatggc cctcgtagta acagccattc tcatccaaac cccctggagc ttcaccggcg | 1200 |
| cagtcattct catgatcgcc cacgggctta tcctcatt actattctgc ctagcaaact | 1260 |
| caaactacga acgcactcac agtcgcatca tgatcctctc tcaaggactt caaactctac | 1320 |
| tcccactaat ggcttttggg tggcttctag caagcccgc taacctcgcc ttaccccca | 1380 |
| ctattaacct actgggagaa ctctctgtgc tagtaaccac gttctcctgg tcaaatatca | 1440 |
| ctctcctact tacaggactc aacatgctag tcacagccct atactccctc tacatgttta | 1500 |
| ccacaacaca atgggctca ctcacccacc acattaacaa catgaaaccc tcattcacac | 1560 |
| gagaaaacac cctcatgttc atgcacctat cccccattct cctcctatcc ctcaaccccg | 1620 |
| acatcattac cgggttttcc tcttaagagc actgggacgc ccaccgcccc tttccctccg | 1680 |
| ctgccaggcg agcatgttgt ggtaattctg gaacacaaga agagaaattg ctgggtttag | 1740 |
| aacaagatta taaacgaatt cggtgctcag tgatcacttg acagtttttt ttttttttaa | 1800 |

| | | |
|---|---|---|
| atattaccca aaatgctccc caaataagaa atgcatcagc tcagtcagtg aatacaaaaa | 1860 | |
| aggaattatt tttcctttg agggtctttt atacatctct cctccaaccc caccctctat | 1920 | |
| tctgtttctt cctcctcaca tgggggtaca catacacagc ttcctctttt ggttccatcc | 1980 | |
| ttaccaccac accacacgca cactccacat gcccagcaga gtggcacttg gtggccagaa | 2040 | |
| agtgtgagcc tcatgatctg ctgtctgtag ttctgtgagc tcaggtccct caaaggcctc | 2100 | |
| ggagcacccc cttccttgtg actgagccag ggcctgcatt tttggttttc ccaccccac | 2160 | |
| acattctcaa ccatagtcct tctaacaata ccaatagcta ggacccggct gctgtgcact | 2220 | |
| gggactgggg attccacatg tttgccttgg gagtctcaag ctggactgcc agccctgtc | 2280 | |
| ctcccttcac ccccattgcg tatgagcatt tcagaactcc aaggagtcac aggcatcttt | 2340 | |
| atagttcacg ttaacatata gacactgttg gaagcagttc cttctaaaag ggtagccctg | 2400 | |
| gacttaatac cagccggata cctctggccc ccaccccatt actgtacctc tggagtcact | 2460 | |
| actgtgggtc gccactcctc tgctacacag cacggctttt tcaaggctgt attgagaagg | 2520 | |
| gaagttagga agaagggtgt gctgggctaa ccagcccaca gagctcacat tcctgtccct | 2580 | |
| tgggtgaaaa atacatgtcc atcctgatat ctcctgaatt cagaaattag cctccacatg | 2640 | |
| tgcaatggct ttaagagcca gaagcagggt tctgggaatt ttgcaagtta cctgtggcca | 2700 | |
| ggtgtggtct cggttaccaa atacggttac ctgcagcttt ttagtccttt gtgctcccac | 2760 | |
| gggtctacag agtcccatct gcccaaaggt cttgaagctt gacaggatgt tttcgattac | 2820 | |
| tcagtctccc agggcactac tggtccgtag gattcgattg gtcggggtag gagagttaaa | 2880 | |
| caacatttaa acagagttct ctcaaaaatg tctaaaggga ttgtaggtag ataacatcca | 2940 | |
| atcactgttt gcacttatct gaaatcttcc ctcttggctg cccccaggta tttactgtgg | 3000 | |
| agaacattgc ataggaatgt ctggaaaaag cttctacaac ttgttacagc cttcacattt | 3060 | |
| gtagaagctt t | 3071 | |

<210> SEQ ID NO 72
<211> LENGTH: 2271
<212> TYPE: DNA
<213> ORGANISM: Artificial Sequence
<220> FEATURE:
<223> OTHER INFORMATION: OPA1-ND4-3'UTR*

<400> SEQUENCE: 72

| | | |
|---|---|---|
| gtgctgcccg cctagaaagg gtgaagtggt tgtttccgtg acggactgag tacgggtgcc | 60 | |
| tgtcaggctc ttgcggaagt ccatgcgcca ttgggagggc ctcggccgcg gctctgtgcc | 120 | |
| cttgctgctg agggccactt cctgggtcat tcctggaccg ggagccgggc tggggctcac | 180 | |
| acggggctc ccgcgtggcc gtctcggcgc ctgcgtgacc tccccgccgg cgggatgtgg | 240 | |
| cgactacgtc gggccgctgt ggcctgatgc taaaactaat cgtcccaaca attatgttac | 300 | |
| taccactgac atggctttcc aaaaaacaca tgatttggat caacacaacc acccacagcc | 360 | |
| taattattag catcatccct ctactatttt ttaaccaaat caacaacaac ctatttagct | 420 | |
| gttccccaac ctttccttcc gacccccctaa caacccccct cctaatgcta actacctggc | 480 | |
| tcctacccct cacaatcatg gcaagccaac gccacttatc cagtgaacca ctatcacgaa | 540 | |
| aaaaactcta cctctctatg ctaatctccc tacaaatctc cttaattatg acattcacag | 600 | |
| ccacagaact aatcatgttt tatatcttct tcgaaaccac acttatcccc accttggcta | 660 | |
| tcatcacccg atggggcaac cagccagaac gcctgaacgc aggcacatac ttcctattct | 720 | |

```
acaccctagt aggctcccctt ccctactca tcgcactaat ttacactcac aacaccctag    780
gctcactaaa cattctacta ctcactctca ctgcccaaga actatcaaac tcctgggcca    840
acaacttaat gtggctagct tacacaatgg ctttttatggt aaagatgcct ctttacggac   900
tccacttatg gctccctaaa gcccatgtcg aagcccccat cgctgggtca atggtacttg    960
ccgcagtact cttaaaacta ggcggctatg gtatgatgcg cctcacactc attctcaacc   1020
ccctgacaaa acatggcc tacccccttcc ttgtactatc cctatgggc atgattatga    1080
caagctccat ctgcctacga caaacagacc taaaatcgct cattgcatac tcttcaatca   1140
gccacatggc cctcgtagta acagccattc tcatccaaac cccctggagc ttcaccggcg   1200
cagtcattct catgatcgcc cacgggctta catcctcatt actattctgc ctagcaaact   1260
caaactacga acgcactcac agtcgcatca tgatcctctc tcaaggactt caaactctac   1320
tcccactaat ggcttttttgg tggcttctag caagcctcgc taacctcgcc ttaccccccca  1380
ctattaaccct actgggagaa ctctctgtgc tagtaaccac gttctcctgg tcaaatatca   1440
ctctcctact tacaggactc aacatgctag tcacagccct atactccctc tacatgttta   1500
ccacaacaca atggggctca ctcacccacc acattaacaa catgaaaccc tcattcacac   1560
gagaaaacac cctcatgttc atgcacctat ccccccattct cctcctatcc ctcaaccccg   1620
acatcattac cgggttttcc tcttaagagc actgggacgc ccaccgcccc ttccctccg    1680
ctgccaggcg agcatgttgt ggtaattctg gaacacaaga agagaaaattg ctgggtttag  1740
aacaagatta taaacgaatt cggtgctcag tgatcacttg acagttttttt ttttttttaa   1800
atattaccca aaatgctccc caaataagaa atgcatcagc tcagtcagtg aatacaaaaa   1860
aggaattatt tttcccttttg agggtctttt atacatctct cctccaaccc cacccctctat 1920
tctgtttctt cctcctcaca tggggtaca catacacagc ttcctcttttt ggttccatcc  1980
ttaccaccac accacacgca cactccacat gcccagcaga gtggcacttg gtggccagaa   2040
agtgtgagcc tcatgatctg ctgtctgtag ttctgtgagc tcaggtccct caaaggcctc   2100
ggagcacccc cttccttgtg actgagccag ggcctgcatt tttggttttc cccacccac    2160
acattctcaa ccatagtcct tctaacaata ccaatagcta ggacccggct gctgtgcact   2220
gggactgggg attccacatg tttgccttgg gagtctcaag ctggactgcc a            2271
```

```
<210> SEQ ID NO 73
<211> LENGTH: 3071
<212> TYPE: DNA
<213> ORGANISM: Artificial Sequence
<220> FEATURE:
<223> OTHER INFORMATION: OPA1-opt_ND4-3'UTR

<400> SEQUENCE: 73
gtgctgcccg cctagaaagg gtgaagtggt tgtttccgtg acggactgag tacgggtgcc    60
tgtcaggctc ttgcggaagt ccatgcgcca ttgggagggc ctcggccgcg gctctgtgcc   120
cttgctgctg agggccactt cctgggtcat tcctggaccg ggagccgggc tggggctcac   180
acggggctc ccgcgtggcc gtctcggcgc ctgcgtgacc tccccgccgg cgggatgtgg    240
cgactacgtc gggccgctgt ggcctgatgc tgaagctgat cgtgcccacc atcatgctgc   300
tgcctctgac ctggctgagc aagaaacaca tgatctggat caacaccacc acgcacagcc   360
tgatcatcag catcatccct ctgctgttct tcaaccagat caacaacaac ctgttcagct   420
gcagccccac cttcagcagc gaccctctga caacacctct gctgatgctg accacctggc   480
tgctgccccct cacaatcatg gcctctcaga gacacctgag cagcgagccc ctgagccgga   540
```

```
agaaactgta cctgagcatg ctgatctccc tgcagatctc tctgatcatg accttcaccg    600
ccaccgagct gatcatgttc tacatctttt tcgagacaac gctgatcccc acactggcca    660
tcatcaccag atggggcaac cagcctgaga gactgaacgc cggcacctac tttctgttct    720
acaccctcgt gggcagcctg ccactgctga ttgccctgat ctacacccac aacaccctgg    780
gctccctgaa catcctgctg ctgacactga cagcccaaga gctgagcaac agctgggcca    840
acaatctgat gtggctggcc tacacaatgg ccttcatggt caagatgccc ctgtacggcc    900
tgcacctgtg gctgcctaaa gctcatgtgg aagcccctat cgccggctct atggtgctgg    960
ctgcagtgct gctgaaactc ggcggctacg gcatgatgcg gctgaccctg attctgaatc   1020
ccctgaccaa gcacatggcc tatccatttc tggtgctgag cctgtggggc atgattatga   1080
ccagcagcat ctgcctgcgg cagaccgatc tgaagtccct gatcgcctac agctccatca   1140
gccacatggc cctggtggtc accgccatcc tgattcagac cccttggagc tttacaggcg   1200
ccgtgatcct gatgattgcc cacggcctga caagcagcct gctgttttgt ctggccaaca   1260
gcaactacga gcggacccac agcagaatca tgatcctgtc tcagggcctg cagaccctcc   1320
tgcctcttat ggcttttttgg tggctgctgg cctctctggc caatctggca ctgcctccta   1380
ccatcaatct gctgggcgag ctgagcgtgc tggtcaccac attcagctgg tccaatatca   1440
ccctgctgct caccggcctg aacatgctgg ttacagccct gtactccctg tacatgttca   1500
ccaccacaca gtggggaagc ctgacacacc acatcaacaa tatgaagccc agcttcaccc   1560
gcgagaacac cctgatgttc atgcatctga gccccattct gctgctgtcc ctgaatcctg   1620
atatcatcac cggcttctcc agctgagagc actgggacgc ccaccgcccc tttccctccg   1680
ctgccaggcg agcatgttgt ggtaattctg aacacaagag agagaaattg ctgggtttag   1740
aacaagatta taaacgaatt cggtgctcag tgatcacttg acagtttttt ttttttttaa   1800
atattaccca aaatgctccc caaataagaa atgcatcagc tcagtcagtg aatacaaaaa   1860
aggaattatt tttcccttttg agggtctttt atacatctct cctccaaccc caccctctat   1920
tctgtttctt cctcctcaca tgggggtaca catacacagc ttcctctttt ggttccatcc   1980
ttaccaccac accacacgca cactccacat gcccagcaga gtggcacttg gtggccagaa   2040
agtgtgagcc tcatgatctg ctgtctgtag ttctgtgagc tcaggtccct caaaggcctc   2100
ggagcacccc cttccttgtg actgagccag ggcctgcatt tttggttttc cccacccccac   2160
acattctcaa ccatagtcct tctaacaata ccaatagcta ggacccggct gctgtgcact   2220
gggactgggg attccacatg tttgccttgg gagtctcaag ctggactgcc agcccctgtc   2280
ctcccttcac ccccattgcg tatgagcatt tcagaactcc aaggagtcac aggcatcttt   2340
atagttcacg ttaacatata gacactgttg gaagcagttc cttctaaaag ggtagccctg   2400
gacttaatac cagccggata cctctggccc ccaccccatt actgtacctc tggagtcact   2460
actgtgggtc gccactcctc tgctacacag cacggctttt tcaaggctgt attgagaagg   2520
gaagttagga agaagggtgt gctgggctaa ccagcccaca gagctcacat tcctgtccct   2580
tgggtgaaaa atacatgtcc atcctgatat ctcctgaatt cagaaattag cctccacatg   2640
tgcaatggct ttaagagcca gaagcagggt tctgggaatt ttgcaagtta cctgtggcca   2700
ggtgtggtct cggttaccaa atacggttac ctgcagcttt ttagtccttt gtgctcccac   2760
gggtctacag agtcccatct gcccaaaggt cttgaagctt gacaggatgt tttcgattac   2820
tcagtctccc agggcactac tggtccgtag gattcgattg gtcggggtag gagagttaaa   2880
```

| caacatttaa acagagttct ctcaaaaatg tctaaaggga ttgtaggtag ataacatcca | 2940 |
| atcactgttt gcacttatct gaaatcttcc ctcttggctg cccccaggta tttactgtgg | 3000 |
| agaacattgc ataggaatgt ctggaaaaag cttctacaac ttgttacagc cttcacattt | 3060 |
| gtagaagctt t | 3071 |

<210> SEQ ID NO 74
<211> LENGTH: 2271
<212> TYPE: DNA
<213> ORGANISM: Artificial Sequence
<220> FEATURE:
<223> OTHER INFORMATION: OPA1-opt_ND4-3'UTR*

<400> SEQUENCE: 74

| gtgctgcccg cctagaaagg gtgaagtggt tgtttccgtg acggactgag tacgggtgcc | 60 |
| tgtcaggctc ttgcggaagt ccatgcgcca ttgggagggc ctcggccgcg gctctgtgcc | 120 |
| cttgctgctg agggccactt cctgggtcat tcctggaccg ggagccgggc tggggctcac | 180 |
| acgggggctc ccgcgtggcc gtctcggcgc ctgcgtgacc tccccgccgg cgggatgtgg | 240 |
| cgactacgtc gggccgctgt ggcctgatgc tgaagctgat cgtgcccacc atcatgctgc | 300 |
| tgcctctgac ctggctgagc aagaaacaca tgatctggat caacaccacc acgcacagcc | 360 |
| tgatcatcag catcatccct ctgctgttct caaccagat caacaacaac ctgttcagct | 420 |
| gcagccccac cttcagcagc gaccctctga caacacctct gctgatgctg accacctggc | 480 |
| tgctgccct cacaatcatg gcctctcaga gacacctgag cagcgagccc ctgagccgga | 540 |
| agaaactgta cctgagcatg ctgatctccc tgcagatctc tctgatcatg accttcaccg | 600 |
| ccaccgagct gatcatgttc tacatctttt tcgagacaac gctgatcccc acactggcca | 660 |
| tcatcaccag atggggcaac cagcctgaga gactgaacgc cggcacctac tttctgttct | 720 |
| acaccctcgt gggcagcctg ccactgctga ttgccctgat ctacacccac aacaccctgg | 780 |
| gctccctgaa catcctgctg ctgacactga gcccaagga gctgagcaac agctgggcca | 840 |
| acaatctgat gtggctggcc tacacaatgg ccttcatggt caagatgccc ctgtacggcc | 900 |
| tgcacctgtg gctgcctaaa gctcatgtgg aagcccctat cgccggctct atggtgctgg | 960 |
| ctgcagtgct gctgaaactc ggcggctacg gcatgatgcg gctgaccctg attctgaatc | 1020 |
| ccctgaccaa gcacatggcc tatccatttc tggtgctgag cctgtggggc atgattatga | 1080 |
| ccagcagcat ctgcctgcgg cagaccgatc tgaagtccct gatcgcctac agctccatca | 1140 |
| gccacatggc cctggtggtc accgccatcc tgattcagac ccttggagc tttacaggcg | 1200 |
| ccgtgatcct gatgattgcc cacggcctga caagcagcct gctgttttgt ctggccaaca | 1260 |
| gcaactacga gcggacccac agcagaatca tgatcctgtc tcagggcctg cagaccctcc | 1320 |
| tgcctcttat ggcttttttgg tggctgctgg cctctctggc caatctggca ctgcctccta | 1380 |
| ccatcaatct gctgggcgag ctgagcgtgc tggtcaccac attcagctgg tccaatatca | 1440 |
| ccctgctgct caccggcctg aacatgctgg ttacagccct gtactccctg tacatgttca | 1500 |
| ccaccacaca gtggggaagc ctgacacacc acatcaacaa tatgaagccc agcttcaccc | 1560 |
| gcgagaacac cctgatgttc atgcatctga gccccattct gctgctgtcc ctgaatcctg | 1620 |
| atatcatcac cggcttctcc agctgagagc actgggacgc ccaccgcccc tttccctccg | 1680 |
| ctgccaggcg agcatgttgt ggtaattctg gaacacaaga agagaaattg ctgggtttag | 1740 |
| aacaagatta taaacgaatt cggtgctcag tgatcacttg acagtttttt ttttttttaa | 1800 |
| atattaccca aaatgctccc caaataagaa atgcatcagc tcagtcagtg aatacaaaaa | 1860 |

```
aggaattatt tttcccttg agggtctttt atacatctct cctccaaccc caccctctat    1920
tctgtttctt cctcctcaca tgggggtaca catacacagc ttcctctttt ggttccatcc    1980
ttaccaccac accacacgca cactccacat gcccagcaga gtggcacttg gtggccagaa    2040
agtgtgagcc tcatgatctg ctgtctgtag ttctgtgagc tcaggtccct caaaggcctc    2100
ggagcacccc cttccttgtg actgagccag ggcctgcatt tttggttttc cccaccccac    2160
acattctcaa ccatagtcct tctaacaata ccaatagcta ggacccggct gctgtgcact    2220
gggactgggg attccacatg tttgccttgg gagtctcaag ctggactgcc a             2271
```

<210> SEQ ID NO 75
<211> LENGTH: 3071
<212> TYPE: DNA
<213> ORGANISM: Artificial Sequence
<220> FEATURE:
<223> OTHER INFORMATION: OPA1-opt_ND4*-3'UTR

<400> SEQUENCE: 75

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc     120
cttgctgctg agggccactt cctgggtcat tcctggaccg ggagccgggc tggggctcac     180 acggggctc ccgcgtggcc gtctcggcgc ctgcgtgacc tccccgccgg cgggatgtgg     240
cgactacgtc gggccgctgt ggcctgatgc tgaagctgat cgtgcccacc atcatgctgc     300
tgcccctgac ctggctgagc aagaagcaca tgatctggat caacaccacc acccacagcc     360
tgatcatcag catcatcccc ctgctgttct tcaaccagat caacaacaac ctgttcagct     420
gcagccccac cttcagcagc gaccccctga ccacccccct gctgatgctg accacctggc     480
tgctgcccct gaccatcatg gccagccagc gccacctgag cagcgagccc tgagccgca      540 agaagctgta cctgagcatg ctgatcagcc tgcagatcag cctgatcatg accttcaccg     600
ccaccgagct gatcatgttc tacatcttct tcgagaccac cctgatcccc accctggcca     660
tcatcacccg ctggggcaac cagcccgagc gcctgaacgc cggcacctac ttcctgttct     720
acaccctggt gggcagcctg cccctgctga tcgccctgat ctacacccac aacaccctgg     780
gcagcctgaa catcctgctg ctgacccctga ccgcccagga gctgagcaac agctgggcca    840
acaacctgat gtggctggcc tacaccatgg ccttcatggt gaagatgccc ctgtacggcc     900
tgcacctgtg gctgcccaag gcccacgtgg aggcccccat cgccggcagc atggtgctgg     960
ccgccgtgct gctgaagctg ggcggctacg gcatgatgcg cctgaccctg atcctgaacc    1020
ccctgaccaa gcacatggcc tacccctcc tggtgctgag cctgtgggc atgatcatga      1080 ccagcagcat ctgcctgcgc cagaccgacc tgaagagcct gatcgcctac agcagcatca    1140
gccacatggc cctggtggtg accgccatcc tgatccagac ccctggagc ttcaccggcg     1200 ccgtgatcct gatgatcgcc cacgcctga ccagcagcc gctgttctgc ctggccaaca      1260
gcaactacga gcgcacccac agccgcatca tgatcctgag ccagggcctg cagaccctgc    1320 tgccctgat ggccttctgg tggctgctgg ccagcctggc caacctggcc ctgccccca      1380 ccatcaacct gctgggcgag ctgagcgtgc tggtgaccac cttcagctgg agcaacatca    1440
ccctgctgct gaccggcctg aacatgctgg tgaccgccct gtacagcctg tacatgttca    1500
ccaccaccca gtggggcagc ctgacccacc acatcaacaa catgaagccc agcttcaccc    1560
gcgagaacac cctgatgttc atgcacctga gccccatcct gctgctgagc ctgaacccg     1620
```

| | |
|---|---:|
| acatcatcac cggcttcagc agctaagagc actgggacgc ccaccgcccc tttccctccg | 1680 |
| ctgccaggcg agcatgttgt ggtaattctg gaacacaaga agagaaattg ctgggtttag | 1740 |
| aacaagatta taaacgaatt cggtgctcag tgatcacttg acagtttttt tttttttttaa | 1800 |
| atattaccca aaatgctccc caaataagaa atgcatcagc tcagtcagtg aatacaaaaa | 1860 |
| aggaattatt tttcccttttg agggtctttt atacatctct cctccaaccc caccctctat | 1920 |
| tctgtttctt cctcctcaca tgggggtaca catacacagc ttcctcttt ggttccatcc | 1980 |
| ttaccaccac accacacgca cactccacat gcccagcaga gtggcacttg gtggccagaa | 2040 |
| agtgtgagcc tcatgatctg ctgtctgtag ttctgtgagc tcaggtccct caaaggcctc | 2100 |
| ggagcacccc cttccttgtg actgagccag ggcctgcatt tttggttttc cccacccac | 2160 |
| acattctcaa ccatagtcct tctaacaata ccaatagcta ggacccggct gctgtgcact | 2220 |
| gggactgggg attccacatg tttgccttgg gagtctcaag ctggactgcc agccctgtc | 2280 |
| ctcccttcac ccccattgcg tatgagcatt tcagaactcc aaggagtcac aggcatcttt | 2340 |
| atagttcacg ttaacatata gacactgttg gaagcagttc cttctaaaag ggtagccctg | 2400 |
| gacttaatac cagccggata cctctggccc ccaccccatt actgtacctc tggagtcact | 2460 |
| actgtgggtc gccactcctc tgctacacag cacggctttt tcaaggctgt attgagaagg | 2520 |
| gaagttagga agaagggtgt gctgggctaa ccagcccaca gagctcacat tcctgtccct | 2580 |
| tgggtgaaaa atacatgtcc atcctgatat ctcctgaatt cagaaattag cctccacatg | 2640 |
| tgcaatggct ttaagagcca gaagcagggt tctgggaatt ttgcaagtta cctgtggcca | 2700 |
| ggtgtggtct cggttaccaa atacggttac ctgcagcttt ttagtccttt gtgctcccac | 2760 |
| gggtctacag agtcccatct gcccaaaggt cttgaagctt gacaggatgt tttcgattac | 2820 |
| tcagtctccc agggcactac tggtccgtag gattcgattg gtcggggtag gagagttaaa | 2880 |
| caacatttaa acagagttct ctcaaaaatg tctaaaggga ttgtaggtag ataacatcca | 2940 |
| atcactgttt gcacttatct gaaatcttcc ctcttggctg cccccaggta tttactgtgg | 3000 |
| agaacattgc ataggaatgt ctggaaaaag cttctacaac ttgttacagc cttcacattt | 3060 |
| gtagaagctt t | 3071 |

<210> SEQ ID NO 76
<211> LENGTH: 2271
<212> TYPE: DNA
<213> ORGANISM: Artificial Sequence
<220> FEATURE:
<223> OTHER INFORMATION: OPA1-opt_ND4*-3'UTR*

<400> SEQUENCE: 76

| | |
|---|---:|
| gtgctgcccg cctagaaagg gtgaagtggt tgtttccgtg acggactgag tacgggtgcc | 60 |
| tgtcaggctc ttgcggaagt ccatgcgcca ttgggagggc ctcggccgcg gctctgtgcc | 120 |
| cttgctgctg agggccactt cctgggtcat tcctggaccg ggagccgggc tggggctcac | 180 |
| acggggctc ccgcgtggcc gtctcggcgc ctgcgtgacc tccccgccgg cgggatgtgg | 240 |
| cgactacgtc gggccgctgt ggcctgatgc tgaagctgat cgtgcccacc atcatgctgc | 300 |
| tgcccctgac ctggctgagc aagaagcaca tgatctggat caacaccacc acccacagcc | 360 |
| tgatcatcag catcatcccc ctgctgttct tcaaccagat caacaacaac ctgttcagct | 420 |
| gcagccccac cttcagcagc gacccccctga ccaccccct gctgatgctg accacctggc | 480 |
| tgctgccct gaccatcatg gccagccagc gccacctgag cagcgagccc ctgagccgca | 540 |
| agaagctgta cctgagcatg ctgatcagcc tgcagatcag cctgatcatg accttcaccg | 600 |

```
ccaccgagct gatcatgttc tacatcttct tcgagaccac cctgatcccc accctggcca      660
tcatcacccg ctggggcaac cagcccgagc gcctgaacgc cggcacctac ttcctgttct      720
acaccctggt gggcagcctg cccctgctga tcgccctgat ctacacccac aacaccctgg      780
gcagcctgaa catcctgctg ctgacccctga ccgcccagga gctgagcaac agctgggcca    840
acaacctgat gtggctggcc tacaccatgg ccttcatggt gaagatgccc ctgtacggcc      900
tgcacctgtg gctgcccaag gcccacgtgg aggcccccat cgccggcagc atggtgctgg      960
ccgccgtgct gctgaagctg gcgggctacg gcatgatgcg cctgaccctg atcctgaacc     1020
ccctgaccaa gcacatggcc tacccttcc tggtgctgag cctgtggggc atgatcatga     1080
ccagcagcat ctgcctgcgc cagaccgacc tgaagagcct gatcgcctac agcagcatca    1140
gccacatggc cctggtggtg accgccatcc tgatccagac ccctggagc ttcaccggcg     1200 ccgtgatcct gatgatcgcc cacggcctga ccagcagcct gctgttctgc ctggccaaca    1260
gcaactacga gcgcacccac agccgcatca tgatcctgag ccagggcctg cagaccctgc    1320 tgccctgat ggccttctgg tggctgctgg ccagcctggc caacctggcc ctgcccccca     1380
ccatcaacct gctgggcgag ctgagcgtgc tggtgaccac cttcagctgg agcaacatca    1440
ccctgctgct gaccggcctg aacatgctgg tgaccgccct gtacagcctg tacatgttca    1500 ccaccccca gtggggcagc ctgacccacc acatcaacaa catgaagccc agcttcaccc     1560
gcgagaacac cctgatgttc atgcacctga gccccatcct gctgctgagc ctgaacccg      1620 acatcatcac cggcttcagc agctaagagc actgggacgc ccaccgcccc tttccctccg    1680
ctgccaggcg agcatgttgt ggtaattctg gaacacaaga agagaaattg ctgggtttag     1740
aacaagatta taaacgaatt cggtgctcag tgatcacttg acagtttttt ttttttttaa    1800 atattccca aaatgctccc caaataagaa atgcatcagc tcagtcagtg aatacaaaaa     1860
aggaattatt tttcccttgg agggtctttt atacatctct cctccaaccc caccctctat    1920
tctgtttctt cctcctcaca tggggtaca catacacagc ttcctctttt ggttccatcc     1980
ttaccaccac accacacgca cactccacat gcccagcaga gtggcacttg gtggccagaa    2040
agtgtgagcc tcatgatctg ctgtctgtag ttctgtgagc tcaggtccct caaaggcctc     2100 ggagcaccc cttccttgtg actgagccag ggcctgcatt tttggttttc cccaccccac     2160
acattctcaa ccatagtcct tctaacaata ccaatagcta ggacccggct gctgtgcact    2220
gggactgggg attccacatg tttgccttgg gagtctcaag ctggactgcc a              2271
```

<210> SEQ ID NO 77
<211> LENGTH: 2216
<212> TYPE: DNA
<213> ORGANISM: Artificial Sequence
<220> FEATURE:
<223> OTHER INFORMATION: OPA1-ND6-3'UTR

<400> SEQUENCE: 77

```
gtgctgcccg cctagaaagg gtgaagtggt tgtttccgtg acggactgag tacgggtgcc       60
tgtcaggctc ttgcggaagt ccatgcgcca ttgggagggc ctcggccgcg gctctgtgcc      120
cttgctgctg agggccactt cctggtcat tcctggaccg ggagccgggc tggggctcac      180 acggggctc ccgcgtggcc gtctcggcgc ctgcgtgacc tccccgccgg cgggatgtgg      240
cgactacgtc gggccgctgt ggcctgatga tgtatgcttt gtttctgttg agtgtgggtt     300
tagtaatggg gtttgtgggg ttttcttcta agccttctcc tatttatggg ggtttagtat    360
```

| | |
|---|---|
| tgattgttag cggtgtggtc gggtgtgtta ttattctgaa ttttggggga ggttatatgg | 420 |
| gtttaatggt tttttttaatt tatttagggg gaatgatggt tgtctttgga tatactacag | 480 |
| cgatggctat tgaggagtat cctgaggcat gggggtcagg ggttgaggtc ttggtgagtg | 540 |
| ttttagtggg gttagcgatg gaggtaggat tggtgctgtg ggtgaaagag tatgatgggg | 600 |
| tggtggttgt ggtaaacttt aatagtgtag gaagctggat gatttatgaa ggagaggggt | 660 |
| cagggttgat tcgggaggat cctattggtg cgggggcttt gtatgattat gggcgttggt | 720 |
| tagtagtagt tactggttgg acattgtttg ttggtgtata tattgtaatt gagattgctc | 780 |
| gggggaatta ggagcactgg gacgcccacc gccccttttcc ctccgctgcc aggcgagcat | 840 |
| gttgtggtaa ttctggaaca caagaagaga aattgctggg tttagaacaa gattataaac | 900 |
| gaattcggtg ctcagtgatc acttgacagt ttttttttttt tttaaatatt acccaaaatg | 960 |
| ctccccaaat aagaaatgca tcagctcagt cagtgaatac aaaaaaggaa ttattttttcc | 1020 |
| ctttgagggt cttttataca tctctcctcc aaccccaccc tctattctgt ttcttcctcc | 1080 |
| tcacatgggg gtacacatac acagcttcct cttttggttc catccttacc accacaccac | 1140 |
| acgcacactc cacatgccca gcagagtggc acttggtggc cagaaagtgt gagcctcatg | 1200 |
| atctgctgtc tgtagttctg tgagctcagg tccctcaaag gcctcggagc accccttcc | 1260 |
| ttgtgactga gccagggcct gcatttttgg ttttccccac cccacacatt ctcaaccata | 1320 |
| gtccttctaa caataccaat agctaggacc cggctgctgt gcactgggac tggggattcc | 1380 |
| acatgtttgc cttgggagtc tcaagctgga ctgccagccc ctgtcctccc ttcaccccca | 1440 |
| ttgcgtatga gcatttcaga actccaagga gtcacaggca tctttatagt tcacgttaac | 1500 |
| atatagacac tgttggaagc agttccttct aaaagggtag ccctggactt aataccagcc | 1560 |
| ggatacctct ggccccccacc ccattactgt acctctggag tcactactgt gggtcgccac | 1620 |
| tcctctgcta cacagcacgg cttttttcaag gctgtattga aagggaagt taggaagaag | 1680 |
| ggtgtgctgg gctaaccagc ccacagagct cacattcctg tcccttgggt gaaaaataca | 1740 |
| tgtccatcct gatatctcct gaattcagaa attagcctcc acatgtgcaa tggctttaag | 1800 |
| agccagaagc agggttctgg gaattttgca agttacctgt ggccaggtgt ggtctcggtt | 1860 |
| accaaatacg gttacctgca gcttttttagt cctttgtgct cccacgggtc tacagagtcc | 1920 |
| catctgccca aagtcttga agcttgacag gatgttttcg attactcagt ctcccagggc | 1980 |
| actactggtc cgtaggattc gattggtcgg ggtaggagag ttaaacaaca tttaaacaga | 2040 |
| gttctctcaa aaatgtctaa agggattgta ggtagataac atccaatcac tgtttgcact | 2100 |
| tatctgaaat cttccctctt ggctgccccc aggtatttac tgtggagaac attgcatagg | 2160 |
| aatgtctgga aaaagcttct acaacttgtt acagccttca catttgtaga agcttt | 2216 |

<210> SEQ ID NO 78
<211> LENGTH: 1416
<212> TYPE: DNA
<213> ORGANISM: Artificial Sequence
<220> FEATURE:
<223> OTHER INFORMATION: OPA1-ND6-3'UTR*

<400> SEQUENCE: 78

| | |
|---|---|
| gtgctgcccg cctagaaagg gtgaagtggt tgtttccgtg acggactgag tacgggtgcc | 60 |
| tgtcaggctc ttgcggaagt ccatgcgcca ttgggagggc ctcggccgcg gctctgtgcc | 120 |
| cttgctgcta agggccactt cctgggtcat tcctggaccg ggagccgggc tggggctcac | 180 |
| acggggggctc ccgcgtggcc gtctcggcgc ctgcgtgacc tccccgccgg cgggatgtgg | 240 |

```
cgactacgtc gggccgctgt ggcctgatga tgtatgcttt gtttctgttg agtgtgggtt      300
tagtaatggg gtttgtgggg ttttcttcta agccttctcc tatttatggg ggtttagtat      360
tgattgttag cggtgtggtc gggtgtgtta ttattctgaa ttttggggga ggttatatgg      420
gtttaatggt ttttttaatt tatttagggg gaatgatggt tgtctttgga tatactacag      480
cgatggctat tgaggagtat cctgaggcat gggggtcagg ggttgaggtc ttggtgagtg      540
ttttagtggg gttagcgatg gaggtaggat tggtgctgtg ggtgaaagag tatgatgggg      600
tggtggttgt ggtaaacttt aatagtgtag gaagctggat gatttatgaa ggagaggggt      660
cagggttgat tcgggaggat cctattggtg cgggggcttt gtatgattat ggcgttggt       720 tagtagtagt tactggttgg acattgtttg ttggtgtata tattgtaatt gagattgctc      780
gggggaatta ggagcactgg gacgcccacc gccccttttcc ctccgctgcc aggcgagcat    840
gttgtggtaa ttctggaaca caagaagaga aattgctggg tttagaacaa gattataaac      900
gaattcggtg ctcagtgatc acttgacagt tttttttttt tttaaatatt acccaaaatg      960
ctccccaaat aagaaatgca tcagctcagt cagtgaatac aaaaaaggaa ttattttttcc     1020 ctttgagggt cttttataca tctctcctcc aaccccaccc tctattctgt ttcttcctcc      1080
tcacatgggg gtacacatac acagcttcct cttttggttc catccttacc accacaccac      1140
acgcacactc cacatgccca gcagagtggc acttggtggc cagaaagtgt gagcctcatg      1200
atctgctgtc tgtagttctg tgagctcagg tccctcaaag gcctcggagc accccttcc      1260 ttgtgactga gccagggcct gcattttttgg tttttcccca cccacacatt ctcaaccata    1320
gtccttctaa caataccaat agctaggacc cggctgctgt gcactgggac tggggattcc     1380
acatgtttgc cttgggagtc tcaagctgga ctgcca                               1416
```

<210> SEQ ID NO 79
<211> LENGTH: 2216
<212> TYPE: DNA
<213> ORGANISM: Artificial Sequence
<220> FEATURE:
<223> OTHER INFORMATION: OPA1-opt_ND6-3'UTR

<400> SEQUENCE: 79

```
gtgctgcccg cctagaaagg gtgaagtggt tgtttccgtg acggactgag tacgggtgcc       60
tgtcaggctc ttgcggaagt ccatgcgcca ttgggagggc ctcggccgcg gctctgtgcc      120
cttgctgctg agggccactt cctgggtcat tcctggaccg ggagccgggc tggggctcac      180 acggggggctc ccgcgtggcc gtctcggcgc ctgcgtgacc tccccgccgg cgggatgtgg      240
cgactacgtc gggccgctgt ggcctgatga tgtacgccct gttcctgctg agcgtgggcc      300
tggtgatggg cttcgtgggc ttcagcagca agcccagccc catctacggc ggcctggtgc      360
tgatcgtgag cggcgtggtg ggctgcgtga tcatcctgaa cttcggcggc ggctacatgg      420
gcctgatggt gttcctgatc tacctgggcg gcatgatggt ggtgttcggc tacaccaccg      480
ccatggccat cgaggagtac cccgaggcct ggggcagcgg cgtggaggtg ctggtgagcg      540
tgctggtggg cctggccatg gaggtgggcc tggtgctgtg ggtgaaggag tacgacggcg      600
tggtggtggt ggtgaacttc aacagcgtgg gcagctggat gatctacgag ggcgagggca      660
gcggcctgat ccgcgaggac cccatcggcg ccggcgccct gtacgactac ggccgctggc      720
tggtggtggt gaccggctgg accctgtttcg tgggcgtgta catcgtgatc gagatcgccc      780
gcggcaacta agagcactgg gacgcccacc gccccttttcc ctccgctgcc aggcgagcat    840
```

```
gttgtggtaa ttctggaaca caagaagaga aattgctggg tttagaacaa gattataaac      900
gaattcggtg ctcagtgatc acttgacagt tttttttttt tttaaatatt acccaaaatg      960
ctccccaaat aagaaatgca tcagctcagt cagtgaatac aaaaaaggaa ttattttttcc    1020 cttttgagggt cttttataca tctctcctcc aacccccaccc tctattctgt ttcttcctcc   1080
tcacatgggg gtacacatac acagcttcct cttttggttc catccttacc accacaccac    1140
acgcacactc cacatgccca gcagagtggc acttggtggc cagaaagtgt gagcctcatg    1200
atctgctgtc tgtagttctg tgagctcagg tccctcaaag gcctcggagc accccttcc    1260 ttgtgactga gccagggcct gcattttggg ttttccccac cccacacatt ctcaaccata    1320
gtccttctaa caataccaat agctaggacc cggctgctgt gcactgggac tggggattcc    1380
acatgtttgc cttgggagtc tcaagctgga ctgccagccc ctgtcctccc ttcacccccca   1440 ttgcgtatga gcatttcaga actccaagga gtcacaggca tctttatagt tcacgttaac    1500
atatagacac tgttggaagc agttccttct aaaagggtag ccctggactt aataccagcc    1560
ggatacctct ggcccccacc ccattactgt acctctggag tcactactgt gggtcgccac    1620
tcctctgcta cacagcacgg ctttttcaag gctgtattga aagggaagt taggaagaag     1680 ggtgtgctgg gctaaccagc ccacagagct cacattcctg tcccttgggt gaaaaataca    1740
tgtccatcct gatatctcct gaattcagaa attagcctcc acatgtgcaa tggctttaag    1800
agccagaagc agggttctgg gaattttgca agttacctgt ggccaggtgt ggtctcggtt    1860
accaaatacg gttacctgca gcttttagt cctttgtgct cccacgggtc tacagagtcc     1920
catctgccca aggtcttga agcttgacag gatgttttcg attactcagt ctcccagggc     1980
actactggtc cgtaggattc gattggtcgg ggtaggagag ttaaacaaca tttaaacaga    2040
gttctctcaa aaatgtctaa agggattgta ggtagataac atccaatcac tgtttgcact    2100
tatctgaaat cttccctctt ggctgccccc aggtatttac tgtggagaac attgcatagg    2160
aatgtctgga aaaagcttct acaacttgtt acagccttca catttgtaga agcttt        2216
```

<210> SEQ ID NO 80
<211> LENGTH: 1416
<212> TYPE: DNA
<213> ORGANISM: Artificial Sequence
<220> FEATURE:
<223> OTHER INFORMATION: OPA1-opt_ND6-3'UTR*

<400> SEQUENCE: 80

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc    120
cttgctgctg agggccactt cctgggtcat tcctggaccg ggagccgggc tggggctcac    180
acgggggctc ccgcgtggcc gtctcggcgc ctgcgtgacc tccccgccgg cgggatgtgg    240
cgactacgtc gggccgctgt ggcctgatga tgtacgccct gttcctgctg agcgtgggcc    300
tggtgatggg cttcgtgggc ttcagcagca agcccagccc catctacggc ggcctggtgc    360
tgatcgtgag cggcgtggtg ggctgcgtga tcatcctgaa cttcggcggc ggctacatgg    420
gcctgatggt gttcctgatc tacctgggcg gcatgatggt ggtgttcggc tacaccaccg    480
ccatggccat cgaggagtac cccgaggcct ggggcagcgg cgtggaggtg ctggtgagcg    540
tgctggtggg cctggccatg gaggtgggcc tggtgctgtg ggtgaaggag tacgacggcg    600
tggtggtggt ggtgaacttc aacagcgtgg gcagctggat gatctacgag ggcgagggca    660
gcggcctgat ccgcgaggac cccatcggcg ccggcgccct gtacgactac ggccgcgctgc    720
```

```
tggtggtggt gaccggctgg accctgttcg tgggcgtgta catcgtgatc gagatcgccc    780
gcggcaacta agagcactgg gacgcccacc gcccctttcc ctccgctgcc aggcgagcat    840
gttgtggtaa ttctggaaca caagaagaga aattgctggg tttagaacaa gattataaac    900
gaattcggtg ctcagtgatc acttgacagt tttttttttt tttaaatatt acccaaaatg    960
ctccccaaat aagaaatgca tcagctcagt cagtgaatac aaaaaaggaa ttattttttcc   1020 cttttgagggt cttttataca tctctcctcc aaccccaccc tctattctgt ttcttcctcc   1080
tcacatgggg gtacacatac acagcttcct cttttggttc catccttacc accacaccac   1140
acgcacactc cacatgccca gcagagtggc acttggtggc cagaaagtgt gagcctcatg   1200
atctgctgtc tgtagttctg tgagctcagg tccctcaaag gcctcggagc accccttcc    1260 ttgtgactga gccagggcct gcattttttgg tttttccccac cccacacatt ctcaaccata   1320
gtccttctaa caataccaat agctaggacc cggctgctgt gcactgggac tggggattcc    1380
acatgtttgc cttgggagtc tcaagctgga ctgcca                              1416
```

<210> SEQ ID NO 81
<211> LENGTH: 2648
<212> TYPE: DNA
<213> ORGANISM: Artificial Sequence
<220> FEATURE:
<223> OTHER INFORMATION: OPA1-ND1-3'UTR

<400> SEQUENCE: 81

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc    120
cttgctgctg agggccactt cctgggtcat tcctggaccg ggagccgggc tggggctcac    180 acggggggctc ccgcgtggcc gtctcggcgc ctgcgtgacc tccccgccgg cgggatgtgg    240
cgactacgtc gggccgctgt ggcctgatgc ccatggccaa cctcctactc ctcattgtac    300
ccattctaat cgcaatggca ttcctaatgc ttaccgaacg aaaaattcta ggctatatgc    360
aactacgcaa aggccccaac gttgtaggcc cctacgggct actacaaccc ttcgctgacg    420
ccatgaaact cttcaccaaa gagcccctaa aacccgccac atctaccatc accctctaca    480
tcaccgcccc gaccttagct ctcaccatcg ctcttctact atggaccccc ctccccatgc    540 ccaacccccct ggtcaacctc aacctaggcc tcctatttat tctagccacc tctagcctag    600
ccgtttactc aatcctctgg tcagggtggg catcaaactc aaactacgcc ctgatcggcg    660
cactgcgagc agtagcccaa acaatctcat atgaagtcac cctagccatc attctactat    720
caacattact aatgagtggc tcctttaacc tctccaccct tatcacaaca caagaacacc    780
tctggttact cctgccatca tggcccttgg ccatgatgtg gtttatctcc acactagcag    840
agaccaaccg aaccccccttc gaccttgccg aaggggagtc cgaactagtc tcaggcttca    900
acatcgaata cgccgcaggc cccttcgccc tattcttcat ggccgaatac acaaacatta    960
ttatgatgaa caccctcacc actacaatct tcctaggaac aacatatgac gcactctccc   1020
ctgaactcta cacaacatat tttgtcacca agaccctact tctaacctcc ctgttcttat   1080
ggattcgaac agcataccc cgattccgct acgaccaact catgcacctc ctatggaaaa    1140
acttcctacc actcacccta gcattactta tgtggtatgt ctccatgccc attacaatct   1200
ccagcattcc ccctcaaacc taagagcact gggacgccca ccgccccttt ccctccgctg    1260
ccaggcgagc atgttgtggt aattctggaa cacaagaaga gaaattgctg ggtttagaac   1320
```

| aagattataa acgaattcgg tgctcagtga tcacttgaca gtttttttt tttttaaata | 1380 |
| ttacccaaaa tgctccccaa ataagaaatg catcagctca gtcagtgaat acaaaaaagg | 1440 |
| aattattttt cccttgagg gtcttttata catctctcct ccaaccccac cctctattct | 1500 |
| gtttcttcct cctcacatgg gggtacacat acacagcttc ctctttggt tccatcctta | 1560 |
| ccaccacacc acacgcacac tccacatgcc cagcagagtg gcacttggtg gccagaaagt | 1620 |
| gtgagcctca tgatctgctg tctgtagttc tgtgagctca ggtccctcaa aggcctcgga | 1680 |
| gcacccctt ccttgtgact gagccagggc ctgcattttt ggttttcccc accccacaca | 1740 |
| ttctcaacca tagtccttct aacaatacca atagctagga cccggctgct gtgcactggg | 1800 |
| actggggatt ccacatgttt gccttgggag tctcaagctg gactgccagc cctgtcctc | 1860 |
| ccttcacccc cattgcgtat gagcatttca gaactccaag gagtcacagg catctttata | 1920 |
| gttcacgtta acatatagac actgttggaa gcagttcctt ctaaagggt agccctggac | 1980 |
| ttaataccag ccggatacct ctggccccca ccccattact gtacctctgg agtcactact | 2040 |
| gtgggtcgcc actcctctgc tacacagcac ggcttttca aggctgtatt gagaagggaa | 2100 |
| gttaggaaga agggtgtgct gggctaacca gcccacagag ctcacattcc tgtcccttgg | 2160 |
| gtgaaaaata catgtccatc ctgatatctc ctgaattcag aaattagcct ccacatgtgc | 2220 |
| aatggcttta agagccagaa gcagggttct gggaattttg caagttacct gtggccaggt | 2280 |
| gtggtctcgg ttaccaaata cggttacctg cagcttttta gtcctttgtg ctcccacggg | 2340 |
| tctacagagt cccatctgcc caaggtctt gaagcttgac aggatgttt cgattactca | 2400 |
| gtctcccagg gcactactgg tccgtaggat tcgattggtc ggggtaggag agttaaacaa | 2460 |
| catttaaaca gagttctctc aaaaatgtct aaagggattg taggtagata acatccaatc | 2520 |
| actgtttgca cttatctgaa atcttccctc ttggctgccc ccaggtattt actgtggaga | 2580 |
| acattgcata ggaatgtctg gaaaaagctt ctacaacttg ttacagcctt cacatttgta | 2640 |
| gaagcttt | 2648 |

<210> SEQ ID NO 82
<211> LENGTH: 1848
<212> TYPE: DNA
<213> ORGANISM: Artificial Sequence
<220> FEATURE:
<223> OTHER INFORMATION: OPA1-ND1-3'UTR*

<400> SEQUENCE: 82

| gtgctgcccg cctagaaagg gtgaagtggt tgtttccgtg acggactgag tacgggtgcc | 60 |
| tgtcaggctc ttgcggaagt ccatgcgcca ttgggagggc ctcggccgcg gctctgtgcc | 120 |
| cttgctgctg agggccactt cctgggtcat tcctggaccg ggagccgggc tggggctcac | 180 |
| acggggctc ccgcgtggcc gtctcggcgc ctgcgtgacc tccccgccgg cgggatgtgg | 240 |
| cgactacgtc gggccgctgt ggcctgatgc ccatggccaa cctcctactc ctcattgtac | 300 |
| ccattctaat cgcaatggca ttcctaatgc ttaccgaacg aaaaattcta ggctatatgc | 360 |
| aactacgcaa aggccccaac gttgtaggcc cctacgggct actacaaccc ttcgctgacg | 420 |
| ccatgaaact cttcaccaaa gagccctaa aacccgccac atctaccatc accctctaca | 480 |
| tcaccgcccc gaccttagct ctcaccatcg ctcttctact atggacccc ctccccatgc | 540 |
| ccaacccct ggtcaacctc aacctaggcc tcctatttat tctagccacc tctagcctag | 600 |
| ccgtttactc aatcctctgg tcagggtggg catcaaactc aaactacgcc ctgatcggcg | 660 |
| cactgcgagc agtagcccaa acaatctcat atgaagtcac cctagccatc attctactat | 720 |

```
caacattact aatgagtggc tcctttaacc tctccaccct tatcacaaca caagaacacc      780
tctggttact cctgccatca tggcccttgg ccatgatgtg gtttatctcc acactagcag      840
agaccaaccg aaccccttc gaccttgccg aaggggagtc cgaactagtc tcaggcttca       900
acatcgaata cgccgcaggc cccttcgccc tattcttcat ggccgaatac acaaacatta     960
ttatgatgaa caccctcacc actacaatct tcctaggaac aacatatgac gcactctccc    1020
ctgaactcta cacaacatat tttgtcacca agaccctact tctaacctcc ctgttcttat    1080
ggattcgaac agcataccccc cgattccgct acgaccaact catgcacctc ctatggaaaa   1140
acttcctacc actcacccta gcattactta tgtggtatgt ctccatgccc attacaatct    1200
ccagcattcc ccctcaaacc taagagcact gggacgccca ccgccccttt ccctccgctg    1260
ccaggcgagc atgttgtggt aattctggaa cacaagaaga gaaattgctg ggtttagaac    1320
aagattataa acgaattcgg tgctcagtga tcacttgaca gtttttttt ttttaaata     1380 ttacccaaaa tgctccccaa ataagaaatg catcagctca gtcagtgaat acaaaaaagg    1440 aattatttt cccttgagg gtctttata catctctcct ccaaccccac cctctattct      1500
gtttcttcct cctcacatgg gggtacacat acacagcttc ctcttttggt tccatcctta    1560
ccaccacacc acacgcacac tccacatgcc cagcagagtg gcacttggtg gccagaaagt    1620
gtgagcctca tgatctgctg tctgtagttc tgtgagctca ggtccctcaa aggcctcgga    1680
gcaccccctt ccttgtgact gagccagggc ctgcattttt ggttttcccc accccacaca    1740
ttctcaacca tagtccttct aacaatacca atagctagga cccggctgct gtgcactggg    1800
actggggatt ccacatgttt gccttgggag tctcaagctg gactgcca                 1848

<210> SEQ ID NO 83
<211> LENGTH: 2648
<212> TYPE: DNA
<213> ORGANISM: Artificial Sequence
<220> FEATURE:
<223> OTHER INFORMATION: OPA1-opt_ND1-3'UTR

<400> SEQUENCE: 83
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc     120
cttgctgctg agggccactt cctgggtcat tcctggaccg ggagccgggc tggggctcac     180 acggggctc ccgcgtggcc gtctcggcgc ctgcgtgacc tccccgccgg cgggatgtgg     240
cgactacgtc gggccgctgt ggcctgatgc ccatggccaa cctgctgctg ctgatcgtgc     300
ccatcctgat cgccatggcc ttcctgatgc tgaccgagcg caagatcctg gctacatgc      360 agctgcgcaa gggccccaac gtggtgggcc ctacggcct gctgcagccc ttcgccgacg    420
ccatgaagct gttcaccaag gagcccctga gcccgccac cagcaccatc accctgtaca     480
tcaccgcccc caccctggcc ctgaccatcc cctgctgct gtgaccccc ctgcccatgc      540 ccaaccccct ggtgaacctg aacctgggcc tgctgttcat cctggccacc agcagcctgg    600
ccgtgtacag catcctgtgg agcggctggg ccagcaacag caactacgcc ctgatcggcg    660
ccctgcgcgc cgtggcccag accatcagct acgaggtgac cctggccatc atcctgctga    720
gcaccctgct gatgagcggc agcttcaacc tgagcaccct gatcaccacc caggagcacc    780
tgtggctgct gctgcccagc tggccccctgg ccatgatgtg gttcatcagc accctggccg   840
agaccaaccg caccccttc gacctggccg agggcgagag cgagctggtg agcggcttca     900
```

| | |
|---|---:|
| acatcgagta cgccgccggc cccttcgccc tgttcttcat ggccgagtac accaacatca | 960 |
| tcatgatgaa caccctgacc accaccatct tcctgggcac cacctacgac gccctgagcc | 1020 |
| ccgagctgta caccacctac ttcgtgacca agaccctgct gctgaccagc ctgttcctgt | 1080 |
| ggatccgcac cgcctacccc cgcttccgct acgaccagct gatgcacctg ctgtggaaga | 1140 |
| acttcctgcc cctgaccctg gccctgctga tgtggtacgt gagcatgccc atcaccatca | 1200 |
| gcagcatccc ccccagacc taagagcact gggacgccca ccgccccttt ccctccgctg | 1260 |
| ccaggcgagc atgttgtggt aattctggaa cacaagaaga gaaattgctg ggtttagaac | 1320 |
| aagattataa acgaattcgg tgctcagtga tcacttgaca gtttttttt tttttaaata | 1380 |
| ttacccaaaa tgctccccaa ataagaaatg catcagctca gtcagtgaat acaaaaaagg | 1440 |
| aattattttt ccctttgagg gtctttata catctctcct ccaacccac cctctattct | 1500 |
| gtttcttcct cctcacatgg gggtacacat acacagcttc ctcttttggt tccatcctta | 1560 |
| ccaccacacc acacgcacac tccacatgcc cagcagagtg gcacttggtg gccagaaagt | 1620 |
| gtgagcctca tgatctgctg tctgtagttc tgtgagctca ggtccctcaa aggcctcgga | 1680 |
| gcaccccctt ccttgtgact gagccagggc ctgcattttt ggttttcccc accccacaca | 1740 |
| ttctcaacca tagtccttct aacaatacca atagctagga cccggctgct gtgcactggg | 1800 |
| actggggatt ccacatgttt gccttgggag tctcaagctg gactgccagc ccctgtcctc | 1860 |
| ccttcacccc cattgcgtat gagcatttca gaactccaag gagtcacagg catctttata | 1920 |
| gttcacgtta acatatagac actgttggaa gcagttcctt ctaaagggt agccctggac | 1980 |
| ttaataccag ccggatacct ctggccccca cccattact gtacctctgg agtcactact | 2040 |
| gtgggtcgcc actcctctgc tacacagcac ggcttttca aggctgtatt gagaagggaa | 2100 |
| gttaggaaga agggtgtgct gggctaacca gcccacagag ctcacattcc tgtcccttgg | 2160 |
| gtgaaaaata catgtccatc ctgatatctc ctgaattcag aaattagcct ccacatgtgc | 2220 |
| aatggcttta agagccagaa gcagggttct gggaattttg caagttacct gtggccaggt | 2280 |
| gtggtctcgg ttaccaaata cggttacctg cagcttttta gtcctttgtg ctcccacggg | 2340 |
| tctacagagt cccatctgcc caaaggtctt gaagcttgac aggatgtttt cgattactca | 2400 |
| gtctcccagg gcactactgg tccgtaggat tcgattggtc ggggtaggag agttaaacaa | 2460 |
| catttaaaca gagttctctc aaaaatgtct aaagggattg taggtagata acatccaatc | 2520 |
| actgtttgca cttatctgaa atcttccctc ttggctgccc ccaggtattt actgtggaga | 2580 |
| acattgcata ggaatgtctg gaaaagctt ctacaacttg ttacagccctt cacatttgta | 2640 |
| gaagcttt | 2648 |

<210> SEQ ID NO 84
<211> LENGTH: 1848
<212> TYPE: DNA
<213> ORGANISM: Artificial Sequence
<220> FEATURE:
<223> OTHER INFORMATION: OPA1-opt_ND1-3'UTR*

<400> SEQUENCE: 84

| | |
|---|---:|
| gtgctgcccg cctagaaagg gtgaagtggt tgtttccgtg acggactgag tacgggtgcc | 60 |
| tgtcaggctc ttgcggaagt ccatgcgcca ttgggagggc ctcggccgcg gctctgtgcc | 120 |
| cttgctgctg agggccactt cctgggtcat tcctggaccg ggagccgggc tggggctcac | 180 |
| acggggctc ccgcgtggcc gtctcggcgc ctgcgtgacc tccccgccgg cgggatgtgg | 240 |
| cgactacgtc gggccgctgt ggcctgatgc ccatggccaa cctgctgctg ctgatcgtgc | 300 |

-continued

```
ccatcctgat cgccatggcc ttcctgatgc tgaccgagcg caagatcctg ggctacatgc      360
agctgcgcaa gggccccaac gtggtgggcc cctacggcct gctgcagccc ttcgccgacg      420
ccatgaagct gttcaccaag gagcccctga agcccgccac cagcaccatc accctgtaca      480
tcaccgcccc cacctggcc ctgaccatcg ccctgctgct gtggacccc ctgcccatgc        540 ccaaccccct ggtgaacctg aacctgggcc tgctgttcat cctggccacc agcagcctgg      600
ccgtgtacag catcctgtgg agcggctggg ccagcaacag caactacgcc ctgatcggcg      660
ccctgcgcgc cgtggcccag accatcagct acgaggtgac cctggccatc atcctgctga      720
gcaccctgct gatgagcggc agcttcaacc tgagcaccct gatcaccacc caggagcacc      780
tgtggctgct gctgcccagc tggcccctgg ccatgatgtg gttcatcagc accctggccg      840
agaccaaccg cacccccttc gacctggccg agggcgagag cgagctggtg agcggcttca      900
acatcgagta cgccgccggc cccttcgccc tgttcttcat ggccgagtac accaacatca      960
tcatgatgaa caccctgacc accaccatct tcctgggcac cacctacgac gccctgagcc     1020
ccgagctgta caccacctac ttcgtgacca agaccctgct gctgaccagc ctgttcctgt     1080
ggatccgcac cgcctacccc cgcttccgct acgaccagct gatgcacctg ctgtggaaga     1140
acttcctgcc cctgaccctg gccctgctga tgtggtacgt gagcatgccc atcaccatca     1200
gcagcatccc ccccagacc taagagcact gggacgccca ccgccccttt ccctccgctg      1260
ccaggcgagc atgttgtggt aattctggaa cacaagaaga gaaattgctg ggtttagaac     1320
aagattataa acgaattcgg tgctcagtga tcacttgaca gttttttttt tttttaaata     1380
ttacccaaaa tgctccccaa ataagaaatg catcagctca gtcagtgaat acaaaaaagg     1440
aattattttt ccctttgagg gtcttttata catctctcct ccaaccccac cctctattct     1500
gtttcttcct cctcacatgg gggtacacat acacagcttc ctcttttggt tccatcctta     1560
ccaccacacc acacgcacac tccacatgcc cagcagagtg gcacttggtg gccagaaagt     1620
gtgagcctca tgatctgctg tctgtagttc tgtgagctca ggtccctcaa aggcctcgga     1680
gcaccccctt ccttgtgact gagccagggc ctgcattttt ggttttcccc accccacaca     1740
ttctcaacca tagtccttct aacaatacca atagctagga cccggctgct gtgcactggg     1800
actggggatt ccacatgttt gccttgggag tctcaagctg gactgcca                 1848
```

<210> SEQ ID NO 85
<211> LENGTH: 18
<212> TYPE: DNA
<213> ORGANISM: Artificial Sequence
<220> FEATURE:
<223> OTHER INFORMATION: beta-actin-S primer

<400> SEQUENCE: 85
cgagatcgtg cgggacat                                                    18

<210> SEQ ID NO 86
<211> LENGTH: 19
<212> TYPE: DNA
<213> ORGANISM: Artificial Sequence
<220> FEATURE:
<223> OTHER INFORMATION: beta-actin-A primer

<400> SEQUENCE: 86
caggaaggag ggctggaac                                                   19

<210> SEQ ID NO 87

```
<211> LENGTH: 19
<212> TYPE: DNA
<213> ORGANISM: Artificial Sequence
<220> FEATURE:
<223> OTHER INFORMATION: ND4-S primer

<400> SEQUENCE: 87
ctgcctacga caaacagac                                                       19

<210> SEQ ID NO 88
<211> LENGTH: 19
<212> TYPE: DNA
<213> ORGANISM: Artificial Sequence
<220> FEATURE:
<223> OTHER INFORMATION: ND4-A primer

<400> SEQUENCE: 88
agtgcgttcg tagtttgag                                                       19

<210> SEQ ID NO 89
<211> LENGTH: 21
<212> TYPE: DNA
<213> ORGANISM: Artificial Sequence
<220> FEATURE:
<223> OTHER INFORMATION: ND6-F primer

<400> SEQUENCE: 89
atgatgtatg ctttgtttct g                                                    21

<210> SEQ ID NO 90
<211> LENGTH: 21
<212> TYPE: DNA
<213> ORGANISM: Artificial Sequence
<220> FEATURE:
<223> OTHER INFORMATION: ND6-R primer

<400> SEQUENCE: 90
ctaattcccc cgagcaatct c                                                    21

<210> SEQ ID NO 91
<211> LENGTH: 18
<212> TYPE: DNA
<213> ORGANISM: Artificial Sequence
<220> FEATURE:
<223> OTHER INFORMATION: ND6-S primer

<400> SEQUENCE: 91
agtgtgggtt tagtaatg                                                        18

<210> SEQ ID NO 92
<211> LENGTH: 18
<212> TYPE: DNA
<213> ORGANISM: Artificial Sequence
<220> FEATURE:
<223> OTHER INFORMATION: ND6-A  primer

<400> SEQUENCE: 92
tgcctcagga tactcctc                                                        18

<210> SEQ ID NO 93
<211> LENGTH: 20
<212> TYPE: DNA
<213> ORGANISM: Artificial Sequence
<220> FEATURE:
<223> OTHER INFORMATION: beta-actin-F primer

<400> SEQUENCE: 93
```

```
ctccatcctg gcctcgctgt                                               20

<210> SEQ ID NO 94
<211> LENGTH: 20
<212> TYPE: DNA
<213> ORGANISM: Artificial Sequence
<220> FEATURE:
<223> OTHER INFORMATION: beta-actin-R primer

<400> SEQUENCE: 94
gctgtcacct tcaccgttcc                                               20

<210> SEQ ID NO 95
<211> LENGTH: 23
<212> TYPE: DNA
<213> ORGANISM: Artificial Sequence
<220> FEATURE:
<223> OTHER INFORMATION: ND6-F primer

<400> SEQUENCE: 95
gggttttctt ctaagccttc tcc                                           23

<210> SEQ ID NO 96
<211> LENGTH: 23
<212> TYPE: DNA
<213> ORGANISM: Artificial Sequence
<220> FEATURE:
<223> OTHER INFORMATION: ND6-R primer

<400> SEQUENCE: 96
ccatcatact ctttcaccca cag                                           23

<210> SEQ ID NO 97
<211> LENGTH: 20
<212> TYPE: DNA
<213> ORGANISM: Artificial Sequence
<220> FEATURE:
<223> OTHER INFORMATION: opt_ND6-F primer

<400> SEQUENCE: 97
cgcctgctga ccggctgcgt                                               20

<210> SEQ ID NO 98
<211> LENGTH: 20
<212> TYPE: DNA
<213> ORGANISM: Artificial Sequence
<220> FEATURE:
<223> OTHER INFORMATION: opt_ND6-R

<400> SEQUENCE: 98
ccaggcctcg gggtactcct                                               20

<210> SEQ ID NO 99
<211> LENGTH: 21
<212> TYPE: DNA
<213> ORGANISM: Artificial Sequence
<220> FEATURE:
<223> OTHER INFORMATION: ND1-F primer

<400> SEQUENCE: 99
atggccgcat ctccgcacac t                                             21

<210> SEQ ID NO 100
<211> LENGTH: 21
<212> TYPE: DNA
```

```
<213> ORGANISM: Artificial Sequence
<220> FEATURE:
<223> OTHER INFORMATION: ND1-R primer

<400> SEQUENCE: 100
ttaggtttga gggggaatgc t                                              21

<210> SEQ ID NO 101
<211> LENGTH: 21
<212> TYPE: DNA
<213> ORGANISM: Artificial Sequence
<220> FEATURE:
<223> OTHER INFORMATION: ND1-F primer

<400> SEQUENCE: 101
aacctcaacc taggcctcct a                                              21

<210> SEQ ID NO 102
<211> LENGTH: 21
<212> TYPE: DNA
<213> ORGANISM: Artificial Sequence
<220> FEATURE:
<223> OTHER INFORMATION: ND1-R primer

<400> SEQUENCE: 102
tggcaggagt aaccagaggt g                                              21

<210> SEQ ID NO 103
<211> LENGTH: 23
<212> TYPE: DNA
<213> ORGANISM: Artificial Sequence
<220> FEATURE:
<223> OTHER INFORMATION: ND1-F primer

<400> SEQUENCE: 103
aggaggctct gtctggtatc ttg                                            23

<210> SEQ ID NO 104
<211> LENGTH: 21
<212> TYPE: DNA
<213> ORGANISM: Artificial Sequence
<220> FEATURE:
<223> OTHER INFORMATION: ND1-R primer

<400> SEQUENCE: 104
ttttaggggc tctttggtga a                                              21

<210> SEQ ID NO 105
<211> LENGTH: 22
<212> TYPE: DNA
<213> ORGANISM: Artificial Sequence
<220> FEATURE:
<223> OTHER INFORMATION: opt-ND1-F primer

<400> SEQUENCE: 105
gccgcctgct gaccggctgc gt                                             22

<210> SEQ ID NO 106
<211> LENGTH: 24
<212> TYPE: DNA
<213> ORGANISM: Artificial Sequence
<220> FEATURE:
<223> OTHER INFORMATION: opt-ND1-R primer

<400> SEQUENCE: 106
tgatgtacag ggtgatggtg ctgg                                           24
```

<210> SEQ ID NO 107
<211> LENGTH: 19
<212> TYPE: DNA
<213> ORGANISM: Artificial Sequence
<220> FEATURE:
<223> OTHER INFORMATION: ND4-S primer

<400> SEQUENCE: 107
gccaacagca actacgagc                                                    19

<210> SEQ ID NO 108
<211> LENGTH: 20
<212> TYPE: DNA
<213> ORGANISM: Artificial Sequence
<220> FEATURE:
<223> OTHER INFORMATION: ND4-A  primer

<400> SEQUENCE: 108
tgatgttgct ccagctgaag                                                   20

<210> SEQ ID NO 109
<211> LENGTH: 20
<212> TYPE: DNA
<213> ORGANISM: Artificial Sequence
<220> FEATURE:
<223> OTHER INFORMATION: opt-ND4-S primer

<400> SEQUENCE: 109
gcctgaccct gatcctgaac                                                   20

<210> SEQ ID NO 110
<211> LENGTH: 20
<212> TYPE: DNA
<213> ORGANISM: Artificial Sequence
<220> FEATURE:
<223> OTHER INFORMATION: opt-ND4-A primer

<400> SEQUENCE: 110
gtgcgctcgt agttgctgtt                                                   20

<210> SEQ ID NO 111
<211> LENGTH: 376
<212> TYPE: DNA
<213> ORGANISM: Homo sapiens

<400> SEQUENCE: 111
gggcagtgcc tccccgcccc gccgctggcg tcaagttcag ctccacgtgt gccatcagtg         60
gatccgatcc gtccagccat ggcttcctat tccaagatgg tgtgaccaga catgcttcct        120 gctcccogct tagcccacgg agtgactgtg gttgtggtgg ggggttctt aaaataactt         180 tttagcccoc gtcttcctat tttgagtttg gttcagatct taagcagctc catgcaactg        240
tatttatttt tgatgacaag actcccatct aaagtttttc tcctgcctga tcatttcatt        300
ggtggctgaa ggattctaga gaacctttg ttcttgcaag gaaaacaaga atccaaaacc         360
agtgactgtt ctgtga                                                       376

<210> SEQ ID NO 112
<211> LENGTH: 146
<212> TYPE: DNA
<213> ORGANISM: Homo sapiens

<400> SEQUENCE: 112

-continued

```
gggGtcttTG tcctctgtac tgtctctctc cttgcccctA acccaaaaag cttcattttt    60
ctgtgtaggc tgcacaagag ccttgattga agatatattc tttctgaaca gtatttaagg   120
tttccaataa aatgtacacc cctcag                                        146

<210> SEQ ID NO 113
<211> LENGTH: 1956
<212> TYPE: DNA
<213> ORGANISM: Homo sapiens

<400> SEQUENCE: 113
tgttgggtcc aagaaggaat ttctttccat ccctgtgagg caatgggtgg gaatgatagg    60
acaggcaaag agaagcttcc tcaggctagc aaaaatatca tttgatgtat tgattaaaaa   120
agcacttgct tgatgtatct ttggcgtgtg tgctactctc atctgtgtgt atgtgtgttg   180
tgtgtgtgtg tgtgtgcatg cacatatgtg ttcactctgc tactttgtaa gttttaggct   240
aggttgcttt accagctgtt tacttctttt ttgttgttgt tttgagacaa ggtttcgctc   300
tgccaccctg gctggagtgc agtggcgtga tcttggctca cggcaacctc tgcctcctgg   360
ggctcaagca attatcccac ctcagcctcc tgagcagctg ggactacagg tgcatgccac   420
aacacctggc tgatatttgt attttttgta gagacaggat tttgccaagt tgcccaggct   480
ggtcttgaac tcctaggctt aagcaatcca cccaccttgg cctcctgaag tgccaggatc   540
acagacgtga gccactacac ccagcccagc tgtttacttc tttaaccata cttttgattt   600
tattttttga ccaaaatgaa ctaacccagg taatcttcca gggaccgcaa ttccagaacc   660
tcatagtatt tcttccattt ccagcagctg attagaagtc caggatcatg tgaagtcagg   720
cagggtcaca gttcctgatg gcacattatg acagagaat tccatttgt tttctaaccc    780 atgatgaaaa cccacgtgag tcagtgtgtg aacagggatc attaattttt tccccctagg   840
tggaaggaaa aaggcactta ctttgcaggt tacagaaatt actgggagag gatatcgtca   900 taaaagagc caggccaaat tggaatattt ttgtgatctg catcatgatg ctgaaaatag    960
caattatttg ggaattgggt ttgaaaactg aattgttgcc agagaattaa accaggtgaa  1020
aggtcctttt gaattcagat tgtcttctga acatccaggc tgatcatctg agagcagtca  1080
aatctacttc cccaaaaaga gaccagggta ggtttatttg cttttatttt taatgtttgc  1140 ctgtgttttcc aagtgtgaac aaaacagtgt gtgatctatt cttggattca ttttgatcag  1200
tatttattca aacccagtct ctctccagga cataaaactg aaatcagata tgttcttttt   1260
aagcccaaac cctctccttt ctagatccaa cccttcaccc ctaattttat gatggctata  1320
gccatggact tccccaagaa aagatcaccc agaaataaga ccacctgtga cagttaccag  1380
cttttattca taaccttagc ttcccaacta ttgagcattt tctaaggtcc ctgctgtctt  1440
ttggtctctg gtttgattg tggcaaacag atgaagtaac agactgctat gaaggaccac   1500
aaaaacggca gcctctggaa aaaccattag aaagtcagtg gcagatccag taaataaat   1560 cgccagcctc agcataatct gctgctgact cgattcagtg gactctaaag tgcccagcct  1620
cctgacctga gctctcctgc catctgtgag actaccagag gtcttatctg ctgtccacat  1680
ggcaactggg catgagtacc tggccacctt gcttccctct ttgcctggtc caagtgagtg  1740
tctgctgcct ctgtcctgcc ttgttttcct ggctctaaac caactccacc cactcttaat  1800
ggaaactcag tctggctttg tgtgtttctg ggaagcacat gacttctggg aatgggcaag  1860
gaagaggagt gaaacaaaaa ctgtcagcta tgtgtgcctg gtctgggatc cttctctggg  1920
tgacagtggc atcatgaatc ttagaatcag ctcccc                             1956
```

<210> SEQ ID NO 114
<211> LENGTH: 411
<212> TYPE: DNA
<213> ORGANISM: Homo sapiens

<400> SEQUENCE: 114

| | | | | | | |
|---|---|---|---|---|---|---|
| gaatcatgca | agcttcctcc | ctcagccatt | gatggaaagt | tcagcaagat | cagcaacaaa | 60 |
| accaagaaaa | atgatccttg | cgtgctgaat | atctgaaaag | agaaattttt | cctacaaaat | 120 |
| ctcttgggtc | aagaaagttc | tagaatttga | attgataaac | atggtgggtt | ggctgagggt | 180 |
| aagagtatat | gaggaacctt | ttaaacgaca | acaatactgc | tagcttttcag | gatgattttt | 240 |
| aaaaaataga | ttcaaatgtg | ttatcctctc | tctgaaacgc | ttcctataac | tcgagtttat | 300 |
| aggggaagaa | aaagctattg | tttacaatta | tatcaccatt | aaggcaactg | ctacaccctg | 360 |
| ctttgtattc | tgggctaaga | ttcattaaaa | actagctgct | cttaacttac | a | 411 |

<210> SEQ ID NO 115
<211> LENGTH: 1465
<212> TYPE: DNA
<213> ORGANISM: Homo sapiens

<400> SEQUENCE: 115

| | | | | | | |
|---|---|---|---|---|---|---|
| gagcactggg | acgcccaccg | cccctttccc | tccgctgcca | ggcgagcatg | ttgtggtaat | 60 |
| tctggaacac | aagaagagaa | attgctgggt | ttagaacaag | attataaacg | aattcggtgc | 120 |
| tcagtgatca | cttgacagtt | tttttttttt | ttaaatatta | cccaaaatgc | tccccaaata | 180 |
| agaaatgcat | cagctcagtc | agtgaataca | aaaaggaat | tattttttccc | tttgagggtc | 240 |
| tttatacatc | tctcctccaa | ccccaccctc | tattctgttt | cttcctcctc | acatgggggt | 300 |
| acacatacac | agcttcctct | tttggttcca | tccttaccac | cacaccacac | gcacactcca | 360 |
| catgcccagc | agagtggcac | ttggtggcca | gaaagtgtga | gcctcatgat | ctgctgtctg | 420 |
| tagttctgtg | agctcaggtc | cctcaaaggc | ctcggagcac | cccctttcctg | gtgactgagc | 480 |
| cagggcctgc | atttttggtt | ttccccaccc | cacacattct | caaccatagt | ccttctaaca | 540 |
| ataccaatag | ctaggacccg | gctgctgtgc | actgggactg | gggattccac | atgtttgcct | 600 |
| tgggagtctc | aagctggact | gccagcccct | gtcctccctt | caccccccatt | gcgtatgagc | 660 |
| atttcagaac | tccaaggagt | cacaggcatc | tttatagttc | acgttaacat | atagacactg | 720 |
| ttggaagcag | ttccttctaa | aagggtagcc | ctggacttaa | taccagccgg | atacctctgg | 780 |
| ccccccacccc | attactgtac | ctctggagtc | actactgtgg | gtcgccactc | ctctgctaca | 840 |
| cagcacggct | ttttcaaggc | tgtattgaga | agggaagtta | ggaagaaggg | tgtgctgggc | 900 |
| taaccagccc | acagagctca | cattcctgtc | ccttgggtga | aaaatacatg | tccatcctga | 960 |
| tatctcctga | attcagaaat | tagcctccac | atgtgcaatg | ctttaagag | ccagaagcag | 1020 |
| ggttctggga | attttgcaag | ttatcctgtg | gccaggtgtg | gtctcggtta | ccaaatacgg | 1080 |
| ttacctgcag | cttttttagtc | ctttgtgctc | ccacgggtct | gcagagtccc | atctgcccaa | 1140 |
| aggtcttgaa | gcttgacagg | atgttttcat | tactcagtct | cccagggcac | tgctggtccg | 1200 |
| tagggattca | ttggtcgggg | tgggagagtt | aaacaacatt | taaacagagt | tctctcaaaa | 1260 |
| atgtctaaag | ggattgtagg | tagataacat | ccaatcactg | tttgcactta | tctgaaatct | 1320 |
| tccctcttgg | ctgcccccag | gtattactg | tggagaacat | tgcataggaa | tgtctggaaa | 1380 |
| aagcctctac | aacttgttac | agccttcaca | tttgtacaat | tcattgattc | tcttttcctt | 1440 |

-continued

| | |
|---|---|
| ccacaataaa atggtataca agaac | 1465 |

<210> SEQ ID NO 116
<211> LENGTH: 288
<212> TYPE: DNA
<213> ORGANISM: Homo sapiens

<400> SEQUENCE: 116

| | |
|---|---|
| gagacttgga ctcaagtcat aggcttcttt cagtctttat gtcacctcag gagacttatt | 60 |
| tgagaggaag ccttctgtac ttgaagttga tttgaaatat gtaagaattg atgatgtatt | 120 |
| tgcaaacatt aatgtgaaat aaattgaatt taatgttgaa actttcagg cattcactta | 180 |
| ataaagacac tgttaagcac tgttatgctc agtcatacac gcgaaaggta caatgtcttt | 240 |
| tagctaattc taattaaaaa ttacagactg gtgtacaaga tacttgtg | 288 |

<210> SEQ ID NO 117
<211> LENGTH: 83
<212> TYPE: DNA
<213> ORGANISM: Homo sapiens

<400> SEQUENCE: 117

| | |
|---|---|
| cccaccaccc tggcctgctg tcctgcgtct atccatgtgg aatgctggac aataaagcga | 60 |
| gtgctgccca ccctccagct gcc | 83 |

<210> SEQ ID NO 118
<211> LENGTH: 66
<212> TYPE: DNA
<213> ORGANISM: Homo sapiens

<400> SEQUENCE: 118

| | |
|---|---|
| tttatattga actgtaaata tgtcactaga gaaataaaat atggacttcc aatctacgta | 60 |
| aactta | 66 |

<210> SEQ ID NO 119
<211> LENGTH: 214
<212> TYPE: DNA
<213> ORGANISM: Homo sapiens

<400> SEQUENCE: 119

| | |
|---|---|
| accacgatcg ttatgctgag tatgttaagc tctttatgac tgtttttgta gtggtataga | 60 |
| gtactgcaga atacagtaag ctgctctatt gtagcatttc ttgatgttgc ttagtcactt | 120 |
| atttcataaa caacttaatg ttctgaataa tttcttacta aacattttgt tattgggcaa | 180 |
| gtgattgaaa atagtaaatg ctttgtgtga ttga | 214 |

<210> SEQ ID NO 120
<211> LENGTH: 286
<212> TYPE: DNA
<213> ORGANISM: Homo sapiens

<400> SEQUENCE: 120

| | |
|---|---|
| tcttggaata taaagaattt cttcaggttg aattacctag aagtttgtca ctgacttgtg | 60 |
| ttcctgaact atgacacatg aatatgtggg ctaagaaata gttcctcttg ataaataaac | 120 |
| aattaacaaa tactttggac agtaagtctt tctcagttct taatgataat gcagggcact | 180 |
| tactagcata agaattggtt tgggatttaa ctgtttatga agctaacttg atttccgtgt | 240 |
| tttgttaaaa tttcattgtt ctagcacatc tttaactgtg atagtt | 286 |

<210> SEQ ID NO 121
<211> LENGTH: 721
<212> TYPE: DNA
<213> ORGANISM: Homo sapiens

<400> SEQUENCE: 121

| | | | | | |
|---|---|---|---|---|---|
| gagacgtgca | cttggtcgtg | cgcccaggga | ggaagccgca | ccaccagcca | gcgcaggccc | 60 |
| tggtggagag | gcctccctgg | ctgcctctgg | gaggggtgct | gccttgtaga | tggagcaagt | 120 |
| gagcactgag | ggtctggtgc | caatcctgta | ggcacaaaac | cagaagtttc | tacattctct | 180 |
| atttttgtta | atcatcttct | cttttttccag | aatttggaag | ctagaatggt | gggaatgtca | 240 |
| gtagtgccag | aaagagagaa | ccaagcttgt | ctttaaagtt | actgatcaca | ggacgttgct | 300 |
| ttttcactgt | ttcctattaa | tcttcagctg | aacacaagca | aaccttctca | ggaggtgtct | 360 |
| cctaccctct | tattgttcct | cttacgctct | gctcaatgaa | accttcctct | tgagggtcat | 420 |
| tttcctttct | gtattaatta | taccagtgtt | aagtgacata | gataagaact | ttgcacactt | 480 |
| caaatcagag | cagtgattct | ctcttctctc | ccctttttcct | tcagagtgaa | tcatccagac | 540 |
| tcctcatgga | taggtcgggt | gttaaagttg | ttttgattat | gtaccttttg | atagatccac | 600 |
| ataaaaagaa | atgtgaagtt | ttcttttact | atcttttcat | ttatcaagca | gagacctttg | 660 |
| ttgggaggcg | gtttgggaga | acacatttct | aatttgaatg | aaatgaaatc | tattttcagt | 720 |
| g | | | | | | 721 |

<210> SEQ ID NO 122
<211> LENGTH: 163
<212> TYPE: DNA
<213> ORGANISM: Homo sapiens

<400> SEQUENCE: 122

| | | | | | |
|---|---|---|---|---|---|
| cagaagaagt | gacggctggg | ggcacagtgg | gctgggcgcc | cctgcagaac | atgaaccttc | 60 |
| cgctcctggc | tgccacaggg | tcctccgatg | ctggcctttg | cgcctctaga | ggcagccact | 120 |
| catggattca | agtcctggct | ccgcctcttc | catcaggacc | act | | 163 |

<210> SEQ ID NO 123
<211> LENGTH: 60
<212> TYPE: DNA
<213> ORGANISM: Homo sapiens

<400> SEQUENCE: 123

| | | | | | |
|---|---|---|---|---|---|
| agaggacaca | ctctgcaccc | ccccacccca | cgaccttggc | ccgagcccct | ccgtgaggaa | 60 |

<210> SEQ ID NO 124
<211> LENGTH: 65
<212> TYPE: DNA
<213> ORGANISM: Homo sapiens

<400> SEQUENCE: 124

| | | | | | |
|---|---|---|---|---|---|
| agcccttccg | ccaggctgtg | tgtcaggccc | gtggtgggtg | ttttgtagta | gtgtagagca | 60 |
| ttgca | | | | | | 65 |

<210> SEQ ID NO 125
<211> LENGTH: 231
<212> TYPE: DNA
<213> ORGANISM: Homo sapiens

<400> SEQUENCE: 125

| | | | | | |
|---|---|---|---|---|---|
| cttatgttct | gtgcgcattc | tggcaggaat | tctgtctctt | cagagactca | tcctcaaaac | 60 |

```
aagacttgac actgtgtcct tgccccagtc ctaggaactg tggcacacag agatgttcat      120
tttaaaaacg gatttcatga aacactcttg tacttatgtt tataagagag cactgggtag      180
ccaagtgatc ttcccattca cagagttagt aaacctctgt actacatgct g               231
```

<210> SEQ ID NO 126
<211> LENGTH: 28
<212> TYPE: PRT
<213> ORGANISM: Homo sapiens

<400> SEQUENCE: 126

Met Ala Ala Ser Pro His Thr Leu Ser Ser Arg Leu Leu Thr Gly Cys
1               5                   10                  15

Val Gly Gly Ser Val Trp Tyr Leu Glu Arg Arg Thr
            20                  25

<210> SEQ ID NO 127
<211> LENGTH: 29
<212> TYPE: PRT
<213> ORGANISM: Homo sapiens

<400> SEQUENCE: 127

Met Ser Val Leu Thr Arg Leu Leu Leu Arg Gly Leu Thr Arg Leu Gly
1               5                   10                  15

Ser Ala Ala Pro Val Arg Arg Ala Arg Ile His Ser Leu
            20                  25

<210> SEQ ID NO 128
<211> LENGTH: 10
<212> TYPE: PRT
<213> ORGANISM: Homo sapiens

<400> SEQUENCE: 128

Met Trp Arg Leu Arg Arg Ala Ala Val Ala
1               5                   10

<210> SEQ ID NO 129
<211> LENGTH: 28
<212> TYPE: PRT
<213> ORGANISM: Homo sapiens

<400> SEQUENCE: 129

Met Ala Ala Ser Pro His Thr Leu Ser Ser Arg Leu Leu Thr Gly Cys
1               5                   10                  15

Val Gly Gly Ser Val Trp Tyr Leu Glu Arg Arg Thr
            20                  25

<210> SEQ ID NO 130
<211> LENGTH: 122
<212> TYPE: PRT
<213> ORGANISM: Saccharomyces cerevisiae

<400> SEQUENCE: 130

Met Ala Phe Lys Ser Phe Ile Tyr Ser Lys Gly Tyr His Arg Ser Ala
1               5                   10                  15

Ala Gln Lys Lys Thr Ala Thr Ser Phe Phe Asp Ser Ser Tyr Gln Tyr
            20                  25                  30

Leu Arg Gln Asn Gln Gly Leu Val Asn Ser Asp Pro Val Leu His Ala
        35                  40                  45

Ser His Leu His Pro His Pro Val Val Val Ala Asn Val Asn Tyr Asn
    50                  55                  60

-continued

Asn Val Asp Asp Ile Leu His Pro His Asp Leu Asp Ser Ser Ile Asn
 65                  70                  75                  80

Asn Thr Asn Asn Pro Leu Thr His Glu Glu Leu Leu Tyr Asn Gln Asn
             85                  90                  95

Val Ser Leu Arg Ser Leu Lys Gln Gln Gln Ser Thr Asn Tyr Val Asn
            100                 105                 110

Asn Asn Asn Asn Asn Gln His Arg Tyr Tyr
        115                 120

<210> SEQ ID NO 131
<211> LENGTH: 174
<212> TYPE: PRT
<213> ORGANISM: Larimichthys crocea

<400> SEQUENCE: 131

Met Arg Lys Arg Ser Leu Arg Cys His Leu Trp Ser Ala Asn Ala Ser
 1               5                  10                  15

Leu Ser Pro Arg Lys Asp Glu Val Thr Ser Arg Lys Glu Ser Glu Asn
            20                  25                  30

Leu Val Lys Gly Lys Lys Asn Lys Lys Ser His Leu His Leu Leu Leu
         35                  40                  45

Phe Thr Ala Ser Lys Ile Gly Thr Asp Ser Val Phe Asp Val Gln Lys
 50                  55                  60

Ser Lys Glu Cys Cys Lys Glu Leu Gly Leu Leu Phe Thr Ser Leu Ile
 65                  70                  75                  80

His Ser Ile Gly Ser Phe Pro Phe Asp Glu Glu Pro Lys Ala Ala Ala
             85                  90                  95

Val Phe Leu Pro Gly Ser Leu Pro Gln Leu Thr Val Leu Val Leu Ala
            100                 105                 110

Pro Gly Ser Gly Ser Cys Pro Thr Gly Lys Ser Thr Pro His Leu Ala
        115                 120                 125

Ala Ser Gly Arg Asn Ala Glu Leu Leu Arg Pro Gln Asn Ser Met Ile
    130                 135                 140

Val Arg Gln Phe Thr Cys Arg Gly Thr Ile Ser Ser His Leu Cys Ala
145                 150                 155                 160

His Leu Arg Lys Pro His Asp Ser Arg Asn Met Ala Arg Pro
                165                 170

<210> SEQ ID NO 132
<211> LENGTH: 56
<212> TYPE: PRT
<213> ORGANISM: Trypanosoma brucei

<400> SEQUENCE: 132

Met Leu Arg Arg Thr Ser Phe Asn Phe Thr Gly Arg Ala Met Ile Ser
 1               5                  10                  15

Arg Gly Ser Pro Glu Trp Ser His Arg Leu Asp Leu Lys Lys Gly Lys
            20                  25                  30

Lys Thr Thr Met Met His Lys Leu Gly Thr Ser Lys Pro Asn Asn Ala
         35                  40                  45

Leu Gln Tyr Ala Gln Met Thr Leu
 50                  55

<210> SEQ ID NO 133
<211> LENGTH: 46
<212> TYPE: PRT
<213> ORGANISM: Neurospora crassa

<400> SEQUENCE: 133

Met Ile Ser Arg Ser Ala Leu Ser Arg Gly Ser Gln Leu Ala Leu Arg
1               5                   10                  15

Arg Pro Ala Ala Ala Lys Thr Ala Gln Arg Gly Phe Ala Ala Ala Ala
            20                  25                  30

Ala Ser Pro Ala Ala Ser Tyr Glu Pro Thr Thr Ile Ala Gly
        35                  40                  45

<210> SEQ ID NO 134
<211> LENGTH: 128
<212> TYPE: PRT
<213> ORGANISM: Homo sapiens

<400> SEQUENCE: 134

Met Pro Glu Leu Ile Leu Tyr Val Ala Ile Thr Leu Ser Val Ala Glu
1               5                   10                  15

Arg Leu Val Gly Pro Gly His Ala Cys Ala Glu Pro Ser Phe Arg Ser
            20                  25                  30

Ser Arg Cys Ser Ala Pro Leu Cys Leu Leu Cys Ser Gly Ser Ser Ser
        35                  40                  45

Pro Ala Thr Ala Pro His Pro Leu Lys Met Phe Ala Cys Ser Lys Phe
50                  55                  60

Val Ser Thr Pro Ser Leu Val Lys Ser Thr Ser Gln Leu Leu Ser Arg
65                  70                  75                  80

Pro Leu Ser Ala Val Val Leu Lys Arg Pro Glu Ile Leu Thr Asp Glu
                85                  90                  95

Ser Leu Ser Ser Leu Ala Val Ser Cys Pro Leu Thr Ser Leu Val Ser
            100                 105                 110

Ser Arg Ser Phe Gln Thr Ser Ala Ile Ser Arg Asp Ile Asp Thr Ala
        115                 120                 125

<210> SEQ ID NO 135
<211> LENGTH: 115
<212> TYPE: PRT
<213> ORGANISM: Homo sapiens

<400> SEQUENCE: 135

Met Tyr Arg Leu Met Ser Ala Val Thr Ala Arg Ala Ala Pro Gly
1               5                   10                  15

Gly Leu Ala Ser Ser Cys Gly Arg Arg Gly Val His Gln Arg Ala Gly
            20                  25                  30

Leu Pro Pro Leu Gly His Gly Trp Val Gly Leu Gly Leu Gly Leu
        35                  40                  45

Gly Leu Ala Leu Gly Val Lys Leu Ala Gly Gly Leu Arg Gly Ala Ala
50                  55                  60

Pro Ala Gln Ser Pro Ala Ala Pro Asp Pro Glu Ala Ser Pro Leu Ala
65                  70                  75                  80

Glu Pro Pro Gln Glu Gln Ser Leu Ala Pro Trp Ser Pro Gln Thr Pro
                85                  90                  95

Ala Pro Pro Cys Ser Arg Cys Phe Ala Arg Ala Ile Glu Ser Ser Arg
            100                 105                 110

Asp Leu Leu
        115

<210> SEQ ID NO 136
<211> LENGTH: 140
<212> TYPE: PRT

<213> ORGANISM: Schizosaccharomyces pombe

<400> SEQUENCE: 136

Met Thr Val Leu Ala Pro Leu Arg Arg Leu His Thr Arg Ala Ala Phe
1               5                   10                  15

Ser Ser Tyr Gly Arg Glu Ile Ala Leu Gln Lys Arg Phe Leu Asn Leu
            20                  25                  30

Asn Ser Cys Ser Ala Val Arg Arg Tyr Gly Thr Gly Phe Ser Asn Asn
        35                  40                  45

Leu Arg Ile Lys Lys Leu Lys Asn Ala Phe Gly Val Val Arg Ala Asn
    50                  55                  60

Ser Thr Lys Ser Thr Ser Thr Val Thr Thr Ala Ser Pro Ile Lys Tyr
65                  70                  75                  80

Asp Ser Ser Phe Val Gly Lys Thr Gly Gly Glu Ile Phe His Asp Met
                85                  90                  95

Met Leu Lys His Asn Val Lys His Val Phe Gly Tyr Pro Gly Gly Ala
            100                 105                 110

Ile Leu Pro Val Phe Asp Ala Ile Tyr Arg Ser Pro His Phe Glu Phe
        115                 120                 125

Ile Leu Pro Arg His Glu Gln Ala Ala Gly His Ala
    130                 135                 140

<210> SEQ ID NO 137
<211> LENGTH: 125
<212> TYPE: PRT
<213> ORGANISM: Glycine max

<400> SEQUENCE: 137

Met Ile Leu Cys Pro Leu Glu Ala Phe Ile Val Gln His Ile Leu Thr
1               5                   10                  15

Ile Ser Val Met Gly Leu Leu Ser Cys Phe Arg Ser Thr Val Leu Arg
            20                  25                  30

Lys Cys Ser Lys Gly Ser Ser Gly Met Ser Arg Phe Leu Tyr Thr Asn
        35                  40                  45

Asn Phe Gln Arg Asn Leu Ile Ser Ser Gly Asn Glu Ser Tyr Tyr
    50                  55                  60

Gly Tyr Phe Asn Arg Arg Ser Tyr Thr Ser Leu Tyr Met Gly Thr Gly
65                  70                  75                  80

Thr Val Gly Gly Ile Thr Ser Ala Arg Ile Arg Val Pro Asn Val Gly
                85                  90                  95

Cys Glu Gly Phe Met Cys Ser Ser His Leu Ser Ile Thr Gln Arg Asn
            100                 105                 110

Ser Arg Leu Ile His Ser Thr Ser Lys Ile Val Pro Asn
        115                 120                 125

<210> SEQ ID NO 138
<211> LENGTH: 107
<212> TYPE: PRT
<213> ORGANISM: Chlamydomonas reinhardtii

<400> SEQUENCE: 138

Met Ala Leu Gln Gln Ala Ala Pro Arg Val Phe Gly Leu Leu Gly Arg
1               5                   10                  15

Ala Pro Val Ala Leu Gly Gln Ser Gly Ile Leu Thr Gly Ser Ser Gly
            20                  25                  30

Phe Lys Asn Gln Gly Phe Asn Gly Ser Leu Gln Ser Val Glu Asn His
        35                  40                  45

```
Val Tyr Ala Gln Ala Phe Ser Thr Ser Ser Gln Glu Gln Ala Ala
         50                  55                  60

Pro Ser Ile Gln Gly Ala Ser Gly Met Lys Leu Pro Gly Met Ala Gly
 65                  70                  75                  80

Ser Met Leu Leu Gly Lys Ser Arg Ser Gly Leu Arg Thr Gly Ser Met
                 85                  90                  95

Val Pro Phe Ala Ala Gln Gln Ala Met Asn Met
            100                 105

<210> SEQ ID NO 139
<211> LENGTH: 87
<212> TYPE: PRT
<213> ORGANISM: Homo sapiens

<400> SEQUENCE: 139

Met Trp Arg Leu Arg Arg Ala Ala Val Ala Cys Glu Val Cys Gln Ser
 1               5                  10                  15

Leu Val Lys His Ser Ser Gly Ile Lys Gly Ser Leu Pro Leu Gln Lys
                 20                  25                  30

Leu His Leu Val Ser Arg Ser Ile Tyr His Ser His His Pro Thr Leu
             35                  40                  45

Lys Leu Gln Arg Pro Gln Leu Arg Thr Ser Phe Gln Gln Phe Ser Ser
         50                  55                  60

Leu Thr Asn Leu Pro Leu Arg Lys Leu Lys Phe Ser Pro Ile Lys Tyr
 65                  70                  75                  80

Gly Tyr Gln Pro Arg Arg Asn
                 85

<210> SEQ ID NO 140
<211> LENGTH: 56
<212> TYPE: PRT
<213> ORGANISM: Homo sapiens

<400> SEQUENCE: 140

Met Ala Val Leu Trp Arg Leu Ser Ala Val Cys Gly Ala Leu Gly Gly
 1               5                  10                  15

Arg Ala Leu Leu Leu Arg Thr Pro Val Val Arg Pro Ala His Ile Ser
                 20                  25                  30

Ala Phe Leu Gln Asp Arg Pro Ile Pro Glu Trp Cys Gly Val Gln His
             35                  40                  45

Ile His Leu Ser Pro Ser His His
         50                  55

<210> SEQ ID NO 141
<211> LENGTH: 162
<212> TYPE: PRT
<213> ORGANISM: Homo sapiens

<400> SEQUENCE: 141

Met Ala Ala Ile Leu Gly Asp Thr Ile Met Val Ala Lys Gly Leu Val
 1               5                  10                  15

Lys Leu Thr Gln Ala Ala Val Glu Thr His Leu Gln His Leu Gly Ile
                 20                  25                  30

Gly Gly Glu Leu Ile Met Ala Ala Arg Ala Leu Gln Ser Thr Ala Val
             35                  40                  45

Glu Gln Ile Gly Met Phe Leu Gly Lys Val Gly Gln Asp Lys His
         50                  55                  60
```

-continued

```
Glu Glu Tyr Phe Ala Glu Asn Phe Gly Gly Pro Gly Glu Phe His
 65                  70                  75                  80

Phe Ser Val Pro His Ala Ala Gly Ala Ser Thr Asp Phe Ser Ser Ala
                 85                  90                  95

Ser Ala Pro Asp Gln Ser Ala Pro Pro Ser Leu Gly His Ala His Ser
            100                 105                 110

Glu Gly Pro Ala Pro Ala Tyr Val Ala Ser Gly Pro Phe Arg Glu Ala
        115                 120                 125

Gly Phe Pro Gly Gln Ala Ser Ser Pro Leu Gly Arg Ala Asn Gly Arg
    130                 135                 140

Leu Phe Ala Asn Pro Arg Asp Ser Phe Ser Ala Met Gly Phe Gln Arg
145                 150                 155                 160

Arg Phe

<210> SEQ ID NO 142
<211> LENGTH: 117
<212> TYPE: PRT
<213> ORGANISM: Oryza sativa

<400> SEQUENCE: 142

Met Ala Leu Leu Leu Arg His Ser Pro Lys Leu Arg Arg Ala His Ala
  1               5                  10                  15

Ile Leu Gly Cys Glu Arg Gly Thr Val Val Arg His Phe Ser Ser Ser
                 20                  25                  30

Thr Cys Ser Ser Leu Val Lys Glu Asp Thr Val Ser Ser Asn Leu
             35                  40                  45

His Pro Glu Tyr Ala Lys Lys Ile Gly Gly Ser Asp Phe Ser His Asp
         50                  55                  60

Arg Gln Ser Gly Lys Glu Leu Gln Asn Phe Lys Val Ser Pro Gln Glu
 65                  70                  75                  80

Ala Ser Arg Ala Ser Asn Phe Met Arg Ala Ser Lys Tyr Gly Met Pro
                 85                  90                  95

Ile Thr Ala Asn Gly Val His Ser Leu Phe Ser Cys Gly Gln Val Val
            100                 105                 110

Pro Ser Arg Cys Phe
        115

<210> SEQ ID NO 143
<211> LENGTH: 66
<212> TYPE: PRT
<213> ORGANISM: Neurospora crassa

<400> SEQUENCE: 143

Met Ala Ser Thr Arg Val Leu Ala Ser Arg Leu Ala Ser Gln Met Ala
  1               5                  10                  15

Ala Ser Ala Lys Val Ala Arg Pro Ala Val Arg Val Ala Gln Val Ser
                 20                  25                  30

Lys Arg Thr Ile Gln Thr Gly Ser Pro Leu Gln Thr Leu Lys Arg Thr
             35                  40                  45

Gln Met Thr Ser Ile Val Asn Ala Thr Thr Arg Gln Ala Phe Gln Lys
         50                  55                  60

Arg Ala
 65

<210> SEQ ID NO 144
<211> LENGTH: 44
<212> TYPE: PRT
```

-continued

<213> ORGANISM: Homo sapiens

<400> SEQUENCE: 144

Met Leu Ala Ala Arg Leu Val Cys Leu Arg Thr Leu Pro Ser Arg Val
1               5                   10                  15

Phe His Pro Ala Phe Thr Lys Ala Ser Pro Val Val Lys Asn Ser Ile
            20                  25                  30

Thr Lys Asn Gln Trp Leu Leu Thr Pro Ser Arg Glu
        35                  40

<210> SEQ ID NO 145
<211> LENGTH: 68
<212> TYPE: PRT
<213> ORGANISM: Homo sapiens

<400> SEQUENCE: 145

Met Ala Ser Arg Val Leu Ser Ala Tyr Val Ser Arg Leu Pro Ala Ala
1               5                   10                  15

Phe Ala Pro Leu Pro Arg Val Arg Met Leu Ala Val Ala Arg Pro Leu
            20                  25                  30

Ser Thr Ala Leu Cys Ser Ala Gly Thr Gln Thr Arg Leu Gly Thr Leu
        35                  40                  45

Gln Pro Ala Leu Val Leu Ala Gln Val Pro Gly Arg Val Thr Gln Leu
    50                  55                  60

Cys Arg Gln Tyr
65

<210> SEQ ID NO 146
<211> LENGTH: 67
<212> TYPE: PRT
<213> ORGANISM: Homo sapiens

<400> SEQUENCE: 146

Met Phe Ala Cys Ala Lys Leu Ala Cys Thr Pro Ser Leu Ile Arg Ala
1               5                   10                  15

Gly Ser Arg Val Ala Tyr Arg Pro Ile Ser Ala Ser Val Leu Ser Arg
            20                  25                  30

Pro Glu Ala Ser Arg Thr Gly Glu Gly Ser Thr Val Phe Asn Gly Ala
        35                  40                  45

Gln Asn Gly Val Ser Gln Leu Ile Gln Arg Glu Phe Gln Thr Ser Ala
    50                  55                  60

Ile Ser Arg
65

<210> SEQ ID NO 147
<211> LENGTH: 273
<212> TYPE: PRT
<213> ORGANISM: Artificial Sequence
<220> FEATURE:
<223> OTHER INFORMATION: crATP6_hsADCK3

<400> SEQUENCE: 147

Met Ala Leu Gln Gln Ala Ala Pro Arg Val Phe Gly Leu Leu Gly Arg
1               5                   10                  15

Ala Pro Val Ala Leu Gly Gln Ser Gly Ile Leu Thr Gly Ser Ser Gly
            20                  25                  30

Phe Lys Asn Gln Gly Phe Asn Gly Ser Leu Gln Ser Val Glu Asn His
        35                  40                  45

Val Tyr Ala Gln Ala Phe Ser Thr Ser Ser Gln Glu Glu Gln Ala Ala

```
                50                  55                  60
Pro Ser Ile Gln Gly Ala Ser Gly Met Lys Leu Pro Gly Met Ala Gly
 65                  70                  75                  80

Ser Met Leu Leu Gly Lys Ser Arg Ser Gly Leu Arg Thr Gly Ser Met
                 85                  90                  95

Val Pro Phe Ala Ala Gln Ala Met Asn Met Gly Met Ala Ala
            100                 105                 110

Ile Leu Gly Asp Thr Ile Met Val Ala Lys Gly Leu Val Lys Leu Thr
            115                 120                 125

Gln Ala Ala Val Glu Thr His Leu Gln His Leu Gly Ile Gly Gly Glu
        130                 135                 140

Leu Ile Met Ala Ala Arg Ala Leu Gln Ser Thr Ala Val Glu Gln Ile
145                 150                 155                 160

Gly Met Phe Leu Gly Lys Val Gln Gly Gln Asp Lys His Glu Glu Tyr
                165                 170                 175

Phe Ala Glu Asn Phe Gly Gly Pro Glu Gly Phe His Phe Ser Val
            180                 185                 190

Pro His Ala Ala Gly Ala Ser Thr Asp Phe Ser Ser Ala Ser Ala Pro
        195                 200                 205

Asp Gln Ser Ala Pro Pro Ser Leu Gly His Ala His Ser Glu Gly Pro
    210                 215                 220

Ala Pro Ala Tyr Val Ala Ser Gly Pro Phe Arg Glu Ala Gly Phe Pro
225                 230                 235                 240

Gly Gln Ala Ser Ser Pro Leu Gly Arg Ala Asn Gly Arg Leu Phe Ala
                245                 250                 255

Asn Pro Arg Asp Ser Phe Ser Ala Met Gly Phe Gln Arg Arg Phe Gly
            260                 265                 270

Gly

<210> SEQ ID NO 148
<211> LENGTH: 132
<212> TYPE: PRT
<213> ORGANISM: Artificial Sequence
<220> FEATURE:
<223> OTHER INFORMATION: ncATP9_ncATP9

<400> SEQUENCE: 148

Met Ala Ser Thr Arg Val Leu Ala Ser Arg Leu Ala Ser Gln Met Ala
 1               5                  10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Met Ala Ser Thr Arg Val Leu Ala Ser Arg Leu Ala Ser Gln
 65                  70                  75                  80

Met Ala Ala Ser Ala Lys Val Ala Arg Pro Ala Val Arg Val Ala Gln
                 85                  90                  95

Val Ser Lys Arg Thr Ile Gln Thr Gly Ser Pro Leu Gln Thr Leu Lys
            100                 105                 110

Arg Thr Gln Met Thr Ser Ile Val Asn Ala Thr Thr Arg Gln Ala Phe
        115                 120                 125

Gln Lys Arg Ala
    130
```

<210> SEQ ID NO 149
<211> LENGTH: 119
<212> TYPE: PRT
<213> ORGANISM: Zea mays

<400> SEQUENCE: 149

```
Met Ala Leu Leu Arg Ala Ala Val Ser Glu Leu Arg Arg Gly Arg
1               5                   10                  15

Gly Ala Leu Thr Pro Leu Pro Ala Leu Ser Ser Leu Leu Ser Ser Leu
                20                  25                  30

Ser Pro Arg Ser Pro Ala Ser Thr Arg Pro Glu Pro Asn Asn Pro His
            35                  40                  45

Ala Asp Arg Arg His Val Ile Ala Leu Arg Arg Cys Pro Pro Leu Pro
50                  55                  60

Ala Ser Ala Val Leu Ala Pro Glu Leu Leu His Ala Arg Gly Leu Leu
65                  70                  75                  80

Pro Arg His Trp Ser His Ala Ser Pro Leu Ser Thr Ser Ser Ser Ser
                85                  90                  95

Ser Arg Pro Ala Asp Lys Ala Gln Leu Thr Trp Val Asp Lys Trp Ile
            100                 105                 110

Pro Glu Ala Ala Arg Pro Tyr
        115
```

<210> SEQ ID NO 150
<211> LENGTH: 391
<212> TYPE: PRT
<213> ORGANISM: Artificial Sequence
<220> FEATURE:
<223> OTHER INFORMATION: ncATP9_zmLOC100282174_spilv1_ncATP9

<400> SEQUENCE: 150

```
Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
                20                  25                  30

Lys Arg Thr Ile Gln Thr Gly Ser Pro Leu Gln Thr Leu Lys Arg Thr
            35                  40                  45

Gln Met Thr Ser Ile Val Asn Ala Thr Thr Arg Gln Ala Phe Gln Lys
50                  55                  60

Arg Ala Met Ala Leu Leu Arg Ala Ala Val Ser Glu Leu Arg Arg Arg
65                  70                  75                  80

Gly Arg Gly Ala Leu Thr Pro Leu Pro Ala Leu Ser Ser Leu Leu Ser
                85                  90                  95

Ser Leu Ser Pro Arg Ser Pro Ala Ser Thr Arg Pro Glu Pro Asn Asn
            100                 105                 110

Pro His Ala Asp Arg Arg His Val Ile Ala Leu Arg Arg Cys Pro Pro
        115                 120                 125

Leu Pro Ala Ser Ala Val Leu Ala Pro Glu Leu Leu His Ala Arg Gly
    130                 135                 140

Leu Leu Pro Arg His Trp Ser His Ala Ser Pro Leu Ser Thr Ser Ser
145                 150                 155                 160

Ser Ser Ser Arg Pro Ala Asp Lys Ala Gln Leu Thr Trp Val Asp Lys
                165                 170                 175

Trp Ile Pro Glu Ala Ala Arg Pro Tyr Met Thr Val Leu Ala Pro Leu
            180                 185                 190
```

Arg Arg Leu His Thr Arg Ala Ala Phe Ser Ser Tyr Gly Arg Glu Ile
            195                 200                 205

Ala Leu Gln Lys Arg Phe Leu Asn Leu Asn Ser Cys Ser Ala Val Arg
210                 215                 220

Arg Tyr Gly Thr Gly Phe Ser Asn Asn Leu Arg Ile Lys Lys Leu Lys
225                 230                 235                 240

Asn Ala Phe Gly Val Val Arg Ala Asn Ser Thr Lys Ser Thr Ser Thr
                245                 250                 255

Val Thr Thr Ala Ser Pro Ile Lys Tyr Asp Ser Ser Phe Val Gly Lys
            260                 265                 270

Thr Gly Gly Glu Ile Phe His Asp Met Met Leu Lys His Asn Val Lys
        275                 280                 285

His Val Phe Gly Tyr Pro Gly Gly Ala Ile Leu Pro Val Phe Asp Ala
    290                 295                 300

Ile Tyr Arg Ser Pro His Phe Glu Phe Ile Leu Pro Arg His Glu Gln
305                 310                 315                 320

Ala Ala Gly His Ala Met Ala Ser Thr Arg Val Leu Ala Ser Arg Leu
                325                 330                 335

Ala Ser Gln Met Ala Ala Ser Ala Lys Val Ala Arg Pro Ala Val Arg
            340                 345                 350

Val Ala Gln Val Ser Lys Arg Thr Ile Gln Thr Gly Ser Pro Leu Gln
        355                 360                 365

Thr Leu Lys Arg Thr Gln Met Thr Ser Ile Val Asn Ala Thr Thr Arg
    370                 375                 380

Gln Ala Phe Gln Lys Arg Ala
385                 390

<210> SEQ ID NO 151
<211> LENGTH: 455
<212> TYPE: PRT
<213> ORGANISM: Artificial Sequence
<220> FEATURE:
<223> OTHER INFORMATION: zmLOC100282174_hsADCK3_crATP6 _hsATP5G3

<400> SEQUENCE: 151

Met Ala Leu Leu Arg Ala Ala Val Ser Glu Leu Arg Arg Arg Gly Arg
1               5                   10                  15

Gly Ala Leu Thr Pro Leu Pro Ala Leu Ser Ser Leu Leu Ser Ser Leu
            20                  25                  30

Ser Pro Arg Ser Pro Ala Ser Thr Arg Pro Glu Pro Asn Asn Pro His
        35                  40                  45

Ala Asp Arg Arg His Val Ile Ala Leu Arg Arg Cys Pro Pro Leu Pro
    50                  55                  60

Ala Ser Ala Val Leu Ala Pro Glu Leu Leu His Ala Arg Gly Leu Leu
65                  70                  75                  80

Pro Arg His Trp Ser His Ala Ser Pro Leu Ser Thr Ser Ser Ser
                85                  90                  95

Ser Arg Pro Ala Asp Lys Ala Gln Leu Thr Trp Val Asp Lys Trp Ile
            100                 105                 110

Pro Glu Ala Ala Arg Pro Tyr Met Ala Ala Ile Leu Gly Asp Thr Ile
        115                 120                 125

Met Val Ala Lys Gly Leu Val Lys Leu Thr Gln Ala Ala Val Glu Thr
    130                 135                 140

His Leu Gln His Leu Gly Ile Gly Gly Glu Leu Ile Met Ala Ala Arg
145                 150                 155                 160

-continued

```
Ala Leu Gln Ser Thr Ala Val Glu Gln Ile Gly Met Phe Leu Gly Lys
                165                 170                 175
Val Gln Gly Gln Asp Lys His Glu Glu Tyr Phe Ala Glu Asn Phe Gly
            180                 185                 190
Gly Pro Glu Gly Glu Phe His Phe Ser Val Pro His Ala Ala Gly Ala
        195                 200                 205
Ser Thr Asp Phe Ser Ser Ala Ser Ala Pro Asp Gln Ser Ala Pro Pro
    210                 215                 220
Ser Leu Gly His Ala His Ser Glu Gly Pro Ala Pro Ala Tyr Val Ala
225                 230                 235                 240
Ser Gly Pro Phe Arg Glu Ala Gly Phe Pro Gly Gln Ala Ser Ser Pro
                245                 250                 255
Leu Gly Arg Ala Asn Gly Arg Leu Phe Ala Asn Pro Arg Asp Ser Phe
            260                 265                 270
Ser Ala Met Gly Phe Gln Arg Phe Met Ala Leu Gln Gln Ala Ala
        275                 280                 285
Pro Arg Val Phe Gly Leu Leu Gly Arg Ala Pro Val Ala Leu Gly Gln
    290                 295                 300
Ser Gly Ile Leu Thr Gly Ser Ser Gly Phe Lys Asn Gln Gly Phe Asn
305                 310                 315                 320
Gly Ser Leu Gln Ser Val Glu Asn His Val Tyr Ala Gln Ala Phe Ser
                325                 330                 335
Thr Ser Ser Gln Glu Gln Ala Ala Pro Ser Ile Gln Gly Ala Ser
            340                 345                 350
Gly Met Lys Leu Pro Gly Met Ala Gly Ser Met Leu Leu Gly Lys Ser
        355                 360                 365
Arg Ser Gly Leu Arg Thr Gly Ser Met Val Pro Phe Ala Ala Gln Gln
    370                 375                 380
Ala Met Asn Met Met Phe Ala Cys Ala Lys Leu Ala Cys Thr Pro Ser
385                 390                 395                 400
Leu Ile Arg Ala Gly Ser Arg Val Ala Tyr Arg Pro Ile Ser Ala Ser
                405                 410                 415
Val Leu Ser Arg Pro Glu Ala Ser Arg Thr Gly Glu Gly Ser Thr Val
            420                 425                 430
Phe Asn Gly Ala Gln Asn Gly Val Ser Gln Leu Ile Gln Arg Glu Phe
        435                 440                 445
Gln Thr Ser Ala Ile Ser Arg
    450                 455

<210> SEQ ID NO 152
<211> LENGTH: 348
<212> TYPE: PRT
<213> ORGANISM: Artificial Sequence
<220> FEATURE:
<223> OTHER INFORMATION: zmLOC100282174_hsADCK3_hsATP5G3

<400> SEQUENCE: 152

Met Ala Leu Leu Arg Ala Ala Val Ser Glu Leu Arg Arg Arg Gly Arg
1               5                   10                  15
Gly Ala Leu Thr Pro Leu Pro Ala Leu Ser Ser Leu Leu Ser Ser Leu
            20                  25                  30
Ser Pro Arg Ser Pro Ala Ser Thr Arg Pro Glu Pro Asn Asn Pro His
        35                  40                  45
Ala Asp Arg Arg His Val Ile Ala Leu Arg Arg Cys Pro Pro Leu Pro
    50                  55                  60
```

```
Ala Ser Ala Val Leu Ala Pro Glu Leu Leu His Ala Arg Gly Leu Leu
 65                  70                  75                  80

Pro Arg His Trp Ser His Ala Ser Pro Leu Ser Thr Ser Ser Ser Ser
                 85                  90                  95

Ser Arg Pro Ala Asp Lys Ala Gln Leu Thr Trp Val Asp Lys Trp Ile
            100                 105                 110

Pro Glu Ala Ala Arg Pro Tyr Met Ala Ala Ile Leu Gly Asp Thr Ile
        115                 120                 125

Met Val Ala Lys Gly Leu Val Lys Leu Thr Gln Ala Ala Val Glu Thr
130                 135                 140

His Leu Gln His Leu Gly Ile Gly Gly Glu Leu Ile Met Ala Ala Arg
145                 150                 155                 160

Ala Leu Gln Ser Thr Ala Val Glu Gln Ile Gly Met Phe Leu Gly Lys
                165                 170                 175

Val Gln Gly Gln Asp Lys His Glu Glu Tyr Phe Ala Glu Asn Phe Gly
            180                 185                 190

Gly Pro Glu Gly Glu Phe His Phe Ser Val Pro His Ala Ala Gly Ala
        195                 200                 205

Ser Thr Asp Phe Ser Ser Ala Ser Ala Pro Asp Gln Ser Ala Pro Pro
210                 215                 220

Ser Leu Gly His Ala His Ser Glu Gly Pro Ala Pro Ala Tyr Val Ala
225                 230                 235                 240

Ser Gly Pro Phe Arg Glu Ala Gly Phe Pro Gly Gln Ala Ser Ser Pro
                245                 250                 255

Leu Gly Arg Ala Asn Gly Arg Leu Phe Ala Asn Pro Arg Asp Ser Phe
            260                 265                 270

Ser Ala Met Gly Phe Gln Arg Arg Phe Met Phe Ala Cys Ala Lys Leu
        275                 280                 285

Ala Cys Thr Pro Ser Leu Ile Arg Ala Gly Ser Arg Val Ala Tyr Arg
290                 295                 300

Pro Ile Ser Ala Ser Val Leu Ser Arg Pro Glu Ala Ser Arg Thr Gly
305                 310                 315                 320

Glu Gly Ser Thr Val Phe Asn Gly Ala Gln Asn Gly Val Ser Gln Leu
                325                 330                 335

Ile Gln Arg Glu Phe Gln Thr Ser Ala Ile Ser Arg
            340                 345

<210> SEQ ID NO 153
<211> LENGTH: 185
<212> TYPE: PRT
<213> ORGANISM: Artificial Sequence
<220> FEATURE:
<223> OTHER INFORMATION: ncATP9_zmLOC100282174

<400> SEQUENCE: 153

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
                20                  25                  30

Lys Arg Thr Ile Gln Thr Gly Ser Pro Leu Gln Thr Leu Lys Arg Thr
            35                  40                  45

Gln Met Thr Ser Ile Val Asn Ala Thr Thr Arg Gln Ala Phe Gln Lys
        50                  55                  60

Arg Ala Met Ala Leu Leu Arg Ala Ala Val Ser Glu Leu Arg Arg Arg
65                  70                  75                  80
```

```
Gly Arg Gly Ala Leu Thr Pro Leu Pro Ala Leu Ser Ser Leu Leu Ser
                    85                  90                  95

Ser Leu Ser Pro Arg Ser Pro Ala Ser Thr Arg Pro Glu Pro Asn Asn
                100                 105                 110

Pro His Ala Asp Arg Arg His Val Ile Ala Leu Arg Arg Cys Pro Pro
                115                 120                 125

Leu Pro Ala Ser Ala Val Leu Ala Pro Glu Leu Leu His Ala Arg Gly
130                 135                 140

Leu Leu Pro Arg His Trp Ser His Ala Ser Pro Leu Ser Thr Ser Ser
145                 150                 155                 160

Ser Ser Ser Arg Pro Ala Asp Lys Ala Gln Leu Thr Trp Val Asp Lys
                165                 170                 175

Trp Ile Pro Glu Ala Ala Arg Pro Tyr
                180                 185

<210> SEQ ID NO 154
<211> LENGTH: 455
<212> TYPE: PRT
<213> ORGANISM: Artificial Sequence
<220> FEATURE:
<223> OTHER INFORMATION: hsADCK3_zmLOC100282174_crATP6_hsATP5G3

<400> SEQUENCE: 154

Met Ala Ala Ile Leu Gly Asp Thr Ile Met Val Ala Lys Gly Leu Val
1               5                   10                  15

Lys Leu Thr Gln Ala Ala Val Glu Thr His Leu Gln His Leu Gly Ile
                20                  25                  30

Gly Gly Glu Leu Ile Met Ala Ala Arg Ala Leu Gln Ser Thr Ala Val
            35                  40                  45

Glu Gln Ile Gly Met Phe Leu Gly Lys Val Gln Gly Gln Asp Lys His
        50                  55                  60

Glu Glu Tyr Phe Ala Glu Asn Phe Gly Gly Pro Glu Gly Glu Phe His
65                  70                  75                  80

Phe Ser Val Pro His Ala Ala Gly Ala Ser Thr Asp Phe Ser Ser Ala
                85                  90                  95

Ser Ala Pro Asp Gln Ser Ala Pro Pro Ser Leu Gly His Ala His Ser
                100                 105                 110

Glu Gly Pro Ala Pro Ala Tyr Val Ala Ser Gly Pro Phe Arg Glu Ala
            115                 120                 125

Gly Phe Pro Gly Gln Ala Ser Ser Pro Leu Gly Arg Ala Asn Gly Arg
        130                 135                 140

Leu Phe Ala Asn Pro Arg Asp Ser Phe Ser Ala Met Gly Phe Gln Arg
145                 150                 155                 160

Arg Phe Met Ala Leu Leu Arg Ala Ala Val Ser Glu Leu Arg Arg
                165                 170                 175

Gly Arg Gly Ala Leu Thr Pro Leu Pro Ala Leu Ser Ser Leu Leu Ser
                180                 185                 190

Ser Leu Ser Pro Arg Ser Pro Ala Ser Thr Arg Pro Glu Pro Asn Asn
                195                 200                 205

Pro His Ala Asp Arg Arg His Val Ile Ala Leu Arg Arg Cys Pro Pro
            210                 215                 220

Leu Pro Ala Ser Ala Val Leu Ala Pro Glu Leu Leu His Ala Arg Gly
225                 230                 235                 240

Leu Leu Pro Arg His Trp Ser His Ala Ser Pro Leu Ser Thr Ser Ser
                245                 250                 255
```

Ser Ser Ser Arg Pro Ala Asp Lys Ala Gln Leu Thr Trp Val Asp Lys
            260                 265                 270

Trp Ile Pro Glu Ala Ala Arg Pro Tyr Met Ala Leu Gln Gln Ala Ala
        275                 280                 285

Pro Arg Val Phe Gly Leu Leu Gly Arg Ala Pro Val Ala Leu Gly Gln
    290                 295                 300

Ser Gly Ile Leu Thr Gly Ser Ser Gly Phe Lys Asn Gln Gly Phe Asn
305                 310                 315                 320

Gly Ser Leu Gln Ser Val Glu Asn His Val Tyr Ala Gln Ala Phe Ser
                325                 330                 335

Thr Ser Ser Gln Glu Glu Gln Ala Ala Pro Ser Ile Gln Gly Ala Ser
            340                 345                 350

Gly Met Lys Leu Pro Gly Met Ala Gly Ser Met Leu Leu Gly Lys Ser
        355                 360                 365

Arg Ser Gly Leu Arg Thr Gly Ser Met Val Pro Phe Ala Ala Gln Gln
    370                 375                 380

Ala Met Asn Met Met Phe Ala Cys Ala Lys Leu Ala Cys Thr Pro Ser
385                 390                 395                 400

Leu Ile Arg Ala Gly Ser Arg Val Ala Tyr Arg Pro Ile Ser Ala Ser
                405                 410                 415

Val Leu Ser Arg Pro Glu Ala Ser Arg Thr Gly Glu Gly Ser Thr Val
            420                 425                 430

Phe Asn Gly Ala Gln Asn Gly Val Ser Gln Leu Ile Gln Arg Glu Phe
        435                 440                 445

Gln Thr Ser Ala Ile Ser Arg
    450                 455

<210> SEQ ID NO 155
<211> LENGTH: 455
<212> TYPE: PRT
<213> ORGANISM: Artificial Sequence
<220> FEATURE:
<223> OTHER INFORMATION: crATP6_hsADCK3_zmLOC100282174_hsATP5G3

<400> SEQUENCE: 155

Met Ala Leu Gln Gln Ala Ala Pro Arg Val Phe Gly Leu Leu Gly Arg
1               5                   10                  15

Ala Pro Val Ala Leu Gly Gln Ser Gly Ile Leu Thr Gly Ser Ser Gly
            20                  25                  30

Phe Lys Asn Gln Gly Phe Asn Gly Ser Leu Gln Ser Val Glu Asn His
        35                  40                  45

Val Tyr Ala Gln Ala Phe Ser Thr Ser Ser Gln Glu Glu Gln Ala Ala
    50                  55                  60

Pro Ser Ile Gln Gly Ala Ser Gly Met Lys Leu Pro Gly Met Ala Gly
65                  70                  75                  80

Ser Met Leu Leu Gly Lys Ser Arg Ser Gly Leu Arg Thr Gly Ser Met
                85                  90                  95

Val Pro Phe Ala Ala Gln Gln Ala Met Asn Met Met Ala Ala Ile Leu
            100                 105                 110

Gly Asp Thr Ile Met Val Ala Lys Gly Leu Val Lys Leu Thr Gln Ala
        115                 120                 125

Ala Val Glu Thr His Leu Gln His Leu Gly Ile Gly Gly Glu Leu Ile
    130                 135                 140

Met Ala Ala Arg Ala Leu Gln Ser Thr Ala Val Glu Gln Ile Gly Met
145                 150                 155                 160

```
Phe Leu Gly Lys Val Gln Gly Gln Asp Lys His Glu Glu Tyr Phe Ala
            165                 170                 175

Glu Asn Phe Gly Gly Pro Glu Gly Glu Phe His Phe Ser Val Pro His
        180                 185                 190

Ala Ala Gly Ala Ser Thr Asp Phe Ser Ser Ala Ser Ala Pro Asp Gln
    195                 200                 205

Ser Ala Pro Pro Ser Leu Gly His Ala His Ser Glu Gly Pro Ala Pro
210                 215                 220

Ala Tyr Val Ala Ser Gly Pro Phe Arg Glu Ala Gly Phe Pro Gly Gln
225                 230                 235                 240

Ala Ser Ser Pro Leu Gly Arg Ala Asn Gly Arg Leu Phe Ala Asn Pro
                245                 250                 255

Arg Asp Ser Phe Ser Ala Met Gly Phe Gln Arg Arg Phe Met Ala Leu
            260                 265                 270

Leu Arg Ala Ala Val Ser Glu Leu Arg Arg Gly Arg Gly Ala Leu
        275                 280                 285

Thr Pro Leu Pro Ala Leu Ser Ser Leu Ser Ser Leu Ser Pro Arg
    290                 295                 300

Ser Pro Ala Ser Thr Arg Pro Glu Pro Asn Asn Pro His Ala Asp Arg
305                 310                 315                 320

Arg His Val Ile Ala Leu Arg Arg Cys Pro Pro Leu Pro Ala Ser Ala
                325                 330                 335

Val Leu Ala Pro Glu Leu Leu His Ala Arg Gly Leu Leu Pro Arg His
            340                 345                 350

Trp Ser His Ala Ser Pro Leu Ser Thr Ser Ser Ser Ser Arg Pro
        355                 360                 365

Ala Asp Lys Ala Gln Leu Thr Trp Val Asp Lys Trp Ile Pro Glu Ala
    370                 375                 380

Ala Arg Pro Tyr Met Phe Ala Cys Ala Lys Leu Ala Cys Thr Pro Ser
385                 390                 395                 400

Leu Ile Arg Ala Gly Ser Arg Val Ala Tyr Arg Pro Ile Ser Ala Ser
                405                 410                 415

Val Leu Ser Arg Pro Glu Ala Ser Arg Thr Gly Glu Gly Ser Thr Val
            420                 425                 430

Phe Asn Gly Ala Gln Asn Gly Val Ser Gln Leu Ile Gln Arg Glu Phe
        435                 440                 445

Gln Thr Ser Ala Ile Ser Arg
    450                 455

<210> SEQ ID NO 156
<211> LENGTH: 285
<212> TYPE: PRT
<213> ORGANISM: Artificial Sequence
<220> FEATURE:
<223> OTHER INFORMATION: hsADCK3_zmLOC100282174

<400> SEQUENCE: 156

Met Ala Ala Ile Leu Gly Asp Thr Ile Met Val Ala Lys Gly Leu Val
1               5                   10                  15

Lys Leu Thr Gln Ala Ala Val Glu Thr His Leu Gln His Leu Gly Ile
            20                  25                  30

Gly Gly Glu Leu Ile Met Ala Ala Arg Ala Leu Gln Ser Thr Ala Val
        35                  40                  45

Glu Gln Ile Gly Met Phe Leu Gly Lys Val Gln Gly Gln Asp Lys His
    50                  55                  60
```

Glu Glu Tyr Phe Ala Glu Asn Phe Gly Gly Pro Glu Gly Glu Phe His
65                  70                  75                  80

Phe Ser Val Pro His Ala Ala Gly Ala Ser Thr Asp Phe Ser Ser Ala
                85                  90                  95

Ser Ala Pro Asp Gln Ser Ala Pro Pro Ser Leu Gly His Ala His Ser
            100                 105                 110

Glu Gly Pro Ala Pro Ala Tyr Val Ala Ser Gly Pro Phe Arg Glu Ala
            115                 120                 125

Gly Phe Pro Gly Gln Ala Ser Ser Pro Leu Gly Arg Ala Asn Gly Arg
            130                 135                 140

Leu Phe Ala Asn Pro Arg Asp Ser Phe Ser Ala Met Gly Phe Gln Arg
145                 150                 155                 160

Arg Phe Gly Gly Met Ala Leu Leu Arg Ala Ala Val Ser Glu Leu Arg
                165                 170                 175

Arg Arg Gly Arg Gly Ala Leu Thr Pro Leu Pro Ala Leu Ser Ser Leu
            180                 185                 190

Leu Ser Ser Leu Ser Pro Arg Ser Pro Ala Ser Thr Arg Pro Glu Pro
            195                 200                 205

Asn Asn Pro His Ala Asp Arg Arg His Val Ile Ala Leu Arg Arg Cys
210                 215                 220

Pro Pro Leu Pro Ala Ser Ala Val Leu Ala Pro Glu Leu Leu His Ala
225                 230                 235                 240

Arg Gly Leu Leu Pro Arg His Trp Ser His Ala Ser Pro Leu Ser Thr
                245                 250                 255

Ser Ser Ser Ser Arg Pro Ala Asp Lys Ala Gln Leu Thr Trp Val
            260                 265                 270

Asp Lys Trp Ile Pro Glu Ala Ala Arg Pro Tyr Gly Gly
            275                 280                 285

<210> SEQ ID NO 157
<211> LENGTH: 394
<212> TYPE: PRT
<213> ORGANISM: Artificial Sequence
<220> FEATURE:
<223> OTHER INFORMATION: hsADCK3_zmLOC100282174_crATP6

<400> SEQUENCE: 157

Met Ala Ala Ile Leu Gly Asp Thr Ile Met Val Ala Lys Gly Leu Val
1               5                   10                  15

Lys Leu Thr Gln Ala Ala Val Glu Thr His Leu Gln His Leu Gly Ile
                20                  25                  30

Gly Gly Glu Leu Ile Met Ala Ala Arg Ala Leu Gln Ser Thr Ala Val
            35                  40                  45

Glu Gln Ile Gly Met Phe Leu Gly Lys Val Gln Gly Gln Asp Lys His
    50                  55                  60

Glu Glu Tyr Phe Ala Glu Asn Phe Gly Gly Pro Glu Gly Glu Phe His
65                  70                  75                  80

Phe Ser Val Pro His Ala Ala Gly Ala Ser Thr Asp Phe Ser Ser Ala
                85                  90                  95

Ser Ala Pro Asp Gln Ser Ala Pro Pro Ser Leu Gly His Ala His Ser
            100                 105                 110

Glu Gly Pro Ala Pro Ala Tyr Val Ala Ser Gly Pro Phe Arg Glu Ala
            115                 120                 125

Gly Phe Pro Gly Gln Ala Ser Ser Pro Leu Gly Arg Ala Asn Gly Arg
            130                 135                 140

```
Leu Phe Ala Asn Pro Arg Asp Ser Phe Ser Ala Met Gly Phe Gln Arg
145                 150                 155                 160

Arg Phe Gly Gly Met Ala Leu Leu Arg Ala Ala Val Ser Glu Leu Arg
                165                 170                 175

Arg Arg Gly Arg Gly Ala Leu Thr Pro Leu Pro Ala Leu Ser Ser Leu
            180                 185                 190

Leu Ser Ser Leu Ser Pro Arg Ser Pro Ala Ser Thr Arg Pro Glu Pro
        195                 200                 205

Asn Asn Pro His Ala Asp Arg Arg His Val Ile Ala Leu Arg Arg Cys
    210                 215                 220

Pro Pro Leu Pro Ala Ser Ala Val Leu Ala Pro Glu Leu Leu His Ala
225                 230                 235                 240

Arg Gly Leu Leu Pro Arg His Trp Ser His Ala Ser Pro Leu Ser Thr
                245                 250                 255

Ser Ser Ser Ser Ser Arg Pro Ala Asp Lys Ala Gln Leu Thr Trp Val
                260                 265                 270

Asp Lys Trp Ile Pro Glu Ala Ala Arg Pro Tyr Gly Gly Met Ala Leu
            275                 280                 285

Gln Gln Ala Ala Pro Arg Val Phe Gly Leu Leu Gly Arg Ala Pro Val
        290                 295                 300

Ala Leu Gly Gln Ser Gly Ile Leu Thr Gly Ser Ser Gly Phe Lys Asn
305                 310                 315                 320

Gln Gly Phe Asn Gly Ser Leu Gln Ser Val Glu Asn His Val Tyr Ala
                325                 330                 335

Gln Ala Phe Ser Thr Ser Ser Ser Glu Glu Gln Ala Ala Pro Ser Ile
            340                 345                 350

Gln Gly Ala Ser Gly Met Lys Leu Pro Gly Met Ala Gly Ser Met Leu
        355                 360                 365

Leu Gly Lys Ser Arg Ser Gly Leu Arg Thr Gly Ser Met Val Pro Phe
    370                 375                 380

Ala Ala Gln Gln Ala Met Asn Met Gly Gly
385                 390

<210> SEQ ID NO 158
<211> LENGTH: 574
<212> TYPE: PRT
<213> ORGANISM: Artificial Sequence
<220> FEATURE:
<223> OTHER INFORMATION: ncATP9_zmLOC100282174_spilv1_GNFP_ncATP9

<400> SEQUENCE: 158

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Met Ala Leu Leu Arg Ala Ala Val Ser Glu Leu Arg Arg Arg
65                  70                  75                  80

Gly Arg Gly Ala Leu Thr Pro Leu Pro Ala Leu Ser Ser Leu Leu Ser
                85                  90                  95

Ser Leu Ser Pro Arg Ser Pro Ala Ser Thr Arg Pro Glu Pro Asn Asn
            100                 105                 110
```

-continued

```
Pro His Ala Asp Arg Arg His Val Ile Ala Leu Arg Cys Pro Pro
            115                 120                 125

Leu Pro Ala Ser Ala Val Leu Ala Pro Glu Leu Leu His Ala Arg Gly
130                 135                 140

Leu Leu Pro Arg His Trp Ser His Ala Ser Pro Leu Ser Thr Ser Ser
145                 150                 155                 160

Ser Ser Ser Arg Pro Ala Asp Lys Ala Gln Leu Thr Trp Val Asp Lys
                165                 170                 175

Trp Ile Pro Glu Ala Ala Arg Pro Tyr Met Thr Val Leu Ala Pro Leu
            180                 185                 190

Arg Arg Leu His Thr Arg Ala Ala Phe Ser Ser Tyr Gly Arg Glu Ile
        195                 200                 205

Ala Leu Gln Lys Arg Phe Leu Asn Leu Asn Ser Cys Ser Ala Val Arg
210                 215                 220

Arg Tyr Gly Thr Gly Phe Ser Asn Asn Leu Arg Ile Lys Lys Leu Lys
225                 230                 235                 240

Asn Ala Phe Gly Val Val Arg Ala Asn Ser Thr Lys Ser Thr Ser Thr
                245                 250                 255

Val Thr Thr Ala Ser Pro Ile Lys Tyr Asp Ser Ser Phe Val Gly Lys
            260                 265                 270

Thr Gly Gly Glu Ile Phe His Asp Met Met Leu Lys His Asn Val Lys
        275                 280                 285

His Val Phe Gly Tyr Pro Gly Gly Ala Ile Leu Pro Val Phe Asp Ala
290                 295                 300

Ile Tyr Arg Ser Pro His Phe Glu Phe Ile Leu Pro Arg His Glu Gln
305                 310                 315                 320

Ala Ala Gly His Ala Val Ser Gly Glu Gly Asp Ala Thr Tyr Gly Lys
                325                 330                 335

Leu Thr Leu Lys Phe Ile Cys Thr Thr Gly Lys Leu Pro Val Pro Trp
            340                 345                 350

Pro Thr Leu Val Thr Thr Leu Thr Tyr Gly Val Gln Cys Phe Ser Arg
        355                 360                 365

Tyr Pro Asp His Met Lys Gln His Asp Phe Phe Lys Ser Ala Met Pro
370                 375                 380

Glu Gly Tyr Val Gln Glu Arg Thr Ile Phe Phe Lys Asp Asp Gly Asn
385                 390                 395                 400

Tyr Lys Thr Arg Ala Glu Val Lys Phe Glu Gly Asp Thr Leu Val Asn
                405                 410                 415

Arg Ile Glu Leu Lys Gly Ile Asp Phe Lys Glu Asp Gly Asn Ile Leu
            420                 425                 430

Gly His Lys Leu Glu Tyr Asn Tyr Asn Ser His Asn Val Tyr Ile Met
        435                 440                 445

Ala Asp Lys Gln Lys Asn Gly Ile Lys Val Asn Phe Lys Ile Arg His
450                 455                 460

Asn Ile Glu Asp Gly Ser Val Gln Leu Ala Asp His Tyr Gln Gln Asn
465                 470                 475                 480

Thr Pro Ile Gly Asp Gly Pro Val Leu Leu Pro Asp Asn His Tyr Leu
                485                 490                 495

Ser Thr Gln Ser Ala Leu Ser Lys Asp Pro Asn Glu Met Ala Ser Thr
            500                 505                 510

Arg Val Leu Ala Ser Arg Leu Ala Ser Gln Met Ala Ala Ser Ala Lys
        515                 520                 525

Val Ala Arg Pro Ala Val Arg Val Ala Gln Val Ser Lys Arg Thr Ile
```

```
              530             535             540
Gln Thr Gly Ser Pro Leu Gln Thr Leu Lys Arg Thr Gln Met Thr Ser
545                 550             555                 560

Ile Val Asn Ala Thr Thr Arg Gln Ala Phe Gln Lys Arg Ala
                565                 570

<210> SEQ ID NO 159
<211> LENGTH: 810
<212> TYPE: PRT
<213> ORGANISM: Artificial Sequence
<220> FEATURE:
<223> OTHER INFORMATION: ncATP9_zmLOC100282174_spilv1_lcSirt5_
      osP0644B06.24-2_hsATP5G2_ncATP9

<400> SEQUENCE: 159

Met Ala Ser Thr Arg Val Leu Ala Ser Arg Leu Ala Ser Gln Met Ala
1               5                   10                  15

Ala Ser Ala Lys Val Ala Arg Pro Ala Arg Val Ala Gln Val Ser
            20                  25                  30

Lys Arg Thr Ile Gln Thr Gly Ser Pro Leu Gln Thr Leu Lys Arg Thr
                35                  40                  45

Gln Met Thr Ser Ile Val Asn Ala Thr Thr Arg Gln Ala Phe Gln Lys
50                  55                  60

Arg Ala Met Ala Leu Leu Arg Ala Ala Val Ser Glu Leu Arg Arg
65                  70                  75                  80

Gly Arg Gly Ala Leu Thr Pro Leu Pro Ala Leu Ser Ser Leu Leu Ser
                85                  90                  95

Ser Leu Ser Pro Arg Ser Pro Ala Ser Thr Arg Pro Glu Pro Asn Asn
                100                 105                 110

Pro His Ala Asp Arg Arg His Val Ile Ala Leu Arg Arg Cys Pro Pro
            115                 120                 125

Leu Pro Ala Ser Ala Val Leu Ala Pro Glu Leu Leu His Ala Arg Gly
130                 135                 140

Leu Leu Pro Arg His Trp Ser His Ala Ser Pro Leu Ser Thr Ser Ser
145                 150                 155                 160

Ser Ser Ser Arg Pro Ala Asp Lys Ala Gln Leu Thr Trp Val Asp Lys
                165                 170                 175

Trp Ile Pro Glu Ala Ala Arg Pro Tyr Met Thr Val Leu Ala Pro Leu
                180                 185                 190

Arg Arg Leu His Thr Arg Ala Ala Phe Ser Ser Tyr Gly Arg Glu Ile
            195                 200                 205

Ala Leu Gln Lys Arg Phe Leu Asn Leu Asn Ser Cys Ser Ala Val Arg
210                 215                 220

Arg Tyr Gly Thr Gly Phe Ser Asn Asn Leu Arg Ile Lys Lys Leu Lys
225                 230                 235                 240

Asn Ala Phe Gly Val Val Arg Ala Asn Ser Thr Lys Ser Thr Ser Thr
                245                 250                 255

Val Thr Thr Ala Ser Pro Ile Lys Tyr Asp Ser Ser Phe Val Gly Lys
            260                 265                 270

Thr Gly Gly Glu Ile Phe His Asp Met Met Leu Lys His Asn Val Lys
            275                 280                 285

His Val Phe Gly Tyr Pro Gly Gly Ala Ile Leu Pro Val Phe Asp Ala
        290                 295                 300

Ile Tyr Arg Ser Pro His Phe Glu Phe Ile Leu Pro Arg His Glu Gln
305                 310                 315                 320
```

-continued

Ala Ala Gly His Ala Met Arg Lys Arg Ser Leu Arg Cys His Leu Trp
            325                 330                 335

Ser Ala Asn Ala Ser Leu Ser Pro Arg Lys Asp Glu Val Thr Ser Arg
            340                 345                 350

Lys Glu Ser Glu Asn Leu Val Lys Gly Lys Lys Asn Lys Lys Ser His
            355                 360                 365

Leu His Leu Leu Leu Phe Thr Ala Ser Lys Ile Gly Thr Asp Ser Val
            370                 375                 380

Phe Asp Val Gln Lys Ser Lys Glu Cys Cys Lys Glu Leu Gly Leu Leu
385                 390                 395                 400

Phe Thr Ser Leu Ile His Ser Ile Gly Ser Phe Pro Phe Asp Glu Glu
            405                 410                 415

Pro Lys Ala Ala Ala Val Phe Leu Pro Gly Ser Leu Pro Gln Leu Thr
            420                 425                 430

Val Leu Val Leu Ala Pro Gly Ser Gly Ser Cys Pro Thr Gly Lys Ser
            435                 440                 445

Thr Pro His Leu Ala Ala Ser Gly Arg Asn Ala Glu Leu Leu Arg Pro
            450                 455                 460

Gln Asn Ser Met Ile Val Arg Gln Phe Thr Cys Arg Gly Thr Ile Ser
465                 470                 475                 480

Ser His Leu Cys Ala His Leu Arg Lys Pro His Asp Ser Arg Asn Met
            485                 490                 495

Ala Arg Pro Met Ala Leu Leu Leu Arg His Ser Pro Lys Leu Arg Arg
            500                 505                 510

Ala His Ala Ile Leu Gly Cys Glu Arg Gly Thr Val Val Arg His Phe
            515                 520                 525

Ser Ser Ser Thr Cys Ser Ser Leu Val Lys Glu Asp Thr Val Ser Ser
530                 535                 540

Ser Asn Leu His Pro Glu Tyr Ala Lys Lys Ile Gly Gly Ser Asp Phe
545                 550                 555                 560

Ser His Asp Arg Gln Ser Gly Lys Glu Leu Gln Asn Phe Lys Val Ser
            565                 570                 575

Pro Gln Glu Ala Ser Arg Ala Ser Asn Phe Met Arg Ala Ser Lys Tyr
            580                 585                 590

Gly Met Pro Ile Thr Ala Asn Gly Val His Ser Leu Phe Ser Cys Gly
            595                 600                 605

Gln Val Val Pro Ser Arg Cys Phe Met Pro Glu Leu Ile Leu Tyr Val
            610                 615                 620

Ala Ile Thr Leu Ser Val Ala Glu Arg Leu Val Gly Pro Gly His Ala
625                 630                 635                 640

Cys Ala Glu Pro Ser Phe Arg Ser Ser Arg Cys Ser Ala Pro Leu Cys
            645                 650                 655

Leu Leu Cys Ser Gly Ser Ser Pro Ala Thr Ala Pro His Pro Leu
            660                 665                 670

Lys Met Phe Ala Cys Ser Lys Phe Val Ser Thr Pro Ser Leu Val Lys
            675                 680                 685

Ser Thr Ser Gln Leu Leu Ser Arg Pro Leu Ser Ala Val Val Leu Lys
            690                 695                 700

Arg Pro Glu Ile Leu Thr Asp Glu Ser Leu Ser Ser Leu Ala Val Ser
705                 710                 715                 720

Cys Pro Leu Thr Ser Leu Val Ser Ser Arg Ser Phe Gln Thr Ser Ala
            725                 730                 735

Ile Ser Arg Asp Ile Asp Thr Ala Met Ala Ser Thr Arg Val Leu Ala

|     |     |     | 740 |     |     |     | 745 |     |     |     | 750 |     |     |
| --- | --- | --- | --- | --- | --- | --- | --- | --- | --- | --- | --- | --- | --- |

Ser Arg Leu Ala Ser Gln Met Ala Ala Ser Ala Lys Val Ala Arg Pro
             755                 760                 765

Ala Val Arg Val Ala Gln Val Ser Lys Arg Thr Ile Gln Thr Gly Ser
770                 775                 780

Pro Leu Gln Thr Leu Lys Arg Thr Gln Met Thr Ser Ile Val Asn Ala
785                 790                 795                 800

Thr Thr Arg Gln Ala Phe Gln Lys Arg Ala
                805                 810

<210> SEQ ID NO 160
<211> LENGTH: 459
<212> TYPE: PRT
<213> ORGANISM: Homo sapiens

<400> SEQUENCE: 160

Met Leu Lys Leu Ile Val Pro Thr Ile Met Leu Leu Pro Leu Thr Trp
1               5                   10                  15

Leu Ser Lys Lys His Met Ile Trp Ile Asn Thr Thr His Ser Leu
                20                  25                  30

Ile Ile Ser Ile Ile Pro Leu Leu Phe Phe Asn Gln Ile Asn Asn Asn
            35                  40                  45

Leu Phe Ser Cys Ser Pro Thr Phe Ser Ser Asp Pro Leu Thr Thr Pro
    50                  55                  60

Leu Leu Met Leu Thr Thr Trp Leu Leu Pro Leu Thr Ile Met Ala Ser
65                  70                  75                  80

Gln Arg His Leu Ser Ser Glu Pro Leu Ser Arg Lys Lys Leu Tyr Leu
                85                  90                  95

Ser Met Leu Ile Ser Leu Gln Ile Ser Leu Ile Met Thr Phe Thr Ala
                100                 105                 110

Thr Glu Leu Ile Met Phe Tyr Ile Phe Phe Glu Thr Thr Leu Ile Pro
            115                 120                 125

Thr Leu Ala Ile Ile Thr Arg Trp Gly Asn Gln Pro Glu Arg Leu Asn
130                 135                 140

Ala Gly Thr Tyr Phe Leu Phe Tyr Thr Leu Val Gly Ser Leu Pro Leu
145                 150                 155                 160

Leu Ile Ala Leu Ile Tyr Thr His Asn Thr Leu Gly Ser Leu Asn Ile
                165                 170                 175

Leu Leu Leu Thr Leu Thr Ala Gln Glu Leu Ser Asn Ser Trp Ala Asn
                180                 185                 190

Asn Leu Met Trp Leu Ala Tyr Thr Met Ala Phe Met Val Lys Met Pro
            195                 200                 205

Leu Tyr Gly Leu His Leu Trp Leu Pro Lys Ala His Val Glu Ala Pro
210                 215                 220

Ile Ala Gly Ser Met Val Leu Ala Ala Val Leu Leu Lys Leu Gly Gly
225                 230                 235                 240

Tyr Gly Met Met Arg Leu Thr Leu Ile Leu Asn Pro Leu Thr Lys His
                245                 250                 255

Met Ala Tyr Pro Phe Leu Val Leu Ser Leu Trp Gly Met Ile Met Thr
                260                 265                 270

Ser Ser Ile Cys Leu Arg Gln Thr Asp Leu Lys Ser Leu Ile Ala Tyr
            275                 280                 285

Ser Ser Ile Ser His Met Ala Leu Val Val Thr Ala Ile Leu Ile Gln
            290                 295                 300

```
Thr Pro Trp Ser Phe Thr Gly Ala Val Ile Leu Met Ile Ala His Gly
305                 310                 315                 320

Leu Thr Ser Ser Leu Leu Phe Cys Leu Ala Asn Ser Asn Tyr Glu Arg
            325                 330                 335

Thr His Ser Arg Ile Met Ile Leu Ser Gln Gly Leu Gln Thr Leu Leu
            340                 345                 350

Pro Leu Met Ala Phe Trp Trp Leu Leu Ala Ser Leu Ala Asn Leu Ala
        355                 360                 365

Leu Pro Pro Thr Ile Asn Leu Leu Gly Glu Leu Ser Val Leu Val Thr
    370                 375                 380

Thr Phe Ser Trp Ser Asn Ile Thr Leu Leu Thr Gly Leu Asn Met
385                 390                 395                 400

Leu Val Thr Ala Leu Tyr Ser Leu Tyr Met Phe Thr Thr Gln Trp
            405                 410                 415

Gly Ser Leu Thr His His Ile Asn Asn Met Lys Pro Ser Phe Thr Arg
            420                 425                 430

Glu Asn Thr Leu Met Phe Met His Leu Ser Pro Ile Leu Leu Leu Ser
            435                 440                 445

Leu Asn Pro Asp Ile Ile Thr Gly Phe Ser Ser
    450                 455

<210> SEQ ID NO 161
<211> LENGTH: 174
<212> TYPE: PRT
<213> ORGANISM: Homo sapiens

<400> SEQUENCE: 161

Met Met Tyr Ala Leu Phe Leu Leu Ser Val Gly Leu Val Met Gly Phe
1               5                   10                  15

Val Gly Phe Ser Ser Lys Pro Ser Pro Ile Tyr Gly Gly Leu Val Leu
            20                  25                  30

Ile Val Ser Gly Val Val Gly Cys Val Ile Ile Leu Asn Phe Gly Gly
        35                  40                  45

Gly Tyr Met Gly Leu Met Val Phe Leu Ile Tyr Leu Gly Gly Met Met
    50                  55                  60

Val Val Phe Gly Tyr Thr Thr Ala Met Ala Ile Glu Glu Tyr Pro Glu
65                  70                  75                  80

Ala Trp Gly Ser Gly Val Glu Val Leu Val Ser Val Leu Val Gly Leu
                85                  90                  95

Ala Met Glu Val Gly Leu Val Leu Trp Val Lys Glu Tyr Asp Gly Val
            100                 105                 110

Val Val Val Asn Phe Asn Ser Val Gly Ser Trp Met Ile Tyr Glu
            115                 120                 125

Gly Glu Gly Ser Gly Leu Ile Arg Glu Asp Pro Ile Gly Ala Gly Ala
    130                 135                 140

Leu Tyr Asp Tyr Gly Arg Trp Leu Val Val Thr Gly Trp Thr Leu
145                 150                 155                 160

Phe Val Gly Val Tyr Ile Val Ile Glu Ile Ala Arg Gly Asn
            165                 170

<210> SEQ ID NO 162
<211> LENGTH: 318
<212> TYPE: PRT
<213> ORGANISM: Homo sapiens

<400> SEQUENCE: 162
```

| | | | | | | | | | | | | | | | |
|---|---|---|---|---|---|---|---|---|---|---|---|---|---|---|---|
|Met|Pro|Met|Ala|Asn|Leu|Leu|Leu|Leu|Ile|Val|Pro|Ile|Leu|Ile|Ala|
|1| | | |5| | | | |10| | | | |15| |
|Met|Ala|Phe|Leu|Met|Leu|Thr|Glu|Arg|Lys|Ile|Leu|Gly|Tyr|Met|Gln|
| | | | |20| | | | |25| | | | |30| |
|Leu|Arg|Lys|Gly|Pro|Asn|Val|Val|Gly|Pro|Tyr|Gly|Leu|Leu|Gln|Pro|
| | | | |35| | | | |40| | | | |45| |
|Phe|Ala|Asp|Ala|Met|Lys|Leu|Phe|Thr|Lys|Glu|Pro|Leu|Lys|Pro|Ala|
| |50| | | | |55| | | | |60| | | | |
|Thr|Ser|Thr|Ile|Thr|Leu|Tyr|Ile|Thr|Ala|Pro|Thr|Leu|Ala|Leu|Thr|
|65| | | | |70| | | | |75| | | | |80|
|Ile|Ala|Leu|Leu|Leu|Trp|Thr|Pro|Leu|Pro|Met|Pro|Asn|Pro|Leu|Val|
| | | | |85| | | | |90| | | | |95| |
|Asn|Leu|Asn|Leu|Gly|Leu|Leu|Phe|Ile|Leu|Ala|Thr|Ser|Ser|Leu|Ala|
| | | | |100| | | | |105| | | | |110| |
|Val|Tyr|Ser|Ile|Leu|Trp|Ser|Gly|Trp|Ala|Ser|Asn|Ser|Asn|Tyr|Ala|
| | | | |115| | | | |120| | | | |125| |
|Leu|Ile|Gly|Ala|Leu|Arg|Ala|Val|Ala|Gln|Thr|Ile|Ser|Tyr|Glu|Val|
| |130| | | | |135| | | | |140| | | | |
|Thr|Leu|Ala|Ile|Ile|Leu|Leu|Ser|Thr|Leu|Leu|Met|Ser|Gly|Ser|Phe|
|145| | | | |150| | | | |155| | | | |160|
|Asn|Leu|Ser|Thr|Leu|Ile|Thr|Thr|Gln|Glu|His|Leu|Trp|Leu|Leu|Leu|
| | | | |165| | | | |170| | | | |175| |
|Pro|Ser|Trp|Pro|Leu|Ala|Met|Met|Trp|Phe|Ile|Ser|Thr|Leu|Ala|Glu|
| | | | |180| | | | |185| | | | |190| |
|Thr|Asn|Arg|Thr|Pro|Phe|Asp|Leu|Ala|Glu|Gly|Glu|Ser|Glu|Leu|Val|
| | | | |195| | | | |200| | | | |205| |
|Ser|Gly|Phe|Asn|Ile|Glu|Tyr|Ala|Ala|Gly|Pro|Phe|Ala|Leu|Phe|Phe|
| |210| | | | |215| | | | |220| | | | |
|Met|Ala|Glu|Tyr|Thr|Asn|Ile|Ile|Met|Met|Asn|Thr|Leu|Thr|Thr|Thr|
|225| | | | |230| | | | |235| | | | |240|
|Ile|Phe|Leu|Gly|Thr|Thr|Tyr|Asp|Ala|Leu|Ser|Pro|Glu|Leu|Tyr|Thr|
| | | | |245| | | | |250| | | | |255| |
|Thr|Tyr|Phe|Val|Thr|Lys|Thr|Leu|Leu|Leu|Thr|Ser|Leu|Phe|Leu|Trp|
| | | | |260| | | | |265| | | | |270| |
|Ile|Arg|Thr|Ala|Tyr|Pro|Arg|Phe|Arg|Tyr|Asp|Gln|Leu|Met|His|Leu|
| | | | |275| | | | |280| | | | |285| |
|Leu|Trp|Lys|Asn|Phe|Leu|Pro|Leu|Thr|Leu|Ala|Leu|Leu|Met|Trp|Tyr|
| |290| | | | |295| | | | |300| | | | |
|Val|Ser|Met|Pro|Ile|Thr|Ile|Ser|Ser|Ile|Pro|Pro|Gln|Thr| | |
|305| | | | |310| | | | |315| | | | | |

<210> SEQ ID NO 163
<211> LENGTH: 957
<212> TYPE: DNA
<213> ORGANISM: Homo sapiens

<400> SEQUENCE: 163

```
atacccatgg ccaacctcct actcctcatt gtacccattc taatcgcaat ggcattccta      60
atgcttaccg aacgaaaaat tctaggctat atacaactac gcaaaggccc caacgttgta     120
ggcccctacg gctactaca  acccttcgct gacgccataa aactcttcac caaagagccc     180
ctaaaacccg ccacatctac catcaccctc tacatcaccg ccccgacctt agctctcacc     240
atcgctcttc tactatgaac ccccctcccc atacccaacc cctggtcaa  cctcaaccta     300
ggcctcctat ttattctagc cacctctagc ctagccgttt actcaatcct ctgatcaggg     360
```

```
tgagcatcaa actcaaacta cgccctgatc ggcgcactgc gagcagtagc ccaaacaatc    420
tcatatgaag tcaccctagc catcattcta ctatcaacat tactaataag tggctccttt    480
aacctctcca cccttatcac aacacaagaa cacctctgat tactcctgcc atcatgaccc    540
ttggccataa tatgatttat ctccacacta gcagagacca accgaacccc cttcgacctt    600
gccgaagggg agtccgaact agtctcaggc ttcaacatcg aatacgccgc aggccccttc    660
gccctattct tcatagccga atacacaaac attattataa taaacaccct caccactaca    720
atcttcctag gaacaacata tgacgcactc tcccctgaac tctacacaac atattttgtc    780
accaagaccc tacttctaac ctccctgttc ttatgaattc gaacagcata ccccgattc    840 cgctacgacc aactcataca cctcctatga aaaaacttcc taccactcac cctagcatta    900
cttatatgat atgtctccat acccattaca atctccagca ttcccccctca aacctaa     957
```

<210> SEQ ID NO 164
<211> LENGTH: 23
<212> TYPE: DNA
<213> ORGANISM: Artificial Sequence
<220> FEATURE:
<223> OTHER INFORMATION: ND1-F primer

<400> SEQUENCE: 164
gaggctctgt ctggtatctt gaa                                            23

<210> SEQ ID NO 165
<211> LENGTH: 18
<212> TYPE: DNA
<213> ORGANISM: Artificial Sequence
<220> FEATURE:
<223> OTHER INFORMATION: ND1-R primer

<400> SEQUENCE: 165
gtcggggcgg tgatgtag                                                  18

<210> SEQ ID NO 166
<211> LENGTH: 20
<212> TYPE: DNA
<213> ORGANISM: Artificial Sequence
<220> FEATURE:
<223> OTHER INFORMATION: GAPDH-F primer

<400> SEQUENCE: 166
cctgtacgcc aacacagtgc                                                20

<210> SEQ ID NO 167
<211> LENGTH: 20
<212> TYPE: DNA
<213> ORGANISM: Artificial Sequence
<220> FEATURE:
<223> OTHER INFORMATION: GAPDH-R primer

<400> SEQUENCE: 167
atactcctgc ttgctgatcc                                                20

<210> SEQ ID NO 168
<211> LENGTH: 1041
<212> TYPE: DNA
<213> ORGANISM: Artificial Sequence
<220> FEATURE:
<223> OTHER INFORMATION: COX10-opt_ND1

<400> SEQUENCE: 168

```
atggccgcat ctccgcacac tctctcctca cgcctcctga caggttgcgt aggaggctct      60
gtctggtatc ttgaaagaag aactatgccc atggccaacc tgctgctgct gatcgtgccc     120
atcctgatcg ccatggcctt cctgatgctg accgagcgca agatcctggg ctacatgcag     180
ctgcgcaagg gccccaacgt ggtgggcccc tacggcctgc tgcagccctt cgccgacgcc     240
atgaagctgt tcaccaagga gcccctgaag cccgccacca gcaccatcac cctgtacatc     300
accgccccca ccctggccct gaccatcgcc ctgctgctgt ggacccccct gcccatgccc     360
aaccccctgg tgaacctgaa cctgggcctg ctgttcatcc tggccaccag cagcctggcc     420
gtgtacagca tcctgtggag cggctgggcc agcaacagca actacgccct gatcggcgcc     480
ctgcgcgccg tggcccagac catcagctac gaggtgaccc tggccatcat cctgctgagc     540
accctgctga tgagcggcag cttcaacctg agcaccctga tcaccaccca ggagcacctg     600
tggctgctgc tgcccagctg gcccctggcc atgatgtggt tcatcagcac cctggccgag     660
accaaccgca ccccttcga cctggccgag ggcgagagcg agctggtgag cggcttcaac     720
atcgagtacg ccgccggccc cttcgccctg ttcttcatgg ccgagtacac caacatcatc     780
atgatgaaca ccctgaccac caccatcttc ctgggcacca cctacgacgc cctgagcccc     840
gagctgtaca ccacctactt cgtgaccaag accctgctgc tgaccagcct gttcctgtgg     900
atccgcaccg cctaccccg cttccgctac gaccagctga tgcacctgct gtggaagaac     960
ttcctgcccc tgaccctggc cctgctgatg tggtacgtga gcatgcccat caccatcagc    1020
agcatccccc cccagaccta a                                              1041

<210> SEQ ID NO 169
<211> LENGTH: 1041
<212> TYPE: DNA
<213> ORGANISM: Artificial Sequence
<220> FEATURE:
<223> OTHER INFORMATION: COX10-ND1

<400> SEQUENCE: 169
atggccgcat ctccgcacac tctctcctca cgcctcctga caggttgcgt aggaggctct      60
gtctggtatc ttgaaagaag aactatgccc atggccaacc tcctactcct cattgtaccc     120
attctaatcg caatggcatt cctaatgctt accgaacgaa aaattctagg ctatatgcaa     180
ctacgcaaag gccccaacgt tgtaggcccc tacgggctac tacaacccit cgctgacgcc     240 atgaaactct tcaccaaaga gcccctaaaa cccgccacat ctaccatcac cctctacatc     300 accgcccga cccttagctct caccatcgct cttctactat ggacccccct ccccatgccc     360
aaccccctgg tcaacctcaa cctaggcctc ctatttattc tagccaccct tagcctagcc     420
gtttactcaa tcctctggtc agggtgggca tcaaactcaa actacgccct gatcggcgca     480
ctgcgagcag tagcccaaac aatctctatat gaagtcaccc tagccatcat tctactatca     540
acattactaa tgagtggctc ctttaacctc tccaccctta tcacaacaca gaacacctc     600 tggttactcc tgccatcatg gcccttggcc atgatgtggt ttatctccac actagcagag     660
accaaccgaa ccccccttcga ccttgccgaa ggggagtccg aactagtctc aggcttcaac     720
```

-continued

| | | | | |
|---|---|---|---|---|
| atcgaatacg | ccgcaggccc | cttcgcccta | ttcttcatgg | ccgaatacac aaacattatt 780 |
| atgatgaaca | ccctcaccac | tacaatcttc | ctaggaacaa | catatgacgc actctcccct 840 |
| gaactctaca | caacatattt | tgtcaccaag | accctacttc | taacctccct gttcttatgg 900 |
| attcgaacag | catacccccg | attccgctac | gaccaactca | tgcacctcct atggaaaaac 960 |
| ttcctaccac | tcaccctagc | attacttatg | tggtatgtct | ccatgcccat tacaatctcc 1020 |
| agcattcccc | ctcaaaccta | a | | 1041 |

COMPOSITIONS AND METHODS FOR TREATING LEBER'S HEREDITARY OPTIC NEUROPATHY WITH NADH DEHYDROGENASE PROTEINS

CROSS-REFERENCE

This application is a continuation of PCT Application No. PCT/CN2020/134859, filed on Dec. 9, 2020, which claims the benefit of Chinese Application No. CN201911250082.4, filed on Dec. 9, 2019, the contents of all of which are incorporated herein by reference in their entireties.

REFERENCE TO A SEQUENCE LISTING

The instant application contains a Sequence Listing which has been submitted in ASCII format via EFS-Web and is hereby incorporated by reference in its entirety. Said ASCII copy, created on Jun. 1, 2021, is named WNBT-011_01US_SeqList_ST25.txt and is about 303 kilobytes in size.

BACKGROUND

Leber's hereditary optic neuropathy (LHON) is a mitochondrially inherited (transmitted from mother to offspring) degeneration of retinal ganglion cells (RGCs) and their axons that leads to an acute or subacute loss of central vision; this affects predominantly young adult males. LHON is only transmitted through the mother, as it is primarily due to mutations in the mitochondrial (not nuclear) genome, and only the egg contributes mitochondria to the embryo. LHON is usually due to one of three pathogenic mitochondrial DNA (mtDNA) point mutations. These mutations are at nucleotide positions 11778 G to A (G11778A), 3460 G to A (G3460A) and 14484 T to C (T14484C), respectively in the NADH dehydrogenase subunit-4 protein (ND4), NADH dehydrogenase subunit-1 protein (ND1) and NADH dehydrogenase subunit-6 protein (ND6) subunit genes of complex I of the oxidative phosphorylation chain in mitochondria. Each mutation is believed to have significant risk of permanent loss of vision. It typically progresses within several weeks to several months without pain, until the binocular vision deteriorate to below 0.1, which seriously affects the quality of life of the patient. Two LHON mutants, G3460A and T14484C, results in the reduction of the patient's platelets isolated mitochondrial NADH dehydrogenase activity by 80%. Ninety percent of the Chinese LHON patients carry the G11778A mutation. The G11778A mutation changes an arginine into histidine in the ND4 protein, resulting the dysfunction and optic nerve damage in LHON patients. There is a need for developing compositions and methods for treating LHON with higher transfection efficiency and treatment efficacy.

SUMMARY

Disclosed here recombinant nucleic acids, pharmaceutical compositions, and methods for treating LHON. In some embodiments, disclosed herein is a recombinant nucleic acid, comprising: a mitochondrial targeting sequence; a mitochondrial protein coding sequence comprising a sequence that is at least 99% identical to SEQ ID NO: 11 or 12; and a 3'UTR nucleic acid sequence.

In some embodiments, the mitochondrial targeting sequence encodes a polypeptide comprising a peptide sequence that is at least 90%, at least 95%, at least 97%, at least 99%, or 100% identical to a sequence selected from the group consisting of SEQ ID NO: 129-159. In some embodiments, the mitochondrial targeting sequence comprises a sequence that is at least 90%, at least 95%, at least 97%, at least 99%, or 100% identical to a sequence as set forth in SEQ ID NO: 2. In some embodiments, the mitochondrial targeting sequence comprises a sequence that is at least 90%, at least 95%, at least 97%, at least 99%, or 100% identical to a sequence as set forth in SEQ ID NO: 3. In some embodiments, the mitochondrial targeting sequence comprises a sequence that is at least 90%, at least 95%, at least 97%, at least 99%, or 100% identical to a sequence as set forth in SEQ ID NO: 4. In some embodiments, the mitochondrial targeting sequence comprises a sequence that is at least 90%, at least 95%, at least 97%, at least 99%, or 100% identical to a sequence as set forth in SEQ ID NO: 5. In some embodiments, the mitochondrial targeting sequence comprises a sequence that is at least 90%, at least 95%, at least 97%, at least 99%, or 100% identical to a sequence as set forth in SEQ ID NO: 1. In some embodiments, the mitochondrial protein coding sequence comprises a sequence that is at least 90%, at least 95%, at least 97%, at least 99%, or 100% identical to a sequence as set forth in SEQ ID NO: 12. In some embodiments, the mitochondrial protein coding sequence comprises a sequence that is at least 90%, at least 95%, at least 97%, at least 99%, or 100% identical to a sequence as set forth in SEQ ID NO: 11. In some embodiments, the 3'UTR nucleic acid sequence comprises a sequence that is at least 90%, at least 95%, at least 97%, at least 99%, or 100% identical to a sequence selected from the group consisting of SEQ ID NO: 111-125. In some embodiments, the 3'UTR nucleic acid sequence comprises a sequence that is at least 90%, at least 95%, at least 97%, at least 99%, or 100% identical to a sequence as set forth in SEQ ID NO: 13 or SEQ ID NO: 14. In some embodiments, the recombinant nucleic acid comprises a sequence that is at least 90%, at least 95%, at least 97%, at least 99%, or 100% identical to a sequence selected from the group consisting of SEQ ID NO: 25-28, 39-42, 53-56, 67-70, and 81-84.

In some embodiments, the disclosure provides recombinant nucleic acids comprising a mitochondrial targeting sequence; a mitochondrial protein coding sequence comprising a sequence that is at least 90%, at least 95%, at least 97%, at least 99%, or 100% identical to SEQ ID NO: 11 or 12; and a 3'UTR nucleic acid sequence. In some embodiments, the mitochondrial targeting sequence comprises a sequence encodes a polypeptide selected from the group consisting of hsCOX10, hsCOX8, scRPM2, lcSirt5, tbNDUS7, ncQCR2, hsATP5G2, hsLACTB, spilv1, gmCOX2, crATP6, hsOPA1, hsSDHD, hsADCK3, osP0644B06.24-2, *Neurospora crassa* ATP9 (ncATP9), hsGHITM, hsNDU-FAB1, hsATP5G3, crATP6_hsADCK3, ncATP9_ncATP9, zmLOC100282174,
ncATP9_zmLOC100282174_spilv1_ncATP9,
zmLOC100282174_hsADCK3_crATP6_hsATP5G3,
zmLOC100282174_hsADCK3_hsATP5G3,
ncATP9_zmLOC100282174,
hsADCK3_zmLOC100282174_crATP6_hsATP5G3,
crATP6_hsADCK3_zmLOC100282174_hsATP5G3,
hsADCK3_zmLOC100282174,
hsADCK3_zmLOC100282174_crATP6,
ncATP9_zmLOC100282174_spilv1_GNFP_ncATP9, and
ncATP9_zmLOC100282174_spilv1_lcSirt5_
osP0644B06.24-2_hsATP5G2_ncATP9. In some embodiments, the mitochondrial targeting sequence encodes a polypeptide comprising a peptide sequence that is at least 90%, at least 95%, at least 97%, at least 99%, or 100% identical to a sequence selected from the group consisting of SEQ ID NO: 129-159. In some embodiments, the mitochondrial targeting sequence comprises a sequence that is at least 90%, at least 95%, at least 97%, at least 99%, or 100% identical to a sequence as set forth in SEQ ID NO: 2 or 3. In some embodiments, the mitochondrial targeting sequence comprises a sequence that is at least 90%, at least 95%, at least 97%, at least 99%, or 100% identical to a sequence as set forth in SEQ ID NO: 4. In some embodiments, the mitochondrial targeting sequence comprises a sequence that is at least 90%, at least 95%, at least 97%, at least 99%, or 100% identical to a sequence as set forth in SEQ ID NO: 5. In some embodiments, the mitochondrial targeting sequence comprises a sequence that is at least 90%, at least 95%, at least 97%, at least 99%, or 100% identical to a sequence as set forth in SEQ ID NO: 1. In some embodiments, the 3'UTR nucleic acid sequence is located at 3' of said mitochondrial targeting sequence. In some embodiments, the 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, rnSOD2, and hsOXA1L. In some embodiments, the 3'UTR nucleic acid sequence comprises a sequence that is at least 90%, at least 95%, at least 97%, at least 99%, or 100% identical to a sequence selected from the group consisting of SEQ ID NO: 111-125 In some embodiments, the 3'UTR nucleic acid sequence comprises a sequence that is at least 90%, at least 95%, at least 97%, at least 99%, or 100% identical to a sequence as set forth in SEQ ID NO: 13 or SEQ ID NO: 14. In some embodiments, the mitochondrial targeting sequence is located at 5' of said 3'UTR nucleic acid sequence. In some embodiments, the mitochondrial targeting sequence is located at 3' of said mitochondrial targeting sequence. In some embodiments, the recombinant nucleic acid comprises a sequence that is at least 90%, at least 95%, at least 97%, at least 99%, or 100% identical to a sequence selected from the group consisting of SEQ ID NO: 25-28, 39-42, 53-56, 67-70, and 81-84. In some embodiments, the mitochondrial protein coding sequence encodes a mitochondrial protein comprising or consisting of a sequence that is at least 90%, at least 95%, at least 97%, at least 99%, or 100% identical to a sequence as set forth in SEQ ID NO: 162.

In some embodiments, the disclosure provides recombinant nucleic acids comprising a mitochondrial protein coding sequence, wherein said mitochondrial protein coding sequence encodes a polypeptide comprising a mitochondrial protein, wherein said mitochondrial protein coding sequence comprises a sequence that is at least 90%, at least 95%, at least 97%, at least 99%, or 100% identical to SEQ ID NO: 11 or 12. In some embodiments, the recombinant nucleic acid further comprises a mitochondrial targeting sequence. In some embodiments, the mitochondrial targeting sequence comprises a sequence encodes a polypeptide selected from the group consisting of hsCOX10, hsCOX8, scRPM2, lcSirt5, tbNDUS7, ncQCR2, hsATP5G2, hsLACTB, spilv1, gmCOX2, crATP6, hsOPA1, hsSDHD, hsADCK3, osP0644B06.24-2, Neurospora crassa ATP9 (ncATP9), hsGHITM, hsNDUFAB1, hsATP5G3, crATP6_hsADCK3, ncATP9_ncATP9, zmLOC100282174, ncATP9_zmLOC100282174_spilv1_ncATP9, zmLOC100282174_hsADCK3_crATP6_hsATP5G3, zmLOC100282174_hsADCK3_hsATP5G3, ncATP9_zmLOC100282174, hsADCK3_zmLOC100282174_crATP6_hsATP5G3, crATP6_hsADCK3_zmLOC100282174_hsATP5G3, hsADCK3_zmLOC100282174, hsADCK3_zmLOC100282174_crATP6, ncATP9_zmLOC100282174_spilv1_GNFP_ncATP9, and ncATP9_zmLOC100282174_spilv1_lcSirt5_osP0644B06.24-2_hsATP5G2_ncATP9. In some embodiments, the mitochondrial targeting sequence encodes a polypeptide comprising a peptide sequence that is at least 90%, at least 95%, at least 97%, at least 99%, or 100% identical to a sequence selected from the group consisting of SEQ ID NO: 129-159. In some embodiments, the mitochondrial targeting sequence comprises a sequence that is at least 90%, at least 95%, at least 97%, at least 99%, or 100% identical to a sequence as set forth in SEQ ID NO: 2. In some embodiments, the mitochondrial targeting sequence comprises a sequence that is at least 90%, at least 95%, at least 97%, at least 99%, or 100% identical to a sequence as set forth in SEQ ID NO: 3. In some embodiments, the mitochondrial targeting sequence comprises a sequence that is at least 90%, at least 95%, at least 97%, at least 99%, or 100% identical to a sequence as set forth in SEQ ID NO: 4. In some embodiments, the mitochondrial targeting sequence comprises a sequence that is at least 90%, at least 95%, at least 97%, at least 99%, or 100% identical to a sequence as set forth in SEQ ID NO: 5. In some embodiments, the mitochondrial targeting sequence comprises a sequence that is at least 90%, at least 95%, at least 97%, at least 99%, or 100% identical to a sequence as set forth in SEQ ID NO: 1. In some embodiments, the recombinant nucleic acid further comprises a 3'UTR nucleic acid sequence. In some embodiments, the 3'UTR nucleic acid sequence is located at 3' of said mitochondrial targeting sequence. In some embodiments, the 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, rnSOD2, and hsOXA1L. In some embodiments, the 3'UTR nucleic acid sequence comprises a sequence that is at least 90%, at least 95%, at least 97%, at least 99%, or 100% identical to a sequence selected from the group consisting of SEQ ID NO: 111-125. In some embodiments, the 3'UTR nucleic acid sequence comprises a sequence that is at least 90%, at least 95%, at least 97%, at least 99%, or 100% identical to a sequence as set forth in SEQ ID NO: 13 or SEQ ID NO: 14. In some embodiments, the mitochondrial targeting sequence is located at 5' of said 3'UTR nucleic acid sequence. In some embodiments, the mitochondrial targeting sequence is located at 3' of said mitochondrial targeting sequence. In some embodiments, the recombinant nucleic acid comprises a sequence that is at least 90%, at least 95%, at least 97%, at least 99%, or 100% identical to a sequence selected from the group consisting of SEQ ID NO: 25-28, 39-42, 53-56, 67-70, and 81-84.

In some embodiments, the disclosure provides viral vectors comprising recombinant nucleic acid of the disclosure. In some embodiments, the viral vector is an adeno-associated virus (AAV) vector. In some embodiments, the AAV vector is selected from the group consisting of AAV1, AAV2, AAV3, AAV4, AAV5, AAV6, AAV7, AAV8, AAV9, AAV10, AAV11, AAV12, AAV13, AAV14, AAV15, and AAV16 vectors. In some embodiments, the AAV vector is a recombinant AAV (rAAV) vector. In some embodiments, the rAAV vector is rAAV2 vector.

In some embodiments, disclosed herein is a pharmaceutical composition, comprising an adeno-associated virus (AAV) comprising any recombinant nucleic acid disclosed herein. In some cases, the pharmaceutical composition further comprises a pharmaceutically acceptable excipient thereof. Also disclosed is a pharmaceutical composition, comprising the viral vector disclosed herein, and a pharmaceutically acceptable excipient thereof, wherein the viral vector comprises any recombinant nucleic acid disclosed herein.

In some cases, the pharmaceutically acceptable excipient comprises phosphate-buffered saline (PBS), α,α-trehalose dehydrate, L-histidine monohydrochloride monohydrate, polysorbate 20, NaCl, NaH2PO4, Na2HPO4, KH2PO4, K2HPO4, poloxamer 188, or any combination thereof. In some cases, the pharmaceutically acceptable excipient is selected from phosphate-buffered saline (PBS), α,α-trehalose dehydrate, L-histidine monohydrochloride monohydrate, polysorbate 20, NaCl, NaH2PO4, Na2HPO4, KH2PO4, K2HPO4, poloxamer 188, and any combination thereof. In some cases, the pharmaceutically acceptable excipient comprises poloxamer 188. In some cases, the pharmaceutically acceptable excipient comprises 0.0001%-0.01% poloxamer 188. In some cases, the pharmaceutically acceptable excipient comprises 0.001% poloxamer 188. In some cases, the pharmaceutically acceptable excipient further comprises one or more salts. In some cases, the one or more salts comprises NaCl, NaH2PO4, Na2HPO4, and KH2PO4. In some cases, the one or more salts comprises 80 mM NaCl, 5 mM NaH2PO4, 40 mM Na2HPO4, and 5 mM KH2PO4. In some cases, the pharmaceutical composition has a pH of 6-8. In some cases, the pharmaceutical composition has a pH of 7.2-7.4. In some cases, the pharmaceutical composition has a pH of 7.3. In some cases, the pharmaceutical composition has a viral titer of at least $1.0 \times 10^{10}$ vg/mL. In some cases, the pharmaceutical composition has a viral titer of at least $5.0 \times 10^{10}$ vg/mL.

In some cases, the pharmaceutical composition is subject to five freeze/thaw cycles, the pharmaceutical composition retains at least 60%, 70%, 80%, or 90% of a viral titer as compared to the viral titer prior to the five freeze/thaw cycles. In some cases, the pharmaceutical composition, when administered to a patient with Leber's hereditary optic neuropathy, generates a higher average recovery of vision than a comparable pharmaceutical composition without the recombinant nucleic acid. In some cases, the pharmaceutical composition, when administered to a patient with Leber's hereditary optic neuropathy, generates a higher average recovery of vision than a comparable pharmaceutical composition comprising a recombinant nucleic acid as set forth in SEQ ID NO: 15.

In another aspect, disclosed herein is a method of treating an eye disorder, comprising administering any pharmaceutical composition disclosed herein to a patient in need thereof. In some cases, the eye disorder is Leber's hereditary optic neuropathy (LHON). In some cases, the method comprises administering the pharmaceutical composition to one or both eyes of the patient. In some cases, the pharmaceutical composition is administered via intraocular or intravitreal injection. In some cases, the pharmaceutical composition is administered via intravitreal injection. In some cases, about 0.01-0.1 mL of the pharmaceutical composition is administered via intravitreal injection. In some cases, about 0.05 mL of the pharmaceutical composition is administered via intravitreal injection.

In some cases, the method further comprises administering methylprednisolone to the patient. In some cases, the methylprednisolone is administered prior to the intravitreal injection of the pharmaceutical composition. In some cases, the methylprednisolone is administered orally In some cases, the methylprednisolone is administered daily for at least 1, 2, 3, 4, 5, 6, or 7 days prior to the intravitreal injection of the pharmaceutical composition. In some cases, the methylprednisolone is administered daily. In some cases, the a daily dosage of about 32 mg/60 kg methylprednisolone is administered. In some cases, the methylprednisolone is administered after the intravitreal injection of the pharmaceutical composition. In some cases, the method further comprises administering creatine phosphate sodium to the patient. In some cases, the creatine phosphate sodium is administered intravenously. In some cases, the methylprednisolone is administered intravenously or orally. In some cases, the method comprises administering methylprednisolone intravenously for at least one day, which is followed by administering methylprednisolone orally for at least a week. In some cases, the method comprises administering methylprednisolone intravenously for about 3 days, which is followed by administering methylprednisolone orally for at least about 6 weeks. In some cases, the methylprednisolone is administered intravenously at a daily dose of about 80 mg/60 kg. In some cases, the administering the pharmaceutical composition generates a higher average recovery of vision than a comparable pharmaceutical composition without the recombinant nucleic acid. In some cases, the administering the pharmaceutical composition generates a higher average recovery of vision than a comparable pharmaceutical composition comprising a recombinant nucleic acid as set forth in SEQ ID NO: 25.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 shows sequence alignment of optimized opt_ND1 gene (SEQ ID NO: 12) and ND1 gene (SEQ ID NO: 11);

FIG. 4 shows sequence alignment of COX10-opt_ND1 (SEQ ID NO: 168) and COX10-ND1 (SEQ ID NO: 169);

FIG. 6 shows mitochondria localization assay of ND1 protein, displaying green fluorescence signal (left), MitoTracker signal (middle) and merged signals (right) showing mitochondria co-localization;

FIG. 10 shows cytokine expression analysis (1-month post-injection and 2-month post-injection) of rabbit intravitreally injected with rAAV2-ND1.

DETAILED DESCRIPTION

Definitions

Figure 1:
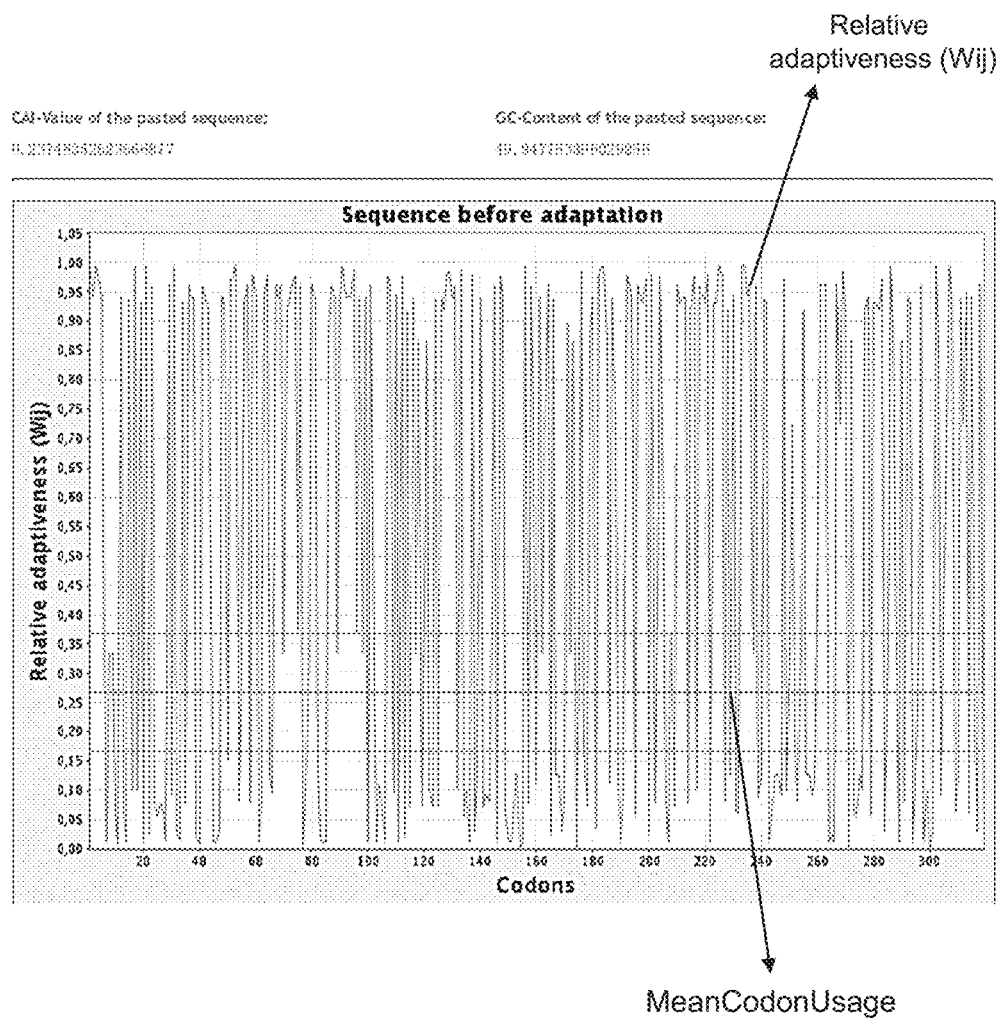
FIG. 1 shows the codon usage frequency of non-optimized ND1 gene.
Figure 2:
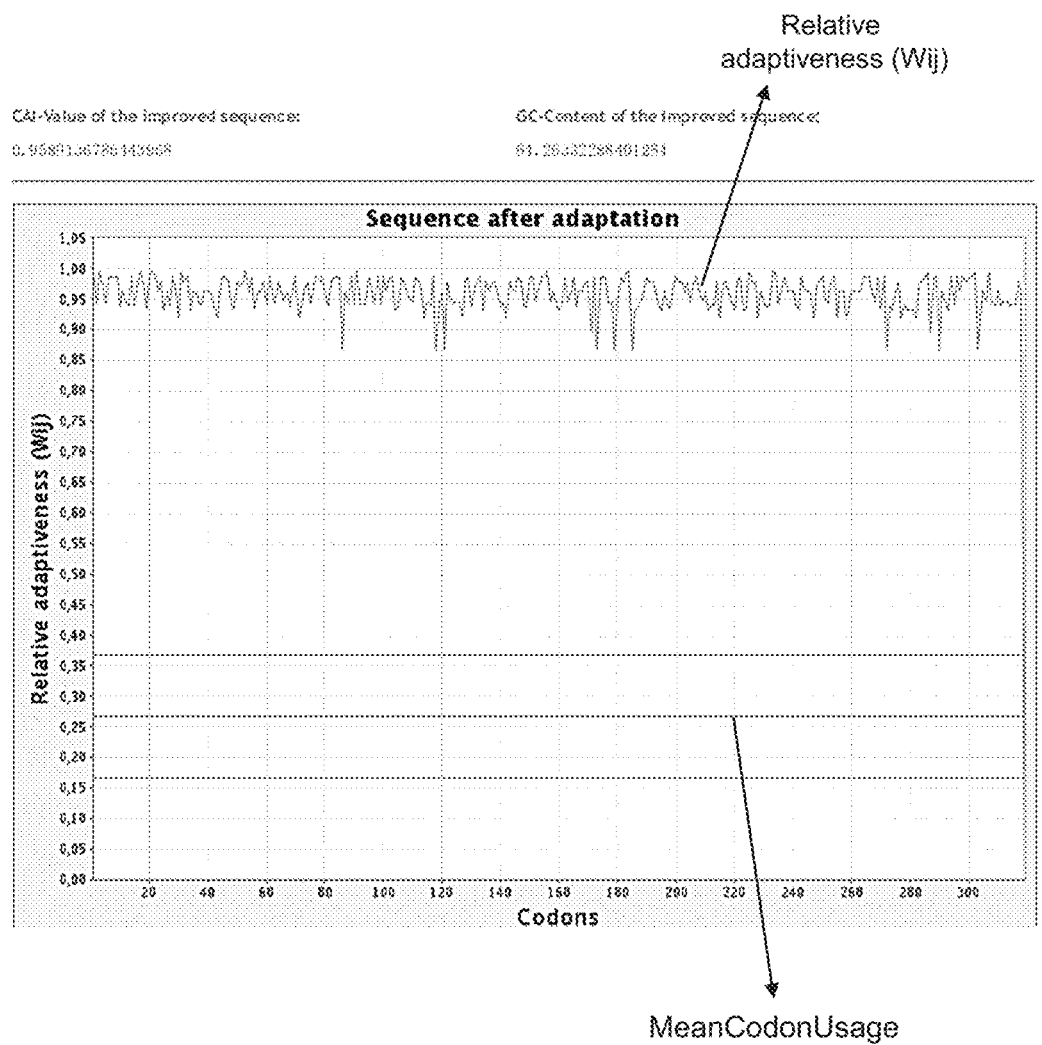
FIG. 2 shows the codon usage frequency of optimized ND1 gene.

Unless defined otherwise, all technical and scientific terms used herein have the same meaning as commonly understood by one of the ordinary skill in the art to which this disclosure belongs. Although any methods and materials similar or equivalent to those described herein can be used in the practice or testing of the formulations or unit doses herein, some methods and materials are now described. Unless mentioned otherwise, the techniques employed or contemplated herein are standard methodologies. The materials, methods and examples are illustrative only and not limiting.

As used herein and in the appended claims, the singular forms "a," "and," and "the" include plural referents unless the context clearly dictates otherwise. Thus, for example, reference to "a compound" includes a plurality of such agents, and reference to "the salt" includes reference to one or more salts (or to a plurality of salts) and equivalents thereof known to those skilled in the art, and so forth.

As used herein, unless otherwise indicated, the term "or" can be conjunctive or disjunctive. As used herein, unless otherwise indicated, any embodiment can be combined with any other embodiment.

As used herein, unless otherwise indicated, some inventive embodiments herein contemplate numerical ranges. When ranges are present, the ranges include the range endpoints. Additionally, every subrange and value within the range is present as if explicitly written out.

The term "about" and its grammatical equivalents in relation to a reference numerical value and its grammatical equivalents as used herein can include a range of values plus or minus 10% from that value, such as a range of values plus or minus 10%, 9%, 8%, 7%, 6%, 5%, 4%, 3%, 2%, or 1% from that value. For example, the amount "about 10" includes amounts from 9 to 11.

The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The term "subject" refers to a mammal that has been or will be the object of treatment, observation or experiment. The term "mammal" is intended to have its standard meaning, and encompasses humans, dogs, cats, sheep, and cows, for example. The methods described herein can be useful in both human therapy and veterinary applications. In some embodiments, the subject is a human.

The term "treating" or "treatment" encompasses administration of at least one compound disclosed herein, or a pharmaceutically acceptable salt thereof, to a mammalian subject, particularly a human subject, in need of such an administration and includes (i) arresting the development of clinical symptoms of the disease, such as cancer, (ii) bringing about a regression in the clinical symptoms of the disease, such as cancer, and/or (iii) prophylactic treatment for preventing the onset of the disease, such as cancer.

The term "therapeutically effective amount" of a chemical entity described herein refers to an amount effective, when administered to a human or non-human subject, to provide a therapeutic benefit such as amelioration of symptoms, slowing of disease progression, or prevention of disease.

As used herein, unless otherwise indicated, the terms "nucleic acid" and "polynucleotide" can be used interchangeably.

Nucleic Acid and Polypeptide Sequences

Table 1 discloses all the nucleic acid and polypeptide sequences disclosed herein. The first column shows the SEQ ID NO of each sequence. The second column describes the nucleic acid or polypeptide construct. For example, the construct COX10-opt_ND1-3'UTR (SEQ ID NO: 27) is a nucleic acid combining the nucleic acid sequences of COX10 (SEQ ID NO: 1), opt_ND1 (SEQ ID NO: 12), and 3'UTR (SEQ ID NO: 13) (from 5' to 3') without linker between the nucleic acid sequences.

TABLE 1 nucleic acid and polypeptide sequences and SEQ ID NOs

| SEQ ID NO: | description | sequence |
|---|---|---|
| 1 | COX10 | ATGGCCGCATCTCCGCACACTCTCTCCTCACGCCTCCTGACAGGTTGCGT AGGAGGCTCTGTCTGGTATCTTGAAAGAAGAACT |
| 2 | opt_COX10 | ATGGCCGCCTCTCCACACACACTGAGTAGCAGACTGCTGACCGGCTGTG TTGGCGGCTCTGTGTGGTATCTGGAACGGCGGACA |
| 3 | opt_COX10 | ATGGCCGCCAGCCCCCACACCCTGAGCAGCCGCCTGCTGACCGGCTGC GTGGGCGGCAGCGTGTGGTACCTGGAGCGCCGCACC |
| 4 | COX8 | ATGTCCGTCCTGACGCGCCTGCTGCTGCGGGGCTTGACACGGCTCGGCT CGGCGGCTCCAGTGCGGCGCGCCAGAATCCATTCGTTG |
| 5 | OPA1 | GTGCTGCCCGCCTAGAAAGGGTGAAGTGGTTGTTTCCGTGACGGACTGA GTACGGGTGCCTGTCAGGCTCTTGCGGAAGTCCATGCGCCATTGGGAGG GCCTCGGCCGCGGCTCTGTGCCCTTGCTGCTGAGGGCCACTTCCTGGGT CATTCCTGGACCGGGAGCCGGGCTGGGGCTCACACGGGGGCTCCCGCG TGGCCGTCTCGGCGCCTGCGTGACCTCCCCGCCGGCGGGATGTGGCGA CTACGTCGGGCCGCTGTGGCCTG |

TABLE 1-continued nucleic acid and polypeptide sequences and SEQ ID NOs

| SEQ ID NO: | description | sequence |
|---|---|---|
| 6 | ND4 | ATGCTAAAACTAATCGTCCCAACAATTATGTTACTACCACTGACATGGCTT
TCCAAAAAACACATGATTTGGATCAACACAACCACCCACAGCCTAATTATT
AGCATCATCCCTCTACTATTTTTAACCAAATCAACAACAACCTATTTAGCT
GTTCCCCAACCTTTTCCTCCGACCCCCTAACAACCCCCCTCCTAATGCTA
ACTACCTGGCTCCTACCCCTCACAATCATGGCAAGCCAACGCCACTTATC
CAGTGAACCACTATCACGAAAAAAACTCTACCTCTCTATGCTAATCTCCCT
ACAAATCTCCTTAATTATGACATTCACAGCCACAGAACTAATCATGTTTTAT
ATCTTCTTCGAAACCACACTTATCCCCACCTTGGCTATCATCACCCGATGG
GGCAACCAGCCAGAACGCCTGAACGCAGGCACATACTTCCTATTCTACAC
CCTAGTAGGCTCCCTTCCCCTACTCATCGCACTAATTTACACTCACAACAC
CCTAGGCTCACTAAACATTCTACTACTCACTCTCACTGCCCAAGAACTATC
AAACTCCTGGGCCAACAACTTAATGTGGCTAGCTTACACAATGGCTTTTAT
GGTAAAGATGCCTCTTTACGGACTCCACTTATGGCTCCCTAAAGCCCATG
TCGAAGCCCCCATCGCTGGGTCAATGGTACTTGCCGCAGTACTCTTAAAA
CTAGGCGGCTATGGTATGATGCGCCTCACACTCATTCTCAACCCCCTGAC
AAAACACATGGCCTACCCCTTCCTTGTACTATCCCTATGGGGCATGATTAT
GACAAGCTCCATCTGCCTACGACAAACAGACCTAAAATCGCTCATTGCAT
ACTCTTCAATCAGCCACATGGCCCTCGTAGTAACAGCCATTCTCATCCAA
ACCCCCTGGAGCTTCACCGGCGCAGTCATTCTCATGATCGCCCACGGGC
TTACATCCTCATTACTATTCTGCCTAGCAAACTCAAACTACGAACGCACTC
ACAGTCGCATCATGATCCTCTCTCAAGGACTTCAAACTCTACTCCCACTAA
TGGCTTTTTGGTGGCTTCTAGCAAGCCTCGCTAACCTCGCCTTACCCCCC
ACTATTAACCTACTGGGAGAACTCTCTGTGCTAGTAACCACGTTCTCCTG
GTCAAATATCACTCTCCTACTTACAGGACTCAACATGCTAGTCACAGCCCT
ATACTCCCTCTACATGTTTACCACAACACAATGGGGCTCACTCACCCACC
ACATTAACAACATGAAACCCTCATTCACACGAGAAAACACCCTCATGTTCA
TGCACCTATCCCCCATTCTCCTCCTATCCCTCAACCCCGACATCATTACC
GGGTTTTCCTCTTAA |
| 7 | opt_ND4 | ATGCTGAAGCTGATCGTGCCCACCATCATGCTGCTGCCTCTGACCTGGCT
GAGCAAGAAACACATGATCTGGATCAACACCACCACGCACAGCCTGATCA
TCAGCATCATCCCTCTGCTGTTCTTCAACCAGATCAACAACAACCTGTTCA
GCTGCAGCCCCACCTTCAGCAGCGACCCTCTGACAACACCTCTGCTGAT
GCTGACCACCTGGCTGCTGCCCCTCACAATCATGGCCTCTCAGAGACAC
CTGAGCAGCGAGCCCCTGAGCCGGAAGAAACTGTACCTGAGCATGCTGA
TCTCCCTGCAGATCTCTCTGATCATGACCTTCACCGCCACCGAGCTGATC
ATGTTCTACATCTTTTTCGAGACAACGCTGATCCCCACACTGGCCATCATC
ACCAGATGGGGCAACCAGCCTGAGAGACTGAACGCCGGCACCTACTTTC
TGTTCTACACCCTCGTGGGCAGCCTGCCACTGCTGATTGCCCTGATCTAC
ACCCACAACACCCTGGGCTCCCTGAACATCCTGCTGCTGACACTGACAG
CCCAAGAGCTGAGCAACAGCTGGGCCAACAATCTGATGTGGCTGGCCTA
CACAATGGCCTTCATGGTCAAGATGCCCCTGTACGGCCTGCACCTGTGG
CTGCCTAAAGCTCATGTGGAAGCCCCTATCGCCGGCTCTATGGTGCTGG
CTGCAGTGCTGCTGAAACTCGGCGGCTACGGCATGATGCGGCTGACCCT
GATTCTGAATCCCCTGACCAAGCACATGGCCTATCCATTTCTGGTGCTGA
GCCTGTGGGGCATGATTATGACCAGCAGCATCTGCCTGCGGCAGACCGA
TCTGAAGTCCCTGATCGCCTACAGCTCCATCAGCCACATGGCCCTGGTG
GTCACCGCCATCCTGATTCAGACCCCTTGGAGCTTTACAGGCGCCGTGAT
CCTGATGATTGCCCACGCCTGACAAGCAGCCTGCTGTTTTGTCTGGCCA
ACAGCAACTACGAGCGGACCCACAGCAGAATCATGATCCTGTCTCAGGG
CCTGCAGACCCTCCTGCCTCTTATGGCTTTTTGGTGGCTGCTGGCCTCTC
TGGCCAATCTGGCACTGCCTCCTACCATCAATCTGCTGGGCGAGCTGAG
CGTGCTGGTCACCACATTCAGCTGGTCCAATATCACCCTGCTGCTCACCG
GCCTGAACATGCTGGTTACAGCCCTGTACTCCCTGTACATGTTCACCACC
ACACAGTGGGGAAGCCTGACACACCACATCAACAATATGAAGCCCAGCTT
CACCCCGCGAGAACACCCTGATGTTCATGCATCTGAGCCCCATTCTGCTGC
TGTCCCTGAATCCTGATATCATCACCGGCTTCTCCAGCTGA |
| 8 | opt_ND4* | ATGCTGAAGCTGATCGTGCCCACCATCATGCTGCTGCCCCTGACCTGGC
TGAGCAAGAAGCACATGATCTGGATCAACACCACCACCCACAGCCTGATC
ATCAGCATCATCCCCCTGCTGTTCTTCAACCAGATCAACAACAACCTGTTC
AGCTGCAGCCCCACCTTCAGCAGCGACCCCCTGACCACCCCCCTGCTGA
TGCTGACCACCTGGCTGCTGCCCCTGACCATCATGGCCAGCCAGCGCCA
CCTGAGCAGCGAGCCCCTGAGCCGCAAGAAGCTGTACCTGAGCATGCTG
ATCAGCCTGCAGATCAGCCTGATCATGACCTTCACCGCCACCGAGCTGAT
CATGTTCTACATCTTCTTCGAGACCACCCTGATCCCCACCCTGGCCATCA
TCACCCGCTGGGGCAACCAGCCCGAGCGCCTGAACGCCGGCACCTACTT
CCTGTTCTACACCCTGGTGGGCAGCCTGCCCCTGCTGATCGCCCTGATC
TACACCCACAACACCCTGGGCAGCCTGAACATCCTGCTGCTGACCCTGA
CCGCCCAGGAGCTGAGCAACAGCTGGGCCAACAACCTGATGTGGCTGG
CCTACACCATGGCCTTCATGGTGAAGATGCCCCTGTACGGCCTGCACCT
GTGGCTGCCCAAGGCCCACGTGGAGGCCCCCATCGCCGGCAGCATGGT
GCTGGCCGCCGTGCTGCTGAAGCTGGGCGGCTACGGCATGATGCGCCT
GACCCTGATCCTGAACCCCCTGACCAAGCACATGGCCTACCCCTTCCTG |

TABLE 1-continued nucleic acid and polypeptide sequences and SEQ ID NOs

| SEQ ID NO: | description | sequence |
|---|---|---|
|  |  | GTGCTGAGCCTGTGGGGCATGATCATGACCAGCAGCATCTGCCTGCGCC
AGACCGACCTGAAGAGCCTGATCGCCTACAGCAGCATCAGCGACATGGC
CCTGGTGGTGACCGCCATCCTGATCCAGACCCCCTGGAGCTTCACCGGC
GCCGTGATCCTGATGATCGCCCACGGCCTGACCAGCAGCCTGCTGTTCT
GCCTGGCCAACAGCAACTACGAGCGCACCCACAGCCGCATCATGATCCT
GAGCCAGGGCCTGCAGACCCTGCTGCCCCTGATGGCCTTCTGGTGGCTG
CTGGCCAGCCTGGCCAACCTGGCCCTGCCCCCCACCATCAACCTGCTGG
GCGAGCTGAGCGTGCTGGTGACCACCTTCAGCTGGAGCAACATCACCCT
GCTGCTGACCGGCCTGAACATGCTGGTGACCGCCCTGTACAGCCTGTAC
ATGTTCACCACCACCCAGTGGGGCAGCCTGACCCACCACATCAACAACAT
GAAGCCCAGCTTCACCCGCGAGAACACCCTGATGTTCATGCACCTGAGC
CCCATCCTGCTGCTGAGCCTGAACCCCGACATCATCACCGGCTTCAGCA
GCTAA |
| 9 | ND6 | ATGATGTATGCTTTGTTTCTGTTGAGTGTGGGTTTAGTAATGGGGTTTGTG
GGGTTTTCTTCTAAGCCTTCTCCTATTTATGGGGGTTTAGTATTGATTGTT
AGCGGTGTGGTCGGGTGTGTTATTATTCTGAATTTTGGGGGAGGTTATAT
GGGTTTAATGGTTTTTTTAATTTATTTAGGGGGAATGATGGTTGTCTTTGG
ATATACTACAGCGATGGCTATTGAGGAGTATCCTGAGGCATGGGGGTCA
GGGGTTGAGGTCTTGGTGAGTGTTTTAGTGGGGTTAGCGATGGAGGTAG
GATTGGTGCTGTGGGTGAAAGAGTATGATGGGGTGGTGGTTGTGGTAAA
CTTTAATAGTGTAGGAAGCTGGATGATTTATGAAGGAGAGGGGTCAGGGT
TGATTCGGGAGGATCCTATTGGTGCGGGGGCTTTGTATGATTATGGGCGT
TGGTTAGTAGTAGTTACTGGTTGGACATTGTTTGTTGGTGTATATATTGTA
ATTGAGATTGCTCGGGGGAATTAG |
| 10 | opt_ND6 | ATGATGTACGCCCTGTTCCTGCTGAGCGTGGGCCTGGTGATGGGCTTCG
TGGGCTTCAGCAGCAAGCCCAGCCCCATCTACGGCGGCCTGGTGCTGAT
CGTGAGCGGCGTGGTGGGCTGCGTGATCATCCTGAACTTCGGCGGCGG
CTACATGGGCCTGATGGTGTTCCTGATCTACCTGGGCGGCATGATGGTG
GTGTTCGGCTACACCACCGCCATGGCCATCGAGGAGTACCCCGAGGCCT
GGGGCAGCGGCGTGGAGGTGCTGGTGAGCGTGCTGGTGGGCCTGGCC
ATGGAGGTGGGCCTGGTGCTGTGGGTGAAGGAGTACGACGGCGTGGTG
GTGGTGGTGAACTTCAACAGCGTGGGCAGCTGGATGATCTACGAGGGCG
AGGGCAGCGGCCTGATCCGCGAGGACCCCATCGGCGCCGGCGCCCTGT
ACGACTACGGCCGCTGGCTGGTGGTGGTGACCGGCTGGACCCTGTTCGT
GGGCGTGTACATCGTGATCGAGATCGCCCGCGGCAACTAA |
| 11 | ND1 | ATGCCCATGGCCAACCTCCTACTCCTCATTGTACCCATTCTAATCGCAATG
GCATTCCTAATGCTTACCGAACGAAAAATTCTAGGCTATATGCAACTACGC
AAAGGCCCCAACGTTGTAGGCCCCTACGGGCTACTACAACCCTTCGCTG
ACGCCATGAAACTCTTCACCAAAGAGCCCCTAAAACCCGCCACATCTACC
ATCACCCTCTACATCACCGCCCCGACCTTAGCTCTCACCATCGCTCTTCT
ACTATGGACCCCCCTCCCCATGCCCAACCCCCTGGTCAACCTCAACCTAG
GCCTCCTATTTATTCTAGCCACCTCTAGCCTAGCCGTTTACTCAATCCTCT
GGTCAGGGTGGGCATCAAACTCAAACTACGCCCTGATCGGCGCACTGCG
AGCAGTAGCCCAAACAATCTCATATGAAGTCACCCTAGCCATCATTCTACT
ATCAACATTACTAATGAGTGGCTCCTTTAACCTCTCCACCCTTATCACAAC
ACAAGAACACCTCTGGTTACTCCTGCCATCATGGCCCTTGGCCATGATGT
GGTTTATCTCCACACTAGCAGAGACCAACCGAACCCCCTTCGACCTTGCC
GAAGGGGAGTCCGAACTAGTCTCAGGCTTCAACATCGAATACGCCGCAG
GCCCCTTCGCCCTATTCTTCATGGCCGAATACACAAACATTATTATGATGA
ACACCCTCACCACTACAATCTTCCTAGGAACAACATATGACGCACTCTCC
CCTGAACTCTACACAACATATTTTGTCACCAAGACCCTACTTCTAACCTCC
CTGTTCTTATGGATTCGAACAGCATACCCCCGATTCCGCTACGACCAACT
CATGCACCTCCTATGGAAAAACTTCCTACCACTCACCCTAGCATTACTTAT
GTGGTATGTCTCCATGCCCATTACAATCTCCAGCATTCCCCCTCAAACCTA
A |
| 12 | opt_ND1 | ATGCCCATGGCCAACCTGCTGCTGCTGATCGTGCCCATCCTGATCGCCAT
GGCCTTCCTGATGCTGACCGAGCGCAAGATCCTGGGCTACATGCAGCTG
CGCAAGGGCCCCAACGTGGTGGGCCCCTACGGCCTGCTGCAGCCCTTC
GCCGACGCCATGAAGCTGTTCACCAAGGAGCCCCTGAAGCCCGCCACCA
GCACCATCACCCTGTACATCACCGCCCCCACCCTGGCCCTGACCATCGC
CCTGCTGCTGTGGACCCCCCTGCCCATGCCCAACCCCCTGGTGAACCTG
AACCTGGGCCTGCTGTTCATCCTGGCCACCAGCAGCCTGGCCGTGTACA
GCATCCTGTGGAGCGGCTGGGCCAGCAACAGCAACTACGCCCTGATCGG
CGCCCTGCGCGCCGTGGCCCAGACCATCAGCTACGAGGTGACCCTGGC
CATCATCCTGCTGAGCACCCTGCTGATGAGCGGCAGCTTCAACCTGAGC
ACCCTGATCACCACCCAGGAGCACCTGTGGCTGCTGCTGCCCAGCTGGC
CCTGGCCATGATGTGGTTCATCAGCACCCTGGCCGAGACCAACCGCAC
CCCCTTCGACCTGGCCGAGGGCGAGAGCGAGCTGGTGAGCGGCTTCAA
CATCGAGTACGCCGCCGGCCCCTTCGCCCTGTTCTTCATGGCCGAGTAC
ACCAACATCATCATGATGAACACCCTGACCACCACCATCTTCCTGGGCAC |

TABLE 1-continued nucleic acid and polypeptide sequences and SEQ ID NOs

| SEQ ID NO: | description | sequence |
|---|---|---|
| | | CACCTACGACGCCCTGAGCCCCGAGCTGTACACCACCTACTTCGTGACC<br>AAGACCCTGCTGCTGACCAGCCTGTTCCTGTGGATCCGCACCGCCTACC<br>CCCGCTTCCGCTACGACCAGCTGATGCACCTGCTGTGGAAGAACTTCCT<br>GCCCCTGACCCTGGCCCTGCTGATGTGGTACGTGAGCATGCCCATCACC<br>ATCAGCAGCATCCCCCCCCAGACCTAA |
| 13 | 3'UTR | GAGCACTGGGACGCCCACCGCCCCTTTCCCTCCGCTGCCAGGCGAGCAT<br>GTTGTGGTAATTCTGGAACACAAGAAGAGAAATTGCTGGGTTTAGAACAA<br>GATTATAAACGAATTCGGTGCTCAGTGATCACTTGACAGTTTTTTTTTTTT<br>TAAATATTACCCAAATGCTCCCCAAATAAGAAATGCATCAGCTCAGTCAG<br>TGAATACAAAAAAGGAATTATTTTTCCCTTTGAGGGTCTTTTATACATCTCT<br>CCTCCAACCCCACCCTCTATTCTGTTTCTTCCTCCTCACATGGGGGTACA<br>CATACACAGCTTCCTCTTTTGGTTCCATCCTTACCACCACACCACACGCAC<br>ACTCCACATGCCCAGCAGAGTGGCACTTGGTGGCCAGAAAGTGTGAGCC<br>TCATGATCTGCTGTCTGTAGTTCTGTGAGCTCAGGTCCCTCAAAGGCCTC<br>GGAGCACCCCCTTCCTTGTGACTGAGCCAGGGCCTGCATTTTTGGTTTTC<br>CCCACCCCACACATTCTCAACCATAGTCCTTCTAACAATACCAATAGCTAG<br>GACCCGGCTGCTGTGCACTGGGACTGGGGATTCCACATGTTTGCCTTGG<br>GAGTCTCAAGCTGGACTGCCAGCCCCTGTCCTCCCTTCACCCCCATTGC<br>GTATGAGCATTTCAGAACTCCAAGGAGTCACAGGCATCTTTATAGTTCAC<br>GTTAACATATAGACACTGTTGGAAGCAGTTCCTTCTAAAAGGGTAGCCCT<br>GGACTTAATACCAGCCGGATACCTCTGGCCCCACCCCATTACTGTACCT<br>CTGGAGTCACTACTGTGGGTCGCCACTCCTCTGCTACACAGCACGGCTTT<br>TTCAAGGCTGTATTGAGAAGGGAAGTTAGGAAGAAGGGTGTGCTGGGCT<br>AACCAGCCCACAGAGCTCACATTCCTGTCCCTTGGGTGAAAAATACATGT<br>CCATCCTGATATCTCCTGAATTCAGAAATTAGCCTCACATGTGCAATGGC<br>TTTAAGAGCCAGAAGCAGGGTTCTGGGAATTTTGCAAGTTACCTGTGGCC<br>AGGTGTGGTCTCGGTTACCAAATACGGTTACCTGCAGCTTTTTAGTCCTTT<br>GTGCTCCCACGGGTCTACAGAGTCCCATCTGCCCAAAGGTCTTGAAGCTT<br>GACAGGATGTTTTCGATTACTCAGTCTCCCAGGGCACTACTGGTCCGTAG<br>GATTCGATTGGTCGGGGTAGGAGAGTTAAACAACATTTAAACAGAGTTCT<br>CTCAAAAATGTCTAAAGGGATTGTAGGTAGATAACATCCAATCACTGTTTG<br>CACTTATCTGAAATCTTCCCTCTTGGCTGCCCCCAGGTATTTACTGTGGA<br>GAACATTGCATAGGAATGTCTGGAAAAAGCTTCTACAACTTGTTACAGCCT<br>TCACATTTGTAGAAGCTTT |
| 14 | 3'UTR* | GAGCACTGGGACGCCCACCGCCCCTTTCCCTCCGCTGCCAGGCGAGCAT<br>GTTGTGGTAATTCTGGAACACAAGAAGAGAAATTGCTGGGTTTAGAACAA<br>GATTATAAACGAATTCGGTGCTCAGTGATCACTTGACAGTTTTTTTTTTTT<br>TAAATATTACCCAAATGCTCCCCAAATAAGAAATGCATCAGCTCAGTCAG<br>TGAATACAAAAAAGGAATTATTTTTCCCTTTGAGGGTCTTTTATACATCTCT<br>CCTCCAACCCCACCCTCTATTCTGTTTCTTCCTCCTCACATGGGGGTACA<br>CATACACAGCTTCCTCTTTTGGTTCCATCCTTACCACCACACCACACGCAC<br>ACTCCACATGCCCAGCAGAGTGGCACTTGGTGGCCAGAAAGTGTGAGCC<br>TCATGATCTGCTGTCTGTAGTTCTGTGAGCTCAGGTCCCTCAAAGGCCTC<br>GGAGCACCCCCTTCCTTGTGACTGAGCCAGGGCCTGCATTTTTGGTTTTC<br>CCCACCCCACACATTCTCAACCATAGTCCTTCTAACAATACCAATAGCTAG<br>GACCCGGCTGCTGTGCACTGGGACTGGGGATTCCACATGTTTGCCTTGG<br>GAGTCTCAAGCTGGACTGCCA |
| 15 | COX10-<br>ND4-<br>3'UTR | ATGGCCGCATCTCCGCACACTCTCTCCTCACGCCTCCTGACAGGTTGCGT<br>AGGAGGCTCTGTCTGGTATCTTGAAAGAAGAACTATGCTAAAACTAATCG<br>TCCCAACAATTATGTTACTACCACTGACATGGCTTTCCAAAAAACACATGA<br>TTTGGATCAACACAACCACCCACAGCCTAATTATTAGCATCATCCCTCTAC<br>TATTTTTTAACCAAATCAACAACAACCTATTTAGCTGTTCCCCAACCTTTTC<br>CTCCGACCCCTAACAACCCCCTCCTAATGCTAACTACCTGGCTCCTAC<br>CCCTCACAATCATGGCAAGCCAACGCCACTTATCCAGTGAACCACTATCA<br>CGAAAAAAACTCTACCTCTCTATGCTAATCTCCCTACAAATCTCCTTAATTA<br>TGACATTCACAGCCACAGAACTAATCATGTTTTATATCTTCTTCGAAACCA<br>CACTTATCCCCACCTTGGCTATCATCACCCGATGGGGCAACCAGCCAGAA<br>CGCCTGAACGCAGGCACATACTTCCTATTCTACACCCTAGTAGGCTCCCT<br>TCCCCTACTCATCGCACTAATTTACACTCACAACACCCTAGGCTCACTAAA<br>CATTCTACTACTCACTCTCACTGCCCAAGAACTATCAAACTCCTGGGCCAA<br>CAACTTAATGTGGCTAGCTTACACAATGGCTTTTATGGTAAAGATGCCTCT<br>TTACGGACTCCACTTATGGCTCCCTAAAGCCCATGTCGAAGCCCCCATCG<br>CTGGGTCAATGGTACTTGCCGCAGTACTCTTAAAACTAGGCGGCTATGGT<br>ATGATGCGCCTCACACTCATTCTCAACCCCCTGACAAAACACATGGCCTA<br>CCCCTTCCTTGTACTATCCCTATGGGGCATGATTATGACAAGCTCCATCT<br>GCCTACGACAAACAGACCTAAAATCGCTCATTGCATACTCTTCAATCAGC<br>CACATGGCCCTCGTAGTAACAGCCATTCTCATCCAAACCCCCTGGAGCTT<br>CACCGGCGCAGTCATTCTCATGATCGCCCACGGGCTTACATCCTCATTAC<br>TATTCTGCCTAGCAAACTCAAACTACGAACGCACTCACAGTCGCATCATG<br>ATCCTCTCTCAAGGACTTCAAACTCTACTCCCACTAATGGCTTTTTGGTGG<br>CTTCTAGCAAGCCTCGCTAACCTCGCCTTACCCCCCACTATTAACCTACT |

TABLE 1-continued nucleic acid and polypeptide sequences and SEQ ID NOs

| SEQ ID NO: | description | sequence |
|---|---|---|
| | | GGGAGAACTCTCTGTGCTAGTAACCACGTTCTCCTGGTCAAATATCACTC
TCCTACTTACAGGACTCAACATGCTAGTCACAGCCCTATACTCCCTCTACA
TGTTTACCACAACACAATGGGGCTCACTCACCCACCACATTAACAACATG
AAACCCTCATTCACACGAGAAAACACCCTCATGTTCATGCACCTATCCCC
CATTCTCCTCCTATCCCTCAACCCCGACATCATTACCGGGTTTTCCTCTTA
AGAGCACTGGGACGCCCACCGCCCCTTTCCCTCCGCTGCCAGGCGAGC
ATGTTGTGGTAATTCTGGAACACAAGAAGAGAAATTGCTGGGTTTAGAAC
AAGATTATAAACGAATTCGGTGCTCAGTGATCACTTGACAGTTTTTTTTTT
TTTAAATATTACCCAAATGCTCCCCAAATAAGAAATGCATCAGCTCAGTC
AGTGAATACAAAAAAGGAATTATTTTTCCCTTTGAGGGTCTTTTATACATCT
CTCCTCCAACCCCACCCTCTATTCTGTTTCTTCCTCCTCACATGGGGGTA
CACATACACAGCTTCCTCTTTTGGTTCCATCCTTACCACCACACCACACGC
ACACTCCACATGCCCAGCAGAGTGGCACTTGGTGGCCAGAAAGTGTGAG
CCTCATGATCTGCTGTCTGTAGTTCTGTGAGCTCAGGTCCCTCAAAGGCC
TCGGAGCACCCCCTTCCTTGTGACTGAGCCAGGGCCTGCATTTTTGGTTT
TCCCCACCCCACACATTCTCAACCATAGTCCTTCTAACAATACCAATAGCT
AGGACCCGGCTGCTGTGCACTGGGACTGGGGATTCCACATGTTTGCCTT
GGGAGTCTCAAGCTGGACTGCCAGCCCTGTCCTCCCTTCACCCCCATT
GCGTATGAGCATTTCAGAACTCCAAGGAGTCACAGGCATTTTATAGTTC
ACGTTAACATATAGACACTGTTGGAAGCAGTTCCTTCTAAAAGGGTAGCC
CTGGACTTAATACCAGCCGGATACCTCTGGCCCCCACCCCATTACTGTAC
CTCTGGAGTCACTACTGTGGGTCGCCACTCCTCTGCTACACAGCACGGC
TTTTTCAAGGCTGTATTGAGAAGGGAAGTTAGGAAGAAGGGTGTGCTGGG
CTAACCAGCCCACAGAGCTCACATTCCTGTCCCTTGGGTGAAAAATACAT
GTCCATCCTGATATCTCCTGAATTCAGAAATTAGCCTCCACATGTGCAATG
GCTTTAAGAGCCAGAAGCAGGGTTCTGGGAATTTTGCAAGTTACCTGTGG
CCAGGTGTGGTCTCGGTTACCAAATACGGTTACCTGCAGCTTTTTAGTCC
TTTGTGCTCCCACGGGTCTACAGAGTCCCATCTGCCCAAAGGTCTTGAAG
CTTGACAGGATGTTTTCGATTACTCAGTCTCCCAGGGCACTACTGGTCCG
TAGGATTCGATTGGTCGGGGTAGGAGAGTTAAACAACATTTAAACAGAGT
TCTCTCAAAAATGTCTAAAGGGATTGTAGGTAGATAACATCCAATCACTGT
TTGCACTTATCTGAAATCTTCCCTCTTGGCTGCCCCCAGGTATTTACTGTG
GAGAACATTGCATAGGAATGTCTGGAAAAAGCTTCTACAACTTGTTACAG
CCTTCACATTTGTAGAAGCTTT |
| 16 | COX10-<br>ND4-<br>3'UTR* | ATGGCCGCATCTCCGCACACTCTCTCCTCACGCCTCCTGACAGGTTGCGT
AGGAGGCTCTGTCTGGTATCTTGAAAGAAGAACTATGCTAAAACTAATCG
TCCCAACAATTATGTTACTACCACTGACATGGCTTTCCAAAAAACACATGA
TTTGGATCAACACAACCACCCACAGCCTAATTATTAGCATCATCCCTCTAC
TATTTTTTAACCAAATCAACAACAACCTATTTAGCTGTTCCCCAACCTTTTC
CTCCGACCCCCTAACAACCCCCCTCCTAATGCTAACTACCTGGCTCCTAC
CCCTCACAATCATGGCAAGCCAACGCCACTTATCCAGTGAACCACTATCA
CGAAAAAAACTCTACCTCTCTATGCTAATCTCCCTACAAATCTCCTTAATTA
TGACATTCACAGCCACAGAACTAATCATGTTTTATATCTTCTTCGAAACCA
CACTTATCCCCACCTTGGCTATCATCACCCGATGGGGCAACCAGCCAGAA
CGCCTGAACGCAGGCACATACTTCCTATTCTACACCCTAGTAGGCTCCCT
TCCCCTACTCATCGCACTAATTTACACTCACAACACCCTAGGCTCACTAAA
CATTCTACTACTCACTCTCACTGCCCAAGAACTATCAAACTCCTGGGCCAA
CAACTTAATGTGGCTAGCTTACACAATGGCTTTTATGGTAAAGATGCCTCT
TTACGGACTCCACTTATGGCTCCCTAAAGCCCATGTCGAAGCCCCCATCG
CTGGGTCAATGGTACTTGCCGCAGTACTCTTAAAACTAGGCGGCTATGGT
ATGATGCGCCTCACACTCATTCTCAACCCCCTGACAAAACACATGGCCTA
CCCCTTCCTTGTACTATCCCTATGGGGCATGATTATGACAAGCTCCATCT
GCCTACGACAAACAGACCTAAAATCGCTCATTGCATACTCTTCAATCAGC
CACATGGCCCTCGTAGTAACAGCCATTCTCATCCAAACCCCCTGGAGCTT
CACCGGCGCAGTCATTCTCATGATCGCCCACGGGCTTACATCCTCATTAC
TATTCTGCCTAGCAAACTCAAACTACGAACGCACTCACAGTCGCATCATG
ATCCTCTCTCAAGGACTTCAAACTCTACTCCCACTAATGGCTTTTTGGTGG
CTTCTAGCAAGCCTCGCTAACCTCGCTTACCCCCCACTATTAACCTACT
GGGAGAACTCTCTGTGCTAGTAACCACGTTCTCCTGGTCAAATATCACTC
TCCTACTTACAGGACTCAACATGCTAGTCACAGCCCTATACTCCCTCTACA
TGTTTACCACAACACAATGGGGCTCACTCACCCACCACATTAACAACATG
AAACCCTCATTCACACGAGAAAACACCCTCATGTTCATGCACCTATCCCC
CATTCTCCTCCTATCCCTCAACCCCGACATCATTACCGGGTTTTCCTCTTA
AGAGCACTGGGACGCCCACCGCCCCTTTCCCTCCGCTGCCAGGCGAGC
ATGTTGTGGTAATTCTGGAACACAAGAAGAGAAATTGCTGGGTTTAGAAC
AAGATTATAAACGAATTCGGTGCTCAGTGATCACTTGACAGTTTTTTTTTT
TTTAAATATTACCCAAATGCTCCCCAAATAAGAAATGCATCAGCTCAGTC
AGTGAATACAAAAAAGGAATTATTTTTCCCTTTGAGGGTCTTTTATACATCT
CTCCTCCAACCCCACCCTCTATTCTGTTTCTTCCTCCTCACATGGGGGTA
CACATACACAGCTTCCTCTTTTGGTTCCATCCTTACCACCACACCACACGC
ACACTCCACATGCCCAGCAGAGTGGCACTTGGTGGCCAGAAAGTGTGAG
CCTCATGATCTGCTGTCTGTAGTTCTGTGAGCTCAGGTCCCTCAAAGGCC
TCGGAGCACCCCCTTCCTTGTGACTGAGCCAGGGCCTGCATTTTTGGTTT |

TABLE 1-continued nucleic acid and polypeptide sequences and SEQ ID NOs

| SEQ ID NO: | description | sequence |
|---|---|---|
| | | TCCCCACCCCACACATTCTCAACCATAGTCCTTCTAACAATACCAATAGCT<br>AGGACCCGGCTGCTGTGCACTGGGACTGGGGATTCCACATGTTTGCCTT<br>GGGAGTCTCAAGCTGGACTGCCA |
| 17 | COX10-<br>opt_ND4-<br>3'UTR | ATGGCCGCATCTCCGCACACTCTCTCCTCACGCCTCCTGACAGGTTGCGT<br>AGGAGGCTCTGTCTGGTATCTTGAAAGAAGAACTATGCTGAAGCTGATCG<br>TGCCCACCATCATGCTGCTGCCTCTGACCTGGCTGAGCAAGAAACACATG<br>ATCTGGATCAACACCACCACGCACAGCCTGATCATCAGCATCATCCCTCT<br>GCTGTTCTTCAACCAGATCAACAACAACCTGTTCAGCTGCAGCCCCACCT<br>TCAGCAGCGACCCTCTGACAACACCTCTGCTGATGCTGACCACCTGGCT<br>GCTGCCCCTCACAATCATGGCCTCTCAGAGACACCTGAGCAGCGAGCCC<br>CTGAGCCGGAAGAAACTGTACCTGAGCATGCTGATCTCCCTGCAGATCTC<br>TCTGATCATGACCTTCACCGCCACCGAGCTGATCATGTTCTACATCTTTTT<br>CGAGACAACGCTGATCCCCACACTGGCCATCATCACCAGATGGGGCAAC<br>CAGCCTGAGAGACTGAACGCCGGCACCTACTTTCTGTTCTACACCCTCGT<br>GGGCAGCCTGCCACTGCTGATTGCCCTGATCTACACCCACAACACCCTG<br>GGCTCCCTGAACATCCTGCTGCTGACACTGACAGCCCAAGAGCTGAGCA<br>ACAGCTGGGCCAACAATCTGATGTGGCTGGCCTACACAATGGCCTTCATG<br>GTCAAGATGCCCCTGTACGGCCTGCACCTGTGGCTGCCTAAAGCTCATG<br>TGGAAGCCCCTATCGCCGGCTCTATGGTGCTGGCTGCAGTGCTGCTGAA<br>ACTCGGCGGCTACGGCATGATGCGGCTGACCCTGATTCTGAATCCCCTG<br>ACCAAGCACATGGCCTATCCATTTCTGGTGCTGAGCCTGTGGGGCATGAT<br>TATGACCAGCAGCATCTGCCTGCGGCAGACCGATCTGAAGTCCCTGATC<br>GCCTACAGCTCCATCAGCCACATGGGCCTGGTGGTCACCGCCATCCTGA<br>TTCAGACCCCTTGGAGCTTTACAGGCGCCGTGATCCTGATGATTGCCCAC<br>GGCCTGACAAGCAGCCTGCTGTTTTGTCTGGCCAACAGCAACTACGAGC<br>GGACCCACAGCAGAATCATGATCCTGTCTCAGGGCCTGCAGACCCTCCT<br>GCCTCTTATGGCTTTTTGGTGGCTGCTGGCCTCTCTGGCCAATCTGGCAC<br>TGCCTCCTACCATCAATCTGCTGGGCGAGCTGAGCGTGCTGGTCACCAC<br>ATTCAGCTGGTCCAATATCACCCTGCTGCTCACCGGCCTGAACATGCTGG<br>TTACAGCCCTGTACTCCCTGTACATGTTCACCACCACAGTGGGGAAGC<br>CTGACACACCACATCAACAATATGAAGCCCAGCTTCACCCGCGAGAACAC<br>CCTGATGTTCATGCATCTGAGCCCCATTCTGCTGCTGTCCCTGAATCCTG<br>ATATCATCACCGGCTTCTCCAGCTGAGAGCACTGGGACGCCCACCGCCC<br>CTTTCCCTCCGCTGCCAGGCGAGCATGTTGTGGTAATTCTGGAACACAAG<br>AAGAGAAATTGCTGGGTTTAGAACAAGATTATAAACGAATTCGGTGCTCA<br>GTGATCACTTGACAGTTTTTTTTTTTTAAATATTACCCAAAATGCTCCCC<br>AAATAAGAAATGCATCAGCTCAGTCAGTGAATACAAAAAAGGAATTATTTT<br>TCCCTTTGAGGGTCTTTTATACATCTCTCCTCCAACCCCACCCTCTATTCT<br>GTTTCTTCCTCCTCACATGGGGGTACACATACACAGCTTCCTCTTTTGTT<br>CCATCCTTACCACCACACCACACGCACACTCCACATGCCCAGCAGAGTG<br>GCACTTGGTGGCCAGAAAGTGTGAGCCTCATGATCTGCTGTCTGTAGTTC<br>TGTGAGCTCAGGTCCCTCAAAGGCCTCGGAGCACCCCCTTCCTTGTGAC<br>TGAGCCAGGGCCTGCATTTTTGGTTTTCCCCACCCCACACATTCTCAACC<br>ATAGTCCTTCTAACAATACCAATAGCTAGGACCCGGCTGCTGTGCACTGG<br>GACTGGGGATTCCACATGTTTGCCTTGGGAGTCTCAAGCTGGACTGCCA<br>GCCCCTGTCCTCCCTTCACCCCCATTGCGTATGAGCATTTCAGAACTCCA<br>AGGAGTCACAGGCATCTTTATAGTTCACGTTAACATATAGACACTGTTGGA<br>AGCAGTTCCTTCTAAAAGGGTAGCCCTGGACTTAATACCAGCCGGATACC<br>TCTGGCCCCCACCCCATTACTGTACCTCTGGAGTCACTACTGTGGGTCGC<br>CACTCCTCTGCTACACAGCACGGCTTTTTCAAGGCTGTATTGAGAAGGGA<br>AGTTAGGAAGAAGGGTGTGCTGGGCTAACCAGCCCACAGAGCTCACATT<br>CCTGTCCCTTGGGTGAAAAATACATGTCCATCCTGATATCTCCTGAATTCA<br>GAAATTAGCCTCCACATGTGCAATGGCTTTAAGAGCCAGAAGCAGGGTTC<br>TGGGAATTTTGCAAGTTACCTGTGGCCAGGTGTGGTCTCGGTTACCAAAT<br>ACGGTTACCTGCAGCTTTTTAGTCCTTTGTGCTCCCACGGGTCTACAGAG<br>TCCCATCTGCCCAAAGGTCTTGAAGCTTGACAGGATGTTTTCGATTACTCA<br>GTCTCCCAGGGCACTACTGGTCCGTAGGATTCGATTGGTCGGGGTAGGA<br>GAGTTAAACAACATTTAAACAGAGTTCTCTCAAAAATGTCTAAAGGGATTG<br>TAGGTAGATAACATCCAATCACTGTTTGCACTTATCTGAAATCTTCCCTCT<br>TGGCTGCCCCCAGGTATTTACTGTGGAGAACATTGCATAGGAATGTCTGG<br>AAAAAGCTTCTACAACTTGTTACAGCCTTCACATTTGTAGAAGCTTT |
| 18 | COX10-<br>opt_ND4-<br>3 UTR* | ATGGCCGCATCTCCGCACACTCTCTCCTCACGCCTCCTGACAGGTTGCGT<br>AGGAGGCTCTGTCTGGTATCTTGAAAGAAGAACTATGCTGAAGCTGATCG<br>TGCCCACCATCATGCTGCTGCCTCTGACCTGGCTGAGCAAGAAACACATG<br>ATCTGGATCAACACCACCACGCACAGCCTGATCATCAGCATCATCCCTCT<br>GCTGTTCTTCAACCAGATCAACAACAACCTGTTCAGCTGCAGCCCCACCT<br>TCAGCAGCGACCCTCTGACAACACCTCTGCTGATGCTGACCACCTGGCT<br>GCTGCCCCTCACAATCATGGCCTCTCAGAGACACCTGAGCAGCGAGCCC<br>CTGAGCCGGAAGAAACTGTACCTGAGCATGCTGATCTCCCTGCAGATCTC<br>TCTGATCATGACCTTCACCGCCACCGAGCTGATCATGTTCTACATCTTTTT<br>CGAGACAACGCTGATCCCCACACTGGCCATCATCACCAGATGGGGCAAC<br>CAGCCTGAGAGACTGAACGCCGGCACCTACTTTCTGTTCTACACCCTCGT |

TABLE 1-continued nucleic acid and polypeptide sequences and SEQ ID NOs

| SEQ ID NO: | description | sequence |
|---|---|---|
| | | GGGCAGCCTGCCACTGCTGATTGCCCTGATCTACACCCACAACACCCTG
GGCTCCCTGAACATCCTGCTGCTGACACTGACAGCCCAAGAGCTGAGCA
ACAGCTGGGCCAACAATCTGATGTGGCTGGCCTACACAATGGCCTTCATG
GTCAAGATGCCCCTGTACGGCCTGCACCTGTGGCTGCCTAAAGCTCATG
TGGAAGCCCCTATCGCCGGCTCTATGGTGCTGGCTGCAGTGCTGCTGAA
ACTCGGCGGCTACGGCATGATGCGGCTGACCCTGATTCTGAATCCCCTG
ACCAAGCACATGGCCTATCCATTTCTGGTGCTGAGCCTGTGGGGCATGAT
TATGACCAGCAGCATCTGCCTGCGGCAGACCGATCTGAAGTCCCTGATC
GCCTACAGCTCCATCAGCCACATGGCCTGGTGGTCACCGCCATCCTGA
TTCAGACCCCTTGGAGCTTTACAGGCGCCGTGATCCTGATGATTGCCCAC
GGCCTGACAAGCAGCCTGCTGTTTTGTCTGGCCAACAGCAACTACGAGC
GGACCCACAGCAGAATCATGATCCTGTCTCAGGGCCTGCAGACCCTCCT
GCCTCTTATGGCTTTTTGGTGGCTGCTGGCCTCTCTGGCCAATCTGGCAC
TGCCTCCTACCATCAATCTGCTGGGCGAGCTGAGCGTGCTGGTCACCAC
ATTCAGCTGGTCCAATATCACCCTGCTGCTCACCGGCCTGAACATGCTGG
TTACAGCCCTGTACTCCCTGTACATGTTCACCACCACACAGTGGGGAAGC
CTGACACACCACATCAACAATATGAAGCCCAGCTTCACCCGCGAGAACAC
CCTGATGTTCATGCATCTGAGCCCCATTCTGCTGCTGTCCCTGAATCCTG
ATATCATCACCGGCTTCTCCAGCTGAGAGCACTGGGACGCCCACCGCCC
CTTTCCCTCCGCTGCCAGGCGAGCATGTTGTGGTAATTCTGGAACACAAG
AAGAGAAATTGCTGGGTTTAGAACAAGATTATAAACGAATTCGGTGCTCA
GTGATCACTTGACAGTTTTTTTTTTTTAAATATTACCCAAAATGCTCCCC
AAATAAGAAATGCATCAGCTCAGTCAGTGAATACAAAAAAGGAATTATTTT
TCCCTTTGAGGGTCTTTTATACATCTCTCCTCCAACCCCACCCTCTATTCT
GTTTCTTCCTCCTCACATGGGGGTACACATACACAGCTTCCTCTTTTGGTT
CCATCCTTACCACCACACCACACGCACACTCCACATGCCCAGCAGAGTG
GCACTTGGTGGCCAGAAAGTGTGAGCCTCATGATCTGCTGTCTGTAGTTC
TGTGAGCTCAGGTCCCTCAAAGGCCTCGGAGCACCCCCTTCCTTGTGAC
TGAGCCAGGGCCTGCATTTTTGGTTTTCCCCACCCCACACATTCTCAACC
ATAGTCCTTCTAACAATACCAATAGCTAGGACCCGGCTGCTGTGCACTGG
GACTGGGGATTCCACATGTTTGCCTTGGGAGTCTCAAGCTGGACTGCCA |
| 19 | COX10-opt_ND4*-3'UTR | ATGGCCGCATCTCCGCACACTCTCTCCTCACGCCTCCTGACAGGTTGCGT
AGGAGGCTCTGTCTGGTATCTTGAAAGAAGAACTATGCTGAAGCTGATCG
TGCCCACCATCATGCTGCTGCCCCTGACCTGGCTGAGCAAGAAGCACAT
GATCTGGATCAACACCACCACCCAGCCTGATCATCAGCATCATCCCCC
TGCTGTTCTTCAACCAGATCAACAACAACCTGTTCAGCTGCAGCCCCACC
TTCAGCAGCGACCCCCTGACCACCCCCCTGCTGATGCTGACCACCTGGC
TGCTGCCCCTGACCATCATGGCCAGCCAGCGCCACCTGAGCAGCGAGCC
CCTGAGCCGCAAGAAGCTGTACCTGAGCATGCTGATCAGCCTGCAGATC
AGCCTGATCATGACCTTCACCGCCACCGAGCTGATCATGTTCTACATCTT
CTTCGAGACCACCCTGATCCCCACCCTGGCCATCATCACCCGCTGGGGC
AACCAGCCCGAGCGCCTGAACGCCGGCACCTACTTCCTGTTCTACACCC
TGGTGGGCAGCCTGCCCCTGCTGATCGCCCTGATCTACACCCACAACAC
CCTGGGCAGCCTGAACATCCTGCTGCTGACCCTGACCGCCCAGGAGCTG
AGCAACAGCTGGGCCAACAACCTGATGTGGCTGGCCTACACCATGGCCT
TCATGGTGAAGATGCCCCTGTACGGCCTGCACCTGTGGCTGCCCAAGGC
CCACGTGGAGGCCCCCATCGCCGGCAGCATGGTGCTGGCCGCCGTGCT
GCTGAAGCTGGGCGGCTACGGCATGATGCGCCTGACCCTGATCCTGAAC
CCCCTGACCAAGCACATGGCCTACCCCTTCCTGGTGCTGAGCCTGTGGG
GCATGATCATGACCAGCAGCATCTGCCTGCGCCAGACCGACCTGAAGAG
CCTGATCGCCTACAGCAGCATCAGCCACATGGCCCTGGTGGTGACCGCC
ATCCTGATCCAGACCCCCTGGAGCTTCACCGGCGCCGTGATCCTGATGA
TCGCCCACGGCCTGACCAGCAGCCTGCTGTTCTGCCTGGCCAACAGCAA
CTACGAGCGCACCCACAGCCGCATCATGATCCTGAGCCAGGGCCTGCAG
ACCCTGCTGCCCCTGATGGCCTTCTGGTGGCTGCTGGCCAGCCTGGCCA
ACCTGGCCCTGCCCCCCACCATCAACCTGCTGGGCGAGCTGAGCGTGCT
GGTGACCACCTTCAGCTGGAGCAACATCACCCTGCTGCTGACCGGCCTG
AACATGCTGGTGACCGCCCTGTACAGCCTGTACATGTTCACCACCACCCA
GTGGGGCAGCCTGACCCACCACATCAACAACATGAAGCCCAGCTTCACC
CGCGAGAACACCCTGATGTTCATGCACCTGAGCCCCATCCTGCTGCTGA
GCCTGAACCCCGACATCATCACCGGCTTCAGCAGCTAAGAGCACTGGGA
CGCCCACCGCCCCTTTCCCTCCGCTGCCAGGCGAGCATGTTGTGGTAAT
TCTGGAACACAAGAAGAGAAATTGCTGGGTTTAGAACAAGATTATAAACG
AATTCGGTGCTCAGTGATCACTTGACAGTTTTTTTTTTTTAAATATTACC
CAAAATGCTCCCCAAATAAGAAATGCATCAGCTCAGTCAGTGAATACAAA
AAAGGAATTATTTTTCCCTTTGAGGGTCTTTTATACATCTCTCCTCCAACC
CCACCCTCTATTCTGTTTCTTCCTCCTCACATGGGGTACACATACACAG
CTTCCTCTTTTGGTTCCATCCTTACCACCACACCACACGCACACTCCACAT
GCCCAGCAGAGTGGCACTTGGTGGCCAGAAAGTGTGAGCCTCATGATCT
GCTGTCTGTAGTTCTGTGAGCTCAGGTCCCTCAAAGGCCTCGGAGCACC
CCCTTCCTTGTGACTGAGCCAGGGCCTGCATTTTTGGTTTTCCCCACCCC
ACACATTCTCAACCATAGTCCTTCTAACAATACCAATAGCTAGGACCCGG
CTGCTGTGCACTGGGACTGGGGATTCCACATGTTTGCCTTGGGAGTCTCA |

TABLE 1-continued nucleic acid and polypeptide sequences and SEQ ID NOs

| SEQ ID NO: | description | sequence |
|---|---|---|
| | | AGCTGGACTGCCAGCCCTGTCCTCCCTTCACCCCCATTGCGTATGAGC<br>ATTTCAGAACTCCAAGGAGTCACAGGCATCTTTATAGTTCACGTTAACATA<br>TAGACACTGTTGGAAGCAGTTCCTTCTAAAAGGGTAGCCCTGGACTTAAT<br>ACCAGCCGGATACCTCTGGCCCCCACCCCATTACTGTACCTCTGGAGTCA<br>CTACTGTGGGTCGCCACTCCTCTGCTACACAGCACGGCTTTTTCAAGGCT<br>GTATTGAGAAGGGAAGTTAGGAAGAAGGGTGTGCTGGGCTAACCAGCCC<br>ACAGAGCTCACATTCCTGTCCCTTGGGTGAAAAATACATGTCCATCCTGA<br>TATCTCCTGAATTCAGAAATTAGCCTCCACATGTGCAATGGCTTTAAGAGC<br>CAGAAGCAGGGTTCTGGGAATTTTGCAAGTTACCTGTGGCAGGTGTGG<br>TCTCGGTTACCAAATACGGTTACCTGCAGCTTTTTAGTCCTTTGTGCTCCC<br>ACGGGTCTACAGAGTCCCATCTGCCCAAAGGTCTTGAAGCTTGACAGGAT<br>GTTTTCGATTACTCAGTCTCCCAGGGCACTACTGGTCCGTAGGATTCGAT<br>TGGTCGGGGTAGGAGAGTTAAACAACATTTAAACAGAGTTCTCTCAAAAA<br>TGTCTAAAGGGATTGTAGGTAGATAACATCCAATCACTGTTTGCACTTATC<br>TGAAATCTTCCCTCTTGGCTGCCCCCAGGTATTTACTGTGGAGAACATTG<br>CATAGGAATGTCTGGAAAAAGCTTCTACAACTTGTTACAGCCTTCACATTT<br>GTAGAAGCTTT |
| 20 | COX10-<br>opt_ND4*-<br>3'UTR* | ATGGCCGCATCTCCGCACACTCTCTCCTCACGCCTCCTGACAGGTTGCGT<br>AGGAGGCTCTGTCTGGTATCTTGAAAGAAGAACTATGCTGAAGCTGATCG<br>TGCCCACCATCATGCTGCTGCCCCTGACCTGGCTGAGCAAGAAGCACAT<br>GATCTGGATCAACACCACCACCCACAGCCTGATCATCAGCATCATCCCCC<br>TGCTGTTCTTCAACCAGATCAACAACAACCTGTTCAGCTGCAGCCCCACC<br>TTCAGCAGCGACCCCCTGACCACCCCCTGCTGATGCTGACCACCTGGC<br>TGCTGCCCCTGACCATCATGGCCAGCCAGCGCCACCTGAGCAGCGAGCC<br>CCTGAGCCGCAAGAAGCTGTACCTGAGCATGCTGATCAGCCTGCAGATC<br>AGCCTGATCATGACCTTCACCGCCACCGAGCTGATCATGTTCTACATCTT<br>CTTCGAGACCACCCTGATCCCCACCCTGGCCATCATCACCCGCTGGGGC<br>AACCAGCCCGAGCGCCTGAACGCCGGCACCTACTTCCTGTTCTACACCC<br>TGGTGGGCAGCCTGCCCCTGCTGATCGCCCTGATCTACACCCACAACAC<br>CCTGGGCAGCCTGAACATCCTGCTGCTGACCCTGACCGCCCAGGAGCTG<br>AGCAACAGCTGGGCCAACAACCTGATGTGGCTGGCCTACACCATGGCCT<br>TCATGGTGAAGATGCCCCTGTACGGCCTGCACCTGTGGCTGCCCAAGGC<br>CCACGTGGAGGCCCCCATCGCCGGCAGCATGGTGCTGGCCGCCGTGCT<br>GCTGAAGCTGGGCGGCTACGGCATGATGCGCCTGACCCTGATCCTGAAC<br>CCCCTGACCAAGCACATGGCCTACCCCTTCCTGGTGCTGAGCCTGTGGG<br>GCATGATCATGACCAGCAGCATCTGCCTGCGCCAGACCGACCTGAAGAG<br>CCTGATCGCCTACAGCAGCATCAGCCACATGGCCCTGGTGGTGACCGCC<br>ATCCTGATCCAGACCCCCTGGAGCTTCACCGGCGCCGTGATCCTGATGA<br>TCGCCCACGGCCTGACCAGCAGCCTGCTGTTCTGCCTGGCCAACAGCAA<br>CTACGAGCGCACCCACAGCCGCATCATGATCCTGAGCCAGGGCCTGCAG<br>ACCCTGCTGCCCCTGATGGCCTTCTGGTGGCTGCTGGCCAGCCTGGCCA<br>ACCTGGCCCTGCCCCCCACCATCAACCTGCTGGGCGAGCTGAGCGTGCT<br>GGTGACCACCTTCAGCTGGAGCAACATCACCCCTGCTGCTGACCGGCCTG<br>AACATGCTGGTGACCGCCCTGTACAGCCTGTACATGTTCACCACCACCCA<br>GTGGGGCAGCCTGACCCACCCACATCAACAACATGAAGCCCAGCTTCACC<br>CGCGAGAACACCCTGATGTTCATGCACCTGAGCCCCATCCTGCTGCTGA<br>GCCTGAACCCCGACATCATCACCGGCTTCAGCAGCTAAGAGCACTGGGA<br>CGCCCACCGCCCCTTTCCCTCCGCTGCCAGGCGAGCATGTTGTGGTAAT<br>TCTGGAACACAAGAAGAGAAATTGCTGGGTTTAGAACAAGATTATAAACG<br>AATTCGGTGCTCAGTGATCACTTGACAGTTTTTTTTTTTTAAATATTACC<br>CAAAATGCTCCCAAATAAGAAATGCATCAGCTCAGTCAGTGAATACAAA<br>AAAGGAATTATTTTTCCCTTTGAGGGTCTTTTATACATCTCTCCTCCAACC<br>CCACCCTCTATTCTGTTTCTTCCTCCTCACATGGGGTACACATACACAG<br>CTTCCTCTTTTGGTTCCATCCTTACCACCACACCACACGCACACTCCACAT<br>GCCCAGCAGAGTGGCACTTGGTGGCCAGAAAGTGTGAGCCTCATGATCT<br>GCTGTCTGTAGTTCTGTGAGCTCAGGTCCCTCAAAGGCCTCGGAGCACC<br>CCCTTCCTTGTGACTGAGCCAGGGCCTGCATTTTTGGTTTTCCCCACCCC<br>ACACATTCTCAACCATAGTCCTTCTAACAATACCAATAGCTAGGACCCGG<br>CTGCTGTGCACTGGGACTGGGGATTCCACATGTTTGCCTTGGGAGTCTCA<br>AGCTGGACTGCCA |
| 21 | COX10-<br>ND6-<br>3'UTR | ATGGCCGCATCTCCGCACACTCTCTCCTCACGCCTCCTGACAGGTTGCGT<br>AGGAGGCTCTGTCTGGTATCTTGAAAGAAGAACTATGATGTATGCTTTGTT<br>TCTGTTGAGTGTGGGTTTAGTAATGGGGTTTGTGGGGTTTTCTTCTAAGC<br>CTTCTCCTATTTATGGGGGTTTAGTATTGATTGTTAGCGGTGTGGTCGGG<br>TGTGTTATTATTCTGAATTTTGGGGGAGGTTATATGGGTTTAATGGTTTTTT<br>TAATTTATTTAGGGGGAATGATGGTTGTCTTTGGATATACTACAGCGATGG<br>CTATTGAGGAGTATCCTGAGGCATGGGGGTCAGGGGTTGAGGTCTTGGT<br>GAGTGTTTTAGTGGGGTTAGCGATGGAGGTAGGATTGGTGCTGTGGGTG<br>AAAGAGTATGATGGGGTGGTGTTGTGGTAAACTTTAATAGTGTAGGAAG<br>CTGGATGATTTATGAAGGAGAGGGGTCAGGGTTGATTCGGGAGGATCCT<br>ATTGGTGCGGGGCTTTGTATGATTATGGGCGTTGGTTAGTAGTAGTTAC<br>TGGTTGGACATTGTTTGTTGGTGTATATATTGTAATTGAGATTGCTCGGGG |

TABLE 1-continued nucleic acid and polypeptide sequences and SEQ ID NOs

| SEQ ID NO: | description | sequence |
|---|---|---|
| | | GAATTAGGAGCACTGGGACGCCCACCGCCCCTTTCCCTCCGCTGCCAGG<br>CGAGCATGTTGTGGTAATTCTGGAACACAAGAAGAGAAATTGCTGGGTTT<br>AGAACAAGATTATAAACGAATTCGGTGCTCAGTGATCACTTGACAGTTTTT<br>TTTTTTTTTAAATATTACCCAAAATGCTCCCCAAATAAGAAATGCATCAGCT<br>CAGTCAGTGAATACAAAAAAGGAATTATTTTTCCCTTTGAGGGTCTTTTAT<br>ACATCTCTCCTCCAACCCCACCCTCTATTCTGTTTCTTCCTCCTCACATGG<br>GGGTACACATACACAGCTTCCTCTTTTGGTTCCATCCTTACCACCACACCA<br>CACGCACACTCCACATGCCCAGCAGAGTGGCACTTGGTGGCCAGAAAGT<br>GTGAGCCTCATGATCTGCTGTCTGTAGTTCTGTGAGCTCAGGTCCCTCAA<br>AGGCCTCGGAGCACCCCCTTCCTTGTGACTGAGCCAGGGCCTGCATTTT<br>TGGTTTTCCCCACCCCACACATTCTCAACCATAGTCCTTCTAACAATACCA<br>ATAGCTAGGACCCGGCTGCTGTGCACTGGGACTGGGGATTCCACATGTT<br>TGCCTTGGGAGTCTCAAGCTGGACTGCCAGCCCCTGTCCTCCCTTCACC<br>CCCATTGCGTATGAGCATTTCAGAACTCCAAGGAGTCACAGGCATCTTTA<br>TAGTTCACGTTAACATATAGACACTGTTGGAAGCAGTTCCTTCTAAAAGGG<br>TAGCCCTGGACTTAATACCAGCCGGATACCTCTGGCCCCCACCCCATTAC<br>TGTACCTCTGGAGTCACTACTGTGGGTCGCCACTCCTCTGCTACACAGCA<br>CGGCTTTTTCAAGGCTGTATTGAGAAGGGAAGTTAGGAAGAAGGGTGTG<br>CTGGGCTAACCAGCCCACAGAGCTCACATTCCTGTCCCTTGGGTGAAAAA<br>TACATGTCCATCCTGATATCTCCTGAATTCAGAAATTAGCCTCCACATGTG<br>CAATGGCTTTAAGAGCCAGAAGCAGGGTTCTGGGAATTTTGCAAGTTACC<br>TGTGGCCAGGTGTGGTCTCGGTTACCAAATACGGTTACCTGCAGCTTTTT<br>AGTCCTTTGTGCTCCCACGGGTCTACAGAGTCCCATCTGCCCAAAGGTCT<br>TGAAGCTTGACAGGATGTTTTCGATTACTCAGTCTCCCAGGGCACTACTG<br>GTCCGTAGGATTCGATTGGTCGGGGTAGGAGAGTTAAACAACATTTAAAC<br>AGAGTTCTCTCAAAAATGTCTAAAGGGATTGTAGGTAGATAACATCCAATC<br>ACTGTTTGCACTTATCTGAAATCTTCCCTCTTGGCTGCCCCCAGGTATTTA<br>CTGTGGAGAACATTGCATAGGAATGTCTGGAAAAAGCTTCTACAACTTGTT<br>ACAGCCTTCACATTTGTAGAAGCTTT |
| 22 | COX10-<br>ND6-<br>3'UTR* | ATGGCCGCATCTCCGCACACTCTCTCCTCACGCCTCCTGACAGGTTGCGT<br>AGGAGGCTCTGTCTGGTATCTTGAAAGAAGAACTATGATGTATGCTTTGTT<br>TCTGTTGAGTGTGGGTTTAGTAATGGGGTTTGTGGGGTTTTCTTCTAAGC<br>CTTCTCCTATTTATGGGGGTTTAGTATTGATTGTTAGCGGTGTGGTCGGG<br>TGTGTTATTATTCTGAATTTTGGGGGAGGTTATATGGGTTTAATGGTTTTTT<br>TAATTTATTTAGGGGGAATGATGGTTGTCTTTGGATATACTACAGCGATGG<br>CTATTGAGGAGTATCCTGAGGCATGGGGGTCAGGGGTTGAGGTCTTGGT<br>GAGTGTTTTAGTGGGGTTAGCGATGGAGGTAGGATTGGTGCTGTGGGTG<br>AAAGAGTATGATGGGGTGGTGGTTGTGGTAAACTTTAATAGTGTAGGAAG<br>CTGGATGATTTATGAAGGAGAGGGGTCAGGGTTGATTCGGGAGGATCCT<br>ATTGGTGCGGGGGCTTTGTATGATTATGGGCGTTGGTTAGTAGTAGTTAC<br>TGGTTGGACATTGTTTGTTGGTGTATATATTGTAATTGAGATTGCTCGGGG<br>GAATTAGGAGCACTGGGACGCCCACCGCCCCTTTCCCTCCGCTGCCAGG<br>CGAGCATGTTGTGGTAATTCTGGAACACAAGAAGAGAAATTGCTGGGTTT<br>AGAACAAGATTATAAACGAATTCGGTGCTCAGTGATCACTTGACAGTTTTT<br>TTTTTTTTTAAATATTACCCAAAATGCTCCCCAAATAAGAAATGCATCAGCT<br>CAGTCAGTGAATACAAAAAAGGAATTATTTTTCCCTTTGAGGGTCTTTTAT<br>ACATCTCTCCTCCAACCCCACCCTCTATTCTGTTTCTTCCTCCTCACATGG<br>GGGTACACATACACAGCTTCCTCTTTTGGTTCCATCCTTACCACCACACCA<br>CACGCACACTCCACATGCCCAGCAGAGTGGCACTTGGTGGCCAGAAAGT<br>GTGAGCCTCATGATCTGCTGTCTGTAGTTCTGTGAGCTCAGGTCCCTCAA<br>AGGCCTCGGAGCACCCCCTTCCTTGTGACTGAGCCAGGGCCTGCATTTT<br>TGGTTTTCCCCACCCCACACATTCTCAACCATAGTCCTTCTAACAATACCA<br>ATAGCTAGGACCCGGCTGCTGTGCACTGGGACTGGGGATTCCACATGTT<br>TGCCTTGGGAGTCTCAAGCTGGACTGCCA |
| 23 | COX10-<br>opt_ND6-<br>3'UTR | ATGGCCGCATCTCCGCACACTCTCTCCTCACGCCTCCTGACAGGTTGCGT<br>AGGAGGCTCTGTCTGGTATCTTGAAAGAAGAACTATGATGTACGCCCTGT<br>TCCTGCTGAGCGTGGGCCTGGTGATGGGCTTCGTGGGCTTCAGCAGCAA<br>GCCCAGCCCCATCTACGGCGGCCTGGTGCTGATCGTGAGCGGCGTGGT<br>GGGCTGCGTGATCATCCTGAACTTCGGCGGCGGCTACATGGGGCCTGATG<br>GTGTTCCTGATCTACCTGGGCGGCATGATGGTGGTGTTCGGCTACACCA<br>CCGCCATGGCCATCGAGGAGTACCCCGAGGCCTGGGCAGCGGCGTGG<br>AGGTGCTGGTGAGCGTGCTGGTGGGCCTGGCCATGGAGGTGGGCCTGG<br>TGCTGTGGGTGAAGGAGTACGACGGCGTGGTGGTGGTGAACTTCAA<br>CAGCGTGGGCAGCTGGATGATCTACGAGGGCGAGGGCAGCGGCCTGAT<br>CCGCGAGGACCCCATCGGCGCCGGCGCCCTGTACGACTACGGCCGCTG<br>GCTGGTGGTGGTGACCGGCTGGACCCTGTTCGTGGGCGTGTACATCGTG<br>ATCGAGATCGCCCGCGGCAACTAAGAGCACTGGGACGCCCACCGCCCCT<br>TTCCCTCCGCTGCCAGGCGAGCATGTTGTGGTAATTCTGGAACACAAGAA<br>GAGAAATTGCTGGGTTTAGAACAAGATTATAAACGAATTCGGTGCTCAGT<br>GATCACTTGACAGTTTTTTTTTTTTAAATATTACCCAAAATGCTCCCCAA<br>ATAAGAAATGCATCAGCTCAGTCAGTGAATACAAAAAAGGAATTATTTTTC<br>CCTTTGAGGGTCTTTTATACATCTCTCCTCCAACCCCACCCTCTATTCTGT |

TABLE 1-continued nucleic acid and polypeptide sequences and SEQ ID NOs

| SEQ ID NO: | description | sequence |
|---|---|---|
| | | TTCTTCCTCCTCACATGGGGTACACATACACAGCTTCCTCTTTTGGTTCC<br>ATCCTTACCACCACACCACACGCACACTCCACATGCCCAGCAGAGTGGC<br>ACTTGGTGGCCAGAAAGTGTGAGCCTCATGATCTGCTGTCTGTAGTTCTG<br>TGAGCTCAGGTCCCTCAAAGGCCTCGGAGCACCCCCTTCCTTGTGACTG<br>AGCCAGGGCCTGCATTTTTGGTTTTCCCCACCCCACACATTCTCAACCAT<br>AGTCCTTCTAACAATACCAATAGCTAGGACCCGGCTGCTGTGCACTGGGA<br>CTGGGGATTCCACATGTTTGCCTTGGGAGTCTCAAGCTGGACTGCCAGC<br>CCCTGTCCTCCCTTCACCCCCATTGCGTATGAGCATTTCAGAACTCCAAG<br>GAGTCACAGGCATCTTTATAGTTCACGTTAACATATAGACACTGTTGGAAG<br>CAGTTCCTTCTAAAAGGGTAGCCCTGGACTTAATACCAGCCGGATACCTC<br>TGGCCCCCACCCCATTACTGTACCTCTGGAGTCACTACTGTGGGTCGCCA<br>CTCCTCTGCTACACAGCACGGCTTTTTCAAGGCTGTATTGAGAAGGGAAG<br>TTAGGAAGAAGGGTGTGCTGGGCTAACCAGCCCACAGAGCTCACATTCC<br>TGTCCCTTGGGTGAAAAATACATGTCCATCCTGATATCTCCTGAATTCAGA<br>AATTAGCCTCCACATGTGCAATGGCTTTAAGAGCCAGAAGCAGGGTTCTG<br>GGAATTTTGCAAGTTACCTGTGGCCAGGTGTGGTCTCGGTTACCAAATAC<br>GGTTACCTGCAGCTTTTTAGTCCTTTGTGCTCCCACGGGTCTACAGAGTC<br>CCATCTGCCCAAAGGTCTTGAAGCTTGACAGGATGTTTTCGATTACTCAG<br>TCTCCCAGGGCACTACTGGTCCGTAGGATTCGATTGGTCGGGGTAGGAG<br>AGTTAAACAACATTTAAACAGAGTTCTCTCAAAAATGTCTAAAGGGATTGT<br>AGGTAGATAACATCCAATCACTGTTTGCACTTATCTGAAATCTTCCCTCTT<br>GGCTGCCCCCAGGTATTTACTGTGGAGAACATTGCATAGGAATGTCTGGA<br>AAAAGCTTCTACAACTTGTTACAGCCTTCACATTTGTAGAAGCTTT |
| 24 | COX10-<br>opt_ND6-<br>3'UTR* | ATGGCCGCATCTCCGCACACTCTCTCCTCACGCCTCCTGACAGGTTGCGT<br>AGGAGGCTCTGTCTGGTATCTTGAAAGAAGAACTATGATGTACGCCCTGT<br>TCCTGCTGAGCGTGGGCCTGGTGATGGGCTTCGTGGGCTTCAGCAGCAA<br>GCCCAGCCCCATCTACGGCGGCCTGGTGCTGATCGTGAGCGGCGTGGT<br>GGGCTGCGTGATCATCCTGAACTTCGGCGGCGGCTACATGGGCCTGATG<br>GTGTTCCTGATCTACCTGGGCGGCATGATGGTGGTGTTCGGCTACACCA<br>CCGCCATGGCCATCGAGGAGTACCCCGAGGGCCTGGGGCAGCGGCGTGG<br>AGGTGCTGGTGAGCGTGCTGGTGGGCCTGGCCATGGAGGTGGGCCTGG<br>TGCTGTGGGTGAAGGAGTACGACGGCGTGGTGGTGGTGAACTTCAA<br>CAGCGTGGGCAGCTGGATGATCTACGAGGGCGAGGGCAGCGGCCTGAT<br>CCGCGAGGACCCCATCGGCGCCGGCGCCCTGTACGACTACGGCCGCTG<br>GCTGGTGGTGGTGACCGGCTGGACCCTGTTCGTGGGCGTGTACATCGTG<br>ATCGAGATCGCCCGCGGCAACTAAGAGCACTGGGACGCCCACCGCCCCT<br>TTCCCTCCGCTGCCAGGCGAGCATGTTGTGGTAATTCTGGAACACAAGAA<br>GAGAAATTGCTGGGTTTAGAACAAGATTATAAACGAATTCGGTGCTCAGT<br>GATCACTTGACAGTTTTTTTTTTTTAAATATTACCCAAAATGCTCCCCAA<br>ATAAGAAATGCATCAGCTCAGTCAGTGAATACAAAAAAGGAATTATTTTTC<br>CCTTTGAGGGTCTTTTATACATCTCTCCTCCAACCCCACCCTCTATTCTGT<br>TTCTTCCTCCTCACATGGGGTACACATACACAGCTTCCTCTTTTGGTTCC<br>ATCCTTACCACCACACCACACGCACACTCCACATGCCCAGCAGAGTGGC<br>ACTTGGTGGCCAGAAAGTGTGAGCCTCATGATCTGCTGTCTGTAGTTCTG<br>TGAGCTCAGGTCCCTCAAAGGCCTCGGAGCACCCCCTTCCTTGTGACTG<br>AGCCAGGGCCTGCATTTTTGGTTTTCCCCACCCCACACATTCTCAACCAT<br>AGTCCTTCTAACAATACCAATAGCTAGGACCCGGCTGCTGTGCACTGGGA<br>CTGGGGATTCCACATGTTTGCCTTGGGAGTCTCAAGCTGGACTGCCA |
| 25 | COX10-<br>ND1-<br>3'UTR | ATGGCCGCATCTCCGCACACTCTCTCCTCACGCCTCCTGACAGGTTGCGT<br>AGGAGGCTCTGTCTGGTATCTTGAAAGAAGAACTATGCCCATGGCCAACC<br>TCCTACTCCTCATTGTACCCATTCTAATCGCAATGGCATTCCTAATGCTTA<br>CCGAACGAAAAATTCTAGGCTATATGCAACTACGCAAAGGCCCCAACGTT<br>GTAGGCCCCTACGGGCTACTACAACCCTTCGCTGACGCCATGAAACTCTT<br>CACCAAAGAGCCCCTAAAACCCGCCACATCTACCATCACCCCTCTACATCA<br>CCGCCCCGACCTTAGCTCTCACCATCGCTCTTCTACTATGGACCCCCCTC<br>CCCATGCCCAACCCCCTGGTCAACCTCAACCTAGGCCTCCTATTTATTCT<br>AGCCACCTCTAGCCTAGCCGTTTACTCAATCCTCTGGTCAGGGTGGGCAT<br>CAAACTCAAACTACGCCCTGATCGGCGCACTGCGAGCAGTAGCCCAAAC<br>AATCTCATATGAAGTCACCCTAGCCATCATTCTACTATCAACATTACTAAT<br>GAGTGGCTCCTTTAACCTCTCCACCCTTATCACAACACAAGAACACCTCT<br>GGTTACTCCTGCCATCATGGCCCTTGGCCATGATGTGGTTTATCTCCACA<br>CTAGCAGAGACCAACCGAACCCCCTTCGACCTTGCCGAAGGGGAGTCCG<br>AACTAGTCTCAGGCTTCAACATCGAATACGCCGCAGGCCCCTTCGCCCTA<br>TTCTTCATGGCCGAATACACAAACATTATTATGATGAACACCCTCACCACT<br>ACAATCTTCCTAGGAACAACATATGACGCACTCTCCCCTGAACTCTACACA<br>ACATATTTTGTCACCAAGACCCTACTTCTAACCTCCCTGTTCTTATGGATT<br>CGAACAGCATACCCCCGATTCCGCTACGACCAACTCATGCACCTCCTATG<br>GAAAAACTTCCTACCACTCACCCTAGCATTACTTATGTGGTATGTCTCCAT<br>GCCCATTACAATCTCCAGCATTCCCCCTCAAACCTAAGAGCACTGGGACG<br>CCCACCGCCCCTTTCCCTCCGCTGCCAGGCGAGCATGTTGTGGTAATTCT<br>GGAACACAAGAAGAGAAATTGCTGGGTTTAGAACAAGATTATAAACGAAT<br>TCGGTGCTCAGTGATCACTTGACAGTTTTTTTTTTTTAAATATTACCCAA |

TABLE 1-continued nucleic acid and polypeptide sequences and SEQ ID NOs

| SEQ ID NO: | description | sequence |
|---|---|---|
| | | AATGCTCCCCAAATAAGAAATGCATCAGCTCAGTCAGTGAATACAAAAAA<br>GGAATTATTTTTCCCTTTGAGGGTCTTTTATACATCTCTCCTCCAACCCCA<br>CCCTCTATTCTGTTTCTTCCTCCTCACATGGGGGTACACATACACAGCTTC<br>CTCTTTTGGTTCCATCCTTACCACCACACCACACGCACACTCCACATGCC<br>CAGCAGAGTGGCACTTGGTGGCCAGAAAGTGTGAGCCTCATGATCTGCT<br>GTCTGTAGTTCTGTGAGCTCAGGTCCCTCAAAGGCCTCGGAGCACCCCC<br>TTCCTTGTGACTGAGCCAGGGCCTGCATTTTTGGTTTTCCCCACCCCACA<br>CATTCTCAACCATAGTCCTTCTAACAATACCAATAGCTAGGACCCGGCTG<br>CTGTGCACTGGGACTGGGGATTCCACATGTTTGCCTTGGGAGTCTCAAG<br>CTGGACTGCCAGCCCCTGTCCTCCCTTCACCCCCATTGCGTATGAGCATT<br>TCAGAACTCCAAGGAGTCACAGGCATCTTTATAGTTCACGTTAACATATAG<br>ACACTGTTGGAAGCAGTTCCTTCTAAAAGGGTAGCCCTGGACTTAATACC<br>AGCCGGATACCTCTGGCCCCCACCCCATTACTGTACCTCTGGAGTCACTA<br>CTGTGGGTCGCCACTCCTCTGCTACACAGCACGGCTTTTTCAAGGCTGTA<br>TTGAGAAGGGAAGTTAGGAAGAAGGGTGTGCTGGGCTAACCAGCCCACA<br>GAGCTCACATTCCTGTCCCTTGGGTGAAAAATACATGTCCATCCTGATATC<br>TCCTGAATTCAGAAATTAGCCTCCACATGTGCAATGGCTTTAAGAGCCAG<br>AAGCAGGGTTCTGGGAATTTTGCAAGTTACCTGTGGCCAGGTGTGGTCTC<br>GGTTACCAAATACGGTTACCTGCAGCTTTTTAGTCCTTTGTGCTCCCACG<br>GGTCTACAGAGTCCCATCTGCCCAAAGGTCTTGAAGCTTGACAGGATGTT<br>TTCGATTACTCAGTCTCCCAGGGCACTACTGGTCCGTAGGATTCGATTGG<br>TCGGGGTAGGAGAGTTAAACAACATTTAAACAGAGTTCTCTCAAAAATGTC<br>TAAAGGGATTGTAGGTAGATAACATCCAATCACTGTTTGCACTTATCTGAA<br>ATCTTCCCTCTTGGCTGCCCCCAGGTATTTACTGTGGAGAACATTGCATA<br>GGAATGTCTGGAAAAAGCTTCTACAACTTGTTACAGCCTTCACATTTGTAG<br>AAGCTTT |
| 26 | COX10-<br>ND1-<br>3'UTR* | ATGGCCGCATCTCCGCACACTCTCTCCTCACGCCTCCTGACAGGTTGCGT<br>AGGAGGCTCTGTCTGGTATCTTGAAAGAAGAACTATGCCCATGGCCAACC<br>TCCTACTCCTCATTGTACCCATTCTAATCGCAATGGCATTCCTAATGCTTA<br>CCGAACGAAAAATTCTAGGCTATATGCAACTACGCAAAGGCCCCAACGTT<br>GTAGGCCCCTACGGGCTACTACAACCCTTCGCTGACGCCATGAAACTCTT<br>CACCAAAGAGCCCCTAAAACCCGCCACATCTACCATCACCCTCTACATCA<br>CCGCCCCGACCTTAGCTCTCACCATCGCTCTTCTACTATGGACCCCCCTC<br>CCCATGCCCAACCCCCTGGTCAACCTCAACCTAGGCCTCCTATTTATTCT<br>AGCCACCTCTAGCCTAGCCGTTTACTCAATCCTCTGGTCAGGGTGGGCAT<br>CAAACTCAAACTACGCCCTGATCGGCGCACTGCGAGCAGTAGCCCAAAC<br>AATCTCATATGAAGTCACCCTAGCCATCATTCTACTATCAACATTACTAAT<br>GAGTGGCTCCTTTAACCTCTCCACCCTTATCACAACACAAGAACACCTCT<br>GGTTACTCCTGCCATCATGGCCCTTGGCCATGATGTGGTTTATCTCCACA<br>CTAGCAGAGACCAACCGAACCCCCTTCGACCTTGCCGAAGGGGAGTCCG<br>AACTAGTCTCAGGCTTCAACATCGAATACGCCGCAGGCCCCTTCGCCCTA<br>TTCTTCATGGCCGAATACACAAACATTATTATGATGAACACCCTCACCACT<br>ACAATCTTCCTAGGAACAACATATGACGCACTCTCCCCTGAACTCTACACA<br>ACATATTTTGTCACCAAGACCCTACTTCTAACCTCCCTGTTCTTATGGATT<br>CGAACAGCATACCCCCGATTCCGCTACGACCAACTCATGCACCTCCTATG<br>GAAAAACTTCCTACCACTCACCCTAGCATTACTTATGTGGTATGTCTCCAT<br>GCCCATTACAATCTCCAGCATTCCCCCTCAAACCTAAGAGCACTGGGACG<br>CCCACCGCCCCTTTCCCTCCGCTGCCAGGCGAGCATGTTGTGGTAATTCT<br>GGAACACAAGAAGAGAAATTGCTGGGTTTAGAACAAGATTATAAACGAAT<br>TCGGTGCTCAGTGATCACTTGACAGTTTTTTTTTTTTAAATATTACCCAA<br>AATGCTCCCCAAATAAGAAATGCATCAGCTCAGTCAGTGAATACAAAAAA<br>GGAATTATTTTTCCCTTTGAGGGTCTTTTATACATCTCTCCTCCAACCCCA<br>CCCTCTATTCTGTTTCTTCCTCCTCACATGGGGGTACACATACACAGCTTC<br>CTCTTTTGGTTCCATCCTTACCACCACACCACACGCACACTCCACATGCC<br>CAGCAGAGTGGCACTTGGTGGCCAGAAAGTGTGAGCCTCATGATCTGCT<br>GTCTGTAGTTCTGTGAGCTCAGGTCCCTCAAAGGCCTCGGAGCACCCCC<br>TTCCTTGTGACTGAGCCAGGGCCTGCATTTTTGGTTTTCCCCACCCCACA<br>CATTCTCAACCATAGTCCTTCTAACAATACCAATAGCTAGGACCCGGCTG<br>CTGTGCACTGGGACTGGGGATTCCACATGTTTGCCTTGGGAGTCTCAAG<br>CTGGACTGCCA |
| 27 | COX10-<br>opt_ND1-<br>3'UTR | ATGGCCGCATCTCCGCACACTCTCTCCTCACGCCTCCTGACAGGTTGCGT<br>AGGAGGCTCTGTCTGGTATCTTGAAAGAAGAACTATGCCCATGGCCAACC<br>TGCTGCTGCTGATCGTGCCCATCCTGATCGCCATGGCCTTCCTGATGCTG<br>ACCGAGCGCAAGATCCTGGGCTACATGCAGCTGCGCAAGGGCCCCAAC<br>GTGGTGGGCCCCTACGGCCTGCTGCAGCCCTTCGCCGACGCCATGAAG<br>CTGTTCACCAAGGAGCCCCTGAAGCCCGCCACCAGCACCATCACCCTGT<br>ACATCACCGCCCCCACCCTGGCCCTGACCATCGCCCTGCTGCTGTGGAC<br>CCCCCTGCCCATGCCCAACCCCCTGGTGAACCTGAACCTGGGCCTGCTG<br>TTCATCCTGGCCACCAGCAGCCTGGCCGTGTACAGCATCCTGTGGAGCG<br>GCTGGGCCAGCAACAGCAACTACGCCCTGATCGGCGCCCTGCGCGCCG<br>TGGCCCAGACCATCAGCTACGAGGTGACCCTGGCCATCATCCTGCTGAG<br>CACCCTGCTGATGAGCGGCAGCTTCAACCTGAGCACCCTGATCACCACC |

TABLE 1-continued nucleic acid and polypeptide sequences and SEQ ID NOs

| SEQ ID NO: | description | sequence |
|---|---|---|
| | | CAGGAGCACCTGTGGCTGCTGCTGCCCAGCTGGCCCCTGGCCATGATGT
GGTTCATCAGCACCCTGGCCGAGACCAACCGCACCCCCTTCGACCTGGC
CGAGGGCGAGAGCGAGCTGGTGAGCGGCTTCAACATCGAGTACGCCGC
CGGCCCCTTCGCCCTGTTCTTCATGGCCGAGTACACCAACATCATCATGA
TGAACACCCTGACCACCACCATCTTCCTGGGCACCACCTACGACGCCCT
GAGCCCCGAGCTGTACACCACCTACTTCGTGACCAAGACCCTGCTGCTG
ACCAGCCTGTTCCTGTGGATCCGCACCGCCTACCCCCGCTTCCGCTACG
ACCAGCTGATGCACCTGCTGTGGAAGAACTTCCTGCCCCTGACCCTGGC
CCTGCTGATGTGGTACGTGAGCATGCCCATCACCATCAGCAGCATCCCC
CCCCAGACCTAAGAGCACTGGGACGCCCACCGCCCCTTTCCCTCCGCTG
CCAGGCGAGCATGTTGTGGTAATTCTGGAACACAAGAAGAGAAATTGCTG
GGTTTAGAACAAGATTATAAACGAATTCGGTGCTCAGTGATCACTTGACA
GTTTTTTTTTTTTAAATATTACCCAAAATGCTCCCCAAATAAGAAATGCA
TCAGCTCAGTCAGTGAATACAAAAAAGGAATTATTTTTCCCTTTGAGGGTC
TTTTATACATCTCTCCTCCAACCCCACCCTCTATTCTGTTTCTTCCTCCTCA
CATGGGGGTACACATACACAGCTTCCTCTTTTGGTTCCATCCTTACCACC
ACACCACACGCACACTCCACATGCCCAGCAGAGTGGCACTTGGTGGCCA
GAAAGTGTGAGCCTCATGATCTGCTGTCTGTAGTTCTGTGAGCTCAGGTC
CCTCAAAGGCCTCGGAGCACCCCCTTCCTTGTGACTGAGCCAGGGCCTG
CATTTTTGGTTTTCCCCACCCCACACATTCTCAACCATAGTCCTTCTAACA
ATACCAATAGCTAGGACCCGGCTGCTGTGCACTGGGACTGGGGATTCCA
CATGTTTGCCTTGGGAGTCTCAAGCTGGACTGCCAGCCCCTGTCCTCCCT
TCACCCCCATTGCGTATGAGCATTTCAGAACTCCAAGGAGTCACAGGCAT
CTTTATAGTTCACGTTAACATATAGACACTGTTGGAAGCAGTTCCTTCTAA
AAGGGGTAGCCCTGGACTTAATACCAGCCGGATACCTCTGGCCCCCACCC
CATTACTGTACCTCTGGAGTCACTACTGTGGGTCGCCACTCCTCTGCTAC
ACAGCACGGCTTTTTCAAGGCTGTATTGAGAAGGGAAGTTAGGAAGAAGG
GTGTGCTGGGCTAACCAGCCCACAGAGCTCACATTCCTGTCCCTTGGGT
GAAAAATACATGTCCATCCTGATATCTCCTGAATTCAGAAATTAGCCTCCA
CATGTGCAATGGCTTTAAGAGCCAGAAGCAGGGTTCTGGGAATTTTGCAA
GTTACCTGTGGCCAGGTGTGGTCTCGGTTACCAAATACGGTTACCTGCAG
CTTTTTAGTCCTTTGTGCTCCCACGGGTCTACAGAGTCCCATCTGCCCAA
AGGTCTTGAAGCTTGACAGGATGTTTTCGATTACTCAGTCTCCCAGGGCA
CTACTGGTCCGTAGGATTCGATTGGTCGGGGTAGGAGAGTTAAACAACAT
TTAAACAGAGTTCTCTCAAAAATGTCTAAAGGGATTGTAGGTAGATAACAT
CCAATCACTGTTTGCACTTATCTGAAATCTTCCCTCTTGGCTGCCCCCAG
GTATTTACTGTGGAGAACATTGCATAGGAATGTCTGGAAAAAGCTTCTACA
ACTTGTTACAGCCTTCACATTTGTAGAAGCTTT |
| 28 | COX10-opt_ND1-3'UTR* | ATGGCCGCATCTCCGCACACTCTCTCCTCACGCCTCCTGACAGGTTGCGT
AGGAGGCTCTGTCTGGTATCTTGAAAGAAGAACTATGCCCATGGCCAACC
TGCTGCTGCTGATCGTGCCCATCCTGATCGCCATGGCCTTCCTGATGCTG
ACCGAGCGCAAGATCCTGGGCTACATGCAGCTGCGCAAGGGCCCCAAC
GTGGTGGGCCCCTACGGCCTGCTGCAGCCCTTCGCCGACGCCATGAAG
CTGTTCACCAAGGAGCCCCTGAAGCCCGCCACCAGCACCATCACCCTGT
ACATCACCGCCCCCACCCTGGCCCTGACCATCGCCCTGCTGCTGTGGAC
CCCCCTGCCCATGCCCAACCCCCTGGTGAACCTGAACCTGGGCCTGCTG
TTCATCCTGGCCACCAGCAGCCTGGCCGTGTACAGCATCCTGTGGAGCG
GCTGGGCCAGCAACAGCAACTACGCCCTGATCGGCGCCCTGCGCGCCG
TGGCCCAGACCATCAGCTACGAGGTGACCCTGGCCATCATCCTGCTGAG
CACCCTGCTGATGAGCGGCAGCTTCAACCTGAGCACCCTGATCACCACC
CAGGAGCACCTGTGGCTGCTGCTGCCCAGCTGGCCCCTGGCCATGATGT
GGTTCATCAGCACCCTGGCCGAGACCAACCGCACCCCCTTCGACCTGGC
CGAGGGCGAGAGCGAGCTGGTGAGCGGCTTCAACATCGAGTACGCCGC
CGGCCCCTTCGCCCTGTTCTTCATGGCCGAGTACACCAACATCATCATGA
TGAACACCCTGACCACCACCATCTTCCTGGGCACCACCTACGACGCCCT
GAGCCCCGAGCTGTACACCACCTACTTCGTGACCAAGACCCTGCTGCTG
ACCAGCCTGTTCCTGTGGATCCGCACCGCCTACCCCCGCTTCCGCTACG
ACCAGCTGATGCACCTGCTGTGGAAGAACTTCCTGCCCCTGACCCTGGC
CCTGCTGATGTGGTACGTGAGCATGCCCATCACCATCAGCAGCATCCCC
CCCCAGACCTAAGAGCACTGGGACGCCCACCGCCCCTTTCCCTCCGCTG
CCAGGCGAGCATGTTGTGGTAATTCTGGAACACAAGAAGAGAAATTGCTG
GGTTTAGAACAAGATTATAAACGAATTCGGTGCTCAGTGATCACTTGACA
GTTTTTTTTTTTTAAATATTACCCAAAATGCTCCCCAAATAAGAAATGCA
TCAGCTCAGTCAGTGAATACAAAAAAGGAATTATTTTTCCCTTTGAGGGTC
TTTTATACATCTCTCCTCCAACCCCACCCTCTATTCTGTTTCTTCCTCCTCA
CATGGGGGTACACATACACAGCTTCCTCTTTTGGTTCCATCCTTACCACC
ACACCACACGCACACTCCACATGCCCAGCAGAGTGGCACTTGGTGGCCA
GAAAGTGTGAGCCTCATGATCTGCTGTCTGTAGTTCTGTGAGCTCAGGTC
CCTCAAAGGCCTCGGAGCACCCCCTTCCTTGTGACTGAGCCAGGGCCTG
CATTTTTGGTTTTCCCCACCCCACACATTCTCAACCATAGTCCTTCTAACA
ATACCAATAGCTAGGACCCGGCTGCTGTGCACTGGGACTGGGGATTCCA
CATGTTTGCCTTGGGAGTCTCAAGCTGGACTGCCA |

TABLE 1-continued nucleic acid and polypeptide sequences and SEQ ID NOs

| SEQ ID NO: | description | sequence |
|---|---|---|
| 29 | opt_COX10-ND4-3'UTR | ATGGCCGCCTCTCCACACACACTGAGTAGCAGACTGCTGACCGGCTGTG<br>TTGGCGGCTCTGTGTGGTATCTGGAACGGCGGACAATGCTAAAACTAATC<br>GTCCCAACAATTATGTTACTACCACTGACATGGCTTTCCAAAAAACACATG<br>ATTTGGATCAACACAACCACCCACAGCCTAATTATTAGCATCATCCCTCTA<br>CTATTTTTTAACCAAATCAACAACAACCTATTTAGCTGTTCCCCAACCTTTT<br>CCTCCGACCCCCTAACAACCCCCCTCCTAATGCTAACTACCTGGCTCCTA<br>CCCCTCACAATCATGGCAAGCCAACGCCACTTATCCAGTGAACCACTATC<br>ACGAAAAAAACTCTACCTCTCTATGCTAATCTCCCTACAAATCTCCTTAATT<br>ATGACATTCACAGCCACAGAACTAATCATGTTTTATATCTTCTTCGAAACC<br>ACACTTATCCCCACCTTGGCTATCATCACCCGATGGGGCAACCAGCCAGA<br>ACGCCTGAACGCAGGCACATACTTCCTATTCTACACCCTAGTAGGCTCCC<br>TTCCCCTACTCATCGCACTAATTTACACTCACAACACCCTAGGCTCACTAA<br>ACATTCTACTACTCACTCTCACTGCCCAAGAACTATCAAACTCCTGGGCCA<br>ACAACTTAATGTGGCTAGCTTACACAATGGCTTTTATGGTAAAGATGCCTC<br>TTTACGGACTCCACTTATGGCTCCCTAAAGCCCATGTCGAAGCCCCCATC<br>GCTGGGTCAATGGTACTTGCCGCAGTACTCTTAAAACTAGGCGGCTATGG<br>TATGATGCGCCTCACACTCATTCTCAACCCCTGACAAAACACATGGCCT<br>ACCCCTTCCTTGTACTATCCCTATGGGGCATGATTATGACAAGCTCCATCT<br>GCCTACGACAAACAGACCTAAAATCGCTCATTGCATACTCTTCAATCAGC<br>CACATGGCCCTCGTAGTAACAGCCATTCTCATCCAAACCCCCTGGAGCTT<br>CACCGGCGCAGTCATTCTCATGATCGCCCACGGGCTTACATCCTCATTAC<br>TATTCTGCCTAGCAAACTCAAACTACGAACGCACTCACAGTCGCATCATG<br>ATCCTCTCTCAAGGACTTCAAACTCTACTCCCACTAATGGCTTTTTGGTGG<br>CTTCTAGCAAGCCTCGCTAACCTCGCCTTACCCCCCACTATTAACCTACT<br>GGGAGAACTCTCTGTGCTAGTAACCACGTTCTCCTGGTCAAATATCACTC<br>TCCTACTTACAGGACTCAACATGCTAGTCACAGCCCTATACTCCCTCTACA<br>TGTTTACCACAACACAATGGGGCTCACTCACCCACCACATTAACAACATG<br>AAACCCTCATTCACACGAGAAAACACCCTCATGTTCATGCACCTATCCCC<br>CATTCTCCTCCTATCCCTCAACCCCGACATCATTACCGGGTTTTCCTCTTA<br>AGAGCACTGGGACGCCACCGCCCCTTTCCCTCCGCTGCCAGGCGAGC<br>ATGTTGTGGTAATTCTGGAACACAAGAAGAGAAATTGCTGGGTTTAGAAC<br>AAGATTATAAACGAATTCGGTGCTCAGTGATCACTTGACAGTTTTTTTTTT<br>TTTAAATATTACCCAAATGCTCCCCAAATAAGAAATGCATCAGCTCAGTC<br>AGTGAATACAAAAAAGGAATTATTTTTCCCTTTGAGGGTCTTTTATACATCT<br>CTCCTCCAACCCCACCCTCTATTCTGTTTCTTCCTCCTCACATGGGGGTA<br>CACATACACAGCTTCCTCTTTTGGTTCCATCCTTACCACCACACCACAGC<br>ACACTCCACATGCCCAGCAGAGTGGCACTTGGTGGCCAGAAAGTGTGAG<br>CCTCATGATCTGCTGTCTGTAGTTCTGTGAGCTCAGGTCCCTCAAAGGCC<br>TCGGAGCACCCCCTTCCTTGTGACTGAGCCAGGGCCTGCATTTTTGGTTT<br>TCCCCACCCCACACATTCTCAACCATAGTCCTTCTAACAATACCAATAGCT<br>AGGACCCGGCTGCTGTGCACTGGGACTGGGGATTCCACATGTTTGCCTT<br>GGGAGTCTCAAGCTGGACTGCCAGCCCCTGTCCTCCCTTCACCCCCATT<br>GCGTATGAGCATTTCAGAACTCCAAGGAGTCACAGGCATCTTTATAGTTC<br>ACGTTAACATATAGACACTGTTGGAAGCAGTTCCTTCTAAAAGGGTAGCC<br>CTGGACTTAATACCAGCCGGATACCTCTGGCCCCCACCCCATTACTGTAC<br>CTCTGGAGTCACTACTGTGGGTCGCCACTCCTCTGCTACACAGCACGGC<br>TTTTTCAAGGCTGTATTGAGAAGGGAAGTTAGGAAGAAGGGTGTGCTGGG<br>CTAACCAGCCCACAGAGCTCACATTCCTGTCCCTTGGGTGAAAAATACAT<br>GTCCATCCTGATATCTCCTGAATTCAGAAATTAGCCTCCACATGTGCAATG<br>GCTTTAAGAGCCAGAAGCAGGGTTCTGGGAATTTTGCAAGTTACCTGTGG<br>CCAGGTGTGGTCTCGGTTACCAAATACGGTTACCTGCAGCTTTTTAGTCC<br>TTTGTGCTCCCACGGGTCTACAGAGTCCCATCTGCCCAAAGGTCTTGAAG<br>CTTGACAGGATGTTTTCGATTACTCAGTCTCCCAGGGCACTACTGGTCCG<br>TAGGATTCGATTGGTCGGGGTAGGAGAGTTAAACAACATTTAAACAGAGT<br>TCTCTCAAAAATGTCTAAAGGGATTGTAGGTAGATAACATCCAATCACTGT<br>TTGCACTTATCTGAAATCTTCCCTCTTGGCTGCCCCAGGTATTTACTGTG<br>GAGAACATTGCATAGGAATGTCTGGAAAAAGCTTCTACAACTTGTTACAG<br>CCTTCACATTTGTAGAAGCTTT |
| 30 | opt_COX10-ND4-3'UTR* | ATGGCCGCCTCTCCACACACACTGAGTAGCAGACTGCTGACCGGCTGTG<br>TTGGCGGCTCTGTGTGGTATCTGGAACGGCGGACAATGCTAAAACTAATC<br>GTCCCAACAATTATGTTACTACCACTGACATGGCTTTCCAAAAAACACATG<br>ATTTGGATCAACACAACCACCCACAGCCTAATTATTAGCATCATCCCTCTA<br>CTATTTTTTAACCAAATCAACAACAACCTATTTAGCTGTTCCCCAACCTTTT<br>CCTCCGACCCCCTAACAACCCCCCTCCTAATGCTAACTACCTGGCTCCTA<br>CCCCTCACAATCATGGCAAGCCAACGCCACTTATCCAGTGAACCACTATC<br>ACGAAAAAAACTCTACCTCTCTATGCTAATCTCCCTACAAATCTCCTTAATT<br>ATGACATTCACAGCCACAGAACTAATCATGTTTTATATCTTCTTCGAAACC<br>ACACTTATCCCCACCTTGGCTATCATCACCCGATGGGGCAACCAGCCAGA<br>ACGCCTGAACGCAGGCACATACTTCCTATTCTACACCCTAGTAGGCTCCC<br>TTCCCCTACTCATCGCACTAATTTACACTCACAACACCCTAGGCTCACTAA<br>ACATTCTACTACTCACTCTCACTGCCCAAGAACTATCAAACTCCTGGGCCA<br>ACAACTTAATGTGGCTAGCTTACACAATGGCTTTTATGGTAAAGATGCCTC<br>TTTACGGACTCCACTTATGGCTCCCTAAAGCCCATGTCGAAGCCCCCATC |

TABLE 1-continued nucleic acid and polypeptide sequences and SEQ ID NOs

| SEQ ID NO: | description | sequence |
|---|---|---|
| | | GCTGGGTCAATGGTACTTGCCGCAGTACTCTTAAAACTAGGCGGCTATGG
TATGATGCGCCTCACACTCATTCTCAACCCCCTGACAAAACACATGGCCT
ACCCCTTCCTTGTACTATCCCTATGGGGCATGATTATGACAAGCTCCATCT
GCCTACGACAAACAGACCTAAAATCGCTCATTGCATACTCTTCAATCAGC
CACATGGCCCTCGTAGTAACAGCCATTCTCATCCAAACCCCCTGGAGCTT
CACCGGCGCAGTCATTCTCATGATCGCCCACGGGCTTACATCCTCATTAC
TATTCTGCCTAGCAAACTCAAACTACGAACGCACTCACAGTCGCATCATG
ATCCTCTCTCAAGGACTTCAAACTCTACTCCCACTAATGGCTTTTTGGTGG
CTTCTAGCAAGCCTCGCTAACCTCGCCTTACCCCCCACTATTAACCTACT
GGGAGAACTCTCTGTGCTAGTAACCACGTTCTCCTGGTCAAATATCACTC
TCCTACTTACAGGACTCAACATGCTAGTCACAGCCCTATACTCCCTCTACA
TGTTTACCACAACACAATGGGGCTCACTCACCCACCACATTAACAACATG
AAACCCTCATTCACACGAGAAAACACCCTCATGTTCATGCACCTATCCCC
CATTCTCCTCCTATCCCTCAACCCCGACATCATTACCGGGTTTTCCTCTTA
AGAGCACTGGGACGCCCACCGCCCCTTTCCCTCCGCTGCCAGGCGAGC
ATGTTGTGGTAATTCTGGAACACAAGAAGAGAAATTGCTGGGTTTAGAAC
AAGATTATAAACGAATTCGGTGCTCAGTGATCACTTGACAGTTTTTTTTTT
TTTAAATATTACCCAAAATGCTCCCCAAATAAGAAATGCATCAGCTCAGTC
AGTGAATACAAAAAAGGAATTATTTTTCCCTTTGAGGGTCTTTTATACATCT
CTCCTCCAACCCCACCCTCTATTCTGTTTCTTCCTCCTCACATGGGGGTA
CACATACACAGCTTCCTCTTTTGGTTCCATCCTTACCACCACACCACACGC
ACACTCCACATGCCCAGCAGAGTGGCACTTGGTGGCCAGAAAGTGTGAG
CCTCATGATCTGCTGTCTGTAGTTCTGTGAGCTCAGGTCCCTCAAAGGCC
TCGGAGCACCCCCTTCCTTGTGACTGAGCCAGGGCCTGCATTTTTGGTTT
TCCCCACCCCACACATTCTCAACCATAGTCCTTCTAACAATACCAATAGCT
AGGACCCGGCTGCTGTGCACTGGGACTGGGGATTCCACATGTTTGCCTT
GGGAGTCTCAAGCTGGACTGCCA |
| 31 | opt_COX10-opt_ND4-3'UTR | ATGGCCGCCTCTCCACACACACTGAGTAGCAGACTGCTGACCGGCTGTG
TTGGCGGCTCTGTGTGGTATCTGGAACGGCGGACAATGCTGAAGCTGAT
CGTGCCCACCATCATGCTGCTGCCTCTGACCTGGCTGAGCAAGAAACAC
ATGATCTGGATCAACACCACCACGCACAGCCTGATCATCAGCATCATCCC
TCTGCTGTTCTTCAACCAGATCAACAACAACCTGTTCAGCTGCAGCCCCA
CCTTCAGCAGCGACCCTCTGACAACACCTCTGCTGATGCTGACCACCTG
GCTGCTGCCCCTCACAATCATGGCCTCTCAGAGACACCTGAGCAGCGAG
CCCCTGAGCCGGAAGAAACTGTACCTGAGCATGCTGATCTCCCTGCAGA
TCTCTCTGATCATGACCTTCACCGCCACCGAGCTGATCATGTTCTACATCT
TTTTCGAGACAACGCTGATCCCCACACTGGCCATCATCACCAGATGGGGC
AACCAGCCTGAGAGACTGAACGCCGGCACCTACTTTCTGTTCTACACCCT
CGTGGGCAGCCTGCCACTGCTGATTGCCCTGATCTACACCCACAACACC
CTGGGCTCCCTGAACATCCTGCTGCTGACACTGACAGCCCAAGAGCTGA
GCAACAGCTGGGCCAACAATCTGATGTGGCTGGCCTACACAATGGCCTT
CATGGTCAAGATGCCCCTGTACGGCCTGCACCTGTGGCTGCCTAAAGCT
CATGTGGAAGCCCCTATCGCCGGCTCTATGGTGCTGGCTGCAGTGCTGC
TGAAACTCGGCGGCTACGGCATGATGCGGCTGACCCTGATTCTGAATCC
CCTGACCAAGCACATGGCCTATCCATTTCTGGTGCTGAGCCTGTGGGGC
ATGATTATGACCAGCAGCATCTGCCTGCGGCAGACCGATCTGAAGTCCCT
GATCGCCTACAGCTCCATCAGCCACATGGCCCTGGTGGTCACCGCCATC
CTGATTCAGACCCCTTGGAGCTTTACAGGCGCCGTGATCCTGATGATTGC
CCACGGCCTGACAAGCAGCCTGCTGTTTTGTCTGGCCAACAGCAACTAC
GAGCGGACCCACAGCAGAATCATGATCCTGTCTCAGGGCCTGCAGACCC
TCCTGCCTCTTATGGCTTTTTGGTGGCTGCTGGCCTCTCTGGCCAATCTG
GCACTGCCTCCTACCATCAATCTGCTGGGCGAGCTGAGCGTGCTGGTCA
CCACATTCAGCTGGTCCAATATCACCCTGCTGCTCACCGGCCTGAACATG
CTGGTTACAGCCCTGTACTCCCTGTACATGTTCACCACCACACAGTGGGG
AAGCCTGACACACCACATCAACAATATGAAGCCCAGCTTCACCCGCGAGA
ACACCCTGATGTTCATGCATCTGAGCCCCATTCTGCTGCTGTCCCTGAAT
CCTGATATCATCACCGGCTTCTCCAGCTGAGAGCACTGGGACGCCCACC
GCCCCTTTCCCTCCGCTGCCAGGCGAGCATGTTGTGGTAATTCTGGAACA
CAAGAAGAGAAATTGCTGGGTTTAGAACAAGATTATAAACGAATTCGGTG
CTCAGTGATCACTTGACAGTTTTTTTTTTTTAAATATTACCCAAAATGCT
CCCCAAATAAGAAATGCATCAGCTCAGTCAGTGAATACAAAAAAGGAATT
ATTTTTCCCTTTGAGGGTCTTTTATACATCTCTCCTCCAACCCCACCCTCT
ATTCTGTTTCTTCCTCCTCACATGGGGGTACACATACACAGCTTCCTCTTT
TGGTTCCATCCTTACCACCACACCACACGCACACTCCACATGCCCAGCAG
AGTGGCACTTGGTGGCCAGAAAGTGTGAGCCTCATGATCTGCTGTCTGTA
GTTCTGTGAGCTCAGGTCCCTCAAAGGCCTCGGAGCACCCCTTCCTTGT
GACTGAGCCAGGGCCTGCATTTTTGGTTTTCCCCACCCCACACATTCTCA
ACCATAGTCCTTCTAACAATACCAATAGCTAGGACCCGGCTGCTGTGCAC
TGGGACTGGGGATTCCACATGTTTGCCTTGGGAGTCTCAAGCTGGACTG
CCAGCCCCTGTCCTCCCTTCACCCCCATTGCGTATGAGCATTTCAGAACT
CCAAGGAGTCACAGGCATCTTTATAGTTCACGTTAACATATAGACACTGTT
GGAAGCAGTTCCTTCTAAAAGGGTAGCCCTGGACTTAATACCAGCCGGAT
ACCTCTGGCCCCCACCCCATTACTGTACCTCTGGAGTCACTACTGTGGGT |

TABLE 1-continued nucleic acid and polypeptide sequences and SEQ ID NOs

| SEQ ID NO: | description | sequence |
|---|---|---|
| | | CGCCACTCCTCTGCTACACAGCACGGCTTTTTCAAGGCTGTATTGAGAAG<br>GGAAGTTAGGAAGAAGGGTGTGCTGGGCTAACCAGCCCACAGAGCTCAC<br>ATTCCTGTCCCTTGGGTGAAAAATACATGTCCATCCTGATATCTCCTGAAT<br>TCAGAAATTAGCCTCCACATGTGCAATGGCTTTAAGAGCCAGAAGCAGGG<br>TTCTGGGAATTTTGCAAGTTACCTGTGGCCAGGTGTGGTCTCGGTTACCA<br>AATACGGTTACCTGCAGCTTTTTAGTCCTTTGTGCTCCCACGGGTCTACA<br>GAGTCCCATCTGCCCAAAGGTCTTGAAGCTTGACAGGATGTTTTCGATTA<br>CTCAGTCTCCCAGGGCACTACTGGTCCGTAGGATTCGATTGGTCGGGGT<br>AGGAGAGTTAAACAACATTTAAACAGAGTTCTCTCAAAAATGTCTAAAGGG<br>ATTGTAGGTAGATAACATCCAATCACTGTTTGCACTTATCTGAAATCTTCC<br>CTCTTGGCTGCCCCCAGGTATTTACTGTGGAGAACATTGCATAGGAATGT<br>CTGGAAAAAGCTTCTACAACTTGTTACAGCCTTCACATTTGTAGAAGCTTT |
| 32 | opt_COX10-<br>opt_ND4-<br>3'UTR* | ATGGCCGCCTCTCCACACACACTGAGTAGCAGACTGCTGACCGGCTGTG<br>TTGGCGGCTCTGTGTGGTATCTGGAACGGCGGACAATGCTGAAGCTGAT<br>CGTGCCCACCATCATGCTGCTGCCCTCTGACCTGGCTGAGCAAGAAACAC<br>ATGATCTGGATCAACACCACCACGCACAGCCTGATCATCAGCATCATCCC<br>TCTGCTGTTCTTCAACCAGATCAACAACAACCTGTTCAGCTGCAGCCCCA<br>CCTTCAGCAGCGACCCTCTGACAACACCTCTGCTGATGCTGACCACCTG<br>GCTGCTGCCCCTCACAATCATGGCCTCTCAGAGACACCTGAGCAGCGAG<br>CCCCTGAGCCGGAAGAAACTGTACCTGAGCATGCTGATCTCCCTGCAGA<br>TCTCTCTGATCATGACCTTCACCGCCACCGAGCTGATCATGTTCTACATCT<br>TTTTCGAGACAACGCTGATCCCCACACTGGCCATCATCACCAGATGGGGC<br>AACCAGCCTGAGAGACTGAACGCCGGCACCTACTTTCTGTTCTACACCCT<br>CGTGGGCAGCCTGCCACTGCTGATTGCCCTGATCTACACCCACAACACC<br>CTGGGCTCCCTGAACATCCTGCTGCTGACACTGACAGCCCAAGAGCTGA<br>GCAACAGCTGGGCCAACAATCTGATGTGGCTGGCCTACACAATGGCCTT<br>CATGGTCAAGATGCCCCTGTACGGCCTGCACCTGTGGCTGCCTAAAGCT<br>CATGTGGAAGCCCCTATCGCCGGCTCTATGGTGCTGGCTGCAGTGCTGC<br>TGAAACTCGGCGGCTACGGCATGATGCGGCTGACCCTGATTCTGAATCC<br>CCTGACCAAGCACATGGCCTATCCATTTCTGGTGCTGAGCCTGTGGGGC<br>ATGATTATGACCAGCAGCATCTGCCTGCGGCAGACCGATCTGAAGTCCCT<br>GATCGCCTACAGCTCCATCAGCCACATGGGCCTGGTGGTCACCGCCATC<br>CTGATTCAGACCCCTTGGAGCTTTACAGGCGCCGTGATCCTGATGATTGC<br>CCACGGCCTGACAAGCAGCCTGCTGTTTTGTCTGGCCAACAGCAACTAC<br>GAGCGGACCCACAGCAGAATCATGATCCTGTCTCAGGGCCTGCAGACCC<br>TCCTGCCTCTTATGGCTTTTTGGTGGCTGCTGGCCTCTCTGGCCAATCTG<br>GCACTGCCTCCTACCATCAATCTGCTGGGCGAGCTGAGCGTGCTGGTCA<br>CCACATTCAGCTGGTCCAATATCACCCTGCTGCTCACCGGCCTGAACATG<br>CTGGTTACAGCCCTGTACTCCCTGTACATGTTCACCACCACACAGTGGGG<br>AAGCCTGACACACCACATCAACAATATGAAGCCCAGCTTCACCCGCGAGA<br>ACACCCTGATGTTCATGCATCTGAGCCCCATTCTGCTGCTGTCCCTGAAT<br>CCTGATATCATCACCGGCTTCTCCAGCTGAGAGCACTGGGACGCCCACC<br>GCCCCTTTCCCTCCGCTGCCAGGCGAGCATGTTGTGGTAATTCTGGAACA<br>CAAGAAGAGAAATTGCTGGGTTTAGAACAAGATTATAAACGAATTCGGTG<br>CTCAGTGATCACTTGACAGTTTTTTTTTTTTAAATATTACCCAAATGCT<br>CCCCAAATAAGAAATGCATCAGCTCAGTCAGTGAATACAAAAAAGGAATT<br>ATTTTTCCCTTTGAGGGTCTTTTATACATCTCTCCTCCAACCCCACCCTCT<br>ATTCTGTTTCTTCCTCCTCACATGGGGGTACACATACACAGCTTCCTCTTT<br>TGGTTCCATCCTTACCACCACACCACACGCACACTCCACATGCCCAGCAG<br>AGTGGCACTTGGTGGCCAGAAAGTGTGAGCCTCATGATCTGCTGTCTGTA<br>GTTCTGTGAGCTCAGGTCCCTCAAAGGCCTCGGAGCACCCCCTTCCTTGT<br>GACTGAGCCAGGGCCTGCATTTTTGGTTTTCCCCACCCCACACATTCTCA<br>ACCATAGTCCTTCTAACAATACCAATAGCTAGGACCCGGCTGCTGTGCAC<br>TGGGACTGGGGATTCCACATGTTTGCCTTGGGAGTCTCAAGCTGGACTG<br>CCA |
| 33 | opt_COX10-<br>opt_ND4*-<br>3'UTR | ATGGCCGCCTCTCCACACACACTGAGTAGCAGACTGCTGACCGGCTGTG<br>TTGGCGGCTCTGTGTGGTATCTGGAACGGCGGACAATGCTGAAGCTGAT<br>CGTGCCCACCATCATGCTGCTGCCCCTGACCTGGCTGAGCAAGAAGCAC<br>ATGATCTGGATCAACACCACCACGCACAGCCTGATCATCAGCATCATCCC<br>CCTGCTGTTCTTCAACCAGATCAACAACAACCTGTTCAGCTGCAGCCCCA<br>CCTTCAGCAGCGACCCCCTGACCACCCCCTGCTGATGCTGACCACCTG<br>GCTGCTGCCCCTGACCATCATGGCCAGCCAGCGCCACCTGAGCAGCGA<br>GCCCCTGAGCCGCAAGAAGCTGTACCTGAGCATGCTGATCAGCCTGCAG<br>ATCAGCCTGATCATGACCTTCACCGCCACCGAGCTGATCATGTTCTACAT<br>CTTCTTCGAGACCACCCTGATCCCCACCCTGGCCATCATCACCCGCTGG<br>GGCAACCAGCCCGAGCGCCTGAACGCCGGCACCTACTTCCTGTTCTACA<br>CCCTGGTGGGCAGCCTGCCCCTGCTGATCGCCCTGATCTACACCCACAA<br>CACCCTGGGCAGCCTGAACATCCTGCTGCTGACCCTGACCGCCCAGGAG<br>CTGAGCAACAGCTGGGCCAACAACCTGATGTGGCTGGCCTACACCATGG<br>CCTTCATGGTGAAGATGCCCCTGTACGGCCTGCACCTGTGGCTGCCCAA<br>GGCCCACGTGGAGGCCCCCATCGCCGGCAGCATGGTGCTGGCCGCCGT<br>GCTGCTGAAGCTGGGCGGCTACGGCATGATGCGCCTGACCCTGATCCTG |

TABLE 1-continued nucleic acid and polypeptide sequences and SEQ ID NOs

| SEQ ID NO: | description | sequence |
|---|---|---|
| | | AACCCCCTGACCAAGCACATGGCCTACCCCTTCCTGGTGCTGAGCCTGT GGGGCATGATCATGACCAGCAGCATCTGCCTGCGCCAGACCGACCTGAA GAGCCTGATCGCCTACAGCAGCATCAGCCACATGGCCCTGGTGGTGACC GCCATCCTGATCCAGACCCCTGGAGCTTCACCGGCGCCGTGATCCTGA TGATCGCCCACGGCCTGACCAGCAGCCTGCTGTTCTGCCTGGCCAACAG CAACTACGAGCGCACCCACAGCCGCATCATGATCCTGAGCCAGGGCCTG CAGACCCTGCTGCCCCTGATGGCCTTCTGGTGGCTGCTGGCCAGCCTGG CCAACCTGGCCCTGCCCCCCACCATCAACCTGCTGGGCGAGCTGAGCGT GCTGGTGACCACCTTCAGCTGGAGCAACATCACCCTGCTGCTGACCGGC CTGAACATGCTGGTGACCGCCCTGTACAGCCTGTACATGTTCACCACCAC CCAGTGGGGCAGCCTGACCCACCACATCAACAACATGAAGCCCAGCTTC ACCCGCGAGAACACCCTGATGTTCATGCACCTGAGCCCCATCCTGCTGC TGAGCCTGAACCCCGACATCATCACCGGCTTCAGCAGCTAAGAGCACTG GGACGCCCACCGCCCCTTTCCCTCCGCTGCCAGGCGAGCATGTTGTGGT AATTCTGGAACACAAGAAGAGAAATTGCTGGGTTTAGAACAAGATTATAAA CGAATTCGGTGCTCAGTGATCACTTGACAGTTTTTTTTTTTTAAATATTA CCCAAAATGCTCCCCAAATAAGAAATGCATCAGCTCAGTCAGTGAATACA AAAAAGGAATTATTTTTCCCTTTGAGGGTCTTTTATACATCTCTCCTCCAAC CCCACCCTCTATTCTGTTTCTTCCTCCTCACATGGGGGTACACATACACA GCTTCCTCTTTTGGTTCCATCCTTACCACCACACCACACGCACACTCCAC ATGCCCAGCAGAGTGGCACTTGGTGGCCAGAAAGTGTGAGCCTCATGAT CTGCTGTCTGTAGTTCTGTGAGCTCAGGTCCCTCAAAGGCCTCGGAGCA CCCCCTTCCTTGTGACTGAGCCAGGGCCTGCATTTTTGGTTTTCCCCACC CCACACATTCTCAACCATAGTCCTTCTAACAATACCAATAGCTAGGACCCG GCTGCTGTGCACTGGGACTGGGGATTCCACATGTTTGCCTTGGGAGTCT CAAGCTGGACTGCCAGCCCCTGTCCTCCCTTCACCCCCATTGCGTATGA GCATTTCAGAACTCCAAGGAGTCACAGGCATCTTTATAGTTCACGTTAACA TATAGACACTGTTGGAAGCAGTTCCTTCTAAAAGGGTAGCCCTGGACTTA ATACCAGCCGGATACCTCTGGCCCCCACCCCATTACTGTACCTCTGGAGT CACTACTGTGGGTCGCCACTCCTCTGCTACACAGCACGGCTTTTTCAAGG CTGTATTGAGAAGGGAAGTTAGGAAGAAGGGTGTGCTGGGCTAACCAGC CCACAGAGCTCACATTCCTGTCCCTTGGGTGAAAAATACATGTCCATCCT GATATCTCCTGAATTCAGAAATTAGCCTCCACATGTGCAATGGCTTTAAGA GCCAGAAGCAGGGTTCTGGGAATTTTGCAAGTTACCTGTGGCCAGGTGT GGTCTCGGTTACCAAATACGGTTACCTGCAGCTTTTTAGTCCTTTGTGCTC CCACGGGTCTACAGAGTCCCATCTGCCCAAAGGTCTTGAAGCTTGACAG GATGTTTTCGATTACTCAGTCTCCCAGGGCACTACTGGTCCGTAGGATTC GATTGGTCGGGTAGGAGAGTTAAACAACATTTAAACAGAGTTCTCTCAA AAATGTCTAAAGGGATTGTAGGTAGATAACATCCAATCACTGTTTGCACTT ATCTGAAATCTTCCCTCTTGGCTGCCCCCAGGTATTTACTGTGGAGAACA TTGCATAGGAATGTCTGGAAAAAGCTTCTACAACTTGTTACAGCCTTCACA TTTGTAGAAGCTTT |
| 34 | opt_COX10- opt_ND4*- 3'UTR* | ATGGCCGCCTCTCCACACACACTGAGTAGCAGACTGCTGACCGGCTGTG TTGGCGGCTCTGTGTGGTATCTGGAACGGCGGACAATGCTGAAGCTGAT CGTGCCCACCATCATGCTGCTGCCCCTGACCTGGCTGAGCAAGAAGCAC ATGATCTGGATCAACACCACCACCCACAGCCTGATCATCAGCATCATCCC CCTGCTGTTCTTCAACCAGATCAACAACAACCTGTTCAGCTGCAGCCCCA CCTTCAGCAGCGACCCCTGACCACCCCCTGCTGATGCTGACCACCTG GCTGCTGCCCCTGACCATCATGGCCAGCAGCGCCACCTGAGCAGCGA GCCCCTGAGCCGCAAGAAGCTGTACCTGAGCATGCTGATCAGCCTGCAG ATCAGCCTGATCATGACCTTCACCGCCACCGAGCTGATCATGTTCTACAT CTTCTTCGAGACCACCCTGATCCCCACCCTGGCCATCATCACCCGCTGG GGCAACCAGCCCGAGCGCCTGAACGCCGGCACCTACTTCCTGTTCTACA CCCTGGTGGGCAGCCTGCCCCTGCTGATCGCCCTGATCTACACCCACAA CACCCTGGGCAGCCTGAACATCCTGCTGCTGACCCTGACCGCCCAGGAG CTGAGCAACAGCTGGGCCAACAACCTGATGTGGCTGGCCTACACCATGG CCTTCATGGTGAAGATGCCCCTGTACGGCCTGCACCTGTGGCTGCCCAA GGCCCACGTGGAGGCCCCATCGCCGGCAGCATGGTGCTGGCCGCCGT GCTGCTGAAGCTGGGCGGCTACGGCATGATGCGCCTGACCCTGATCCTG AACCCCCTGACCAAGCACATGGCCTACCCCTTCCTGGTGCTGAGCCTGT GGGGCATGATCATGACCAGCAGCATCTGCCTGCGCCAGACCGACCTGAA GAGCCTGATCGCCTACAGCAGCATCAGCCACATGGCCCTGGTGGTGACC GCCATCCTGATCCAGACCCCTGGAGCTTCACCGGCGCCGTGATCCTGA TGATCGCCCACGGCCTGACCAGCAGCCTGCTGTTCTGCCTGGCCAACAG CAACTACGAGCGCACCCACAGCCGCATCATGATCCTGAGCCAGGGCCTG CAGACCCTGCTGCCCCTGATGGCCTTCTGGTGGCTGCTGGCCAGCCTGG CCAACCTGGCCCTGCCCCCCACCATCAACCTGCTGGGCGAGCTGAGCGT GCTGGTGACCACCTTCAGCTGGAGCAACATCACCCTGCTGCTGACCGGC CTGAACATGCTGGTGACCGCCCTGTACAGCCTGTACATGTTCACCACCAC CCAGTGGGGCAGCCTGACCCACCACATCAACAACATGAAGCCCAGCTTC ACCCGCGAGAACACCCTGATGTTCATGCACCTGAGCCCCATCCTGCTGC TGAGCCTGAACCCCGACATCATCACCGGCTTCAGCAGCTAAGAGCACTG GGACGCCCACCGCCCCTTTCCCTCCGCTGCCAGGCGAGCATGTTGTGGT |

TABLE 1-continued nucleic acid and polypeptide sequences and SEQ ID NOs

| SEQ ID NO: | description | sequence |
|---|---|---|
| | | AATTCTGGAACACAAGAAGAGAAATTGCTGGGTTTAGAACAAGATTATAAA<br>CGAATTCGGTGCTCAGTGATCACTTGACAGTTTTTTTTTTTTTAAATATTA<br>CCCAAAATGCTCCCCAAATAAGAAATGCATCAGCTCAGTCAGTGAATACA<br>AAAAAGGAATTATTTTTCCCTTTGAGGGTCTTTTATACATCTCTCCTCCAAC<br>CCCACCCTCTATTCTGTTTCTTCCTCCTCACATGGGGGTACACATACACA<br>GCTTCCTCTTTTGGTTCCATCCTTACCACCACACCACACGCACACTCCAC<br>ATGCCCAGCAGAGTGGCACTTGGTGGCCAGAAAGTGTGAGCCTCATGAT<br>CTGCTGTCTGTAGTTCTGTGAGCTCAGGTCCCTCAAAGGCCTCGGAGCA<br>CCCCCTTCCTTGTGACTGAGCCAGGGCCTGCATTTTTGGTTTTCCCCACC<br>CCACACATTCTCAACCATAGTCCTTCTAACAATACCAATAGCTAGGACCCG<br>GCTGCTGTGCACTGGGACTGGGGATTCCACATGTTTGCCTTGGGAGTCT<br>CAAGCTGGACTGCCA |
| 35 | opt_COX10-<br>ND6-<br>3'UTR | ATGGCCGCCTCTCCACACACACTGAGTAGCAGACTGCTGACCGGCTGTG<br>TTGGCGGCTCTGTGTGGTATCTGGAACGGCGGACAATGATGTATGCTTTG<br>TTTCTGTTGAGTGTGGGTTTAGTAATGGGGTTTGTGGGGTTTTCTTCTAAG<br>CCTTCTCCTATTTATGGGGGTTTAGTATTGATTGTTAGCGGTGTGGTCGG<br>GTGTGTTATTATTCTGAATTTTGGGGGAGGTTATATGGGTTTAATGGTTTT<br>TTTAATTTATTTAGGGGGAATGATGGTTGTCTTTGGATATACTACAGCGAT<br>GGCTATTGAGGAGTATCCTGAGGCATGGGGGTCAGGGGTTGAGGTCTTG<br>GTGAGTGTTTTAGTGGGGTTAGCGATGGAGGTAGGATTGGTGCTGTGGG<br>TGAAAGAGTATGATGGGGTGGTGGTTGTGGTAAACTTTAATAGTGTAGGA<br>AGCTGGATGATTTATGAAGGAGAGGGGTCAGGGTTGATTCGGGAGGATC<br>CTATTGGTGCGGGGCTTTGTATGATTATGGGCGTTGGTTAGTAGTAGTT<br>ACTGGTTGGACATTGTTTGTTGGTGTATATATTGTAATTGAGATTGCTCGG<br>GGGAATTAGGAGCACTGGGACGCCCACCGCCCCTTTCCCTCCGCTGCCA<br>GGCGAGCATGTTGTGGTAATTCTGGAACACAAGAAGAGAAATTGCTGGGT<br>TTAGAACAAGATTATAAACGAATTCGGTGCTCAGTGATCACTTGACAGTTT<br>TTTTTTTTTTAAATATTACCCAAAATGCTCCCAAATAAGAAATGCATCAG<br>CTCAGTCAGTGAATACAAAAAAGGAATTATTTTTCCCTTTGAGGGTCTTTT<br>ATACATCTCTCCTCCAACCCCACCCTCTATTCTGTTTCTTCCTCCTCACAT<br>GGGGGTACACATACACAGCTTCCTCTTTTGGTTCCATCCTTACCACCACA<br>CCACACGCACACTCCACATGCCCAGCAGAGTGGCACTTGGTGGCCAGAA<br>AGTGTGAGCCTCATGATCTGCTGTCTGTAGTTCTGTGAGCTCAGGTCCCT<br>CAAAGGCCTCGGAGCACCCCCTTCCTTGTGACTGAGCCAGGGCCTGCAT<br>TTTTGGTTTTCCCCACCCCACACATTCTCAACCATAGTCCTTCTAACAATA<br>CCAATAGCTAGGACCCGGCTGCTGTGCACTGGGACTGGGGATTCCACAT<br>GTTTGCCTTGGGAGTCTCAAGCTGGACTGCCAGCCCCTGTCCTCCCTTCA<br>CCCCCATTGCGTATGAGCATTTCAGAACTCCAAGGAGTCACAGGCATCTT<br>TATAGTTCACGTTAACATATAGACACTGTTGGAAGCAGTTCCTTCTAAAAG<br>GGTAGCCCTGGACTTAATACCAGCCGGATACCTCTGGCCCCCACCCCAT<br>TACTGTACCTCTGGAGTCACTACTGTGGGTCGCCACTCCTCTGCTACACA<br>GCACGGCTTTTTCAAGGCTGTATTGAGAAGGGAAGTTAGGAAGAAGGGT<br>GTGCTGGGCTAACCAGCCCACAGAGCTCACATTCCTGTCCCTTGGGTGA<br>AAAATACATGTCCATCCTGATATCTCCTGAATTCAGAAATTAGCCTCCACA<br>TGTGCAATGGCTTTAAGAGCCAGAAGCAGGGTTCTGGGAATTTTGCAAGT<br>TACCTGTGGCCAGGTGTGGTCTCGGTTACCAAATACGGTTACCTGCAGCT<br>TTTTAGTCCTTTGTGCTCCCACGGGTCTACAGAGTCCCATCTGCCCAAAG<br>GTCTTGAAGCTTGACAGGATGTTTTCGATTACTCAGTCTCCCAGGGCACT<br>ACTGGTCCGTAGGATTCGATTGGTCGGGGTAGGAGAGTTAAACAACATTT<br>AAACAGAGTTCTCTCAAAAATGTCTAAAGGGATTGTAGGTAGATAACATCC<br>AATCACTGTTTGCACTTATCTGAAATCTTCCCTCTTGGCTGCCCCCAGGTA<br>TTTACTGTGGAGAACATTGCATAGGAATGTCTGGAAAAAGCTTCTACAACT<br>TGTTACAGCCTTCACATTTGTAGAAGCTTT |
| 36 | opt_COX10-<br>ND6-<br>3'UTR* | ATGGCCGCCTCTCCACACACACTGAGTAGCAGACTGCTGACCGGCTGTG<br>TTGGCGGCTCTGTGTGGTATCTGGAACGGCGGACAATGATGTATGCTTTG<br>TTTCTGTTGAGTGTGGGTTTAGTAATGGGGTTTGTGGGGTTTTCTTCTAAG<br>CCTTCTCCTATTTATGGGGGTTTAGTATTGATTGTTAGCGGTGTGGTCGG<br>GTGTGTTATTATTCTGAATTTTGGGGGAGGTTATATGGGTTTAATGGTTTT<br>TTTAATTTATTTAGGGGGAATGATGGTTGTCTTTGGATATACTACAGCGAT<br>GGCTATTGAGGAGTATCCTGAGGCATGGGGGTCAGGGGTTGAGGTCTTG<br>GTGAGTGTTTTAGTGGGGTTAGCGATGGAGGTAGGATTGGTGCTGTGGG<br>TGAAAGAGTATGATGGGGTGGTGGTTGTGGTAAACTTTAATAGTGTAGGA<br>AGCTGGATGATTTATGAAGGAGAGGGGTCAGGGTTGATTCGGGAGGATC<br>CTATTGGTGCGGGGCTTTGTATGATTATGGGCGTTGGTTAGTAGTAGTT<br>ACTGGTTGGACATTGTTTGTTGGTGTATATATTGTAATTGAGATTGCTCGG<br>GGGAATTAGGAGCACTGGGACGCCCACCGCCCCTTTCCCTCCGCTGCCA<br>GGCGAGCATGTTGTGGTAATTCTGGAACACAAGAAGAGAAATTGCTGGGT<br>TTAGAACAAGATTATAAACGAATTCGGTGCTCAGTGATCACTTGACAGTTT<br>TTTTTTTTTTAAATATTACCCAAAATGCTCCCAAATAAGAAATGCATCAG<br>CTCAGTCAGTGAATACAAAAAAGGAATTATTTTTCCCTTTGAGGGTCTTTT<br>ATACATCTCTCCTCCAACCCCACCCTCTATTCTGTTTCTTCCTCCTCACAT<br>GGGGGTACACATACACAGCTTCCTCTTTTGGTTCCATCCTTACCACCACA |

TABLE 1-continued nucleic acid and polypeptide sequences and SEQ ID NOs

| SEQ ID NO: | description | sequence |
|---|---|---|
| | | CCACACGCACACTCCACATGCCCAGCAGAGTGGCACTTGGTGGCCAGAA
AGTGTGAGCCTCATGATCTGCTGTCTGTAGTTCTGTGAGCTCAGGTCCCT
CAAAGGCCTCGGAGCACCCCCTTCCTTGTGACTGAGCCAGGGCCTGCAT
TTTTGGTTTTCCCCACCCCACACATTCTCAACCATAGTCCTTCTAACAATA
CCAATAGCTAGGACCCGGCTGCTGTGCACTGGGACTGGGGATTCCACAT
GTTTGCCTTGGGAGTCTCAAGCTGGACTGCCA |
| 37 | opt_COX10-opt_ND6-3'UTR | ATGGCCGCCTCTCCACACACACTGAGTAGCAGACTGCTGACCGGCTGTG
TTGGCGGCTCTGTGTGGTATCTGGAACGGCGGACAATGATGTACGCCCT
GTTCCTGCTGAGCGTGGGCCTGGTGATGGGCTTCGTGGGCTTCAGCAGC
AAGCCCAGCCCCATCTACGGCGGCCTGGTGCTGATCGTGAGCGGCGTG
GTGGGCTGCGTGATCATCCTGAACTTCGGCGGCGGCTACATGGGCCTGA
TGGTGTTCCTGATCTACCTGGGCGGCATGATGGTGGTGTTCGGCTACAC
CACCGCCATGGCCATCGAGGAGTACCCCGAGGCCTGGGGCAGCGGCGT
GGAGGTGCTGGTGAGCGTGCTGGTGGGCCTGGCCATGGAGGTGGGCCT
GGTGCTGTGGGTGAAGGAGTACGACGGCGTGGTGGTGGTGAACTT
CAACAGCGTGGGCAGCTGGATGATCTACGAGGGCGAGGGCAGCGGCCT
GATCCGCGAGGACCCCATCGGCGCCGGCGCCCTGTACGACTACGGCCG
CTGGCTGGTGGTGGTGACCGGCTGGACCCTGTTCGTGGGCGTGTACATC
GTGATCGAGATCGCCCGCGGCAACTAAGAGCACTGGGACGCCCACCGC
CCCTTTCCCTCCGCTGCCAGGCGAGCATGTTGTGGTAATTCTGGAACACA
AGAAGAGAAATTGCTGGGTTTAGAACAAGATTATAAACGAATTCGGTGCT
CAGTGATCACTTGACAGTTTTTTTTTTTTAAATATTACCCAAATGCTCC
CCAAATAAGAAATGCATCAGCTCAGTCAGTGAATACAAAAAAGGAATTATT
TTTCCCTTTGAGGGTCTTTTATACATCTCTCCTCCAACCCCACCCTCTATT
CTGTTTCTTCCTCCTCACATGGGGGTACACATACACAGCTTCCTCTTTTGG
TTCCATCCTTACCACCACACCACACGCACACTCCACATGCCCAGCAGAGT
GGCACTTGGTGGCCAGAAAGTGTGAGCCTCATGATCTGCTGTCTGTAGTT
CTGTGAGCTCAGGTCCCTCAAAGGCCTCGGAGCACCCCCTTCCTTGTGA
CTGAGCCAGGGCCTGCATTTTTGGTTTTCCCCACCCCACACATTCTCAAC
CATAGTCCTTCTAACAATACCAATAGCTAGGACCCGGCTGCTGTGCACTG
GGACTGGGGATTCCACATGTTTGCCTTGGGAGTCTCAAGCTGGACTGCC
AGCCCCTGTCCTCCCTTCACCCCATTGCGTATGAGCATTTCAGAACTCC
AAGGAGTCACAGGCATCTTTATAGTTCACGTTAACATATAGACACTGTTGG
AAGCAGTTCCTTCTAAAAGGGTAGCCCTGGACTTAATACCAGCCGGATAC
CTCTGGCCCCCACCCCATTACTGTACCTCTGGAGTCACTACTGTGGGTCG
CCACTCCTCTGCTACACAGCACGGCTTTTTCAAGGCTGTATTGAGAAGGG
AAGTTAGGAAGAAGGGTGTGCTGGGCTAACCAGCCCACAGAGCTCACAT
TCCTGTCCCTTGGGTGAAAAATACATGTCCATCCTGATATCTCCTGAATTC
AGAAATTAGCCTCCACATGTGCAATGGCTTTAAGAGCCAGAAGCAGGGTT
CTGGGAATTTTGCAAGTTACCTGTGGCCAGGTGTGGTCTCGGTTACCAAA
TACGGTTACCTGCAGCTTTTTAGTCCTTTGTGCTCCCACGGGTCTACAGA
GTCCCATCTGCCCAAAGGTCTTGAAGCTTGACAGGATGTTTTCGATTACT
CAGTCTCCCAGGGCACTACTGGTCCGTAGGATTCGATTGGTCGGGGTAG
GAGAGTTAAACAACATTTAAACAGAGTTCTCTCAAAAATGTCTAAAGGGAT
TGTAGGTAGATAACATCCAATCACTGTTTGCACTTATCTGAAATCTTCCCT
CTTGGCTGCCCCCAGGTATTTACTGTGGAGAACATTGCATAGGAATGTCT
GGAAAAAGCTTCTACAACTTGTTACAGCCTTCACATTTGTAGAAGCTTT |
| 38 | opt_COX10-opt_ND6-3'UTR* | ATGGCCGCCTCTCCACACACACTGAGTAGCAGACTGCTGACCGGCTGTG
TTGGCGGCTCTGTGTGGTATCTGGAACGGCGGACAATGATGTACGCCCT
GTTCCTGCTGAGCGTGGGCCTGGTGATGGGCTTCGTGGGCTTCAGCAGC
AAGCCCAGCCCCATCTACGGCGGCCTGGTGCTGATCGTGAGCGGCGTG
GTGGGCTGCGTGATCATCCTGAACTTCGGCGGCGGCTACATGGGCCTGA
TGGTGTTCCTGATCTACCTGGGCGGCATGATGGTGGTGTTCGGCTACAC
CACCGCCATGGCCATCGAGGAGTACCCCGAGGCCTGGGGCAGCGGCGT
GGAGGTGCTGGTGAGCGTGCTGGTGGGCCTGGCCATGGAGGTGGGCCT
GGTGCTGTGGGTGAAGGAGTACGACGGCGTGGTGGTGGTGAACTT
CAACAGCGTGGGCAGCTGGATGATCTACGAGGGCGAGGGCAGCGGCCT
GATCCGCGAGGACCCCATCGGCGCCGGCGCCCTGTACGACTACGGCCG
CTGGCTGGTGGTGGTGACCGGCTGGACCCTGTTCGTGGGCGTGTACATC
GTGATCGAGATCGCCCGCGGCAACTAAGAGCACTGGGACGCCCACCGC
CCCTTTCCCTCCGCTGCCAGGCGAGCATGTTGTGGTAATTCTGGAACACA
AGAAGAGAAATTGCTGGGTTTAGAACAAGATTATAAACGAATTCGGTGCT
CAGTGATCACTTGACAGTTTTTTTTTTTTAAATATTACCCAAATGCTCC
CCAAATAAGAAATGCATCAGCTCAGTCAGTGAATACAAAAAAGGAATTATT
TTTCCCTTTGAGGGTCTTTTATACATCTCTCCTCCAACCCCACCCTCTATT
CTGTTTCTTCCTCCTCACATGGGGGTACACATACACAGCTTCCTCTTTTGG |

TABLE 1-continued nucleic acid and polypeptide sequences and SEQ ID NOs

| SEQ ID NO: | description | sequence |
|---|---|---|
| | | TTCCATCCTTACCACCACACCACACGCACACTCCACATGCCCAGCAGAGT GGCACTTGGTGGCCAGAAAGTGTGAGCCTCATGATCTGCTGTCTGTAGTT CTGTGAGCTCAGGTCCCTCAAAGGCCTCGGAGCACCCCCTTCCTTGTGA CTGAGCCAGGGCCTGCATTTTTGGTTTTCCCCACCCCACACATTCTCAAC CATAGTCCTTCTAACAATACCAATAGCTAGGACCCGGCTGCTGTGCACTG GGACTGGGGATTCCACATGTTTGCCTTGGGAGTCTCAAGCTGGACTGCC A |
| 39 | opt_COX10-ND1-3'UTR | ATGGCCGCCTCTCCACACACACTGAGTAGCAGACTGCTGACCGGCTGTG TTGGCGGCTCTGTGTGGTATCTGGAACGGCGGACAATGCCCATGGCCAA CCTCCTACTCCTCATTGTACCCATTCTAATCGCAATGGCATTCCTAATGCT TACCGAACGAAAAATTCTAGGCTATATGCAACTACGCAAAGGCCCCAACG TTGTAGGCCCCTACGGGCTACTACAACCCTTCGCTGACGCCATGAAACTC TTCACCAAAGAGCCCCTAAAACCCGCCACATCTACCATCACCCTCTACAT CACCGCCCCGACCTTAGCTCTCACCATCGCTCTTCTACTATGGACCCCCC TCCCCATGCCCAACCCCCTGGTCAACCTCAACCTAGGCCTCCTATTTATT CTAGCCACCTCTAGCCTAGCCGTTTACTCAATCCTCTGGTCAGGGTGGGC ATCAAACTCAAACTACGCCCTGATCGGCGCACTGCGAGCAGTAGCCCAA ACAATCTCATATGAAGTCACCCTAGCCATCATTCTACTATCAACATTACTA ATGAGTGGCTCCTTTAACCTCTCCACCCTTATCACAACACAAGAACACCTC TGGTTACTCCTGCCATCATGGCCCTTGGCCATGATGTGGTTTATCTCCAC ACTAGCAGAGACCAACCGAACCCCCTTCGACCTTGCCGAAGGGGAGTCC GAACTAGTCTCAGGCTTCAACATCGAATACGCCGCAGGCCCCTTCGCCCT ATTCTTCATGGCCGAATACACAAACATTATTATGATGAACACCCTCACCAC TACAATCTTCCTAGGAACAACATATGACGCACTCTCCCCTGAACTCTACAC AACATATTTTGTCACCAAGACCCTACTTCTAACCTCCCTGTTCTTATGGAT TCGAACAGCATACCCCCGATTCCGCTACGACCAACTCATGCACCTCCTAT GGAAAAACTTCCTACCACTCACCCTAGCATTACTTATGTGGTATGTCTCCA TGCCCATTACAATCTCCAGCATTCCCCTCAAACCTAAGAGCACTGGGAC GCCCACCGCCCCTTTCCCTCCGCTGCCAGGCGAGCATGTTGTGGTAATT CTGGAACACAAGAAGAGAAATTGCTGGGTTTAGAACAAGATTATAAACGA ATTCGGTGCTCAGTGATCACTTGACAGTTTTTTTTTTTTAAATATTACCC AAAATGCTCCCCAAATAAGAAATGCATCAGCTCAGTCAGTGAATACAAAAA AGGAATTATTTTTCCCTTTGAGGGTCTTTTATACATCTCTCCTCCAACCCC ACCCTCTATTCTGTTTCTTCCTCCTCACATGGGGGTACACATACACAGCTT CCTCTTTTGGTTCCATCCTTACCACCACACCACACGCACACTCCACATGC CCAGCAGAGTGGCACTTGGTGGCCAGAAAGTGTGAGCCTCATGATCTGC TGTCTGTAGTTCTGTGAGCTCAGGTCCCTCAAAGGCCTCGGAGCACCCC CTTCCTTGTGACTGAGCCAGGGCCTGCATTTTTGGTTTTCCCCACCCCAC ACATTCTCAACCATAGTCCTTCTAACAATACCAATAGCTAGGACCCGGCT GCTGTGCACTGGGACTGGGGATTCCACATGTTTGCCTTGGGAGTCTCAA GCTGGACTGCCAGCCCCTGTCCTCCCTTCACCCCCATTGCGTATGAGCAT TTCAGAACTCCAAGGAGTCACAGGCATCTTTATAGTTCACGTTAACATATA GACACTGTTGGAAGCAGTTCCTTCTAAAAGGGTAGCCCTGGACTTAATAC CAGCCGGATACCTCTGGCCCCCACCCCATTACTGTACCTCTGGAGTCACT ACTGTGGGTCGCCACTCCTCTGCTACACAGCACGGCTTTTTCAAGGCTGT ATTGAGAAGGGAAGTTAGGAAGAAGGGTGTGCTGGGCTAACCAGCCCAC AGAGCTCACATTCCTGTCCCTTGGGTGAAAAATACATGTCCATCCTGATAT CTCCTGAATTCAGAAATTAGCCTCCACATGTGCAATGGCTTTAAGAGCCA GAAGCAGGGTTCTGGGAATTTTGCAAGTTACCTGTGGCCAGGTGTGGTCT CGGTTACCAAATACGGTTACCTGCAGCTTTTTAGTCCTTTGTGCTCCCAC GGGTCTACAGAGTCCCATCTGCCCAAAGGTCTTGAAGCTTGACAGGATGT TTTCGATTACTCAGTCTCCCAGGGCACTACTGGTCCGTAGGATTCGATTG GTCGGGGTAGGAGAGTTAAACAACATTTAAACAGAGTTCTCTCAAAAATG TCTAAAGGGATTGTAGGTAGATAACATCCAATCACTGTTTGCACTTATCTG AAATCTTCCCTCTTGGCTGCCCCCAGGTATTTACTGTGGAGAACATTGCA TAGGAATGTCTGGAAAAAGCTTCTACAACTTGTTACAGCCTTCACATTTGT AGAAGCTTT |
| 40 | opt_COX10-ND1-3'UTR* | ATGGCCGCCTCTCCACACACACTGAGTAGCAGACTGCTGACCGGCTGTG TTGGCGGCTCTGTGTGGTATCTGGAACGGCGGACAATGCCCATGGCCAA CCTCCTACTCCTCATTGTACCCATTCTAATCGCAATGGCATTCCTAATGCT TACCGAACGAAAAATTCTAGGCTATATGCAACTACGCAAAGGCCCCAACG TTGTAGGCCCCTACGGGCTACTACAACCCTTCGCTGACGCCATGAAACTC TTCACCAAAGAGCCCCTAAAACCCGCCACATCTACCATCACCCTCTACAT CACCGCCCCGACCTTAGCTCTCACCATCGCTCTTCTACTATGGACCCCCC TCCCCATGCCCAACCCCCTGGTCAACCTCAACCTAGGCCTCCTATTTATT CTAGCCACCTCTAGCCTAGCCGTTTACTCAATCCTCTGGTCAGGGTGGGC ATCAAACTCAAACTACGCCCTGATCGGCGCACTGCGAGCAGTAGCCCAA ACAATCTCATATGAAGTCACCCTAGCCATCATTCTACTATCAACATTACTA ATGAGTGGCTCCTTTAACCTCTCCACCCTTATCACAACACAAGAACACCTC TGGTTACTCCTGCCATCATGGCCCTTGGCCATGATGTGGTTTATCTCCAC ACTAGCAGAGACCAACCGAACCCCCTTCGACCTTGCCGAAGGGGAGTCC GAACTAGTCTCAGGCTTCAACATCGAATACGCCGCAGGCCCCTTCGCCCT |

TABLE 1-continued nucleic acid and polypeptide sequences and SEQ ID NOs

| SEQ ID NO: | description | sequence |
|---|---|---|
| | | ATTCTTCATGGCCGAATACACAAACATTATTATGATGAACACCCTCACCAC<br>TACAATCTTCCTAGGAACAACATATGACGCACTCTCCCCTGAACTCTACAC<br>AACATATTTTGTCACCAAGACCCTACTTCTAACCTCCCTGTTCTTATGGAT<br>TCGAACAGCATACCCCCGATTCCGCTACGACCAACTCATGCACCTCCTAT<br>GGAAAAACTTCCTACCACTCACCCTAGCATTACTTATGTGGTATGTCTCCA<br>TGCCCATTACAATCTCCAGCATTCCCCCTCAAACCTAAGAGCACTGGGAC<br>GCCCACCGCCCCTTTCCCTCCGCTGCCAGGCGAGCATGTTGTGGTAATT<br>CTGGAACACAAGAAGAGAAATTGCTGGGTTTAGAACAAGATTATAAACGA<br>ATTCGGTGCTCAGTGATCACTTGACAGTTTTTTTTTTTTTTAAATATTACCC<br>AAAATGCTCCCCAAATAAGAAATGCATCAGCTCAGTCAGTGAATACAAAAA<br>AGGAATTATTTTTCCCTTTGAGGGTCTTTTATACATCTCTCCTCCAACCCC<br>ACCCTCTATTCTGTTTCTTCCTCCTCACATGGGGGTACACATACACAGCTT<br>CCTCTTTTGGTTCCATCCTTACCACCACACCACACGCACACTCCACATGC<br>CCAGCAGAGTGGCACTTGGTGGCCAGAAAGTGTGAGCCTCATGATCTGC<br>TGTCTGTAGTTCTGTGAGCTCAGGTCCCTCAAAGGCCTCGGAGCACCCC<br>CTTCCTTGTGACTGAGCCAGGGCCTGCATTTTTGGTTTTCCCCACCCCAC<br>ACATTCTCAACCATAGTCCTTCTAACAATACCAATAGCTAGGACCCGGCT<br>GCTGTGCACTGGGACTGGGGATTCCACATGTTTGCCTTGGGAGTCTCAA<br>GCTGGACTGCCA |
| 41 | opt_COX10-<br>opt_ND1-<br>3'UTR | ATGGCCGCCTCTCCACACACACTGAGTAGCAGACTGCTGACCGGCTGTG<br>TTGGCGGCTCTGTGTGGTATCTGGAACGGCGGACAATGCCCATGGCCAA<br>CCTGCTGCTGCTGATCGTGCCCATCCTGATCGCCATGGCCTTCCTGATGC<br>TGACCGAGCGCAAGATCCTGGGCTACATGCAGCTGCGCAAGGGCCCCAA<br>CGTGGTGGGCCCCTACGGCCTGCTGCAGCCCTTCGCCGACGCCATGAA<br>GCTGTTCACCAAGGAGCCCCTGAAGCCCGCCACCAGCACCATCACCCTG<br>TACATCACCGCCCCCACCCTGGCCCTGACCATCGCCCTGCTGCTGTGGA<br>CCCCCCTGCCCATGCCCAACCCCCTGGTGAACCTGAACCTGGGCCTGCT<br>GTTCATCCTGGCCACCAGCAGCCTGGCCGTGTACAGCATCCTGTGGAGC<br>GGCTGGGCCAGCAACAGCAACTACGCCCTGATCGGCGCCCTGCGCGCC<br>GTGGCCCAGACCATCAGCTACGAGGTGACCCTGGCCATCATCCTGCTGA<br>GCACCCTGCTGATGAGCGGCAGCTTCAACCTGAGCACCCTGATCACCAC<br>CCAGGAGCACCTGTGGCTGCTGCTGCCCAGCTGGCCCCTGGCCATGATG<br>TGGTTCATCAGCACCCTGGCCGAGACCAACCGCACCCCCTTCGACCTGG<br>CCGAGGGCGAGAGCGAGCTGGTGAGCGGCTTCAACATCGAGTACGCCG<br>CCGGCCCCTTCGCCCTGTTCTTCATGGCCGAGTACACCAACATCATCATG<br>ATGAACACCCTGACCACCACCATCTTCCTGGGCACCACCTACGACGCCCT<br>GAGCCCCGAGCTGTACACCACCTACTTCGTGACCAAGACCCTGCTGCTG<br>ACCAGCCTGTTCCTGTGGATCCGCACCGCCTACCCCCGCTTCCGCTACG<br>ACCAGCTGATGCACCTGCTGTGGAAGAACTTCCTGCCCCTGACCCTGGC<br>CCTGCTGATGTGGTACGTGAGCATGCCCATCACCATCAGCAGCATCCCC<br>CCCCAGACCTAAGAGCACTGGGACGCCCACCGCCCCTTTCCCTCCGCTG<br>CCAGGCGAGCATGTTGTGGTAATTCTGGAACACAAGAAGAGAAATTGCTG<br>GGTTTAGAACAAGATTATAAACGAATTCGGTGCTCAGTGATCACTTGACA<br>GTTTTTTTTTTTTTAAATATTACCCAAAATGCTCCCCAAATAAGAAATGCA<br>TCAGCTCAGTCAGTGAATACAAAAAAGGAATTATTTTTCCCTTTGAGGGTC<br>TTTTATACATCTCTCCTCCAACCCCACCCTCTATTCTGTTTCTTCCTCCTCA<br>CATGGGGGTACACATACACAGCTTCCTCTTTTGGTTCCATCCTTACCACC<br>ACACCACACGCACACTCCACATGCCCAGCAGAGTGGCACTTGGTGGCCA<br>GAAAGTGTGAGCCTCATGATCTGCTGTCTGTAGTTCTGTGAGCTCAGGTC<br>CCTCAAAGGCCTCGGAGCACCCCCTTCCTTGTGACTGAGCCAGGGCCTG<br>CATTTTTGGTTTTCCCCACCCCACACATTCTCAACCATAGTCCTTCTAACA<br>ATACCAATAGCTAGGACCCGGCTGCTGTGCACTGGGACTGGGGATTCCA<br>CATGTTTGCCTTGGGAGTCTCAAGCTGGACTGCCAGCCCCTGTCCTCCCT<br>TCACCCCCATTGCGTATGAGCATTTCAGAACTCCAAGGAGTCACAGGCAT<br>CTTTATAGTTCACGTTAACATATAGACACTGTTGGAAGCAGTTCCTTCTAA<br>AAGGGTAGCCCTGGACTTAATACCAGCCGGATACCTCTGGCCCCCACCC<br>CATTACTGTACCTCTGGAGTCACTACTGTGGGTCGCCACTCCTCTGCTAC<br>ACAGCACGGCTTTTTCAAGGCTGTATTGAGAAGGGAAGTTAGGAAGAAGG<br>GTGTGCTGGGCTAACCAGCCCACAGAGCTCACATTCCTGTCCCTTGGGT<br>GAAAAATACATGTCCATCCTGATATCTCCTGAATTCAGAAATTAGCCTCCA<br>CATGTGCAATGGCTTTAAGAGCCAGAAGCAGGGTTCTGGGAATTTTGCAA<br>GTTACCTGTGGCCAGGTGTGGTCTCGGTTACCAAATACGGTTACCTGCAG<br>CTTTTTAGTCCTTTGTGCTCCCACGGGTCTACAGAGTCCCATCTGCCCAA<br>AGGTCTTGAAGCTTGACAGGATGTTTTCGATTACTCAGTCTCCCAGGGCA<br>CTACTGGTCCGTAGGATTCGATTGGTCGGGGTAGGAGAGTTAAACAACAT<br>TTAAACAGAGTTCTCTCAAAAATGTCTAAAGGGATTGTAGGTAGATAACAT<br>CCAATCACTGTTTGCACTTATCTGAAATCTTCCCTCTTGGCTGCCCCCAG<br>GTATTTACTGTGGAGAACATTGCATAGGAGTGTCTGGAAAAAGCTTCTACA<br>ACTTGTTACAGCCTTCACATTTGTAGAAGCTTT |
| 42 | opt_COX10-<br>opt_ND1-<br>3'UTR* | ATGGCCGCCTCTCCACACACACTGAGTAGCAGACTGCTGACCGGCTGTG<br>TTGGCGGCTCTGTGTGGTATCTGGAACGGCGGACAATGCCCATGGCCAA<br>CCTGCTGCTGCTGATCGTGCCCATCCTGATCGCCATGGCCTTCCTGATGC |

TABLE 1-continued nucleic acid and polypeptide sequences and SEQ ID NOs

| SEQ ID NO: | description | sequence |
|---|---|---|
| | | TGACCGAGCGCAAGATCCTGGGCTACATGCAGCTGCGCAAGGGCCCCAA<br>CGTGGTGGGCCCCTACGGCCTGCTGCAGCCCTTCGCCGACGCCATGAA<br>GCTGTTCACCAAGGAGCCCCTGAAGCCCGCCACCAGCACCATCACCCTG<br>TACATCACCGCCCCCACCCTGGCCCTGACCATCGCCCTGCTGCTGTGGA<br>CCCCCCTGCCCATGCCCAACCCCCTGGTGAACCTGAACCTGGGCCTGCT<br>GTTCATCCTGGCCCACCAGCAGCCTGGCCGTGTACAGCATCCTGTGGAGC<br>GGCTGGGCCAGCAACAGCAACTACGCCCTGATCGGCGCCCTGCGCGCC<br>GTGGCCCAGACCATCAGCTACGAGGTGACCCTGGCCATCATCCTGCTGA<br>GCACCCTGCTGATGAGCGGCAGCTTCAACCTGAGCACCCTGATCACCAC<br>CCAGGAGCACCTGTGGCTGCTGCTGCCCAGCTGGCCCCTGGCCATGATG<br>TGGTTCATCAGCACCCTGGCCGAGACCAACCGCACCCCCTTCGACCTGG<br>CCGAGGGCGAGAGCGAGCTGGTGAGCGGCTTCAACATCGAGTACGCCG<br>CCGGCCCCTTCGCCCTGTTCTTCATGGCCGAGTACACCAACATCATCATG<br>ATGAACACCCTGACCACCACCATCTTCCTGGGCACCACCTACGACGCCCT<br>GAGCCCCGAGCTGTACACCACCTACTTCGTGACCAAGACCCTGCTGCTG<br>ACCAGCCTGTTCCTGTGGATCCGCACCGCCTACCCCCGCTTCCGCTACG<br>ACCAGCTGATGCACCTGCTGTGGAAGAACTTCCTGCCCCTGACCCTGGC<br>CCTGCTGATGTGGTACGTGAGCATGCCCATCACCATCAGCAGCATCCCC<br>CCCCAGACCTAAGAGCACTGGGACGCCCACCGCCCCTTTCCCTCCGCTG<br>CCAGGCGAGCATGTTGTGGTAATTCTGGAACACAAGAAGAGAAATTGCTG<br>GGTTTAGAACAAGATTATAAACGAATTCGGTGCTCAGTGATCACTTGACA<br>GTTTTTTTTTTTTAAATATTACCCAAAATGCTCCCCAAATAAGAAATGCA<br>TCAGCTCAGTCAGTGAATACAAAAAAGGAATTATTTTTCCCTTTGAGGGTC<br>TTTTATACATCTCTCCTCCAACCCCACCCTCTATTCTGTTTCTTCCTCCTCA<br>CATGGGGGTACACATACACAGCTTCCTCTTTTGGTTCCATCCTTACCACC<br>ACACCACACGCACACTCCACATGCCCAGCAGAGTGGCACTTGGTGGCCA<br>GAAAGTGTGAGCCTCATGATCTGCTGTCTGTAGTTCTGTGAGCTCAGGTC<br>CCTCAAAGGCCTCGGAGCACCCCCTTCCTTGTGACTGAGCCAGGGCCTG<br>CATTTTTGGTTTTCCCCACCCCACACATTCTCAACCATAGTCCTTCTAACA<br>ATACCAATAGCTAGGACCCGGCTGCTGTGCACTGGGACTGGGGATTCCA<br>CATGTTTGCCTTGGGAGTCTCAAGCTGGACTGCCA |
| 43 | opt_COX10*-<br>ND4-<br>3'UTR | ATGGCCGCCAGCCCCCACACCCTGAGCAGCCGCCTGCTGACCGGCTGC<br>GTGGGCGGCAGCGTGTGGTACCTGGAGCGCCGCACCATGCTAAAACTAA<br>TCGTCCCAACAATTATGTTACTACCACTGACATGGCTTTCCAAAAAACACA<br>TGATTTGGATCAACACAACCACCCACAGCCTAATTATTAGCATCATCCCTC<br>TACTATTTTTAACCAAATCAACAACAACCTATTTAGCTGTTCCCCAACCTT<br>TTCCTCCGACCCCCTAACAACCCCCCTCCTAATGCTAACTACCTGGCTCC<br>TACCCCTCACAATCATGGCAAGCCAACGCCACTTATCCAGTGAACCACTA<br>TCACGAAAAAAACTCTACCTCTCTATGCTAATCTCCCTACAAATCTCCTTA<br>ATTATGACATTCACAGCCACAGAACTAATCATGTTTTATATCTTCTTCGAAA<br>CCACACTTATCCCCACCTTGGCTATCATCACCCGATGGGGCAACCAGCCA<br>GAACGCCTGAACGCAGGCACATACTTCCTATTCTACACCCTAGTAGGCTC<br>CCTTCCCCTACTCATCGCACTAATTTACACTCACAACACCCTAGGCTCACT<br>AAACATTCTACTACTCACTCTCACTGCCCAAGAACTATCAAACTCCTGGGC<br>CAACAACTTAATGTGGCTAGCTTACACAATGGCTTTTATGGTAAAGATGCC<br>TCTTTACGGACTCCACTTATGGCTCCCTAAAGCCCATGTCGAAGCCCCCA<br>TCGCTGGGTCAATGGTACTTGCCGCAGTACTCTTAAAACTAGGCGGCTAT<br>GGTATGATGCGCCTCACACTCATTCTCAACCCCCTGACAAAACACATGGC<br>CTACCCCTTCCTTGTACTATCCCTATGGGGCATGATTATGACAAGCTCCAT<br>CTGCCTACGACAAACAGACCTAAAATCGCTCATTGCATACTCTTCAATCAG<br>CCACATGGCCCTCGTAGTAACAGCCATTCTCATCCAAACCCCCTGGAGCT<br>TCACCGGCGCAGTCATTCTCATGATCGCCCACGGGCTTACATCCTCATTA<br>CTATTCTGCCTAGCAAACTCAAACTACGAACGCACTCACAGTCGCATCAT<br>GATCCTCTCTCAAGGACTTCAAACTCTACTCCCACTAATGGCTTTTTGGTG<br>GCTTCTAGCAAGCCTCGCTAACCTCGCCTTACCCCCCACTATTAACCTAC<br>TGGGAGAACTCTCTGTGCTAGTAACCACGTTCTCCTGGTCAAATATCACT<br>CTCCTACTTACAGGACTCAACATGCTAGTCACAGCCCTATACTCCCTCTAC<br>ATGTTTACCACAACACAATGGGGCTCACTCACCCACCACATTAACAACAT<br>GAAACCCTCATTCACACGAGAAAACACCCTCATGTTCATGCACCTATCCC<br>CCATTCTCCTCCTATCCCTCAACCCCGACATCATTACCGGGTTTTCCTCTT<br>AAGAGCACTGGGACGCCCACCGCCCCTTTCCCTCCGCTGCCAGGCGAG<br>CATGTTGTGGTAATTCTGGAACACAAGAAGAGAAATTGCTGGGTTTAGAA<br>CAAGATTATAAACGAATTCGGTGCTCAGTGATCACTTGACAGTTTTTTTTT<br>TTTTAAATATTACCCAAAATGCTCCCCAAATAAGAAATGCATCAGCTCAGT<br>CAGTGAATACAAAAAAGGAATTATTTTTCCCTTTGAGGGTCTTTTATACATC<br>TCTCCTCCAACCCCACCCTCTATTCTGTTTCTTCCTCCTCACATGGGGGTA<br>CACATACACAGCTTCCTCTTTTGGTTCCATCCTTACCACCACACCACACGC<br>ACACTCCACATGCCCAGCAGAGTGGCACTTGGTGGCCAGAAAGTGTGAG<br>CCTCATGATCTGCTGTCTGTAGTTCTGTGAGCTCAGGTCCCTCAAAGGCC<br>TCGGAGCACCCCCTTCCTTGTGACTGAGCCAGGGCCTGCATTTTTGGTTT<br>TCCCCACCCCACACATTCTCAACCATAGTCCTTCTAACAATACCAATAGCT<br>AGGACCCGGCTGCTGTGCACTGGGACTGGGGATTCCACATGTTTGCCTT<br>GGGAGTCTCAAGCTGGACTGCCAGCCCCTGTCCTCCCTTCACCCCCATT |

TABLE 1-continued nucleic acid and polypeptide sequences and SEQ ID NOs

| SEQ ID NO: | description | sequence |
|---|---|---|
| | | GCGTATGAGCATTTCAGAACTCCAAGGAGTCACAGGCATCTTTATAGTTC<br>ACGTTAACATATAGACACTGTTGGAAGCAGTTCCTTCTAAAAGGGTAGCC<br>CTGGACTTAATACCAGCCGGATACCTCTGGCCCCCACCCCATTACTGTAC<br>CTCTGGAGTCACTACTGTGGGTCGCCACTCCTCTGCTACACAGCACGGC<br>TTTTTCAAGGCTGTATTGAGAAGGGAAGTTAGGAAGAAGGGTGTGCTGGG<br>CTAACCAGCCCACAGAGCTCACATTCCTGTCCCTTGGGTGAAAAATACAT<br>GTCCATCCTGATATCTCCTGAATTCAGAAATTAGCCTCCACATGTGCAATG<br>GCTTTAAGAGCCAGAAGCAGGGTTCTGGGAATTTTGCAAGTTACCTGTGG<br>CCAGGTGTGGTCTCGGTTACCAAATACGGTTACCTGCAGCTTTTTAGTCC<br>TTTGTGCTCCCACGGGTCTACAGAGTCCCATCTGCCCAAAGGTCTTGAAG<br>CTTGACAGGATGTTTTCGATTACTCAGTCTCCCAGGGCACTACTGGTCCG<br>TAGGATTCGATTGGTCGGGGTAGGAGAGTTAAACAACATTTAAACAGAGT<br>TCTCTCAAAAATGTCTAAAGGGATTGTAGGTAGATAACATCCAATCACTGT<br>TTGCACTTATCTGAAATCTTCCCTCTTGGCTGCCCCCAGGTATTTACTGTG<br>GAGAACATTGCATAGGAATGTCTGGAAAAAGCTTCTACAACTTGTTACAG<br>CCTTCACATTTGTAGAAGCTTT |
| 44 | opt_COX10*-<br>ND4-<br>3'UTR* | ATGGCCGCCAGCCCCCACACCCTGAGCAGCCGCCTGCTGACCGGCTGC<br>GTGGGCGGCAGCGTGTGGTACCTGGAGCGCCGCACCATGCTAAAACTAA<br>TCGTCCCAACAATTATGTTACTACCACTGACATGGCTTTCAAAAAACACA<br>TGATTTGGATCAACACAACCACCCACAGCCTAATTATTAGCATCATCCCTC<br>TACTATTTTTTAACCAAATCAACAACAACCTATTTAGCTGTTCCCCAACCTT<br>TTCCTCCGACCCCCTAACAACCCCCCTCCTAATGCTAACTACCTGGCTCC<br>TACCCCTCACAATCATGGCAAGCCAACGCCACTTATCCAGTGAACCACTA<br>TCACGAAAAAAACTCTACCTCTCTATGCTAATCTCCCTACAAATCTCCTTA<br>ATTATGACATTCACAGCCACAGAACTAATCATGTTTTATATCTTCTTCGAAA<br>CCACACTTATCCCCACCTTGGCTATCATCACCCGATGGGGCAACCAGCCA<br>GAACGCCTGAACGCAGGCACATACTTCCTATTCTACACCCTAGTAGGCTC<br>CCTTCCCCTACTCATCGCACTAATTTACACTCACAACACCCTAGGCTCACT<br>AAACATTCTACTACTCACTCTCACTGCCCAAGAACTATCAAACTCCTGGGC<br>CAACAACTTAATGTGGCTAGCTTACACAATGGCTTTTATGGTAAAGATGCC<br>TCTTTACGGACTCCACTTATGGCTCCCTAAAGCCCATGTCGAAGCCCCCA<br>TCGCTGGGTCAATGGTACTTGCCGCAGTACTCTTAAAAACTAGGCGGCTAT<br>GGTATGATGCGCCTCACACTCATTCTCAACCCCCTGACAAAACACATGGC<br>CTACCCCTTCCTTGTACTATCCCTATGGGGCATGATTATGACAAGCTCCAT<br>CTGCCTACGACAAACAGACCTAAAATCGCTCATTGCATACTCTTCAATCAG<br>CCACATGGCCCTCGTAGTAACAGCCATTCTCATCCAAACCCCCTGGAGCT<br>TCACCGGCGCAGTCATTCTCATGATCGCCCACGGGCTTACATCCTCATTA<br>CTATTCTGCCTAGCAAACTCAAACTACGAACGCACTCACAGTCGCATCAT<br>GATCCTCTCTCAAGGACTTCAAACTCTACTCCCACTAATGGCTTTTTGGTG<br>GCTTCTAGCAAGCCTCGCTAACCTCGCCTTACCCCCCACTATTAACCTAC<br>TGGGAGAACTCTCTGTGCTAGTAACCACGTTCTCCTGGTCAAATATCACT<br>CTCCTACTTACAGGACTCAACATGCTAGTCACAGCCCTATACTCCCTCTAC<br>ATGTTTACCACAACACAATGGGGCTCACTCACCCACCACATTAACAACAT<br>GAAACCCTCATTCACACGAGAAAACACCCTCATGTTCATGCACCTATCCC<br>CCATTCTCCTCCTATCCCTCAACCCCGACATCATTACCGGGTTTTCCTCTT<br>AAGAGCACTGGGACGCCCACCGCCCCTTTCCCTCCGCTGCCAGGCGAG<br>CATGTTGTGGTAATTCTGGAACACAAGAAGAGAAATTGCTGGGTTTAGAA<br>CAAGATTATAAACGAATTCGGTGCTCAGTGATCACTTGACAGTTTTTTTTTT<br>TTTTAAATATTACCCAAAATGCTCCCCAAATAAGAAATGCATCAGCTCAGT<br>CAGTGAATACAAAAAAGGAATTATTTTTCCCTTTGAGGGTCTTTTATACATC<br>TCTTCCTCCAACCCCACCCTCTATTCTGTTTCTTCCTCCTCACATGGGGTA<br>CACATACACAGCTTCCTCTTTTGGTTCCATCCTTACCACCACACCACACGC<br>ACACTCCACATGCCCAGCAGAGTGGCACTTGGTGGCCAGAAAGTGTGAG<br>CCTCATGATCTGCTGTCTGTAGTTCTGTGAGCTCAGGTCCCTCAAAGGCC<br>TCGGAGCACCCCCTTCCTTGTGACTGAGCCAGGGCCTGCATTTTTGGTTT<br>TCCCCACCCCACACATTCTCAACCATAGTCCTTCTAACAATACCAATAGCT<br>AGGACCCGGCTGCTGTGCACTGGGACTGGGGATTCCACATGTTTGCCTT<br>GGGAGTCTCAAGCTGGACTGCCA |
| 45 | opt_COX10*-<br>opt_ND4-<br>3'UTR | ATGGCCGCCAGCCCCCACACCCTGAGCAGCCGCCTGCTGACCGGCTGC<br>GTGGGCGGCAGCGTGTGGTACCTGGAGCGCCGCACCATGCTGAAGCTG<br>ATCGTGCCCACCATCATGCTGCTGCCTCTGACCTGGCTGAGCAAGAAACA<br>CATGATCTGGATCAACACCACCACGCACAGCCTGATCATCAGCATCATCC<br>CTCTGCTGTTCTTCAACCAGATCAACAACAACCTGTTCAGCTGCAGCCCC<br>ACCTTCAGCAGCGACCCTCTGACAACACCTCTGCTGATGCTGACCACCTG<br>GCTGCTGCCCCTCACAATCATGGCCTCTCAGAGACACCTGAGCAGCGAG<br>CCCCTGAGCCGGAAGAAACTGTACCTGAGCATGCTGATCTCCCTGCAGA<br>TCTCTCTGATCATGACCTTCACCGCCACCGAGCTGATCATGTTCTACATCT<br>TTTTCGAGACAACGCTGATCCCCACACTGGCCATCATCACCAGATGGGGC<br>AACCAGCCTGAGAGACTGAACGCCGGCACCTACTTTCTGTTCTACACCCT<br>CGTGGGCAGCCTGCCACTGCTGATTGCCCTGATCTACACCCACAACACC<br>CTGGGCTCCCTGAACATCTGCTGCTGACACTGACAGCCCAAGAGCTGA<br>GCAACAGCTGGGCCAACAATCTGATGTGGCTGGCCTACACAATGGCCTT |

TABLE 1-continued nucleic acid and polypeptide sequences and SEQ ID NOs

| SEQ ID NO: | description | sequence |
|---|---|---|
| | | CATGGTCAAGATGCCCCTGTACGGCCTGCACCTGTGGCTGCCTAAAGCT
CATGTGGAAGCCCCTATCGCCGGCTCTATGGTGCTGGCTGCAGTGCTGC
TGAAACTCGGCGGCTACGGCATGATGCGGCTGACCCTGATTCTGAATCC
CCTGACCAAGCACATGGCCTATCCATTTCTGGTGCTGAGCCTGTGGGGC
ATGATTATGACCAGCAGCATCTGCCTGCGGCAGACCGATCTGAAGTCCCT
GATCGCCTACAGCTCCATCAGCCACATGGCCCTGGTGGTCACCGCCATC
CTGATTCAGACCCCTTGGAGCTTTACAGGCGCCGTGATCCTGATGATTGC
CCACGGCCTGACAAGCAGCCTGCTGTTTTGTCTGGCCAACAGCAACTAC
GAGCGGACCCACAGCAGAATCATGATCCTGTCTCAGGGCCTGCAGACCC
TCCTGCCTCTTATGGCTTTTTGGTGGCTGCTGGCCTCTCTGGCCAATCTG
GCACTGCCTCCTACCATCAATCTGCTGGGCGAGCTGAGCGTGCTGGTCA
CCACATTCAGCTGGTCCAATATCACCCTGCTGCTCACCGGCCTGAACATG
CTGGTTACAGCCCTGTACTCCCTGTACATGTTCACCACCACACAGTGGGG
AAGCCTGACACACCACATCAACAATATGAAGCCCAGCTTCACCCGCGAGA
ACACCCTGATGTTCATGCATCTGAGCCCCATTCTGCTGCTGTCCCTGAAT
CCTGATATCATCACCGGCTTCTCCAGCTGAGAGCACTGGGACGCCCACC
GCCCCTTTCCCTCCGCTGCCAGGCGAGCATGTTGTGGTAATTCTGGAACA
CAAGAAGAGAAATTGCTGGGTTTAGAACAAGATTATAAACGAATTCGGTG
CTCAGTGATCACTTGACAGTTTTTTTTTTTTTTAAATATTACCCAAATGCT
CCCCAAATAAGAAATGCATCAGCTCAGTCAGTGAATACAAAAAAGGAATT
ATTTTTCCCTTTGAGGGTCTTTTATACATCTCTCCTCCAACCCCACCCTCT
ATTCTGTTTCTTCCTCCTCACATGGGGGTACACATACACAGCTTCCTCTTT
TGGTTCCATCCTTACCACCACACCACACGCACACTCCACATGCCCAGCAG
AGTGGCACTTGGTGGCCAGAAAGTGTGAGCCTCATGATCTGCTGTCTGTA
GTTCTGTGAGCTCAGGTCCCTCAAAGGCCTCGGAGCACCCCCTTCCTTGT
GACTGAGCCAGGGCCTGCATTTTTGGTTTTCCCCACCCCACACATTCTCA
ACCATAGTCCTTCTAACAATACCAATAGCTAGGACCCGGCTGCTGTGCAC
TGGGACTGGGGATTCCACATGTTTGCCTTGGGAGTCTCAAGCTGGACTG
CCAGCCCCTGTCCTCCCTTCACCCCCATTGCGTATGAGCATTTCAGAACT
CCAAGGAGTCACAGGCATCTTTATAGTTCACGTTAACATATAGACACTGTT
GGAAGCAGTTCCTTCTAAAAGGGTAGCCCTGGACTTAATACCAGCCGGAT
ACCTCTGGCCCCCACCCCATTACTGTACCTCTGGAGTCACTACTGTGGGT
CGCCACTCCTCTGCTACACAGCACGGCTTTTTCAAGGCTGTATTGAGAAG
GGAAGTTAGGAAGAAGGGTGTGCTGGGCTAACCAGCCCACAGAGCTCAC
ATTCCTGTCCCTTGGGTGAAAAATACATGTCCATCCTGATATCTCCTGAAT
TCAGAAATTAGCCTCCACATGTGCAATGGCTTTAAGAGCCAGAAGCAGGG
TTCTGGGAATTTTGCAAGTTACCTGTGGCCAGGTGTGGTCTCGGTTACCA
AATACGGTTACCTGCAGCTTTTTAGTCCTTTGTGCTCCCACGGGTCTACA
GAGTCCCATCTGCCCAAAGGTCTTGAAGCTTGACAGGATGTTTTCGATTA
CTCAGTCTCCCAGGGCACTACTGGTCCGTAGGATTCGATTGGTCGGGGT
AGGAGAGTTAAACAACATTTAAACAGAGTTCTCTCAAAAATGTCTAAAGGG
ATTGTAGGTAGATAACATCCAATCACTGTTTGCACTTATCTGAAATCTTCC
CTCCTTGGCTGCCCCCAGGTATTTACTGTGGAGAACATTGCATAGGAATGT
CTGGAAAAAGCTTCTACAACTTGTTACAGCCTTCACATTTGTAGAAGCTTT |
| 46 | opt_COX10*-opt_ND4-3'UTR* | ATGGCCGCCAGCCCCCACACCCTGAGCAGCCGCCTGCTGACCGGCTGC
GTGGGCGGCAGCGTGTGGTACCTGGAGCGCCGCACCATGCTGAAGCTG
ATCGTGCCCACCATCATGCTGCTGCCTCTGACCTGGCTGAGCAAGAAACA
CATGATCTGGATCAACACCACCACGCACAGCCTGATCATCAGCATCATCC
CTCTGCTGTTCTTCAACCAGATCAACAACAACCTGTTCAGCTGCAGCCCC
ACCTTCAGCAGCGACCCTCTGACAACACCTCTGCTGATGCTGACCACCTG
GCTGCTGCCCCTCACAATCATGGCCTCTCAGAGACACCTGAGCAGCGAG
CCCCTGAGCCGGAAGAAACTGTACCTGAGCATGCTGATCTCCCTGCAGA
TCTCTCTGATCATGACCTTCACCGCCACCGAGCTGATCATGTTCTACATCT
TTTTCGAGACAACGCTGATCCCCACACTGGCCATCATCACCAGATGGGGC
AACCAGCCTGAGAGACTGAACGCCGGCACCTACTTTCTGTTCTACACCCT
CGTGGGCAGCCTGCCACTGCTGATTGCCCTGATCTACACCCCACAACACC
CTGGGCTCCCTGAACATCCTGCTGCTGACACTGACAGCCCAAGAGCTGA
GCAACAGCTGGGCCAACAATCTGATGTGGCTGGCCTACACAATGGCCTT
CATGGTCAAGATGCCCCTGTACGGCCTGCACCTGTGGCTGCCTAAAGCT
CATGTGGAAGCCCCTATCGCCGGCTCTATGGTGCTGGCTGCAGTGCTGC
TGAAACTCGGCGGCTACGGCATGATGCGGCTGACCCTGATTCTGAATCC
CCTGACCAAGCACATGGCCTATCCATTTCTGGTGCTGAGCCTGTGGGGC
ATGATTATGACCAGCAGCATCTGCCTGCGGCAGACCGATCTGAAGTCCCT
GATCGCCTACAGCTCCATCAGCCACATGGCCCTGGTGGTCACCGCCATC
CTGATTCAGACCCCTTGGAGCTTTACAGGCGCCGTGATCCTGATGATTGC
CCACGGCCTGACAAGCAGCCTGCTGTTTTGTCTGGCCAACAGCAACTAC
GAGCGGACCCACAGCAGAATCATGATCCTGTCTCAGGGCCTGCAGACCC
TCCTGCCTCTTATGGCTTTTTGGTGGCTGCTGGCCTCTCTGGCCAATCTG
GCACTGCCTCCTACCATCAATCTGCTGGGCGAGCTGAGCGTGCTGGTCA
CCACATTCAGCTGGTCCAATATCACCCTGCTGCTCACCGGCCTGAACATG
CTGGTTACAGCCCTGTACTCCCTGTACATGTTCACCACCACACAGTGGGG
AAGCCTGACACACCACATCAACAATATGAAGCCCAGCTTCACCCGCGAGA
ACACCCTGATGTTCATGCATCTGAGCCCCATTCTGCTGCTGTCCCTGAAT |

TABLE 1-continued nucleic acid and polypeptide sequences and SEQ ID NOs

| SEQ ID NO: | description | sequence |
|---|---|---|
|  |  | CCTGATATCATCACCGGCTTCTCCAGCTGAGAGCACTGGGACGCCCACC<br>GCCCCTTTCCCTCCGCTGCCAGGCGAGCATGTTGTGGTAATTCTGGAACA<br>CAAGAAGAGAAATTGCTGGGTTTAGAACAAGATTATAAACGAATTCGGTG<br>CTCAGTGATCACTTGACAGTTTTTTTTTTTTAAATATTACCCAAAATGCT<br>CCCCAAATAAGAAATGCATCAGCTCAGTCAGTGAATACAAAAAAGGAATT<br>ATTTTTCCCTTTGAGGGTCTTTTATACATCTCTCCTCCAACCCCACCCTCT<br>ATTCTGTTTCTTCCTCCTCACATGGGGGTACACATACACAGCTTCCTCTTT<br>TGGTTCCATCCTTACCACCACACCACACGCACACTCCACATGCCCAGCAG<br>AGTGGCACTTGGTGGCCAGAAAGTGTGAGCCTCATGATCTGCTGTCTGTA<br>GTTCTGTGAGCTCAGGTCCCTCAAAGGCTCGGAGCACCCCCTTCCTTGT<br>GACTGAGCCAGGGCCTGCATTTTTGGTTTTCCCCACCCCACACATTCTCA<br>ACCATAGTCCTTCTAACAATACCAATAGCTAGGACCCGGCTGCTGTGCAC<br>TGGGACTGGGGATTCCACATGTTTGCCTTGGGAGTCTCAAGCTGGACTG<br>CCA |
| 47 | opt_COX10*-<br>opt_ND4*-<br>3'UTR | ATGGCCGCCAGCCCCCACACCCTGAGCAGCCGCCTGCTGACCGGCTGC<br>GTGGGCGGCAGCGTGTGGTACCTGGAGCGCCGCACCATGCTGAAGCTG<br>ATCGTGCCCACCATCATGCTGCTGCCCCTGACCTGGCTGAGCAAGAAGC<br>ACATGATCTGGATCAACACCACCACCCACAGCCTGATCATCAGCATCATC<br>CCCCTGCTGTTCTTCAACCAGATCAACAACAACCTGTTCAGCTGCAGCCC<br>CACCTTCAGCAGCGACCCCCTGACCACCCCCTGCTGATGCTGACCACC<br>TGGCTGCTGCCCCTGACCATCATGGCCAGCCAGCGCCACCTGAGCAGCG<br>AGCCCCTGAGCCGCAAGAAGCTGTACCTGAGCATGCTGATCAGCCTGCA<br>GATCAGCCTGATCATGACCTTCACCGCCACCGAGCTGATCATGTTCTACA<br>TCTTCTTCGAGACCACCCTGATCCCCACCCTGGCCATCATCACCCGCTGG<br>GGCAACCAGCCCGAGCGCCTGAACGCCGGCACCTACTTCCTGTTCTACA<br>CCCTGGTGGGCAGCCTGCCCCTGCTGATCGCCCTGATCTACACCCACAA<br>CACCCTGGGCAGCCTGAACATCCTGCTGCTGACCCTGACCGCCCAGGAG<br>CTGAGCAACAGCTGGGCCAACAACCTGATGTGGCTGGCCTACACCATGG<br>CCTTCATGGTGAAGATGCCCCTGTACGGCCTGCACCTGTGGCTGCCCAA<br>GGCCCACGTGGAGGCCCCCATCGCCGGCAGCATGGTGCTGGCCGCCGT<br>GCTGCTGAAGCTGGGCGGCTACGGCATGATGCGCCTGACCCTGATCCTG<br>AACCCCCTGACCAAGCACATGGCCTACCCCTTCCTGGTGCTGAGCCTGT<br>GGGGCATGATCATGACCAGCAGCATCTGCCTGCGCCAGACCGACCTGAA<br>GAGCCTGATCGCCTACAGCAGCATCAGCCACATGGCCCTGGTGGTGACC<br>GCCATCCTGATCCAGACCCCCTGGAGCTTCACCGGCGCCGTGATCCTGA<br>TGATCGCCCACGGCCTGACCAGCAGCCTGCTGTTCTGCCTGGCCAACAG<br>CAACTACGAGCGCACCCACAGCCGCATCATGATCCTGAGCCAGGGCCTG<br>CAGACCCTGCTGCCCCTGATGGCCTTCTGGTGGCTGCTGGCCAGCCTGG<br>CCAACCTGGCCCTGCCCCCCACCATCAACCTGCTGGGCGAGCTGAGCGT<br>GCTGGTGACCACCTTCAGCTGGAGCAACATCACCCTGCTGCTGACCGGC<br>CTGAACATGCTGGTGACCGCCCTGTACAGCCTGTACATGTTCACCACCAC<br>CCAGTGGGGCAGCCTGACCCACCCACATCAACAACATGAAGCCCAGCTTC<br>ACCCGCGAGAACACCCTGATGTTCATGCACCTGAGCCCCATCCTGCTGC<br>TGAGCCTGAACCCCGACATCATCACCGGCTTCAGCAGCTAAGAGCACTG<br>GACGCCCACCGCCCCTTTCCCTCCGCTGCCAGGCGAGCATGTTGTGGT<br>AATTCTGGAACACAAGAAGAGAAATTGCTGGGTTTAGAACAAGATTATAAA<br>CGAATTCGGTGCTCAGTGATCACTTGACAGTTTTTTTTTTTTAAATATTA<br>CCCAAAATGCTCCCCAAATAAGAAATGCATCAGCTCAGTCAGTGAATACA<br>AAAAAGGAATTATTTTTCCCTTTGAGGGTCTTTTATACATCTCTCCTCCAAC<br>CCCACCCTCTATTCTGTTTCTTCCTCCTCACATGGGGGTACACATACACA<br>GCTTCCTCTTTTGGTTCCATCCTTACCACCACACCACACGCACACTCCAC<br>ATGCCCAGCAGAGTGGCACTTGGTGGCCAGAAAGTGTGAGCCTCATGAT<br>CTGCTGTCTGTAGTTCTGTGAGCTCAGGTCCCTCAAAGGCTCGGAGCA<br>CCCCCTTCCTTGTGACTGAGCCAGGGCCTGCATTTTTGGTTTTCCCCACC<br>CCACACATTCTCAACCATAGTCCTTCTAACAATACCAATAGCTAGGACCCG<br>GCTGCTGTGCACTGGGACTGGGGATTCCACATGTTTGCCTTGGGAGTCT<br>CAAGCTGGACTGCCAGCCCCTGTCCTCCCTTCACCCCCATTGCGTATGA<br>GCATTTCAGAACTCCAAGGAGTCACAGGCATCTTTATAGTTCACGTTAACA<br>TATAGACACTGTTGGAAGCAGTTCCTTCTAAAAGGGTAGCCCTGGACTTA<br>ATACCAGCCGGATACCTCTGGCCCCCACCCCATTACTGTACCTCTGGAGT<br>CACTACTGTGGGTCGCCACTCCTCTGCTACACAGCACGGCTTTTTCAAGG<br>CTGTATTGAGAAGGGAAGTTAGGAAGAAGGGTGTGCTGGGCTAACCAGC<br>CCACAGAGCTCACATTCCTGTCCCTTGGGTGAAAAATACATGTCCATCCT<br>GATATCTCCTGAATTCAGAAATTAGCCTCCACATGTGCAATGGCTTTAAGA<br>GCCAGAAGCAGGGTTCTGGGAATTTTGCAAGTTACCTGTGGCCAGGTGT<br>GGTCTCGGTTACCAAATACGGTTACCTGCAGCTTTTTAGTCCTTTGTGCTC<br>CCACGGGTCTACAGAGTCCCATCTGCCCAAAGGTCTTGAAGCTTGACAG<br>GATGTTTTCGATTACTCAGTCTCCCAGGGCACTACTGGTCCGTAGGATTC<br>GATTGGTCGGGGTAGGAGAGTTAAACAACATTTAAACAGAGTTCTCTCAA<br>AAATGTCTAAAGGGATTGTAGGTAGATAACATCCAATCACTGTTTTGCACTT<br>ATCTGAAATCTTCCCTCTTGGCTGCCCCCAGGTATTTACTGTGGAGAACA<br>TTGCATAGGAATGTCTGGAAAAAGCTTCTACAACTTGTTACAGCCTTCACA<br>TTTGTAGAAGCTTT |

TABLE 1-continued nucleic acid and polypeptide sequences and SEQ ID NOs

| SEQ ID NO: | description | sequence |
|---|---|---|
| 48 | opt_COX10*-opt_ND4*-3'UTR* | ATGGCCGCCAGCCCCCACACCCTGAGCAGCCGCCTGCTGACCGGCTGC<br>GTGGGCGGCAGCGTGTGGTACCTGGAGCGCCGCACCATGCTGAAGCTG<br>ATCGTGCCCACCATCATGCTGCTGCCCCTGACCTGGCTGAGCAAGAAGC<br>ACATGATCTGGATCAACACCACCACCCACAGCCTGATCATCAGCATCATC<br>CCCCTGCTGTTCTTCAACCAGATCAACAACAACCTGTTCAGCTGCAGCCC<br>CACCTTCAGCAGCGACCCCCTGACCACCCCCCTGCTGATGCTGACCACC<br>TGGCTGCTGCCCCTGACCATCATGGCCAGCCAGCGCCACCTGAGCAGCG<br>AGCCCCTGAGCCGCAAGAAGCTGTACCTGAGCATGCTGATCAGCCTGCA<br>GATCAGCCTGATCATGACCTTCACCGCCACCGAGCTGATCATGTTCTACA<br>TCTTCTTCGAGACCACCCTGATCCCCACCCTGGCCATCATCACCCGCTGG<br>GGCAACCAGCCCGAGCGCCTGAACGCCGGCACCTACTTCCTGTTCTACA<br>CCCTGGTGGGCAGCCTGCCCCTGCTGATCGCCCTGATCTACACCCACAA<br>CACCCTGGGCAGCCTGAACATCCTGCTGCTGACCCTGACCGCCCAGGAG<br>CTGAGCAACAGCTGGGCCAACAACCTGATGTGGCTGGCCTACACCATGG<br>CCTTCATGGTGAAGATGCCCCTGTACGGCCTGCACCTGTGGCTGCCCAA<br>GGCCCACGTGGAGGCCCCCATCGCCGGCAGCATGGTGCTGGCCGCCGT<br>GCTGCTGAAGCTGGGCGGCTACGGCATGATGCGCCTGACCCTGATCCTG<br>AACCCCCTGACCAAGCACATGGCCTACCCCTTCCTGGTGCTGAGCCTGT<br>GGGGCATGATCATGACCAGCAGCATCTGCCTGCGCCAGACCGACCTGAA<br>GAGCCTGATCGCCTACAGCAGCATCAGCCACATGGCCCTGGTGGTGACC<br>GCCATCCTGATCCAGACCCCCTGGAGCTTCACCGGCGCCGTGATCCTGA<br>TGATCGCCCACGGCCTGACCAGCAGCCTGCTGTTCTGCCTGGCCAACAG<br>CAACTACGAGCGCACCCACAGCCGCATCATGATCCTGAGCCAGGGCCTG<br>CAGACCCTGCTGCCCCTGATGGCCTTCTGGTGGCTGCTGGCCAGCCTGG<br>CCAACCTGGCCCTGCCCCCCACCATCAACCTGCTGGGCGAGCTGAGCGT<br>GCTGGTGACCACCTTCAGCTGGAGCAACATCACCCTGCTGCTGACCGGC<br>CTGAACATGCTGGTGACCGCCCTGTACAGCCTGTACATGTTCACCACCAC<br>CCAGTGGGCAGCCTGACCCACCACATCAACAACATGAAGCCCAGCTTC<br>ACCCGCGAGAACACCCTGATGTTCATGCACCTGAGCCCCATCCTGCTGC<br>TGAGCCTGAACCCCGACATCATCACCGGCTTCAGCAGCTAAGAGCACTG<br>GGACGCCCACCGCCCCTTTCCCTCCGCTGCCAGGCGAGCATGTTGTGGT<br>AATTCTGGAACACAAGAAGAGAAATTGCTGGGTTTAGAACAAGATTATAAA<br>CGAATTCGGTGCTCAGTGATCACTTGACAGTTTTTTTTTTTTTTAAATATTA<br>CCCAAAATGCTCCCCAAATAAGAAATGCATCAGCTCAGTCAGTGAATACA<br>AAAAAGGAATTATTTTTCCCTTTGAGGGTCTTTTATACATCTCTCCTCCAAC<br>CCCACCCTCTATTCTGTTTCTTCCTCCTCACATGGGGGTACACATACACA<br>GCTTCCTCTTTTGGTTCCATCCTTACCACCACACCACACGCACACTCCAC<br>ATGCCCAGCAGAGTGGCACTTGGTGGCCAGAAAGTGTGAGCCTCATGAT<br>CTGCTGTCTGTAGTTCTGTGAGCTCAGGTCCCTCAAAGGCCTCGGAGCA<br>CCCCCTTCCTTGTGACTGAGCCAGGGCCTGCATTTTTGGTTTTCCCCACC<br>CCACACATTCTCAACCATAGTCCTTCTAACAATACCAATAGCTAGGACCCG<br>GCTGCTGTGCACTGGGACTGGGGATTCCACATGTTTGCCTTGGGAGTCT<br>CAAGCTGGACTGCCA |
| 49 | opt_COX10*-ND6-3'UTR | ATGGCCGCCAGCCCCCACACCCTGAGCAGCCGCCTGCTGACCGGCTGC<br>GTGGGCGGCAGCGTGTGGTACCTGGAGCGCCGCACCATGATGTATGCTT<br>TGTTTCTGTTGAGTGTGGGTTTAGTAATGGGGTTTGTGGGGTTTCTTCTA<br>AGCCTTCTCCTATTTATGGGGGTTTAGTATTGATTGTTAGCGGTGTGGTC<br>GGGTGTGTTATTATTCTGAATTTTGGGGGAGGTTATATGGGTTTAATGGTT<br>TTTTTAATTTATTTAGGGGGAATGATGGTTGTCTTTGGATATACTACAGCG<br>ATGGCTATTGAGGAGTATCCTGAGGCATGGGGGTCAGGGGTTGAGGTCT<br>TGGTGAGTGTTTTAGTGGGGTTAGCGATGGAGGTAGGATTGGTGCTGTG<br>GGTGAAAGAGTATGATGGGGTGGTGGTTGTGGTAAACTTTAATAGTGTAG<br>GAAGCTGGATGATTTATGAAGGAGAGGGGTCAGGGTTGATTCGGGAGGA<br>TCCTATTGGTGCGGGGGCTTTGTATGATTATGGGCGTTGGTTAGTAGTAG<br>TTACTGGTTGGACATTGTTTGTTGGTGTATATATTGTAATTGAGATTGCTC<br>GGGGGAATTAGGAGCACTGGGACGCCCACCGCCCCTTTCCCTCCGCTGC<br>CAGGCGAGCATGTTGTGGTAATTCTGGAACACAAGAAGAGAAATTGCTGG<br>GTTTAGAACAAGATTATAAACGAATTCGGTGCTCAGTGATCACTTGACAGT<br>TTTTTTTTTTTTAAATATTACCCAAAATGCTCCCCAAATAAGAAATGCATC<br>AGCTCAGTCAGTGAATACAAAAAAGGAATTATTTTTCCCTTTGAGGGTCTT<br>TTATACATCTCTCCTCCAACCCCACCCTCTATTCTGTTTCTTCCTCCTCAC<br>ATGGGGGTACACATACACAGCTTCCTCTTTTGGTTCCATCCTTACCACCA<br>CACCACACGCACACTCCACATGCCCAGCAGAGTGGCACTTGGTGGCCAG<br>AAAGTGTGAGCCTCATGATCTGCTGTCTGTAGTTCTGTGAGCTCAGGTCC<br>CTCAAAGGCCTCGGAGCACCCCCTTCCTTGTGACTGAGCCAGGGCCTGC<br>ATTTTTGGTTTTCCCCACCCCACACATTCTCAACCATAGTCCTTCTAACAA<br>TACCAATAGCTAGGACCCGGCTGCTGTGCACTGGGACTGGGGATTCCAC<br>ATGTTTGCCTTGGGAGTCTCAAGCTGGACTGCCAGCCCCGTCCTCCCTT<br>CACCCCCATTGCGTATGAGCATTTCAGAACTCCAAGGAGTCACAGGCATC<br>TTTTATAGTTCACGTTAACATATAGACACTGTTGGAAGCAGTTCCTTCTAAA<br>AGGGTAGCCCTGGACTTAATACCAGCCGGATACCTCTGGCCCCCACCCC<br>ATTACTGTACCTCTGGAGTCACTACTGTGGGTCGCCACTCCTCTGCTACA |

TABLE 1-continued nucleic acid and polypeptide sequences and SEQ ID NOs

| SEQ ID NO: | description | sequence |
|---|---|---|
| | | CAGCACGGCTTTTTCAAGGCTGTATTGAGAAGGGAAGTTAGGAAGAAGG<br>GTGTGCTGGGCTAACCAGCCCACAGAGCTCACATTCCTGTCCCTTGGGT<br>GAAAAATACATGTCCATCCTGATATCTCCTGAATTCAGAAATTAGCCTCCA<br>CATGTGCAATGGCTTTAAGAGCCAGAAGCAGGGTTCTGGGAATTTTGCAA<br>GTTACCTGTGGCCAGGTGTGGTCTCGGTTACCAAATACGGTTACCTGCAG<br>CTTTTTAGTCCTTTGTGCTCCCACGGGTCTACAGAGTCCCATCTGCCCAA<br>AGGTCTTGAAGCTTGACAGGATGTTTTCGATTACTCAGTCTCCCAGGGCA<br>CTACTGGTCCGTAGGATTCGATTGGTCGGGGTAGGAGAGTTAAACAACAT<br>TTAAACAGAGTTCTCTCAAAAATGTCTAAAGGGATTGTAGGTAGATAACAT<br>CCAATCACTGTTTGCACTTATCTGAAATCTTCCCTCTTGGCTGCCCCCAG<br>GTATTTACTGTGGAGAACATTGCATAGGAATGTCTGGAAAAAGCTTCTACA<br>ACTTGTTACAGCCTTCACATTTGTAGAAGCTTT |
| 50 | opt_COX10*-<br>ND6-<br>3'UTR* | ATGGCCGCCAGCCCCCACACCCTGAGCAGCCGCCTGCTGACCGGCTGC<br>GTGGGCGGCAGCGTGTGGTACCTGGAGCGCCGCACCATGATGTATGCTT<br>TGTTTCTGTTGAGTGTGGGTTTAGTAATGGGGTTTGTGGGGTTTTCTTCTA<br>AGCCTTCTCCTATTTATGGGGGTTTAGTATTGATTGTTAGCGGTGTGGTC<br>GGGTGTGTTATTATTCTGAATTTTGGGGGAGGTTATATGGGTTTAATGGTT<br>TTTTTAATTTATTTAGGGGGAATGATGGTTGTCTTTGGATATACTACAGCG<br>ATGGCTATTGAGGAGTATCCTGAGGCATGGGGGTCAGGGGTTGAGGTCT<br>TGGTGAGTGTTTTAGTGGGGTTAGCGATGGAGGTAGGATTGGTGCTGTG<br>GGTGAAAGAGTATGATGGGGTGGTGGTTGTGGTAAACTTTAATAGTGTAG<br>GAAGCTGGATGATTTATGAAGGAGAGGGGTCAGGGTTGATTCGGGAGGA<br>TCCTATTGGTGCGGGGGCTTTGTATGATTATGGGCGTTGGTTAGTAGTAG<br>TTACTGGTTGGACATTGTTTGTTGGTGTATATATTGTAATTGAGATTGCTC<br>GGGGGAATTAGGAGCACTGGGACGCCCACCGCCCCTTTCCCTCCGCTGC<br>CAGGCGAGCATGTTGTGGTAATTCTGGAACACAAGAAGAGAAATTGCTGG<br>GTTTAGAACAAGATTATAAACGAATTCGGTGCTCAGTGATCACTTGACAGT<br>TTTTTTTTTTTTTAAATATTACCCAAAATGCTCCCCAAATAAGAAATGCATC<br>AGCTCAGTCAGTGAATACAAAAAAGGAATTATTTTTCCCTTTGAGGGTCTT<br>TTATACATCTCTCCTCCAACCCCACCCTCTATTCTGTTTCTTCCTCCTCAC<br>ATGGGGGTACACATACACAGCTTCCTCTTTTGGTTCCATCCTTACCACCA<br>CACCACACGCACACTCCACATGCCCAGCAGAGTGGCACTTGGTGGCCAG<br>AAAGTGTGAGCCTCATGATCTGCTGTCTGTAGTTCTGTGAGCTCAGGTCC<br>CTCAAAGGCCTCGGAGCACCCCCTTCCTTGTGACTGAGCCAGGGCCTGC<br>ATTTTTGGTTTTCCCCACCCCACACATTCTCAACCATAGTCCTTCTAACAA<br>TACCAATAGCTAGGACCCGGCTGCTGTGCACTGGGACTGGGGATTCCAC<br>ATGTTTGCCTTGGGAGTCTCAAGCTGGACTGCCA |
| 51 | opt_COX10*-<br>opt_ND6-<br>3'UTR | ATGGCCGCCAGCCCCCACACCCTGAGCAGCCGCCTGCTGACCGGCTGC<br>GTGGGCGGCAGCGTGTGGTACCTGGAGCGCCGCACCATGATGTACGCC<br>CTGTTCCTGCTGAGCGTGGGCCTGGTGATGGGCTTCGTGGGCTTCAGCA<br>GCAAGCCCAGCCCCATCTACGGCGGCCTGGTGCTGATCGTGAGCGGCG<br>TGGTGGGCTGCGTGATCATCCTGAACTTCGGCGGCGGCTACATGGGCCT<br>GATGGTGTTCCTGATCTACCTGGGCGGCATGATGGTGGTGTTCGGCTAC<br>ACCACCGCCATGGCCATCGAGGAGTACCCCGAGGCCTGGGGCAGCGGC<br>GTGGAGGTGCTGGTGAGCGTGCTGGTGGGCCTGGCCATGGAGGTGGGC<br>CTGGTGCTGTGGGTGAAGGAGTACGACGGCGTGGTGGTGGTGGTGAAC<br>TTCAACAGCGTGGGCAGCTGGATGATCTACGAGGGCGAGGGCAGCGGC<br>CTGATCCGCGAGGACCCCATCGGCGCCGGCGCCCTGTACGACTACGGC<br>CGCTGGCTGGTGGTGGTGACCGGCTGGACCCGTTCGTGGGCGTGTAC<br>ATCGTGATCGAGATCGCCCGCGGCAACTAAGAGCACTGGGACGCCCACC<br>GCCCCTTTCCCTCCGCTGCCAGGCGAGCATGTTGTGGTAATTCTGGAACA<br>CAAGAAGAGAAATTGCTGGGTTTAGAACAAGATTATAAACGAATTCGGTG<br>CTCAGTGATCACTTGACAGTTTTTTTTTTTTAAATATTACCCAAAATGCT<br>CCCCAAATAAGAAATGCATCAGCTCAGTCAGTGAATACAAAAAAGGAATT<br>ATTTTTCCCTTTGAGGGTCTTTTATACATCTCTCCTCCAACCCCACCCTCT<br>ATTCTGTTTCTTCCTCCTCACATGGGGGTACACATACACAGCTTCCTCTTT<br>TGGTTCCATCCTTACCACCACACCACACGCACACTCCACATGCCCAGCAG<br>AGTGGCACTTGGTGGCCAGAAAGTGTGAGCCTCATGATCTGCTGTCTGTA<br>GTTCTGTGAGCTCAGGTCCCTCAAAGGCCTCGGAGCACCCCCTTCCTTGT<br>GACTGAGCCAGGGCCTGCATTTTTGGTTTTCCCCACCCCACACATTCTCA<br>ACCATAGTCCTTCTAACAATACCAATAGCTAGGACCCGGCTGCTGTGCAC<br>TGGGACTGGGGATTCCACATGTTTGCCTTGGGAGTCTCAAGCTGGACTG<br>CCAGCCCCTGTCCTCCCTTCACCCCCATTGCGTATGAGCATTTCAGAACT<br>CCAAGGAGTCACAGGCATCTTTATAGTTCACGTTAACATATAGACACTGTT<br>GGAAGCAGTTCCTTCTAAAAGGGTAGCCCTGGACTTAATACCAGCCGGAT<br>ACCTCTGGCCCCCACCCCATTACTGTACCTCTGGAGTCACTACTGTGGGT<br>CGCCACTCCTCTGCTACACAGCACGGCTTTTTCAAGGCTGTATTGAGAAG<br>GGAAGTTAGGAAGAAGGGTGTGCTGGGCTAACCAGCCCACAGAGCTCAC<br>ATTCCTGTCCCTTGGGTGAAAAATACATGTCCATCCTGATATCTCCTGAAT<br>TCAGAAATTAGCCTCCACATGTGCAATGGCTTTAAGAGCCAGAAGCAGGG<br>TTCTGGGAATTTTGCAAGTTACCTGTGGCCAGGTGTGGTCTCGGTTACCA<br>AATACGGTTACCTGCAGCTTTTTAGTCCTTTGTGCTCCCACGGGTCTACA |

TABLE 1-continued nucleic acid and polypeptide sequences and SEQ ID NOs

| SEQ ID NO: | description | sequence |
|---|---|---|
|  |  | GAGTCCCATCTGCCCAAAGGTCTTGAAGCTTGACAGGATGTTTTCGATTA<br>CTCAGTCTCCCAGGGCACTACTGGTCCGTAGGATTCGATTGGTCGGGGT<br>AGGAGAGTTAAACAACATTTAAACAGAGTTCTCTCAAAAATGTCTAAAGGG<br>ATTGTAGGTAGATAACATCCAATCACTGTTTGCACTTATCTGAAATCTTCC<br>CTCTTGGCTGCCCCCAGGTATTTACTGTGGAGAACATTGCATAGGAATGT<br>CTGGAAAAAGCTTCTACAACTTGTTACAGCCTTCACATTTGTAGAAGCTTT |
| 52 | opt_COX10*-<br>opt_ND6-<br>3'UTR* | ATGGCCGCCAGCCCCCACACCCTGAGCAGCCGCCTGCTGACCGGCTGC<br>GTGGGCGGCAGCGTGTGGTACCTGGAGCGCCGCACCATGATGTACGCC<br>CTGTTCCTGCTGAGCGTGGGCCTGGTGATGGGCTTCGTGGGCTTCAGCA<br>GCAAGCCCAGCCCCATCTACGGCGGCCTGGTGCTGATCGTGAGCGGCG<br>TGGTGGGCTGCGTGATCATCCTGAACTTCGGCGGCGGCTACATGGGCCT<br>GATGGTGTTCCTGATCTACCTGGGCGGCATGATGGTGGTGTTCGGCTAC<br>ACCACCGCCATGGCCATCGAGGAGTACCCCGAGGCCTGGGGCAGCGGC<br>GTGGAGGTGCTGGTGAGCGTGCTGGTGGGCCTGGCCATGGAGGTGGC<br>CTGGTGCTGTGGGTGAAGGAGTACGACGGCGTGGTGGTGGTGGTGAAC<br>TTCAACAGCGTGGGCAGCTGGATGATCTACGAGGGCGAGGGCAGCGGC<br>CTGATCCGCGAGGACCCCATCGGCGCCGGCGCCCTGTACGACTACGGC<br>CGCTGGCTGGTGGTGGTGACCGGCTGGACCCTGTTCGTGGGCGTGTAC<br>ATCGTGATCGAGATCGCCCGCGGCAACTAAGAGCACTGGGACGCCCACC<br>GCCCCTTTCCCTCCGCTGCCAGGCGAGCATGTTGTGGTAATTCTGGAACA<br>CAAGAAGAGAAATTGCTGGGTTTAGAACAAGATTATAAACGAATTCGGTG<br>CTCAGTGATCACTTGACAGTTTTTTTTTTTTTAAATATTACCCAAATGCT<br>CCCCAAATAAGAAATGCATCAGCTCAGTCAGTGAATACAAAAAAGGAATT<br>ATTTTTCCCTTTGAGGGTCTTTTATACATCTCTCCTCCAACCCCACCCTCT<br>ATTCTGTTTCTTCCTCCTCACATGGGGGTACACATACACAGCTTCCTCTTT<br>TGGTTCCATCCTTACCACCACACCACACGCACACTCCACATGCCCAGCAG<br>AGTGGCACTTGGTGGCCAGAAAGTGTGAGCCTCATGATCTGCTGTCTGTA<br>GTTCTGTGAGCTCAGGTCCCTCAAAGGCCTCGGAGCACCCCCTTCCTTGT<br>GACTGAGCCAGGGCCTGCATTTTTGGTTTTCCCCACCCCACACATTCTCA<br>ACCATAGTCCTTCTAACAATACCAATAGCTAGGACCCGGCTGCTGTGCAC<br>TGGGACTGGGGATTCCACATGTTTGCCTTGGGAGTCTCAAGCTGGACTG<br>CCA |
| 53 | opt_COX10*-<br>ND1-<br>3'UTR | ATGGCCGCCAGCCCCCACACCCTGAGCAGCCGCCTGCTGACCGGCTGC<br>GTGGGCGGCAGCGTGTGGTACCTGGAGCGCCGCACCATGCCCATGGCC<br>AACCTCCTACTCCTCATTGTACCCATTCTAATCGCAATGGCATTCCTAATG<br>CTTACCGAACGAAAAATTCTAGGCTATATGCAACTACGCAAAGGCCCCAA<br>CGTTGTAGGCCCCTACGGGCTACTACAACCCTTCGCTGACGCCATGAAA<br>CTCTTCACCAAAGAGCCCCTAAAACCCGCCACATCTACCATCACCCTCTA<br>CATCACCGCCCCGACCTTAGCTCTCACCATCGCTCTTCTACTATGGACCC<br>CCCTCCCCATGCCCAACCCCTGGTCAACCTCAACCTAGGCCTCCTATTT<br>ATTCTAGCCACCTCTAGCCTAGCCGTTTACTCAATCCTCTGGTCAGGGTG<br>GGCATCAAACTCAAACTACGCCCTGATCGGCGCACTGCGAGCAGTAGCC<br>CAAACAATCTCATATGAAGTCACCCTAGCCATCATTCTACTATCAACATTA<br>CTAATGAGTGGCTCCTTTAACCTCTCCACCCTTATCACAACACAAGAACAC<br>CTCTGGTTACTCCTGCCATCATGGCCCTTGGCCATGATGTGGTTTATCTC<br>CACACTAGCAGAGACCAACCGAACCCCCTTCGACCTTGCCGAAGGGGAG<br>TCCGAACTAGTCTCAGGCTTCAACATCGAATACGCCGCAGGCCCCTTCGC<br>CCTATTCTTCATGGCCGAATACACAAACATTATTATGATGAACACCCTCAC<br>CACTACAATCTTCCTAGGAACAACATATGACGCACTCTCCCCTGAACTCTA<br>CACAACATATTTTGTCACCAAGACCCTACTTCTAACCTCCCTGTTCTTATG<br>GATTCGAACAGCATACCCCCGATTCCGCTACGACCAACTCATGCACCTCC<br>TATGGAAAAACTTCCTACCACTCACCCTAGCATTACTTATGTGGTATGTCT<br>CCATGCCCATTACAATCTCCAGCATTCCCCCTCAAACCTAAGAGCACTGG<br>GACGCCCACCGCCCCTTTCCCTCCGCTGCCAGGCGAGCATGTTGTGGTA<br>ATTCTGGAACACAAGAAGAGAAATTGCTGGGTTTAGAACAAGATTATAAAC<br>GAATTCGGTGCTCAGTGATCACTTGACAGTTTTTTTTTTTTAAATATTAC<br>CCAAAATGCTCCCCAAATAAGAAATGCATCAGCTCAGTCAGTGAATACAA<br>AAAAGGAATTATTTTTCCCTTTGAGGGTCTTTTATACATCTCTCCTCCAACC<br>CCACCCTCTATTCTGTTTCTTCCTCCTCACATGGGGGTACACATACACAG<br>CTTCCTCTTTTGGTTCCATCCTTACCACCACACCACACGCACACTCCACAT<br>GCCCAGCAGAGTGGCACTTGGTGGCCAGAAAGTGTGAGCCTCATGATCT<br>GCTGTCTGTAGTTCTGTGAGCTCAGGTCCCTCAAAGGCCTCGGAGCACC<br>CCCTTCCTTGTGACTGAGCCAGGGCCTGCATTTTTGGTTTTCCCCACCCC<br>ACACATTCTCAACCATAGTCCTTCTAACAATACCAATAGCTAGGACCCGG<br>CTGCTGTGCACTGGGACTGGGGATTCCACATGTTTGCCTTGGGAGTCTCA<br>AGCTGGACTGCCAGCCCCTGTCCTCCCTTCACCCCATTGCGTATGAGC<br>ATTTCAGAACTCCAAGGAGTCACAGGCATCTTTATAGTTCACGTTAACATA<br>TAGACACTGTTGGAAGCAGTTCCTTCTAAAAGGGTAGCCCTGGACTTAAT<br>ACCAGCCGGATACCTCTGGCCCCCACCCCATTACTGTACCTCTGGAGTCA<br>CTACTGTGGGTCGCCACTCCTCTGCTACACAGCACGGCTTTTTCAAGGCT<br>GTATTGAGAAGGGAAGTTAGGAAGAAGGGTGTGCTGGGCTAACCAGCCC<br>ACAGAGCTCACATTCCTGTCCCTTGGGTGAAAAATACATGTCCATCCTGA |

TABLE 1-continued nucleic acid and polypeptide sequences and SEQ ID NOs

| SEQ ID NO: | description | sequence |
|---|---|---|
| | | TATCTCCTGAATTCAGAAATTAGCCTCCACATGTGCAATGGCTTTAAGAGC
CAGAAGCAGGGTTCTGGGAATTTTGCAAGTTACCTGTGGCCAGGTGTGG
TCTCGGTTACCAAATACGGTTACCTGCAGCTTTTTAGTCCTTTGTGCTCCC
ACGGGTCTACAGAGTCCCATCTGCCCAAAGGTCTTGAAGCTTGACAGGAT
GTTTTCGATTACTCAGTCTCCCAGGGCACTACTGGTCCGTAGGATTCGAT
TGGTCGGGGTAGGAGAGTTAAACAACATTTAAACAGAGTTCTCTCAAAAA
TGTCTAAAGGGATTGTAGGTAGATAACATCCAATCACTGTTTGCACTTATC
TGAAATCTTCCCTCTTGGCTGCCCCCAGGTATTTACTGTGGAGAACATTG
CATAGGAATGTCTGGAAAAAGCTTCTACAACTTGTTACAGCCTTCACATTT
GTAGAAGCTTT |
| 54 | opt_COX10*-
ND1-
3'UTR* | ATGGCCGCCAGCCCCCACACCCTGAGCAGCCGCCTGCTGACCGGCTGC
GTGGGCGGCAGCGTGTGGTACCTGGAGCGCCGCACCATGCCCATGGCC
AACCTCCTACTCCTCATTGTACCCATTCTAATCGCAATGGCATTCCTAATG
CTTACCGAACGAAAAATTCTAGGCTATATGCAACTACGCAAAGGCCCCAA
CGTTGTAGGCCCCTACGGGCTACTACAACCCTTCGCTGACGCCATGAAA
CTCTTCACCAAAGAGCCCCTAAAACCCGCCACATCTACCATCACCCTCTA
CATCACCGCCCCGACCTTAGCTCTCACCATCGCTCTTCTACTATGGACCC
CCCTCCCCATGCCCAACCCCCTGGTCAACCTCAACCTAGGCCTCCTATTT
ATTCTAGCCACCTCTAGCCTAGCCGTTTACTCAATCCTCTGGTCAGGGTG
GGCATCAAACTCAAACTACGCCCTGATCGGCGCACTGCGAGCAGTAGCC
CAAACAATCTCATATGAAGTCACCCTAGCCATCATTCTACTATCAACATTA
CTAATGAGTGGCTCCTTTAACCTCTCCACCCTTATCACAACACAAGAACAC
CTCTGGTTACTCCTGCCATCATGGCCCTTGGCCATGATGTGGTTTATCTC
CACACTAGCAGAGACCAACCGAACCCCCTTCGACCTTGCCGAAGGGGAG
TCCGAACTAGTCTCAGGCTTCAACATCGAATACGCCGCAGGCCCCTTCGC
CCTATTCTTCATGGCCGAATACACAAACATTATTATGATGAACACCCTCAC
CACTACAATCTTCCTAGGAACAACATATGACGCACTCTCCCCTGAACTCTA
CACAACATATTTTGTCACCAAGACCCTACTTCTAACCTCCCTGTTCTTATG
GATTCGAACAGCATACCCCCGATTCCGCTACGACCAACTCATGCACCTCC
TATGGAAAAACTTCCTACCACTCACCCTAGCATTACTTATGGTATGTCT
CCATGCCCATTACAATCTCCAGCATTCCCCCTCAAACCTAAGAGCACTGG
GACGCCCACCGCCCCTTTCCCTCCGCTGCCAGGCGAGCATGTTGTGGTA
ATTCTGGAACACAAGAAGAGAAATTGCTGGGTTTAGAACAAGATTATAAAC
GAATTCGGTGCTCAGTGATCACTTGACAGTTTTTTTTTTTTTAAATATTAC
CCAAAATGCTCCCAAATAAGAAATGCATCAGCTCAGTCAGTGAATACAA
AAAAGGAATTATTTTTCCCTTTGAGGGTCTTTTATACATCTCTCCTCCAACC
CCACCCTCTATTCTGTTTCTTCCTCCTCACATGGGGTACACATACACAG
CTTCCTCTTTTGGTTCCATCCTTACCACCACACCACACGCACACTCCACAT
GCCCAGCAGAGTGGCACTTGGTGGCCAGAAAGTGTGAGCCTCATGATCT
GCTGTCTGTAGTTCTGTGAGCTCAGGTCCCTCAAAGGCCTCGGAGCACC
CCCTTCCTTGTGACTGAGCCAGGGCCTGCATTTTTGGTTTTCCCCACCCC
ACACATTCTCAACCATAGTCCTTCTAACAATACCAATAGCTAGGACCCGG
CTGCTGTGCACTGGGACTGGGGATTCCACATGTTTGCCTTGGGAGTCTCA
AGCTGGACTGCCA |
| 55 | opt_COX10*-
opt_ND1-
3'UTR | ATGGCCGCCAGCCCCCACACCCTGAGCAGCCGCCTGCTGACCGGCTGC
GTGGGCGGCAGCGTGTGGTACCTGGAGCGCCGCACCATGCCCATGGCC
AACCTGCTGCTGCTGATCGTGCCCATCCTGATCGCCATGGCCTTCCTGAT
GCTGACCGAGCGCAAGATCCTGGGCTACATGCAGCTGCGCAAGGGCCC
CAACGTGGTGGGCCCCTACGGCCTGCTGCAGCCCTTCGCCGACGCCAT
GAAGCTGTTCACCAAGGAGCCCCTGAAGCCCGCCACCAGCACCATCACC
CTGTACATCACCGCCCCCACCCTGGCCCTGACCATCGCCCTGCTGCTGT
GGACCCCCCTGCCCATGCCCAACCCCCTGGTGAACCTGAACCTGGGCCT
GCTGTTCATCCTGGCCACCAGCAGCCTGGCCGTGTACAGCATCCTGTGG
AGCGGCTGGGCCAGCAACAGCAACTACGCCCTGATCGGCGCCCTGCGC
GCCGTGGCCCAGACCATCAGCTACGAGGTGACCCTGGCCATCATCCTGC
TGAGCACCCTGCTGATGAGCGGCAGCTTCAACCTGAGCACCCTGATCAC
CACCCAGGAGCACCTGTGGCTGCTGCTGCCCAGCTGGCCCCTGGCCAT
GATGTGGTTCATCAGCACCCTGGCCGAGACCAACCGCACCCCCTTCGAC
CTGGCCGAGGGCGAGAGCGAGCTGGTGAGCGGCTTCAACATCGAGTAC
GCCGCCGGCCCCTTCGCCCTGTTCTTCATGGCCGAGTACACCAACATCA
TCATGATGAACACCCTGACCACCACCATCTTCCTGGGCACCACCTACGAC
GCCCTGAGCCCCGAGCTGTACACCACCTACTTCGTGACCAAGACCCTGC
TGCTGACCAGCCTGTTCCTGTGGATCCGCACCGCCTACCCCCGCTTCCG
CTACGACCAGCTGATGCACCTGCTGTGGAAGAACTTCCTGCCCCTGACC
CTGGCCCTGCTGATGTGGTACGTGAGCATGCCCATCACCATCAGCAGCA
TCCCCCCCCAGACCTAAGAGCACTGGGACGCCCACCGCCCCTTTCCCTC
CGCTGCCAGGCGAGCATGTTGTGGTAATTCTGGAACACAAGAAGAGAAAT
TGCTGGGTTTAGAACAAGATTATAAACGAATTCGGTGCTCAGTGATCACTT
GACAGTTTTTTTTTTTTTAAATATTACCCAAAATGCTCCCAAATAAGAAA
TGCATCAGCTCAGTCAGTGAATACAAAAAAGGAATTATTTTTCCCTTTGAG
GGTCTTTTATACATCTCTCCTCCAACCCCACCCTCTATTCTGTTTCTTCCT
CCTCACATGGGGTACACATACACAGCTTCCTCTTTTGGTTCCATCCTTAC |

TABLE 1-continued nucleic acid and polypeptide sequences and SEQ ID NOs

| SEQ ID NO: | description | sequence |
|---|---|---|
| | | CACCACACCACACGCACACTCCACATGCCCAGCAGAGTGGCACTTGGTG
GCCAGAAAGTGTGAGCCTCATGATCTGCTGTCTGTAGTTCTGTGAGCTCA
GGTCCCTCAAAGGCCTCGGAGCACCCCCTTCCTTGTGACTGAGCCAGGG
CCTGCATTTTTGGTTTTCCCCACCCCACACATTCTCAACCATAGTCCTTCT
AACAATACCAATAGCTAGGACCCGGCTGCTGTGCACTGGGACTGGGGAT
TCCACATGTTTGCCTTGGGAGTCTCAAGCTGGACTGCCAGCCCCTGTCCT
CCCTTCACCCCCATTGCGTATGAGCATTTCAGAACTCCAAGGAGTCACAG
GCATCTTTATAGTTCACGTTAACATATAGACACTGTTGGAAGCAGTTCCTT
CTAAAAGGGTAGCCCTGGACTTAATACCAGCCGGATACCTCTGGCCCCC
ACCCCATTACTGTACCTCTGGAGTCACTACTGTGGGTCGCCACTCCTCTG
CTACACAGCACGGCTTTTTCAAGGCTGTATTGAGAAGGGAAGTTAGGAAG
AAGGGTGTGCTGGGCTAACCAGCCCACAGAGCTCACATTCCTGTCCCTT
GGGTGAAAAATACATGTCCATCCTGATATCTCCTGAATTCAGAAATTAGCC
TCCACATGTGCAATGGCTTTAAGAGCCAGAAGCAGGGTTCTGGGAATTTT
GCAAGTTACCTGTGGCCAGGTGTGGTCTCGGTTACCAAATACGGTTACCT
GCAGCTTTTTAGTCCTTTGTGCTCCCACGGGTCTACAGAGTCCCATCTGC
CCAAAGGTCTTGAAGCTTGACAGGATGTTTTCGATTACTCAGTCTCCCAG
GGCACTACTGGTCCGTAGGATTCGATTGGTCGGGGTAGGAGAGTTAAAC
AACATTTAAACAGAGTTCTCTCAAAAATGTCTAAAGGGATTGTAGGTAGAT
AACATCCAATCACTGTTTGCACTTATCTGAAATCTTCCCTCTTGGCTGCCC
CCAGGTATTTACTGTGGAGAACATTGCATAGGAATGTCTGGAAAAAGCTT
CTACAACTTGTTACAGCCTTCACATTTGTAGAAGCTTT |
| 56 | opt_COX10*-
opt_ND1-
3'UTR* | ATGGCCGCCAGCCCCCACACCCTGAGCAGCCGCCTGCTGACCGGCTGC
GTGGGCGGCAGCGTGTGGTACCTGGAGCGCCGCACCATGCCCATGGCC
AACCTGCTGCTGCTGATCGTGCCCATCCTGATCGCCATGGCCTTCCTGAT
GCTGACCGAGCGCAAGATCCTGGGCTACATGCAGCTGCGCAAGGGCCC
CAACGTGGTGGGCCCCTACGGCCTGCTGCAGCCCTTCGCCGACGCCAT
GAAGCTGTTCACCAAGGAGCCCCTGAAGCCCGCCACCAGCACCATCACC
CTGTACATCACCGCCCCCACCCTGGGCCCTGACCATCGCCTGCTGCTGT
GGACCCCCCTGCCCATGCCCAACCCCCTGGTGAACCTGAACCTGGGCCT
GCTGTTCATCCTGGCCACCAGCAGCCTGGCCGTGTACAGCATCCTGTGG
AGCGGCTGGGCCAGCAACAGCAACTACGCCCTGATCGGCGCCCTGCGC
GCCGTGGCCCAGACCATCAGCTACGAGGTGACCCTGGCCATCATCCTGC
TGAGCACCCTGCTGATGAGCGGCAGCTTCAACCTGAGCACCCTGATCAC
CACCCAGGAGCACCTGTGGCTGCTGCTGCCCAGCTGGCCCCTGGCCAT
GATGTGGTTCATCAGCACCCTGGCCGAGACCAACCGCACCCCCTTCGAC
CTGGCCGAGGGCGAGAGCGAGCTGGTGAGCGGCTTCAACATCGAGTAC
GCCGCCGGCCCCTTCGCCCTGTTCTTCATGGCCGAGTACACCAACATCA
TCATGATGAACACCCTGACCACCACCATCTTCCTGGGCACCACCTACGAC
GCCCTGAGCCCCGAGCTGTACACCACCTACTTCGTGACCAAGACCCTGC
TGCTGACCAGCCTGTTCCTGTGGATCCGCACCGCCTACCCCCGCTTCCG
CTACGACCAGCTGATGCACCTGCTGTGGAAGAACTTCCTGCCCCTGACC
CTGGCCCTGCTGATGTGGTACGTGAGCATGCCCATCACCATCAGCAGCA
TCCCCCCCCAGACCTAAGAGCACTGGGACGCCCACCGCCCCTTTCCCTC
CGCTGCCAGGCGAGCATGTTGTGGTAATTCTGGAACACAAGAAGAGAAAT
TGCTGGGTTTAGAACAAGATTATAAACGAATTCGGTGCTCAGTGATCACTT
GACAGTTTTTTTTTTTTTAAATATTACCCAAAATGCTCCCCAAATAAGAAA
TGCATCAGCTCAGTCAGTGAATACAAAAAAGGAATTATTTTTCCCTTTGAG
GGTCTTTTATACATCTCTCCTCCAACCCCACCCTCTATTCTGTTTCTTCCT
CCTCACATGGGGGTACACATACACAGCTTCCTCTTTTGGTTCCATCCTTAC
CACCACACCACACGCACACTCCACATGCCCAGCAGAGTGGCACTTGGTG
GCCAGAAAGTGTGAGCCTCATGATCTGCTGTCTGTAGTTCTGTGAGCTCA
GGTCCCTCAAAGGCCTCGGAGCACCCCCTTCCTTGTGACTGAGCCAGGG
CCTGCATTTTTGGTTTTCCCCACCCCACACATTCTCAACCATAGTCCTTCT
AACAATACCAATAGCTAGGACCCGGCTGCTGTGCACTGGGACTGGGGAT
TCCACATGTTTGCCTTGGGAGTCTCAAGCTGGACTGCCA |
| 57 | COX8-
ND4-
3'UTR | ATGTCCGTCCTGACGCGCCTGCTGCTGCGGGGCTTGACACGGCTCGGCT
CGGCGGCTCCAGTGCGGCGCGCCAGAATCCATTCGTTGATGCTAAAACT
AATCGTCCCAACAATTATGTTACTACCACTGACATGGCTTTCCAAAAAACA
CATGATTTGGATCAACACAACCACCCACAGCCTAATTATTAGCATCATCCC
TCTACTATTTTTTAACCAAATCAACAACAACCTATTTAGCTGTTCCCCAACC
TTTTCCTCCGACCCCCTAACAACCCCCCTCCTAATGCTAACTACCTGGCT
CCTACCCCTCACAATCATGGCAAGCCAACGCCACTTATCCAGTGAACCAC
TATCACGAAAAAAACTCTACCTCTCTATGCTAATCTCCCTACAAATCTCCTT
AATTATGACATTCACAGCCACAGAACTAATCATGTTTTATATCTTCTTCGAA
ACCACACTTATCCCCACCTTGGCTATCATCACCCGATGGGCAACCAGCC
AGAACGCCTGAACGCAGGCACATACTTCCTATTCTACACCCTAGTAGGCT
CCCTTCCCCTACTCATCGCACTAATTTACACTCACAACACCCTAGGCTCAC
TAAACATTCTACTACTCACTCTCACTGCCCAAGAACTATCAAACTCCTGGG
CCAACAACTTAATGTGGCTAGCTTACACAATGGCTTTTATGGTAAAGATGC
CTCTTTACGGACTCCACTTATGGCTCCCTAAAGCCCATGTCGAAGCCCCC
ATCGCTGGGTCAATGGTACTTGCCGCAGTACTCTTAAAACTAGGCGGCTA |

TABLE 1-continued nucleic acid and polypeptide sequences and SEQ ID NOs

| SEQ ID NO: | description | sequence |
|---|---|---|
| | | TGGTATGATGCGCCTCACACTCATTCTCAACCCCCTGACAAAACACATGG
CCTACCCCTTCCTTGTACTATCCCTATGGGCATGATTATGACAAGCTCC
ATCTGCCTACGACAAACAGACCTAAAATCGCTCATTGCATACTCTTCAATC
AGCCACATGGCCCTCGTAGTAACAGCCATTCTCATCCAAACCCCCTGGAG
CTTCACCGGCGCAGTCATTCTCATGATCGCCCACGGGCTTACATCCTCAT
TACTATTCTGCCTAGCAAACTCAAACTACGAACGCACTCACAGTCGCATC
ATGATCCTCTCTCAAGGACTTCAAACTCTACTCCCACTAATGGCTTTTTGG
TGGCTTCTAGCAAGCCTCGCTAACCTCGCCTTACCCCCCACTATTAACCT
ACTGGGAGAACTCTCTGTGCTAGTAACCACGTTCTCCTGGTCAAATATCA
CTCTCCTACTTACAGGACTCAACATGCTAGTCACAGCCCTATACTCCCTCT
ACATGTTTACCACAACACAATGGGGCTCACTCACCCACCACATTAACAAC
ATGAAACCCTCATTCACACGAGAAAACACCCTCATGTTCATGCACCTATCC
CCCATTCTCCTCCTATCCCTCAACCCCGACATCATTACCGGGTTTTCCTCT
TAAGAGCACTGGGACGCCCACCGCCCCTTTCCCTCCGCTGCCAGGCGAG
CATGTTGTGGTAATTCTGGAACACAAGAAGAGAAATTGCTGGGTTTAGAA
CAAGATTATAAACGAATTCGGTGCTCAGTGATCACTTGACAGTTTTTTTTTT
TTTTAAATATTACCCAAAATGCTCCCCAAATAAGAAATGCATCAGCTCAGT
CAGTGAATACAAAAAAGGAATTATTTTTCCCTTTGAGGGTCTTTTATACATC
TCTCCTCCAACCCCACCCTCTATTCTGTTTCTTCCTCCTCACATGGGGGTA
CACATACACAGCTTCCTCTTTTGGTTCCATCCTTACCACCACACCACACGC
ACACTCCACATGCCCAGCAGAGTGGCACTTGGTGGCCAGAAAGTGTGAG
CCTCATGATCTGCTGTCTGTAGTTCTGTGAGCTCAGGTCCCTCAAAGGCC
TCGGAGCACCCCCTTCCTTGTGACTGAGCCAGGGCCTGCATTTTTGGTTT
TCCCCACCCCACACATTCTCAACCATAGTCCTTCTAACAATACCAATAGCT
AGGACCCGGCTGCTGTGCACTGGGACTGGGGATTCCACATGTTTGCCTT
GGGAGTCTCAAGCTGGACTGCCAGCCCCTGTCCTCCCTTCACCCCCATT
GCGTATGAGCATTTCAGAACTCCAAGGAGTCACAGGCATCTTTATAGTTC
ACGTTAACATATAGACACTGTTGGAAGCAGTTCCTTCTAAAAGGGTAGCC
CTGGACTTAATACCAGCCGGATACCTCTGGCCCCCACCCCATTACTGTAC
CTCTGGAGTCACTACTGTGGGTCGCCACTCCTCTGCTACACAGCACGGC
TTTTTCAAGGCTGTATTGAGAAGGGAAGTTAGGAAGAAGGGTGTGCTGGG
CTAACCAGCCCACAGAGCTCACATTCCTGTCCCTTGGGTGAAAAATACAT
GTCCATCCTGATATCTCCTGAATTCAGAAATTAGCCTCCACATGTGCAATG
GCTTTAAGAGCCAGAAGCAGGGTTCTGGGAATTTTGCAAGTTACCTGTGG
CCAGGTGTGGTCTCGGTTACCAAATACGGTTACCTGCAGCTTTTTAGTCC
TTTGTGCTCCCACGGGTCTACAGAGTCCCATCTGCCCAAAGGTCTTGAAG
CTTGACAGGATGTTTTCGATTACTCAGTCTCCCAGGGCACTACTGGTCCG
TAGGATTCGATTGGTCGGGTAGGAGAGTTAAACAACATTTAAACAGAGT
TCTCTCAAAAATGTCTAAAGGGATTGTAGGTAGATAACATCCAATCACTGT
TTGCACTTATCTGAAATCTTTCCCTCTTGGCTGCCCCCAGGTATTTACTGTG
GAGAACATTGCATAGGAATGTCTGGAAAAAGCTTCTACAACTTGTTACAG
CCTTCACATTTGTAGAAGCTTT |
| 58 | COX8-ND4-3'UTR* | ATGTCCGTCCTGACGCGCCTGCTGCTGCGGGGCTTGACACGGCTCGGCT
CGGCGGCTCCAGTGCGGCGCGCCAGAATCCATTCGTTGATGCTAAAACT
AATCGTCCCAACAATTATGTTACTACCACTGACATGGCTTTCCAAAAAACA
CATGATTTGGATCAACACAACCACCCACAGCCTAATTATTAGCATCATCCC
TCTACTATTTTTTAACCAAATCAACAACAACCTATTTAGCTGTTCCCCAACC
TTTTCCTCCGACCCCCTAACAACCCCCCTCCTAATGCTAACTACCTGGCT
CCTACCCCTCACAATCATGGCAAGCCAACGCCACTTATCCAGTGAACCAC
TATCACGAAAAAAACTCTACCTCTCTATGCTAATCTCCCTACAAATCTCCTT
AATTATGACATTCACAGCCACAGAACTAATCATGTTTTATATCTTCTTCGAA
ACCACACTTATCCCCACCTTGGCTATCATCACCCGATGGGCAACCAGCC
AGAACGCCTGAACGCAGGCACATACTTCCTATTCTACACCCTAGTAGGCT
CCCTTCCCCTACTCATCGCACTAATTTACACTCACAACACCCTAGGCTCAC
TAAACATTCTACTACTCACTCTCACTGCCCAAGAACTATCAAACTCCTGGG
CCAACAACTTAATGTGGCTAGCTTACACAATGGCTTTTATGGTAAAGATGC
CTCTTTACGGACTCCACTTATGGCTCCCTAAAGCCCATGTCGAAGCCCCC
ATCGCTGGGTCAATGGTACTTGCCGCAGTACTCTTAAAACTAGGCGGCTA
TGGTATGATGCGCCTCACACTCATTCTCAACCCCCTGACAAAACACATGG
CCTACCCCTTCCTTGTACTATCCCTATGGGCATGATTATGACAAGCTCC
ATCTGCCTACGACAAACAGACCTAAAATCGCTCATTGCATACTCTTCAATC
AGCCACATGGCCCTCGTAGTAACAGCCATTCTCATCCAAACCCCCTGGAG
CTTCACCGGCGCAGTCATTCTCATGATCGCCCACGGGCTTACATCCTCAT
TACTATTCTGCCTAGCAAACTCAAACTACGAACGCACTCACAGTCGCATC
ATGATCCTCTCTCAAGGACTTCAAACTCTACTCCCACTAATGGCTTTTTGG
TGGCTTCTAGCAAGCCTCGCTAACCTCGCCTTACCCCCCACTATTAACCT
ACTGGGAGAACTCTCTGTGCTAGTAACCACGTTCTCCTGGTCAAATATCA
CTCTCCTACTTACAGGACTCAACATGCTAGTCACAGCCCTATACTCCCTCT
ACATGTTTACCACAACACAATGGGGCTCACTCACCCACCACATTAACAAC
ATGAAACCCTCATTCACACGAGAAAACACCCTCATGTTCATGCACCTATCC
CCCATTCTCCTCCTATCCCTCAACCCCGACATCATTACCGGGTTTTCCTCT
TAAGAGCACTGGGACGCCCACCGCCCCTTTCCCTCCGCTGCCAGGCGAG
CATGTTGTGGTAATTCTGGAACACAAGAAGAGAAATTGCTGGGTTTAGAA |

TABLE 1-continued nucleic acid and polypeptide sequences and SEQ ID NOs

| SEQ ID NO: | description | sequence |
|---|---|---|
| | | CAAGATTATAAACGAATTCGGTGCTCAGTGATCACTTGACAGTTTTTTTTT<br>TTTTAAATATTACCCAAAATGCTCCCCAAATAAGAAATGCATCAGCTCAGT<br>CAGTGAATACAAAAAAGGAATTATTTTTCCCTTTGAGGGTCTTTTATACATC<br>TCTCCTCCAACCCCACCCTCTATTCTGTTTCTTCCTCCTCACATGGGGGTA<br>CACATACACAGCTTCCTCTTTTGGTTCCATCCTTACCACCACACCACACGC<br>ACACTCCACATGCCCAGCAGAGTGGCACTTGGTGGCCAGAAAGTGTGAG<br>CCTCATGATCTGCTGTCTGTAGTTCTGTGAGCTCAGGTCCCTCAAAGGCC<br>TCGGAGCACCCCCTTCCTTGTGACTGAGCCAGGGCCTGCATTTTTGGTTT<br>TCCCCACCCCACACATTCTCAACCATAGTCCTTCTAACAATACCAATAGCT<br>AGGACCCGGCTGCTGTGCACTGGGACTGGGGATTCCACATGTTTGCCTT<br>GGGAGTCTCAAGCTGGACTGCCA |
| 59 | COX8-<br>opt_ND4-<br>3'UTR | ATGTCCGTCCTGACGCGCCTGCTGCTGCGGGGCTTGACACGGCTCGGCT<br>CGGCGGCTCCAGTGCGGCGCGCCAGAATCCATTCGTTGATGCTGAAGCT<br>GATCGTGCCCACCATCATGCTGCTGCCTCTGACCTGGCTGGCAGCAAGAAA<br>CACATGATCTGGATCAACACCACCACGCACAGCCTGATCATCAGCATCAT<br>CCCTCTGCTGTTCTTCAACCAGATCAACAACAACCTGTTCAGCTGCAGCC<br>CCACCTTCAGCAGCGACCCTCTGACAACACCTCTGCTGATGCTGACCACC<br>TGGCTGCTGCCCCTCACAATCATGGCCTCTCAGAGACACCTGAGCAGCG<br>AGCCCCTGAGCCGGAAGAAACTGTACCTGAGCATGCTGATCTCCCTGCA<br>GATCCTCTCTGATCATGACCTTCACCGCCACCGAGCTGATCATGTTCTACA<br>TCTTTTTCGAGACAACGCTGATCCCCACACTGGCCATCATCACCAGATGG<br>GGCAACCAGCCTGAGAGACTGAACGCCGGCACCTACTTTCTGTTCTACAC<br>CCTCGTGGGCAGCCTGCCACTGCTGATTGCCCTGATCTACACCCACAAC<br>ACCCTGGGCTCCTGAACATCCTGCTGCTGACACTGACAGCCCAAGAGC<br>TGAGCAACAGCTGGGCCAACAATCTGATGTGGCTGGCCTACACAATGGC<br>CTTCATGGTCAAGATGCCCCTGTACGGCCTGCACCTGTGGCTGCCTAAA<br>GCTCATGTGGAAGCCCCTATCGCCGGCTCTATGGTGCTGGCTGCAGTGC<br>TGCTGAAACTCGGCGGCTACGGCATGATGCGGCTGACCCTGATTCTGAA<br>TCCCCTGACCAAGCACATGGCCTATCCATTTCTGGTGCTGAGCCTGTGGG<br>GCATGATTATGACCAGCAGCATCTGCCTGCGGCAGACCGATCTGAAGTC<br>CCTGATCGCCTACAGCTCCATCAGCCACATGGCCCTGGTGGTCACCGCC<br>ATCCTGATTCAGACCCCTTGGAGCTTTACAGGCGCCGTGATCCTGATGAT<br>TGCCCACGGCCTGACAAGCAGCCTGCTGTTTTGTCTGGCCAACAGCAAC<br>TACGAGCGGACCCACAGCAGAATCATGATCCTGTCTCAGGGCCTGCAGA<br>CCCTCCTGCCTCTTATGGCTTTTTGGTGGCTGCTGGCCTCTCTGGCCAAT<br>CTGGCACTGCCTCCTACCATCAATCTGCTGGGCGAGCTGAGCGTGCTGG<br>TCACCACATTCAGCTGGTCCAATATCACCCTGCTGCTCACCGGCCTGAAC<br>ATGCTGGTTACAGCCCTGTACTCCCTGTACATGTTCACCACCACACAGTG<br>GGGAAGCCTGACACACCACATCAACAATATGAAGCCCAGCTTCACCCGC<br>GAGAACACCCTGATGTTCATGCATCTGAGCCCCATTCTGCTGCTGTCCCT<br>GAATCCTGATATCATCACCGGCTTCTCCAGCTGAGAGCACTGGGACGCC<br>CACCGCCCCTTTCCCTCCGCTGCCAGGCGAGCATGTTGTGGTAATTCTG<br>GAACACAAGAAGAGAAATTGCTGGGTTTAGAACAAGATTATAAACGAATT<br>CGGTGCTCAGTGATCACTTGACAGTTTTTTTTTTTTAAATATTACCCAAA<br>ATGCTCCCCAAATAAGAAATGCATCAGCTCAGTCAGTGAATACAAAAAAG<br>GAATTATTTTTCCCTTTGAGGGTCTTTTATACATCTCTCCTCCAACCCCAC<br>CCTCTATTCTGTTTCTTCCTCCTCACATGGGGGTACACATACACAGCTTCC<br>TCTTTTGGTTCCATCCTTACCACCACACCACACGCACACTCCACATGCCC<br>AGCAGAGTGGCACTTGGTGGCCAGAAAGTGTGAGCCTCATGATCTGCTG<br>TCTGTAGTTCTGTGAGCTCAGGTCCCTCAAAGGCCTCGGAGCACCCCCTT<br>CCTTGTGACTGAGCCAGGGCCTGCATTTTTGGTTTTCCCCACCCCACACA<br>TTCTCAACCATAGTCCTTCTAACAATACCAATAGCTAGGACCCGGCTGCT<br>GTGCACTGGGACTGGGGATTCCACATGTTTGCCTTGGGAGTCTCAAGCT<br>GGACTGCCAGCCCCTGTCCTCCCTTCACCCCCATTGCGTATGAGCATTTC<br>AGAACTCCAAGGAGTCACAGGCATCTTTATAGTTCACGTTAACATATAGAC<br>ACTGTTGGAAGCAGTTCCTTCTAAAAGGGTAGCCCTGGACTTAATACCAG<br>CCGGATACCTCTGGCCCCCACCCCATTACTGTACCTCTGGAGTCACTACT<br>GTGGGTCGCCACTCCTCTGCTACACAGCACGGCTTTTTCAAGGCTGTATT<br>GAGAAGGGAAGTTAGGAAGAAGGGTGTGCGGGCTAACCAGCCCACAGA<br>GCTCACATTCCTGTCCCTTGGGTGAAAAATACATGTCCATCCTGATATCTC<br>CTGAATTCAGAAATTAGCCTCCACATGTGCAATGGCTTTAAGAGCCAGAA<br>GCAGGGTTCTGGGAATTTTGCAAGTTACCTGTGGCCAGGTGTGGTCTCG<br>GTTACCAAATACGGTTACCTGCAGCTTTTTAGTCCTTTGTGCTCCCACGG<br>GTCTACAGAGTCCCATCTGCCCAAGGTCTTGAAGCTTGACAGGATGTTT<br>TCGATTACTCAGTCTCCCAGGGCACTACTGGTCCGTAGGATTCGATTGGT<br>CGGGGTAGGAGAGTTAAACAACATTTAAACAGAGTTCTCTCAAAAATGTCT<br>AAAGGGATTGTAGGTAGATAACATCCAATCACTGTTTGCACTTATCTGAAA<br>TCTTCCCTCTTGGCTGCCCCCAGGTATTTACTGTGGAGAACATTGCATAG<br>GAATGTCTGGAAAAAGCTTCTACAACTTGTTACAGCCTTCACATTTGTAGA<br>AGCTTT |

TABLE 1-continued nucleic acid and polypeptide sequences and SEQ ID NOs

| SEQ ID NO: | description | sequence |
|---|---|---|
| 60 | COX8-opt_ND4-3'UTR* | ATGTCCGTCCTGACGCGCCTGCTGCTGCGGGGCTTGACACGGCTCGGCT<br>CGGCGGCTCCAGTGCGGCGCGCCAGAATCCATTCGTTGATGCTGAAGCT<br>GATCGTGCCCACCATCATGCTGCTGCCTCTGACCTGGCTGAGCAAGAAA<br>CACATGATCTGGATCAACACCACCACGCACAGCCTGATCATCAGCATCAT<br>CCCTCTGCTGTTCTTCAACCAGATCAACAACAACCTGTTCAGCTGCAGCC<br>CCACCTTCAGCAGCGACCCTCTGACAACACCTCTGCTGATGCTGACCACC<br>TGGCTGCTGCCCCTCACAATCATGGCCTCTCAGAGACACCTGAGCAGCG<br>AGCCCCTGAGCCGGAAGAAACTGTACCTGAGCATGCTGATCTCCCTGCA<br>GATCTCTCTGATCATGACCTTCACCGCCACCGAGCTGATCATGTTCTACA<br>TCTTTTTCGAGACAACGCTGATCCCCACACTGGCCATCATCACCAGATGG<br>GGCAACCAGCCTGAGAGACTGAACGCCGGCACCTACTTTCTGTTCTACAC<br>CCTCGTGGGCAGCCTGCCACTGCTGATTGCCCTGATCTACACCCACAAC<br>ACCCTGGGCTCCCTGAACATCCTGCTGCTGACACTGACAGCCCAAGAGC<br>TGAGCAACAGCTGGGCCAACAATCTGATGTGGCTGGCCTACACAATGGC<br>CTTCATGGTCAAGATGCCCCTGTACGGCCTGCACCTGTGGCTGCCTAAA<br>GCTCATGTGGAAGCCCCTATCGCCGGCTCTATGGTGCTGGCTGCAGTGC<br>TGCTGAAACTCGGCGGCTACGGCATGATGCGGCTGACCCTGATTCTGAA<br>TCCCCTGACCAAGCACATGGCCTATCCATTTCTGGTGCTGAGCCTGTGGG<br>GCATGATTATGACCAGCAGCATCTGCCTGCGGCAGACCGATCTGAAGTC<br>CCTGATCGCCTACAGCTCCATCAGCCACATGGGCCCTGGTGGTCACCGCC<br>ATCCTGATTCAGACCCCTTGGAGCTTTACAGGCGCCGTGATCCTGATGAT<br>TGCCCACGGCCTGACAAGCAGCCTGCTGTTTTGTCTGGCCAACAGCAAC<br>TACGAGCGGACCCACAGCAGAATCATGATCCTGTCTCAGGGCCTGCAGA<br>CCCTCCTGCCTCTTATGGCTTTTTGGTGGCTGCTGGCCTCTCTGGCCAAT<br>CTGGCACTGCCTCCTACCATCAATCTGCTGGGCGAGCTGAGCGTGCTGG<br>TCACCACATTCAGCTGGTCCAATATCACCCTGCTGCTCACCGGCCTGAAC<br>ATGCTGGTTACAGCCCTGTACTCCCTGTACATGTTCACCACCACACAGTG<br>GGGAAGCCTGACACACCCACATCAACAATATGAAGCCCAGCTTCACCCGC<br>GAGAACACCCTGATGTTCATGCATCTGAGCCCCATTCTGCTGCTGTCCCT<br>GAATCCTGATATCATCACCGGCTTCTCCAGCTGAGAGCACTGGGACGCC<br>CACCGCCCCTTTCCCTCCGCTGCCAGGCGAGCATGTTGTGGTAATTCTG<br>GAACACAAGAAGAGAAATTGCTGGGTTTAGAACAAGATTATAAACGAATT<br>CGGTGCTCAGTGATCACTTGACAGTTTTTTTTTTTTAAATATTACCCAAA<br>ATGCTCCCAAATAAGAAATGCATCAGCTCAGTCAGTAATACAAAAAAG<br>GAATTATTTTTCCCTTTGAGGGTCTTTTATACATCTCTCCTCCAACCCCAC<br>CCTCTATTCTGTTTCTTCCTCCTCACATGGGGTACACATACACAGCTTCC<br>TCTTTTGGTTCCATCCTTACCACCACACCACACGCACACTCCACATGCCC<br>AGCAGAGTGGCACTTGGTGGCCAGAAAGTGTGAGCCTCATGATCTGCTG<br>TCTGTAGTTCTGTGAGCTCAGGTCCCTCAAAGGCCTCGGAGCACCCCCTT<br>CCTTGTGACTGAGCCAGGGCCTGCATTTTTGGTTTTCCCCACCCCACACA<br>TTCTCAACCATAGTCCTTCTAACAATACCAATAGCTAGGACCCGGCTGCT<br>GTGCACTGGGACTGGGGATTCCACATGTTTGCCTTGGGAGTCTCAAGCT<br>GGACTGCCA |
| 61 | COX8-opt_ND4*-3'UTR | ATGTCCGTCCTGACGCGCCTGCTGCTGCGGGGCTTGACACGGCTCGGCT<br>CGGCGGCTCCAGTGCGGCGCGCCAGAATCCATTCGTTGATGCTGAAGCT<br>GATCGTGCCCACCATCATGCTGCTGCCCCTGACCTGGCTGAGCAAGAAG<br>CACATGATCTGGATCAACAGCACCACCCACAGCCTGATCATCAGCATCAT<br>CCCCCTGCTGTTCTTCAACCAGATCAACAACAACCTGTTCAGCTGCAGCC<br>CCACCTTCAGCAGCGACCCCCTGACCACCCCCTGCTGATGCTGACCAC<br>CTGGCTGCTGCCCCTGACCATCATGGCCAGCCAGCGCCACCTGAGCAGC<br>GAGCCCCTGAGCCGCAAGAAGCTGTACCTGAGCATGCTGATCAGCCTGC<br>AGATCAGCCTGATCATGACCTTCACCGCCACCGAGCTGATCATGTTCTAC<br>ATCTTCTTCGAGACCACCCTGATCCCCACCCTGGCCATCATCACCCGCTG<br>GGGCAACCAGCCCGAGCGCCTGAACGCCGGCACCTACTTCCTGTTCTAC<br>ACCCTGGTGGGCAGCCTGCCCCTGCTGATCGCCCTGATCTACACCCACA<br>ACACCCTGGGCAGCCTGAACATCCTGCTGCTGACCCTGACCGCCCAGGA<br>GCTGAGCAACAGCTGGGCCAACAACCTGATGTGGCTGGCCTACACCATG<br>GCCTTCATGGTGAAGATGCCCCTGTACGCCCTGCACCTGTGGCTGCCCA<br>AGGCCCACGTGGAGGCCCCATCGCCGGCAGCATGGTGCTGGCCGCCG<br>TGCTGCTGAAGCTGGGCGGCTACGGCATGATGCGCCTGACCCTGATCCT<br>GAACCCCCTGACCAAGCACATGGCCTACCCCTTCCTGGTGCTGAGCCTG<br>TGGGGCATGATCATGACCAGCAGCATCTGCCTGCGCCAGACCGACCTGA<br>AGAGCCTGATCGCCTACAGCAGCATCAGCCACATGGGCCCTGGTGGTGAC<br>CGCCATCCTGATCCAGACCCCCTGGAGCTTCACCGGCGCCGTGATCCTG<br>ATGATCGCCCACGGCCTGACCAGCAGCCTGCTGTTCTGCCTGGCCAACA<br>GCAACTACGAGCGCACCCACAGCCGCATCATGATCCTGAGCCAGGGCCT<br>GCAGACCCTGCTGCCCCTGATGGCCTTCTGGTGGCTGCTGGCCAGCCTG<br>GCCAACCTGGCCCTGCCCCCCACCATCAACCTGCTGGGCGAGCTGAGC<br>GTGCTGGTGACCACCTTCAGCTGGAGCAACATCACCCTGCTGCTGACCG<br>GCCTGAACATGCTGGTGACCGCCCTGTACAGCCTGTACATGTTCACCACC<br>ACCCAGTGGGGCAGCCTGACCCACCACATCAACAACATGAAGCCCAGCT<br>TCACCCGCGAGAACACCCTGATGTTCATGCACCTGAGCCCCATCCTGCT<br>GCTGAGCCTGAACCCCGACATCATCACCGGCTTCAGCAGCTAAGAGCAC |

TABLE 1-continued nucleic acid and polypeptide sequences and SEQ ID NOs

| SEQ ID NO: | description | sequence |
|---|---|---|
| | | TGGGACGCCCACCGCCCCTTTCCCTCCGCTGCCAGGCGAGCATGTTGTG
GTAATTCTGGAACACAAGAAGAGAAATTGCTGGGTTTAGAACAAGATTATA
AACGAATTCGGTGCTCAGTGATCACTTGACAGTTTTTTTTTTTTTAAATAT
TACCCAAAATGCTCCCCAAATAAGAAATGCATCAGCTCAGTCAGTGAATA
CAAAAAAGGAATTATTTTTCCCTTTGAGGGTCTTTTATACATCTCTCCTCCA
ACCCCACCCTCTATTCTGTTTCTTCCTCCTCACATGGGGGTACACATACAC
AGCTTCCTCTTTTGGTTCCATCCTTACCACCACACCACACGCACACTCCA
CATGCCCAGCAGAGTGGCACTTGGTGGCCAGAAAGTGTGAGCCTCATGA
TCTGCTGTCTGTAGTTCTGTGAGCTCAGGTCCCTCAAAGGCCTCGGAGCA
CCCCCTTCCTTGTGACTGAGCCAGGGCCTGCATTTTTGGTTTTCCCCACC
CCACACATTCTCAACCATAGTCCTTCTAACAATACCAATAGCTAGGACCCG
GCTGCTGTGCACTGGGACTGGGGATTCCACATGTTTGCCTTGGGAGTCT
CAAGCTGGACTGCCAGCCCCTGTCCTCCCTTCACCCCCATTGCGTATGA
GCATTTCAGAACTCCAAGGAGTCACAGGCATCTTTATAGTTCACGTTAACA
TATAGACACTGTTGGAAGCAGTTCCTTCTAAAAGGGTAGCCCTGGACTTA
ATACCAGCCGGATACCTCGGCCCCCACCCCATTACTGTACCTCTGGAGT
CACTACTGTGGGTCGCCACTCCTCTGCTACACAGCACGGCTTTTTCAAGG
CTGTATTGAGAAGGGAAGTTAGGAAGAAGGGTGTGCTGGGCTAACCAGC
CCACAGAGCTCACATTCCTGTCCCTTGGGTGAAAAATACATGTCCATCCT
GATATCTCCTGAATTCAGAAATTAGCCTCCACATGTGCAATGGCTTTAAGA
GCCAGAAGCAGGGTTCTGGGAATTTTGCAAGTTACCTGTGGCCAGGTGT
GGTCTCGGTTACCAAATACGGTTACCTGCAGCTTTTTAGTCCTTTGTGCTC
CCACGGGTCTACAGAGTCCCATCTGCCCAAAGGTCTTGAAGCTTGACAG
GATGTTTTCGATTACTCAGTCTCCCAGGGCACTACTGGTCCGTAGGATTC
GATTGGTCGGGTAGGAGAGTTAAACAACATTTAAACAGAGTTCTCTCAA
AAATGTCTAAAGGGATTGTAGGTAGATAACATCCAATCACTGTTTGCACTT
ATCTGAAATCTTCCCTCTTGGCTGCCCCAGGTATTTACTGTGGAGAACA
TTGCATAGGAATGTCTGGAAAAAGCTTCTACAACTTGTTACAGCCTTCACA
TTTGTAGAAGCTTT |
| 62 | COX8-opt_ND4*-3'UTR* | ATGTCCGTCCTGACGCGCCTGCTGCTGCGGGGCTTGACACGGCTCGGCT
CGGCGGCTCCAGTGCGGCGCGCCAGAATCCATTCGTTGATGCTGAAGCT
GATCGTGCCCACCATCATGCTGCTGCCCCTGACCTGGCTGAGCAAGAAG
CACATGATCTGGATCAACACCACCACCCACAGCCTGATCATCAGCATCAT
CCCCCTGCTGTTCTTCAACCAGATCAACAACAACCTGTTCAGCTGCAGCC
CCACCTTCAGCAGCGACCCCCTGACCACCCCCCTGCTGATGCTGACCAC
CTGGCTGCTGCCCCTGACCATCATGGGCCAGCAGCGCCACCTGAGCAGC
GAGCCCCTGAGCCGCAAGAAGCTGTACCTGAGCATGCTGATCAGCCTGC
AGATCAGCCTGATCATGACCTTCACCGCCACCGAGCTGATCATGTTCTAC
ATCTTCTTCGAGACCACCCTGATCCCCACCCTGGCCATCATCACCCGCTG
GGGCAACCAGCCCGAGCGCCTGAACGCCGGCACCTACTTCCTGTTCTAC
ACCCTGGTGGGCAGCCTGCCCCTGCTGATCGCCCTGATCTACACCCACA
ACACCCTGGGCAGCCTGAACATCCTGCTGCTGACCCTGACCGCCCAGGA
GCTGAGCAACAGCTGGGCCAACAACCTGATGTGGCTGGCCTACACCATG
GCCTTCATGGTGAAGATGCCCCTGTACGGCCTGCACCTGTGGCTGCCCA
AGGCCCACGTGGAGGCCCCCATCGCCGGCAGCATGGTGCTGGCCGCCG
TGCTGCTGAAGCTGGGCGGCTACGGCATGATGCGCCTGACCCTGATCCT
GAACCCCCTGACCAAGCACATGGCCTACCCCTTCCTGGTGCTGAGCCTG
TGGGGCATGATCATGACCAGCAGCATCTGCCTGCGCCAGACCGACCTGA
AGAGCCTGATCGCCTACAGCAGCATCAGCCACATGGCCCTGGTGGTGAC
CGCCATCCTGATCCAGACCCCCTGGAGCTTCACCGGCGCCGTGATCCTG
ATGATCGCCCACGGCCTGACCAGCAGCCTGCTGTTCTGCCTGGCCAACA
GCAACTACGAGCGCACCCACAGCCGCATCATGATCCTGAGCCAGGGCCT
GCAGACCCTGCTGCCCCTGATGGCCTTCTGGTGGCTGCTGGCCAGCCTG
GCCAACCTGGCCCTGCCCCCCACCATCAACCTGCTGGGCGAGCTGAGC
GTGCTGGTGACCACCTTCAGCTGGAGCAACATCACCCTGCTGCTGACCG
GCCTGAACATGCTGGTGACCGCCCCTGTACAGCCTGTACATGTTCACCACC
ACCCAGTGGGGCAGCCTGACCCACCCACATCAACAACATGAAGCCCAGCT
TCACCCGCGAGAACACCCTGATGTTCATGCACCTGAGCCCCATCCTGCT
GCTGAGCCTGAACCCCGACATCATCACCGGCTTCAGCAGCTAAGAGCAC
TGGGACGCCCACCGCCCCTTTCCCTCCGCTGCCAGGCGAGCATGTTGTG
GTAATTCTGGAACACAAGAAGAGAAATTGCTGGGTTTAGAACAAGATTATA
AACGAATTCGGTGCTCAGTGATCACTTGACAGTTTTTTTTTTTTTAAATAT
TACCCAAAATGCTCCCCAAATAAGAAATGCATCAGCTCAGTCAGTGAATA
CAAAAAAGGAATTATTTTTCCCTTTGAGGGTCTTTTATACATCTCTCCTCCA
ACCCCACCCTCTATTCTGTTTCTTCCTCCTCACATGGGGGTACACATACAC
AGCTTCCTCTTTTGGTTCCATCCTTACCACCACACCACACGCACACTCCA
CATGCCCAGCAGAGTGGCACTTGGTGGCCAGAAAGTGTGAGCCTCATGA
TCTGCTGTCTGTAGTTCTGTGAGCTCAGGTCCCTCAAAGGCCTCGGAGCA
CCCCCTTCCTTGTGACTGAGCCAGGGCCTGCATTTTTGGTTTTCCCCACC
CCACACATTCTCAACCATAGTCCTTCTAACAATACCAATAGCTAGGACCCG
GCTGCTGTGCACTGGGACTGGGGATTCCACATGTTTGCCTTGGGAGTCT
CAAGCTGGACTGCCA |

TABLE 1-continued nucleic acid and polypeptide sequences and SEQ ID NOs

| SEQ ID NO: | description | sequence |
|---|---|---|
| 63 | COX8-ND6-3'UTR | ATGTCCGTCCTGACGCGCCTGCTGCTGCGGGGCTTGACACGGCTCGGCT<br>CGGCGGCTCCAGTGCGGCGCGCCAGAATCCATTCGTTGATGATGTATGC<br>TTTGTTTCTGTTGAGTGTGGGTTTAGTAATGGGGTTTGTGGGGTTTTCTTC<br>TAAGCCTTCTCCTATTTATGGGGGTTTAGTATTGATTGTTAGCGGTGTGGT<br>CGGGTGTGTTATTATTCTGAATTTTGGGGGAGGTTATATGGGTTTAATGGT<br>TTTTTTAATTTATTTAGGGGGAATGATGGTTGTCTTTGGATATACTACAGC<br>GATGGCTATTGAGGAGTATCCTGAGGCATGGGGGTCAGGGGTTGAGGTC<br>TTGGTGAGTGTTTTAGTGGGGTTAGCGATGGAGGTAGGATTGGTGCTGT<br>GGGTGAAAGAGTATGATGGGGTGGTGGTTGTGGTAAACTTTAATAGTGTA<br>GGAAGCTGGATGATTTATGAAGGAGAGGGGTCAGGGTTGATTCGGGAGG<br>ATCCTATTGGTGCGGGGGCTTTGTATGATTATGGGCGTTGGTTAGTAGTA<br>GTTACTGGTTGGACATTGTTTGTTGGTGTATATATTGTAATTGAGATTGCT<br>CGGGGGAATTAGGAGCACTGGGACGCCCACCGCCCCTTTCCCTCCGCTG<br>CCAGGCGAGCATGTTGTGGTAATTCTGGAACACAAGAAGAGAAATTGCTG<br>GGTTTAGAACAAGATTATAAACGAATTCGGTGCTCAGTGATCACTTGACA<br>GTTTTTTTTTTTTAAATATTACCCAAAATGCTCCCCAAATAAGAAATGCA<br>TCAGCTCAGTCAGTGAATACAAAAAAGGAATTATTTTTCCCTTTGAGGGTC<br>TTTTTATACATCTCTCCTCCAACCCCACCCTCTATTCTGTTTCTTCCTCCTCA<br>CATGGGGGTACACATACACAGCTTCCTCTTTTGGTTCCATCCTTACCACC<br>ACACCACACGCACACTCCACATGCCCAGCAGAGTGGCACTTGGTGGCCA<br>GAAAGTGTGAGCCTCATGATCTGCTGTCTGTAGTTCTGTGAGCTCAGGTC<br>CCTCAAAGGCCTCGGAGCACCCCCTTCCTTGTGACTGAGCCAGGGCCTG<br>CATTTTTGGTTTTCCCCACCCCACACATTCTCAACCATAGTCCTTCTAACA<br>ATACCAATAGCTAGGACCCGGCTGCTGTGCACTGGGACTGGGGATTCCA<br>CATGTTTGCCTTGGGAGTCTCAAGCTGGACTGCCAGCCCCTGTCCTCCCT<br>TCACCCCCATTGCGTATGAGCATTTCAGAACTCCAAGGAGTCACAGGCAT<br>CTTTATAGTTCACGTTAACATATAGACACTGTTGGAAGCAGTTCCTTCTAA<br>AAGGGTAGCCCTGGACTTAATACCAGCCGGATACCTCTGGCCCCCACCC<br>CATTACTGTACCTCTGGAGTCACTACTGTGGGTCGCCACTCCTCTGCTAC<br>ACAGCACGGCTTTTTCAAGGCTGTATTGAGAAGGGAAGTTAGGAAGAAGG<br>GTGTGCTGGGCTAACCAGCCCACAGAGCTCACATTCCTGTCCCTTGGGT<br>GAAAAATACATGTCCATCCTGATATCTCCTGAATTCAGAAATTAGCCTCCA<br>CATGTGCAATGGCTTTAAGAGCCAGAAGCAGGGTTCTGGGAATTTTGCAA<br>GTTACCTGTGGCCAGGTGTGGTCTCGGTTACCAAATACGGTTACCTGCAG<br>CTTTTTTAGTCCTTTGTGCTCCCACGGGTCTACAGAGTCCCATCTGCCCAA<br>AGGTCTTGAAGCTTGACAGGATGTTTTCGATTACTCAGTCTCCCAGGGCA<br>CTACTGGTCCGTAGGATTCGATTGGTCGGGGTAGGAGAGTTAAACAACAT<br>TTAAACAGAGTTCTCTCAAAAATGTCTAAAGGGATTGTAGGTAGATAACAT<br>CCAATCACTGTTTGCACTTATCTGAAATCTTCCCTCTTGGCTGCCCCCAG<br>GTATTTACTGTGGAGAACATTGCATAGGAATGTCTGGAAAAAGCTTCTACA<br>ACTTGTTACAGCCTTCACATTTGTAGAAGCTTT |
| 64 | COX8-ND6-3'UTR* | ATGTCCGTCCTGACGCGCCTGCTGCTGCGGGGCTTGACACGGCTCGGCT<br>CGGCGGCTCCAGTGCGGCGCGCCAGAATCCATTCGTTGATGATGTATGC<br>TTTGTTTCTGTTGAGTGTGGGTTTAGTAATGGGGTTTGTGGGGTTTTCTTC<br>TAAGCCTTCTCCTATTTATGGGGGTTTAGTATTGATTGTTAGCGGTGTGGT<br>CGGGTGTGTTATTATTCTGAATTTTGGGGGAGGTTATATGGGTTTAATGGT<br>TTTTTTAATTTATTTAGGGGGAATGATGGTTGTCTTTGGATATACTACAGC<br>GATGGCTATTGAGGAGTATCCTGAGGCATGGGGGTCAGGGGTTGAGGTC<br>TTGGTGAGTGTTTTAGTGGGGTTAGCGATGGAGGTAGGATTGGTGCTGT<br>GGGTGAAAGAGTATGATGGGGTGGTGGTTGTGGTAAACTTTAATAGTGTA<br>GGAAGCTGGATGATTTATGAAGGAGAGGGGTCAGGGTTGATTCGGGAGG<br>ATCCTATTGGTGCGGGGGCTTTGTATGATTATGGGCGTTGGTTAGTAGTA<br>GTTACTGGTTGGACATTGTTTGTTGGTGTATATATTGTAATTGAGATTGCT<br>CGGGGGAATTAGGAGCACTGGGACGCCCACCGCCCCTTTCCCTCCGCTG<br>CCAGGCGAGCATGTTGTGGTAATTCTGGAACACAAGAAGAGAAATTGCTG<br>GGTTTAGAACAAGATTATAAACGAATTCGGTGCTCAGTGATCACTTGACA<br>GTTTTTTTTTTTTAAATATTACCCAAAATGCTCCCCAAATAAGAAATGCA<br>TCAGCTCAGTCAGTGAATACAAAAAAGGAATTATTTTTCCCTTTGAGGGTC<br>TTTTTATACATCTCTCCTCCAACCCCACCCTCTATTCTGTTTCTTCCTCCTCA<br>CATGGGGGTACACATACACAGCTTCCTCTTTTGGTTCCATCCTTACCACC<br>ACACCACACGCACACTCCACATGCCCAGCAGAGTGGCACTTGGTGGCCA<br>GAAAGTGTGAGCCTCATGATCTGCTGTCTGTAGTTCTGTGAGCTCAGGTC<br>CCTCAAAGGCCTCGGAGCACCCCCTTCCTTGTGACTGAGCCAGGGCCTG<br>CATTTTTGGTTTTCCCCACCCCACACATTCTCAACCATAGTCCTTCTAACA<br>ATACCAATAGCTAGGACCCGGCTGCTGTGCACTGGGACTGGGGATTCCA<br>CATGTTTGCCTTGGGAGTCTCAAGCTGGACTGCCA |
| 65 | COX8-opt_ND6-3'UTR | ATGTCCGTCCTGACGCGCCTGCTGCTGCGGGGCTTGACACGGCTCGGCT<br>CGGCGGCTCCAGTGCGGCGCGCCAGAATCCATTCGTTGATGATGTACGC<br>CCTGTTCCTGCTGAGCGTGGGCCTGGTGATGGGCTTCGTGGGCTTCAGC<br>AGCAAGCCCAGCCCCATCTACGGCGGCCTGGTGCTGATCGTGAGCGGC<br>GTGGTGGGCTGCGTGATCATCCTGAACTTCGGCGGCGGCTACATGGGCC<br>TGATGGTGTTCCTGATCTACCTGGGCGGCATGATGGTGGTGTTCGGCTA |

TABLE 1-continued nucleic acid and polypeptide sequences and SEQ ID NOs

| SEQ ID NO: | description | sequence |
|---|---|---|
| | | CACCACCGCCATGGCCATCGAGGAGTACCCCGAGGCCTGGGGCAGCGG<br>CGTGGAGGTGCTGGTGAGCGTGCTGGTGGGCCTGGCCATGGAGGTGGG<br>CCTGGTGCTGTGGGTGAAGGAGTACGACGGCGTGGTGGTGGTGGTGAA<br>CTTCAACAGCGTGGGCAGCTGGATGATCTACGAGGGCGAGGGCAGCGG<br>CCTGATCCGCGAGGACCCCATCGGCGCCGGCGCCCTGTACGACTACGG<br>CCGCTGGCTGGTGGTGGTGACCGGCTGGACCCTGTTCGTGGGCGTGTA<br>CATCGTGATCGAGATCGCCCGCGGCAACTAAGAGCACTGGGACGCCCAC<br>CGCCCCTTTCCCTCCGCTGCCAGGCGAGCATGTTGTGGTAATTCTGGAA<br>CACAAGAAGAGAAATTGCTGGGTTTAGAACAAGATTATAAACGAATTCGG<br>TGCTCAGTGATCACTTGACAGTTTTTTTTTTTTAAATATTACCCAAAATG<br>CTCCCCAAATAAGAAATGCATCAGCTCAGTCAGTGAATACAAAAAAGGAA<br>TTATTTTTCCCTTTGAGGGTCTTTTATACATCTCTCCTCCAACCCCACCCT<br>CTATTCTGTTTCTTCCTCCTCACATGGGGGTACACATACACAGCTTCCTCT<br>TTTGGTTCCATCCTTACCACCACACCACACGCACACTCCACATGCCCAGC<br>AGAGTGGCACTTGGTGGCCAGAAAGTGTGAGCCTCATGATCTGCTGTCT<br>GTAGTTCTGTGAGCTCAGGTCCCTCAAAGGCCTCGGAGCACCCCCTTCC<br>TTGTGACTGAGCCAGGGCCTGCATTTTTGGTTTTCCCCACCCCACACATT<br>CTCAACCATAGTCCTTCTAACAATACCAATAGCTAGGACCCGGCTGCTGT<br>GCACTGGGACTGGGGATTCCACATGTTTGCCTTGGGAGTCTCAAGCTGG<br>ACTGCCAGCCCCTGTCCTCCCTTCACCCCCATTGCGTATGAGCATTTCAG<br>AACTCCAAGGAGTCACAGGCATCTTTATAGTTCACGTTAACATATAGACAC<br>TGTTGGAAGCAGTTCCTTCTAAAAGGGTAGCCCTGGACTTAATACCAGCC<br>GGATACCTCTGGCCCCCACCCCATTACTGTACCTCTGGAGTCACTACTGT<br>GGGTCGCCACTCCTCTGCTACACAGCACGGCTTTTTCAAGGCTGTATTGA<br>GAAGGGAAGTTAGGAAGAAGGGTGTGCTGGGCTAACCAGCCCACAGAG<br>CTCACATTCCTGTCCCTTGGGTGAAAAATACATGTCCATCCTGATATCTCC<br>TGAATTCAGAAATTAGCCTCCACATGTGCAATGGCTTTAAGAGCCAGAAG<br>CAGGGTTCTGGGAATTTTGCAAGTTACCTGTGGCCAGGTGTGGTCTCGGT<br>TACCAAATACGGTTACCTGCAGCTTTTTAGTCCTTTGTGCTCCCACGGGT<br>CTACAGAGTCCCATCGCCCAAAGGTCTTGAAGCTTGACAGGATGTTTTC<br>GATTACTCAGTCTCCCAGGGCACTACTGGTCCGTAGGATTCGATTGGTCG<br>GGGTAGGAGAGTTAAACAACATTTAAACAGAGTTCTCTCAAAAATGTCTAA<br>AGGGATTGTAGGTAGATAACATCCAATCACTGTTTGCACTTATCTGAAATC<br>TTCCCTCTTGGCTGCCCCCAGGTATTTACTGTGGAGAACATTGCATAGGA<br>ATGTCTGGAAAAAGCTTCTACAACTTGTTACAGCCTTCACATTTGTAGAAG<br>CTTT |
| 66 | COX8-<br>opt_ND6-<br>3'UTR* | ATGTCCGTCCTGACGCGCCTGCTGCTGCGGGGCTTGACACGGCTCGGCT<br>CGGCGGCTCCAGTGCGGCGCGCCAGAATCCATTCGTTGATGATGTACGC<br>CCTGTTCCTGCTGAGCGTGGGCCTGGTGATGGGCTTCGTGGGCTTCAGC<br>AGCAAGCCCAGCCCCATCTACGGCGGCCTGGTGCTGATCGTGAGCGGC<br>GTGGTGGGCTGCGTGATCATCCTGAACTTCGGCGGCGGCTACATGGGCC<br>TGATGGTGTTCCTGATCTACCTGGGCGGCATGATGGTGGTGTTCGGCTA<br>CACCACCGCCATGGCCATCGAGGAGTACCCCGAGGCCTGGGGCAGCGG<br>CGTGGAGGTGCTGGTGAGCGTGCTGGTGGGCCTGGCCATGGAGGTGGG<br>CCTGGTGCTGTGGGTGAAGGAGTACGACGGCGTGGTGGTGGTGGTGAA<br>CTTCAACAGCGTGGGCAGCTGGATGATCTACGAGGGCGAGGGCAGCGG<br>CCTGATCCGCGAGGACCCCATCGGCGCCGGCGCCCTGTACGACTACGG<br>CCGCTGGCTGGTGGTGGTGACCGGCTGGACCCTGTTCGTGGGCGTGTA<br>CATCGTGATCGAGATCGCCCGCGGCAACTAAGAGCACTGGGACGCCCAC<br>CGCCCCTTTCCCTCCGCTGCCAGGCGAGCATGTTGTGGTAATTCTGGAA<br>CACAAGAAGAGAAATTGCTGGGTTTAGAACAAGATTATAAACGAATTCGG<br>TGCTCAGTGATCACTTGACAGTTTTTTTTTTTTAAATATTACCCAAAATG<br>CTCCCCAAATAAGAAATGCATCAGCTCAGTCAGTGAATACAAAAAAGGAA<br>TTATTTTTCCCTTTGAGGGTCTTTTATACATCTCTCCTCCAACCCCACCCT<br>CTATTCTGTTTCTTCCTCCTCACATGGGGGTACACATACACAGCTTCCTCT<br>TTTGGTTCCATCCTTACCACCACACCACACGCACACTCCACATGCCCAGC<br>AGAGTGGCACTTGGTGGCCAGAAAGTGTGAGCCTCATGATCTGCTGTCT<br>GTAGTTCTGTGAGCTCAGGTCCCTCAAAGGCCTCGGAGCACCCCCTTCC<br>TTGTGACTGAGCCAGGGCCTGCATTTTTGGTTTTCCCCACCCCACACATT<br>CTCAACCATAGTCCTTCTAACAATACCAATAGCTAGGACCCGGCTGCTGT<br>GCACTGGGACTGGGGATTCCACATGTTTGCCTTGGGAGTCTCAAGCTGG<br>ACTGCCA |
| 67 | COX8-<br>ND1-<br>3'UTR | ATGTCCGTCCTGACGCGCCTGCTGCTGCGGGGCTTGACACGGCTCGGCT<br>CGGCGGCTCCAGTGCGGCGCGCCAGAATCCATTCGTTGATGCCCATGGC<br>CAACCTCCTACTCCTCATTGTACCCATTCTAATCGCAATGGCATTCCTAAT<br>GCTTACCGAACGAAAAATTCTAGGCTATATGCAACTACGCAAAGGCCCCA<br>ACGTTGTAGGCCCCTACGGGCTACTACAACCCTTCGCTGACGCCATGAAA<br>CTCTTCACCAAAGAGCCCCTAAAACCCGCCACATCTACCATCACCCTCTA<br>CATCACCGCCCCGACCTTAGCTCTCACCATCGCTCTTCTACTATGGACCC<br>CCCTCCCCATGCCCAACCCCCTGGTCAACCTCAACCTAGGCCTCCTATTT<br>ATTCTAGCCACCTCTAGCCTAGCCGTTTACTCAATCCTCTGGTCAGGGTG<br>GGCATCAAACTCAAACTACGCCCTGATCGGCGCACTGCGAGCAGTAGCC |

TABLE 1-continued nucleic acid and polypeptide sequences and SEQ ID NOs

| SEQ ID NO: | description | sequence |
|---|---|---|
| | | CAAACAATCTCATATGAAGTCACCCTAGCCATCATTCTACTATCAACATTA
CTAATGAGTGGCTCCTTTAACCTCTCCACCCTTATCACAACACAAGAACAC
CTCTGGTTACTCCTGCCATCATGGCCCTTGGCCATGATGTGGTTTATCTC
CACACTAGCAGAGACCAACCGAACCCCCTTCGACCTTGCCGAAGGGGAG
TCCGAACTAGTCTCAGGCTTCAACATCGAATACGCCGCAGGCCCCTTCGC
CCTATTCTTCATGGCCGAATACACAAACATTATTATGATGAACACCCTCAC
CACTACAATCTTCCTAGGAACAACATATGACGCACTCTCCCCTGAACTCTA
CACAACATATTTTGTCACCAAGACCCTACTTCTAACCTCCCTGTTCTTATG
GATTCGAACAGCATACCCCCGATTCCGCTACGACCAACTCATGCACCTCC
TATGGAAAAACTTCCTACCACTCACCCTAGCATTACTTATGTGGTATGTCT
CCATGCCCATTACAATCTCCAGCATTCCCCCTCAAACCTAAGAGCACTGG
GACGCCCACCGCCCCTTTCCCTCCGCTGCCAGGCGAGCATGTTGTGGTA
ATTCTGGAACACAAGAAGAGAAATTGCTGGGTTTAGAACAAGATTATAAAC
GAATTCGGTGCTCAGTGATCACTTGACAGTTTTTTTTTTTTAAATATTAC
CCAAAATGCTCCCAAATAAGAAATGCATCAGCTCAGTCAGTGAATACAA
AAAAGGAATTATTTTTCCCTTTGAGGGTCTTTTATACATCTCTCCTCCAACC
CCACCCTCTATTCTGTTTCTTCCTCCTCACATGGGGGTACACATACACAG
CTTCCTCTTTTGGTTCCATCCTTACCACCACACCACACGCACACTCCACAT
GCCCAGCAGAGTGGCACTTGGTGGCCAGAAAGTGTGAGCCTCATGATCT
GCTGTCTGTAGTTCTGTGAGCTCAGGTCCCTCAAAGGCCTCGGAGCACC
CCCTTCCTTGTGACTGAGCCAGGGCCTGCATTTTTGGTTTTCCCCACCCC
ACACATTCTCAACCATAGTCCTTCTAACAATACCAATAGCTAGGACCCGG
CTGCTGTGCACTGGGACTGGGGATTCCACATGTTTGCCTTGGGAGTCTCA
AGCTGGACTGCCAGCCCCTGTCCTCCCTTCACCCCCATTGCGTATGAGC
ATTTCAGAACTCCAAGGAGTCACAGGCATCTTTATAGTTCACGTTAACATA
TAGACACTGTTGGAAGCAGTTCCTTCTAAAAGGGTAGCCCTGGACTTAAT
ACCAGCCGGATACCTCTGGCCCCCACCCCATTACTGTACCTCTGGAGTCA
CTACTGTGGGTCGCCACTCCTCTGCTACACAGCACGGCTTTTTCAAGGCT
GTATTGAGAAGGGAAGTTAGGAAGAAGGGTGTGCTGGGCTAACCAGCCC
ACAGAGCTCACATTCCTGTCCCTTGGGTGAAAAATACATGTCCATCCTGA
TATCTCCTGAATTCAGAAATTAGCCTCCACATGTGCAATGGCTTTAAGAGC
CAGAAGCAGGGTTCTGGGAATTTTGCAAGTTACCTGTGGCCAGGTGTGG
TCTCGGTTACCAAATACGGTTACCTGCAGCTTTTTAGTCCTTTGTGCTCCC
ACGGGTCTACAGAGTCCCATCTGCCCAAAGGTCTTGAAGCTTGACAGGAT
GTTTTCGATTACTCAGTCTCCCAGGGCACTACTGGTCCGTAGGATTCGAT
TGGTCGGGGTAGGAGAGTTAAACAACATTTAAACAGAGTTCTCTCAAAAA
TGTCTAAAGGGATTGTAGGTAGATAACATCCAATCACTGTTTGCACTTATC
TGAAATCTTCCCTCTTGGCTGCCCCCAGGTATTTACTGTGGAGAACATTG
CATAGGAATGTCTGGAAAAAGCTTCTACAACTTGTTACAGCCTTCACATTT
GTAGAAGCTTT |
| 68 | COX8-ND1-3'UTR* | ATGTCCGTCCTGACGCGCCTGCTGCTGCGGGGCTTGACACGGCTCGGCT
CGGCGGCTCCAGTGCGGCGCGCCAGAATCCATTCGTTGATGCCCATGGC
CAACCTCCTACTCCTCATTGTACCCATTCTAATCGCAATGGCATTCCTAAT
GCTTACCGAACGAAAAATTCTAGGCTATATGCAACTACGCAAAGGCCCCA
ACGTTGTAGGCCCCTACGGGCTACTACAACCCTTCGCTGACGCCATGAAA
CTCTTCACCAAAGAGCCCCTAAAACCCGCCACATCTACCATCACCCTCTA
CATCACCGCCCCGACCTTAGCTCTCACCATCGCTCTTCTACTATGGACCC
CCCTCCCCATGCCCAACCCCCTGGTCAACCTCAACCTAGGCCTCCTATTT
ATTCTAGCCACCTCTAGCCTAGCCGTTTACTCAATCCTCTGGTCAGGGTG
GGCATCAAACTCAAACTACGCCCTGATCGGCGCACTGCGAGCAGTAGCC
CAAACAATCTCATATGAAGTCACCCTAGCCATCATTCTACTATCAACATTA
CTAATGAGTGGCTCCTTTAACCTCTCCACCCTTATCACAACACAAGAACAC
CTCTGGTTACTCCTGCCATCATGGCCCTTGGCCATGATGTGGTTTATCTC
CACACTAGCAGAGACCAACCGAACCCCCTTCGACCTTGCCGAAGGGGAG
TCCGAACTAGTCTCAGGCTTCAACATCGAATACGCCGCAGGCCCCTTCGC
CCTATTCTTCATGGCCGAATACACAAACATTATTATGATGAACACCCTCAC
CACTACAATCTTCCTAGGAACAACATATGACGCACTCTCCCCTGAACTCTA
CACAACATATTTTGTCACCAAGACCCTACTTCTAACCTCCCTGTTCTTATG
GATTCGAACAGCATACCCCCGATTCCGCTACGACCAACTCATGCACCTCC
TATGGAAAAACTTCCTACCACTCACCCTAGCATTACTTATGTGGTATGTCT
CCATGCCCATTACAATCTCCAGCATTCCCCCTCAAACCTAAGAGCACTGG
GACGCCCACCGCCCCTTTCCCTCCGCTGCCAGGCGAGCATGTTGTGGTA
ATTCTGGAACACAAGAAGAGAAATTGCTGGGTTTAGAACAAGATTATAAAC
GAATTCGGTGCTCAGTGATCACTTGACAGTTTTTTTTTTTTAAATATTAC
CCAAAATGCTCCCAAATAAGAAATGCATCAGCTCAGTCAGTGAATACAA
AAAAGGAATTATTTTTCCCTTTGAGGGTCTTTTATACATCTCTCCTCCAACC
CCACCCTCTATTCTGTTTCTTCCTCCTCACATGGGGGTACACATACACAG
CTTCCTCTTTTGGTTCCATCCTTACCACCACACCACACGCACACTCCACAT |

TABLE 1-continued nucleic acid and polypeptide sequences and SEQ ID NOs

| SEQ ID NO: | description | sequence |
|---|---|---|
| | | GCCCAGCAGAGTGGCACTTGGTGGCCAGAAAGTGTGAGCCTCATGATCT GCTGTCTGTAGTTCTGTGAGCTCAGGTCCCTCAAAGGCCTCGGAGCACC CCCTTCCTTGTGACTGAGCCAGGGCCTGCATTTTTGGTTTTCCCCACCCC ACACATTCTCAACCATAGTCCTTCTAACAATACCAATAGCTAGGACCCGG CTGCTGTGCACTGGGACTGGGGATTCCACATGTTTGCCTTGGGAGTCTCA AGCTGGACTGCCA |
| 69 | COX8-opt_ND1-3'UTR | ATGTCCGTCCTGACGCGCCTGCTGCTGCGGGGCTTGACACGGCTCGGCT CGGCGGCTCCAGTGCGGCGCGCCAGAATCCATTCGTTGATGCCCATGGC CAACCTGCTGCTGCTGATCGTGCCCATCCTGATCGCCATGGCCTTCCTGA TGCTGACCGAGCGCAAGATCCTGGGCTACATGCAGCTGCGCAAGGGCCC CAACGTGGTGGGCCCCTACGGCCTGCTGCAGCCCTTCGCCGACGCCAT GAAGCTGTTCACCAAGGAGCCCCTGAAGCCCGCCACCAGCACCATCACC CTGTACATCACCGCCCCCACCCTGGCCCTGACCATCGCCCTGCTGCTGT GGACCCCCCTGCCCATGCCCAACCCCCTGGTGAACCTGAACCTGGGCCT GCTGTTCATCCTGGCCACCAGCAGCCTGGCCGTGTACAGCATCCTGTGG AGCGGCTGGGCCAGCAACAGCAACTACGCCCTGATCGGCGCCCTGCGC GCCGTGGCCCAGACCATCAGCTACGAGGTGACCCTGGCCATCATCCTGC TGAGCACCCTGCTGATGAGCGGCAGCTTCAACCTGAGCACCCTGATCAC CACCCAGGAGCACCTGTGGCTGCTGCTGCCCAGCTGGCCCCTGGCCAT GATGTGGTTCATCAGCACCCTGGCCGAGACCAACCGCACCCCCTTCGAC CTGGCCGAGGGCGAGAGCGAGCTGGTGAGCGGCTTCAACATCGAGTAC GCCGCCGGCCCCTTCGCCCTGTTCTTCATGGCCGAGTACACCAACATCA TCATGATGAACACCCTGACCACCACCATCTTCCTGGGCACCACCTACGAC GCCCTGAGCCCCGAGCTGTACACCACCTACTTCGTGACCAAGACCCTGC TGCTGACCAGCCTGTTCCTGTGGATCCGCACCGCCTACCCCCGCTTCCG CTACGACCAGCTGATGCACCTGCTGTGGAAGAACTTCCTGCCCCTGACC CTGGCCCTGCTGATGTGGTACGTGAGCATGCCCATCACCATCAGCAGCA TCCCCCCCCAGACCTAAGAGCACTGGGACGCCCACCGCCCCTTTCCCTC CGCTGCCAGGCGAGCATGTTGTGGTAATTCTGGAACACAAGAAGAGAAAT TGCTGGGTTTAGAACAAGATTATAAACGAATTCGGTGCTCAGTGATCACTT GACAGTTTTTTTTTTTTAAATATTACCCAAAATGCTCCCAAATAAGAAA TGCATCAGCTCAGTCAGTGAATACAAAAAAGGAATTATTTTTCCCTTTGAG GTCTTTTATACATCTCTCCTCCAACCCCACCCTCTATTCTGTTTCTTCCT CCTCACATGGGGGTACACATACACAGCTTCCTCTTTTGGTTCCATCCTTAC CACCACACCACACGCACACTCCACATGCCCAGCAGAGTGGCACTTGGTG GCCAGAAAGTGTGAGCCTCATGATCTGCTGTCTGTAGTTCTGTGAGCTCA GGTCCCTCAAAGGCCTCGGAGCACCCCCTTCCTTGTGACTGAGCCAGGG CCTGCATTTTTGGTTTTCCCCACCCCACACATTCTCAACCATAGTCCTTCT AACAATACCAATAGCTAGGACCCGGCTGCTGTGCACTGGGACTGGGGAT TCCACATGTTTGCCTTGGGAGTCTCAAGCTGGACTGCCAGCCCCTGTCCT CCCTTCACCCCCATTGCGTATGAGCATTTCAGAACTCCAAGGAGTCACAG GCATCTTTATAGTTCACGTTAACATATAGACACTGTTGGAAGCAGTTCCTT CTAAAAGGGTAGCCCTGGACTTAATACCAGCCGGATACCTCTGGCCCCC ACCCCATTACTGTACCTCTGGAGTCACTACTGTGGGTCGCCACTCCTCTG CTACACAGCACGGCTTTTTCAAGGCTGTATTGAGAAGGGAAGTTAGGAAG AAGGGTGTGCTGGGCTAACCAGCCCACAGAGCTCACATTCCTGTCCCTT GGGTGAAAAATACATGTCCATCCTGATATCTCCTGAATTCAGAAATTAGCC TCCACATGTGCAATGGCTTTAAGAGCCAGAAGCAGGGTTCTGGGAATTTT GCAAGTTACCTGTGGCCAGGTGTGGTCTCGGTTACCAAATACGGTTACCT GCAGCTTTTTAGTCCTTTGTGCTCCCACGGGTCTACAGAGTCCCATCTGC CCAAAGGTCTTGAAGCTTGACAGGATGTTTTCGATTACTCAGTCTCCCAG GGCACTACTGGTCCGTAGGATTCGATTGGTCGGGGTAGGAGAGTTAAAC AACATTTAAACAGAGTTCTCTCAAAAATGTCTAAAGGGATTGTAGGTAGAT AACATCCAATCACTGTTTGCACTTATCTGAAATCTTCCCTCTTGGCTGCCC CCAGGTATTTACTGTGGAGAACATTGCATAGGAATGTCTGGAAAAAGCTT CTACAACTTGTTACAGCCTTCACATTTGTAGAAGCTTT |
| 70 | COX8-opt_ND1-3'UTR* | ATGTCCGTCCTGACGCGCCTGCTGCTGCGGGGCTTGACACGGCTCGGCT CGGCGGCTCCAGTGCGGCGCGCCAGAATCCATTCGTTGATGCCCATGGC CAACCTGCTGCTGCTGATCGTGCCCATCCTGATCGCCATGGCCTTCCTGA TGCTGACCGAGCGCAAGATCCTGGGCTACATGCAGCTGCGCAAGGGCCC CAACGTGGTGGGCCCCTACGGCCTGCTGCAGCCCTTCGCCGACGCCAT GAAGCTGTTCACCAAGGAGCCCCTGAAGCCCGCCACCAGCACCATCACC CTGTACATCACCGCCCCCACCCTGGCCCTGACCATCGCCCTGCTGCTGT GGACCCCCCTGCCCATGCCCAACCCCCTGGTGAACCTGAACCTGGGCCT GCTGTTCATCCTGGCCACCAGCAGCCTGGCCGTGTACAGCATCCTGTGG AGCGGCTGGGCCAGCAACAGCAACTACGCCCTGATCGGCGCCCTGCGC GCCGTGGCCCAGACCATCAGCTACGAGGTGACCCTGGCCATCATCCTGC TGAGCACCCTGCTGATGAGCGGCAGCTTCAACCTGAGCACCCTGATCAC CACCCAGGAGCACCTGTGGCTGCTGCTGCCCAGCTGGCCCCTGGCCAT GATGTGGTTCATCAGCACCCTGGCCGAGACCAACCGCACCCCCTTCGAC CTGGCCGAGGGCGAGAGCGAGCTGGTGAGCGGCTTCAACATCGAGTAC GCCGCCGGCCCCTTCGCCCTGTTCTTCATGGCCGAGTACACCAACATCA |

TABLE 1-continued nucleic acid and polypeptide sequences and SEQ ID NOs

| SEQ ID NO: | description | sequence |
|---|---|---|
| | | TCATGATGAACACCCTGACCACCACCATCTTCCTGGGCACCACCTACGAC
GCCCTGAGCCCCGAGCTGTACACCACCTACTTCGTGACCAAGACCCTGC
TGCTGACCAGCCTGTTCCTGTGTGGATCCGCACCGCCTACCCCCGCTTCCG
CTACGACCAGCTGATGCACCTGCTGTGGAAGAACTTCCTGCCCCTGACC
CTGGCCCTGCTGATGTGGTACGTGAGCATGCCCATCACCATCAGCAGCA
TCCCCCCCCAGACCTAAGAGCACTGGGACGCCCACCGCCCCTTTCCCTC
CGCTGCCAGGCGAGCATGTTGTGGTAATTCTGGAACACAAGAAGAGAAAT
TGCTGGGTTTAGAACAAGATTATAAACGAATTCGGTGCTCAGTGATCACTT
GACAGTTTTTTTTTTTTAAATATTACCCAAAATGCTCCCCAAATAAGAAA
TGCATCAGCTCAGTCAGTGAATACAAAAAAGGAATTATTTTTCCCTTTGAG
GGTCTTTTATACATCTCTCCTCCAACCCCACCCTCTATTCTGTTTCTTCCT
CCTCACATGGGGTACACATACACAGCTTCCTCTTTTGGTTCCATCCTTAC
CACCACACCACACGCACACTCCACATGCCCAGCAGAGTGGCACTTGGTG
GCCAGAAAGTGTGAGCCTCATGATCTGCTGTCTGTAGTTCTGTGAGCTCA
GGTCCCTCAAAGGCCTCGGAGCACCCCCTTCCTTGTGACTGAGCCAGGG
CCTGCATTTTTGGTTTTCCCCACCCCACACATTCTCAACCATAGTCCTTCT
AACAATACCAATAGCTAGGACCCGGCTGCTGTGCACTGGGACTGGGGAT
TCCACATGTTTGCCTTGGGAGTCTCAAGCTGGACTGCCA |
| 71 | OPA1-ND4-3'UTR | GTGCTGCCCGCCTAGAAAGGGTGAAGTGGTTGTTTCCGTGACGGACTGA
GTACGGGTGCCTGTCAGGCTCTTGCGGAAGTCCATGCGCCATTGGGAGG
GCCTCGGCCGCGGCTCTGTGCCCTTGCTGCTGAGGGCCACTTCCTGGGT
CATTCCTGGACCGGGAGCCGGGCTGGGGCTCACACGGGGGCTCCCGCG
TGGCCGTCTCGGCGCCTGCGTGACCTCCCCGCCGGCGGGATGTGGCGA
CTACGTCGGGCCGCTGTGGCCTGATGCTAAAACTAATCGTCCCAACAATT
ATGTTACTACCACTGACATGGCTTTCCAAAAAACACATGATTTGGATCAAC
ACAACCACCCACAGCCTAATTATTAGCATCATCCCTCTACTATTTTTTAAC
CAAATCAACAACAACCTATTTAGCTGTTCCCCAACCTTTTCCTCCGACCCC
CTAACAACCCCCCTCCTAATGCTAACTACCTGGCTCCTACCCCTCACAAT
CATGGCAAGCCAACGCCACTTATCCAGTGAACCACTATCACGAAAAAAAC
TCTACCTCTCTATGCTAATCTCCCTACAAATCTCTTAATTATGACATTCAC
AGCCACAGAACTAATCATGTTTTATATCTTCTTCGAAACCACACTTATCCC
CACCTTGGCTATCATCACCCGATGGGGCAACCAGCCAGAACGCCTGAAC
GCAGGCACATACTTCCTATTCTACACCCTAGTAGGCTCCCTTCCCCTACT
CATCGCACTAATTTACACTCACAACACCCTAGGCTCACTAAACATTCTACT
ACTCACTCTCACTGCCCAAGAACTATCAAACTCCTGGGCCAACAACTTAAT
GTGGCTAGCTTACACAATGGCTTTTATGGTAAAGATGCCTCTTTACGGACT
CCACTTATGGCTCCCTAAAGCCCATGTCGAAGCCCCCATCGCTGGGTCAA
TGGTACTTGCCGCAGTACTCTTAAAACTAGGCGGCTATGGTATGATGCGC
CTCACACTCATTCTCAACCCCCTGACAAAACACATGGCCTACCCCTTCCTT
GTACTATCCCTATGGGGCATGATTATGACAAGCTCCATCTGCCTACGACA
AACAGACCTAAAATCGCTCATTGCATACTCTTCAATCAGCCACATGGCCCT
CGTAGTAACAGCCATTCTCATCCAAACCCCCTGGAGCTTCACCGGCGCA
GTCATTCTCATGATCGCCCACGGGCTTACATCCTCATTACTATTCTGCCTA
GCAAACTCAAACTACGAACGCACTCACAGTCGCATCATGATCCTCTCTCA
AGGACTTCAAACTCTACTCCCACTAATGGCTTTTTGGTGGCTTCTAGCAAG
CCTCGCTAACCTCGCCTTACCCCCCACTATTAACCTACTGGGAGAACTCT
CTGTGCTAGTAACCACGTTCTCCTGGTCAAATATCACTCTCCTACTTACAG
GACTCAACATGCTAGTCACAGCCCTATACTCCCTCTACATGTTTACCACAA
CACAATGGGGCTCACTCACCCACCACATTAACAACATGAAACCCTCATTC
ACACGAGAAAACACCCTCATGTTCATGCACCTATCCCCCATTCTCCTCCTA
TCCCTCAACCCCGACATCATTACCGGGTTTTCCTCTTAAGAGCACTGGGA
CGCCCACCGCCCCTTTCCCTCCGCTGCCAGGCGAGCATGTTGTGGTAAT
TCTGGAACACAAGAAGAGAAATTGCTGGGTTTAGAACAAGATTATAAACG
AATTCGGTGCTCAGTGATCACTTGACAGTTTTTTTTTTTTAAATATTACC
CAAAATGCTCCCCAAATAAGAAATGCATCAGCTCAGTCAGTGAATACAAA
AAAGGAATTATTTTTCCCTTTGAGGGTCTTTTATACATCTCTCCTCCAACC
CCACCCTCTATTCTGTTTCTTCCTCCTCACATGGGGTACACATACACAG
CTTCCTCTTTTGGTTCCATCCTTACCACCACACCACACGCACACTCCACAT
GCCCAGCAGAGTGGCACTTGGTGGCCAGAAAGTGTGAGCCTCATGATCT
GCTGTCTGTAGTTCTGTGAGCTCAGGTCCCTCAAAGGCCTCGGAGCACC
CCCTTCCTTGTGACTGAGCCAGGGCCTGCATTTTTGGTTTTCCCCACCCC
ACACATTCTCAACCATAGTCCTTCTAACAATACCAATAGCTAGGACCCGG
CTGCTGTGCACTGGGACTGGGGATTCCACATGTTTGCCTTGGGAGTCTCA
AGCTGGACTGCCAGCCCCTGTCCTCCCTTCACCCCCATTGCGTATGAGC
ATTTCAGAACTCCAAGGAGTCACAGGCATCTTTATAGTTCACGTTAACATA
TAGACACTGTTGGAAGCAGTTCCTTCTAAAAGGGTAGCCCTGGACTTAAT
ACCAGCCGGATACCTCTGGCCCCCACCCCATTACTGTACCTCTGGAGTCA
CTACTGTGGGTCGCCACTCCTCTGCTACACAGCACGGCTTTTTCAAGGCT
GTATTGAGAAGGGAAGTTAGGAAGAAGGGTGTGCTGGGCTAACCAGCCC
ACAGAGCTCACATTCCTGTCCCTTGGGTGAAAATACATGTCCATCCTGA
TATCTCCTGAATTCAGAAATTAGCCTCCACATGTGCAATGGCTTTAAGAGC
CAGAAGCAGGGTTCTGGGAATTTTGCAAGTTACCTGTGGCCAGGTGTGG
TCTCGGTTACCAAATACGGTTACCTGCAGCTTTTTAGTCCTTTGTGCTCCC |

TABLE 1-continued nucleic acid and polypeptide sequences and SEQ ID NOs

| SEQ ID NO: | description | sequence |
|---|---|---|
| | | ACGGGTCTACAGAGTCCCATCTGCCCAAAGGTCTTGAAGCTTGACAGGAT
GTTTTCGATTACTCAGTCTCCCAGGGCACTACTGGTCCGTAGGATTCGAT
TGGTCGGGGTAGGAGAGTTAAACAACATTTAAACAGAGTTCTCTCAAAAA
TGTCTAAAGGGATTGTAGGTAGATAACATCCAATCACTGTTTGCACTTATC
TGAAATCTTCCCTCTTGGCTGCCCCCAGGTATTTACTGTGGAGAACATTG
CATAGGAATGTCTGGAAAAAGCTTCTACAACTTGTTACAGCCTTCACATTT
GTAGAAGCTTT |
| 72 | OPA1-
ND4-
3'UTR* | GTGCTGCCCGCCTAGAAAGGGTGAAGTGGTTGTTTCCGTGACGGACTGA
GTACGGGTGCCTGTCAGGCTCTTGCGGAAGTCCATGCGCCATTGGGAGG
GCCTCGGCCGCGGCTCTGTGCCCTTGCTGCTGAGGGCCACTTCCTGGGT
CATTCCTGGACCGGGAGCCGGGCTGGGGCTCACACGGGGGCTCCCGCG
TGGCCGTCTCGGCGCCTGCGTGACCTCCCCGCCGGCGGGATGTGGCGA
CTACGTCGGGCCGCTGTGGCCTGATGCTAAAACTAATCGTCCCAACAATT
ATGTTACTACCACTGACATGGCTTTCCAAAAAACACATGATTTGGATCAAC
ACAACCACCCACAGCCTAATTATTAGCATCATCCCTCTACTATTTTTTAAC
CAAATCAACAACAACCTATTTAGCTGTTCCCCAACCTTTTCCTCCGACCCC
CTAACAACCCCCTCCTAATGCTAACTACCTGGCTCCTACCCCTCACAAT
CATGGCAAGCCAACGCCACTTATCCAGTGAACCACTATCACGAAAAAAAC
TCTACCTCTCTATGCTAATCTCCCTACAAATCTCCTTAATTATGACATTCAC
AGCCACAGAACTAATCATGTTTTATATCTTCTTCGAAACCACACTTATCCC
CACCTTGGCTATCATCACCCGATGGGGCAACCAGCCAGAACGCCTGAAC
GCAGGCACATACTTCCTATTCTACACCCTAGTAGGCTCCCTTCCCCTACT
CATCGCACTAATTTACACTCACAACACCCTAGGCTCACTAAACATTCTACT
ACTCACTCTCACTGCCCAAGAACTATCAAACTCCTGGGCCAACAACTTAAT
GTGGCTAGCTTACACAATGGCTTTTATGGTAAAGATGCCTCTTTACGGACT
CCACTTATGGCTCCCTAAAGCCCATGTCGAAGCCCCCATCGCTGGGTCAA
TGGTACTTGCCGCAGTACTCTTAAAACTAGGCGGCTATGGTATGATGCGC
CTCACACTCATTCTCAACCCCCTGACAAAACACATGGCCTACCCCTTCCTT
GTACTATCCCTATGGGGCATGATTATGACAAGCTCCATCTGCCTACGACA
AACAGACCTAAAATCGCTCATTGCATACTCTTCAATCAGCCACATGGCCCT
CGTAGTAACAGCCATTCTCATCCAAACCCCCTGGAGCTTCACCGGCGCA
GTCATTCTCATGATCGCCCACGGGCTTACATCCTCATTACTATTCTGCCTA
GCAAACTCAAACTACGAACGCACTCACAGTCGCATCATGATCCTCTCTCA
AGGACTTCAAACTCTACTCCCACTAATGGCTTTTTGGTGGCTTCTAGCAAG
CCTCGCTAACCTCGCCTTACCCCCCACTATTAACCTACTGGGAGAACTCT
CTGTGCTAGTAACCACGTTCTCCTGGTCAAATATCACTCTCCTACTTACAG
GACTCAACATGCTAGTCACAGCCCTATACTCCCTCTACATGTTTACCACAA
CACAATGGGGCTCACTCACCCACCACATTAACAACATGAAACCCTCATTC
ACACGAGAAAACACCCTCATGTTCATGCACCTATCCCCATTCTCCTCCTA
TCCCTCAACCCCGACATCATTACCGGGTTTTCCTCTTAAGAGCACTGGGA
CGCCCACCGCCCCTTTCCCTCCGCTGCCAGGCGAGCATGTTGTGGTAAT
TCTGGAACACAAGAAGAGAAATTGCTGGGTTTAGAACAAGATTATAAACG
AATTCGGTGCTCAGTGATCACTTGACAGTTTTTTTTTTTTAAATATTACC
CAAAATGCTCCCCAAATAAGAAATGCATCAGCTCAGTCAGTGAATACAAA
AAAGGAATTATTTTTCCCTTTGAGGGTCTTTTATACATCTCTCCTCCAACC
CCACCCTCTATTCTGTTTCTTCCTCCTCACATGGGGGTACACATACACAG
CTTCCTCTTTTGGTTCCATCCTTACCACCACACCACACGCACACTCCACAT
GCCCAGCAGAGTGGCACTTGGTGGCCAGAAAGTGTGAGCCTCATGATCT
GCTGTCTGTAGTTCTGTGAGCTCAGGTCCCTCAAAGGCCTCGGAGCACC
CCCTTCCTTGTGACTGAGCCAGGGCCTGCATTTTTGGTTTTCCCCACCCC
ACACATTCTCAACCATAGTCCTTCTAACAATACCAATAGCTAGGACCCGG
CTGCTGTGCACTGGGACTGGGGATTCCACATGTTTGCCTTGGGAGTCTCA
AGCTGGACTGCCA |
| 73 | OPA1-
opt_ND4-
3'UTR | GTGCTGCCCGCCTAGAAAGGGTGAAGTGGTTGTTTCCGTGACGGACTGA
GTACGGGTGCCTGTCAGGCTCTTGCGGAAGTCCATGCGCCATTGGGAGG
GCCTCGGCCGCGGCTCTGTGCCCTTGCTGCTGAGGGCCACTTCCTGGGT
CATTCCTGGACCGGGAGCCGGGCTGGGGCTCACACGGGGGCTCCCGCG
TGGCCGTCTCGGCGCCTGCGTGACCTCCCCGCCGGCGGGATGTGGCGA
CTACGTCGGGCCGCTGTGGCCTGATGCTGAAGCTGATCGTGCCCACCAT
CATGCTGCTGCCTCTGACCTGGCTGAGCAAGAAACACATGATCTGGATCA
ACACCACCACGCACAGCCTGATCATCAGCATCATCCCTCTGCTGTTCTTC
AACCAGATCAACAACAACCTGTTCAGCTGCAGCCCCACCTTCAGCAGCGA
CCCTCTGACAACACCTCTGCTGATGCTGACCACCTGGCTGCTGCCCCTCA
CAATCATGGCCTCTCAGAGACACCTGAGCAGCGAGCCCCTGAGCCGGAA
GAAACTGTACCTGAGCATGCTGATCTCCCTGCAGATCTCTCTGATCATGA
CCTTCACCGCCACCGAGCTGATCATGTTCTACATCTTTTTCGAGACAACG
CTGATCCCCACACTGGCCATCATCACCGATGGGGCAACCAGCCTGAGA
GACTGAACGCCGGCACCTACTTTCTGTTCTACACCCTCGTGGGCAGCCT
GCCACTGCTGATTGCCCTGATCTACACCCACAACACCCTGGGCTCCCTGA
ACATCCTGCTGCTGACACTGACAGCCCAAGAGCTGAGCAACAGCTGGGC
CAACAATCTGATGTGGCTGGCCTACACAATGGCCTTCATGGTCAAGATGC
CCCTGTACGGCCTGCACCTGTGGCTGCCTAAAGCTCATGTGGAAGCCCC |

TABLE 1-continued nucleic acid and polypeptide sequences and SEQ ID NOs

| SEQ ID NO: | description | sequence |
|---|---|---|
| | | TATCGCCGGCTCTATGGTGCTGGCTGCAGTGCTGCTGAAACTCGGCGGC
TACGGCATGATGCGGCTGACCCTGATTCTGAATCCCCTGACCAAGCACAT
GGCCTATCCATTTCTGGTGCTGAGCCTGTGGGGCATGATTATGACCAGCA
GCATCTGCCTGCGGCAGACCGATCTGAAGTCCCTGATCGCCTACAGCTC
CATCAGCCACATGGCCCTGGTGGTCACCGCCATCCTGATTCAGACCCCTT
GGAGCTTTACAGGCGCCGTGATCCTGATGATTGCCCACGGCCTGACAAG
CAGCCTGCTGTTTTGTCTGGCCAACAGCAACTACGAGCGGACCCACAGC
AGAATCATGATCCTGTCTCAGGGCCTGCAGACCCTCCTGCCTCTTATGGC
TTTTTGGTGGCTGCTGGCCTCTCTGGCCAATCTGGCACTGCCTCCTACCA
TCAATCTGCTGGGCGAGCTGAGCGTGCTGGTCACCACATTCAGCTGGTC
CAATATCACCCTGCTGCTCACCGGCCTGAACATGCTGGTTACAGCCCTGT
ACTCCCTGTACATGTTCACCACCACACAGTGGGGAAGCCTGACACACCAC
ATCAACAATATGAAGCCCAGCTTCACCCGCGAGAACACCCTGATGTTCAT
GCATCTGAGCCCCATTCTGCTGCTGTCCCTGAATCCTGATATCATCACCG
GCTTCTCCAGCTGAGAGCACTGGACGCCCACCGCCCCTTTCCCTCCGC
TGCCAGGCGAGCATGTTGTGGTAATTCTGGAACACAAGAAGAGAAATTGC
TGGGTTTAGAACAAGATTATAAACGAATTCGGTGCTCAGTGATCACTTGAC
AGTTTTTTTTTTTTTAAATATTACCCAAAATGCTCCCCAAATAAGAAATGC
ATCAGCTCAGTCAGTGAATACAAAAAAGGAATTATTTTTCCCTTTGAGGGT
CTTTTATACATCTCTCCTCCAACCCCACCCTCTATTCTGTTTCTTCCTCCTC
ACATGGGGTACACATACACAGCTTCCTCTTTTGGTTCCATCCTTACCAC
CACACCACACGCACACTCCACATGCCCAGCAGAGTGGCACTTGGTGGCC
AGAAAGTGTGAGCCTCATGATCTGCTGTCTGTAGTTCTGTGAGCTCAGGT
CCCTCAAAGGCCTCGGAGCACCCCCTTCCTTGTGACTGAGCCAGGGCCT
GCATTTTTGGTTTTCCCCACCCCACACATTCTCAACCATAGTCCTTCTAAC
AATACCAATAGCTAGGACCCGGCTGCTGTGCACTGGGACTGGGGATTCC
ACATGTTTGCCTTGGGAGTCTCAAGCTGGACTGCCAGCCCCTGTCCTCCC
TTCACCCCCATTGCGTATGAGCATTTCAGAACTCCAAGGAGTCACAGGCA
TCTTTATAGTTCACGTTAACATATAGACACTGTTGGAAGCAGTTCCTTCTA
AAAGGGTAGCCCTGGACTTAATACCAGCCGGATACCTCTGGCCCCCACC
CCATTACTGTACCTCTGGAGTCACTACTGTGGGTCGCCACTCCTCTGCTA
CACAGCACGGCTTTTTCAAGGCTGTATTGAGAAGGGAAGTTAGGAAGAAG
GGTGTGCTGGGCTAACCAGCCCACAGAGCTCACATTCCTGTCCCTTGGG
TGAAAAATACATGTCCATCCTGATATCTCCTGAATTCAGAAATTAGCCTCC
ACATGTGCAATGGCTTTAAGAGCCAGAAGCAGGGTTCTGGGAATTTTGCA
AGTTACCTGTGGCCAGGTGTGGTCTCGGTTACCAAATACGGTTACCTGCA
GCTTTTTAGTCCTTTGTGCTCCCACGGGTCTACAGAGTCCCATCTGCCCA
AAGGTCTTGAAGCTTGACAGGATGTTTTCGATTACTCAGTCTCCCAGGGC
ACTACTGGTCCGTAGGATTCGATTGGTCGGGTAGGAGAGTTAAACAACA
TTTAAACAGAGTTCTCTCAAAAATGTCTAAAGGGATTGTAGGTAGATAACA
TCCAATCACTGTTTGCACTTATCTGAAATCTTCCCTCTTGGCTGCCCCCAG
GTATTTACTGTGGAGAACATTGCATAGGAATGTCTGGAAAAAGCTTCTACA
ACTTGTTACAGCCTTCACATTTGTAGAAGCTTT |
| 74 | OPA1-opt_ND4-3'UTR* | GTGCTGCCCGCCTAGAAAGGGTGAAGTGGTTGTTTCCGTGACGGACTGA
GTACGGGTGCCTGTCAGGCTCTTGCGGAAGTCCATGCGCCATTGGGAGG
GCCTCGGCCGCGGCTCTGTGCCCTTGCTGCTGAGGGCCACTTCCTGGGT
CATTCCTGGACCGGGAGCCGGGCTGGGGCTCACACGGGGGCTCCCGCG
TGGCCGTCTCGGCGCCTGCGTGACCTCCCCGCCGGCGGGATGTGGCGA
CTACGTCGGGCCGCTGTGGCCTGATGCTGAAGCTGATCGTGCCCACCAT
CATGCTGCTGCCTCTGACCTGGCTGAGCAAGAAACACATGATCTGGATCA
ACACCACCACGCACAGCCTGATCATCAGCATCATCCCTCTGCTGTTCTTC
AACCAGATCAACAACAACCTGTTCAGCTGCAGCCCCACCTTCAGCAGCGA
CCCTCTGACAACACCTCTGCTGATGCTGACCACCTGGCTGCTGCCCCTCA
CAATCATGGCCTCTCAGAGACACCTGAGCAGCGAGCCCCTGAGCCGGAA
GAAACTGTACCTGAGCATGCTGATCTCCCTGCAGATCTCTCTGATCATGA
CCTTCACCGCCACCGAGCTGATCATGTTCTACATCTTTTTCGAGACAACG
CTGATCCCCACACTGGCCATCATCACCAGATGGGGCAACCAGCCTGAGA
GACTGAACGCCGGCACCTACTTTCTGTTCTACACCCTCGTGGGCAGCCT
GCCACTGCTGATTGCCCTGATCTACACCCACAACACCCTGGGCTCCCTGA
ACATCCTGCTGCTGACACTGACAGCCCAAGAGCTGAGCAACAGCTGGGC
CAACAATCTGATGTGGCTGGCCTACACAATGGCCTTCATGGTCAAGATGC
CCCTGTACGGCCTGCACCTGTGGCTGCCTAAAGCTCATGTGGAAGCCCC
TATCGCCGGCTCTATGGTGCTGGCTGCAGTGCTGCTGAAACTCGGCGGC
TACGGCATGATGCGGCTGACCCTGATTCTGAATCCCCTGACCAAGCACAT
GGCCTATCCATTTCTGGTGCTGAGCCTGTGGGGCATGATTATGACCAGCA
GCATCTGCCTGCGGCAGACCGATCTGAAGTCCCTGATCGCCTACAGCTC
CATCAGCCACATGGCCCTGGTGGTCACCGCCATCCTGATTCAGACCCCTT
GGAGCTTTACAGGCGCCGTGATCCTGATGATTGCCCACGGCCTGACAAG
CAGCCTGCTGTTTTGTCTGGCCAACAGCAACTACGAGCGGACCCACAGC
AGAATCATGATCCTGTCTCAGGGCCTGCAGACCCTCCTGCCTCTTATGGC
TTTTTGGTGGCTGCTGGCCTCTCTGGCCAATCTGGCACTGCCTCCTACCA
TCAATCTGCTGGGCGAGCTGAGCGTGCTGGTCACCACATTCAGCTGGTC
CAATATCACCCTGCTGCTCACCGGCCTGAACATGCTGGTTACAGCCCTGT |

TABLE 1-continued nucleic acid and polypeptide sequences and SEQ ID NOs

| SEQ ID NO: | description | sequence |
|---|---|---|
| | | ACTCCCTGTACATGTTCACCACCACACAGTGGGGAAGCCTGACACACCAC<br>ATCAACAATATGAAGCCCAGCTTCACCCGCGAGAACACCCTGATGTTCAT<br>GCATCTGAGCCCCATTCTGCTGCTGTCCCTGAATCCTGATATCATCACCG<br>GCTTCTCCAGCTGAGAGCACTGGGACGCCCACCGCCCCTTTCCCTCCGC<br>TGCCAGGCGAGCATGTTGTGGTAATTCTGGAACACAAGAAGAGAAATTGC<br>TGGGTTTAGAACAAGATTATAAACGAATTCGGTGCTCAGTGATCACTTGAC<br>AGTTTTTTTTTTTTTAAATATTACCCAAAATGCTCCCCAAATAAGAAATGC<br>ATCAGCTCAGTCAGTAATACAAAAAAGGAATTATTTTTCCCTTTGAGGGT<br>CTTTTATACATCTCTCCTCCAACCCCACCCTCTATTCTGTTTCTTCCTCCTC<br>ACATGGGGTACACATACACAGCTTCCTCTTTTGGTTCCATCCTTACCAC<br>CACACCACACGCACACTCCACATGCCCAGCAGAGTGGCACTTGGTGGCC<br>AGAAAGTGTGAGCCTCATGATCTGCTGTCTGTAGTTCTGTGAGCTCAGGT<br>CCCTCAAAGGCCTCGGAGCACCCCCTTCCTTGTGACTGAGCCAGGGCCT<br>GCATTTTTGGTTTTCCCCACCCCACACATTCTCAACCATAGTCCTTCTAAC<br>AATACCAATAGCTAGGACCCGGCTGCTGTGCACTGGGACTGGGGATTCC<br>ACATGTTTGCCTTGGGAGTCTCAAGCTGGACTGCCA |
| 75 | OPA1-<br>opt_ND4*-<br>3'UTR | GTGCTGCCCGCCTAGAAAGGGTGAAGTGGTTGTTTCCGTGACGGACTGA<br>GTACGGGTGCCTGTCAGGCTCTTGCGGAAGTCCATGCGCCATTGGGAGG<br>GCCTCGGCCGCGGCTCTGTGCCCTTGCTGCTGAGGGCCACTTCCTGGGT<br>CATTCCTGGACCGGGAGCCGGGCTGGGGCTCACACGGGGGCTCCCGCG<br>TGGCCGTCTCGGCGCCTGCGTGACCTCCCCGCCGGCGGGATGTGGCGA<br>CTACGTCGGGCCGCTGTGGCCTGATGCTGAAGCTGATCGTGCCCACCAT<br>CATGCTGCTGCCCCTGACCTGGCTGAGCAAGAAGCACATGATCTGGATC<br>AACACCACCACCCACAGCCTGATCATCAGCATCATCCCCCTGCTGTTCTT<br>CAACCAGATCAACAACAACCTGTTCAGCTGCAGCCCCACCTTCAGCAGCG<br>ACCCCCTGACCACCCCCCTGCTGATGCTGACCACCTGGCTGCTGCCCCT<br>GACCATCATGGCCAGCCAGCGCCACCTGAGCAGCGAGCCCCTGAGCCG<br>CAAGAAGCTGTACCTGAGCATGCTGATCAGCCTGCAGATCAGCCTGATCA<br>TGACCTTCACCGCCACCGAGCTGATCATGTTCTACATCTTCTTCGAGACC<br>ACCCTGATCCCCACCCTGGCCATCATCACCCGCTGGGGCAACCAGCCCG<br>AGCGCCTGAACGCCGGCACCTACTTCCTGTTCTACACCCTGGTGGGCAG<br>CCTGCCCCTGCTGATCGCCCTGATCTACACCCACAACACCCTGGGCAGC<br>CTGAACATCCTGCTGCTGACCCTGACCGCCCAGGAGCTGAGCAACAGCT<br>GGGCCAACAACCTGATGTGGCTGGCCTACACCATGGCCTTCATGGTGAA<br>GATGCCCCTGTACGGCCTGCACCTGTGGCTGCCCAAGGCCCACGTGGA<br>GGCCCCCATCGCCGGCAGCATGGTGCTGGCCGCCGTGCTGCTGAAGCT<br>GGGCGGCTACGGCATGATGCGCCTGACCCTGATCCTGAACCCCCTGACC<br>AAGCACATGGCCTACCCCTTCCTGGTGCTGAGCCTGTGGGGCATGATCA<br>TGACCAGCAGCATCTGCCTGCGCCAGACCGACCTGAAGAGCCTGATCGC<br>CTACAGCAGCATCAGCCACATGGCCCTGGTGGTGACCGCCATCCTGATC<br>CAGACCCCCTGGAGCTTCACCGGCGCCGTGATCCTGATGATCGCCCACG<br>GCCTGACCAGCAGCCTGCTGTTCTGCCTGGCCAACAGCAACTACGAGCG<br>CACCCACAGCCGCATCATGATCCTGAGCCAGGGCCTGCAGACCCTGCTG<br>CCCCTGATGGCCTTCTGGTGGCTGCTGGCCAGCCTGGCCAACCTGGCCC<br>TGCCCCCCACCATCAACCTGCTGGGCGAGCTGAGCGTGCTGGTGACCAC<br>CTTCAGCTGGAGCAACATCACCCTGCTGCTGACCGGCCTGAACATGCTG<br>GTGACCGCCCTGTACAGCCGTGTACATGTTCACCACCACCCAGTGGGCA<br>GCCTGACCCACCACATCAACAACATGAAGCCCAGCTTCACCCGCGAGAA<br>CACCCTGATGTTCATGCACCTGAGCCCCATCCTGCTGCTGAGCCTGAACC<br>CCGACATCATCACCGGCTTCAGCAGCTAAGAGCACTGGGACGCCCACCG<br>CCCCTTTCCCTCCGCTGCCAGGCGAGCATGTTGTGGTAATTCTGGAACAC<br>AAGAAGAGAAATTGCTGGGTTTAGAACAAGATTATAAACGAATTCGGTGC<br>TCAGTGATCACTTGACAGTTTTTTTTTTTTAAATATTACCCAAAATGCTC<br>CCCAAATAAGAAATGCATCAGCTCAGTCAGTAATACAAAAAAGGAATTAT<br>TTTTCCCTTTGAGGGTCTTTTATACATCTCTCCTCCAACCCCACCCTCTAT<br>TCTGTTTCTTCCTCCTCACATGGGGGTACACATACACAGCTTCCTCTTTTG<br>GTTCCATCCTTACCACCACACCACACGCACACTCCACATGCCCAGCAGAG<br>TGGCACTTGGTGGCCAGAAAGTGTGAGCCTCATGATCTGCTGTCTGTAGT<br>TCTGTGAGCTCAGGTCCCTCAAAGGCCTCGGAGCACCCCCTTCCTTGTG<br>ACTGAGCCAGGGCCTGCATTTTTGGTTTTCCCCACCCCACACATTCTCAA<br>CCATAGTCCTTCTAACAATACCAATAGCTAGGACCCGGCTGCTGTGCACT<br>GGGACTGGGGATTCCACATGTTTGCCTTGGGAGTCTCAAGCTGGACTGC<br>CAGCCCCTGTCCTCCCTTCACCCCCATTGCGTATGAGCATTTCAGAACTC<br>CAAGGAGTCACAGGCATCTTTATAGTTCACGTTAACATATAGACACTGTTG<br>GAAGCAGTTCCTTCTAAAAGGGTAGCCCTGGACTTAATACCAGCCGGATA<br>CCTCTGGCCCCACCCCATTACTGTACCTCTGGAGTCACTACTGTGGGTC<br>GCCACTCCTCTGCTACACAGCACGGCTTTTTCAAGGCTGTATTGAGAAGG<br>GAAGTTAGGAAGAAGGGTGTGCTGGGCTAACCAGCCCACAGAGCTCACA<br>TTCCTGTCCCTTGGGTGAAAAATACATGTCCATCCTGATATCTCCTGAATT<br>CAGAAATTAGCCTCCACATGTGCAATGGCTTTAAGAGCCAGAAGCAGGGT<br>TCTGGGAATTTTGCAAGTTACCTGTGGCCAGGTGTGGTCTCGGTTACCAA<br>ATACGGTTACCTGCAGCTTTTTAGTCCTTTGTGCTCCCACGGGTCTACAG<br>AGTCCCATCTGCCCAAAGGTCTTGAAGCTTGACAGGATGTTTTCGATTAC |

TABLE 1-continued nucleic acid and polypeptide sequences and SEQ ID NOs

| SEQ ID NO: | description | sequence |
|---|---|---|
| | | TCAGTCTCCCAGGGCACTACTGGTCCGTAGGATTCGATTGGTCGGGGTA<br>GGAGAGTTAAACAACATTTAAACAGAGTTCTCTCAAAAATGTCTAAAGGGA<br>TTGTAGGTAGATAACATCCAATCACTGTTTGCACTTATCTGAAATCTTCCC<br>TCTTGGCTGCCCCAGGTATTTACTGTGGAGAACATTGCATAGGAATGTC<br>TGGAAAAAGCTTCTACAACTTGTTACAGCCTTCACATTTGTAGAAGCTTT |
| 76 | OPA1-opt_ND4*-3'UTR* | GTGCTGCCCGCCTAGAAAGGGTGAAGTGGTTGTTTCCGTGACGGACTGA<br>GTACGGGTGCCTGTCAGGCTCTTGCGGAAGTCCATGCGCCATTGGGAGG<br>GCCTCGGCCGCGGCTCTGTGCCCTTGCTGCTGAGGGCCACTTCCTGGGT<br>CATTCCTGGACCGGGAGCCGGGCTGGGGCTCACACGGGGGCTCCCGCG<br>TGGCCGTCTCGGCGCCTGCGTGACCTCCCCGCCGGCGGGATGTGGCGA<br>CTACGTCGGGCCGCTGTGGCCTGATGCTGAAGCTGATCGTGCCCACCAT<br>CATGCTGCTGCCCCTGACCTGGCTGAGCAAGAAGCACATGATCTGGATC<br>AACACCACCACCCACAGCCTGATCATCAGCATCATCCCCCTGCTGTTCTT<br>CAACCAGATCAACAACAACCTGTTCAGCTGCAGCCCCACCTTCAGCAGCG<br>ACCCCCTGACCACCCCCCTGCTGATGCTGACCACCTGGCTGCTGCCCCT<br>GACCATCATGGCCAGCCAGCGCCACCTGAGCAGCGAGCCCTGAGCCG<br>CAAGAAGCTGTACCTGAGCATGCTGATCAGCCTGCAGATCAGCCTGATCA<br>TGACCTTCACCGCCACCGAGCTGATCATGTTCTACATCTTCTTCGAGACC<br>ACCCTGATCCCCACCCTGGCCATCATCACCCGCTGGGGCAACCAGCCCG<br>AGCGCCTGAACGCCGGCACCTACTTCCTGTTCTACACCCTGGTGGGCAG<br>CCTGCCCCTGCTGATCGCCCTGATCTACACCCACAACACCCTGGGCAGC<br>CTGAACATCCTGCTGCTGACCCTGACCGCCCAGGAGCTGAGCAACAGCT<br>GGGCCAACAACCTGATGTGGCTGGCCTACACCATGGCCTTCATGGTGAA<br>GATGCCCCTGTACGGCCTGCACCTGTGGCTGCCCAAGGCCCACGTGGA<br>GGCCCCCATCGCCGGCAGCATGGTGCTGGCCGCCGTGCTGCTGAAGCT<br>GGGCGGCTACGGCATGATGCGCCTGACCCTGATCCTGAACCCCCTGACC<br>AAGCACATGGCCTACCCCTTCCTGGTGCTGAGCCTGTGGGGCATGATCA<br>TGACCAGCAGCATCTGCCTGCGCCAGACCGACCTGAAGAGCCTGATCGC<br>CTACAGCAGCATCAGCCACATGGCCCTGGTGGTGACCGCCATCCTGATC<br>CAGACCCCCTGGAGCTTCACCGGCGCCGTGATCCTGATGATCGCCCACG<br>GCCTGACCAGCAGCCTGCTGTTCTGCCTGGCCAACAGCAACTACGAGCG<br>CACCCACAGCCGCATCATGATCCTGAGCCAGGGCCTGCAGACCCTGCTG<br>CCCCTGATGGCCTTCTGGTGGCTGCTGGCCAGCCTGGCCAACCTGGCCC<br>TGCCCCCCACCATCAACCTGCTGGGCGAGCTGAGCGTGCTGGTGACCAC<br>CTTCAGCTGGAGCAACATCACCCTGCTGCTGACCGGCCTGAACATGCTG<br>GTGACCGCCCTGTACAGCCTGTACATGTTCACCACCACCCAGTGGGGCA<br>GCCTGACCCACCACATCAACAACATGAAGCCCAGCTTCACCCGCGAGAA<br>CACCCTGATGTTCATGCACCTGAGCCCCATCCTGCTGCTGAGCCTGAACC<br>CCGACATCATCACCGGCTTCAGCAGCTAAGAGCACTGGGACGCCCACCG<br>CCCCTTTCCCTCCGCTGCCAGGCGAGCATGTTGTGGTAATTCTGGAACAC<br>AAGAAGAGAAATTGCTGGGTTTAGAACAAGATTATAAACGAATTCGGTGC<br>TCAGTGATCACTTGACAGTTTTTTTTTTTTTAAATATTACCCAAAATGCTC<br>CCCAAATAAGAAATGCATCAGCTCAGTCAGTGAATACAAAAAAGGAATTAT<br>TTTTCCCTTTGAGGGTCTTTTATACATCTCTCCTCCAACCCCACCCTCTAT<br>TCTGTTTCTTCCTCCTCACATGGGGGTACACATACACAGCTTCCTCTTTTG<br>GTTCCATCCTTACCACCACACCACACGCACACTCCACATGCCCAGCAGAG<br>TGGCACTTGGTGGCCAGAAAGTGTGAGCCTCATGATCTGCTGTCTGTAGT<br>TCTGTGAGCTCAGGTCCCTCAAAGGCCTCGGAGCACCCCCTTCCTTGTG<br>ACTGAGCCAGGGCCTGCATTTTTGGTTTTCCCCACCCCACACATTCTCAA<br>CCATAGTCCTTCTAACAATACCAATAGCTAGGACCCGGCTGCTGTGCACT<br>GGGACTGGGGATTCCACATGTTTGCCTTGGGAGTCTCAAGCTGGACTGC<br>CA |
| 77 | OPA1-ND6-3'UTR | GTGCTGCCCGCCTAGAAAGGGTGAAGTGGTTGTTTCCGTGACGGACTGA<br>GTACGGGTGCCTGTCAGGCTCTTGCGGAAGTCCATGCGCCATTGGGAGG<br>GCCTCGGCCGCGGCTCTGTGCCCTTGCTGCTGAGGGCCACTTCCTGGGT<br>CATTCCTGGACCGGGAGCCGGGCTGGGGCTCACACGGGGGCTCCCGCG<br>TGGCCGTCTCGGCGCCTGCGTGACCTCCCCGCCGGCGGGATGTGGCGA<br>CTACGTCGGGCCGCTGTGGCCTGATGATGTATGCTTTGTTTCTGTTGAGT<br>GTGGGTTTAGTAATGGGGTTTGTGGGGTTTTCTTCTAAGCCTTCTCCTATT<br>TATGGGGGTTTAGTATTGATTGTTAGCGGTGTGGTCGGGTGTGTTATTATT<br>CTGAATTTTGGGGGAGGTTATATGGGTTTAATGGTTTTTTTAATTTATTTAG<br>GGGGAATGATGGTTGTCTTTGGATATACTACAGCGATGGCTATTGAGGAG<br>TATCCTGAGGCATGGGGGTCAGGGGTTGAGGTCTTGGTGAGTGTTTTAG<br>TGGGGTTAGCGATGGAGGTAGGATTGGTGCTGTGGGTGAAAGAGTATGA<br>TGGGGTGGTGGTTGTGGTAAACTTTAATAGTGTAGGAAGCTGGATGATTT<br>ATGAAGGAGAGGGGTCAGGGTTGATTCGGGAGGATCCTATTGGTGCGGG<br>GGCTTTGTATGATTATGGGCGTTGGTTAGTAGTAGTTACTGGTTGGACATT<br>GTTTGTTGGTGTATATATTGTAATTGAGATTGCTCGGGGGAATTAGGAGC<br>ACTGGGACGCCCACCGCCCCTTTCCCTCCGCTGCCAGGCGAGCATGTTG<br>TGGTAATTCTGGAACACAAGAAGAGAAATTGCTGGGTTTAGAACAAGATT<br>ATAAACGAATTCGGTGCTCAGTGATCACTTGACAGTTTTTTTTTTTTAAA<br>TATTACCCAAAATGCTCCCCAAATAAGAAATGCATCAGCTCAGTCAGTGAA |

TABLE 1-continued nucleic acid and polypeptide sequences and SEQ ID NOs

| SEQ ID NO: | description | sequence |
|---|---|---|
| | | TACAAAAAAGGAATTATTTTTCCCTTTGAGGGTCTTTTATACATCTCTCCTC
CAACCCCACCCTCTATTCTGTTTCTTCCTCCTCACATGGGGGTACACATAC
ACAGCTTCCTCTTTTGGTTCCATCCTTACCACCACACCACACGCACACTC
CACATGCCCAGCAGAGTGGCACTTGGTGGCCAGAAAGTGTGAGCCTCAT
GATCTGCTGTCTGTAGTTCTGTGAGCTCAGGTCCCTCAAAGGCCTCGGAG
CACCCCCTTCCTTGTGACTGAGCCAGGGCCTGCATTTTTGGTTTTCCCCA
CCCCACACATTCTCAACCATAGTCCTTCTAACAATACCAATAGCTAGGACC
CGGCTGCTGTGCACTGGGACTGGGGATTCCACATGTTTGCCTTGGGAGT
CTCAAGCTGGACTGCCAGCCCCTGTCCTCCCTTCACCCCCATTGCGTATG
AGCATTTCAGAACTCCAAGGAGTCACAGGCATCTTTATAGTTCACGTTAAC
ATATAGACACTGTTGGAAGCAGTTCCTTCTAAAAGGGTAGCCCTGGACTT
AATACCAGCCGGATACCTCTGGCCCCCACCCCATTACTGTACCTCTGGAG
TCACTACTGTGGGTCGCCACTCCTCTGCTACACAGCACGGCTTTTTCAAG
GCTGTATTGAGAAGGGAAGTTAGGAAGAAGGGTGTGCTGGGCTAACCAG
CCCACAGAGCTCACATTCCTGTCCCTTGGGTGAAAAATACATGTCCATCC
TGATATCTCCTGAATTCAGAAATTAGCCTCCACATGTGCAATGGCTTTAAG
AGCCAGAAGCAGGGTTCTGGGAATTTTGCAAGTTACCTGTGGCCAGGTG
TGGTCTCGGTTACCAAATACGGTTACCTGCAGCTTTTTAGTCCTTTGTGCT
CCCACGGGTCTACAGAGTCCCATCTGCCCAAAGGTCTTGAAGCTTGACA
GGATGTTTTCGATTACTCAGTCTCCCAGGGCACTACTGGTCCGTAGGATT
CGATTGGTCGGGGTAGGAGAGTTAAACAACATTTAAACAGAGTTCTCTCA
AAAATGTCTAAAGGGATTGTAGGTAGATAACATCCAATCACTGTTTGCACT
TATCTGAAATCTTCCCTCTTGGCTGCCCCCAGGTATTTACTGTGGAGAAC
ATTGCATAGGAATGTCTGGAAAAAAGCTTCTACAACTTGTTACAGCCTTCAC
ATTTGTAGAAGCTTT |
| 78 | OPA1-ND6-3'UTR* | GTGCTGCCCGCCTAGAAAGGGTGAAGTGGTTGTTTCCGTGACGGACTGA
GTACGGGTGCCTGTCAGGCTCTTGCGGAAGTCCATGCGCCATTGGGAGG
GCCTCGGCCGCGGCTCTGTGCCCTTGCTGCTGAGGGCCACTTCCTGGGT
CATTCCTGGACCGGGAGCCGGGCTGGGGCTCACACGGGGCTCCCGCG
TGGCCGTCTCGGCGCCTGCGTGACCTCCCCGCCGGCGGGATGTGGCGA
CTACGTCGGGCCGCTGTGGCCTGATGATGTATGCTTTGTTTCTGTTGAGT
GTGGGTTTAGTAATGGGGTTTGTGGGGTTTTCTTCTAAGCCTTCTCCTATT
TATGGGGGTTTAGTATTGATTGTTAGCGGTGTGGTCGGGTGTGTTATTATT
CTGAATTTTGGGGGAGGTTATATGGGTTTAATGGTTTTTTTAATTTATTTAG
GGGGAATGATGGTTGTCTTTGGATATACTACAGCGATGGCTATTGAGGAG
TATCCTGAGGCATGGGGGTCAGGGGTTGAGGTCTTGGTGAGTGTTTTAG
TGGGGTTAGCGATGGAGGTAGGATTGGTGCTGTGGGTGAAAAGAGTATGA
TGGGGTGGTGGTTGTGGTAAACTTTAATAGTGTAGGAAGCTGGATGATTT
ATGAAGGAGAGGGGTCAGGGTTGATTCGGGAGGATCCTATTGGTGCGGG
GGCTTTGTATGATTATGGGCGTTGGTTAGTAGTAGTTACTGGTTGGACATT
GTTTGTTGGTGTATATATTGTAATTGAGATTGCTCGGGGGAATTAGGAGC
ACTGGGACGCCCACCGCCCCTTTCCCTCCGCTGCCAGGCGAGCATGTTG
TGGTAATTCTGGAACACAAGAAGAGAAATTGCTGGGTTTAGAACAAGATT
ATAAACGAATTCGGTGCTCAGTGATCACTTGACAGTTTTTTTTTTTTTTAAA
TATTACCCAAAATGCTCCCCAAATAAGAAATGCATCAGCTCAGTCAGTGAA
TACAAAAAAGGAATTATTTTTCCCTTTGAGGGTCTTTTATACATCTCTCCTC
CAACCCCACCCTCTATTCTGTTTCTTCCTCCTCACATGGGGGTACACATAC
ACAGCTTCCTCTTTTGGTTCCATCCTTACCACCACACCACACGCACACTC
CACATGCCCAGCAGAGTGGCACTTGGTGGCCAGAAAGTGTGAGCCTCAT
GATCTGCTGTCTGTAGTTCTGTGAGCTCAGGTCCCTCAAAGGCCTCGGAG
CACCCCCTTCCTTGTGACTGAGCCAGGGCCTGCATTTTTGGTTTTCCCCA
CCCCACACATTCTCAACCATAGTCCTTCTAACAATACCAATAGCTAGGACC
CGGCTGCTGTGCACTGGGACTGGGGATTCCACATGTTTGCCTTGGGAGT
CTCAAGCTGGACTGCCA |
| 79 | OPA1-opt_ND6-3'UTR | GTGCTGCCCGCCTAGAAAGGGTGAAGTGGTTGTTTCCGTGACGGACTGA
GTACGGGTGCCTGTCAGGCTCTTGCGGAAGTCCATGCGCCATTGGGAGG
GCCTCGGCCGCGGCTCTGTGCCCTTGCTGCTGAGGGCCACTTCCTGGGT
CATTCCTGGACCGGGAGCCGGGCTGGGGCTCACACGGGGCTCCCGCG
TGGCCGTCTCGGCGCCTGCGTGACCTCCCCGCCGGCGGGATGTGGCGA
CTACGTCGGGCCGCTGTGGCCTGATGATGTACGCCCTGTTCCTGCTGAG
CGTGGGCCTGGTGATGGGCTTCGTGGGCTTCAGCAGCAAGCCCAGCCC
CATCTACGGCGGCCTGGTGCTGATCGTGAGCGGCGTGGTGGGCTGCGT
GATCATCCTGAACTTCGGCGGCGGCTACATGGGCCTGATGGTGTTCCTG
ATCTACCTGGGCGGCATGATGGTGGTGTTCGGCTACACCACCGCCATGG
CCATCGAGGAGTACCCCGAGGCCTGGGGCAGCGGCGTGGAGGTGCTGG
TGAGCGTGCTGGTGGGCCTGGCCATGGAGGTGGGCCTGGTGCTGTGGG
TGAAGGAGTACGACGGCGTGGTGGTGGTGAGCTTCAACAGCGTGGC
CAGCTGGATGATCTACGAGGGCGAGGGCAGCGGCCTGATCCGCGAGGA
CCCCATCGGCGCCGGCGCCCTGTACGACTACGGCCGCTGCTGGTGGT
GGTGACCGGCTGGACCCTGTTCGTGGGCGTGTACATCGTGATCGAGATC
GCCCGCGGCAACTAAGAGCACTGGGACGCCCACCGCCCCTTTCCCTCCG
CTGCCAGGCGAGCATGTTGTGGTAATTCTGGAACACAAGAAGAGAAATTG |

TABLE 1-continued nucleic acid and polypeptide sequences and SEQ ID NOs

| SEQ ID NO: | description | sequence |
|---|---|---|
| | | CTGGGTTTAGAACAAGATTATAAACGAATTCGGTGCTCAGTGATCACTTGA<br>CAGTTTTTTTTTTTTTAAATATTACCCAAAATGCTCCCCAAATAAGAAATG<br>CATCAGCTCAGTCAGTGAATACAAAAAAGGAATTATTTTTCCCTTTGAGGG<br>TCTTTTATACATCTCTCCTCCAACCCCACCCTCTATTCTGTTTCTTCCTCCT<br>CACATGGGGGTACACATACACAGCTTCCTCTTTTGGTTCCATCCTTACCA<br>CCACACCACACGCACACTCCACATGCCCAGCAGAGTGGCACTTGGTGGC<br>CAGAAAGTGTGAGCCTCATGATCTGCTGTCTGTAGTTCTGTGAGCTCAGG<br>TCCCTCAAAGGCCTCGGAGCACCCCCTTCCTTGTGACTGAGCCAGGGCC<br>TGCATTTTTGGTTTTCCCCACCCCACACATTCTCAACCATAGTCCTTCTAA<br>CAATACCAATAGCTAGGACCCGGCTGCTGTGCACTGGGACTGGGGATTC<br>CACATGTTTGCCTTGGGAGTCTCAAGCTGGACTGCCAGCCCCTGTCCTCC<br>CTTCACCCCCATTGCGTATGAGCATTTCAGAACTCCAAGGAGTCACAGGC<br>ATCTTTATAGTTCACGTTAACATATAGACACTGTTGGAAGCAGTTCCTTCT<br>AAAAGGGTAGCCCTGGACTTAATACCAGCCGGATACCTCTGGCCCCCAC<br>CCCATTACTGTACCTCTGGAGTCACTACTGTGGGTCGCCACTCCTCTGCT<br>ACACAGCACGGCTTTTTCAAGGCTGTATTGAGAAGGGAAGTTAGGAAGAA<br>GGGTGTGCTGGGCTAACCAGCCCACAGAGCTCACATTCCTGTCCCTTGG<br>GTGAAAAATACATGTCCATCCTGATATCTCCTGAATTCAGAAATTAGCCTC<br>CACATGTGCAATGGCTTTAAGAGCCAGAAGCAGGGTTCTGGGAATTTTGC<br>AAGTTACCTGTGGCCAGGTGTGGTCTCGGTTACCAAATACGGTTACCTGC<br>AGCTTTTTAGTCCTTTGTGCTCCCACGGGTCTACAGAGTCCCATCTGCCC<br>AAAGGTCTTGAAGCTTGACAGGATGTTTTCGATTACTCAGTCTCCCAGGG<br>CACTACTGGTCCGTAGGATTCGATTGGTCGGGGTAGGAGAGTTAAACAAC<br>ATTTAAACAGAGTTCTCTCAAAAATGTCTAAAGGGATTGTAGGTAGATAAC<br>ATCCAATCACTGTTTGCACTTATCTGAAATCTTCCCTCTTGGCTGCCCCCA<br>GGTATTTACTGTGGAGAACATTGCATAGGAATGTCTGGAAAAAGCTTCTA<br>CAACTTGTTACAGCCTTCACATTTGTAGAAGCTTT |
| 80 | OPA1-<br>opt_ND6-<br>3'UTR* | GTGCTGCCCGCCTAGAAAGGGTGAAGTGGTTGTTTCCGTGACGGACTGA<br>GTACGGGTGCCTGTCAGGCTCTTGCGGAAGTCCATGCGCCATTGGGAGG<br>GCCTCGGCCGCGGCTCTGTGCCCTTGCTGCTGAGGGCCACTTCCTGGGT<br>CATTCCTGGACCGGGAGCCGGGCTGGGGCTCACACGGGGGCTCCCGCG<br>TGGCCGTCTCGGCGCCTGCGTGACCTCCCCGCCGGCGGGATGTGGCGA<br>CTACGTCGGGCCGCTGTGGCCTGATGATGTACGCCCTGTTCCTGCTGAG<br>CGTGGGCCTGGTGATGGGCTTCGTGGGCTTCAGCAGCAAGCCCAGCCC<br>CATCTACGGCGGCCTGGTGCTGATCGTGAGCGGCGTGGTGGGCTGCGT<br>GATCATCCTGAACTTCGGCGGCGGCTACATGGGCCTGATGGTGTTCCTG<br>ATCTACCTGGGCGGCATGATGGTGGTGTTCGGCTACACCACCGCCATGG<br>CCATCGAGGAGTACCCCGAGGCCTGGGGCAGCGGCGTGGAGGTGCTGG<br>TGAGCGTGCTGGTGGGCCTGGCCATGGAGGTGGGCCTGGTGCTGTGGG<br>TGAAGGAGTACGACGCGTGGTGGTGGTGGTGAACTTCAACAGCGTGGG<br>CAGCTGGATGATCTACGAGGGCGAGGGCAGCGGCCTGATCCGCGAGGA<br>CCCCATCGGCGCCGGCGCCCTGTACGACTACGGCCGCTGGCTGGTGGT<br>GGTGACCGGCTGGACCCTGTTCGTGGGCGTGTACATCGTGATCGAGATC<br>GCCCGCGGCAACTAAGAGCACTGGGACGCCCACCGCCCCTTTCCCTCCG<br>CTGCCAGGCGAGCATGTTGTGGTAATTCTGGAACACAAGAAGAGAAATTG<br>CTGGGTTTAGAACAAGATTATAAACGAATTCGGTGCTCAGTGATCACTTGA<br>CAGTTTTTTTTTTTTTAAATATTACCCAAAATGCTCCCCAAATAAGAAATG<br>CATCAGCTCAGTCAGTGAATACAAAAAAGGAATTATTTTTCCCTTTGAGGG<br>TCTTTTATACATCTCTCCTCCAACCCCACCCTCTATTCTGTTTCTTCCTCCT<br>CACATGGGGGTACACATACACAGCTTCCTCTTTTGGTTCCATCCTTACCA<br>CCACACCACACGCACACTCCACATGCCCAGCAGAGTGGCACTTGGTGGC<br>CAGAAAGTGTGAGCCTCATGATCTGCTGTCTGTAGTTCTGTGAGCTCAGG<br>TCCCTCAAAGGCCTCGGAGCACCCCCTTCCTTGTGACTGAGCCAGGGCC<br>TGCATTTTTGGTTTTCCCCACCCCACACATTCTCAACCATAGTCCTTCTAA<br>CAATACCAATAGCTAGGACCCGGCTGCTGTGCACTGGGACTGGGGATTC<br>CACATGTTTGCCTTGGGAGTCTCAAGCTGGACTGCCA |
| 81 | OPA1-<br>ND1-<br>3'UTR | GTGCTGCCCGCCTAGAAAGGGTGAAGTGGTTGTTTCCGTGACGGACTGA<br>GTACGGGTGCCTGTCAGGCTCTTGCGGAAGTCCATGCGCCATTGGGAGG<br>GCCTCGGCCGCGGCTCTGTGCCCTTGCTGCTGAGGGCCACTTCCTGGGT<br>CATTCCTGGACCGGGAGCCGGGCTGGGGCTCACACGGGGGCTCCCGCG<br>TGGCCGTCTCGGCGCCTGCGTGACCTCCCCGCCGGCGGGATGTGGCGA<br>CTACGTCGGGCCGCTGTGGCCTGATGCCCATGGCCAACCTCCTACTCCT<br>CATTGTACCCATTCTAATCGCAATGGCATTCCTAATGCTTACCGAACAGAA<br>AATTCTAGGCTATATGCAACTACGCAAAGGCCCCAACGTTGTAGGCCCCT<br>ACGGGCTACTACAACCCTTCGCTGACGCCATGAAACTCTTCACCAAAGAG<br>CCCCTAAAACCCGCCACATCTACCATCACCCTCTACATCACCGCCCCGAC<br>CTTAGCTCTCACCATCGCTCTTCTACTATGGACCCCCCTCCCCATGCCCA<br>ACCCCCTGGTCAACCTCAACCTAGGCCTCCTATTTATTCTAGCCACCTCTA<br>GCCTAGCCGTTTACTCAATCCTCTGGTCAGGGTGGGCATCAAACTCAAAC<br>TACGCCCTGATCGGCGCACTGCGAGCAGTAGCCCAAACAATCTCATATGA<br>AGTCACCCTAGCCATCATTCTACTATCAACATTACTAATGAGTGGCTCCTT<br>TAACCTCTCCACCCTTATCACAACACAAGAACACCTCTGGTTACTCCTGCC

TABLE 1-continued nucleic acid and polypeptide sequences and SEQ ID NOs

| SEQ ID NO: | description | sequence |
|---|---|---|
| | | ATCATGGCCCTTGGCCATGATGTGGTTTATCTCCACACTAGCAGAGACCA<br>ACCGAACCCCCTTCGACCTTGCCGAAGGGGAGTCCGAACTAGTCTCAGG<br>CTTCAACATCGAATACGCCGCAGGCCCCTTCGCCCTATTCTTCATGGCCG<br>AATACACAAACATTATTATGATGAACACCCTCACCACTACAATCTTCCTAG<br>GAACAACATATGACGCACTCTCCCCTGAACTCTACACAACATATTTTGTCA<br>CCAAGACCCTACTTCTAACCTCCCTGTTCTTATGGATTCGAACAGCATACC<br>CCCGATTCCGCTACGACCAACTCATGCACCTCCTATGGAAAAACTTCCTA<br>CCACTCACCCTAGCATTACTTATGTGGTATGTCTCCATGCCCATTACAATC<br>TCCAGCATTCCCCCTCAAACCTAAGAGCACTGGGACGCCCACCGCCCCT<br>TTCCCTCCGCTGCCAGGCGAGCATGTTGTGGTAATTCTGGAACACAAGAA<br>GAGAAATTGCTGGGTTTAGAACAAGATTATAAACGAATTCGGTGCTCAGT<br>GATCACTTGACAGTTTTTTTTTTTTAAATATTACCCAAAATGCTCCCCAA<br>ATAAGAAATGCATCAGCTCAGTCAGTGAATACAAAAAAGGAATTATTTTTC<br>CCTTTGAGGGTCTTTTATACATCTCTCCTCCAACCCCACCCTCTATTCTGT<br>TTCTTCCTCCTCACATGGGGGTACACATACACAGCTTCCTCTTTTGGTTCC<br>ATCCTTACCACCACACCACACGCACACTCCACATGCCCAGCAGAGTGGC<br>ACTTGGTGGCCAGAAAGTGTGAGCCTCATGATCTGCTGTCTGTAGTTCTG<br>TGAGCTCAGGTCCCTCAAAGGCCTCGGAGCACCCCCTTCCTTGTGACTG<br>AGCCAGGGCCTGCATTTTTGGTTTTCCCCACCCCACACATTCTCAACCAT<br>AGTCCTTCTAACAATACCAATAGCTAGGACCCGGCTGCTGTGCACTGGGA<br>CTGGGGATTCCACATGTTTGCCTTGGGAGTCTCAAGCTGGACTGCCAGC<br>CCCTGTCCTCCCTTCACCCCCATTGCGTATGAGCATTTCAGAACTCCAAG<br>GAGTCACAGGCATCTTTATAGTTCACGTTAACATATAGACACTGTTGGAAG<br>CAGTTCCTTCTAAAAGGGTAGCCCTGGACTTAATACCAGCCGGATACCTC<br>TGGCCCCCACCCCATTACTGTACCTCTGGAGTCACTACTGTGGGTCGCCA<br>CTCCTCTGCTACACAGCACGGCTTTTTCAAGGCTGTATTGAGAAGGGAAG<br>TTAGGAAGAAGGGTGTGCTGGGCTAACCAGCCCACAGAGCTCACATTCC<br>TGTCCCTTGGGTGAAAAATACATGTCCATCCTGATATCTCCTGAATTCAGA<br>AATTAGCCTCCACATGTGCAATGGCTTTAAGAGCCAGAAGCAGGGTTCTG<br>GGAATTTTGCAAGTTACCTGTGGCCAGGTGTGGTCTCGGTTACCAAATAC<br>GGTTACCTGCAGCTTTTTAGTCCTTTGTGCTCCCACGGGTCTACAGAGTC<br>CCATCTGCCCAAAGGTCTTGAAGCTTGACAGGATGTTTTCGATTACTCAG<br>TCTCCCAGGGCACTACTGGTCCGTAGGATTCGATTGGTCGGGGTAGGAG<br>AGTTAAACAACATTTAAACAGAGTTCTCTCAAAAATGTCTAAAGGGATTGT<br>AGGTAGATAACATCCAATCACTGTTTGCACTTATCTGAAATCTTCCCTCTT<br>GGCTGCCCCCAGGTATTTACTGTGGAGAACATTGCATAGGAATGTCTGGA<br>AAAAGCTTCTACAACTTGTTACAGCCTTCACATTTGTAGAAGCTTT |
| 82 | OPA1-<br>ND1-<br>3'UTR* | GTGCTGCCCGCCTAGAAAGGGTGAAGTGGTTGTTTCCGTGACGGACTGA<br>GTACGGGTGCCTGTCAGGCTCTTGCGGAAGTCCATGCGCCATTGGGAGG<br>GCCTCGGCCGCGGCTCTGTGCCCTTGCTGCTGAGGGCCACTTCCTGGGT<br>CATTCCTGGACCGGGAGCCGGGCTGGGGCTCACACGGGGGCTCCCGCG<br>TGGCCGTCTCGGCGCCTGCGTGACCTCCCCGCCGGCGGGATGTGGCGA<br>CTACGTCGGGCCGCTGTGGCCTGATGCCCATGGCCAACCTCCTACTCCT<br>CATTGTACCCATTCTAATCGCAATGGCATTCCTAATGCTTACCGAACGAAA<br>AATTCTAGGCTATATGCAACTACGCAAAGGCCCCAACGTTGTAGGCCCCT<br>ACGGGCTACTACAACCCTTCGCTGACGCCATGAAACTCTTCACCAAAGAG<br>CCCCTAAAACCCGCCACATCTACCATCACCCTCTACATCACCGCCCCGAC<br>CTTAGCTCTCACCATCGCTCTTCTACTATGGACCCCCCTCCCCATGCCCA<br>ACCCCCTGGTCAACCTCAACCTAGGCCTCCTATTTATTCTAGCCACCTCTA<br>GCCTAGCCGTTTACTCAATCCTCTGGTCAGGGTGGGCATCAAACTCAAAC<br>TACGCCCTGATCGGCGCACTGCGAGCAGTAGCCCAAACAATCTCATATGA<br>AGTCACCCTAGCCATCATTCTACTATCAACATTACTAATGAGTGGCTCCTT<br>TAACCTCTCCACCCTTATCACAACACAAGAACACCTCTGGTTACTCCTGCC<br>ATCATGGCCCTTGGCCATGATGTGGTTTATCTCCACACTAGCAGAGACCA<br>ACCGAACCCCCTTCGACCTTGCCGAAGGGGAGTCCGAACTAGTCTCAGG<br>CTTCAACATCGAATACGCCGCAGGCCCCTTCGCCCTATTCTTCATGGCCG<br>AATACACAAACATTATTATGATGAACACCCTCACCACTACAATCTTCCTAG<br>GAACAACATATGACGCACTCTCCCCTGAACTCTACACAACATATTTTGTCA<br>CCAAGACCCTACTTCTAACCTCCCTGTTCTTATGGATTCGAACAGCATACC<br>CCCGATTCCGCTACGACCAACTCATGCACCTCCTATGGAAAAACTTCCTA<br>CCACTCACCCTAGCATTACTTATGTGGTATGTCTCCATGCCCATTACAATC<br>TCCAGCATTCCCCCTCAAACCTAAGAGCACTGGGACGCCCACCGCCCCT<br>TTCCCTCCGCTGCCAGGCGAGCATGTTGTGGTAATTCTGGAACACAAGAA<br>GAGAAATTGCTGGGTTTAGAACAAGATTATAAACGAATTCGGTGCTCAGT<br>GATCACTTGACAGTTTTTTTTTTTTAAATATTACCCAAAATGCTCCCCAA<br>ATAAGAAATGCATCAGCTCAGTCAGTGAATACAAAAAAGGAATTATTTTTC<br>CCTTTGAGGGTCTTTTATACATCTCTCCTCCAACCCCACCCTCTATTCTGT<br>TTCTTCCTCCTCACATGGGGGTACACATACACAGCTTCCTCTTTTGGTTCC |

TABLE 1-continued nucleic acid and polypeptide sequences and SEQ ID NOs

| SEQ ID NO: | description | sequence |
|---|---|---|
|  |  | ATCCTTACCACCACACCACACGCACACTCCACATGCCCAGCAGAGTGGC<br>ACTTGGTGGCCAGAAAGTGTGAGCCTCATGATCTGCTGTCTGTAGTTCTG<br>TGAGCTCAGGTCCCTCAAAGGCCTCGGAGCACCCCCTTCCTTGTGACTG<br>AGCCAGGGCCTGCATTTTTGGTTTTCCCCACCCCACACATTCTCAACCAT<br>AGTCCTTCTAACAATACCAATAGCTAGGACCCGGCTGCTGTGCACTGGGA<br>CTGGGGATTCCACATGTTTGCCTTGGGAGTCTCAAGCTGGACTGCCA |
| 83 | OPA1-opt_ND1-3'UTR | GTGCTGCCCGCCTAGAAAGGGTGAAGTGGTTGTTTCCGTGACGGACTGA<br>GTACGGGTGCCTGTCAGGCTCTTGCGGAAGTCCATGCGCCATTGGGAGG<br>GCCTCGGCCGCGGCTCTGTGCCCTTGCTGCTGAGGGCCACTTCCTGGGT<br>CATTCCTGGACCGGGAGCCGGGCTGGGGCTCACACGGGGGCTCCCGCG<br>TGGCCGTCTCGGCGCCTGCGTGACCTCCCCGCCGGCGGGATGTGGCGA<br>CTACGTCGGGCCGCTGTGGCCTGATGCCCATGGCCAACCTGCTGCTGCT<br>GATCGTGCCCATCCTGATCGCCATGGCCTTCCTGATGCTGACCGAGCGC<br>AAGATCCTGGGCTACATGCAGCTGCGCAAGGGCCCCAACGTGGTGGGC<br>CCCTACGGCCTGCTGCAGCCCTTCGCCGACGCCATGAAGCTGTTCACCA<br>AGGAGCCCCTGAAGCCCGCCACCAGCACCATCACCCTGTACATCACCGC<br>CCCCACCCTGGCCCTGACCATCGCCCTGCTGCTGTGGACCCCCCTGCCC<br>ATGCCCAACCCCCTGGTGAACCTGAACCTGGGCCTGCTGTTCATCCTGG<br>CCACCAGCAGCCTGGCCGTGTACAGCATCCTGTGGAGCGGCTGGGCCA<br>GCAACAGCAACTACGCCCTGATCGGCGCCCTGCGCGCCGTGGCCCAGA<br>CCATCAGCTACGAGGTGACCCTGGCCATCATCCTGCTGAGCACCCTGCT<br>GATGAGCGGCAGCTTCAACCTGAGCACCCTGATCACCACCCAGGAGCAC<br>CTGTGGCTGCTGCTGCCCAGCTGGCCCCTGGCCATGATGTGGTTCATCA<br>GCACCCTGGCCGAGACCAACCGCACCCCCTTCGACCTGGCCGAGGGCG<br>AGAGCGAGCTGGTGAGCGGCTTCAACATCGAGTACGCCGCCGGCCCCTT<br>CGCCCTGTTCTTCATGGCCGAGTACACCAACATCATCATGATGAACACCC<br>TGACCACCACCATCTTCCTGGGCACCACCTACGACGCCCTGAGCCCCGA<br>GCTGTACACCACCTACTTCGTGACCAAGACCCTGCTGCTGACCAGCCTGT<br>TCCTGTGGATCCGCACCGCCTACCCCCGCTTCCGCTACGACCAGCTGAT<br>GCACCTGCTGTGGAAGAACTTCCTGCCCCTGACCCTGGCCCTGCTGATG<br>TGGTACGTGAGCATGCCCATCACCATCAGCAGCATCCCCCCCCAGACCT<br>AAGAGCACTGGGACGCCCACCGCCCCTTTCCCTCCGCTGCCAGGCGAG<br>CATGTTGTGGTAATTCTGGAACACAAGAAGAGAAATTGCTGGGTTTAGAA<br>CAAGATTATAAACGAATTCGGTGCTCAGTGATCACTTGACAGTTTTTTTTT<br>TTTTAAATATTACCCAAAATGCTCCCCAAATAAGAAATGCATCAGCTCAGT<br>CAGTGAATACAAAAAAGGAATTATTTTTCCCTTTGAGGGTCTTTTATACATC<br>TCTCCTCCAACCCCACCCTCTATTCTGTTTCTTCCTCCTCACATGGGGGTA<br>CACATACACAGCTTCCTCTTTTGGTTCCATCCTTACCACCACACCACACGC<br>ACACTCCACATGCCCAGCAGAGTGGCACTTGGTGGCCAGAAAGTGTGAG<br>CCTCATGATCTGCTGTCTGTAGTTCTGTGAGCTCAGGTCCCTCAAAGGCC<br>TCGGAGCACCCCCTTCCTTGTGACTGAGCCAGGGCCTGCATTTTTGGTTT<br>TCCCCACCCCACACATTCTCAACCATAGTCCTTCTAACAATACCAATAGCT<br>AGGACCCGGCTGCTGTGCACTGGGACTGGGGATTCCACATGTTTGCCTT<br>GGGAGTCTCAAGCTGGACTGCCAGCCCCTGTCCTCCCTTCACCCCCATT<br>GCGTATGAGCATTTCAGAACTCCAAGGAGTCACAGGCATCTTTATAGTTC<br>ACGTTAACATATAGACACTGTTGGAAGCAGTTCCTTCTAAAAGGGTAGCC<br>CTGGACTTAATACCAGCCGGATACCTCTGGCCCCCACCCCATTACTGTAC<br>CTCTGGAGTCACTACTGTGGGTCGCCACTCCTCTGCTACACAGCACGGC<br>TTTTTCAAGGCTGTATTGAGAAGGGAAGTTAGGAAGAAGGGTGTGCTGGG<br>CTAACCAGCCCACAGAGCTCACATTCCTGTCCCTTGGGTGAAAAATACAT<br>GTCCATCCTGATATCTCCTGAATTCAGAAATTAGCCTCCACATGTGCAATG<br>GCTTTAAGAGCCAGAAGCAGGGTTCTGGGAATTTTGCAAGTTACCTGTGG<br>CCAGGTGTGGTCTCGGTTACCAAATACGGTTACCTGCAGCTTTTTAGTCC<br>TTTGTGCTCCCACGGGTCTACAGAGTCCCATCTGCCCAAAGGTCTTGAAG<br>CTTGACAGGATGTTTTCGATTACTCAGTCTCCCAGGGCACTACTGGTCCG<br>TAGGATTCGATTGGTCGGGTAGGAGAGTTAAACAACATTTAAACAGAGT<br>TCTCTCAAAAATGTCTAAAGGGATTGTAGGTAGATAACATCCAATCACTGT<br>TTGCACTTATCTGAAATCTTCCCTCTTGGCTGCCCCAGGTATTTACTGTG<br>GAGAACATTGCATAGGAATGTCTGGAAAAAGCTTCTACAACTTGTTACAG<br>CCTTCACATTTGTAGAAGCTTT |
| 84 | OPA1-opt_ND1-3'UTR* | GTGCTGCCCGCCTAGAAAGGGTGAAGTGGTTGTTTCCGTGACGGACTGA<br>GTACGGGTGCCTGTCAGGCTCTTGCGGAAGTCCATGCGCCATTGGGAGG<br>GCCTCGGCCGCGGCTCTGTGCCCTTGCTGCTGAGGGCCACTTCCTGGGT<br>CATTCCTGGACCGGGAGCCGGGCTGGGGCTCACACGGGGGCTCCCGCG<br>TGGCCGTCTCGGCGCCTGCGTGACCTCCCCGCCGGCGGGATGTGGCGA<br>CTACGTCGGGCCGCTGTGGCCTGATGCCCATGGCCAACCTGCTGCTGCT<br>GATCGTGCCCATCCTGATCGCCATGGCCTTCCTGATGCTGACCGAGCGC<br>AAGATCCTGGGCTACATGCAGCTGCGCAAGGGCCCCAACGTGGTGGGC<br>CCCTACGGCCTGCTGCAGCCCTTCGCCGACGCCATGAAGCTGTTCACCA<br>AGGAGCCCCTGAAGCCCGCCACCAGCACCATCACCCTGTACATCACCGC<br>CCCCACCCTGGCCCTGACCATCGCCCTGCTGCTGTGGACCCCCCTGCCC<br>ATGCCCAACCCCCTGGTGAACCTGAACCTGGGCCTGCTGTTCATCCTGG |

TABLE 1-continued nucleic acid and polypeptide sequences and SEQ ID NOs

| SEQ ID NO: | description | sequence |
|---|---|---|
| | | CCACCAGCAGCCTGGCCGTGTACAGCATCCTGTGGAGCGGCTGGGCCA GCAACAGCAACTACGCCCTGATCGGCGCCCTGCGCGCCGTGGCCCAGA CCATCAGCTACGAGGTGACCCTGGCCATCATCCTGCTGAGCACCCTGCT GATGAGCGGCAGCTTCAACCTGAGCACCCTGATCACCACCCAGGAGCAC CTGTGGCTGCTGCTGCCCAGCTGGCCCCTGGCCATGATGTGGTTCATCA GCACCCTGGCCGAGACCAACCGCACCCCCTTCGACCTGGCCGAGGGCG AGAGCGAGCTGGTGAGCGGCTTCAACATCGAGTACGCCGCCGGCCCCTT CGCCCTGTTCTTCATGGCCGAGTACACCAACATCATCATGATGAACACCC TGACCACCACCATCTTCCTGGGCACCACCTACGACGCCCTGAGCCCCGA GCTGTACACCACCTACTTCGTGACCAAGACCCTGCTGCTGACCAGCCTGT TCCTGTGGATCCGCACCGCCTACCCCCGCTTCCGCTACGACCAGCTGAT GCACCTGCTGTGGAAGAACTTCCTGCCCCTGACCCTGGCCCTGCTGATG TGGTACGTGAGCATGCCCATCACCATCAGCAGCATCCCCCCCCCAGACCT AA |
| | | GAGCACTGGGACGCCCACCGCCCCTTTCCCTCCGCTGCCAGGCGAGCAT GTTGTGGTAATTCTGGAACACAAGAAGAGAAATTGCTGGGTTTAGAACAA GATTATAAACGAATTCGGTGCTCAGTGATCACTTGACAGTTTTTTTTTTTT TAAATATTACCCAAAATGCTCCCCAAATAAGAAATGCATCAGCTCAGTCAG TGAATACAAAAAGGAATTATTTTTCCCTTTGAGGGTCTTTTATACATCTCT CCTCCAACCCCACCCTCTATTCTGTTTCTTCCTCCTCACATGGGGGTACA CATACACAGCTTCCTCTTTTGGTTCCATCCTTACCACCACACCACACGCAC ACTCCACATGCCCAGCAGAGTGGCACTTGGTGGCCAGAAAGTGTGAGCC TCATGATCTGCTGTCTGTAGTTCTGTGAGCTCAGGTCCCTCAAAGGCCTC GGAGCACCCCCTTCCTTGTGACTGAGCCAGGGCCTGCATTTTTGGTTTTC CCCACCCCACACATTCTCAACCATAGTCCTTCTAACAATACCAATAGCTAG GACCCGGCTGCTGTGCACTGGGACTGGGGATTCCACATGTTTGCCTTGG GAGTCTCAAGCTGGACTGCCA |
| 85 | β-actin-S primer | CGAGATCGTGCGGGACAT |
| 86 | β-actin-A primer | CAGGAAGGAGGGCTGGAAC |
| 87 | ND4-S primer | CTGCCTACGACAAACAGAC |
| 88 | ND4-A primer | AGTGCGTTCGTAGTTTGAG |
| 89 | ND6-F primer | ATGATGTATGCTTTGTTTCTG |
| 90 | ND6-R primer | CTAATTCCCCCGAGCAATCTC |
| 91 | ND6-S primer | AGTGTGGGTTTAGTAATG |
| 92 | ND6-A primer | TGCCTCAGGATACTCCTC |
| 93 | β-actin-F primer | CTCCATCCTGGCCTCGCTGT |
| 94 | β-actin-R primer | GCTGTCACCTTCACCGTTCC |
| 95 | ND6-F primer | GGGTTTTCTTCTAAGCCTTCTCC |
| 96 | ND6-R primer | CCATCATACTCTTTCACCCACAG |
| 97 | opt_ND6-F primer | CGCCTGCTGACCGGCTGCGT |
| 98 | opt_ND6-R | CCAGGCCTCGGGGTACTCCT |

TABLE 1-continued nucleic acid and polypeptide sequences and SEQ ID NOs

| SEQ ID NO: | description | sequence |
|---|---|---|
| 99 | ND1-F primer | ATGGCCGCATCTCCGCACACT |
| 100 | ND1-R primer | TTAGGTTTGAGGGGGAATGCT |
| 101 | ND1-F primer | AACCTCAACCTAGGCCTCCTA |
| 102 | ND1-R primer | TGGCAGGAGTAACCAGAGGTG |
| 103 | N1-F primer | AGGAGGCTCTGTCTGGTATCTTG |
| 104 | ND1-R primer | TTTTAGGGGCTCTTTGGTGAA |
| 105 | opt-ND1-F primer | GCCGCCTGCTGACCGGCTGCGT |
| 106 | opt-ND1-R primer | TGATGTACAGGGTGATGGTGCTGG |
| 107 | ND4-S primer | GCCAACAGCAACTACGAGC |
| 108 | ND4-A primer | TGATGTTGCTCCAGCTGAAG |
| 109 | opt-ND4-S primer | GCCTGACCCTGATCCTGAAC |
| 110 | opt-ND4-A primer | GTGCGCTCGTAGTTGCTGTT |
| 111 | hsACO2 | GGGCAGTGCCTCCCCGCCCCGCCGCTGGCGTCAAGTTCAGCTCCACGT GTGCCATCAGTGGATCCGATCCGTCCAGCCATGGCTTCCTATTCCAAGAT GGTGTGACCAGACATGCTTCCTGCTCCCCGCTTAGCCCACGGAGTGACT GTGGTTGTGGTGGGGGGGTTCTTAAAATAACTTTTTAGCCCCCGTCTTCC TATTTTGAGTTTGGTTCAGATCTTAAGCAGCTCCATGCAACTGTATTTATTT TTGATGACAAGACTCCCATCTAAAGTTTTTCTCCTGCCTGATCATTTCATT GGTGGCTGAAGGATTCTAGAGAACCTTTTGTTCTTGCAAGGAAAACAAGA ATCCAAAACCAGTGACTGTTCTGTGA |
| 112 | hsATP5B | GGGGTCTTTGTCCTCTGTACTGTCTCTCCTTGCCCCTAACCCAAAAAG CTTCATTTTTCTGTGTAGGCTGCACAAGAGCCTTGATTGAAGATATATTCT TTCTGAACAGTATTTAAGGTTTCCAATAAAATGTACACCCCTCAG TGTTGGGTCCAAGAAGGAATTTCTTTCCATCCCTGTGAGGCAATGGGTGG GAATGATAGGACAGGCAAAGAGAAGCTTCCTCAGGCTAGCAAAAATATCA TTTGATGTATTGATTAAAAAAGCACTTGCTTGATGTATCTTTGGCGTGTGT GCTACTCTCATCTGTGTGTATGTGTGTTGTGTGTGTGTGTGTGCATGC ACATATGTGTTCACTCTGCTACTTTGTAAGTTTTAGGCTAGGTTGCTTTAC CAGCTGTTTACTTCTTTTTTGTTGTTGTTTGAGACAAGGTTTCGCTCTGC CACCCTGGCTGGAGTGCAGTGGCGTGATCTTGGCTCACGGCAACCTCTG CCTCCTGGGGCTCAAGCAATTATCCCACCTCAGCCTCCTGAGCAGCTGG GACTACAGGTGCATGCCACAACACCTGGCTGATATTTGTATTTTTTGTAGA GACAGGATTTTGCCAAGTTGCCCAGGCTGGTCTTGAACTCCTAGGCTTAA GCAATCCACCCACCTTGGCCTCCTGAAGTGCCAGGATCACAGACGTGAG CCACTACACCCAGCCCAGCTGTTTACTTCTTTAACCATACTTTTGATTTTAT TTTTTGACCAAAATGAACTAACCCAGGTAATCTTCCAGGGACCGCAATTCC AGAACCTCATAGTATTTCTTCCATTTCCAGCAGCTGATTAGAAGTCCAGGA TCATGTGAAGTCAGGCAGGGTCACAGTTCCTGATGGCACATTATGGACAG AGAATTCCATTTTGTTTTCTAACCCATGATGAAAACCCACGTGAGTCAGTG TGTGAACAGGGATCATTAATTTTTTCCCCCTAGGTGGAAGGAAAAAGGCA CTTACTTTGCAGGTTACAGAAATTACTGGGAGAGGATATCGTCATAAAAAG AGCCAGGCCAAATTGGAATATTTTTGTGATCTGCATCATGATGCTGAAAAT |
| 113 | hsAK2 | AGCAATTATTTGGGAATTGGGTTTGAAAACTGAATTGTTGCCAGAGAATTA AACCAGGTGAAAGGTCCTTTTGAATTCAGATTGTTCTGAACATCCAGG CTGATCATCTGAGAGCAGTCAAATCTACTTCCCAAAAAGAGACCAGGGT AGGTTTATTTGCTTTTATTTTTAATGTTTGCCTGTGTTTCCAAGTGTGAACA AAACAGTGTGTGATCTATTCTTGGATTCATTTTGATCAGTATTTATTCAAAC CCAGTCTCTCTCCAGGACATAAAACTGAAATCAGATATGTTCTTTTTAAGC CCAAACCCTCTCCTTTCTAGATCCAACCCTTCACCCCTAATTTTATGATGG |

TABLE 1-continued nucleic acid and polypeptide sequences and SEQ ID NOs

| SEQ ID NO: | description | sequence |
|---|---|---|
| | | CTATAGCCATGGACTTCCCCAAGAAAAGATCACCCAGAAATAAGACCACC<br>TGTGACAGTTACCAGCTTTTATTCATAACCTTAGCTTCCCAACTATTGAGC<br>ATTTTCTAAGGTCCCTGCTGTCTTTTGGTCTCTGGTTTGATTTGTGGCAAA<br>CAGATGAAGTAACAGACTGCTATGAAGGACCACAAAAACGGCAGCCTCT<br>GGAAAAACCATTAGAAAGTCAGTGGCAGATCCAGTAAATAATATCGCCAG<br>CCTCAGCATAATCTGCTGCTGACTCGATTCAGTGGACTCTAAAGTGCCCA<br>GCCTCCTGACCTGAGCTCTCCTGCCATCTGTGAGACTACCAGAGGTCTTA<br>TCTGCTGTCCACATGGCAACTGGGCATGAGTACCTGGCCACCTTGCTTCC<br>CTCTTTGCCTGGTCCAAGTGAGTGTCTGCTGCCTCTGTCCTGCCTTGTTT<br>TCCTGGCTCTAAACCAACTCCACCCACTCTTAATGGAAACTCAGTCTGGC<br>TTTGTGTGTTTCTGGGAAGCACATGACTTCTGGGAATGGGCAAGGAAGAG<br>GAGTGAAACAAAAACTGTCAGCTATGTGTGCCTGGTCTGGGATCCTTCTC<br>TGGGTGACAGTGGCATCATGAATCTTAGAATCAGCTCCCC |
| 114 | hsALDH2 | GAATCATGCAAGCTTCCTCCCTCAGCCATTGATGGAAAGTTCAGCAAGAT<br>CAGCAACAAAACCAAGAAAAATGATCCTTGCGTGCTGAATATCTGAAAAG<br>AGAAATTTTTCCTACAAAATCTCTTGGGTCAAGAAAGTTCTAGAATTTGAAT<br>TGATAAACATGGTGGGTTGGCTGAGGGTAAGAGTATATGAGGAACCTTTT<br>AAACGACAACAATACTGCTAGCTTTCAGGATGATTTTTAAAAAATAGATTC<br>AAATGTGTTATCCTCTCTCTGAAACGCTTCCTATAACTCGAGTTTATAGGG<br>GAAGAAAAAGCTATTGTTTACAATTATATCACCATTAAGGCAACTGCTACA<br>CCCTGCTTTGTATTCTGGGCTAAGATTCATTAAAAACTAGCTGCTCTTAAC<br>TTACA |
| 115 | hsCOX10 | GAGCACTGGGACGCCCACCGCCCCTTTCCCTCCGCTGCCAGGCGAGCAT<br>GTTGTGGTAATTCTGGAACACAAGAAGAGAAATTGCTGGGTTTAGAACAA<br>GATTATAAACGAATTCGGTGCTCAGTGATCACTTGACAGTTTTTTTTTTTT<br>TAAATATTACCCAAAATGCTCCCCAAATAAGAAATGCATCAGCTCAGTCAG<br>TGAATACAAAAAAGGAATTATTTTTCCCTTTGAGGGTCTTTATACATCTCTC<br>CTCCAACCCCACCCTCTATTCTGTTTCTTCCTCCTCACATGGGGGTACAC<br>ATACACAGCTTCCTCTTTTGGTTCCATCCTTACCACCACACCACACGCACA<br>CTCCACATGCCCAGCAGAGTGGCACTTGGTGGCCAGAAAGTGTGAGCCT<br>CATGATCTGCTGTCTGTAGTTCTGTGAGCTCAGGTCCCTCAAAGGCCTCG<br>GAGCACCCCCTTCCTGGTGACTGAGCCAGGGCCTGCATTTTTGGTTTTCC<br>CCACCCCACACATTCTCAACCATAGTCCTTCTAACAATACCAATAGCTAGG<br>ACCCGGCTGCTGTGCACTGGGACTGGGGATTCCACATGTTTGCCTTGGG<br>AGTCTCAAGCTGGACTGCCAGCCCCTGTCCTCCCTTCACCCCCATTGCGT<br>ATGAGCATTTCAGAACTCCAAGGAGTCACAGGCATCTTTATAGTTCACGTT<br>AACATATAGACACTGTTGGAAGCAGTTCCTTCTAAAAGGGTAGCCCTGGA<br>CTTAATACCAGCCGGATACCTCTGGCCCCCACCCCATTACTGTACCTCTG<br>GAGTCACTACTGTGGGTCGCCACTCCTCTGCTACACAGCACGGCTTTTTC<br>AAGGCTGTATTGAGAAGGGAAGTTAGGAAGAAGGGTGTGCTGGGCTAAC<br>CAGCCCACAGAGCTCACATTCCTGTCCCTTGGGTGAAAAATACATGTCCA<br>TCCTGATATCTCCTGAATTCAGAAATTAGCCTCCACATGTGCAATGGCTTT<br>AAGAGCCAGAAGCAGGGTTCTGGGAATTTTGCAAGTTATCCTGTGGCCAG<br>GTGTGGTCTCGGTTACCAAATACGGTTACCTGCAGCTTTTTAGTCCTTTGT<br>GCTCCCACGGGTCTGCAGAGTCCCATCTGCCCAAAGGTCTTGAAGCTTG<br>ACAGGATGTTTTCATTACTCAGTCTCCCAGGGCACTGCTGGTCCGTAGGG<br>ATTCATTGGTCGGGTGGGAGAGTTAAACAACATTTAAACAGAGTTCTCT<br>CAAAAATGTCTAAAGGGATTGTAGGTAGATAACATCCAATCACTGTTTGCA<br>CTTATCTGAAATCTTCCCTCTTGGCTGCCCCCAGGTATTTACTGTGGAGAA<br>CATTGCATAGGAATGTCTGGAAAAAGCCTCTACAACTTGTTACAGCCTTCA<br>CATTTGTACAATTCATTGATTCTCTTTTCCTTCCACAATAAAATGGTATACA<br>AGAAC |
| 116 | hsUQCRFS1 | GAGACTTGGACTCAAGTCATAGGCTTCTTTCAGTCTTTATGTCACCTCAGG<br>AGACTTATTTGAGAGGAAGCCTTCTGTACTTGAAGTTGATTTGAAATATGT<br>AAGAATTGATGATGTATTTGCAAACATTAATGTGAAATAAATTGAATTTAAT<br>GTTGAATACTTTCAGGCATTCACTTAATAAAGACACTGTTAAGCACTGTTA<br>TGCTCAGTCATACACGCGAAAGGTACAATGTCTTTTAGCTAATTCTAATTA<br>AAAATTACAGACTGGTGTACAAGATACTTGTG |
| 117 | hsNDUFV1 | CCCACCACCCTGGCCTGCTGTCCTGCGTCTATCCATGTGGAATGCTGGA<br>CAATAAAGCGAGTGCTGCCCACCCTCCAGCTGCC |
| 118 | hsNDUFV2 | TTTATATTGAACTGTAAATATGTCACTAGAGAAATAAAATATGGACTTCCAA<br>TCTACGTAAACTTA |
| 119 | hsSOD2 | ACCACGATCGTTATGCTGAGTATGTTAAGCTCTTTATGACTGTTTTTGTAG<br>TGGTATAGAGTACTGCAGAATACAGTAAGCTGCTCTATTGTAGCATTTCTT<br>GATGTTGCTTAGTCACTTATTTCATAAACAACTTAATGTCTGAATAATTTC<br>TTACTAAACATTTTGTTATTGGGCAAGTGATTGAAAATAGTAAATGCTTTGT<br>GTGATTGA |

TABLE 1-continued nucleic acid and polypeptide sequences and SEQ ID NOs

| SEQ ID NO: | description | sequence |
|---|---|---|
| 120 | hsCOX6c | TCTTGGAATATAAAGAATTTCTTCAGGTTGAATTACCTAGAAGTTTGTCACT GACTTGTGTTCCTGAACTATGACACATGAATATGTGGGCTAAGAAATAGTT CCTCTTGATAAATAAACAATTAACAAATACTTTGGACAGTAAGTCTTTCTCA GTTCTTAATGATAATGCAGGGCACTTACTAGCATAAGAATTGGTTTGGGAT TTAACTGTTTATGAAGCTAACTTGATTTCCGTGTTTTGTTAAAATTTCATTG TTCTAGCACATCTTTAACTGTGATAGTT |
| 121 | hsIRP1 | GAGACGTGCACTTGGTCGTGCGCCCAGGGAGGAAGCCGCACCACCAGC CAGCGCAGGCCCTGGTGGAGAGGCCTCCCTGGCTGCCTCTGGGAGGGG TGCTGCCTTGTAGATGGAGCAAGTGAGCACTGAGGGTCTGGTGCCAATC CTGTAGGCACAAAACCAGAAGTTTCTACATTCTCTATTTTTGTTAATCATCT TCTCTTTTTCCAGAATTTGGAAGCTAGAATGGTGGGAATGTCAGTAGTGC CAGAAAGAGAGAACCAAGCTTGTCTTTAAAGTTACTGATCACAGGACGTT GCTTTTTCACTGTTTCCTATTAATCTTCAGCTGAACACAAGCAAACCTTCT CAGGAGGTGTCTCCTACCCTCTTATTGTTCCTCTTACGCTCTGCTCAATGA AACCTTCCTCTTGAGGGTCATTTTCCTTTCTGTATTAATTATACCAGTGTTA AGTGACATAGATAAGAACTTTGCACACTTCAAATCAGAGCAGTGATTCTCT CTTCTCTCCCCTTTTCCTTCAGAGTGAATCATCCAGACTCCTCATGGATAG GTCGGGTGTTAAAGTTGTTTTGATTATGTACCTTTTGATAGATCCACATAA AAAGAAATGTGAAGTTTTCTTTTACTATCTTTTCATTTATCAAGCAGAGACC TTTGTTGGGAGGCGGTTTGGGAGAACACATTTCTAATTTGAATGAAATGAA ATCTATTTTCAGTG |
| 122 | hsMRPS12 | CAGAAGAAGTGACGGCTGGGGGCACAGTGGGCTGGGCGCCCCTGCAGA ACATGAACCTTCCGCTCCTGGCTGCCACAGGGTCCTCCGATGCTGGCCT TGCGCCTCTAGAGGCAGCCACTCATGGATTCAAGTCCTGGCTCCGCCT CTTCCATCAGGACCACT |
| 123 | hsATP5J2 | AGAGGACACACTCTGCACCCCCCCACCCCACGACCTTGGCCCGAGCCCC TCCGTGAGGAA |
| 124 | rnSOD2 | AGCCCTTCCGCCAGGCTGTGTGTCAGGCCCGTGGTGGGTGTTTTGTAGT AGTGTAGAGCATTGCA |
| 125 | hsOXA1L | CTTATGTTCTGTGCGCATTCTGGCAGGAATTCTGTCTCTTCAGAGACTCAT CCTCAAAACAAGACTTGACACTGTGTCCTTGCCCCAGTCCTAGGAACTGT GGCACACAGAGATGTTCATTTTAAAAACGGATTTCATGAAACACTCTTGTA CTTATGTTTATAAGAGAGCACTGGGTAGCCAAGTGATCTTCCCATTCACA GAGTTAGTAAACCTCTGTACTACATGCTG |
| 126 | MTS-COX10 | MAASPHTLSSRLLTGCVGGSVWYLERRT |
| 127 | MTS-COX8 | MSVLTRLLLRGLTRLGSAAPVRRARIHSL |
| 128 | MTS-OPA1 | MWRLRRAAVA |
| 129 | hsCOX10 | MAASPHTLSSRLLTGCVGGSVWYLERRT |
| 130 | scRPM2 | MAFKSFIYSKGYHRSAAQKKTATSFFDSSYQYLRQNQGLVNSDPVLHASHLH PHPVVVANVNYNNVDDILHPHDLDSSINNTNNPLTHEELLYNQNVSLRSLKQ QQSTNYVNNNNNNQHRYY |
| 131 | lcSirt5 | MRKRSLRCHLWSANASLSPRKDEVTSRKESENLVKGKKNKKSHLHLLLFTAS KIGTDSVFDVQKSKECCKELGLLFTSLIHSIGSFPFDEEPKAAAVFLPGSLPQL TVLVLAPGSGSCPTGKSTPHLAASGRNAELLRPQNSMIVRQFTCRGTISSHL CAHLRKPHDSRNMARP |
| 132 | tbNDUS7 | MLRRTSFNFTGRAMISRGSPEWSHRLDLKKGKKTTMMHKLGTSKPNNALQY AQMTL |
| 133 | ncQCR2 | MISRSALSRGSQLALRRPAAAKTAQRGFAAAAASPAASYEPTTIAG |
| 134 | hsATP5G2 | MPELILYVAITLSVAERLVGPGHACAEPSFRSSRCSAPLCLLCSGSSSPATAP HPLKMFACSKFVSTPSLVKSTSQLLSRPLSAVVLKRPEILTDESLSSLAVSCPL TSLVSSRSFQTSAISRDIDTA |

TABLE 1-continued nucleic acid and polypeptide sequences and SEQ ID NOs

| SEQ ID NO: | description | sequence |
|---|---|---|
| 135 | hsLACTB | MYRLMSAVTARAAAPGGLASSCGRRGVHQRAGLPPLGHGWVGGLGLGLGL<br>ALGVKLAGGLRGAAPAQSPAAPDPEASPLAEPPQEQSLAPWSPQTPAPPCS<br>RCFARAIESSRDLL |
| 136 | spilv1 | MTVLAPLRRLHTRAAFSSYGREIALQKRFLNLNSCSAVRRYGTGFSNNLRIKK<br>LKNAFGVVRANSTKSTSTVTTASPIKYDSSFVGKTGGEIFHDMMLKHNVKHV<br>FGYPGGAILPVFDAIYRSPHFEFILPRHEQAAGHA |
| 137 | gmCOX2 | MILCPLEAFIVQHILTISVMGLLSCFRSTVLRKCSKGSSGMSRFLYTNNFQRNL<br>ISSGGNESYYGYFNRRSYTSLYMGTGTVGGITSARIRVPNVGCEGFMCSSHL<br>SITQRNSRLIHSTSKIVPN |
| 138 | crATP6 | MALQQAAPRVFGLLGRAPVALGQSGILTGSSGFKNQGFNGSLQSVENHVYA<br>QAFSTSSQEEQAAPSIQGASGMKLPGMAGSMLLGKSRSGLRTGSMVPFAA<br>QQAMNM |
| 139 | hsOPA1 | MWRLRRAAVACEVCQSLVKHSSGIKGSLPLQKLHLVSRSIYHSHHPTLKLQR<br>PQLRTSFQQFSSLTNLPLRKLKFSPIKYGYQPRRN |
| 140 | hsSDHD | MAVLWRLSAVCGALGGRALLLRTPVVRPAHISAFLQDRPIPEWCGVQHIHLS<br>PSHH |
| 141 | hsADCK3 | MAAILGDTIMVAKGLVKLTQAAVETHLQHLGIGGELIMAARALQSTAVEQIGM<br>FLGKVQGQDKHEEYFAENFGGPEGEFHFSVPHAAGASTDFSSASAPDQSAP<br>PSLGHAHSEGPAPAYVASGPFREAGFPGQASSPLGRANGRLFANPRDSFSA<br>MGFQRRF |
| 142 | osP0644B06.24-2 | MALLLRHSPKLRRAHAILGCERGTVVRHFSSSTCSSLVKEDTVSSSNLHPEY<br>AKKIGGSDFSHDRQSGKELQNFKVSPQEASRASNFMRASKYGMPITANGVH<br>SLFSCGQVVPSRCF |
| 143 | Neurospora crassa ATP9 (ncATP9) | MASTRVLASRLASQMAASAKVARPAVRVAQVSKRTIQTGSPLQTLKRTQMT<br>SIVNATTRQAFQKRA |
| 144 | hsGHITM | MLAARLVCLRTLPSRVFHPAFTKASPVVKNSITKNQWLLTPSRE |
| 145 | hsNDUFAB1 | MASRVLSAYVSRLPAAFAPLPRVRMLAVARPLSTALCSAGTQTRLGTLQPAL<br>VLAQVPGRVTQLCRQY |
| 146 | hsATP5G3 | MFACAKLACTPSLIRAGSRVAYRPISASVLSRPEASRTGEGSTVFNGAQNGV<br>SQLIQREFQTSAISR |
| 147 | crATP6_hsADCK3 | MALQQAAPRVFGLLGRAPVALGQSGILTGSSGFKNQGFNGSLQSVENHVYA<br>QAFSTSSQEEQAAPSIQGASGMKLPGMAGSMLLGKSRSGLRTGSMVPFAA<br>QQAMNMGGMAAILGDTIMVAKGLVKLTQAAVETHLQHLGIGGELIMAARALQ<br>STAVEQIGMFLGKVQGQDKHEEYFAENFGGPEGEFHFSVPHAAGASTDFSS<br>ASAPDQSAPPSLGHAHSEGPAPAYVASGPFREAGFPGQASSPLGRANGRLF<br>ANPRDSFSAMGFQRRFGG |
| 148 | ncATP9_ncATP9 | MASTRVLASRLASQMAASAKVARPAVRVAQVSKRTIQTGSPLQTLKRTQMT<br>SIVNATTRQAFQKRAMASTRVLASRLASQMAASAKVARPAVRVAQVSKRTIQ<br>TGSPLQTLKRTQMTSIVNATTRQAFQKRA |
| 149 | znnLOC100282174 | MALLRAAVSELRRRGRGALTPLPALSSLLSSLSPRSPASTRPEPNNPHADRR<br>HVIALRRCPPLPASAVLAPELLHARGLLPRHWSHASPLSTSSSSSRPADKAQ<br>LTWVDKWIPEAARPY |
| 150 | ncATP9_zmLOC100282174_spilvi_ncATP9 | MASTRVLASRLASQMAASAKVARPAVRVAQVSKRTIQTGSPLQTLKRTQMT<br>SIVNATTRQAFQKRAMALLRAAVSELRRRGRGALTPLPALSSLLSSLSPRSPA<br>STRPEPNNPHADRRHVIALRRCPPLPASAVLAPELLHARGLLPRHWSHASPL<br>STSSSSSRPADKAQLTWVDKWIPEAARPYMTVLAPLRRLHTRAAFSSYGREI<br>ALQKRFLNLNSCSAVRRYGTGFSNNLRIKKLKNAFGVVRANSTKSTSTVTTA<br>SPIKYDSSFVGKTGGEIFHDMMLKHNVKHVFGYPGGAILPVFDAIYRSPHFEF<br>ILPRHEQAAGHAMASTRVLASRLASQMAASAKVARPAVRVAQVSKRTIQTGS<br>PLQTLKRTQMTSIVNATTRQAFQKRA |
| 151 | zmLOC100282174_hsADCK-3_crATP6_hsATP5G3 | MALLRAAVSELRRRGRGALTPLPALSSLLSSLSPRSPASTRPEPNNPHADRR<br>HVIALRRCPPLPASAVLAPELLHARGLLPRHWSHASPLSTSSSSSRPADKAQ<br>LTWVDKWIPEAARPYMAAILGDTIMVAKGLVKLTQAAVETHLQHLGIGGELIM<br>AARALQSTAVEQIGMFLGKVQGQDKHEEYFAENFGGPEGEFHFSVPHAAGA<br>STDFSSASAPDQSAPPSLGHAHSEGPAPAYVASGPFREAGFPGQASSPLGR<br>ANGRLFANPRDSFSAMGFQRRFMALQQAAPRVFGLLGRAPVALGQSGILTG |

TABLE 1-continued nucleic acid and polypeptide sequences and SEQ ID NOs

| SEQ ID NO: | description | sequence |
|---|---|---|
| | | SSGFKNQGFNGSLQSVENHVYAQAFSTSSQEEQAAPSIQGASGMKLPGMA GSMLLGKSRSGLRTGSMVPFAAQQAMNMMFACAKLACTPSLIRAGSRVAYR PISASVLSRPEASRTGEGSTVFNGAQNGVSQLIQREFQTSAISR |
| 152 | zmLOC100282174_ hsADCK3_ hsATP5G3 | MALLRAAVSELRRGRGALTPLPALSSLLSSLSPRSPASTRPEPNNPHADRR HVIALRRCPPLPASAVLAPELLHARGLLPRHWSHASPLSTSSSSSRPADKAQ LTWVDKWIPEAARPYMAAILGDTIMVAKGLVKLTQAAVETHLQHLGIGGELIM AARALQSTAVEQIGMFLGKVQGQDKHEEYFAENFGGPEGEFHFSVPHAAGA STDFSSASAPDQSAPPSLGHAHSEGPAPAYVASGPFREAGFPGQASSPLGR ANGRLFANPRDSFSAMGFQRRFMFACAKLACTPSLIRAGSRVAYRPISASVL SRPEASRTGEGSTVFNGAQNGVSQLIQREFQTSAISR |
| 153 | ncATP9_ zmLOC100282174 | MASTRVLASRLASQMAASAKVARPAVRVAQVSKRTIQTGSPLQTLKRTQMT SIVNATTRQAFQKRAMALLRAAVSELRRGRGALTPLPALSSLLSSLSPRSPA STRPEPNNPHADRRHVIALRRCPPLPASAVLAPELLHARGLLPRHWSHASPL STSSSSSRPADKAQLTWVDKWIPEAARPY |
| 154 | hsADCK3_ zmLOC100282174_ crATP6_ hsATP5G3 | MAAILGDTIMVAKGLVKLTQAAVETHLQHLGIGGELIMAARALQSTAVEQIGM FLGKVQGQDKHEEYFAENFGGPEGEFHFSVPHAAGASTDFSSASAPDQSAP PSLGHAHSEGPAPAYVASGPFREAGFPGQASSPLGRANGRLFANPRDSFSA MGFQRRFMALLRAAVSELRRGRGALTPLPALSSLLSSLSPRSPASTRPEPN NPHADRRHVIALRRCPPLPASAVLAPELLHARGLLPRHWSHASPLSTSSSSS RPADKAQLTWVDKWIPEAARPYMALQQAAPRVFGLLGRAPVALGQSGILTG SSGFKNQGFNGSLQSVENHVYAQAFSTSSQEEQAAPSIQGASGMKLPGMA GSMLLGKSRSGLRTGSMVPFAAQQAMNMMFACAKLACTPSLIRAGSRVAYR PISASVLSRPEASRTGEGSTVFNGAQNGVSQLIQREFQTSAISR |
| 155 | crATP6_ hsADCK3_ zmLOC100282174_ hsATP5G3 | MALQQAAPRVFGLLGRAPVALGQSGILTGSSGFKNQGFNGSLQSVENHVYA QAFSTSSQEEQAAPSIQGASGMKLPGMAGSMLLGKSRSGLRTGSMVPFAA QQAMNMMAAILGDTIMVAKGLVKLTQAAVETHLQHLGIGGELIMAARALQST AVEQIGMFLGKVQGQDKHEEYFAENFGGPEGEFHFSVPHAAGASTDFSSAS APDQSAPPSLGHAHSEGPAPAYVASGPFREAGFPGQASSPLGRANGRLFA NPRDSFSAMGFQRRFMALLRAAVSELRRGRGALTPLPALSSLLSSLSPRSP ASTRPEPNNPHADRRHVIALRRCPPLPASAVLAPELLHARGLLPRHWSHASP LSTSSSSSRPADKAQLTWVDKWIPEAARPYMFACAKLACTPSLIRAGSRVAY RPISASVLSRPEASRTGEGSTVFNGAQNGVSQLIQREFQTSAISR |
| 156 | hsADCK3_ zmLOC100282174 | MAAILGDTIMVAKGLVKLTQAAVETHLQHLGIGGELIMAARALQSTAVEQIGM FLGKVQGQDKHEEYFAENFGGPEGEFHFSVPHAAGASTDFSSASAPDQSAP PSLGHAHSEGPAPAYVASGPFREAGFPGQASSPLGRANGRLFANPRDSFSA MGFQRRFGGMALLRAAVSELRRGRGALTPLPALSSLLSSLSPRSPASTRP EPNNPHADRRHVIALRRCPPLPASAVLAPELLHARGLLPRHWSHASPLSTSS SSSRPADKAQLTWVDKWIPEAARPYGG |
| 157 | hsADCK3_ zmLOC100282174_ crATP6 | MAAILGDTIMVAKGLVKLTQAAVETHLQHLGIGGELIMAARALQSTAVEQIGM FLGKVQGQDKHEEYFAENFGGPEGEFHFSVPHAAGASTDFSSASAPDQSAP PSLGHAHSEGPAPAYVASGPFREAGFPGQASSPLGRANGRLFANPRDSFSA MGFQRRFGGMALLRAAVSELRRGRGALTPLPALSSLLSSLSPRSPASTRP EPNNPHADRRHVIALRRCPPLPASAVLAPELLHARGLLPRHWSHASPLSTSS SSSRPADKAQLTWVDKWIPEAARPYGGMALQQAAPRVFGLLGRAPVALGQ SGILTGSSGFKNQGFNGSLQSVENHVYAQAFSTSSQEEQAAPSIQGASGMK LPGMAGSMLLGKSRSGLRTGSMVPFAAQQAMNMGG |
| 158 | ncATP9_ zmnnLOC100282174_ spilv1_ GNFP_ ncATP9 | MASTRVLASRLASQMAASAKVARPAVRVAQVSKRTIQTGSPLQTLKRTQMT SIVNATTRQAFQKRAMALLRAAVSELRRGRGALTPLPALSSLLSSLSPRSPA STRPEPNNPHADRRHVIALRRCPPLPASAVLAPELLHARGLLPRHWSHASPL STSSSSSRPADKAQLTWVDKWIPEAARPYMTVLAPLRRLHTRAAFSSYGREI ALQKRFLNLNSCSAVRRYGTGFSNNLRIKKLKNAFGVVRANSTKSTSTVTTA SPIKYDSSFVGKTGGEIFHDMMLKHNVKHVFGYPGGAILPVFDAIYRSPHFEF ILPRHEQAAGHAVSGEGDATYGKLTLKFICTTGKLPVPWPTLVTTLTYGVQCF SRYPDHMKQHDFFKSAMPEGYVQERTIFFKDDGNYKTRAEVKFEGDTLVNR IELKGIDFKEDGNILGHKLEYNYNSHNVYIMADKQKNGIKVNFKIRHNIEDGSV QLADHYQQNTPIGDGPVLLPDNHYLSTQSALSKDPNEMASTRVLASRLASQ MAASAKVARPAVRVAQVSKRTIQTGSPLQTLKRTQMTSIVNATTRQAFQKRA |
| 159 | ncATP9_ zmLOC100282174_ spilv1_ lcSirt5_ osP0644B06.240 2_hsATP5G2_ ncATP9 | MASTRVLASRLASQMAASAKVARPAVRVAQVSKRTIQTGSPLQTLKRTQMT SIVNATTRQAFQKRAMALLRAAVSELRRGRGALTPLPALSSLLSSLSPRSPA STRPEPNNPHADRRHVIALRRCPPLPASAVLAPELLHARGLLPRHWSHASPL STSSSSSRPADKAQLTWVDKWIPEAARPYMTVLAPLRRLHTRAAFSSYGREI ALQKRFLNLNSCSAVRRYGTGFSNNLRIKKLKNAFGVVRANSTKSTSTVTTA SPIKYDSSFVGKTGGEIFHDMMLKHNVKHVFGYPGGAILPVFDAIYRSPHFEF ILPRHEQAAGHAMRKRSLRCHLWSANASLSPRKDEVTSRKESENLVKGKKN KKSHLHLLLFTASKIGTDSVFDVQKSKECCKELGLLFTSLIHSIGSFPFDEEPK AAAVFLPGSLPQLTVLVLAPGSGSCPTGKSTPHLAASGRNAELLRPQNSMIV |

TABLE 1-continued nucleic acid and polypeptide sequences and SEQ ID NOs

| SEQ ID NO: | description | sequence |
|---|---|---|
| | | RQFTCRGTISSHLCAHLRKPHDSRNMARPMALLLRHSPKLRRAHAILGCERG<br>TVVRHFSSSTCSSLVKEDTVSSSNLHPEYAKKIGGSDFSHDRQSGKELQNFK<br>VSPQEASRASNFMRASKYGMPITANGVHSLFSCGQVVPSRCFMPELILYVAI<br>TLSVAERLVGPGHACAEPSFRSSRCSAPLCLLCSGSSSPATAPHPLKMFACS<br>KFVSTPSLVKSTSQLLSRPLSAVVLKRPEILTDESLSSLAVSCPLTSLVSSRSF<br>QTSAISRDIDTAMASTRVLASRLASQMAASAKVARPAVRVAQVSKRTIQTGS<br>PLQTLKRTQMTSIVNATTRQAFQKRA |
| 160 | ND4 | MLKLIVPTIMLLPLTWLSKKHMIWINTTTHSLIISIIPLLFFNQINNNLFSCSPTFS<br>SDPLTTPLLMLTTWLLPLTIMASQRHLSSEPLSRKKLYLSMLISLQISLIMTFTA<br>TELIMFYIFFETTLIPTLAIITRWGNQPERLNAGTYFLFYTLVGSLPLLIALIYTHN<br>TLGSLNILLLTLTAQELSNSWANNLMWLAYTMAFMVKMPLYGLHLWLPKAHV<br>EAPIAGSMVLAAVLLKLGGYGMMRLTLILNPLTKHMAYPFLVLSLWGMIMTSS<br>ICLRQTDLKSLIAYSSISHMALVVTAILIQTPWSFTGAVILMIAHGLTSSLLFCLA<br>NSNYERTHSRIMILSQGLQTLLPLMAFWWLLASLANLALPPTINLLGELSVLVT<br>TFSWSNITLLLTGLNMLVTALYSLYMFTTTQWGSLTHHINNMKPSFTRENTLM<br>FMHLSPILLLSLNPDIITGFSS |
| 161 | ND6 | MMYALFLLSVGLVMGFVGFSSKPSPIYGGLVLIVSGVVGCVIILNFGGGYMGL<br>MVFLIYLGGMMVVFGYTTAMAIEEYPEAWGSGVEVLVSVLVGLAMEVGLVL<br>WVKEYDGVVVVVNFNSVGSWMIYEGEGSGLIREDPIGAGALYDYGRWLVVV<br>TGWTLFVGVYIVIEIARGN |
| 162 | ND1 | MPMANLLLLIVPILIAMAFLMLTERKILGYMQLRKGPNVVGPYGLLQPFADAM<br>KLFTKEPLKPATSTITLYITAPTLALTIALLLWTPLPMPNPLVNLNLGLLFILATSS<br>LAVYSILWSGWASNSNYALIGALRAVAQTISYEVTLAIILLSTLLMSGSFNLSTLI<br>TTQEHLWLLLPSWPLAMMWFISTLAETNRTPFDLAEGESELVSGFNIEYAAG<br>PFALFFMAEYTNIIMMNTLTTTIFLGTTYDALSPELYTTYFVTKTLLLTSLFLWIR<br>TAYPRFRYDQLMHLLWKNFLPLTLALLMWYVSMPITISSIPPQT |
| 163 | ND1<br>[homo sapiens] | ATACCCATGGCCAACCTCCTACTCCTCATTGTACCCATTCTAATCGCAATG<br>GCATTCCTAATGCTTACCGAACGAAAAATTCTAGGCTATATACAACTACGC<br>AAAGGCCCCAACGTTGTAGGCCCCTACGGGCTACTACAACCCTTCGCTG<br>ACGCCATAAAACTCTTCACCAAAGAGCCCCTAAAACCCGCCACATCTACC<br>ATCACCCTCTACATCACCGCCCCGACCTTAGCTCTCACCATCGCTCTTCT<br>ACTATGAACCCCCCTCCCCATACCCAACCCCCTGGTCAACCTCAACCTAG<br>GCCTCCTATTTATTCTAGCCACCTCTAGCCTAGCCGTTTACTCAATCCTCT<br>GATCAGGGTGAGCATCAAACTCAAACTACGCCCTGATCGGCGCACTGCG<br>AGCAGTAGCCCAAACAATCTCATATGAAGTCACCCTAGCCATCATTCTACT<br>ATCAACATTACTAATAAGTGGCTCCTTTAACCTCTCCACCCTTATCACAAC<br>ACAAGAACACCTCTGATTACTCCTGCCATCATGACCCTTGGCCATAATATG<br>ATTTATCTCCACACTAGCAGAGACCAACCGAACCCCCTTCGACCTTGCCG<br>AAGGGGAGTCCGAACTAGTCTCAGGCTTCAACATCGAATACGCCGCAGG<br>CCCCTTCGCCCTATTCTTCATAGCCGAATACACAAACATTATTATAATAAA<br>CACCCTCACCACTACAATCTTCCTAGGAACAACATATGACGCACTCTCCC<br>CTGAACTCTACACAACATATTTTGTCACCAAGACCCTACTTCTAACCTCCC<br>TGTTCTTATGAATTCGAACAGCATACCCCCGATTCCGCTACGACCAACTC<br>ATACACCTCCTATGAAAAAACTTCCTACCACTCACCCTAGCATTACTTATA<br>TGATATGTCTCCATACCCATTACAATCTCCAGCATTCCCCCTCAAACCTAA |

Adeno-Associated Virus (AAV)

Adeno-associated virus (AAV) is a small virus that infects humans and some other primate species. The compositions disclosed herein comprises firstly an adeno-associated virus (AAV) genome or a derivative thereof.

An AAV genome is a polynucleotide sequence which encodes functions needed for production of an AAV viral particle. These functions include those operating in the replication and packaging cycle for AAV in a host cell, including encapsidation of the AAV genome into an AAV viral particle. Naturally occurring AAV viruses are replication-deficient and rely on the provision of helper functions in trans for completion of a replication and packaging cycle. Accordingly, the AAV genome of the vector of the invention is typically replication-deficient.

The AAV genome can be in single-stranded form, either positive or negative-sense, or alternatively in double-stranded form. The use of a double-stranded form allows bypass of the DNA replication step in the target cell and so can accelerate transgene expression.

The AAV genome may be from any naturally derived serotype or isolate or Glade of AAV. Thus, the AAV genome may be the full genome of a naturally occurring AAV virus. As is known to the skilled person, AAV viruses occurring in nature may be classified according to various biological systems.

Commonly, AAV viruses are referred to in terms of their serotype. A serotype corresponds to a variant subspecies of AAV which owing to its profile of expression of capsid surface antigens has a distinctive reactivity which can be used to distinguish it from other variant subspecies. Typically, a virus having a particular AAV serotype does not efficiently cross-react with neutralising antibodies specific for any other AAV serotype. AAV serotypes include AAV1, AAV2, AAV3, AAV4, AAV5, AAV6, AAV7, AAV8, AAV9, AAV10, AAV11, AAV12, AAV13, AAV14, AAV15, and AAV16, also recombinant serotypes, such as Rec2 and Rec3, recently identified from primate brain. In some embodiments, the AAV viruses comprising the recombinant nucleic acid of the disclosure has a serotype selected from the group consisting of AAV2, AAV5, AAV7, AAV8, AAV9, AAV10, AAV-DJ, and a combination thereof.

A preferred serotype of AAV for use in the invention is AAV2. Other serotypes of particular interest for use in the invention include AAV4, AAV5 and AAV8 which efficiently transduce tissue in the eye, such as the retinal pigmented epithelium. The serotype of AAV which is used can be an AAV serotype which is not AAV4. Reviews of AAV serotypes may be found in Choi et al (Curr Gene Ther. 2005; 5(3); 299-310) and Wu et al (Molecular Therapy. 2006; 14(3), 316-327). The sequences of AAV genomes or of elements of AAV genomes including ITR sequences, rep or cap genes for use in the invention may be derived from the following accession numbers for AAV whole genome sequences: Adeno-associated virus 1 NC_002077, AF063497; Adeno-associated virus 2 NC_001401; Adeno-associated virus 3 NC_001729; Adeno-associated virus 3B NC_001863; Adeno-associated virus 4 NC_001829; Adeno-associated virus 5 Y18065, AF085716; Adeno-associated virus 6 NC_001862; Avian AAV ATCC VR-865 AY186198, AY629583, NC_004828; Avian AAV strain DA-1 NC_006263, AY629583; Bovine AAV NC_005889, AY388617.

AAV viruses may also be referred to in terms of clades or clones. This refers to the phylogenetic relationship of naturally derived AAV viruses, and typically to a phylogenetic group of AAV viruses which can be traced back to a common ancestor, and includes all descendants thereof. Additionally, AAV viruses may be referred to in terms of a specific isolate, i.e. a genetic isolate of a specific AAV virus found in nature. The term genetic isolate describes a population of AAV viruses which has undergone limited genetic mixing with other naturally occurring AAV viruses, thereby defining a recognisably distinct population at a genetic level.

Examples of clades and isolates of AAV that may be used in the invention include: Clade A: AAV1 NC_002077, AF063497, AAV6 NC_001862, Hu. 48 AY530611, Hu 43 AY530606, Hu 44 AY530607, Hu 46 AY530609; Clade B: Hu. 19 AY530584, Hu. 20 AY530586, Hu 23 AY530589, Hu22 AY530588, Hu24 AY530590, Hu21 AY530587, Hu27 AY530592, Hu28 AY530593, Hu 29 AY530594, Hu63 AY530624, Hu64 AY530625, Hu13 AY530578, Hu56 AY530618, Hu57 AY530619, Hu49 AY530612, Hu58 AY530620, Hu34 AY530598, Hu35 AY530599, AAV2 NC_001401, Hu45 AY530608, Hu47 AY530610, Hu51 AY530613, Hu52 AY530614, Hu T41 AY695378, Hu S17 AY695376, Hu T88 AY695375, Hu T71 AY695374, Hu T70 AY695373, Hu T40 AY695372, Hu T32 AY695371, Hu T17 AY695370, Hu LG15 AY695377; Clade C: Hu9 AY530629, Hu10 AY530576, Hu11 AY530577, Hu53 AY530615, Hu55 AY530617, Hu54 AY530616, Hu7 AY530628, Hu18 AY530583, Hu15 AY530580, Hu16 AY530581, Hu25 AY530591, Hu60 AY530622, Ch5 AY243021, Hu3 AY530595, Hu1 AY530575, Hu4 AY530602 Hu2, AY530585, Hu61 AY530623; Clade D: Rh62 AY530573, Rh48 AY530561, Rh54 AY530567, Rh55 AY530568, Cy2 AY243020, AAV7 AF513851, Rh35 AY243000, Rh37 AY242998, Rh36 AY242999, Cy6 AY243016, Cy4 AY243018, Cy3 AY243019, Cy5 AY243017, Rh13 AY243013; Clade E: Rh38 AY530558, Hu66 AY530626, Hu42 AY530605, Hu67 AY530627, Hu40 AY530603, Hu41 AY530604, Hu37 AY530600, Rh40 AY530559, Rh2 AY243007, Bb1 AY243023, Bb2 AY243022, Rh10 AY243015, Hu17 AY530582, Hu6 AY530621, Rh25 AY530557, Pi2 AY530554, Pi1 AY530553, Pi3 AY530555, Rh57 AY530569, Rh50 AY530563, Rh49 AY530562, Hu39 AY530601, Rh58 AY530570, Rh61 AY530572, Rh52 AY530565, Rh53 AY530566, Rh51 AY530564, Rh64 AY530574, Rh43 AY530560, AAV8 AF513852, Rh8 AY242997, Rh1 AY530556; Clade F: Hu14 (AAV9) AY530579, Hu31 AY530596, Hu32 AY530597, Clonal Isolate AAV5 Y18065, AF085716, AAV 3 NC_001729, AAV 3B NC_001863, AAV4 NC_001829, Rh34 AY243001, Rh33 AY243002, Rh32 AY243003.

The skilled person can select an appropriate serotype, Glade, clone or isolate of AAV for use in the present invention on the basis of their common general knowledge. For instance, the AAV5 capsid has been shown to transduce primate cone photoreceptors efficiently as evidenced by the successful correction of an inherited color vision defect (Mancuso et al., Nature 2009, 461:784-7).

It should be understood however that the invention also encompasses use of an AAV genome of other serotypes that may not yet have been identified or characterised. The AAV serotype determines the tissue specificity of infection (or tropism) of an AAV virus. Accordingly, preferred AAV serotypes for use in AAV viruses administered to patients in accordance with the invention are those which have natural tropism for or a high efficiency of infection of target cells within eye in LHON. Thus, AAV serotypes for use in AAV viruses administered to patients can be ones which infect cells of the neurosensory retina and retinal pigment epithelium.

Typically, the AAV genome of a naturally derived serotype or isolate or Glade of AAV comprises at least one inverted terminal repeat sequence (ITR). An ITR sequence acts in cis to provide a functional origin of replication, and allows for integration and excision of the vector from the genome of a cell. In preferred embodiments, one or more ITR sequences flank the polynucleotide sequence encoding ND4, ND6, or ND1 or a variant thereof. Preferred ITR sequences are those of AAV2, and variants thereof. The AAV genome typically also comprises packaging genes, such as rep and/or cap genes which encode packaging functions for an AAV viral particle. The rep gene encodes one or more of the proteins Rep78, Rep68, Rep52 and Rep40 or variants thereof. The cap gene encodes one or more capsid proteins such as VP1, VP2 and VP3 or variants thereof. These proteins make up the capsid of an AAV viral particle. Capsid variants are discussed below.

A promoter will be operably linked to each of the packaging genes. Specific examples of such promoters include the p5, p19 and p40 promoters (Laughlin et al., 1979, PNAS, 76:5567-5571). For example, the p5 and p19 promoters are generally used to express the rep gene, while the p40 promoter is generally used to express the cap gene.

As discussed above, the AAV genome used in the vector of the invention may therefore be the full genome of a naturally occurring AAV virus. For example, a vector comprising a full AAV genome may be used to prepare AAV virus in vitro. However, while such a vector may in principle be administered to patients, this will be done rarely in practice. Preferably the AAV genome will be derivatised for the purpose of administration to patients. Such derivatisation is standard in the art and the present invention encompasses the use of any known derivative of an AAV genome, and derivatives which could be generated by applying techniques known in the art. Derivatisation of the AAV genome and of the AAV capsid are reviewed in Coura and Nardi (Virology Journal, 2007, 4:99), and in Choi et al and Wu et al, referenced above.

Derivatives of an AAV genome include any truncated or modified forms of an AAV genome which allow for expression of a ND4, ND6, or ND1 transgene from a vector of the invention in vivo. Typically, it is possible to truncate the AAV genome significantly to include minimal viral sequence yet retain the above function. This is preferred for safety reasons to reduce the risk of recombination of the vector with wild-type virus, and also to avoid triggering a cellular immune response by the presence of viral gene proteins in the target cell.

Typically, a derivative will include at least one inverted terminal repeat sequence (ITR), preferably more than one ITR, such as two ITRs or more. One or more of the ITRs may be derived from AAV genomes having different serotypes, or may be a chimeric or mutant ITR. A preferred mutant ITR is one having a deletion of a trs (terminal resolution site). This deletion allows for continued replication of the genome to generate a single-stranded genome which contains both coding and complementary sequences i.e. a self-complementary AAV genome. This allows for bypass of DNA replication in the target cell, and so enables accelerated transgene expression.

The one or more ITRs will preferably flank the polynucleotide sequence encoding ND4, ND6, ND1, or a variant thereof at either end. The inclusion of one or more ITRs is preferred to aid concatamer formation of the vector of the invention in the nucleus of a host cell, for example following the conversion of single-stranded vector DNA into double-stranded DNA by the action of host cell DNA polymerases. The formation of such episomal concatamers protects the vector construct during the life of the host cell, thereby allowing for prolonged expression of the transgene in vivo.

In preferred embodiments, ITR elements will be the only sequences retained from the native AAV genome in the derivative. Thus, a derivative will preferably not include the rep and/or cap genes of the native genome and any other sequences of the native genome. This is preferred for the reasons described above, and also to reduce the possibility of integration of the vector into the host cell genome. Additionally, reducing the size of the AAV genome allows for increased flexibility in incorporating other sequence elements (such as regulatory elements) within the vector in addition to the transgene.

With reference to the AAV2 genome, the following portions could therefore be removed in a derivative of the invention: One inverted terminal repeat (ITR) sequence, the replication (rep) and capsid (cap) genes (NB: the rep gene in the wildtype AAV genome should not to be confused with ND4, ND6, or ND1, the human gene affected in LHON). However, in some embodiments, including in vitro embodiments, derivatives may additionally include one or more rep and/or cap genes or other viral sequences of an AAV genome. Naturally occurring AAV virus integrates with a high frequency at a specific site on human chromosome 19, and shows a negligible frequency of random integration, such that retention of an integrative capacity in the vector may be tolerated in a therapeutic setting.

Where a derivative genome comprises genes encoding capsid proteins i.e. VP1, VP2 and/or VP3, the derivative may be a chimeric, shuffled or capsid-modified derivative of one or more naturally occurring AAV viruses. In particular, the invention encompasses the provision of capsid protein sequences from different serotypes, clades, clones, or isolates of AAV within the same vector i.e. pseudotyping.

Chimeric, shuffled or capsid-modified derivatives will be typically selected to provide one or more desired functionalities for the viral vector. Thus, these derivatives may display increased efficiency of gene delivery, decreased immunogenicity (humoral or cellular), an altered tropism range and/or improved targeting of a particular cell type compared to an AAV viral vector comprising a naturally occurring AAV genome, such as that of AAV2. Increased efficiency of gene delivery may be effected by improved receptor or co-receptor binding at the cell surface, improved internalisation, improved trafficking within the cell and into the nucleus, improved uncoating of the viral particle and improved conversion of a single-stranded genome to double-stranded form. Increased efficiency may also relate to an altered tropism range or targeting of a specific cell population, such that the vector dose is not diluted by administration to tissues where it is not needed.

Chimeric capsid proteins include those generated by recombination between two or more capsid coding sequences of naturally occurring AAV serotypes. This may be performed for example by a marker rescue approach in which non-infectious capsid sequences of one serotype are cotransfected with capsid sequences of a different serotype, and directed selection is used to select for capsid sequences having desired properties. The capsid sequences of the different serotypes can be altered by homologous recombination within the cell to produce novel chimeric capsid proteins.

Chimeric capsid proteins also include those generated by engineering of capsid protein sequences to transfer specific capsid protein domains, surface loops or specific amino acid residues between two or more capsid proteins, for example between two or more capsid proteins of different serotypes.

Shuffled or chimeric capsid proteins may also be generated by DNA shuffling or by error-prone PCR. Hybrid AAV capsid genes can be created by randomly fragmenting the sequences of related AAV genes e.g. those encoding capsid proteins of multiple different serotypes and then subsequently reassembling the fragments in a self-priming polymerase reaction, which may also cause crossovers in regions of sequence homology. A library of hybrid AAV genes created in this way by shuffling the capsid genes of several serotypes can be screened to identify viral clones having a desired functionality. Similarly, error prone PCR may be used to randomly mutate AAV capsid genes to create a diverse library of variants which may then be selected for a desired property.

The sequences of the capsid genes may also be genetically modified to introduce specific deletions, substitutions or insertions with respect to the native wild-type sequence. In particular, capsid genes may be modified by the insertion of a sequence of an unrelated protein or peptide within an open reading frame of a capsid coding sequence, or at the N- and/or C-terminus of a capsid coding sequence.

The unrelated protein or peptide may advantageously be one which acts as a ligand for a particular cell type, thereby conferring improved binding to a target cell or improving the specificity of targeting of the vector to a particular cell population. An example might include the use of RGD peptide to block uptake in the retinal pigment epithelium and thereby enhance transduction of surrounding retinal tissues (Cronin et al., 2008 ARVO Abstract: D1048). The unrelated protein may also be one which assists purification of the viral particle as part of the production process i.e. an epitope or affinity tag. The site of insertion will typically be selected so as not to interfere with other functions of the viral particle e.g. internalisation, trafficking of the viral particle. The skilled person can identify suitable sites for insertion based on their common general knowledge. Particular sites are disclosed in Choi et al, referenced above.

The invention additionally encompasses the provision of sequences of an AAV genome in a different order and configuration to that of a native AAV genome. The invention also encompasses the replacement of one or more AAV sequences or genes with sequences from another virus or with chimeric genes composed of sequences from more than one virus. Such chimeric genes may be composed of sequences from two or more related viral proteins of different viral species.

The vector of the invention takes the form of a polynucleotide sequence comprising an AAV genome or derivative thereof and a sequence encoding ND4, ND6, ND1 or a variant thereof.

For the avoidance of doubt, the invention also provides an AAV viral particle comprising a vector of the invention. The AAV particles of the invention include transcapsidated forms wherein an AAV genome or derivative having an ITR of one serotype is packaged in the capsid of a different serotype. The AAV particles of the invention also include mosaic forms wherein a mixture of unmodified capsid proteins from two or more different serotypes makes up the viral envelope. The AAV particle also includes chemically modified forms bearing ligands adsorbed to the capsid surface. For example, such ligands may include antibodies for targeting a particular cell surface receptor.

The invention additionally provides a host cell comprising a vector or AAV viral particle of the invention.

Recombinant Nucleic Acid Sequences

Also disclosed herein are recombinant nucleic acid sequences comprising a polynucleotide sequence encoding a NADH dehydrogenase subunit-4 (ND4), NADH dehydrogenase subunit-1 (ND1) and NADH dehydrogenase subunit-6 (ND6) polypeptide or a variant thereof.

The polynucleotide sequence for ND4 is shown in SEQ ID NO: 6 and encodes the protein shown in SEQ ID NO: 160. Further nucleic acid sequences for ND4 are SEQ ID NO: 7 and 8. The polynucleotide sequence for ND6 is shown in SEQ ID NO: 9 and encodes the protein shown in SEQ ID NO: 161. A further nucleic acid sequence for ND6 is SEQ ID NO: 10. The polynucleotide sequence for ND1 is shown in SEQ ID NO: 11 and encodes the protein shown in SEQ ID NO: 162. A further nucleic acid sequence for ND1 is SEQ ID NO: 12.

A variant of any one of SEQ ID NO: 160, 161, or 162 may comprise truncations, mutants or homologues thereof, and any transcript variants thereof which encode a functional ND4, ND6, or ND1 polypeptide. Any homologues mentioned herein are typically at least 70% homologous to a relevant region of ND4, ND6, or ND1, and can functionally compensate for the polypeptide deficiency.

Homology can be measured using known methods. For example the UWGCG Package provides the BESTFIT program which can be used to calculate homology (for example used on its default settings) (Devereux et at (1984) Nucleic Acids Research 12, 387-395). The PILEUP and BLAST algorithms can be used to calculate homology or line up sequences (typically on their default settings), for example as described in Altschul S. F. (1993) J Mol Evol 36:290-300; Altschul, S, F et at (1990) J Mol Biol 215:403-10. Software for performing BLAST analyses is publicly available through the National Center for Biotechnology Information (http://www.ncbi.nlm.nih.gov/).

In preferred embodiments, a recombinant nucleic acid sequence may encode a polypeptide which is at least 55%, 65%, 70%, 75%, 80%, 85%, 90% and more preferably at least 95%, 97%, 99%, 99.5%, or 100% homologous to a relevant region of ND4, ND6, or ND1 (SEQ ID NO: 160, 161, or 162) over at least 20, preferably at least 30, for instance at least 40, 60, 100, 200, 300, 400 or more contiguous amino acids, or even over the entire sequence of the recombinant nucleic acid. The relevant region will be one which provides for functional activity of ND4, ND6, or ND1.

Alternatively, and preferably the recombinant nucleic acid sequence may encode a polypeptide having at least 70%, 75%, 80%, 85%, 90% and more preferably at least 95%, 97%, 99%, 99.5%, or 100% homologous to full-length ND4, ND6, or ND1 (SEQ ID NO: 160, 161, or 162) over its entire sequence. Typically the recombinant nucleic acid sequence differs from the relevant region of ND4, ND6, or ND1 (SEQ ID NO: 160, 161, or 162) by at least, or less than, 2, 5, 10, 20, 40, 50 or 60 mutations (each of which can be substitutions, insertions or deletions).

A recombinant nucleic acid ND4, ND6, or ND1 polypeptide may have a percentage identity with a particular region of SEQ ID NO: 160, 161, or 162 which is the same as any of the specific percentage homology values (i.e. it may have at least 70%, 80% or 90% and more preferably at least 95%, 97%, 99% identity) across any of the lengths of sequence mentioned above.

Variants of ND4, ND6, or ND1 (SEQ ID NO: 160, 161, or 162) also include truncations. Any truncation may be used so long as the variant is still functional. Truncations will typically be made to remove sequences that are non-essential for the protein activity and/or do not affect conformation of the folded protein, in particular folding of the active site. Appropriate truncations can routinely be identified by systematic truncation of sequences of varying length from the N- or C-terminus. Preferred truncations are N-terminal and may remove all other sequences except for the catalytic domain.

Variants of ND4, ND6, or ND1 (SEQ ID NO: 160, 161, or 162) further include mutants which have one or more, for example, 2, 3, 4, 5 to 10, 10 to 20, 20 to 40 or more, amino acid insertions, substitutions or deletions with respect to a particular region of ND4, ND6, or ND1 (SEQ ID NO: 160, 161, or 162). Deletions and insertions are made preferably outside of the catalytic domain as described below. Substitutions are also typically made in regions that are non-essential for protease activity and/or do not affect conformation of the folded protein.

Substitutions preferably introduce one or more conservative changes, which replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative change may introduce another amino acid that is aromatic or aliphatic in the place of a pre-existing aromatic or aliphatic amino acid. Conservative amino acid changes are well known in the art and may be selected in accordance with the properties of the amino acids.

Similarly, preferred variants of the polynucleotide sequence of ND4, ND6, or ND1 (SEQ ID NO: 6, 9, or 11) include polynucleotides having at least 70%, 75%, 80%, 85%, 90% and more preferably at least 95%, 96%, 97%, 98%, 99%, or 99.5% homologous to a relevant region of ND4, ND6, or ND1 (SEQ ID NO: 6, 9, or 11). Preferably the variant displays these levels of homology to full-length ND4, ND6, or ND1 (SEQ ID NO: 6, 9, or 11) over its entire sequence.

Mitochondrial targeting sequences (MTSs) and three prime untranslated regions (3'UTRs) can be used to target proteins or mRNA to the mitochondria. The charge, length, and structure of the MTS can be important for protein import into the mitochondria. Particular 3'UTRs may drive mRNA localization to the mitochondrial surface and thus facilitate cotranslational protein import into the mitochondria.

The polynucleotide sequence for a mitochondrial targeting sequence can encode a polypeptide selected from hsCOX10, hsCOX8, scRPM2, lcSirt5, tbNDUS7, ncQCR2, hsATP5G2, hsLACTB, spilv1, gmCOX2, crATP6, hsOPA1, hsSDHD, hsADCK3, osP0644B06.24-2, *Neurospora crassa* ATP9 (ncATP9), hsGHITM, hsNDUFAB1, hsATP5G3, crATP6_hsADCK3, ncATP9_ncATP9, zmLOC100282174, ncATP9_zmLOC100282174_spilv1_ncATP9, zmLOC100282174_hsADCK3_crATP6_hsATP5G3, zmLOC100282174_hsADCK3_hsATP5G3, ncATP9_zmLOC100282174, hsADCK3_zmLOC100282174_crATP6_hsATP5G3, crATP6_hsADCK3_zmLOC100282174_hsATP5G3, hsADCK3_zmLOC100282174, hsADCK3_zmLOC100282174_crATP6, ncATP9_zmLOC100282174_spilv1_GNFP_ncATP9, and ncATP9_zmLOC100282174_spilv1_lcSirt5_osP0644B06.24-2_hsATP5G2_ncATP9 (see Table 1 for SEQ ID NO). In one example, the polynucleotide sequences, COX10 (SEQ ID NO: 1, 2, or 3) can encode the mitochondrial targeting sequence, MTS-COX10 (SEQ ID NO: 126). In another example, the polynucleotide sequences, COX8 (SEQ ID NO: 4) can encode the mitochondrial targeting sequence, MTS-COX8 (SEQ ID NO: 127). In another example, the polynucleotide sequences, OPA1 (SEQ ID NO: 5) can encode the mitochondrial targeting sequence, MTS-OPA1 (SEQ ID NO: 128).

The 3'UTR nucleic acid sequence can be selected from hsACO2 (SEQ ID NO: 111), hsATP5B (SEQ ID NO: 112), hsAK2 (SEQ ID NO: 113), hsALDH2 (SEQ ID NO: 114), hsCOX10 (SEQ ID NO: 115), hsUQCRFS1 (SEQ ID NO: 116), hsNDUFV1 (SEQ ID NO: 117), hsNDUFV2 (SEQ ID NO: 118), hsSOD2 (SEQ ID NO: 119), hsCOX6c (SEQ ID NO: 120), hsIRP1 (SEQ ID NO: 121), hsMRPS12 (SEQ ID NO: 122), hsATP5J2 (SEQ ID NO: 123), rnSOD2 (SEQ ID NO: 124), and hsOXA1L (SEQ ID NO: 125). The 3'UTR nucleic acid sequence can also be a variant having at least 70%, 75%, 80%, 85%, 90% and more preferably at least 95%, 96%, 97%, 98%, 99%, 99.5%, or 100% homologous to any 3'UTR nucleic acid sequence listed here. For example, the 3'UTR nucleic acid sequence can be SEQ ID NO: 13 or 14.

Also disclosed herein are recombinant nucleic acid sequences comprising a mitochondrial targeting sequence, a mitochondrial protein coding sequence, and a 3'UTR nucleic acid sequence. For example, the recombinant nucleic acid sequence can be selected from SEQ ID NO: 15-84. The recombinant nucleic acid sequence can also be a variant having at least 70%, 75%, 80%, 85%, 90% and more preferably at least 95%, 96%, 97%, 98%, 99%, 99.5%, or 100% homologous to any recombinant nucleic acid sequence listed here.

Promoters and Regulatory Sequences

The vector of the invention also includes elements allowing for the expression of the disclosed transgene in vitro or in vivo. Thus, the vector typically comprises a promoter sequence operably linked to the polynucleotide sequence encoding the ND4, ND6, or ND1 transgene or a variant thereof.

Any suitable promoter may be used. The promoter sequence may be constitutively active i.e. operational in any host cell background, or alternatively may be active only in a specific host cell environment, thus allowing for targeted expression of the transgene in a particular cell type. The promoter may show inducible expression in response to presence of another factor, for example a factor present in a host cell. In any event, where the vector is administered for therapy, the promoter must be functional in a retinal cell background.

In some embodiments, it is preferred that the promoter shows retinal-cell specific expression in order to allow for the transgene to only be expressed in retinal cell populations. Thus, expression from the promoter may be retinal-cell specific, for example confined only to cells of the neurosensory retina and retinal pigment epithelium.

Preferred promoters for the ND4, ND6, or ND1 transgene include the chicken beta-actin (CBA) promoter, optionally in combination with a cytomegalovirus (CME) enhancer element. In some cases, the preferred promoters for the ND4, ND6, or ND1 transgene comprises the CAG promoter. A particularly preferred promoter is a hybrid CBA/CAG promoter, for example the promoter used in the rAVE expression cassette. Examples of promoters based on human sequences that would induce retina specific gene expression include rhodospin kinase for rods and cones (Allocca et al., 2007, J Viol 81:11372-80), PR2.1 for cones only (Mancuso et al. 2009, Nature) and/or RPE65 for the retinal pigment epithelium (Bainbridge et al., 2008, N Eng J Med).

The vector of the invention may also comprise one or more additional regulatory sequences with may act pre- or post-transcriptionally. The regulatory sequence may be part of the native ND4, ND6, or ND1 gene locus or may be a heterologous regulatory sequence. The vector of the invention may comprise portions of the 5'UTR or 3'UTR from the native ND4, ND6, or ND1 transcript.

Regulatory sequences are any sequences which facilitate expression of the transgene i.e. act to increase expression of a transcript, improve nuclear export of mRNA or enhance its stability. Such regulatory sequences include for example enhancer elements, postregulatory elements and polyadenylation sites. A preferred polyadenylation site is the Bovine Growth Hormone poly-A signal. In the context of the vector of the invention such regulatory sequences will be cis-acting. However, the invention also encompasses the use of trans-acting regulatory sequences located on additional genetic constructs.

A preferred postregulatory element for use in a vector of the invention is the woodchuck hepatitis postregulatory element (WPRE) or a variant thereof. Another regulatory sequence which may be used in a vector of the present invention is a scaffold-attachment region (SAR). Additional regulatory sequences may be selected by the skilled person on the basis of their common general knowledge.

Preparation of Vector

The vector of the invention may be prepared by standard means known in the art for provision of vectors for gene therapy. Thus, well established public domain transfection, packaging and purification methods can be used to prepare a suitable vector preparation.

As discussed above, a vector of the invention may comprise the full genome of a naturally occurring AAV virus in addition to a polynucleotide sequence encoding ND4, ND6, or ND1 or a variant thereof. However, commonly a derivatised genome will be used, for instance a derivative which has at least one inverted terminal repeat sequence (ITR), but which may lack any AAV genes such as rep or cap.

In such embodiments, in order to provide for assembly of the derivatised genome into an AAV viral particle, additional genetic constructs providing AAV and/or helper virus functions will be provided in a host cell in combination with the derivatised genome. These additional constructs will typically contain genes encoding structural AAV capsid proteins i.e. cap, VP1, VP2, VP3, and genes encoding other functions required for the AAV life cycle, such as rep. The selection of structural capsid proteins provided on the additional construct will determine the serotype of the packaged viral vector.

A particularly preferred packaged viral vector for use in the invention comprises a derivatised genome of AAV2 in combination with AAV5 or AAV8 capsid proteins. This packaged viral vector typically comprises one or more AAV2 ITRs.

As mentioned above, AAV viruses are replication incompetent and so helper virus functions, preferably adenovirus helper functions will typically also be provided on one or more additional constructs to allow for AAV replication.

All of the above additional constructs may be provided as plasmids or other episomal elements in the host cell, or alternatively one or more constructs may be integrated into the genome of the host cell.

In these aspects, the invention provides a method for production of a vector of the invention. The method comprises providing a vector which comprises an adeno-associated virus (AAV) genome or a derivative thereof and a polynucleotide sequence encoding ND4, ND6, or ND1 or a variant thereof in a host cell, and providing means for replication and assembly of the vector into an AAV viral particle. Preferably, the method comprises providing a vector comprising a derivative of an AAV genome and a polynucleotide sequence encoding ND4, ND6, or ND1 or a variant thereof, together with one or more additional genetic constructs encoding AAV and/or helper virus functions. Typically, the derivative of an AAV genome comprises at least one ITR. Optionally, the method further comprises a step of purifying the assembled viral particles. Additionally, the method may comprise a step of formulating the viral particles for therapeutic use.

Methods of Therapy and Medical Uses

As discussed above, the present inventors have surprisingly demonstrated that a vector of the invention may be used to address the cellular dysfunction underlying LHON. In particular, they have shown that use of the vector can correct the defect associated with LHON. This provides a means whereby the degenerative process of the disease can be treated, arrested, palliated or prevented.

The invention therefore provides a method of treating or preventing LHON in a patient in need thereof, comprising administering a therapeutically effective amount of a vector of the invention to the patient by direct retinal, subretinal or intravitreal injection. Accordingly, LHON is thereby treated or prevented in the patient.

In a related aspect, the invention provides for use of a vector of the invention in a method of treating or preventing LHON by administering said vector to a patient by direct retinal, subretinal or intravitreal injection. Additionally, the invention provides the use of a vector of the invention in the manufacture of a medicament for treating or preventing LHON by direct retinal, subretinal or intravitreal injection.

In all these embodiments, the vector of the invention may be administered in order to prevent the onset of one or more symptoms of LHON. The patient may be asymptomatic. The subject may have a predisposition to the disease. The method or use may comprise a step of identifying whether or not a subject is at risk of developing, or has, LHON. A prophylactically effective amount of the vector is administered to such a subject. A prophylactically effective amount is an amount which prevents the onset of one or more symptoms of the disease.

Alternatively, the vector may be administered once the symptoms of the disease have appeared in a subject i.e. to cure existing symptoms of the disease. A therapeutically effective amount of the antagonist is administered to such a subject. A therapeutically effective amount is an amount which is effective to ameliorate one or more symptoms of the disease. Such an amount may also arrest, slow or reverse some loss of peripheral vision associated with LHON. Such an amount may also arrest, slow or reverse onset of LHON.

A typical single dose is between $10^{10}$ and $10^{12}$ genome particles, depending on the amount of remaining retinal tissue that requires transduction. A genome particle is defined herein as an AAV capsid that contains a single stranded DNA molecule that can be quantified with a sequence specific method (such as real-time PCR). That dose may be provided as a single dose, but may be repeated for the fellow eye or in cases where vector may not have targeted the correct region of retina for whatever reason (such as surgical complication). The treatment is preferably a single permanent treatment for each eye, but repeat injections, for example in future years and/or with different AAV serotypes may be considered.

The invention also provides a method of monitoring treatment or prevention of LHON in a patient comprising measuring activity ex vivo in retinal cells obtained from said patient following administration of the AAV vector of the invention by direct retinal, subretinal or intravitreal injection. This method can allow for determination of the efficacy of treatment.

Pharmaceutical Compositions

The vector of the invention can be formulated into pharmaceutical compositions. These compositions may comprise, in addition to the vector, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may be determined by the skilled person according to the route of administration, i.e. here direct retinal, subretinal or intravitreal injection.

The pharmaceutical composition is typically in liquid form. Liquid pharmaceutical compositions generally include a liquid carrier such as water, petroleum, animal or vegetable oils, mineral oil or synthetic oil. Physiological saline solution, magnesium chloride, dextrose or other saccharide solution or glycols such as ethylene glycol, propylene glycol or polyethylene glycol may be included. In some cases, a surfactant, such as pluronic acid (PF68) 0.001% may be used.

In some embodiments, the pharmaceutical composition of the disclosure comprises between $10^9$ and $10^{16}$ viral vectors. In some embodiments, the pharmaceutical composition of the disclosure comprises between $10^{10}$ and $10^{12}$ viral vectors per milliliter.

For injection at the site of affliction, the active ingredient will be in the form of an aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

For delayed release, the vector may be included in a pharmaceutical composition which is formulated for slow release, such as in microcapsules formed from biocompatible polymers or in liposomal carrier systems according to methods known in the art.

Samples

Samples that are suitable for use in the methods described herein can be nucleic acid samples from a subject. A "nucleic acid sample" as used herein can include RNA or DNA, or a combination thereof. In another embodiment, a "polypeptide sample" (e.g., peptides or proteins, or fragments therefrom) can be used to ascertain information that an amino acid change has occurred, which is the result of a genetic variant. Nucleic acids and polypeptides can be extracted from one or more samples including but not limited to, blood, saliva, urine, mucosal scrapings of the lining of the mouth, expectorant, serum, tears, skin, tissue, or hair. A nucleic acid sample can be assayed for nucleic acid information. "Nucleic acid information," as used herein, includes a nucleic acid sequence itself, the presence/absence of genetic variation in the nucleic acid sequence, a physical property which varies depending on the nucleic acid sequence (e.g., Tm), and the amount of the nucleic acid (e.g., number of mRNA copies). A "nucleic acid" means any one of DNA, RNA, DNA including artificial nucleotides, or RNA including artificial nucleotides. As used herein, a "purified nucleic acid" includes cDNAs, fragments of genomic nucleic acids, nucleic acids produced using the polymerase chain reaction (PCR), nucleic acids formed by restriction enzyme treatment of genomic nucleic acids, recombinant nucleic acids, and chemically synthesized nucleic acid molecules. A "recombinant" nucleic acid molecule includes a nucleic acid molecule made by an artificial combination of two otherwise separated segments of sequence, e.g., by chemical synthesis or by the manipulation of isolated segments of nucleic acids by genetic engineering techniques. As used herein, a "polypeptide" includes proteins, fragments of proteins, and peptides, whether isolated from natural sources, produced by recombinant techniques, or chemically synthesized. A polypeptide may have one or more modifications, such as a post-translational modification (e.g., glycosylation, phosphorylation, etc.) or any other modification (e.g., pegylation, etc.). The polypeptide may contain one or more non-naturally-occurring amino acids (e.g., such as an amino acid with a side chain modification).

In some embodiments, the nucleic acid sample can comprise cells or tissue, for example, cell lines. Exemplary cell types from which nucleic acids can be obtained using the methods described herein include, but are not limited to, the following: a blood cell such as a B lymphocyte, T lymphocyte, leukocyte, erythrocyte, macrophage, or neutrophil; a muscle cell such as a skeletal cell, smooth muscle cell or cardiac muscle cell; a germ cell, such as a sperm or egg; an epithelial cell; a connective tissue cell, such as an adipocyte, chondrocyte; fibroblast or osteoblast; a neuron; an astrocyte; a stromal cell; an organ specific cell, such as a kidney cell, pancreatic cell, liver cell, or a keratinocyte; a stem cell; or any cell that develops therefrom. A cell from which nucleic acids can be obtained can be a blood cell or a particular type of blood cell including, for example, a hematopoietic stem cell or a cell that arises from a hematopoietic stem cell such as a red blood cell, B lymphocyte, T lymphocyte, natural killer cell, neutrophil, basophil, eosinophil, monocyte, macrophage, or platelet. Generally, any type of stem cell can be used including, without limitation, an embryonic stem cell, adult stem cell, or pluripotent stem cell.

In some embodiments, a nucleic acid sample can be processed for RNA or DNA isolation, for example, RNA or DNA in a cell or tissue sample can be separated from other components of the nucleic acid sample. Cells can be harvested from a nucleic acid sample using standard techniques, for example, by centrifuging a cell sample and resuspending the pelleted cells, for example, in a buffered solution, for example, phosphate-buffered saline (PBS). In some embodiments, after centrifuging the cell suspension to obtain a cell pellet, the cells can be lysed to extract DNA. In some embodiments, the nucleic acid sample can be concentrated and/or purified to isolate DNA. All nucleic acid samples obtained from a subject, including those subjected to any sort of further processing, are considered to be obtained from the subject. In some embodiments, standard techniques and kits known in the art can be used to extract RNA or DNA from a nucleic acid sample, including, for example, phenol extraction, a QIAAMP® Tissue Kit (Qiagen, Chatsworth, Calif.), a WIZARD® Genomic DNA purification kit (Promega), or a Qiagen Autopure method using Puregene chemistry, which can enable purification of highly stable DNA well-suited for archiving.

In some embodiments, determining the identity of an allele or determining copy number can, but need not, include obtaining a nucleic acid sample comprising RNA and/or DNA from a subject, and/or assessing the identity, copy number, presence or absence of one or more genetic variations and their chromosomal locations within the genomic DNA (i.e. subject's genome) derived from the nucleic acid sample.

The individual or organization that performs the determination need not actually carry out the physical analysis of a nucleic acid sample from a subject. In some embodiments, the methods can include using information obtained by analysis of the nucleic acid sample by a third party. In some embodiments, the methods can include steps that occur at more than one site. For example, a nucleic acid sample can be obtained from a subject at a first site, such as at a health care provider or at the subject's home in the case of a self-testing kit. The nucleic acid sample can be analyzed at the same or a second site, for example, at a laboratory or other testing facility.

Nucleic Acids

The nucleic acids and polypeptides described herein can be used in methods and kits of the present disclosure. In some embodiments, aptamers that specifically bind the nucleic acids and polypeptides described herein can be used in methods and kits of the present disclosure. As used herein, a nucleic acid can comprise a deoxyribonucleotide (DNA) or ribonucleotide (RNA), whether singular or in polymers, naturally occurring or non-naturally occurring, double-stranded or single-stranded, coding, for example a translated gene, or non-coding, for example a regulatory region, or any fragments, derivatives, mimetics or complements thereof. In some embodiments, nucleic acids can comprise oligonucleotides, nucleotides, polynucleotides, nucleic acid sequences, genomic sequences, complementary DNA (cDNA), antisense nucleic acids, DNA regions, probes, primers, genes, regulatory regions, introns, exons, open-reading frames, binding sites, target nucleic acids and allele-specific nucleic acids.

A "probe," as used herein, includes a nucleic acid fragment for examining a nucleic acid in a specimen using the hybridization reaction based on the complementarity of nucleic acid.

A "hybrid" as used herein, includes a double strand formed between any one of the abovementioned nucleic acid, within the same type, or across different types, including DNA-DNA, DNA-RNA, RNA-RNA or the like.

"Isolated" nucleic acids, as used herein, are separated from nucleic acids that normally flank the gene or nucleotide sequence (as in genomic sequences) and/or has been completely or partially purified from other transcribed sequences (e.g., as in an RNA library). For example, isolated nucleic acids of the disclosure can be substantially isolated with respect to the complex cellular milieu in which it naturally occurs, or culture medium when produced by recombinant techniques, or chemical precursors or other chemicals when chemically synthesized. In some instances, the isolated material can form part of a composition, for example, a crude extract containing other substances, buffer system or reagent mix. In some embodiments, the material can be purified to essential homogeneity using methods known in the art, for example, by polyacrylamide gel electrophoresis (PAGE) or column chromatography (e.g., HPLC). With regard to genomic DNA (gDNA), the term "isolated" also can refer to nucleic acids that are separated from the chromosome with which the genomic DNA is naturally associated. For example, the isolated nucleic acid molecule can contain less than about 250 kb, 200 kb, 150 kb, 100 kb, 75 kb, 50 kb, 25 kb, 10 kb, 5 kb, 4 kb, 3 kb, 2 kb, 1 kb, 0.5 kb or 0.1 kb of the nucleotides that flank the nucleic acid molecule in the gDNA of the cell from which the nucleic acid molecule is derived.

Nucleic acids can be fused to other coding or regulatory sequences can be considered isolated. For example, recombinant DNA contained in a vector is included in the definition of "isolated" as used herein. In some embodiments, isolated nucleic acids can include recombinant DNA molecules in heterologous host cells or heterologous organisms, as well as partially or substantially purified DNA molecules in solution. Isolated nucleic acids also encompass in vivo and in vitro RNA transcripts of the DNA molecules of the present disclosure. An isolated nucleic acid molecule or nucleotide sequence can be synthesized chemically or by recombinant means. Such isolated nucleotide sequences can be useful, for example, in the manufacture of the encoded polypeptide, as probes for isolating homologous sequences (e.g., from other mammalian species), for gene mapping (e.g., by in situ hybridization with chromosomes), or for detecting expression of the gene, in tissue (e.g., human tissue), such as by Northern blot analysis or other hybridization techniques disclosed herein. The disclosure also pertains to nucleic acid sequences that hybridize under high stringency hybridization conditions, such as for selective hybridization, to a nucleotide sequence described herein Such nucleic acid sequences can be detected and/or isolated by allele- or sequence-specific hybridization (e.g., under high stringency conditions). Stringency conditions and methods for nucleic acid hybridizations are well known to the skilled person (see, e.g., Current Protocols in Molecular Biology, Ausubel, F. et al., John Wiley & Sons, (1998), and Kraus, M. and Aaronson, S., Methods Enzymol., 200:546-556 (1991), the entire teachings of which are incorporated by reference herein.

Calculations of "identity" or "percent identity" between two or more nucleotide or amino acid sequences can be determined by aligning the sequences for optimal comparison purposes (e.g., gaps can be introduced in the sequence of a first sequence). The nucleotides at corresponding positions are then compared, and the percent identity between the two sequences is a function of the number of identical positions shared by the sequences (i.e. % identity=# of identical positions/total # of positions×100). For example, a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

In some embodiments, the length of a sequence aligned for comparison purposes is at least 30%, at least 40%, at least 50%, at least 60%, at least 70%, at least 80%, at least 90%, or at least 95%, of the length of the reference sequence. The actual comparison of the two sequences can be accomplished by well-known methods, for example, using a mathematical algorithm. A non-limiting example of such a mathematical algorithm is described in Karlin, S. and Altschul, S., Proc. Natl. Acad. Sci. USA, 90-5873-5877 (1993). Such an algorithm is incorporated into the NBLAST and XBLAST programs (version 2.0), as described in Altschul, S. et al., Nucleic Acids Res., 25:3389-3402 (1997). When utilizing BLAST and Gapped BLAST programs, any relevant parameters of the respective programs (e.g., NBLAST) can be used. For example, parameters for sequence comparison can be set at score=100, word length=12, or can be varied (e.g., W=5 or W=20). Other examples include the algorithm of Myers and Miller, CABIOS (1989), ADVANCE, ADAM, BLAT, and FASTA. In some embodiments, the percent identity between two amino acid sequences can be accomplished using, for example, the GAP program in the GCG software package (Accelrys, Cambridge, UK).

"Probes" or "primers" can be oligonucleotides that hybridize in a base-specific manner to a complementary strand of a nucleic acid molecule. Probes can include primers, which can be a single-stranded oligonucleotide probe that can act as a point of initiation of template-directed DNA synthesis using methods including but not limited to, polymerase chain reaction (PCR) and ligase chain reaction (LCR) for amplification of a target sequence. Oligonucleotides, as described herein, can include segments or fragments of nucleic acid sequences, or their complements. In some embodiments, DNA segments can be between 5 and 10,000 contiguous bases, and can range from 5, 10, 12, 15, 20, or 25 nucleotides to 10, 15, 20, 25, 30, 40, 50, 100, 200, 500, 1000 or 10,000 nucleotides. In addition to DNA and RNA, probes and primers can include polypeptide nucleic acids (PNA), as described in Nielsen, P. et al., Science 254: 1497-1500 (1991). A probe or primer can comprise a region of nucleotide sequence that hybridizes to at least about 15, typically about 20-25, and in certain embodiments about 40, 50, 60 or 75, consecutive nucleotides of a nucleic acid molecule.

The present disclosure also provides isolated nucleic acids, for example, probes or primers, that contain a fragment or portion that can selectively hybridize to a nucleic acid that comprises, or consists of, a nucleotide sequence, wherein the nucleotide sequence can comprise at least one polymorphism or polymorphic allele contained in the genetic variations described herein or the wild-type nucleotide that is located at the same position, or the complements thereof. In some embodiments, the probe or primer can be at least 70% identical, at least 80% identical, at least 85% identical, at least 90% identical, or at least 95% identical, to the contiguous nucleotide sequence or to the complement of the contiguous nucleotide sequence.

In some embodiments, a nucleic acid probe can be an oligonucleotide capable of hybridizing with a complementary region of a gene associated with a condition (e.g., LHON) containing a genetic variation described herein. The nucleic acid fragments of the disclosure can be used as probes or primers in assays such as those described herein.

The nucleic acids of the disclosure, such as those described above, can be identified and isolated using standard molecular biology techniques well known to the skilled person. In some embodiments, DNA can be amplified and/or can be labeled (e.g., radiolabeled, fluorescently labeled) and used as a probe for screening, for example, a cDNA library derived from an organism. cDNA can be derived from mRNA and can be contained in a suitable vector. For example, corresponding clones can be isolated, DNA obtained fallowing in vivo excision, and the cloned insert can be sequenced in either or both orientations by art-recognized methods to identify the correct reading frame encoding a polypeptide of the appropriate molecular weight. Using these or similar methods, the polypeptide and the DNA encoding the polypeptide can be isolated, sequenced and further characterized.

In some embodiments, nucleic acid can comprise one or more polymorphisms, variations, or mutations, for example, single nucleotide polymorphisms (SNPs), single nucleotide variations (SNVs), copy number variations (CNVs), for example, insertions, deletions, inversions, and translocations. In some embodiments, nucleic acids can comprise analogs, for example, phosphorothioates, phosphoramidates, methyl phosphonate, chiralmethyl phosphonates, 2-O-methyl ribonucleotides, or modified nucleic acids, for example, modified backbone residues or linkages, or nucleic acids combined with carbohydrates, lipids, polypeptide or other materials, or peptide nucleic acids (PNAs), for example, chromatin, ribosomes, and transcriptosomes. In some embodiments nucleic acids can comprise nucleic acids in various structures, for example, A DNA, B DNA, Z-form DNA, siRNA, tRNA, and ribozymes. In some embodiments, the nucleic acid may be naturally or non-naturally polymorphic, for example, having one or more sequence differences, for example, additions, deletions and/or substitutions, as compared to a reference sequence. In some embodiments, a reference sequence can be based on publicly available information, for example, the U.C. Santa Cruz Human Genome Browser Gateway (genome.ucsc.edu/cgi-bin/hg-Gateway) or the NCBI website (www.ncbi.nlm.nih.gov). In some embodiments, a reference sequence can be determined by a practitioner of the present disclosure using methods well known in the art, for example, by sequencing a reference nucleic acid.

In some embodiments, a probe can hybridize to an allele, SNP, SNV, or CNV as described herein. In some embodiments, the probe can bind to another marker sequence associated with LHON as described herein.

One of skill in the art would know how to design a probe so that sequence specific hybridization can occur only if a particular allele is present in a genomic sequence from a test nucleic acid sample. The disclosure can also be reduced to practice using any convenient genotyping method, including commercially available technologies and methods for genotyping particular genetic variations.

Control probes can also be used, for example, a probe that binds a less variable sequence, for example, a repetitive DNA associated with a centromere of a chromosome, can be used as a control. In some embodiments, probes can be obtained from commercial sources. In some embodiments, probes can be synthesized, for example, chemically or in vitro, or made from chromosomal or genomic DNA through standard techniques. In some embodiments sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification using PCR.

One or more nucleic acids for example, a probe or primer, can also be labeled, for example, by direct labeling, to comprise a detectable label. A detectable label can comprise any label capable of detection by a physical, chemical, or a biological process for example, a radioactive label, such as $32P$ or $3H$, a fluorescent label, such as FITC, a chromophore label, an affinity-ligand label, an enzyme label, such as alkaline phosphatase, horseradish peroxidase, or 12 galactosidase, an enzyme cofactor label, a hapten conjugate label, such as digoxigenin or dinitrophenyl, a Raman signal generating label, a magnetic label, a spin label, an epitope label, such as the FLAG or HA epitope, a luminescent label, a heavy atom label, a nanoparticle label, an electrochemical label, a light scattering label, a spherical shell label, semiconductor nanocrystal label, such as quantum dots (described in U.S. Pat. No. 6,207,392), and probes labeled with any other signal generating label known to those of skill in the art, wherein a label can allow the probe to be visualized with or without a secondary detection molecule. A nucleotide can be directly incorporated into a probe with standard techniques, for example, nick translation, random priming, and PCR labeling. A "signal," as used herein, include a signal suitably detectable and measurable by appropriate means, including fluorescence, radioactivity, chemiluminescence, and the like.

Non-limiting examples of label moieties useful for detection include, without limitation, suitable enzymes such as horseradish peroxidase, alkaline phosphatase, beta-galactosidase, or acetylcholinesterase; members of a binding pair that are capable of forming complexes such as streptavidin/biotin, avidin/biotin or an antigen/antibody complex including, for example, rabbit IgG and anti-rabbit IgG; fluorophores such as umbelliferone, fluorescein, fluorescein isothiocyanate, rhodamine, tetramethyl rhodamine, eosin, green fluorescent protein, erythrosin, coumarin, methyl coumarin, pyrene, malachite green, stilbene, lucifer yellow, Cascade Blue, Texas Red, dichlorotriazinylamine fluorescein, dansyl chloride, phycoerythrin, fluorescent lanthanide complexes such as those including Europium and Terbium, cyanine dye family members, such as Cy3 and Cy5, molecular beacons and fluorescent derivatives thereof, as well as others known in the art as described, for example, in Principles of Fluorescence Spectroscopy, Joseph R. Lakowicz (Editor), Plenum Pub Corp, 2nd edition (July 1999) and the 6th Edition of the Molecular Probes Handbook by Richard P. Hoagland; a luminescent material such as luminol; light scattering or plasmon resonant materials such as gold or silver particles or quantum dots; or radioactive material include 14C, 123I, 124I, 125I, Tc99m, 32P, 33P, 35S or 3H.

Other labels can also be used in the methods of the present disclosure, for example, backbone labels. Backbone labels comprise nucleic acid stains that bind nucleic acids in a sequence independent manner. Non-limiting examples include intercalating dyes such as phenanthridines and acridines (e.g., ethidium bromide, propidium iodide, hexidium iodide, dihydroethidium, ethidium homodimer-1 and -2, ethidium monoazide, and ACMA); some minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes, Inc. Still other examples of nucleic acid stains include the following dyes from Molecular Probes: cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red).

In some embodiments, fluorophores of different colors can be chosen, for example, 7-amino-4-methylcoumarin-3-acetic acid (AMCA), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, TRITC, rhodamine, tetramethylrhodamine, R-phycoerythrin, Cy-3, Cy-5, Cy-7, Texas Red, Phar-Red, allophycocyanin (APC), and CASCADE™ blue acetylazide, such that each probe in or not in a set can be distinctly visualized. In some embodiments, fluorescently labeled probes can be viewed with a fluorescence microscope and an appropriate filter for each fluorophore, or by using dual or triple bandpass filter sets to observe multiple fluorophores. In some embodiments, techniques such as flow cytometry can be used to examine the hybridization pattern of the probes.

In other embodiments, the probes can be indirectly labeled, for example, with biotin or digoxygenin, or labeled with radioactive isotopes such as 32P and/or 3H. As a non-limiting example, a probe indirectly labeled with biotin can be detected by avidin conjugated to a detectable marker. For example, avidin can be conjugated to an enzymatic marker such as alkaline phosphatase or horseradish peroxidase. In some embodiments, enzymatic markers can be detected using colorimetric reactions using a substrate and/or a catalyst for the enzyme. In some embodiments, catalysts for alkaline phosphatase can be used, for example, 5-bromo-4-chloro-3-indolylphosphate and nitro blue tetrazolium. In some embodiments, a catalyst can be used for horseradish peroxidase, for example, diaminobenzoate.

Formulations, Routes of Administration, and Effective Doses

Yet another aspect of the present disclosure relates to formulations, routes of administration and effective doses for pharmaceutical compositions comprising an agent or combination of agents of the instant disclosure. Such pharmaceutical compositions can be used to treat a condition (e.g., LHON) as described above.

Compounds of the disclosure can be administered as pharmaceutical formulations including those suitable for oral (including buccal and sub-lingual), rectal, nasal, topical, transdermal patch, pulmonary, vaginal, suppository, or parenteral (including intraocular, intravitreal, intramuscular, intraarterial, intrathecal, intradermal, intraperitoneal, subcutaneous and intravenous) administration or in a form suitable for administration by aerosolization, inhalation or insufflation. General information on drug delivery systems can be found in Ansel et al., Pharmaceutical Dosage Forms and Drug Delivery Systems (Lippencott Williams & Wilkins, Baltimore Md. (1999).

In various embodiments, the pharmaceutical composition includes carriers and excipients (including but not limited to buffers, carbohydrates, mannitol, polypeptides, amino acids, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In some embodiments, the pharmaceutical preparation is substantially free of preservatives. In other embodiments, the pharmaceutical preparation can contain at least one preservative. General methodology on pharmaceutical dosage forms is found in Ansel et al., Pharmaceutical Dosage Forms and Drug Delivery Systems (Lippencott, Williams, & Wilkins, Baltimore Md. (1999)). It can be recognized that, while any suitable carrier known to those of ordinary skill in the art can be employed to administer the compositions of this disclosure, the type of carrier can vary depending on the mode of administration.

Compounds can also be encapsulated within liposomes using well-known technology. Biodegradable microspheres can also be employed as carriers for the pharmaceutical compositions of this disclosure. Suitable biodegradable microspheres are disclosed, for example, in U.S. Pat. Nos. 4,897,268, 5,075,109, 5,928,647, 5,811,128, 5,820,883, 5,853,763, 5,814,344 and 5,942,252.

The compound can be administered in liposomes or microspheres (or microparticles). Methods for preparing liposomes and microspheres for administration to a subject are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, and along with surfactants if required, and the material dialyzed or sonicated, as necessary. A review of known methods is provided by G. Gregoriadis, Chapter 14, "Liposomes," Drug Carriers in Biology and Medicine, pp. 2.sup.87-341 (Academic Press, 1979).

Microspheres formed of polymers or polypeptides are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

The concentration of drug can be adjusted, the pH of the solution buffered and the isotonicity adjusted to be compatible with intraocular or intravitreal injection.

The compounds of the disclosure can be formulated as a sterile solution or suspension, in suitable vehicles. The pharmaceutical compositions can be sterilized by conventional, well-known sterilization techniques, or can be sterile filtered. The resulting aqueous solutions can be packaged for use as is, or lyophilized, the lyophilized preparation being combined with a sterile solution prior to administration. Suitable formulations and additional carriers are described in Remington "The Science and Practice of Pharmacy" (20th Ed., Lippincott Williams & Wilkins, Baltimore Md.), the teachings of which are incorporated by reference in their entirety herein.

The agents or their pharmaceutically acceptable salts can be provided alone or in combination with one or more other agents or with one or more other forms. For example, a formulation can comprise one or more agents in particular proportions, depending on the relative potencies of each agent and the intended indication. For example, in compositions for targeting two different host targets, and where potencies are similar, about a 1:1 ratio of agents can be used. The two forms can be formulated together, in the same dosage unit e.g., in one cream, suppository, tablet, capsule, aerosol spray, or packet of powder to be dissolved in a beverage, or each form can be formulated in a separate unit, e.g., two creams, two suppositories, two tablets, two capsules, a tablet and a liquid for dissolving the tablet, two aerosol sprays, or a packet of powder and a liquid for dissolving the powder, etc.

The term "pharmaceutically acceptable salt" means those salts which retain the biological effectiveness and properties of the agents used in the present disclosure, and which are not biologically or otherwise undesirable.

Typical salts are those of the inorganic ions, such as, for example, sodium, potassium, calcium, magnesium ions, and the like. Such salts include salts with inorganic or organic acids, such as hydrochloric acid, hydrobromic acid, phosphoric acid, nitric acid, sulfuric acid, methanesulfonic acid, p toluenesulfonic acid, acetic acid, fumaric acid, succinic acid, lactic acid, mandelic acid, malic acid, citric acid, tartaric acid or maleic acid. In addition, if the agent(s) contain a carboxyl group or other acidic group, it can be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

A pharmaceutically acceptable ester or amide refers to those which retain biological effectiveness and properties of the agents used in the present disclosure, and which are not biologically or otherwise undesirable. Typical esters include ethyl, methyl, isobutyl, ethylene glycol, and the like. Typical amides include unsubstituted amides, alkyl amides, dialkyl amides, and the like.

In some embodiments, an agent can be administered in combination with one or more other compounds, forms, and/or agents, e.g., as described above. Pharmaceutical compositions with one or more other active agents can be formulated to comprise certain molar ratios. For example, molar ratios of about 99:1 to about 1:99 of a first active agent to the other active agent can be used. In some subset of the embodiments, the range of molar ratios of a first active agent: other active agents are selected from about 80:20 to about 20:80; about 75:25 to about 25:75, about 70:30 to about 30:70, about 66:33 to about 33:66, about 60:40 to about 40:60; about 50:50; and about 90:10 to about 10:90. The molar ratio of a first active: other active agents can be about 1:9, and in some embodiments can be about 1:1. The two agents, forms and/or compounds can be formulated together, in the same dosage unit e.g., in one cream, suppository, tablet, capsule, or packet of powder to be dissolved in a beverage; or each agent, form, and/or compound can be formulated in separate units, e.g., two creams, suppositories, tablets, two capsules, a tablet and a liquid for dissolving the tablet, an aerosol spray a packet of powder and a liquid for dissolving the powder, etc.

If necessary or desirable, the agents and/or combinations of agents can be administered with still other agents. The choice of agents that can be co-administered with the agents and/or combinations of agents of the instant disclosure can depend, at least in part, on the condition being treated.

The agent(s) (or pharmaceutically acceptable salts, esters or amides thereof) can be administered per se or in the form of a pharmaceutical composition wherein the active agent(s) is in an admixture or mixture with one or more pharmaceutically acceptable carriers. A pharmaceutical composition, as used herein, can be any composition prepared for administration to a subject. Pharmaceutical compositions for use in accordance with the present disclosure can be formulated in conventional manner using one or more physiologically acceptable carriers, comprising excipients, diluents, and/or auxiliaries, e.g., which facilitate processing of the active agents into preparations that can be administered. Proper formulation can depend at least in part upon the route of administration chosen. The agent(s) useful in the present disclosure, or pharmaceutically acceptable salts, esters, or amides thereof, can be delivered to a subject using a number of routes or modes of administration, including oral, buccal, topical, rectal, transdermal, transmucosal, subcutaneous, intravenous, intraocular, intravitreal, and intramuscular applications, as well as by inhalation.

In some embodiments, oils or non-aqueous solvents can be used to bring the agents into solution, due to, for example, the presence of large lipophilic moieties. Alternatively, emulsions, suspensions, or other preparations, for example, liposomal preparations, can be used. With respect to liposomal preparations, any known methods for preparing liposomes for treatment of a condition can be used. See, for example, Bangham et al., J. Mol. Biol. 23: 238-252 (1965) and Szoka et al., Proc. Natl Acad. Sci. USA 75: 4194-4198 (1978), incorporated herein by reference. Ligands can also be attached to the liposomes to direct these compositions to particular sites of action. Agents of this disclosure can also be integrated into foodstuffs, e.g., cream cheese, butter, salad dressing, or ice cream to facilitate solubilization, administration, and/or compliance in certain subject populations.

The compounds of the disclosure can be formulated for parenteral administration (e.g., by injection, for example, intraocular or intravitreal injection) and can be presented in unit dose form in ampoules, pre-filled syringes, small volume infusion or in multi-dose containers with an added preservative. The compositions can take such forms as suspensions, solutions, or emulsions in oily or aqueous vehicles, for example, solutions in aqueous polyethylene glycol.

For injectable formulations, the vehicle can be chosen from those known in art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation can also comprise polymer compositions which are biocompatible, biodegradable, such as poly(lactic-co-glycolic)acid. These materials can be made into micro or nanospheres, loaded with drug and further coated or derivatized to provide superior sustained release performance. Vehicles suitable for periocular or intraocular injection include, for example, suspensions of therapeutic agent in injection grade water, liposomes and vehicles suitable for lipophilic substances. Other vehicles for periocular or intraocular injection are well known in the art.

In some embodiments, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

When administration is by injection, the active compound can be formulated in aqueous solutions, specifically in physiologically compatible buffers such as Hanks solution, Ringer's solution, or physiological saline buffer. The solution can contain formulatory agents such as suspending, stabilizing and/or dispersing agents. Alternatively, the active compound can be in powder form for constitution with a suitable vehicle, e.g., sterile pyrogen-free water, before use. In some embodiments, the pharmaceutical composition does not comprise an adjuvant or any other substance added to enhance the immune response stimulated by the peptide. In some embodiments, the pharmaceutical composition comprises a substance that inhibits an immune response to the peptide. Methods of formulation are known in the art, for example, as disclosed in Remington's Pharmaceutical Sciences, latest edition, Mack Publishing Co., Easton P.

In some embodiments, eye disorders can be effectively treated with ophthalmic solutions, suspensions, ointments or inserts comprising an agent or combination of agents of the present disclosure. Eye drops can be prepared by dissolving the active ingredient in a sterile aqueous solution such as physiological saline, buffering solution, etc., or by combining powder compositions to be dissolved before use. Other vehicles can be chosen, as is known in the art, including but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

The solubility of the components of the present compositions can be enhanced by a surfactant or other appropriate co-solvent in the composition. Such cosolvents include polysorbate 20, 60, and 80, Pluronic F68, F-84 and P-103, cyclodextrin, or other agents known to those skilled in the art. Such co-solvents can be employed at a level of from about 0.01% to 2% by weight.

The compositions of the disclosure can be packaged in multidose form. Preservatives can be preferred to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. In the prior art ophthalmic products, such preservatives can be employed at a level of from 0.004% to 0.02%. In the compositions of the present application the preservative, preferably benzalkonium chloride, can be employed at a level of from 0.001% to less than 0.01%, e.g., from 0.001% to 0.008%, preferably about 0.005% by weight. It has been found that a concentration of benzalkonium chloride of 0.005% can be sufficient to preserve the compositions of the present disclosure from microbial attack.

/In some embodiments, the agents of the present disclosure are delivered in soluble rather than suspension form, which allows for more rapid and quantitative absorption to the sites of action. In general, formulations such as jellies, creams, lotions, suppositories and ointments can provide an area with more extended exposure to the agents of the present disclosure, while formulations in solution, e.g., sprays, provide more immediate, short-term exposure.

It is envisioned additionally, that the compounds of the disclosure can be attached releasably to biocompatible polymers for use in sustained release formulations on, in or attached to inserts for topical, intraocular, periocular, or systemic administration. The controlled release from a biocompatible polymer can be utilized with a water soluble polymer to form an instillable formulation, as well. The controlled release from a biocompatible polymer, such as for example, PLGA microspheres or nanospheres, can be utilized in a formulation suitable for intra ocular implantation or injection for sustained release administration, as well any suitable biodegradable and biocompatible polymer can be used.

Further Numbered Embodiments

Further numbered embodiments of the disclosure are provided here as follows:
Embodiment 1. A recombinant nucleic acid, comprising:
a mitochondrial targeting sequence;
a mitochondrial protein coding sequence comprising a sequence that is at least 99% identical to SEQ ID NO: 11 or 12; and
a 3'UTR nucleic acid sequence.
Embodiment 2. The recombinant nucleic acid of Embodiment 1, wherein said mitochondrial targeting sequence encodes a polypeptide comprising a peptide sequence that is at least 90%, at least 95%, at least 97%, at least 99%, or 100% identical to a sequence selected from the group consisting of SEQ ID NO: 129-159.

Embodiment 3. The recombinant nucleic acid of Embodiment 1, wherein said mitochondrial targeting sequence comprises a sequence that is at least 90%, at least 95%, at least 97%, at least 99%, or 100% identical to a sequence as set forth in SEQ ID NO: 2.

Embodiment 4. The recombinant nucleic acid of Embodiment 1, wherein said mitochondrial targeting sequence comprises a sequence that is at least 90%, at least 95%, at least 97%, at least 99%, or 100% identical to a sequence as set forth in SEQ ID NO: 3.

Embodiment 5. The recombinant nucleic acid of Embodiment 1, wherein said mitochondrial targeting sequence comprises a sequence that is at least 90%, at least 95%, at least 97%, at least 99%, or 100% identical to a sequence as set forth in SEQ ID NO: 4.

Embodiment 6. The recombinant nucleic acid of Embodiment 1, wherein said mitochondrial targeting sequence comprises a sequence that is at least 90%, at least 95%, at least 97%, at least 99%, or 100% identical to a sequence as set forth in SEQ ID NO: 5.

Embodiment 7. The recombinant nucleic acid of Embodiment 1, wherein said mitochondrial targeting sequence comprises a sequence that is at least 90%, at least 95%, at least 97%, at least 99%, or 100% identical to a sequence as set forth in SEQ ID NO: 1.

Embodiment 8. The recombinant nucleic acid of Embodiment 1, wherein said mitochondrial protein coding sequence comprises a sequence that is at least 90%, at least 95%, at least 97%, at least 99%, or 100% identical to a sequence as set forth in SEQ ID NO: 12.

Embodiment 8.1. The recombinant nucleic acid of Embodiment 1, wherein said mitochondrial protein coding sequence comprises a sequence that is at least 90%, at least 95%, at least 97%, at least 99%, or 100% identical to a sequence as set forth in SEQ ID NO: 11.

Embodiment 9. The recombinant nucleic acid of any one of Embodiments 1-8 and 8.1, wherein said 3'UTR nucleic acid sequence comprises a sequence that is at least 90%, at least 95%, at least 97%, at least 99%, or 100% identical to a sequence selected from the group consisting of SEQ ID NO: 111-125.

Embodiment 10. The recombinant nucleic acid of any one of Embodiments 1-8 and 8.1, wherein said 3'UTR nucleic acid sequence comprises a sequence that is at least 90%, at least 95%, at least 97%, at least 99%, or 100% identical to a sequence as set forth in SEQ ID NO: 13 or SEQ ID NO: 14.

Embodiment 11. The recombinant nucleic acid of Embodiment 1, wherein said recombinant nucleic acid comprises a sequence that is at least 90%, at least 95%, at least 97%, at least 99%, or 100% identical to a sequence selected from the group consisting of SEQ ID NO: 25-28, 39-42, 53-56, 67-70, and 81-84.

Embodiment 12. A recombinant nucleic acid, comprising:
a mitochondrial targeting sequence;
a mitochondrial protein coding sequence comprising a sequence that is at least 90%, at least 95%, at least 97%, at least 99%, or 100% identical to SEQ ID NO: 11 or 12; and
a 3'UTR nucleic acid sequence.

Embodiment 13. The recombinant nucleic acid of Embodiment 12, wherein said mitochondrial targeting sequence comprises a sequence encodes a polypeptide selected from the group consisting of hsCOX10, hsCOX8, scRPM2, lcSirt5, tbNDUS7, ncQCR2, hsATP5G2, hsLACTB, spilv1, gmCOX2, crATP6, hsOPA1, hsSDHD, hsADCK3, osP0644B06.24-2, *Neurospora crassa* ATP9 (ncATP9), hsGHITM, hsNDUFAB1, hsATP5G3, crATP6_hsADCK3, ncATP9_ncATP9, zmLOC100282174, ncATP9_zmLOC100282174_spilv1_ncATP9, zmLOC100282174_hsADCK3_crATP6_hsATP5G3, zmLOC100282174_hsADCK3_hsATP5G3, ncATP9_zmLOC100282174, hsADCK3_zmLOC100282174_crATP6_hsATP5G3, crATP6_hsADCK3_zmLOC100282174_hsATP5G3, hsADCK3_zmLOC100282174, hsADCK3_zmLOC100282174_crATP6, ncATP9_zmLOC100282174_spilv1_GNFP_ncATP9, and ncATP9_zmLOC100282174_spilv1_lcSirt5_osP0644B06.24-2_hsATP5G2_ncATP9.

Embodiment 14. The recombinant nucleic acid of Embodiment 12 or 13, wherein said mitochondrial targeting sequence encodes a polypeptide comprising a peptide sequence that is at least 90%, at least 95%, at least 97%, at least 99%, or 100% identical to a sequence selected from the group consisting of SEQ ID NO: 129-159.

Embodiment 15. The recombinant nucleic acid of any one of Embodiments 12-14, wherein said mitochondrial targeting sequence comprises a sequence that is at least 90%, at least 95%, at least 97%, at least 99%, or 100% identical to a sequence as set forth in SEQ ID NO: 2 or 3.

Embodiment 16. The recombinant nucleic acid of any one of Embodiments 12-14, wherein said mitochondrial targeting sequence comprises a sequence that is at least 90%, at least 95%, at least 97%, at least 99%, or 100% identical to a sequence as set forth in SEQ ID NO: 4.

Embodiment 17. The recombinant nucleic acid of any one of Embodiments 12-14, wherein said mitochondrial targeting sequence comprises a sequence that is at least 90%, at least 95%, at least 97%, at least 99%, or 100% identical to a sequence as set forth in SEQ ID NO: 5.

Embodiment 18. The recombinant nucleic acid of any one of Embodiments 12-14, wherein said mitochondrial targeting sequence comprises a sequence that is at least 90%, at least 95%, at least 97%, at least 99%, or 100% identical to a sequence as set forth in SEQ ID NO: 1.

Embodiment 19. The recombinant nucleic acid of any one of Embodiments 12-18, wherein said 3'UTR nucleic acid sequence is located at 3' of said mitochondrial targeting sequence.

Embodiment 20. The recombinant nucleic acid of any one of Embodiments 12-19, wherein said 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, rnSOD2, and hsOXA1L.

Embodiment 21. The recombinant nucleic acid of any one of Embodiments 12-20, wherein said 3'UTR nucleic acid sequence comprises a sequence that is at least 90%, at least 95%, at least 97%, at least 99%, or 100% identical to a sequence selected from the group consisting of SEQ ID NO: 111-125.

Embodiment 22. The recombinant nucleic acid of any one of Embodiments 12-21, wherein said 3'UTR nucleic acid sequence comprises a sequence that is at least 90%, at least 95%, at least 97%, at least 99%, or 100% identical to a sequence as set forth in SEQ ID NO: 13 or SEQ ID NO: 14.

Embodiment 23. The recombinant nucleic acid of any one of Embodiments 12-22, wherein said mitochondrial targeting sequence is located at 5' of said 3'UTR nucleic acid sequence.

Embodiment 24. The recombinant nucleic acid of any one of Embodiments 12-22, wherein said mitochondrial targeting sequence is located at 3' of said mitochondrial targeting sequence.

Embodiment 25. The recombinant nucleic acid of any one of Embodiments 12-24, wherein said recombinant nucleic acid comprises a sequence that is at least 90%, at least 95%, at least 97%, at least 99%, or 100% identical to a sequence selected from the group consisting of SEQ ID NO: 25-28, 39-42, 53-56, 67-70, and 81-84.

Embodiment 26. The recombinant nucleic acid of any one of Embodiments 12-25, wherein said mitochondrial protein coding sequence encodes a mitochondrial protein comprising or consisting of a sequence that is at least 90%, at least 95%, at least 97%, at least 99%, or 100% identical to a sequence as set forth in SEQ ID NO: 162.

Embodiment 27. A recombinant nucleic acid, comprising a mitochondrial protein coding sequence, wherein said mitochondrial protein coding sequence encodes a polypeptide comprising a mitochondrial protein, wherein said mitochondrial protein coding sequence comprises a sequence that is at least 90%, at least 95%, at least 97%, at least 99%, or 100% identical to SEQ ID NO: 11 or 12.

Embodiment 28. The recombinant nucleic acid of Embodiment 27, further comprising a mitochondrial targeting sequence.

Embodiment 29. The recombinant nucleic acid of Embodiment 27 or 28, wherein said mitochondrial targeting sequence comprises a sequence encodes a polypeptide selected from the group consisting of hsCOX10, hsCOX8, scRPM2, lcSirt5, tbNDUS7, ncQCR2, hsATP5G2, hsLACTB, spilv1, gmCOX2, crATP6, hsOPA1, hsSDHD, hsADCK3, osP0644B06.24-2, Neurospora crassa ATP9 (ncATP9), hsGHITM hsNDUFAB1, hsATP5G3, crATP6_hsADCK3, ncATP9_ncATP9, zmLOC100282174, ncATP9_zmLOC100282174_spilv1_ncATP9, zmLOC100282174_hsADCK3_crATP6_hsATP5G3, zmLOC100282174_hsADCK3_hsATP5G3, ncATP9_zmLOC100282174, hsADCK3_zmLOC100282174_crATP6_hsATP5G3, crATP6_hsADCK3_zmLOC100282174_hsATP5G3, hsADCK3_zmLOC100282174, hsADCK3_zmLOC100282174_crATP6, ncATP9_zmLOC100282174_spilv1_GNFP_ncATP9, and ncATP9_zmLOC100282174_spilv1_lcSirt5_osP0644B06.24-2_hsATP5G2_ncATP9.

Embodiment 30. The recombinant nucleic acid of any one of Embodiments 27-29, wherein said mitochondrial targeting sequence encodes a polypeptide comprising a peptide sequence that is at least 90%, at least 95%, at least 97%, at least 99%, or 100% identical to a sequence selected from the group consisting of SEQ ID NO: 129-159.

Embodiment 31. The recombinant nucleic acid of any one of Embodiments 27-30, wherein said mitochondrial targeting sequence comprises a sequence that is at least 90%, at least 95%, at least 97%, at least 99%, or 100% identical to a sequence as set forth in SEQ ID NO: 2.

Embodiment 32. The recombinant nucleic acid of any one of Embodiments 27-31, wherein said mitochondrial targeting sequence comprises a sequence that is at least 90%, at least 95%, at least 97%, at least 99%, or 100% identical to a sequence as set forth in SEQ ID NO: 3.

Embodiment 33. The recombinant nucleic acid of any one of Embodiments 27-32, wherein said mitochondrial targeting sequence comprises a sequence that is at least 90%, at least 95%, at least 97%, at least 99%, or 100% identical to a sequence as set forth in SEQ ID NO: 4.

Embodiment 34. The recombinant nucleic acid of any one of Embodiments 27-33, wherein said mitochondrial targeting sequence comprises a sequence that is at least 90%, at least 95%, at least 97%, at least 99%, or 100% identical to a sequence as set forth in SEQ ID NO: 5.

Embodiment 35. The recombinant nucleic acid of any one of Embodiments 27-34, wherein said mitochondrial targeting sequence comprises a sequence that is at least 90%, at least 95%, at least 97%, at least 99%, or 100% identical to a sequence as set forth in SEQ ID NO: 1.

Embodiment 36. The recombinant nucleic acid of any one of Embodiments 27-35, further comprising a 3'UTR nucleic acid sequence.

Embodiment 37. The recombinant nucleic acid of Embodiment 36, wherein said 3'UTR nucleic acid sequence is located at 3' of said mitochondrial targeting sequence.

Embodiment 38. The recombinant nucleic acid of Embodiment 36 or 37, wherein said 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, mSOD2, and hsOXA1L.

Embodiment 39. The recombinant nucleic acid of any one of Embodiments 36-38, wherein said 3'UTR nucleic acid sequence comprises a sequence that is at least 90%, at least 95%, at least 97%, at least 99%, or 100% identical to a sequence selected from the group consisting of SEQ ID NO: 111-125.

Embodiment 40. The recombinant nucleic acid of any one of Embodiments 36-39, wherein said 3'UTR nucleic acid sequence comprises a sequence that is at least 90%, at least 95%, at least 97%, at least 99%, or 100% identical to a sequence as set forth in SEQ ID NO: 13 or SEQ ID NO: 14.

Embodiment 41. The recombinant nucleic acid of any one of Embodiments 36-40, wherein said mitochondrial targeting sequence is located at 5' of said 3'UTR nucleic acid sequence.

Embodiment 42. The recombinant nucleic acid of any one of Embodiments 36-41, wherein said mitochondrial targeting sequence is located at 3' of said mitochondrial targeting sequence.

Embodiment 43. The recombinant nucleic acid of any one of Embodiments 36-42, wherein said recombinant nucleic acid comprises a sequence that is at least 90%, at least 95%, at least 97%, at least 99%, or 100% identical to a sequence selected from the group consisting of SEQ ID NO: 25-28, 39-42, 53-56, 67-70, and 81-84.

Embodiment 44. A viral vector comprising said recombinant nucleic acid of any one of Embodiments 1-43.

Embodiment 45. The viral vector of Embodiment 44, wherein said viral vector is an adeno-associated virus (AAV) vector.

Embodiment 46. The viral vector of Embodiment 45, wherein said AAV vector is selected from the group consisting of AAV1, AAV2, AAV3, AAV4, AAV5, AAV6, AAV7, AAV8, AAV9, AAV10, AAV11, AAV12, AAV13, AAV14, AAV15, and AAV16 vectors.

Embodiment 47. The viral vector of Embodiment 45 or 46, wherein said AAV vector is a recombinant AAV (rAAV) vector.

Embodiment 48. The viral vector of Embodiment 47, wherein said rAAV vector is rAAV2 vector.

Embodiment 49. A pharmaceutical composition, comprising an adeno-associated virus (AAV) comprising said recombinant nucleic acid of any one of Embodiments 1-43.

Embodiment 50. The pharmaceutical composition of Embodiment 49, further comprising a pharmaceutically acceptable excipient thereof.

Embodiment 51. A pharmaceutical composition, comprising said viral vector of any one of Embodiments 44-48, and a pharmaceutically acceptable excipient thereof.

Embodiment 52. The pharmaceutical composition of Embodiment 50 or 51, wherein said pharmaceutically acceptable excipient comprises phosphate-buffered saline (PBS), α,α-trehalose dehydrate, L-histidine monohydrochloride monohydrate, polysorbate 20, NaCl, NaH2PO4, Na2HPO4, KH2PO4, K2HPO4, poloxamer 188, or any combination thereof.

Embodiment 53. The pharmaceutical composition of Embodiment 50 or 51, wherein said pharmaceutically acceptable excipient is selected from phosphate-buffered saline (PBS), α,α-trehalose dehydrate, L-histidine monohydrochloride monohydrate, polysorbate 20, NaCl, NaH2PO4, Na2HPO4, KH2PO4, K2HPO4, poloxamer 188, and any combination thereof.

Embodiment 54. The pharmaceutical composition of Embodiment 50 or 51, wherein said pharmaceutically acceptable excipient comprises poloxamer 188.

Embodiment 55. The pharmaceutical composition of Embodiment 54, wherein said pharmaceutically acceptable excipient comprises 0.0001%-0.01% poloxamer 188.

Embodiment 56. The pharmaceutical composition of Embodiment 55, wherein said pharmaceutically acceptable excipient comprises 0.001% poloxamer 188.

Embodiment 57. The pharmaceutical composition of any one of Embodiments 50-56, wherein said pharmaceutically acceptable excipient further comprises one or more salts.

Embodiment 58. The pharmaceutical composition of Embodiment 57, wherein said one or more salts comprises NaCl, NaH2PO4, Na2HPO4, and KH2PO4.

Embodiment 59. The pharmaceutical composition of Embodiment 57, wherein said one or more salts comprises 80 mM NaCl, 5 mM NaH2PO4, 40 mM Na2HPO4, and 5 mM KH2PO4.

Embodiment 60. The pharmaceutical composition of any one of Embodiments 49-59, wherein said pharmaceutical composition has a pH of 6-8.

Embodiment 61. The pharmaceutical composition of Embodiment 60, wherein said pharmaceutical composition has a pH of 7.2-7.4.

Embodiment 62. The pharmaceutical composition of Embodiment 61, wherein said pharmaceutical composition has a pH of 7.3.

Embodiment 63. The pharmaceutical composition of any one of Embodiments 49-62, wherein said pharmaceutical composition has a viral titer of at least $1.0 \times 10^{10}$ vg/mL.

Embodiment 64. The pharmaceutical composition of Embodiment 63, wherein said pharmaceutical composition has a viral titer of at least $5.0 \times 10^{10}$ vg/mL.

Embodiment 65. The pharmaceutical composition of any one of Embodiments 49-64, when said pharmaceutical composition is subject to five freeze/thaw cycles, said pharmaceutical composition retains at least 60%, 70%, 80%, or 90% of a viral titer as compared to the viral titer prior to the five freeze/thaw cycles.

Embodiment 66. The pharmaceutical composition of any one of Embodiments 49-65, wherein said pharmaceutical composition, when administered to a patient with Leber's hereditary optic neuropathy, generates a higher average recovery of vision than a comparable pharmaceutical composition without said recombinant nucleic acid.

Embodiment 67. The pharmaceutical composition of any one of Embodiments 49-66, wherein said pharmaceutical composition, when administered to a patient with Leber's hereditary optic neuropathy, generates a higher average recovery of vision than a comparable pharmaceutical composition comprising a recombinant nucleic acid as set forth in SEQ ID NO: 15.

Embodiment 68. A method of treating an eye disorder, comprising administering said pharmaceutical composition of any one of Embodiments 49-67 to a patient in need thereof.

Embodiment 69. The method of Embodiment 68, wherein said eye disorder is Leber's hereditary optic neuropathy (LHON).

Embodiment 70. The method of Embodiment 68 or 69, comprising administering said pharmaceutical composition to one or both eyes of said patient.

Embodiment 71. The method of any one of Embodiments 68-70, wherein said pharmaceutical composition is administered via intraocular or intravitreal injection.

Embodiment 72. The method of Embodiment 71, wherein said pharmaceutical composition is administered via intravitreal injection.

Embodiment 73. The method of Embodiment 72, wherein about 0.01-0.1 mL of said pharmaceutical composition is administered via intravitreal injection.

Embodiment 74. The method of Embodiment 73, wherein about 0.05 mL of said pharmaceutical composition is administered via intravitreal injection.

Embodiment 75. The method of any one of Embodiments 68-74, further comprising administering methylprednisolone to said patient.

Embodiment 76. The method of Embodiment 75, wherein said methylprednisolone is administered prior to said intravitreal injection of said pharmaceutical composition.

Embodiment 77. The method of Embodiment 75 or 76, wherein said methylprednisolone is administered orally.

Embodiment 78. The method of any one of Embodiments 75-77, wherein said methylprednisolone is administered daily for at least 1, 2, 3, 4, 5, 6, or 7 days prior to said intravitreal injection of said pharmaceutical composition.

Embodiment 79. The method of any one of Embodiments 75-78, wherein said methylprednisolone is administered daily.

Embodiment 80. The method of any one of Embodiments 75-79, wherein a daily dosage of about 32 mg/60 kg methylprednisolone is administered.

Embodiment 81. The method of any one of Embodiments 75-80, wherein said methylprednisolone is administered after said intravitreal injection of said pharmaceutical composition.

Embodiment 82. The method of any one of Embodiments 75-81, further comprising administering creatine phosphate sodium to said patient.

Embodiment 83. The method of Embodiment 82, wherein said creatine phosphate sodium is administered intravenously.

Embodiment 84. The method of any one of Embodiments 75-83, wherein said methylprednisolone is administered intravenously or orally.

Embodiment 85. The method of any one of Embodiments 75-84, comprising administering methylprednisolone intravenously for at least one day, which is followed by administering methylprednisolone orally for at least a week.

Embodiment 86. The method of Embodiment 85, comprising administering methylprednisolone intravenously for about 3 days, which is followed by administering methylprednisolone orally for at least about 6 weeks.

Embodiment 87. The method of any one of Embodiments 75-86, wherein said methylprednisolone is administered intravenously at a daily dose of about 80 mg/60 kg.

Embodiment 88. The method of any one of Embodiments 75-87, wherein said administering said pharmaceutical composition generates a higher average recovery of vision than a comparable pharmaceutical composition without said recombinant nucleic acid.

Embodiment 89. The method of any one of Embodiments 75-88, wherein said administering said pharmaceutical composition generates a higher average recovery of vision than a comparable pharmaceutical composition comprising a recombinant nucleic acid as set forth in SEQ ID NO: 25.

EXAMPLES

The following exemplary embodiments further describe the present invention. It should be understood that these examples are only intended to illustrate the invention, but not to limit the scope of the present invention. Unless otherwise indicated, the methods and conditions disclosed in e.g., sambrook et al, molecular cloning: a laboratory manual (New York: cold spring harbor laboratory press, 1989) or the conditions recommended by the manufacturer can be used in the examples below.

Example 1—ND1 Plasmid and Virus Preparation 1.1 Plasmid Preparation

The nucleotide sequence for human ND1 was obtained based on US National Center for Biotechnology Information reference Gene ID 4535 (SEQ ID NO: 163). The mitochondrial targeting sequence is derived from COX10 (e.g., as shown in SEQ ID NO: 1 and 3). The optimized nucleotide sequence of human ND1 (e.g., SEQ ID NO: 11 and 12, referred herein as ND1 and optimized ND1) were designed to improve the transcription efficiency and/or the translation efficiency. The optimized COX10-opt_ND1 sequence is about 81% homology to COX10-ND1 (as shown in FIG. 4), and the GC content is raised from 49.45% to 64.26% after codon-optimization, and therefore has improved gene transcription efficiency and protein translation efficiency. The 3' of the optimized opt_ND1 gene was followed by an untranslated region (i.e., 3'UTR, SEQ ID NO: 13) to form a recombinant nucleic acid, COX10-opt_ND1-3'UTR (as shown in SEQ ID NO: 27).

The synthesized recombinant nucleic acid, COX10-opt_ND1-3'UTR and the AAV vector was cut by restriction enzymes to form cohesive ends, and then the recombinant nucleic acid was embedded into the rAAV vector to form generate the rAAV-optimized ND1 plasmid (i.e., the rAAV2-opt_ND1 plasmid). The rAAV2-opt_ND1 plasmid was compared to the rAAV2-ND1 plasmid which comprises the COX10-ND1 nucleic acid. The plasmid was cultured at 37° C. in a LB plate with Kanamycin. Blue colonies and white colonies appeared, where white colonies were recombinant clones. The white colonies were picked, added to 100 mg/L kanamycin-containing LB culture medium, cultured at 37° C., 200 rpm for 8 hours and then the plasmid were extracted from the cultured bacterial medium.

1.2 Cell Transfection

One day before transfection, HEK293 cells were inoculated to 225 cm2 cell culture bottle: at the inoculation density of 3.0×107 cells/ml, the culture medium was the Dulbecco's Modified Eagle Medium (DMEM) with 10% bovine serum, at 37° C. in a 5% C02 incubator overnight. The culture medium were replaced with fresh DMEM with 10% bovine serum on the day of transfection. After the cells grow to 80-90%, the culture medium was discarded and cells were transfected with the rAAV2-ND1 and rAAV2-opt_ND1 plasmid. The cells were collected 48 h after the transfection.

1.3 Collection, Concentration and Purification of the Recombinant Adeno-Associated Virus Virus collection: 1) dry ice ethanol bath (or liquid nitrogen) and a 37° C. water bath were prepared; 2) the transfected cells along with media were collected in a 15 ml centrifuge tube; 3) the cells were centrifuged for 3 minutes at 1000 rpm/min; the cells and supernatant were separated; the supernatant were stored separately; and the cells were re-suspended in 1 ml of PBS; 4) the cell suspension were transferred between the dry ice-ethanol bath and 37° C. water bath repeatedly, freeze thawing for four times for 10 minutes each, slightly shaking after each thawing.

Virus concentration: 1) cell debris were removed with 10,000 g centrifugation; the centrifugal supernatant was transferred to a new centrifuge tube; 2) adding benzonase nuclease was added to remove residual plasmid DNA (final concentration at 50 U/ml). The tube was inverted several times to mix thoroughly and then incubated at 37° C. for 30 minutes; 3) the sample was filtered with a 0.45 μm filtration head; the filtrate is the concentrated rAAV2 virus.

Virus purification: 1) Iodixanol at final concentrations of 60%, 50%, 40%, or 25% was added to the concentrated virus solution; 2) samples were centrifuged at 50,000 g for 4 hours to form a density gradient. The enriched rAAV2 particles were collected near the fraction with 50% iodixanol; 3) viruses were loaded to a dialysis column bag and eluted for 10 times to obtain the purified recombinant AAV virus.

Accordingly, the concentrated, purified AAV particles comprising rAAV2-ND1 and rAAV2-opt_ND1 were obtained.

Similarly, other mitochondrial targeting sequences (MTS), such as OPA1 (SEQ ID NO: 5) can be used to replace COX10 in the above example and create AAV with recombinant plasmids. Mitochondria targeting peptide encoded by COX10 and OPA1 can direct the protein encoded by the optimized ND1 nucleic acid to the inner membrane of mitochondria, thereby achieving mitochondria targeted expression of protein.

Figure 5:
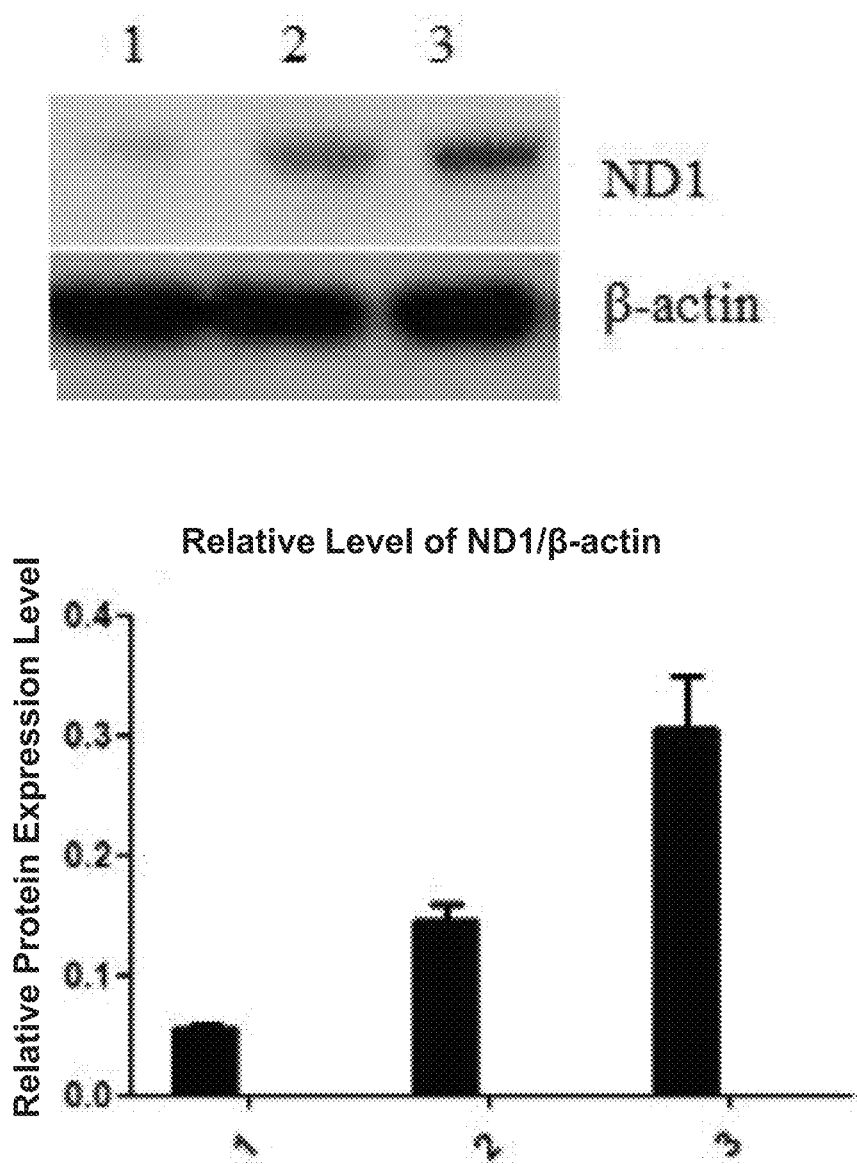
FIG. 5 shows the protein expression level analysis of COX10-opt_ND1 construct and COX10-ND1 construct in human HEK293 cells. Upper figure shows Western blotting result and lower figure is a bar graph showing analysis result.

Example 2—Expression of ND1 Protein in HEK293 Cells Using COX10-ND1 and Further Optimized COX10-Opt_ND1 Vectors HEK293 cells were transduced with viral particle comprising 1) rAAV2-COX10-opt_ND1 (comprising SEQ ID NO: 27) or 2) rAAV2-COX10-ND1 (comprising SEQ ID NO: 25) at MOI of 10,000. PBS was used for the control group. Cellular proteins were extracted 48 hours after transduction for analysis by western blotting. β-actin was used as loading control. As shown in FIG. 5, the results indicated that ND1 expression level in cells transduced with the optimized rAAV2-COX10-opt_ND1 is 2.1 times of the ND1 expression level in cells transduced with the non-optimized COX10-ND1. In FIG. 5, lane 1 is PBS control, lane 2 is rAAV2-COX10-ND1 group, and lane 3 is rAAV2-COX10-opt_ND1 group.

Example 3—Expression and Mitochondria Localization of Human AAV2-ND1 in HEK293 Cells We have conducted fluorescence microscopy/staining experiment to show that the mitochondria targeting sequence (MTS) can direct ND1 protein into mitochondria, suggesting that it is feasible to use these constructs to treat LHON.

Here, 293 cells and RGC-5 cells were transduced with corresponding rAAV2-ND1-ZsGreen at MOI of 106. 48 hours after viral transduction, we used fluorescence microscopy to monitor the expression of green fluorescence protein and cell condition. Mitochondria was stained with MitoTracker and cell nucleus were stained with DAPI after fixation using 4% paraformadyhyde.

As shown in FIG. 6, mitochondria was labeled with MitoTracker and shown in red color, ND1-ZsGreen protein was shown in green color. According to laser confocal microscopy, ND1 proteins were co-localized with mitochondria (as shown in the merged yellow color) in 293 cells and RGC-5 cells. The results showed that the ND1 constructs carrying MTS result in expression of ND1 protein in mitochondria.

Example 4—Dynamics of Expression of AAV2-ND1 in HEK293 Cells

To study the change of ND1 mRNA expression over time after rAAV2-ND1 transduction in cells, we collected cell samples at different time points and analyzed ND1 mRNA expression level using RT-PCT.

Briefly, 293 cells were cultured and transduced with viral particles at MOI of 104 or 105. RT-PCR was conducted using the following primers for ND1 and GAPDH (as control):

```
ND1-F:
                                        (SEQ ID NO: 164)
GAGGCTCTGTCTGGTATCTTGAA

ND1-R:
                                        (SEQ ID NO: 165)
GTCGGGGCGGTGATGTAG

GAPDH-F:
                                        (SEQ ID NO: 166)
CCTGTACGCCAACACAGTGC

GAPDH-R:
                                        (SEQ ID NO: 167)
ATACTCCTGCTTGCTGATCC
```

Figure 7:
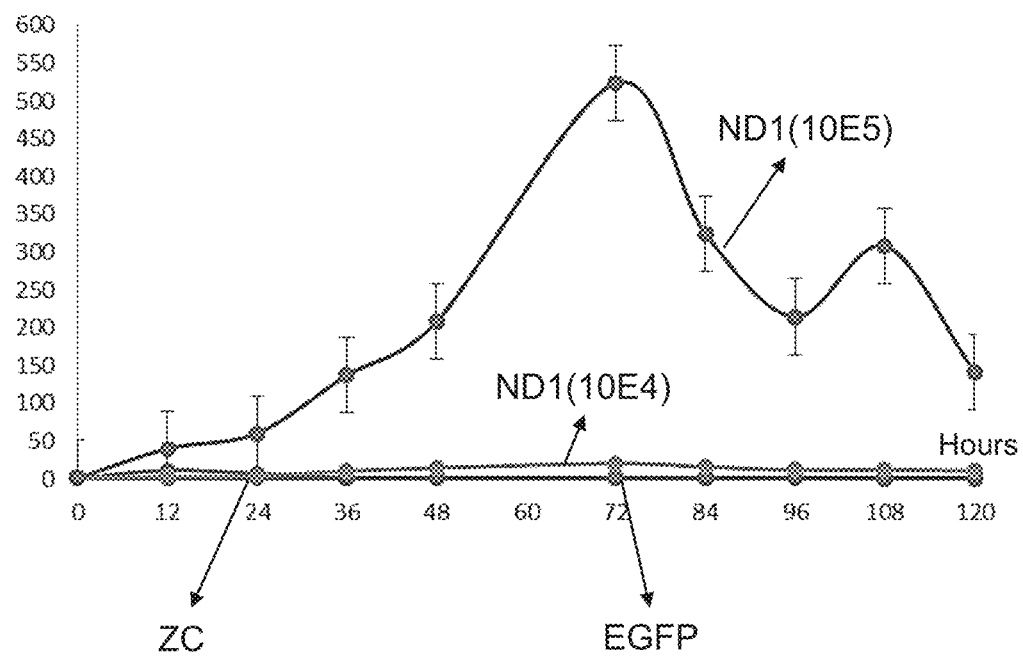
FIG. 7 shows ND1 expression dynamics in HEK293 cells transduced with rAAV2-ND1.

According to FIG. 7, the results showed that ND1 mRNA expression reached peak value at about 72 hours after transduction at MOI of 105, and decreased afterwards, suggesting that rAAV2-ND1 can effectively transduce cells.

Example 5—Exploratory Study of ND1 Expression in C57BL/6J Mice with Intravitreal Injection of rAAV2-ND1

Figure 8:
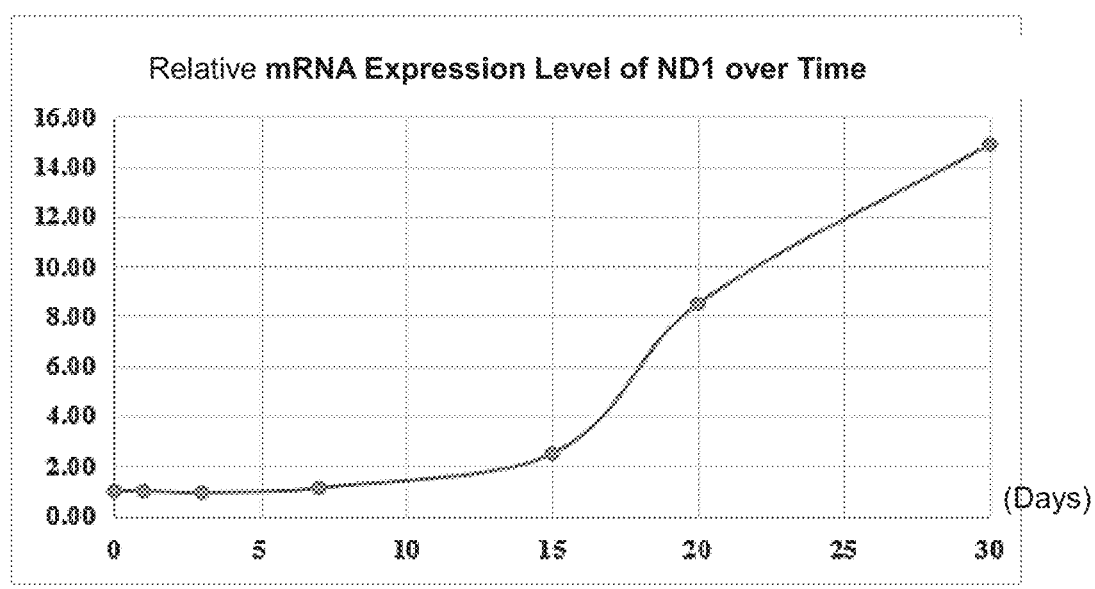
FIG. 8 shows change of ND1 mRNA expression level in C57BL/6J mice intravitreally injected with rAAV2-ND1.

C57BL/6J mice received intravitreal injection of rAAV2-ND1 (at 1 μL injection volume) and eye samples were analyzed 1 day, 5 days, 10 days, or 30 days after injection. RNA were extracted from the sample and RT-PCT was performed to analyze the expression level. As shown in FIG. 8, the results indicated that rAAV-ND1 can be expressed in mice eye and the mRNA expression level continued to increase from 7 days post-injection to 30 days post-injection.

Example 6—ND1 Protein Expression in HEK293 Cells Transduced with rAAV2-ND1

Figure 9:
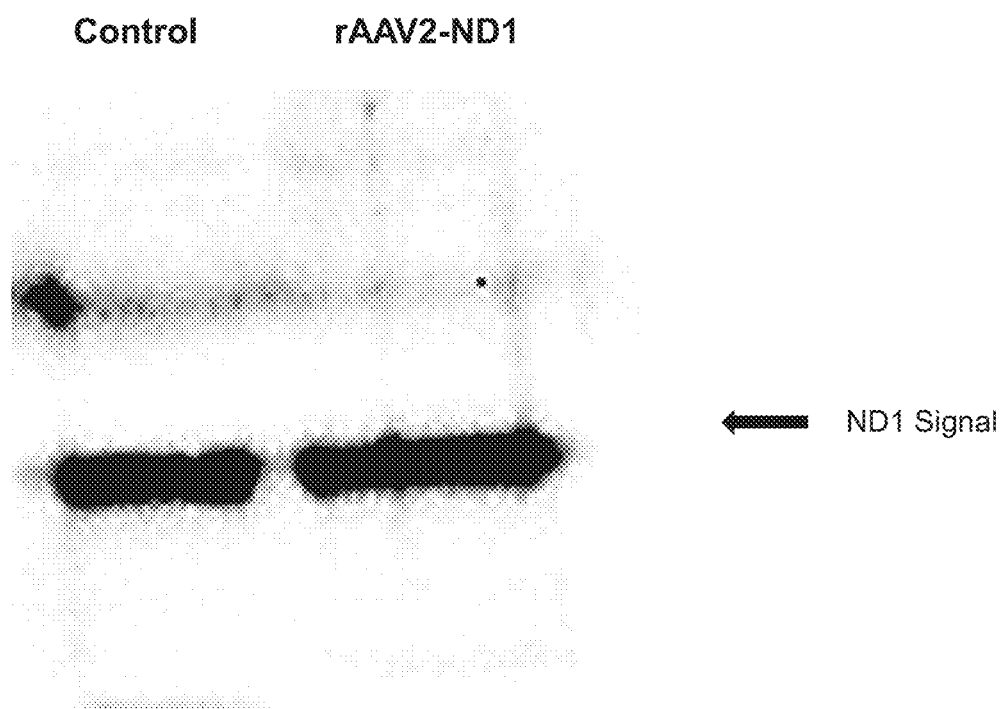
FIG. 9 shows the ND1 protein expression level in HEK293 cells transduced with AAV2-ND1.

293 cells were transduced with rAAV2-ND1 viruses at MOI of 105 and ND1 protein expression was analyzed by Western blotting. As shown in FIG. 9, the results indicated that rAAV2-ND1 can successfully transduce cells and induce ND1 expression.

Example 7—Safety Study of rAAV2-ND1 Using Rabbit Model

Eight rabbits were divided into 2 group. rAAV2-ND1 virus solution (1×1010 vg/0.05 mL) or PBS control solution was punctured into the vitreous cavity from 3 mm outside the corneal limbus at the pars plana. Blood samples were collected for routine blood tests and cytokine analysis 1-month and 2-month post-injection.

Tables 2 and 3 below showed the results of the routine blood tests, including white blood cell count (WBC), red blood cell count (RBC), hemoglobulin (HGB), hematocrit (HCT), platelet (PLT), mean platelet volume (MPV), platelet hematocrit (PCT), mean corpuscular volume (MCV), mean corpuscular hemoglobin (MCH), mean corpuscular hemoglobin concentration (MCHC) and neutrophil ratio (NEUT %). The results showed no significant differences between the rAAV2-ND1 virus injected group and the PBS control group, indicating that injection of rAAV2-ND1 is safe.

TABLE 2

Routine Blood Test Results: 1-month Post-injection

| 1-month | WBC | RBC | HGB | HCT | PLT | MPV |
|---|---|---|---|---|---|---|
| PBS Control | 10.0 ± 1.7 | 6.1 ± 0.4 | 128.4 ± 7.6 | 39.2 ± 2.3 | 425.0 ± 74.3 | 6.6 ± 0.2 |
| rAAV2-ND1 | 10.9 ± 2.6 | 6.3 ± 0.4 | 132.0 ± 6.7 | 40.4 ± 2.0 | 363.9 ± 144.1 | 7.1 ± 0.4 |

| 1-month | PCT | MCV | MCH | MCHC | NEUT% |
|---|---|---|---|---|---|
| PBS Control | 0.3 ± 0.1 | 64.6 ± 1.9 | 21.2 ± 0.5 | 327.4 ± 6.5 | 48.4 ± 8.5 |
| rAAV2-ND1 | 0.3 ± 0.1 | 64.5 ± 3.4 | 21.1 ± 0.9 | 326.9 ± 6.1 | 38.7 ± 8.6 |

TABLE 3

Routine Blood Test Results: 2-month Post-injection

| 2-month | WBC | RBC | HGB | HCT | PLT | MPV |
|---|---|---|---|---|---|---|
| PBS Control | 8.9 ± 4.1 | 6.5 ± 0.5 | 139.6 ± 10.2 | 41.6 ± 3.1 | 284.0 ± 120 | 7.8 ± 0.6 |
| rAAV2-ND1 | 7.6 ± 1.6 | 6.8 ± 0.2 | 144.7 ± 5.7 | 42.8 ± 1.4 | 326.6 ± 130 | 7.9 ± 0.6 |

TABLE 3-continued

| Routine Blood Test Results: 2-month Post-injection | | | | | |
|---|---|---|---|---|---|
| 2-month | PCT | MCV | MCH | MCHC | NEUT % |
| PBS Control | 0.2 ± 0.1 | 64.4 ± 3.2 | 21.6 ± 1.1 | 335.6 ± 6.9 | 32.9 ± 6.9 |
| rAAV2-ND1 | 0.3 ± 0.1 | 63.0 ± 1.7 | 21.3 ± 0.5 | 338.1 ± 8.9 | 40.2 ± 8.3 |

As shown in FIG. 10, cytokine analysis of blood samples 1-month and 2-month post-injection showed that there was no significant differences of cytokine levels (TNF-α, IFN-γ, IL-6) between rAAV2-ND1 virus injected group and the PBS control group, indicating that injection of rAAV2-ND1 does not generate immune response, is safe and without immunogenicity.

Example 8—Other Fusion Proteins

Similar experimental methods in examples 1-7 can be followed using other fusion proteins as set forth in SEQ ID NO: 15-84. And similar results are expected to be achieved.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A recombinant nucleic acid, comprising:
a mitochondrial targeting sequence;
a mitochondrial protein coding sequence comprising a sequence that is at least 99% identical to SEQ ID NO: 11 or 12; and
a 3'UTR nucleic acid sequence.

2. The recombinant nucleic acid of claim 1, wherein said mitochondrial targeting sequence comprises a sequence that is at least 90% identical to a sequence selected from the group consisting of SEQ ID NO: 1-5.

3. The recombinant nucleic acid of claim 1, wherein said mitochondrial targeting sequence comprises a sequence encodes a polypeptide selected from the group consisting of hsCOX10, hsCOX8, scRPM2, lcSirt5, tbNDUS7, ncQCR2, hsATP5G2, hsLACTB, spilv1, gmCOX2, crATP6, hsOPA1, hsSDHD, hsADCK3, osP0644B06.24-2, Neurospora crassa ATPS (ncATP9), hsGHITM, hsNDUFAB1, hsATP5G3, crATP6_hsADCK3, ncATP9_ncATP9, zmLOC100282174, ncATP9_zmLOC100282174_spilv1_ncATP9, zmLOC100282174_hsADCK3_crATP6_hsATP5G3, zmLOC100282174_hsADCK3_hsATP5G3, ncATP9_zmLOC100282174, hsADCK3_zmLOC100282174_crATP6_hsATP5G3, crATP6_hsADCK3_zmLOC100282174_hsATP5G3, hsADCK3_zmLOC100282174, hsADCK3_zmLOC100282174_crATP6, ncATP9_zmLOC100282174_spilv1_GNFP_ncATP9, and ncATP9_zmLOC100282174_spilv1_lcSirt5_osP0644B06.24-2_hsATP5G2_ncATP9.

4. The recombinant nucleic acid of claim 1, wherein said mitochondrial targeting sequence encodes a polypeptide comprising a peptide sequence that is at least 90% identical to a sequence selected from the group consisting of SEQ ID NO: 129-159.

5. The recombinant nucleic acid of claim 1, wherein said 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, rnSOD2, and hsOXA1L.

6. The recombinant nucleic acid of claim 1, wherein said 3'UTR nucleic acid sequence comprises a sequence that is at least 90% identical to a sequence selected from the group consisting of SEQ ID NO: 13, 14, and 111-125.

7. The recombinant nucleic acid of claim 1, wherein said recombinant nucleic acid comprises a sequence that is at least 90% identical to a sequence selected from the group consisting of SEQ ID NO: 25-28, 39-42, 53-56, 67-70, and 81-84.

8. The recombinant nucleic acid of claim 1, wherein said mitochondrial protein coding sequence encodes a mitochondrial protein comprising or consisting of a sequence that is at least 90% identical to a sequence as set forth in SEQ ID NO: 162.

9. A viral vector comprising said recombinant nucleic acid of claim 1.

10. The viral vector of claim 9, wherein said viral vector is an adeno-associated virus (AAV) vector.

11. The viral vector of claim 10, wherein said AAV vector is a recombinant AAV (rAAV) vector.

12. The viral vector of claim 11, wherein said rAAV vector is rAAV2 vector.

13. A pharmaceutical composition, comprising a viral vector comprising said recombinant nucleic acid of claim 1 and a pharmaceutically acceptable excipient thereof.

14. The pharmaceutical composition of claim 13, wherein said viral vector is an adeno-associated virus (AAV) vector.

15. The pharmaceutical composition of claim 13, wherein said pharmaceutically acceptable excipient comprises phosphate-buffered saline (PBS), α,α-trehalose dehydrate, L-histidine monohydrochloride monohydrate, polysorbate 20, NaCl, $NaH_2PO_4$, $Na_2HPO_4$, $KH_2PO_4$, $K_2HPO_4$, poloxamer 188, or any combination thereof.

16. The pharmaceutical composition of claim 13, wherein said pharmaceutically acceptable excipient comprises poloxamer 188.

17. The pharmaceutical composition of claim 16, wherein said pharmaceutically acceptable excipient comprises 0.0001%-0.01% poloxamer 188.

18. The pharmaceutical composition of claim 13, wherein said pharmaceutical composition has a viral titer of at least $5.0 \times 10^{10}$ vg/mL.

19. The pharmaceutical composition of claim 13, when said pharmaceutical composition is subject to five freeze/thaw cycles, said pharmaceutical composition retains at least 60% of a viral titer as compared to the viral titer prior to the five freeze/thaw cycles.

20. A method of treating Leber's hereditary optic neuropathy (LHON), comprising intravitreally administering a pharmaceutical composition to a patient in need thereof, wherein said pharmaceutical composition comprises a therapeutically effective amount of an adeno-associated virus (AAV) comprising the recombinant nucleic acid of claim 1.

21. The method of claim 20, wherein about 0.01-0.1 mL of said pharmaceutical composition is administered via intravitreal injection.

22. The method of claim 20, further comprising administering methylprednisolone to said patient.

23. The method of claim 22, wherein said methylprednisolone is administered daily for at least 2 days prior to intravitreal injection of said pharmaceutical composition.

24. The method of claim 22, comprising administering methylprednisolone intravenously for at least one day, which is followed by administering methylprednisolone orally for at least a week.

25. The method of claim 22, wherein said methylprednisolone is administered intravenously at a daily dose of about 80 mg/60 kg.

26. The method of claim 20, further comprising administering creatine phosphate sodium to said patient.

27. The method of claim 20, wherein said administering said pharmaceutical composition generates a higher average recovery of vision than a comparable pharmaceutical composition without said recombinant nucleic acid.

28. The method of claim 20, wherein said administering said pharmaceutical composition generates a higher average recovery of vision than a comparable pharmaceutical composition comprising a recombinant nucleic acid as set forth in SEQ ID NO: 25.

29. A recombinant nucleic acid, comprising a mitochondrial protein coding sequence, wherein said mitochondrial protein coding sequence encodes a polypeptide comprising a mitochondrial protein, wherein said mitochondrial protein coding sequence comprises a sequence that is at least 99% identical to SEQ ID NO: 11 or 12.

* * * * *